United States Patent
Kida et al.

(10) Patent No.: US 11,634,778 B2
(45) Date of Patent: Apr. 25, 2023

(54) KIT, DEVICE, AND METHOD FOR DETECTING LUNG CANCER

(71) Applicants: TORAY INDUSTRIES, INC., Tokyo (JP); NATIONAL CANCER CENTER, Tokyo (JP)

(72) Inventors: Yuho Kida, Kamakura (JP); Satoko Kozono, Kamakura (JP); Hiroko Sudo, Kamakura (JP); Satoshi Kondou, Kamakura (JP); Junpei Kawauchi, Kamakura (JP); Takahiro Ochiya, Tokyo (JP); Shun-Ichi Watanabe, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 26 days.

(21) Appl. No.: 16/626,781

(22) PCT Filed: Jun. 29, 2018

(86) PCT No.: PCT/JP2018/024834
§ 371 (c)(1),
(2) Date: Dec. 26, 2019

(87) PCT Pub. No.: WO2019/004436
PCT Pub. Date: Jan. 3, 2019

(65) Prior Publication Data
US 2020/0140958 A1 May 7, 2020

(30) Foreign Application Priority Data

Jun. 29, 2017 (JP) .............................. JP2017-126933

(51) Int. Cl.
*C12Q 1/6886* (2018.01)
*C12Q 1/6816* (2018.01)

(52) U.S. Cl.
CPC ......... *C12Q 1/6886* (2013.01); *C12Q 1/6816* (2013.01); *C12Q 2600/112* (2013.01); *C12Q 2600/178* (2013.01); *G01N 2800/7028* (2013.01)

(58) Field of Classification Search
None
See application file for complete search history.

(56) References Cited

U.S. PATENT DOCUMENTS

| | | |
|---|---|---|
| 2001/0053519 A1 | 12/2001 | Fodor |
| 2011/0053158 A1 | 3/2011 | Mambo et al. |
| 2012/0108462 A1 | 5/2012 | Keller et al. |
| 2015/0080243 A1 | 3/2015 | Whitney et al. |
| 2015/0337332 A1* | 11/2015 | Ruohoa-Baker ..... C12N 15/113 514/44 R |
| 2017/0121779 A1 | 5/2017 | Kondou et al. |
| 2017/0130278 A1 | 5/2017 | Sudo et al. |
| 2017/0166975 A1 | 6/2017 | Kondou et al. |

FOREIGN PATENT DOCUMENTS

| | | |
|---|---|---|
| CN | 103173448 A | 6/2013 |
| EP | 3156500 A1 | 4/2017 |
| JP | 2011-505143 A | 2/2011 |
| JP | 2013-502931 A | 1/2013 |
| WO | WO 2009/070653 A1 | 6/2009 |
| WO | WO 2010/139810 A1 | 12/2010 |
| WO | WO 2011/025919 A | 3/2011 |
| WO | WO 2011/076144 A1 | 6/2011 |
| WO | WO 2011/146937 A1 | 11/2011 |
| WO | WO 2014/013258 A | 1/2014 |
| WO | WO 2014/192907 A1 | 12/2014 |
| WO | WO 2015/115923 A2 | 8/2015 |
| WO | WO 2015/190542 A1 | 12/2015 |
| WO | WO 2015/190584 A1 | 12/2015 |
| WO | WO 2015/194610 A1 | 12/2015 |
| WO | WO 2015/194615 A1 | 12/2015 |

OTHER PUBLICATIONS

Cobb et al. (Crit Care Med 2002 vol. 30 p. 2711) (Year: 2002).*
Enard et al. (Science 2002 vol 296 p. 340) (Year: 2002).*
Ondracek et al., "Global MicroRNA Expression Profiling Identifies Unique MicroRNA Pattern of Radioresistant Glioblastoma Cells", Anticancer Research 37, pp. 1099-1104, 2017.
Persson et al., "identification of New MicroRNAs in Paired Normal and Tumor Breast Tissue Suggests a Dual Role for the ERBB2/Her2 Gene", Cancer Research 71(1), pp. 78-86, 2011.
Supplementary Partial European Search Report issued in Application No. 18823484.3 dated Mar. 12, 2021.
Foss et al., "miR-1254 and miR-574-5p Serum-Based microRNA Biomarkers for Early-Stage Non-small Cell Lung Cancer", Journal of Thoracic Oncology, Mar. 2011, vol. 6, No. 3, pp. 482-488.
International Search Report, issued in PCT/JP2018/024834, dated Oct. 2, 2018.
Leidinger et al., "What makes a blood cell based miRNA expression pattern disease specific?—A miRNome analysis of blood cell subsets in lung cancer patients and healthy controls", Oncotarget, Sep. 19, 2014, vol. 5, No. 19, pp. 9484-9497.
Rani et al., "Global analysis of serum microRNAs as potential biomarkers for lung adenocarcinoma", Cancer Biology & Therapy, 2013, vol. 14, issue 12, pp. 1104-1112.
Roth et al., "Low Levels of Cell-Free Circulating miR-361-3p and miR-625* as Blood-Based Markers for Discriminating Malignant from Benign Lung Tumors", PLoS ONE, Jun. 2012, vol. 7, Issue 6, e38248, pp. 1-10.
Schmidt et al., "Liquid Profiling in Lung Cancer—Quantification of Extracellular miRNAs in Bronchial Lavage", Adv Exp Med Biol., 2016, vol. 924, pp. 33-37.

(Continued)

Primary Examiner — Katherine D Salmon
(74) Attorney, Agent, or Firm — Birch, Stewart, Kolasch & Birch, LLP

(57) ABSTRACT

This application provides a kit or a device for detection of lung cancer, comprising a nucleic acid(s) for detecting a miRNA(s) in a sample from a subject, and a method for detecting lung cancer, comprising measuring the miRNA(s) in vitro.

7 Claims, 3 Drawing Sheets
Specification includes a Sequence Listing.

(56) References Cited

OTHER PUBLICATIONS

Tai et al., "Blood-borne miRNA profile-based diagnostic classifier for lung adenocarcinoma", Scientific Reports, Aug. 10, 2016, 6: 31389, total 9 pages.
Written Opinion of the International Searching Authority, issued in PCT/JP2018/024834, dated Oct. 2, 2018.
Dissertation of Xin Wang, "Microrna: Profiling and Functional Implications in Cancer and Metabolism" from University of Houston, Dec. 2012, available online at https://uh-ir.tdl.org/bitstream/handle/10657/540/Diss_XinWang_20121.pdf?sequence=1&isAllowed=y.
GenBank Locus NR_ 106826. "*Homo sapiens* micro RNA 6768 (MIR6768), micro RNA", (Apr. 3, 2014) from/www.ncbi.nlm.nih.gov, printed pp. 1-3.
Qiagen Product Description "miScript™ miRNA PCR Array (384-well, 384HC) Human miRBase Profiler HC Plate 3" document 1073798, Aug. 2012, from https://b2b.qiagen.com/~media/genetable/mi/hs/34/mihs-3403z.
American Cancer Society. "Luna Cancer (Non-Small Cell)", 2013, total 77 pages, pp. 2-7 and 37-56.
Bai et al., "MiR-296-3p regulates cell growth and multi-drug resistance of human glioblastoma by targeting ether-á-go-go (EAG1)," European Journal of Cancer. vol. 49, No. 3, 2013 (available online Sep. 18, 2012), pp. 710-724.
Chen et al., "Identification of ten serum microRNAs from a genome-wide serum microRNA expression profile as novel noninvasive biomarkers for nonsmall cell lung cancer diagnosis", International Journal Cancer, vol. 130, May 9, 2011, pp. 1620-1628.
Cheung et al., "Natural variation in human qene expression assessed In lymphobiastoid cells", Nature Genetics, vol. 33, Mar. 2003, pp. 422-425.
Eto et al., "Prospect of microRNA toward laboratory medicine Gastrointestinal Cancer and microRNA", Clinical Chemistry, 2014, vol. 43, pp. 99-105.
Hoshikawa et al., "Hypoxia induces different genes in the lungs of rats compared with mice", Physiological Genomics, vol. 12, 2003, pp. 209-213.
International Search Report, issued in PCT/JP2015/067533, dated Sep. 15, 2015.
Japanese Office Action for Japanese Application No. 2019-527064, dated Jun. 7, 2022.
Jin et al., "Circulating microRNA: a novel potential biomarker for early diagnosis of Intracranial Aneurysm Rupture a case control study." Journal of Translational Medicine (2013), vol. 11, No. 296, pp. 1-9.
Keller et al., "Stable serum miRNA profiles as potential tool for non-invasive lung cancer diagnosis", RNA Biology, May 1, 2011, vol. 8, No. 3, pp. 506-516, Supplemental Content.
Kozomara et al., "miRBase: annotating high confidence microRNAs using deep sequencing data", Nucleic Acids Research, Nov. 25, 2013, vol. 42, Database issue, pp. D68-D73.
MiScript™ miRNA PCR Array (384-well, 384HC) Human miRBase Profiler HC Plate 5, Qiagen, 2012, 10 pages, from https://b2b.qiagen.com/-/media/genetable/mi/hs/34/mihs-3403z.
Office Action dated Aug. 23, 2021, in Republic of Korea Patent Application No. 10-2017-7000867.
Okamura et al., "Diagnostic value of CEA and CYFRA21-1 tumor markers in primary lung cancer", Lung Cancer, 2013, vol. 80, pp. 45-49.
Partial Supplementary European Search Report, dated Dec. 14, 2017, for European Application No. 15809623.0.
Shen et al., "Applications of MicroRNAs in the Diagnosis and Prognosis of Lung Cancer," Expert Opin. Med. Diagn. (2012), vol. 6, No. 3, pp. 197-207.
Sobin et al., "TNM Classification of Malignant Tumours, the 7th edition", International Union Against Cancer; 2010, pp. 129-134.
Takizawa el al., "miRNA Profiling in Serum Samples Using DNA Chip 3D-Gene®" BIO Clinica, Jun. 10, 2014, vol. 29, No. 6, pp. 588-589.
U.S. Office Action for U.S. Appl. No. 16/800,755, dated Feb. 2, 2022.
U.S. Office Action for U.S. Appl. No. 16/800,755, dated Oct. 8, 2021.
Written Opinion of the International Searching Authority, issued in PCT/JP2015/067533, dated Sep. 15, 2015.
Yanaihara et al., "Unique microRNA molecular profiles in lung cancer diagnosis and prognosis," Cancer Cell, vol. 9, No. 3, Mar. 13, 2006, pp. 189-198.

* cited by examiner

SEQUENCE LISTING

<160> NUMBER OF SEQ ID NOS: 1000

<210> SEQ ID NO 1
<211> LENGTH: 22
<212> TYPE: RNA
<213> ORGANISM: Homo sapiens

<400> SEQUENCE: 1
uggcgggggu agagcuggcu gc

```
<210> SEQ ID NO 2
<211> LENGTH: 20
<212> TYPE: RNA
<213> ORGANISM: Homo sapiens

<400> SEQUENCE: 2
ggggagcugu ggaagcagua                                               20

<210> SEQ ID NO 3
<211> LENGTH: 22
<212> TYPE: RNA
<213> ORGANISM: Homo sapiens

<400> SEQUENCE: 3
caggcacggg agcucaggug ag                                            22

<210> SEQ ID NO 4
<211> LENGTH: 22
<212> TYPE: RNA
<213> ORGANISM: Homo sapiens

<400> SEQUENCE: 4
auauacaggg ggagacucuu au                                            22

<210> SEQ ID NO 5
<211> LENGTH: 19
<212> TYPE: RNA
<213> ORGANISM: Homo sapiens

<400> SEQUENCE: 5
ggcuugcaug ggggacugg                                                19

<210> SEQ ID NO 6
<211> LENGTH: 20
<212> TYPE: RNA
<213> ORGANISM: Homo sapiens

<400> SEQUENCE: 6
gcggagagag aaugggggagc                                              20

<210> SEQ ID NO 7
<211> LENGTH: 20
<212> TYPE: RNA
<213> ORGANISM: Homo sapiens

<400> SEQUENCE: 7
gugagucagg gugggcugg                                                20

<210> SEQ ID NO 8
<211> LENGTH: 21
<212> TYPE: RNA
<213> ORGANISM: Homo sapiens

<400> SEQUENCE: 8
ccgucgccgc cacccgagcc g                                             21

<210> SEQ ID NO 9
<211> LENGTH: 22
<212> TYPE: RNA
<213> ORGANISM: Homo sapiens

<400> SEQUENCE: 9
```
auauacaggg ggagacucuc au                                                    22

<210> SEQ ID NO 10
<211> LENGTH: 23
<212> TYPE: RNA
<213> ORGANISM: Homo sapiens

<400> SEQUENCE: 10
gggaugguag accggugacg ugc                                                   23

<210> SEQ ID NO 11
<211> LENGTH: 21
<212> TYPE: RNA
<213> ORGANISM: Homo sapiens

<400> SEQUENCE: 11
uggcagggag gcugggaggg g                                                     21

<210> SEQ ID NO 12
<211> LENGTH: 23
<212> TYPE: RNA
<213> ORGANISM: Homo sapiens

<400> SEQUENCE: 12
gugaguggga gccccagugu gug                                                   23

<210> SEQ ID NO 13
<211> LENGTH: 19
<212> TYPE: RNA
<213> ORGANISM: Homo sapiens

<400> SEQUENCE: 13
aauggauuuu uggagcagg                                                        19

<210> SEQ ID NO 14
<211> LENGTH: 24
<212> TYPE: RNA
<213> ORGANISM: Homo sapiens

<400> SEQUENCE: 14
aggagggagg agaugggcca aguu                                                  24

<210> SEQ ID NO 15
<211> LENGTH: 20
<212> TYPE: RNA
<213> ORGANISM: Homo sapiens

<400> SEQUENCE: 15
ucgcgccccg gcucccguuc                                                       20

<210> SEQ ID NO 16
<211> LENGTH: 22
<212> TYPE: RNA
<213> ORGANISM: Homo sapiens

<400> SEQUENCE: 16
cucggcgcgg ggcgcgggcu cc                                                    22

<210> SEQ ID NO 17
<211> LENGTH: 21
<212> TYPE: RNA
<213> ORGANISM: Homo sapiens

<400> SEQUENCE: 17
gcccuccgcc cgugcacccc g                                         21

<210> SEQ ID NO 18
<211> LENGTH: 23
<212> TYPE: RNA
<213> ORGANISM: Homo sapiens

<400> SEQUENCE: 18
cggguagaga gggcaguggg agg                                       23

<210> SEQ ID NO 19
<211> LENGTH: 22
<212> TYPE: RNA
<213> ORGANISM: Homo sapiens

<400> SEQUENCE: 19
gagcuuuugg cccgguuau ac                                         22

<210> SEQ ID NO 20
<211> LENGTH: 22
<212> TYPE: RNA
<213> ORGANISM: Homo sapiens

<400> SEQUENCE: 20
uuggggaaac ggccgcugag ug                                        22

<210> SEQ ID NO 21
<211> LENGTH: 21
<212> TYPE: RNA
<213> ORGANISM: Homo sapiens

<400> SEQUENCE: 21
gcagggacag caaaggggug c                                         21

<210> SEQ ID NO 22
<211> LENGTH: 22
<212> TYPE: RNA
<213> ORGANISM: Homo sapiens

<400> SEQUENCE: 22
agcagaggca gagaggcuca gg                                        22

<210> SEQ ID NO 23
<211> LENGTH: 22
<212> TYPE: RNA
<213> ORGANISM: Homo sapiens

<400> SEQUENCE: 23
guugggacaa gaggacgguc uu                                        22

<210> SEQ ID NO 24
<211> LENGTH: 19
<212> TYPE: RNA
<213> ORGANISM: Homo sapiens

<400> SEQUENCE: 24
gagggcgggu ggaggagga                                            19

<210> SEQ ID NO 25
<211> LENGTH: 22
<212> TYPE: RNA
<213> ORGANISM: Homo sapiens

```
<400> SEQUENCE: 25
aaagaucugg aagugggaga ca                                              22

<210> SEQ ID NO 26
<211> LENGTH: 21
<212> TYPE: RNA
<213> ORGANISM: Homo sapiens

<400> SEQUENCE: 26
ccugcagaga ggaagcccuu c                                               21

<210> SEQ ID NO 27
<211> LENGTH: 22
<212> TYPE: RNA
<213> ORGANISM: Homo sapiens

<400> SEQUENCE: 27
ggcuuucuag ucucagcucu cc                                              22

<210> SEQ ID NO 28
<211> LENGTH: 22
<212> TYPE: RNA
<213> ORGANISM: Homo sapiens

<400> SEQUENCE: 28
uggggcggag cuuccggagg cc                                              22

<210> SEQ ID NO 29
<211> LENGTH: 23
<212> TYPE: RNA
<213> ORGANISM: Homo sapiens

<400> SEQUENCE: 29 ugggacgua gcuggccaga cag                                              23

<210> SEQ ID NO 30
<211> LENGTH: 22
<212> TYPE: RNA
<213> ORGANISM: Homo sapiens

<400> SEQUENCE: 30
agcucugcug cucacuggca gu                                              22

<210> SEQ ID NO 31
<211> LENGTH: 22
<212> TYPE: RNA
<213> ORGANISM: Homo sapiens

<400> SEQUENCE: 31
aaaagcuggg uugagagggc aa                                              22

<210> SEQ ID NO 32
<211> LENGTH: 23
<212> TYPE: RNA
<213> ORGANISM: Homo sapiens

<400> SEQUENCE: 32
gggggggcag gaggggcuca ggg                                             23

<210> SEQ ID NO 33
<211> LENGTH: 20
<212> TYPE: RNA
<213> ORGANISM: Homo sapiens
```

```
<400> SEQUENCE: 33
gaaucggaaa ggaggcgccg                                              20

<210> SEQ ID NO 34
<211> LENGTH: 22
<212> TYPE: RNA
<213> ORGANISM: Homo sapiens

<400> SEQUENCE: 34
gggaccaucc ugccugcugu gg                                           22

<210> SEQ ID NO 35
<211> LENGTH: 22
<212> TYPE: RNA
<213> ORGANISM: Homo sapiens

<400> SEQUENCE: 35
gugggcuggg cugggcuggg cc                                           22

<210> SEQ ID NO 36
<211> LENGTH: 22
<212> TYPE: RNA
<213> ORGANISM: Homo sapiens

<400> SEQUENCE: 36
gccugcuggg guggaaccug gu                                           22

<210> SEQ ID NO 37
<211> LENGTH: 22
<212> TYPE: RNA
<213> ORGANISM: Homo sapiens

<400> SEQUENCE: 37
acucaaaaug ggggcgcuuu cc                                           22

<210> SEQ ID NO 38
<211> LENGTH: 20
<212> TYPE: RNA
<213> ORGANISM: Homo sapiens

<400> SEQUENCE: 38
gcucggacug agcagguggg                                              20

<210> SEQ ID NO 39
<211> LENGTH: 23
<212> TYPE: RNA
<213> ORGANISM: Homo sapiens

<400> SEQUENCE: 39
acaggcggcu guagcaaugg ggg                                          23

<210> SEQ ID NO 40
<211> LENGTH: 22
<212> TYPE: RNA
<213> ORGANISM: Homo sapiens

<400> SEQUENCE: 40 caguugdggguc uagdgggucag ga                                        22

<210> SEQ ID NO 41
<211> LENGTH: 18
<212> TYPE: RNA
```

```
<213> ORGANISM: Homo sapiens

<400> SEQUENCE: 41
gggucccggg gagggggg                                                18

<210> SEQ ID NO 42
<211> LENGTH: 17
<212> TYPE: RNA
<213> ORGANISM: Homo sapiens

<400> SEQUENCE: 42
gggagucuac agcaggg                                                 17

<210> SEQ ID NO 43
<211> LENGTH: 18
<212> TYPE: RNA
<213> ORGANISM: Homo sapiens

<400> SEQUENCE: 43
gaggcugaag gaagaugg                                                18

<210> SEQ ID NO 44
<211> LENGTH: 22
<212> TYPE: RNA
<213> ORGANISM: Homo sapiens

<400> SEQUENCE: 44
caaggagacg ggaacaugga gc                                           22

<210> SEQ ID NO 45
<211> LENGTH: 20
<212> TYPE: RNA
<213> ORGANISM: Homo sapiens

<400> SEQUENCE: 45
aaaagcuggg cugagaggcg                                              20

<210> SEQ ID NO 46
<211> LENGTH: 21
<212> TYPE: RNA
<213> ORGANISM: Homo sapiens

<400> SEQUENCE: 46
acaggagugg ggugggaca u                                             21

<210> SEQ ID NO 47
<211> LENGTH: 17
<212> TYPE: RNA
<213> ORGANISM: Homo sapiens

<400> SEQUENCE: 47
ggugggggcu guuguuu                                                 17

<210> SEQ ID NO 48
<211> LENGTH: 22
<212> TYPE: RNA
<213> ORGANISM: Homo sapiens

<400> SEQUENCE: 48
cgucccgggg cugcgcgagg ca                                           22

<210> SEQ ID NO 49
<211> LENGTH: 22
```

```
<212> TYPE: RNA
<213> ORGANISM: Homo sapiens

<400> SEQUENCE: 49
ccaggaggcg gaggaggugg ag                                        22

<210> SEQ ID NO 50
<211> LENGTH: 21
<212> TYPE: RNA
<213> ORGANISM: Homo sapiens

<400> SEQUENCE: 50
agccaagugg aaguuacuuu a                                         21

<210> SEQ ID NO 51
<211> LENGTH: 16
<212> TYPE: RNA
<213> ORGANISM: Homo sapiens

<400> SEQUENCE: 51
accgccugcc caguga                                               16

<210> SEQ ID NO 52
<211> LENGTH: 17
<212> TYPE: RNA
<213> ORGANISM: Homo sapiens

<400> SEQUENCE: 52
gcugggcgag gcuggca                                              17

<210> SEQ ID NO 53
<211> LENGTH: 18
<212> TYPE: RNA
<213> ORGANISM: Homo sapiens

<400> SEQUENCE: 53 aggggggcggg cuccggcg                                            18

<210> SEQ ID NO 54
<211> LENGTH: 21
<212> TYPE: RNA
<213> ORGANISM: Homo sapiens

<400> SEQUENCE: 54
uggggcuagu gaugcaggac g                                         21

<210> SEQ ID NO 55
<211> LENGTH: 18
<212> TYPE: RNA
<213> ORGANISM: Homo sapiens

<400> SEQUENCE: 55
aggcugggcu gggacgga                                             18

<210> SEQ ID NO 56
<211> LENGTH: 22
<212> TYPE: RNA
<213> ORGANISM: Homo sapiens

<400> SEQUENCE: 56
agacugacgg cuggaggccc au                                        22

<210> SEQ ID NO 57
```

```
<211> LENGTH: 22
<212> TYPE: RNA
<213> ORGANISM: Homo sapiens

<400> SEQUENCE: 57
aggacuggac ucccggcagc cc                                              22

<210> SEQ ID NO 58
<211> LENGTH: 18
<212> TYPE: RNA
<213> ORGANISM: Homo sapiens

<400> SEQUENCE: 58
cccagcagga cgggagcg                                                   18

<210> SEQ ID NO 59
<211> LENGTH: 17
<212> TYPE: RNA
<213> ORGANISM: Homo sapiens

<400> SEQUENCE: 59
guggaccugg cugggac                                                    17

<210> SEQ ID NO 60
<211> LENGTH: 21
<212> TYPE: RNA
<213> ORGANISM: Homo sapiens

<400> SEQUENCE: 60
ucuugaaguc agaacccgca a                                               21

<210> SEQ ID NO 61
<211> LENGTH: 23
<212> TYPE: RNA
<213> ORGANISM: Homo sapiens

<400> SEQUENCE: 61
ugggccaggg agcagcuggu ggg                                             23

<210> SEQ ID NO 62
<211> LENGTH: 22
<212> TYPE: RNA
<213> ORGANISM: Homo sapiens

<400> SEQUENCE: 62
acugggaaga ggagcugagg ga                                              22

<210> SEQ ID NO 63
<211> LENGTH: 23
<212> TYPE: RNA
<213> ORGANISM: Homo sapiens

<400> SEQUENCE: 63
ugggcugagg gcaggaggcc ugu                                             23

<210> SEQ ID NO 64
<211> LENGTH: 24
<212> TYPE: RNA
<213> ORGANISM: Homo sapiens

<400> SEQUENCE: 64
agcugagcuc cauggacgug cagu                                            24
```

```
<210> SEQ ID NO 65
<211> LENGTH: 23
<212> TYPE: RNA
<213> ORGANISM: Homo sapiens

<400> SEQUENCE: 65 cuggggacg cgugagcgcg agc                                              23

<210> SEQ ID NO 66
<211> LENGTH: 25
<212> TYPE: RNA
<213> ORGANISM: Homo sapiens

<400> SEQUENCE: 66
agcggggagg aaguggggcgc ugcuu                                          25

<210> SEQ ID NO 67
<211> LENGTH: 23
<212> TYPE: RNA
<213> ORGANISM: Homo sapiens

<400> SEQUENCE: 67
gccccggcgc gggcgggguuc ugg                                            23

<210> SEQ ID NO 68
<211> LENGTH: 22
<212> TYPE: RNA
<213> ORGANISM: Homo sapiens

<400> SEQUENCE: 68
agcaaggcgg caucucucug au                                              22

<210> SEQ ID NO 69
<211> LENGTH: 18
<212> TYPE: RNA
<213> ORGANISM: Homo sapiens

<400> SEQUENCE: 69
gggugagggc aggugguu                                                   18

<210> SEQ ID NO 70
<211> LENGTH: 21
<212> TYPE: RNA
<213> ORGANISM: Homo sapiens

<400> SEQUENCE: 70
agcuguaccu gaaaccaagc a                                               21

<210> SEQ ID NO 71
<211> LENGTH: 23
<212> TYPE: RNA
<213> ORGANISM: Homo sapiens

<400> SEQUENCE: 71
ggcaggaggg cugugccagg uug                                             23

<210> SEQ ID NO 72
<211> LENGTH: 22
<212> TYPE: RNA
<213> ORGANISM: Homo sapiens

<400> SEQUENCE: 72 auaguggga gcuggcagau uc                                               22
```

```
<210> SEQ ID NO 73
<211> LENGTH: 23
<212> TYPE: RNA
<213> ORGANISM: Homo sapiens

<400> SEQUENCE: 73
cuggcggagc ccauuccaug cca                                    23

<210> SEQ ID NO 74
<211> LENGTH: 22
<212> TYPE: RNA
<213> ORGANISM: Homo sapiens

<400> SEQUENCE: 74
gcugcgggcu gcggucaggg cg                                     22

<210> SEQ ID NO 75
<211> LENGTH: 22
<212> TYPE: RNA
<213> ORGANISM: Homo sapiens

<400> SEQUENCE: 75
aggacugauc cucucgggca gg                                     22

<210> SEQ ID NO 76
<211> LENGTH: 22
<212> TYPE: RNA
<213> ORGANISM: Homo sapiens

<400> SEQUENCE: 76
aaggcccggg cuuuccuccc ag                                     22

<210> SEQ ID NO 77
<211> LENGTH: 22
<212> TYPE: RNA
<213> ORGANISM: Homo sapiens

<400> SEQUENCE: 77
ugcggggaca ggccagggca uc                                     22

<210> SEQ ID NO 78
<211> LENGTH: 22
<212> TYPE: RNA
<213> ORGANISM: Homo sapiens

<400> SEQUENCE: 78
agccaggcuc ugaagggaaa gu                                     22

<210> SEQ ID NO 79
<211> LENGTH: 21
<212> TYPE: RNA
<213> ORGANISM: Homo sapiens

<400> SEQUENCE: 79
cgccugccca gcccuccugc u                                      21

<210> SEQ ID NO 80
<211> LENGTH: 24
<212> TYPE: RNA
<213> ORGANISM: Homo sapiens

<400> SEQUENCE: 80
gaugcgccgc ccacugcccc gcgc                                   24
```

```
<210> SEQ ID NO 81
<211> LENGTH: 22
<212> TYPE: RNA
<213> ORGANISM: Homo sapiens

<400> SEQUENCE: 81
ugaggcccuu ggggcacagu gg                                              22

<210> SEQ ID NO 82
<211> LENGTH: 22
<212> TYPE: RNA
<213> ORGANISM: Homo sapiens

<400> SEQUENCE: 82
agggggaugg cagagcaaaa uu                                              22

<210> SEQ ID NO 83
<211> LENGTH: 21
<212> TYPE: RNA
<213> ORGANISM: Homo sapiens

<400> SEQUENCE: 83
gggagugcag ggcaggguuu c                                               21

<210> SEQ ID NO 84
<211> LENGTH: 23
<212> TYPE: RNA
<213> ORGANISM: Homo sapiens

<400> SEQUENCE: 84
ccggggcaga uugguguagg gug                                             23

<210> SEQ ID NO 85
<211> LENGTH: 22
<212> TYPE: RNA
<213> ORGANISM: Homo sapiens

<400> SEQUENCE: 85
uucagauccc agcggugccu cu                                              22

<210> SEQ ID NO 86
<211> LENGTH: 22
<212> TYPE: RNA
<213> ORGANISM: Homo sapiens

<400> SEQUENCE: 86
agggaagggg acgaggguug gg                                              22

<210> SEQ ID NO 87
<211> LENGTH: 22
<212> TYPE: RNA
<213> ORGANISM: Homo sapiens

<400> SEQUENCE: 87
gaaaucaagc gugggugaga cc                                              22

<210> SEQ ID NO 88
<211> LENGTH: 23
<212> TYPE: RNA
<213> ORGANISM: Homo sapiens

<400> SEQUENCE: 88
```

-continued

```
guuugcacgg gugggccuug ucu                                    23

<210> SEQ ID NO 89
<211> LENGTH: 20
<212> TYPE: RNA
<213> ORGANISM: Homo sapiens

<400> SEQUENCE: 89
gggcuggggc gcggggaggu                                        20

<210> SEQ ID NO 90
<211> LENGTH: 19
<212> TYPE: RNA
<213> ORGANISM: Homo sapiens

<400> SEQUENCE: 90
ggggagcgag gggcggggc                                         19

<210> SEQ ID NO 91
<211> LENGTH: 20
<212> TYPE: RNA
<213> ORGANISM: Homo sapiens

<400> SEQUENCE: 91
gggaaaagga aggggagga                                         20

<210> SEQ ID NO 92
<211> LENGTH: 19
<212> TYPE: RNA
<213> ORGANISM: Homo sapiens

<400> SEQUENCE: 92
agcagggcug gggauugca                                         19

<210> SEQ ID NO 93
<211> LENGTH: 22
<212> TYPE: RNA
<213> ORGANISM: Homo sapiens

<400> SEQUENCE: 93
cagcagggga gagagaggag uc                                     22

<210> SEQ ID NO 94
<211> LENGTH: 24
<212> TYPE: RNA
<213> ORGANISM: Homo sapiens

<400> SEQUENCE: 94
cugcaggcag aagugggcu gaca                                    24

<210> SEQ ID NO 95
<211> LENGTH: 20
<212> TYPE: RNA
<213> ORGANISM: Homo sapiens

<400> SEQUENCE: 95
ucucuucauc uaccccccag                                        20

<210> SEQ ID NO 96
<211> LENGTH: 22
<212> TYPE: RNA
<213> ORGANISM: Homo sapiens

<400> SEQUENCE: 96
```

| | |
|---|---|
| ugugggccg cagaacaugu gc | 22 |

<210> SEQ ID NO 97
<211> LENGTH: 25
<212> TYPE: RNA
<213> ORGANISM: Homo sapiens

<400> SEQUENCE: 97

| | |
|---|---|
| ggcggaggga aguagguccg uuggu | 25 |

<210> SEQ ID NO 98
<211> LENGTH: 19
<212> TYPE: RNA
<213> ORGANISM: Homo sapiens

<400> SEQUENCE: 98

| | |
|---|---|
| ugcgccucgg gugagcaug | 19 |

<210> SEQ ID NO 99
<211> LENGTH: 20
<212> TYPE: RNA
<213> ORGANISM: Homo sapiens

<400> SEQUENCE: 99

| | |
|---|---|
| aggcgcaccc gaccacaugc | 20 |

<210> SEQ ID NO 100
<211> LENGTH: 23
<212> TYPE: RNA
<213> ORGANISM: Homo sapiens

<400> SEQUENCE: 100

| | |
|---|---|
| cugggcccgc ggcgggcgug ggg | 23 |

<210> SEQ ID NO 101
<211> LENGTH: 21
<212> TYPE: RNA
<213> ORGANISM: Homo sapiens

<400> SEQUENCE: 101

| | |
|---|---|
| ucauccccu cgcccucuca g | 21 |

<210> SEQ ID NO 102
<211> LENGTH: 21
<212> TYPE: RNA
<213> ORGANISM: Homo sapiens

<400> SEQUENCE: 102

| | |
|---|---|
| uuggggugu cggcccugga g | 21 |

<210> SEQ ID NO 103
<211> LENGTH: 23
<212> TYPE: RNA
<213> ORGANISM: Homo sapiens

<400> SEQUENCE: 103

| | |
|---|---|
| agggugggc uggagguggg gcu | 23 |

<210> SEQ ID NO 104
<211> LENGTH: 23
<212> TYPE: RNA
<213> ORGANISM: Homo sapiens

```
<400> SEQUENCE: 104
cggggccaug gagcagccug ugu                                          23

<210> SEQ ID NO 105
<211> LENGTH: 21
<212> TYPE: RNA
<213> ORGANISM: Homo sapiens

<400> SEQUENCE: 105
cuccccggcc ucugccccca g                                            21

<210> SEQ ID NO 106
<211> LENGTH: 24
<212> TYPE: RNA
<213> ORGANISM: Homo sapiens

<400> SEQUENCE: 106
cgggugggag cagaucuuau ugag                                         24

<210> SEQ ID NO 107
<211> LENGTH: 21
<212> TYPE: RNA
<213> ORGANISM: Homo sapiens

<400> SEQUENCE: 107
agguggguau ggaggagccc u                                            21

<210> SEQ ID NO 108
<211> LENGTH: 22
<212> TYPE: RNA
<213> ORGANISM: Homo sapiens

<400> SEQUENCE: 108
cucgggaggg caugggccag gc                                           22

<210> SEQ ID NO 109
<211> LENGTH: 21
<212> TYPE: RNA
<213> ORGANISM: Homo sapiens

<400> SEQUENCE: 109 gcggugggc cggaggggcg u                                             21

<210> SEQ ID NO 110
<211> LENGTH: 24
<212> TYPE: RNA
<213> ORGANISM: Homo sapiens

<400> SEQUENCE: 110
guaggggcgu cccgggcgcg cggg                                         24

<210> SEQ ID NO 111
<211> LENGTH: 20
<212> TYPE: RNA
<213> ORGANISM: Homo sapiens

<400> SEQUENCE: 111 caggggacu gggggugagc                                               20

<210> SEQ ID NO 112
<211> LENGTH: 21
<212> TYPE: RNA
<213> ORGANISM: Homo sapiens
```

-continued

```
<400> SEQUENCE: 112
gaagcucucc cuccccgca g                                          21

<210> SEQ ID NO 113
<211> LENGTH: 25
<212> TYPE: RNA
<213> ORGANISM: Homo sapiens

<400> SEQUENCE: 113
aggagggaag gggcugagaa cagga                                     25

<210> SEQ ID NO 114
<211> LENGTH: 21
<212> TYPE: RNA
<213> ORGANISM: Homo sapiens

<400> SEQUENCE: 114
caccucuccu ggcaucgccc c                                         21

<210> SEQ ID NO 115
<211> LENGTH: 20
<212> TYPE: RNA
<213> ORGANISM: Homo sapiens

<400> SEQUENCE: 115
cuaggugggg ggcuugaagc                                           20

<210> SEQ ID NO 116
<211> LENGTH: 22
<212> TYPE: RNA
<213> ORGANISM: Homo sapiens

<400> SEQUENCE: 116 cuggggugg ggggcugggc gu                                         22

<210> SEQ ID NO 117
<211> LENGTH: 23
<212> TYPE: RNA
<213> ORGANISM: Homo sapiens

<400> SEQUENCE: 117
uugcucugcu cccccgcccc cag                                       23

<210> SEQ ID NO 118
<211> LENGTH: 22
<212> TYPE: RNA
<213> ORGANISM: Homo sapiens

<400> SEQUENCE: 118 uaggggcgg cuuguggagu gu                                         22

<210> SEQ ID NO 119
<211> LENGTH: 22
<212> TYPE: RNA
<213> ORGANISM: Homo sapiens

<400> SEQUENCE: 119
gugagccagu ggaauggaga gg                                        22

<210> SEQ ID NO 120
<211> LENGTH: 25
<212> TYPE: RNA
```

```
<213> ORGANISM: Homo sapiens

<400> SEQUENCE: 120 augggugag auggggagga gcagc                                            25

<210> SEQ ID NO 121
<211> LENGTH: 22
<212> TYPE: RNA
<213> ORGANISM: Homo sapiens

<400> SEQUENCE: 121
uuggggugga gggccaagga gc                                              22

<210> SEQ ID NO 122
<211> LENGTH: 20
<212> TYPE: RNA
<213> ORGANISM: Homo sapiens

<400> SEQUENCE: 122
cagggaacca guugggcuu                                                  20

<210> SEQ ID NO 123
<211> LENGTH: 22
<212> TYPE: RNA
<213> ORGANISM: Homo sapiens

<400> SEQUENCE: 123 guagggagg uugggccagg ga                                               22

<210> SEQ ID NO 124
<211> LENGTH: 23
<212> TYPE: RNA
<213> ORGANISM: Homo sapiens

<400> SEQUENCE: 124
ucaauaggaa agagguggga ccu                                             23

<210> SEQ ID NO 125
<211> LENGTH: 22
<212> TYPE: RNA
<213> ORGANISM: Homo sapiens

<400> SEQUENCE: 125
gugcggaacg cuggccgggg cg                                              22

<210> SEQ ID NO 126
<211> LENGTH: 22
<212> TYPE: RNA
<213> ORGANISM: Homo sapiens

<400> SEQUENCE: 126
gugaggaggg gcuggcaggg ac                                              22

<210> SEQ ID NO 127
<211> LENGTH: 22
<212> TYPE: RNA
<213> ORGANISM: Homo sapiens

<400> SEQUENCE: 127 acugguagg uggggcucca gg                                               22

<210> SEQ ID NO 128
<211> LENGTH: 21
```

```
<212> TYPE: RNA
<213> ORGANISM: Homo sapiens

<400> SEQUENCE: 128
ccgccuucuc uccucccca g                                              21

<210> SEQ ID NO 129
<211> LENGTH: 22
<212> TYPE: RNA
<213> ORGANISM: Homo sapiens

<400> SEQUENCE: 129
ucggccuggg gaggaggaag gg                                            22

<210> SEQ ID NO 130
<211> LENGTH: 21
<212> TYPE: RNA
<213> ORGANISM: Homo sapiens

<400> SEQUENCE: 130
cuggggggag gagacccugc u                                             21

<210> SEQ ID NO 131
<211> LENGTH: 21
<212> TYPE: RNA
<213> ORGANISM: Homo sapiens

<400> SEQUENCE: 131
ucuguggagu ggggugccug u                                             21

<210> SEQ ID NO 132
<211> LENGTH: 19
<212> TYPE: RNA
<213> ORGANISM: Homo sapiens

<400> SEQUENCE: 132
cggggucggc ggcgacgug                                                19

<210> SEQ ID NO 133
<211> LENGTH: 21
<212> TYPE: RNA
<213> ORGANISM: Homo sapiens

<400> SEQUENCE: 133
cagcggagcc uggagagaag g                                             21

<210> SEQ ID NO 134
<211> LENGTH: 22
<212> TYPE: RNA
<213> ORGANISM: Homo sapiens

<400> SEQUENCE: 134
cgggacugua gagggcauga gc                                            22

<210> SEQ ID NO 135
<211> LENGTH: 24
<212> TYPE: RNA
<213> ORGANISM: Homo sapiens

<400> SEQUENCE: 135
ccaugaagca gugguagga ggac                                           24

<210> SEQ ID NO 136
```

-continued

```
<211> LENGTH: 20
<212> TYPE: RNA
<213> ORGANISM: Homo sapiens

<400> SEQUENCE: 136 cguggacug gaguggugg                                                       20

<210> SEQ ID NO 137
<211> LENGTH: 22
<212> TYPE: RNA
<213> ORGANISM: Homo sapiens

<400> SEQUENCE: 137
accuggcagc agggagcguc gu                                                  22

<210> SEQ ID NO 138
<211> LENGTH: 23
<212> TYPE: RNA
<213> ORGANISM: Homo sapiens

<400> SEQUENCE: 138
cggccccacg caccagggua aga                                                 23

<210> SEQ ID NO 139
<211> LENGTH: 21
<212> TYPE: RNA
<213> ORGANISM: Homo sapiens

<400> SEQUENCE: 139
gcugggaagg caaagggacg u                                                   21

<210> SEQ ID NO 140
<211> LENGTH: 22
<212> TYPE: RNA
<213> ORGANISM: Homo sapiens

<400> SEQUENCE: 140
cagaagggga guugggagca ga                                                  22

<210> SEQ ID NO 141
<211> LENGTH: 20
<212> TYPE: RNA
<213> ORGANISM: Homo sapiens

<400> SEQUENCE: 141
ggcggcggcg gaggcggggg                                                     20

<210> SEQ ID NO 142
<211> LENGTH: 21
<212> TYPE: RNA
<213> ORGANISM: Homo sapiens

<400> SEQUENCE: 142
cgucccaccc cccacuccug u                                                   21

<210> SEQ ID NO 143
<211> LENGTH: 17
<212> TYPE: RNA
<213> ORGANISM: Homo sapiens

<400> SEQUENCE: 143
agggugugug uguuuuu                                                        17
```

```
<210> SEQ ID NO 144
<211> LENGTH: 23
<212> TYPE: RNA
<213> ORGANISM: Homo sapiens

<400> SEQUENCE: 144
ugacacggag gguggcuugg gaa                                          23

<210> SEQ ID NO 145
<211> LENGTH: 22
<212> TYPE: RNA
<213> ORGANISM: Homo sapiens

<400> SEQUENCE: 145
caggaaggau uuagggacag gc                                           22

<210> SEQ ID NO 146
<211> LENGTH: 17
<212> TYPE: RNA
<213> ORGANISM: Homo sapiens

<400> SEQUENCE: 146
gcggggcugg gcgcgcg                                                 17

<210> SEQ ID NO 147
<211> LENGTH: 21
<212> TYPE: RNA
<213> ORGANISM: Homo sapiens

<400> SEQUENCE: 147
uggcuguugg aggggggcagg c                                           21

<210> SEQ ID NO 148
<211> LENGTH: 22
<212> TYPE: RNA
<213> ORGANISM: Homo sapiens

<400> SEQUENCE: 148
cagcccuccu cccgcaccca aa                                           22

<210> SEQ ID NO 149
<211> LENGTH: 23
<212> TYPE: RNA
<213> ORGANISM: Homo sapiens

<400> SEQUENCE: 149
uguagagcag ggagcaggaa gcu                                          23

<210> SEQ ID NO 150
<211> LENGTH: 21
<212> TYPE: RNA
<213> ORGANISM: Homo sapiens

<400> SEQUENCE: 150
agcagacuug accuacaauu a                                            21

<210> SEQ ID NO 151
<211> LENGTH: 22
<212> TYPE: RNA
<213> ORGANISM: Homo sapiens

<400> SEQUENCE: 151
agacacauuu ggagagggaa cc                                           22
```

```
<210> SEQ ID NO 152
<211> LENGTH: 20
<212> TYPE: RNA
<213> ORGANISM: Homo sapiens

<400> SEQUENCE: 152 uaggggugg caggcuggcc                                               20

<210> SEQ ID NO 153
<211> LENGTH: 23
<212> TYPE: RNA
<213> ORGANISM: Homo sapiens

<400> SEQUENCE: 153
cagggagaag guggaagugc aga                                          23

<210> SEQ ID NO 154
<211> LENGTH: 20
<212> TYPE: RNA
<213> ORGANISM: Homo sapiens

<400> SEQUENCE: 154
ggggaggugu gcagggcugg                                              20

<210> SEQ ID NO 155
<211> LENGTH: 19
<212> TYPE: RNA
<213> ORGANISM: Homo sapiens

<400> SEQUENCE: 155
ugcggcagag cugggguca                                               19

<210> SEQ ID NO 156
<211> LENGTH: 23
<212> TYPE: RNA
<213> ORGANISM: Homo sapiens

<400> SEQUENCE: 156
gugcguggug gcucgaggcg ggg                                          23

<210> SEQ ID NO 157
<211> LENGTH: 20
<212> TYPE: RNA
<213> ORGANISM: Homo sapiens

<400> SEQUENCE: 157
ugggcugcug agaaggggca                                              20

<210> SEQ ID NO 158
<211> LENGTH: 21
<212> TYPE: RNA
<213> ORGANISM: Homo sapiens

<400> SEQUENCE: 158
caggcaggug uaggguggag c                                            21

<210> SEQ ID NO 159
<211> LENGTH: 20
<212> TYPE: RNA
<213> ORGANISM: Homo sapiens

<400> SEQUENCE: 159
acccgcccgu cuccccacag                                              20
```

```
<210> SEQ ID NO 160
<211> LENGTH: 22
<212> TYPE: RNA
<213> ORGANISM: Homo sapiens

<400> SEQUENCE: 160 uggggagga aggacaggcc au                                              22

<210> SEQ ID NO 161
<211> LENGTH: 24
<212> TYPE: RNA
<213> ORGANISM: Homo sapiens

<400> SEQUENCE: 161 ccugggaca ggggauuggg gcag                                            24

<210> SEQ ID NO 162
<211> LENGTH: 22
<212> TYPE: RNA
<213> ORGANISM: Homo sapiens

<400> SEQUENCE: 162
aggcagcggg guguagugga ua                                             22

<210> SEQ ID NO 163
<211> LENGTH: 22
<212> TYPE: RNA
<213> ORGANISM: Homo sapiens

<400> SEQUENCE: 163
uauugcacuc gucccggccu cc                                             22

<210> SEQ ID NO 164
<211> LENGTH: 22
<212> TYPE: RNA
<213> ORGANISM: Homo sapiens

<400> SEQUENCE: 164 cuccugggc ccgcacucuc gc                                              22

<210> SEQ ID NO 165
<211> LENGTH: 22
<212> TYPE: RNA
<213> ORGANISM: Homo sapiens

<400> SEQUENCE: 165
ccgggagaag gagguggccu gg                                             22

<210> SEQ ID NO 166
<211> LENGTH: 22
<212> TYPE: RNA
<213> ORGANISM: Homo sapiens

<400> SEQUENCE: 166
acuggacuua gggucagaag gc                                             22

<210> SEQ ID NO 167
<211> LENGTH: 22
<212> TYPE: RNA
<213> ORGANISM: Homo sapiens

<400> SEQUENCE: 167
```

```
ggcuacaaca caggacccgg gc                                              22

<210> SEQ ID NO 168
<211> LENGTH: 23
<212> TYPE: RNA
<213> ORGANISM: Homo sapiens

<400> SEQUENCE: 168
gagggcagcg uggguguggc gga                                             23

<210> SEQ ID NO 169
<211> LENGTH: 22
<212> TYPE: RNA
<213> ORGANISM: Homo sapiens

<400> SEQUENCE: 169
ccccuggggc ugggcaggcg ga                                              22

<210> SEQ ID NO 170
<211> LENGTH: 23
<212> TYPE: RNA
<213> ORGANISM: Homo sapiens

<400> SEQUENCE: 170
agcagcauug uacagggcua uga                                             23

<210> SEQ ID NO 171
<211> LENGTH: 23
<212> TYPE: RNA
<213> ORGANISM: Homo sapiens

<400> SEQUENCE: 171
agcagcauug uacagggcua uca                                             23

<210> SEQ ID NO 172
<211> LENGTH: 20
<212> TYPE: RNA
<213> ORGANISM: Homo sapiens

<400> SEQUENCE: 172
ccugagcccg ggccgcgcag                                                 20

<210> SEQ ID NO 173
<211> LENGTH: 22
<212> TYPE: RNA
<213> ORGANISM: Homo sapiens

<400> SEQUENCE: 173
ugagccccug ugccgccccc ag                                              22

<210> SEQ ID NO 174
<211> LENGTH: 22
<212> TYPE: RNA
<213> ORGANISM: Homo sapiens

<400> SEQUENCE: 174
guggguacgg cccaguggg gg                                               22

<210> SEQ ID NO 175
<211> LENGTH: 21
<212> TYPE: RNA
<213> ORGANISM: Homo sapiens

<400> SEQUENCE: 175
```
gugggcgggg gcaggugugu g                                                    21

<210> SEQ ID NO 176
<211> LENGTH: 24
<212> TYPE: RNA
<213> ORGANISM: Homo sapiens

<400> SEQUENCE: 176
guggguaggg uuuggggggag agcg                                                24

<210> SEQ ID NO 177
<211> LENGTH: 22
<212> TYPE: RNA
<213> ORGANISM: Homo sapiens

<400> SEQUENCE: 177
agugggaggc cagggcacgg ca                                                   22

<210> SEQ ID NO 178
<211> LENGTH: 21
<212> TYPE: RNA
<213> ORGANISM: Homo sapiens

<400> SEQUENCE: 178
cgggggcggg gccgaagcgc g                                                    21

<210> SEQ ID NO 179
<211> LENGTH: 24
<212> TYPE: RNA
<213> ORGANISM: Homo sapiens

<400> SEQUENCE: 179
ccccgggaac gucgagacug gagc                                                 24

<210> SEQ ID NO 180
<211> LENGTH: 22
<212> TYPE: RNA
<213> ORGANISM: Homo sapiens

<400> SEQUENCE: 180
acgcccuucc cccccuucuu ca                                                   22

<210> SEQ ID NO 181
<211> LENGTH: 24
<212> TYPE: RNA
<213> ORGANISM: Homo sapiens

<400> SEQUENCE: 181
agccuggaag cuggagccug cagu                                                 24

<210> SEQ ID NO 182
<211> LENGTH: 19
<212> TYPE: RNA
<213> ORGANISM: Homo sapiens

<400> SEQUENCE: 182
aucccaccac ugccaccau                                                       19

<210> SEQ ID NO 183
<211> LENGTH: 18
<212> TYPE: RNA
<213> ORGANISM: Homo sapiens

```
<400> SEQUENCE: 183
cgggcguggu ggugggg                                                  18

<210> SEQ ID NO 184
<211> LENGTH: 20
<212> TYPE: RNA
<213> ORGANISM: Homo sapiens

<400> SEQUENCE: 184
cgggcguggu gguggggug                                                20

<210> SEQ ID NO 185
<211> LENGTH: 21
<212> TYPE: RNA
<213> ORGANISM: Homo sapiens

<400> SEQUENCE: 185
accacugcac uccagccuga g                                             21

<210> SEQ ID NO 186
<211> LENGTH: 23
<212> TYPE: RNA
<213> ORGANISM: Homo sapiens

<400> SEQUENCE: 186
cggggccgua gcacugucug aga                                           23

<210> SEQ ID NO 187
<211> LENGTH: 23
<212> TYPE: RNA
<213> ORGANISM: Homo sapiens

<400> SEQUENCE: 187
gggggccgau acacuguacg aga                                           23

<210> SEQ ID NO 188
<211> LENGTH: 19
<212> TYPE: RNA
<213> ORGANISM: Homo sapiens

<400> SEQUENCE: 188
uggauuuuug gaucaggga                                                19

<210> SEQ ID NO 189
<211> LENGTH: 22
<212> TYPE: RNA
<213> ORGANISM: Homo sapiens

<400> SEQUENCE: 189
cugguacagg ccuggggac ag                                             22

<210> SEQ ID NO 190
<211> LENGTH: 22
<212> TYPE: RNA
<213> ORGANISM: Homo sapiens

<400> SEQUENCE: 190
acugcaguga aggcacuugu ag                                            22

<210> SEQ ID NO 191
<211> LENGTH: 21
<212> TYPE: RNA
<213> ORGANISM: Homo sapiens
```

```
<400> SEQUENCE: 191
cggcggggac ggcgauuggu c                                              21

<210> SEQ ID NO 192
<211> LENGTH: 22
<212> TYPE: RNA
<213> ORGANISM: Homo sapiens

<400> SEQUENCE: 192
cgcaggggcc gggugcucac cg                                             22

<210> SEQ ID NO 193
<211> LENGTH: 22
<212> TYPE: RNA
<213> ORGANISM: Homo sapiens

<400> SEQUENCE: 193 ggagggguccc cgcacuggga gg                                            22

<210> SEQ ID NO 194
<211> LENGTH: 20
<212> TYPE: RNA
<213> ORGANISM: Homo sapiens

<400> SEQUENCE: 194
ccccagggcg acgcggcggg                                                20

<210> SEQ ID NO 195
<211> LENGTH: 23
<212> TYPE: RNA
<213> ORGANISM: Homo sapiens

<400> SEQUENCE: 195
caacggaauc ccaaaagcag cug                                            23

<210> SEQ ID NO 196
<211> LENGTH: 22
<212> TYPE: RNA
<213> ORGANISM: Homo sapiens

<400> SEQUENCE: 196
aagcugccag uugaagaacu gu                                             22

<210> SEQ ID NO 197
<211> LENGTH: 21
<212> TYPE: RNA
<213> ORGANISM: Homo sapiens

<400> SEQUENCE: 197
aucacauugc cagggauuac c                                              21

<210> SEQ ID NO 198
<211> LENGTH: 22
<212> TYPE: RNA
<213> ORGANISM: Homo sapiens

<400> SEQUENCE: 198
uggcucaguu cagcaggaac ag                                             22

<210> SEQ ID NO 199
<211> LENGTH: 22
<212> TYPE: RNA
```

```
<213> ORGANISM: Homo sapiens

<400> SEQUENCE: 199
gaggguuggg uggaggcucu cc                                            22

<210> SEQ ID NO 200
<211> LENGTH: 21
<212> TYPE: RNA
<213> ORGANISM: Homo sapiens

<400> SEQUENCE: 200 agggccccccc cucaauccug u                                            21

<210> SEQ ID NO 201
<211> LENGTH: 23
<212> TYPE: RNA
<213> ORGANISM: Homo sapiens

<400> SEQUENCE: 201
ucgaggacug guggaagggc cuu                                           23

<210> SEQ ID NO 202
<211> LENGTH: 23
<212> TYPE: RNA
<213> ORGANISM: Homo sapiens

<400> SEQUENCE: 202
uuagggagua aagggguggg gag                                           23

<210> SEQ ID NO 203
<211> LENGTH: 23
<212> TYPE: RNA
<213> ORGANISM: Homo sapiens

<400> SEQUENCE: 203
agaggcuuug ugcggauacg ggg                                           23

<210> SEQ ID NO 204
<211> LENGTH: 18
<212> TYPE: RNA
<213> ORGANISM: Homo sapiens

<400> SEQUENCE: 204
cggggcggca ggggccuc                                                 18

<210> SEQ ID NO 205
<211> LENGTH: 23
<212> TYPE: RNA
<213> ORGANISM: Homo sapiens

<400> SEQUENCE: 205
ggaggcgcag gcucggaaag gcg                                           23

<210> SEQ ID NO 206
<211> LENGTH: 22
<212> TYPE: RNA
<213> ORGANISM: Homo sapiens

<400> SEQUENCE: 206
aaaagcuggg uugagagggc ga                                            22

<210> SEQ ID NO 207
<211> LENGTH: 21
```

```
<212> TYPE: RNA
<213> ORGANISM: Homo sapiens

<400> SEQUENCE: 207
aggggugcua ucugugauug a                                          21

<210> SEQ ID NO 208
<211> LENGTH: 20
<212> TYPE: RNA
<213> ORGANISM: Homo sapiens

<400> SEQUENCE: 208
cgcgggucgg ggucugcagg                                            20

<210> SEQ ID NO 209
<211> LENGTH: 21
<212> TYPE: RNA
<213> ORGANISM: Homo sapiens

<400> SEQUENCE: 209
agccgcgggg aucgccgagg g                                          21

<210> SEQ ID NO 210
<211> LENGTH: 17
<212> TYPE: RNA
<213> ORGANISM: Homo sapiens

<400> SEQUENCE: 210
ggcgggugcg gggugg                                                17

<210> SEQ ID NO 211
<211> LENGTH: 23
<212> TYPE: RNA
<213> ORGANISM: Homo sapiens

<400> SEQUENCE: 211
agggacuuuu gggggcagau gug                                        23

<210> SEQ ID NO 212
<211> LENGTH: 18
<212> TYPE: RNA
<213> ORGANISM: Homo sapiens

<400> SEQUENCE: 212
agcaggugcg gggcggcg                                              18

<210> SEQ ID NO 213
<211> LENGTH: 23
<212> TYPE: RNA
<213> ORGANISM: Homo sapiens

<400> SEQUENCE: 213
ugaggauaug gcagggaagg gga                                        23

<210> SEQ ID NO 214
<211> LENGTH: 20
<212> TYPE: RNA
<213> ORGANISM: Homo sapiens

<400> SEQUENCE: 214
acucaaacug uggggcacu                                             20

<210> SEQ ID NO 215
```

```
<211> LENGTH: 20
<212> TYPE: RNA
<213> ORGANISM: Homo sapiens

<400> SEQUENCE: 215
guggguuggg gcgggcucug                                                   20

<210> SEQ ID NO 216
<211> LENGTH: 23
<212> TYPE: RNA
<213> ORGANISM: Homo sapiens

<400> SEQUENCE: 216
ugaggggcag agagcgagac uuu                                               23

<210> SEQ ID NO 217
<211> LENGTH: 18
<212> TYPE: RNA
<213> ORGANISM: Homo sapiens

<400> SEQUENCE: 217
ccagaggugg ggacugag                                                     18

<210> SEQ ID NO 218
<211> LENGTH: 20
<212> TYPE: RNA
<213> ORGANISM: Homo sapiens

<400> SEQUENCE: 218
ucagggaguc agggagggc                                                    20

<210> SEQ ID NO 219
<211> LENGTH: 19
<212> TYPE: RNA
<213> ORGANISM: Homo sapiens

<400> SEQUENCE: 219
gggggaagaa aaggugggg                                                    19

<210> SEQ ID NO 220
<211> LENGTH: 17
<212> TYPE: RNA
<213> ORGANISM: Homo sapiens

<400> SEQUENCE: 220
accccacucc ugguacc                                                      17

<210> SEQ ID NO 221
<211> LENGTH: 22
<212> TYPE: RNA
<213> ORGANISM: Homo sapiens

<400> SEQUENCE: 221
cugggacagg aggaggaggc ag                                                22

<210> SEQ ID NO 222
<211> LENGTH: 18
<212> TYPE: RNA
<213> ORGANISM: Homo sapiens

<400> SEQUENCE: 222
ggugggcuuc ccggaggg                                                     18
```

```
<210> SEQ ID NO 223
<211> LENGTH: 17
<212> TYPE: RNA
<213> ORGANISM: Homo sapiens

<400> SEQUENCE: 223
gccggacaag agggagg                                                  17

<210> SEQ ID NO 224
<211> LENGTH: 22
<212> TYPE: RNA
<213> ORGANISM: Homo sapiens

<400> SEQUENCE: 224
cagggcuggc agugacaugg gu                                            22

<210> SEQ ID NO 225
<211> LENGTH: 20
<212> TYPE: RNA
<213> ORGANISM: Homo sapiens

<400> SEQUENCE: 225
ggcuccuugg ucuaggggua                                               20

<210> SEQ ID NO 226
<211> LENGTH: 20
<212> TYPE: RNA
<213> ORGANISM: Homo sapiens

<400> SEQUENCE: 226
ggauccgagu cacggcacca                                               20

<210> SEQ ID NO 227
<211> LENGTH: 22
<212> TYPE: RNA
<213> ORGANISM: Homo sapiens

<400> SEQUENCE: 227
uggcggcggu aguuaugggc uu                                            22

<210> SEQ ID NO 228
<211> LENGTH: 18
<212> TYPE: RNA
<213> ORGANISM: Homo sapiens

<400> SEQUENCE: 228 ggugggggu guuguuuu                                                  18

<210> SEQ ID NO 229
<211> LENGTH: 20
<212> TYPE: RNA
<213> ORGANISM: Homo sapiens

<400> SEQUENCE: 229
cugguugggg cugggcuggg                                               20

<210> SEQ ID NO 230
<211> LENGTH: 17
<212> TYPE: RNA
<213> ORGANISM: Homo sapiens

<400> SEQUENCE: 230
gggagaaggg ucggggc                                                  17
```

```
<210> SEQ ID NO 231
<211> LENGTH: 22
<212> TYPE: RNA
<213> ORGANISM: Homo sapiens

<400> SEQUENCE: 231
aaaccguuac cauuacugag uu                                              22

<210> SEQ ID NO 232
<211> LENGTH: 24
<212> TYPE: RNA
<213> ORGANISM: Homo sapiens

<400> SEQUENCE: 232
ugggcgaggg gugggcucuc agag                                            24

<210> SEQ ID NO 233
<211> LENGTH: 20
<212> TYPE: RNA
<213> ORGANISM: Homo sapiens

<400> SEQUENCE: 233
cggggugggu gaggucgggc                                                 20

<210> SEQ ID NO 234
<211> LENGTH: 26
<212> TYPE: RNA
<213> ORGANISM: Homo sapiens

<400> SEQUENCE: 234
cucggccgcg gcgcguagcc cccgcc                                          26

<210> SEQ ID NO 235
<211> LENGTH: 21
<212> TYPE: RNA
<213> ORGANISM: Homo sapiens

<400> SEQUENCE: 235
cugggcucgg gacgcgcggc u                                               21

<210> SEQ ID NO 236
<211> LENGTH: 22
<212> TYPE: RNA
<213> ORGANISM: Homo sapiens

<400> SEQUENCE: 236
ggggcuguga uugaccagca gg                                              22

<210> SEQ ID NO 237
<211> LENGTH: 22
<212> TYPE: RNA
<213> ORGANISM: Homo sapiens

<400> SEQUENCE: 237
uugaggagac auggugggggg cc                                             22

<210> SEQ ID NO 238
<211> LENGTH: 22
<212> TYPE: RNA
<213> ORGANISM: Homo sapiens

<400> SEQUENCE: 238
caggaggcag ugggcgagca gg                                              22
```

```
<210> SEQ ID NO 239
<211> LENGTH: 22
<212> TYPE: RNA
<213> ORGANISM: Homo sapiens

<400> SEQUENCE: 239 aggggggcgca gucacugacg ug                                          22

<210> SEQ ID NO 240
<211> LENGTH: 22
<212> TYPE: RNA
<213> ORGANISM: Homo sapiens

<400> SEQUENCE: 240
uggggaaggc gucagugucg gg                                           22

<210> SEQ ID NO 241
<211> LENGTH: 25
<212> TYPE: RNA
<213> ORGANISM: Homo sapiens

<400> SEQUENCE: 241
aagggaggag gagcggaggg gcccu                                        25

<210> SEQ ID NO 242
<211> LENGTH: 23
<212> TYPE: RNA
<213> ORGANISM: Homo sapiens

<400> SEQUENCE: 242 ugagugggc ucccgggacg gcg                                           23

<210> SEQ ID NO 243
<211> LENGTH: 24
<212> TYPE: RNA
<213> ORGANISM: Homo sapiens

<400> SEQUENCE: 243
aggcaggggc uggugcuggg cggg                                         24

<210> SEQ ID NO 244
<211> LENGTH: 18
<212> TYPE: RNA
<213> ORGANISM: Homo sapiens

<400> SEQUENCE: 244
cggugagcgc ucgcuggc                                                18

<210> SEQ ID NO 245
<211> LENGTH: 21
<212> TYPE: RNA
<213> ORGANISM: Homo sapiens

<400> SEQUENCE: 245
cggggcagcu caguacagga u                                            21

<210> SEQ ID NO 246
<211> LENGTH: 24
<212> TYPE: RNA
<213> ORGANISM: Homo sapiens

<400> SEQUENCE: 246
```

```
agggcuggac ucagcggcgg agcu                                          24

<210> SEQ ID NO 247
<211> LENGTH: 21
<212> TYPE: RNA
<213> ORGANISM: Homo sapiens

<400> SEQUENCE: 247
auccaguucu cugaggggc u                                              21

<210> SEQ ID NO 248
<211> LENGTH: 23
<212> TYPE: RNA
<213> ORGANISM: Homo sapiens

<400> SEQUENCE: 248
agugccugag ggaguaagag ccc                                           23

<210> SEQ ID NO 249
<211> LENGTH: 22
<212> TYPE: RNA
<213> ORGANISM: Homo sapiens

<400> SEQUENCE: 249 uggggagug cagugauugu gg                                             22

<210> SEQ ID NO 250
<211> LENGTH: 21
<212> TYPE: RNA
<213> ORGANISM: Homo sapiens

<400> SEQUENCE: 250
acggcccagg cggcauuggu g                                             21

<210> SEQ ID NO 251
<211> LENGTH: 20
<212> TYPE: RNA
<213> ORGANISM: Homo sapiens

<400> SEQUENCE: 251
agagaugaag cgggggggcg                                               20

<210> SEQ ID NO 252
<211> LENGTH: 24
<212> TYPE: RNA
<213> ORGANISM: Homo sapiens

<400> SEQUENCE: 252
ggaggccggg gugggcggg gcgg                                           24

<210> SEQ ID NO 253
<211> LENGTH: 20
<212> TYPE: RNA
<213> ORGANISM: Homo sapiens

<400> SEQUENCE: 253
gcggaaggcg gagcggcgga                                               20

<210> SEQ ID NO 254
<211> LENGTH: 18
<212> TYPE: RNA
<213> ORGANISM: Homo sapiens

<400> SEQUENCE: 254
```

-continued gugaaggccc ggcggaga                                                18

<210> SEQ ID NO 255
<211> LENGTH: 23
<212> TYPE: RNA
<213> ORGANISM: Homo sapiens

<400> SEQUENCE: 255
gaacgccugu ucuugccagg ugg                                          23

<210> SEQ ID NO 256
<211> LENGTH: 22
<212> TYPE: RNA
<213> ORGANISM: Homo sapiens

<400> SEQUENCE: 256
gggggucccc ggugcucgga uc                                           22

<210> SEQ ID NO 257
<211> LENGTH: 22
<212> TYPE: RNA
<213> ORGANISM: Homo sapiens

<400> SEQUENCE: 257
gcugggauua caggcaugag cc                                           22

<210> SEQ ID NO 258
<211> LENGTH: 25
<212> TYPE: RNA
<213> ORGANISM: Homo sapiens

<400> SEQUENCE: 258
agggaucgcg ggcggguggc ggccu                                        25

<210> SEQ ID NO 259
<211> LENGTH: 22
<212> TYPE: RNA
<213> ORGANISM: Homo sapiens

<400> SEQUENCE: 259
agacacauuu ggagagggac cc                                           22

<210> SEQ ID NO 260
<211> LENGTH: 21
<212> TYPE: RNA
<213> ORGANISM: Homo sapiens

<400> SEQUENCE: 260
aggaggcagc gcucucagga c                                            21

<210> SEQ ID NO 261
<211> LENGTH: 22
<212> TYPE: RNA
<213> ORGANISM: Homo sapiens

<400> SEQUENCE: 261
aggcggggcg ccgcgggacc gc                                           22

<210> SEQ ID NO 262
<211> LENGTH: 22
<212> TYPE: RNA
<213> ORGANISM: Homo sapiens

```
<400> SEQUENCE: 262
gguggcccgg ccgugccuga gg                                              22

<210> SEQ ID NO 263
<211> LENGTH: 22
<212> TYPE: RNA
<213> ORGANISM: Homo sapiens

<400> SEQUENCE: 263
aggcgaugug gggauguaga ga                                              22

<210> SEQ ID NO 264
<211> LENGTH: 23
<212> TYPE: RNA
<213> ORGANISM: Homo sapiens

<400> SEQUENCE: 264
ugggcagggg cuuauuguag gag                                             23

<210> SEQ ID NO 265
<211> LENGTH: 21
<212> TYPE: RNA
<213> ORGANISM: Homo sapiens

<400> SEQUENCE: 265
cgggagcugg ggucugcagg u                                               21

<210> SEQ ID NO 266
<211> LENGTH: 23
<212> TYPE: RNA
<213> ORGANISM: Homo sapiens

<400> SEQUENCE: 266
cucggggcag gcggcuggga gcg                                             23

<210> SEQ ID NO 267
<211> LENGTH: 23
<212> TYPE: RNA
<213> ORGANISM: Homo sapiens

<400> SEQUENCE: 267 cgaggggguag aagagcacag ggg                                            23

<210> SEQ ID NO 268
<211> LENGTH: 22
<212> TYPE: RNA
<213> ORGANISM: Homo sapiens

<400> SEQUENCE: 268
gugggugcug gugggagccg ug                                              22

<210> SEQ ID NO 269
<211> LENGTH: 22
<212> TYPE: RNA
<213> ORGANISM: Homo sapiens

<400> SEQUENCE: 269
ucgggccugg gguuggggga gc                                              22

<210> SEQ ID NO 270
<211> LENGTH: 22
<212> TYPE: RNA
<213> ORGANISM: Homo sapiens
```

```
<400> SEQUENCE: 270 gggggggugug gagccagggg gc                                        22

<210> SEQ ID NO 271
<211> LENGTH: 23
<212> TYPE: RNA
<213> ORGANISM: Homo sapiens

<400> SEQUENCE: 271
uggugcggag agggcccaca gug                                        23

<210> SEQ ID NO 272
<211> LENGTH: 22
<212> TYPE: RNA
<213> ORGANISM: Homo sapiens

<400> SEQUENCE: 272
uagggauggg aggccaggau ga                                         22

<210> SEQ ID NO 273
<211> LENGTH: 19
<212> TYPE: RNA
<213> ORGANISM: Homo sapiens

<400> SEQUENCE: 273
cuggggagug gcuggggag                                             19

<210> SEQ ID NO 274
<211> LENGTH: 25
<212> TYPE: RNA
<213> ORGANISM: Homo sapiens

<400> SEQUENCE: 274
gugaggcggg gccaggaggg ugugu                                      25

<210> SEQ ID NO 275
<211> LENGTH: 25
<212> TYPE: RNA
<213> ORGANISM: Homo sapiens

<400> SEQUENCE: 275
ucggggcaug ggggagggag gcugg                                      25

<210> SEQ ID NO 276
<211> LENGTH: 23
<212> TYPE: RNA
<213> ORGANISM: Homo sapiens

<400> SEQUENCE: 276 ugggggaaggc uuggcaggga aga                                       23

<210> SEQ ID NO 277
<211> LENGTH: 25
<212> TYPE: RNA
<213> ORGANISM: Homo sapiens

<400> SEQUENCE: 277 uaggggugggg ggaauucagg ggugu                                     25

<210> SEQ ID NO 278
<211> LENGTH: 20
<212> TYPE: RNA
```

```
<213> ORGANISM: Homo sapiens

<400> SEQUENCE: 278
gccggggcuu ugggugaggg                                            20

<210> SEQ ID NO 279
<211> LENGTH: 21
<212> TYPE: RNA
<213> ORGANISM: Homo sapiens

<400> SEQUENCE: 279
guaggugaca gucaggggcg g                                          21

<210> SEQ ID NO 280
<211> LENGTH: 24
<212> TYPE: RNA
<213> ORGANISM: Homo sapiens

<400> SEQUENCE: 280
uguaggcaug aggcagggcc cagg                                       24

<210> SEQ ID NO 281
<211> LENGTH: 22
<212> TYPE: RNA
<213> ORGANISM: Homo sapiens

<400> SEQUENCE: 281
gcccaggacu uugugcgggg ug                                         22

<210> SEQ ID NO 282
<211> LENGTH: 23
<212> TYPE: RNA
<213> ORGANISM: Homo sapiens

<400> SEQUENCE: 282 uggggggcugg gaugggccau ggu                                       23

<210> SEQ ID NO 283
<211> LENGTH: 23
<212> TYPE: RNA
<213> ORGANISM: Homo sapiens

<400> SEQUENCE: 283
aggagguggu acuaggggcc agc                                        23

<210> SEQ ID NO 284
<211> LENGTH: 19
<212> TYPE: RNA
<213> ORGANISM: Homo sapiens

<400> SEQUENCE: 284 uggggggagau gggggguuga                                           19

<210> SEQ ID NO 285
<211> LENGTH: 21
<212> TYPE: RNA
<213> ORGANISM: Homo sapiens

<400> SEQUENCE: 285
cccaugccuc cugccgcggu c                                          21

<210> SEQ ID NO 286
<211> LENGTH: 21
```

-continued

```
<212> TYPE: RNA
<213> ORGANISM: Homo sapiens

<400> SEQUENCE: 286
ugagggaccc aggacaggag a                                            21

<210> SEQ ID NO 287
<211> LENGTH: 22
<212> TYPE: RNA
<213> ORGANISM: Homo sapiens

<400> SEQUENCE: 287
agggccgaag gguggaagcu gc                                           22

<210> SEQ ID NO 288
<211> LENGTH: 22
<212> TYPE: RNA
<213> ORGANISM: Homo sapiens

<400> SEQUENCE: 288
cagggcaggg aagugggag ag                                            22

<210> SEQ ID NO 289
<211> LENGTH: 22
<212> TYPE: RNA
<213> ORGANISM: Homo sapiens

<400> SEQUENCE: 289
ugguggagga agagggcagc uc                                           22

<210> SEQ ID NO 290
<211> LENGTH: 25
<212> TYPE: RNA
<213> ORGANISM: Homo sapiens

<400> SEQUENCE: 290
aggggggcac ugcgcaagca aagcc                                        25

<210> SEQ ID NO 291
<211> LENGTH: 23
<212> TYPE: RNA
<213> ORGANISM: Homo sapiens

<400> SEQUENCE: 291
uggggggaca gauggagagg aca                                          23

<210> SEQ ID NO 292
<211> LENGTH: 21
<212> TYPE: RNA
<213> ORGANISM: Homo sapiens

<400> SEQUENCE: 292
guguggccgg caggcgggug g                                            21

<210> SEQ ID NO 293
<211> LENGTH: 22
<212> TYPE: RNA
<213> ORGANISM: Homo sapiens

<400> SEQUENCE: 293
gggacccagg gagagacgua ag                                           22

<210> SEQ ID NO 294
```

```
<211> LENGTH: 23
<212> TYPE: RNA
<213> ORGANISM: Homo sapiens

<400> SEQUENCE: 294
ccucccugcc cgccucucug cag                                              23

<210> SEQ ID NO 295
<211> LENGTH: 22
<212> TYPE: RNA
<213> ORGANISM: Homo sapiens

<400> SEQUENCE: 295
ugcggggcua gggcuaacag ca                                               22

<210> SEQ ID NO 296
<211> LENGTH: 20
<212> TYPE: RNA
<213> ORGANISM: Homo sapiens

<400> SEQUENCE: 296
cggcucuggg ucugugggga                                                  20

<210> SEQ ID NO 297
<211> LENGTH: 21
<212> TYPE: RNA
<213> ORGANISM: Homo sapiens

<400> SEQUENCE: 297
aagggacagg gagggucgug g                                                21

<210> SEQ ID NO 298
<211> LENGTH: 21
<212> TYPE: RNA
<213> ORGANISM: Homo sapiens

<400> SEQUENCE: 298
cguggaggac gaggaggagg c                                                21

<210> SEQ ID NO 299
<211> LENGTH: 18
<212> TYPE: RNA
<213> ORGANISM: Homo sapiens

<400> SEQUENCE: 299
uucccagcca acgcacca                                                    18

<210> SEQ ID NO 300
<211> LENGTH: 22
<212> TYPE: RNA
<213> ORGANISM: Homo sapiens

<400> SEQUENCE: 300
ggggaacugu agaugaaaag gc                                               22

<210> SEQ ID NO 301
<211> LENGTH: 22
<212> TYPE: RNA
<213> ORGANISM: Homo sapiens

<400> SEQUENCE: 301
ucaaaaucag gagucggggc uu                                               22
```

```
<210> SEQ ID NO 302
<211> LENGTH: 20
<212> TYPE: RNA
<213> ORGANISM: Homo sapiens

<400> SEQUENCE: 302
ggcggcgggg agguaggcag                                              20

<210> SEQ ID NO 303
<211> LENGTH: 22
<212> TYPE: RNA
<213> ORGANISM: Homo sapiens

<400> SEQUENCE: 303
cugcccuggc ccgagggacc ga                                           22

<210> SEQ ID NO 304
<211> LENGTH: 22
<212> TYPE: RNA
<213> ORGANISM: Homo sapiens

<400> SEQUENCE: 304
ggguggggau uuguugcauu ac                                           22

<210> SEQ ID NO 305
<211> LENGTH: 22
<212> TYPE: RNA
<213> ORGANISM: Homo sapiens

<400> SEQUENCE: 305
agggacggga cgcggugcag ug                                           22

<210> SEQ ID NO 306
<211> LENGTH: 21
<212> TYPE: RNA
<213> ORGANISM: Homo sapiens

<400> SEQUENCE: 306
aaggcagggc ccccgcuccc c                                            21

<210> SEQ ID NO 307
<211> LENGTH: 20
<212> TYPE: RNA
<213> ORGANISM: Homo sapiens

<400> SEQUENCE: 307
ucacaccugc cucgccccccc                                             20

<210> SEQ ID NO 308
<211> LENGTH: 17
<212> TYPE: RNA
<213> ORGANISM: Homo sapiens

<400> SEQUENCE: 308 guggggaga ggcuguc                                                  17

<210> SEQ ID NO 309
<211> LENGTH: 22
<212> TYPE: RNA
<213> ORGANISM: Homo sapiens

<400> SEQUENCE: 309
acucggcgug gcgucggucg ug                                           22
```

```
<210> SEQ ID NO 310
<211> LENGTH: 22
<212> TYPE: RNA
<213> ORGANISM: Homo sapiens

<400> SEQUENCE: 310 ugggggagcgg cccccggguug gg                                          22

<210> SEQ ID NO 311
<211> LENGTH: 21
<212> TYPE: RNA
<213> ORGANISM: Homo sapiens

<400> SEQUENCE: 311
aucacauugc cagggauuuc c                                             21

<210> SEQ ID NO 312
<211> LENGTH: 23
<212> TYPE: RNA
<213> ORGANISM: Homo sapiens

<400> SEQUENCE: 312
uagcaccauu ugaaaucagu guu                                           23

<210> SEQ ID NO 313
<211> LENGTH: 22
<212> TYPE: RNA
<213> ORGANISM: Homo sapiens

<400> SEQUENCE: 313
ggcuggagcg agugcagugg ug                                            22

<210> SEQ ID NO 314
<211> LENGTH: 23
<212> TYPE: RNA
<213> ORGANISM: Homo sapiens

<400> SEQUENCE: 314
agaagaaggc ggucggucug cgg                                           23

<210> SEQ ID NO 315
<211> LENGTH: 17
<212> TYPE: RNA
<213> ORGANISM: Homo sapiens

<400> SEQUENCE: 315
ccccggggag cccggcg                                                  17

<210> SEQ ID NO 316
<211> LENGTH: 22
<212> TYPE: RNA
<213> ORGANISM: Homo sapiens

<400> SEQUENCE: 316
gagcaggcga ggcugggcug aa                                            22

<210> SEQ ID NO 317
<211> LENGTH: 23
<212> TYPE: RNA
<213> ORGANISM: Homo sapiens

<400> SEQUENCE: 317
gugaguggga gccgguggg cug                                            23
```

```
<210> SEQ ID NO 318
<211> LENGTH: 23
<212> TYPE: RNA
<213> ORGANISM: Homo sapiens

<400> SEQUENCE: 318
ccccgguguu ggggcgcguc ugc                                              23

<210> SEQ ID NO 319
<211> LENGTH: 19
<212> TYPE: RNA
<213> ORGANISM: Homo sapiens

<400> SEQUENCE: 319
ggcuggucag augggagug                                                   19

<210> SEQ ID NO 320
<211> LENGTH: 22
<212> TYPE: RNA
<213> ORGANISM: Homo sapiens

<400> SEQUENCE: 320
gacuauagaa cuuuccccu ca                                                22

<210> SEQ ID NO 321
<211> LENGTH: 23
<212> TYPE: RNA
<213> ORGANISM: Homo sapiens

<400> SEQUENCE: 321
caggcagaag ugggcugac agg                                               23

<210> SEQ ID NO 322
<211> LENGTH: 21
<212> TYPE: RNA
<213> ORGANISM: Homo sapiens

<400> SEQUENCE: 322
ucaccuggcu ggcccgccca g                                                21

<210> SEQ ID NO 323
<211> LENGTH: 21
<212> TYPE: RNA
<213> ORGANISM: Homo sapiens

<400> SEQUENCE: 323 ugggcgggg cagguccug c                                                  21

<210> SEQ ID NO 324
<211> LENGTH: 22
<212> TYPE: RNA
<213> ORGANISM: Homo sapiens

<400> SEQUENCE: 324
uggggaggug uggagucagc au                                               22

<210> SEQ ID NO 325
<211> LENGTH: 19
<212> TYPE: RNA
<213> ORGANISM: Homo sapiens

<400> SEQUENCE: 325
```
cggggccaga gcagagagc                                                  19

<210> SEQ ID NO 326
<211> LENGTH: 18
<212> TYPE: RNA
<213> ORGANISM: Homo sapiens

<400> SEQUENCE: 326
cuggcagggg gagaggua                                                   18

<210> SEQ ID NO 327
<211> LENGTH: 19
<212> TYPE: RNA
<213> ORGANISM: Homo sapiens

<400> SEQUENCE: 327
uugaucucgg aagcuaagc                                                  19

<210> SEQ ID NO 328
<211> LENGTH: 18
<212> TYPE: RNA
<213> ORGANISM: Homo sapiens

<400> SEQUENCE: 328
auccuaguca cggcacca                                                   18

<210> SEQ ID NO 329
<211> LENGTH: 22
<212> TYPE: RNA
<213> ORGANISM: Homo sapiens

<400> SEQUENCE: 329
uauugcacuu gucccggccu gu                                              22

<210> SEQ ID NO 330
<211> LENGTH: 61
<212> TYPE: RNA
<213> ORGANISM: Homo sapiens

<400> SEQUENCE: 330
ucggcuggcg ggguagagc uggcugcagg cccggccccu cucagcugcu gcccucucca      60
g                                                                     61

<210> SEQ ID NO 331
<211> LENGTH: 75
<212> TYPE: RNA
<213> ORGANISM: Homo sapiens

<400> SEQUENCE: 331
guaguuguuc uacagaagac cuggaugugu aggagcuaag acacacucca ggggagcugu     60
ggaagcagua acacg                                                      75

<210> SEQ ID NO 332
<211> LENGTH: 83
<212> TYPE: RNA
<213> ORGANISM: Homo sapiens

<400> SEQUENCE: 332
aauagagggu gcacaggcac gggagcucag gugaggcagg gagcugagcu caccugaccu     60
cccaugccug ugcacccucu auu                                             83

-continued

```
<210> SEQ ID NO 333
<211> LENGTH: 86
<212> TYPE: RNA
<213> ORGANISM: Homo sapiens

<400> SEQUENCE: 333
uuugguacuu gaagagagga uacccuuugu auguucacuu gauuaauggc gaauauacag      60
ggggagacuc uuauuugcgu aucaaa                                          86

<210> SEQ ID NO 334
<211> LENGTH: 85
<212> TYPE: RNA
<213> ORGANISM: Homo sapiens

<400> SEQUENCE: 334
ggccugggua ggcuugcaug ggggacuggg aagagaccau gaacagguua guccagggag      60
uucucaucaa gccuuuacuc aguag                                           85

<210> SEQ ID NO 335
<211> LENGTH: 80
<212> TYPE: RNA
<213> ORGANISM: Homo sapiens

<400> SEQUENCE: 335
gguuggcuau aacuaucauu uccaagguug ugcuuuuagg aaauguuggc uguccugcgg      60
agagagaaug gggagccagg                                                 80

<210> SEQ ID NO 336
<211> LENGTH: 86
<212> TYPE: RNA
<213> ORGANISM: Homo sapiens

<400> SEQUENCE: 336
agcacugccc ccggugaguc aggguggggc uggccccug cuucgugccc auccgcgcuc       60
ugacucucug cccaccugca ggagcu                                          86

<210> SEQ ID NO 337
<211> LENGTH: 81
<212> TYPE: RNA
<213> ORGANISM: Homo sapiens

<400> SEQUENCE: 337
uccacugcug ccgccgucgc cgccacccga gccggagcgg gcugggccgc caaggcaaga      60
ugguggacua cagcgugugg g                                               81

<210> SEQ ID NO 338
<211> LENGTH: 86
<212> TYPE: RNA
<213> ORGANISM: Homo sapiens

<400> SEQUENCE: 338
uuugguacuu aaagagagga uacccuuugu auguucacuu gauuaauggc gaauauacag      60
ggggagacuc ucauuugcgu aucaaa                                          86

<210> SEQ ID NO 339
<211> LENGTH: 78
<212> TYPE: RNA
<213> ORGANISM: Homo sapiens

<400> SEQUENCE: 339
```

```
guagcugagg ggaugguaga ccggugacgu gcacuucauu uacgauguag gucacccguu    60
ugacuaucca ccagcgcc                                                 78

<210> SEQ ID NO 340
<211> LENGTH: 87
<212> TYPE: RNA
<213> ORGANISM: Homo sapiens

<400> SEQUENCE: 340
gcagggcugg cagggaggcu gggaggggcu ggcugggucu gguagugggc aucagcuggc    60
ccucauuucu uaagacagca cuucugu                                       87

<210> SEQ ID NO 341
<211> LENGTH: 83
<212> TYPE: RNA
<213> ORGANISM: Homo sapiens

<400> SEQUENCE: 341
gugaguggga gccccagugu gugguuggg ccauggcggg ugggcagccc agccucugag    60
ccuuccucgu cugucugccc cag                                           83

<210> SEQ ID NO 342
<211> LENGTH: 73
<212> TYPE: RNA
<213> ORGANISM: Homo sapiens

<400> SEQUENCE: 342
uguauccuug aauggauuuu uggagcagga guggacaccu gacccaaagg aaaucaaucc    60
auaggcuagc aau                                                      73

<210> SEQ ID NO 343
<211> LENGTH: 66
<212> TYPE: RNA
<213> ORGANISM: Homo sapiens

<400> SEQUENCE: 343
gggaggaggg aggagauggg ccaaguuccc ucuggcugga acgcccuucc ccccuucuu    60 caccug                                                              66

<210> SEQ ID NO 344
<211> LENGTH: 66
<212> TYPE: RNA
<213> ORGANISM: Homo sapiens

<400> SEQUENCE: 344
ccugggaacg gguuccggca gacgcugagg uugcguugac gcucgcgccc cggcucccgu    60
uccagg                                                              66

<210> SEQ ID NO 345
<211> LENGTH: 47
<212> TYPE: RNA
<213> ORGANISM: Homo sapiens

<400> SEQUENCE: 345
cucggcgcgg ggcgcgggcu ccggguuggg gcgagccaac gccgggg                 47

<210> SEQ ID NO 346
<211> LENGTH: 61
<212> TYPE: RNA
<213> ORGANISM: Homo sapiens
```

<400> SEQUENCE: 346
gcccuccgcc cgugcacccc ggggcaggag accccgcggg acgcgccgag guagggggga    60
c                                                                    61

<210> SEQ ID NO 347
<211> LENGTH: 75
<212> TYPE: RNA
<213> ORGANISM: Homo sapiens

<400> SEQUENCE: 347
ggcugugccg gguagagagg gcagugggag guaagagcuc uucacccuuc accaccuucu    60
ccacccagca uggcc                                                     75

<210> SEQ ID NO 348
<211> LENGTH: 71
<212> TYPE: RNA
<213> ORGANISM: Homo sapiens

<400> SEQUENCE: 348
ugacgggcga gcuuuuggcc cggguuauac cugaugcuca cguauaagac gagcaaaaag    60
cuuguugguc a                                                         71

<210> SEQ ID NO 349
<211> LENGTH: 75
<212> TYPE: RNA
<213> ORGANISM: Homo sapiens

<400> SEQUENCE: 349
cagggguuug gggaaacggc cgcugaguga ggcgucggcu guguucuca ccgcggucuu     60 uuccucccac ucuug                                                     75

<210> SEQ ID NO 350
<211> LENGTH: 110
<212> TYPE: RNA
<213> ORGANISM: Homo sapiens

<400> SEQUENCE: 350
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 351
<211> LENGTH: 81
<212> TYPE: RNA
<213> ORGANISM: Homo sapiens

<400> SEQUENCE: 351
ggacaggcac cugaggcucu guuagccuug gcucuggguc cugcuccuua gagcagaggc    60
agagaggcuc agggucuguc u                                              81

<210> SEQ ID NO 352
<211> LENGTH: 73
<212> TYPE: RNA
<213> ORGANISM: Homo sapiens

<400> SEQUENCE: 352
accagcucug uugggacaag aggacggucu ucuuuuggaa ggaagaccau caucuugucc    60
gaagagagcu ggu                                                       73

<210> SEQ ID NO 353
<211> LENGTH: 61
<212> TYPE: RNA
<213> ORGANISM: Homo sapiens

<400> SEQUENCE: 353
ucacccggug agggcggug gaggaggagg gucccacca ucagccuuca cugggacggg    60
a    61

<210> SEQ ID NO 354
<211> LENGTH: 75
<212> TYPE: RNA
<213> ORGANISM: Homo sapiens

<400> SEQUENCE: 354
gcagaagaaa gaucuggaag ugggagacac uuuuacuaua uauaguggcu cccacuucca    60
gaucuuucuc ucugu    75

<210> SEQ ID NO 355
<211> LENGTH: 77
<212> TYPE: RNA
<213> ORGANISM: Homo sapiens

<400> SEQUENCE: 355
ugcagaagaa agaucuggaa gugggagaca cuuucacuau auaguggc ucccacuucc    60 agaucuuucu cucugua    77

<210> SEQ ID NO 356
<211> LENGTH: 77
<212> TYPE: RNA
<213> ORGANISM: Homo sapiens

<400> SEQUENCE: 356
ugcagaagaa agaucuggaa gugggagaca cuuucacuau auaguggc ucccacuucc    60 ugaucuuucu cucugua    77

<210> SEQ ID NO 357
<211> LENGTH: 81
<212> TYPE: RNA
<213> ORGANISM: Homo sapiens

<400> SEQUENCE: 357
auucaggccg guccugcaga gaggaagccc uucugcuuac agguauugga agggcuuccu    60
cucugcagga ccggccugaa u    81

<210> SEQ ID NO 358
<211> LENGTH: 81
<212> TYPE: RNA
<213> ORGANISM: Homo sapiens

<400> SEQUENCE: 358
auucaggccg guccugcaga gaggaagccc uuccaauacc uguaagcaga agggcuuccu    60
cucugcagga ccggccugaa u    81

<210> SEQ ID NO 359
<211> LENGTH: 85
<212> TYPE: RNA
<213> ORGANISM: Homo sapiens

<400> SEQUENCE: 359

```
ggaccugccc ugggcuuucu agucucagcu cuccuccagc ucagcugguc aggagagcug    60
agacuagaaa gcccagggca gguuc                                         85

<210> SEQ ID NO 360
<211> LENGTH: 81
<212> TYPE: RNA
<213> ORGANISM: Homo sapiens

<400> SEQUENCE: 360
accugcccug ggcuuucuag ucucagcucu ccugaccagc ugagcuggag gagagcugag    60
acuagaaagc ccagggcagg u                                             81

<210> SEQ ID NO 361
<211> LENGTH: 94
<212> TYPE: RNA
<213> ORGANISM: Homo sapiens

<400> SEQUENCE: 361
cagugcgacg ggcggagcuu ccagacgcuc cgccccacgu cgcaugcgcc ccgggaaagc    60 gugggggcgga gcuuccggag gccccgcccu gcug                              94

<210> SEQ ID NO 362
<211> LENGTH: 88
<212> TYPE: RNA
<213> ORGANISM: Homo sapiens

<400> SEQUENCE: 362
gcgacgggcg gagcuuccag acgcuccgcc ccacgucgca ugcgcccggg aaagcgugg    60 ggcggagcuu ccggaggccc cgcccugc                                      88

<210> SEQ ID NO 363
<211> LENGTH: 94
<212> TYPE: RNA
<213> ORGANISM: Homo sapiens

<400> SEQUENCE: 363
cagugcgacg ggcggagcuu ccagacgcuc cgccccacgu cgcaugcgcc ccgggaaagc    60 gugggggcgga gcuuccggag gccccgcccu gcug                              94

<210> SEQ ID NO 364
<211> LENGTH: 76
<212> TYPE: RNA
<213> ORGANISM: Homo sapiens

<400> SEQUENCE: 364
ggggucaccu cucuggccgu cuaccuucca cacugacaag ggccguggg acguagcugg    60 ccagacaggu gacccc                                                   76

<210> SEQ ID NO 365
<211> LENGTH: 73
<212> TYPE: RNA
<213> ORGANISM: Homo sapiens

<400> SEQUENCE: 365
agguggcagg gccagccacc aggagggcug cgugccaccc gggcagcucu gcugucacu    60 ggcaguguca ccu                                                      73

<210> SEQ ID NO 366
```

```
<211> LENGTH: 79
<212> TYPE: RNA
<213> ORGANISM: Homo sapiens

<400> SEQUENCE: 366
aauuaauccc ucucuuucua guucuuccua gagugaggaa aagcugggu gagagggcaa    60 acaaauuaac uaauuaauu                                                79

<210> SEQ ID NO 367
<211> LENGTH: 138
<212> TYPE: RNA
<213> ORGANISM: Homo sapiens

<400> SEQUENCE: 367
uguuauuuuu ugucuucuac cuaagaauuc ugucucuuag gcuuucucuu cccagauuuc    60
ccaaaguugg gaaaagcugg guugagaggg caaaaggaaa aaaaaagaau ucgucucug   120 acauaauuag auagggaa                                                138

<210> SEQ ID NO 368
<211> LENGTH: 75
<212> TYPE: RNA
<213> ORGANISM: Homo sapiens

<400> SEQUENCE: 368 uggaguggg gggcaggagg ggcucaggga gaaagugcau acagcccug gcccucucug     60 cccuuccguc cccug                                                    75

<210> SEQ ID NO 369
<211> LENGTH: 73
<212> TYPE: RNA
<213> ORGANISM: Homo sapiens

<400> SEQUENCE: 369
aagagccgcg gcguaacggc agccaucuug uuuguuugag ugaaucggaa aggaggcgcc    60
ggcuguggcg gcg                                                      73

<210> SEQ ID NO 370
<211> LENGTH: 83
<212> TYPE: RNA
<213> ORGANISM: Homo sapiens

<400> SEQUENCE: 370
acggcaucuu ugcacucagc aggcaggcug gugcagcccg ugguggggga ccauccugcc    60 ugcuguggg uaaggacggc ugu                                            83

<210> SEQ ID NO 371
<211> LENGTH: 79
<212> TYPE: RNA
<213> ORGANISM: Homo sapiens

<400> SEQUENCE: 371 gugaggugg ggccagcagg gagugggcug ggcugggcug ggccaaggua caaggccuca     60
cccugcaucc cgcacccag                                                79

<210> SEQ ID NO 372
<211> LENGTH: 75
<212> TYPE: RNA
<213> ORGANISM: Homo sapiens

<400> SEQUENCE: 372
```

```
agacagagaa gccaggucac gucucugcag uuacacagcu cacgagugcc ugcuggggug    60
gaaccugguc ugucu                                                    75

<210> SEQ ID NO 373
<211> LENGTH: 69
<212> TYPE: RNA
<213> ORGANISM: Homo sapiens

<400> SEQUENCE: 373
gggauacuca aaauggggge gcuuuccuuu uugucuguac ugggaagugc uucgauuuug    60
ggguguccc                                                           69

<210> SEQ ID NO 374
<211> LENGTH: 93
<212> TYPE: RNA
<213> ORGANISM: Homo sapiens

<400> SEQUENCE: 374
ggcgcuuuug ugcgcgcccg ggucuguugg ugcucagagu guggucaggc ggcucggacu    60
gagcaggugg gugcggggcu cggaggaggc ggc                                93

<210> SEQ ID NO 375
<211> LENGTH: 106
<212> TYPE: RNA
<213> ORGANISM: Homo sapiens

<400> SEQUENCE: 375
agaagaaugc ccaaccagcc cucaguugcu acaguucccu guuguuucag cucgacaaca    60
acaggcggcu guagcaaugg ggggcuggau gggcaucuca augugc                  106

<210> SEQ ID NO 376
<211> LENGTH: 101
<212> TYPE: RNA
<213> ORGANISM: Homo sapiens

<400> SEQUENCE: 376
gaugggcccc uugugaccug aauugggugg gggcucugag uggggaaagu gggggccuag    60
gggaggucac aguugggucu aggggucagg agggcccagg a                       101

<210> SEQ ID NO 377
<211> LENGTH: 62
<212> TYPE: RNA
<213> ORGANISM: Homo sapiens

<400> SEQUENCE: 377
gcuggggguc ccccgacagu guggagcugg ggccgggucc cggggagggg gguucugggc    60
ag                                                                  62

<210> SEQ ID NO 378
<211> LENGTH: 76
<212> TYPE: RNA
<213> ORGANISM: Homo sapiens

<400> SEQUENCE: 378
ccgaugccuc gggagucuac agcagggcca ugucugugag ggcccaaggg ugcaugiguc    60 ucccagguuu cggugc                                                   76

<210> SEQ ID NO 379
```

```
<211> LENGTH: 68
<212> TYPE: RNA
<213> ORGANISM: Homo sapiens

<400> SEQUENCE: 379
cucaggcuca guggugcaug cuuauagucc cagccacucu ggaggcugaa ggaagauggc      60
uugagccu                                                              68

<210> SEQ ID NO 380
<211> LENGTH: 73
<212> TYPE: RNA
<213> ORGANISM: Homo sapiens

<400> SEQUENCE: 380
uuggcaggug ccauguugcc ugcuccuuac uguacacgug gcuggcaagg agacgggaac     60
auggagccgc cau                                                        73

<210> SEQ ID NO 381
<211> LENGTH: 73
<212> TYPE: RNA
<213> ORGANISM: Homo sapiens

<400> SEQUENCE: 381
agggagaaaa gcugggcuga gaggcgacug gugucuaauu uguuugucuc uccaacucag     60
acugccuggc cca                                                        73

<210> SEQ ID NO 382
<211> LENGTH: 81
<212> TYPE: RNA
<213> ORGANISM: Homo sapiens

<400> SEQUENCE: 382
cauccuccuu acgucccacc ccccacuccu guuucggug aaauauucaa acaggagugg      60 ggguggggaca uaaggaggau a                                              81

<210> SEQ ID NO 383
<211> LENGTH: 91
<212> TYPE: RNA
<213> ORGANISM: Homo sapiens

<400> SEQUENCE: 383
guucuagagc augguuucuc aucauuugca cuacugauac uuggggucag auaauuguuu     60 guggugggg cuguuguuug cauuguagga u                                     91

<210> SEQ ID NO 384
<211> LENGTH: 66
<212> TYPE: RNA
<213> ORGANISM: Homo sapiens

<400> SEQUENCE: 384
agcagcccuc ggcggccccgg ggggcgggcg gcggugcccg ucccggggcu gcgcgaggca    60
caggcg                                                                66

<210> SEQ ID NO 385
<211> LENGTH: 66
<212> TYPE: RNA
<213> ORGANISM: Homo sapiens

<400> SEQUENCE: 385
acccaggagg cggaggaggu ggagguugca gugagccaag aucguggcac ugacuccagc     60
```

```
cugggg                                                              66

<210> SEQ ID NO 386
<211> LENGTH: 71
<212> TYPE: RNA
<213> ORGANISM: Homo sapiens

<400> SEQUENCE: 386
gcagaggvga guugaccucc acagggccac ccagggagua aguagccaag uggaaguuac    60
uuuaccucug u                                                        71
```

Note: line 1 of SEQ 386 should read:
```
gcagaggvga guugaccucc acagggccac ccagggagua aguagccaag uggaaguuac    60
```

<210> SEQ ID NO 387
<211> LENGTH: 57
<212> TYPE: RNA
<213> ORGANISM: Homo sapiens

<400> SEQUENCE: 387
agaggcaccg ccugcccagu gacaugcguu uaacggccgc gguacccuaa cugugca      57

<210> SEQ ID NO 388
<211> LENGTH: 63
<212> TYPE: RNA
<213> ORGANISM: Homo sapiens

<400> SEQUENCE: 388
gcaugcuggg cgaggcuggc aucuagcaca ggcgguagau gcuugcucuu gccauugcaa   60
uga                                                                 63

<210> SEQ ID NO 389
<211> LENGTH: 62
<212> TYPE: RNA
<213> ORGANISM: Homo sapiens

<400> SEQUENCE: 389 gguaggggc gggcuccggc gcugggaccc cacuagggug gcgccuuggc cccgccccgc    60
cc                                                                  62

<210> SEQ ID NO 390
<211> LENGTH: 62
<212> TYPE: RNA
<213> ORGANISM: Homo sapiens

<400> SEQUENCE: 390 ggggguggg cuagugaugc aggacgcugg ggacuggaga aguccugccu gacccugucc    60
ca                                                                  62

<210> SEQ ID NO 391
<211> LENGTH: 73
<212> TYPE: RNA
<213> ORGANISM: Homo sapiens

<400> SEQUENCE: 391
ggaggcuggg cugggacgga cacccggccu ccacuuucug uggcagguac cuccuccaug   60
ucggcccgcc uug                                                      73

<210> SEQ ID NO 392
<211> LENGTH: 86
<212> TYPE: RNA
<213> ORGANISM: Homo sapiens

<400> SEQUENCE: 392
auucuaggug gggagacuga cggcuggagg cccauaagcu gucuaaaacu ucggccccca          60
gauuucuggu cuccccacuu cagaac          86

<210> SEQ ID NO 393
<211> LENGTH: 81
<212> TYPE: RNA
<213> ORGANISM: Homo sapiens

<400> SEQUENCE: 393
gcgggaggug uaacaggacu ggacucccgg cagccccagg cagggggcgu ggggagcugg          60
uccuagcuca gcgcucccgg a          81

<210> SEQ ID NO 394
<211> LENGTH: 56
<212> TYPE: RNA
<213> ORGANISM: Homo sapiens

<400> SEQUENCE: 394
cgaccgcacc cgcccgaagc ugggucaagg agcccagcag gacgggagcg cggcgc          56

<210> SEQ ID NO 395
<211> LENGTH: 59
<212> TYPE: RNA
<213> ORGANISM: Homo sapiens

<400> SEQUENCE: 395
aacugggucc cagucuucac aguugguuuc ugacacgugg accuggcugg gacgaugug          59

<210> SEQ ID NO 396
<211> LENGTH: 79
<212> TYPE: RNA
<213> ORGANISM: Homo sapiens

<400> SEQUENCE: 396
ccgggacuuu gugggguucug accccacuug gaucacgccg acaacacugg ucuugaaguc          60
agaacccgca aaguccugg          79

<210> SEQ ID NO 397
<211> LENGTH: 90
<212> TYPE: RNA
<213> ORGANISM: Homo sapiens

<400> SEQUENCE: 397
cugugggcug ggccagggag cagcuggugg gugggaagua agaucugacc uggacuccau          60
cccacccacc cccuguuucc uggcccacag          90

<210> SEQ ID NO 398
<211> LENGTH: 63
<212> TYPE: RNA
<213> ORGANISM: Homo sapiens

<400> SEQUENCE: 398
acugggaaga ggagcugagg gacauugcgg agagggucuc acauugcccc ucucccuucc          60
cag          63

<210> SEQ ID NO 399
<211> LENGTH: 75
<212> TYPE: RNA
<213> ORGANISM: Homo sapiens

```
<400> SEQUENCE: 399
aggcuggcgu gggcugaggg caggaggccu guggccgguc ccaggccucc ugcuuccugg    60
gcucaggcuc gguuu                                                    75

<210> SEQ ID NO 400
<211> LENGTH: 76
<212> TYPE: RNA
<213> ORGANISM: Homo sapiens

<400> SEQUENCE: 400
cuguggugga gcugagcucc auggacgugc aguggcaucu gcauugcug ccuuccugga    60 gcucaggccc uugcag                                                   76

<210> SEQ ID NO 401
<211> LENGTH: 79
<212> TYPE: RNA
<213> ORGANISM: Homo sapiens

<400> SEQUENCE: 401
cucgaggugc uggggacgc gugagcgcga ccgcuuccu cacggcucgg ccgcggcgcg    60 uagccccgc cacaucggg                                                 79

<210> SEQ ID NO 402
<211> LENGTH: 82
<212> TYPE: RNA
<213> ORGANISM: Homo sapiens

<400> SEQUENCE: 402
gcuacgggga gcggggagga aguggcgcu gcuucugcgu uaucuggaag gagcagccca    60
cuccuguccu gggcucugug gu                                            82

<210> SEQ ID NO 403
<211> LENGTH: 80
<212> TYPE: RNA
<213> ORGANISM: Homo sapiens

<400> SEQUENCE: 403
gguuccggag ccccggcgcg ggcggguucu ggggguguaga cgcugcuggc cagcccgccc    60
cagccgaggu ucucggcacc                                               80

<210> SEQ ID NO 404
<211> LENGTH: 67
<212> TYPE: RNA
<213> ORGANISM: Homo sapiens

<400> SEQUENCE: 404
uuuaggagag agaugccgcc uugcuccuug aacaggagga gcaaggcggc aucucucuga    60
uacuaaa                                                             67

<210> SEQ ID NO 405
<211> LENGTH: 56
<212> TYPE: RNA
<213> ORGANISM: Homo sapiens

<400> SEQUENCE: 405
gaccgagugg ggugagggca ggugguucuu cccgaagcag cucucgccuc uucguc       56

<210> SEQ ID NO 406
```

```
<211> LENGTH: 51
<212> TYPE: RNA
<213> ORGANISM: Homo sapiens

<400> SEQUENCE: 406
agcuguaccu gaaaccaagc accuguuugu gacuuggcuu caguuacuag c            51

<210> SEQ ID NO 407
<211> LENGTH: 60
<212> TYPE: RNA
<213> ORGANISM: Homo sapiens

<400> SEQUENCE: 407
ggcaggaggg cugugccagg uuggcugggc caggccugac cugccagcac cucccugcag   60

<210> SEQ ID NO 408
<211> LENGTH: 55
<212> TYPE: RNA
<213> ORGANISM: Homo sapiens

<400> SEQUENCE: 408
aaucugccag cuuccacagu ggcagauuuu cccauagugg gaagcuggca gauuc        55

<210> SEQ ID NO 409
<211> LENGTH: 76
<212> TYPE: RNA
<213> ORGANISM: Homo sapiens

<400> SEQUENCE: 409
cgcaggccuc uggcggagcc cauuccaugc cagaugcuga gcgauggcug gugugugcug   60
cuccacaggc cuggug                                                  76

<210> SEQ ID NO 410
<211> LENGTH: 70
<212> TYPE: RNA
<213> ORGANISM: Homo sapiens

<400> SEQUENCE: 410
cucgggcccg accgcgccgg cccgcaccuc ccggcccgga gcugcgggcu gcggucaggg   60
cgaucccggg                                                         70

<210> SEQ ID NO 411
<211> LENGTH: 63
<212> TYPE: RNA
<213> ORGANISM: Homo sapiens

<400> SEQUENCE: 411
gccaaggacu gauccucucg ggcagggagu cagaggggac cgcccgagag gauccguccc   60
ugc                                                                63

<210> SEQ ID NO 412
<211> LENGTH: 54
<212> TYPE: RNA
<213> ORGANISM: Homo sapiens

<400> SEQUENCE: 412
agggaaggag gcuuggucuu agcacggggu cuaaggcccg ggcuuccuc ccag          54

<210> SEQ ID NO 413
<211> LENGTH: 61
<212> TYPE: RNA
<213> ORGANISM: Homo sapiens
```

```
<400> SEQUENCE: 413
ccugcgggga caggccaggg caucuaggcu gugcacagug acgccccucc ugccccaca      60 g                                                                    61

<210> SEQ ID NO 414
<211> LENGTH: 72
<212> TYPE: RNA
<213> ORGANISM: Homo sapiens

<400> SEQUENCE: 414
agauucagcu uucccuucag agccuggcuu uggcaucuau gaaagccagg cucugaaggg     60
aaaguugaau cu                                                        72

<210> SEQ ID NO 415
<211> LENGTH: 92
<212> TYPE: RNA
<213> ORGANISM: Homo sapiens

<400> SEQUENCE: 415 ccuguccuc cugcccugcg ccugcccagc ccuccugcuc uggugacuga ggaccgccag      60
gcaggggcug gugcugggcg gggggcggcg gg                                  92

<210> SEQ ID NO 416
<211> LENGTH: 84
<212> TYPE: RNA
<213> ORGANISM: Homo sapiens

<400> SEQUENCE: 416
cgguccagac guggcggggg uggcggcggc aucccggacg gccugugagg gaugcgccgc     60
ccacugcccc gcgccgccug accg                                           84

<210> SEQ ID NO 417
<211> LENGTH: 94
<212> TYPE: RNA
<213> ORGANISM: Homo sapiens

<400> SEQUENCE: 417
gggcugaccc cuaggucag gugaggcccu uggggcacag uggugccauc uccccugugc      60
ucccagggcc ucgccugucc cuugaggucg gccc                                94

<210> SEQ ID NO 418
<211> LENGTH: 120
<212> TYPE: RNA
<213> ORGANISM: Homo sapiens

<400> SEQUENCE: 418
gauccaggga acccuagagc aggggaugga cagagcaaaa uucauggccu acagcugccu     60
cuugccaaac ugcacuggau uuugucucuc ccauccccca gagcugucug aggugcuuug    120

<210> SEQ ID NO 419
<211> LENGTH: 83
<212> TYPE: RNA
<213> ORGANISM: Homo sapiens

<400> SEQUENCE: 419
gcugcuguug ggagacccug gucugcacuc uaucuguauu cuuacugaag ggagugcagg     60 gcagggguuuc ccauacagag ggc                                           83
```

```
<210> SEQ ID NO 420
<211> LENGTH: 85
<212> TYPE: RNA
<213> ORGANISM: Homo sapiens

<400> SEQUENCE: 420
ucugagguac ccggggcaga uugguguagg gugcaaagcc ugcccgcccc cuaagccuuc    60
ugcccccaac uccagccugu cagga                                         85

<210> SEQ ID NO 421
<211> LENGTH: 119
<212> TYPE: RNA
<213> ORGANISM: Homo sapiens

<400> SEQUENCE: 421
ccaugaggag cuggcagugg gauggccugg ggguaggagc guggcuucug gagcuagacc    60
acauggguuc agaucccagc ggugccucua acuggccaca ggaccuuggg cagucagcu   119

<210> SEQ ID NO 422
<211> LENGTH: 115
<212> TYPE: RNA
<213> ORGANISM: Homo sapiens

<400> SEQUENCE: 422
ucugaggaga ccugggcugu cagaggccag ggaaggggac gaggguuggg gaacaggugg    60
uuagcacuuc auccucgucu cccucccagg uuagaagggc ccccucucu gaagg         115

<210> SEQ ID NO 423
<211> LENGTH: 96
<212> TYPE: RNA
<213> ORGANISM: Homo sapiens

<400> SEQUENCE: 423
agaugugcuc uccuggccca ugaaaucaag cgugggugag accuggugca gaacgggaag    60
gcgacccaua cuugguuuca gaggcuguga gaauaa                             96

<210> SEQ ID NO 424
<211> LENGTH: 98
<212> TYPE: RNA
<213> ORGANISM: Homo sapiens

<400> SEQUENCE: 424
agaaugggca aaugaacagu aaauuuggag gccuggggcc cucccugcug cuggagaagu    60
guuugcacgg gugggccuug ucuuugaaag gaggugga                           98

<210> SEQ ID NO 425
<211> LENGTH: 55
<212> TYPE: RNA
<213> ORGANISM: Homo sapiens

<400> SEQUENCE: 425
gggggcuggg gcgcggggag gugcuagguc ggccucggcu cccgcgccgc acccc         55

<210> SEQ ID NO 426
<211> LENGTH: 60
<212> TYPE: RNA
<213> ORGANISM: Homo sapiens

<400> SEQUENCE: 426
cgcuggguuc gcgcgcccug ggccgggcga uguccgcuug ggggagcgag gggcggggcg    60
```

-continued

```
<210> SEQ ID NO 427
<211> LENGTH: 85
<212> TYPE: RNA
<213> ORGANISM: Homo sapiens

<400> SEQUENCE: 427
ggggagguag ggaaaaggaa gggggaggag aaggugagac caauguccug ggugccacuc      60
cugcccagug ccucccuucc ucguu                                           85

<210> SEQ ID NO 428
<211> LENGTH: 109
<212> TYPE: RNA
<213> ORGANISM: Homo sapiens

<400> SEQUENCE: 428
ugcuauuguc uuacugcuac agcagggcug gggauugcag uauccgcugu ugcugcugcu      60
cccaguccug ccccugcugc uaccaguccc agccucaccg caucccaga               109

<210> SEQ ID NO 429
<211> LENGTH: 54
<212> TYPE: RNA
<213> ORGANISM: Homo sapiens

<400> SEQUENCE: 429
agcagcaggg gagagagagg aguccucuag acaccgacuc ugucuccugc agau            54

<210> SEQ ID NO 430
<211> LENGTH: 85
<212> TYPE: RNA
<213> ORGANISM: Homo sapiens

<400> SEQUENCE: 430
gggacggggc cugcaggcag aaguggggcu gacagggcag aggguugcgc ccccucacca      60
ccccuucugc cugcagcggu gggcu                                           85

<210> SEQ ID NO 431
<211> LENGTH: 71
<212> TYPE: RNA
<213> ORGANISM: Homo sapiens

<400> SEQUENCE: 431
ggggccugca ggcagaagug gggcugacag ggcagagggu ugcgccccu caccacccu       60 ucugccugca g                                                          71

<210> SEQ ID NO 432
<211> LENGTH: 57
<212> TYPE: RNA
<213> ORGANISM: Homo sapiens

<400> SEQUENCE: 432
cauuggaggg uguggaagac aucugggcca acucugaucu cuucaucuac ccccag          57

<210> SEQ ID NO 433
<211> LENGTH: 81
<212> TYPE: RNA
<213> ORGANISM: Homo sapiens

<400> SEQUENCE: 433
ggguaagugg aaagauggug ggccgcagaa caugugcuga guucgugcca uaugucugcu      60
```

```
gaccaucacc uuuagaagcc c                                           81
```

<210> SEQ ID NO 434
<211> LENGTH: 100
<212> TYPE: RNA
<213> ORGANISM: Homo sapiens

<400> SEQUENCE: 434

```
gcucgguugc cgugguugcg ggcccugccc gcccgccagc ucgcugacag cacgacucag    60
ggcggaggga aguagguccg uuggucgguc gggaacgagg                         100
```

<210> SEQ ID NO 435
<211> LENGTH: 66
<212> TYPE: RNA
<213> ORGANISM: Homo sapiens

<400> SEQUENCE: 435

```
gguaagugcg ccucggguga gcaugcacuu aaugugggug uaugucacuc ggcucggccc    60
acuacc                                                              66
```

<210> SEQ ID NO 436
<211> LENGTH: 78
<212> TYPE: RNA
<213> ORGANISM: Homo sapiens

<400> SEQUENCE: 436

```
ggccucaggc aggcgcaccc gaccacaugc auggcuggug gcggcgugca ggggucgggu    60
gggccaggcu guggggcg                                                 78
```

<210> SEQ ID NO 437
<211> LENGTH: 92
<212> TYPE: RNA
<213> ORGANISM: Homo sapiens

<400> SEQUENCE: 437

```
cgcugcgcuu cuggggcccgc ggcgggcgug gggcugcccg ggccggucga ccagcgcgcc    60
guagcucccg aggcccgagc cgcgacccgc gg                                  92
```

<210> SEQ ID NO 438
<211> LENGTH: 65
<212> TYPE: RNA
<213> ORGANISM: Homo sapiens

<400> SEQUENCE: 438

```
gagggugggc gagggcggcu gagcggcucc auccccggc cugcucaucc cccucgcccu    60
cucag                                                               65
```

<210> SEQ ID NO 439
<211> LENGTH: 70
<212> TYPE: RNA
<213> ORGANISM: Homo sapiens

<400> SEQUENCE: 439

```
uuggguuggg gugucggcc cuggagggg uuuguuugcu auucccccuc ugugcuuac       60 cccuacccag                                                          70
```

<210> SEQ ID NO 440
<211> LENGTH: 63
<212> TYPE: RNA
<213> ORGANISM: Homo sapiens

<400> SEQUENCE: 440
acccuagggu ggggcuggag gugggggcuga ggcugagucu uccucccccuu ccucccugcc    60 cag    63

<210> SEQ ID NO 441
<211> LENGTH: 86
<212> TYPE: RNA
<213> ORGANISM: Homo sapiens

<400> SEQUENCE: 441
agagccgggg ccauggagca gccuguguag acggggaccu gcccugcaug ggcaccccu    60 cacuggcugc uucccuuggu cuccag    86

<210> SEQ ID NO 442
<211> LENGTH: 65
<212> TYPE: RNA
<213> ORGANISM: Homo sapiens

<400> SEQUENCE: 442
uucuccuggg gaguggcugg ggagcagaca gacccaaccu caugcucccc ggccucugcc    60
cccag    65

<210> SEQ ID NO 443
<211> LENGTH: 72
<212> TYPE: RNA
<213> ORGANISM: Homo sapiens

<400> SEQUENCE: 443
augagcgggu gggagcagau cuuauugaga guuccuucuc cugcuccuga uugucuuccc    60 ccaccccucac ag    72

<210> SEQ ID NO 444
<211> LENGTH: 73
<212> TYPE: RNA
<213> ORGANISM: Homo sapiens

<400> SEQUENCE: 444
aggccaggug gguauggagg agcccucaua uggcaguugg cgagggccca gugagccccu    60
cucugcucuc cag    73

<210> SEQ ID NO 445
<211> LENGTH: 60
<212> TYPE: RNA
<213> ORGANISM: Homo sapiens

<400> SEQUENCE: 445
ggugccucgg gagggcaugg gccaggccac auaaugagcc aaaccccugu cuacccgcag    60

<210> SEQ ID NO 446
<211> LENGTH: 113
<212> TYPE: RNA
<213> ORGANISM: Homo sapiens

<400> SEQUENCE: 446 gccgggugg gcggggcggc cucaggaggg gcccagcucc ccuggaugug cugcgguggg    60
gccggagggg cgucacgugc acccaaguga cgccccuucu gauucugccu cag    113

<210> SEQ ID NO 447

```
<211> LENGTH: 98
<212> TYPE: RNA
<213> ORGANISM: Homo sapiens

<400> SEQUENCE: 447
cgagguaggg gcgucccggg cgcgcgggcg gguccaggc ugggcccuc ggaggccggg    60 ugcucacugc cccgucccgg cgcccguguc uccuccag                         98

<210> SEQ ID NO 448
<211> LENGTH: 68
<212> TYPE: RNA
<213> ORGANISM: Homo sapiens

<400> SEQUENCE: 448
gggcgcaggg ggacuggggg ugagcaggcc cagaacccag cucgugcuca cucucagucc    60
cucccuag                                                            68

<210> SEQ ID NO 449
<211> LENGTH: 62
<212> TYPE: RNA
<213> ORGANISM: Homo sapiens

<400> SEQUENCE: 449
uuaccuugug ggguuggaga gcuggcuggu ccagcccuc agaagcucuc ccuccccgc    60 ag                                                                62

<210> SEQ ID NO 450
<211> LENGTH: 72
<212> TYPE: RNA
<213> ORGANISM: Homo sapiens

<400> SEQUENCE: 450
cagccaggag ggaaggggcu gagaacagga ccugugcuca cuggggccug caugacccuu    60
cccuccccac ag                                                       72

<210> SEQ ID NO 451
<211> LENGTH: 82
<212> TYPE: RNA
<213> ORGANISM: Homo sapiens

<400> SEQUENCE: 451
accuguaggu gacagucagg ggcggggugu ggugggcug ggcuggccc ccuccucaca    60 ccucuccugg caucgccccc ag                                            82

<210> SEQ ID NO 452
<211> LENGTH: 65
<212> TYPE: RNA
<213> ORGANISM: Homo sapiens

<400> SEQUENCE: 452
gagggcuagg uggggggcuu gaagcccga gaugccucac gucuucaccc cucucaccua    60
agcag                                                               65

<210> SEQ ID NO 453
<211> LENGTH: 65
<212> TYPE: RNA
<213> ORGANISM: Homo sapiens

<400> SEQUENCE: 453
cuccucuggg gguggggggc ugggcguggu ggacagcgau gcaucccucg ccuucucacc    60
``` cucag                                                              65

<210> SEQ ID NO 454
<211> LENGTH: 62
<212> TYPE: RNA
<213> ORGANISM: Homo sapiens

<400> SEQUENCE: 454
uggccuaggg ggcggcuugu ggaguguaug ggcugagccu ugcucugcuc ccccgccccc    60
ag                                                                 62

<210> SEQ ID NO 455
<211> LENGTH: 92
<212> TYPE: RNA
<213> ORGANISM: Homo sapiens

<400> SEQUENCE: 455
gugagccagu ggaauggaga ggcuguggc aggggagau gugaaggaaa gaacuaggac    60
ccauucaucc acugcauucc ugcuuggccc ag                                 92

<210> SEQ ID NO 456
<211> LENGTH: 64
<212> TYPE: RNA
<213> ORGANISM: Homo sapiens

<400> SEQUENCE: 456
ugaggauggg gugagauggg gaggagcagc caguccuguc ucaccgcucu uccccugacc    60
ccag                                                               64

<210> SEQ ID NO 457
<211> LENGTH: 61
<212> TYPE: RNA
<213> ORGANISM: Homo sapiens

<400> SEQUENCE: 457 gagggguuggg guggagggcc aaggagcugg gugggugcc aagccucugu ccccacccca    60
g                                                                  61

<210> SEQ ID NO 458
<211> LENGTH: 61
<212> TYPE: RNA
<213> ORGANISM: Homo sapiens

<400> SEQUENCE: 458
uggcccaggg aaccaguugg ggcuuccgcu cugcagaggc ucuaacuggc uuucccugca    60
g                                                                  61

<210> SEQ ID NO 459
<211> LENGTH: 63
<212> TYPE: RNA
<213> ORGANISM: Homo sapiens

<400> SEQUENCE: 459
gagguguagg ggagguuggg ccagggaugc cuucacugug ucucucuggu cuugccaccc    60
cag                                                                63

<210> SEQ ID NO 460
<211> LENGTH: 98
<212> TYPE: RNA

<213> ORGANISM: Homo sapiens

<400> SEQUENCE: 460

| cuuggucaau aggaaagagg ugggaccucc uggcuuuucc ucugcagcau ggcucggacc | 60 |
| uagugcaaug uuuaagcucc ccucucuuuc cuguucag | 98 |

<210> SEQ ID NO 461
<211> LENGTH: 61
<212> TYPE: RNA
<213> ORGANISM: Homo sapiens

<400> SEQUENCE: 461

| gugcggaacg cuggccgggg cgggaggggga agggacgccc ggccggaacg ccgcacucac | 60 |
| g | 61 |

<210> SEQ ID NO 462
<211> LENGTH: 67
<212> TYPE: RNA
<213> ORGANISM: Homo sapiens

<400> SEQUENCE: 462

| gugaggaggg gcuggcaggg accccuccaa guuggggacg gcagccagcc ccugcucacc | 60 |
| ccucgcc | 67 |

<210> SEQ ID NO 463
<211> LENGTH: 64
<212> TYPE: RNA
<213> ORGANISM: Homo sapiens

<400> SEQUENCE: 463

| gaggcacugg guaggugggg cuccagggcu ccugacaccu ggaccucucc uccccaggcc | 60 |
| caca | 64 |

<210> SEQ ID NO 464
<211> LENGTH: 62
<212> TYPE: RNA
<213> ORGANISM: Homo sapiens

<400> SEQUENCE: 464

| gaggguggug gaggaagagg gcagcuccca ugacugccug accgccuucu cuccucccc | 60 |
| ag | 62 |

<210> SEQ ID NO 465
<211> LENGTH: 80
<212> TYPE: RNA
<213> ORGANISM: Homo sapiens

<400> SEQUENCE: 465

| ugccgucggc cugggaagga ggaagggcaa guccaaaggu auacaguugg ucuguucauu | 60 |
| cucucuuuuu ggccuacaag | 80 |

<210> SEQ ID NO 466
<211> LENGTH: 65
<212> TYPE: RNA
<213> ORGANISM: Homo sapiens

<400> SEQUENCE: 466

| gucuccuggg gggaggagac ccugcucucc cuggcagcaa gccucuccug cccuuccaga | 60 |
| uuagc | 65 |

```
<210> SEQ ID NO 467
<211> LENGTH: 61
<212> TYPE: RNA
<213> ORGANISM: Homo sapiens

<400> SEQUENCE: 467
uccgcucugu ggagugggu gccugucccc ugccacuggg ugacccaccc cucuccacca    60
g                                                                  61

<210> SEQ ID NO 468
<211> LENGTH: 59
<212> TYPE: RNA
<213> ORGANISM: Homo sapiens

<400> SEQUENCE: 468
cggggucggc ggcgacgugc ucagcuuggc acccaaguuc ugccgcuccg acgcccggc    59

<210> SEQ ID NO 469
<211> LENGTH: 96
<212> TYPE: RNA
<213> ORGANISM: Homo sapiens

<400> SEQUENCE: 469
gccccgccgc cuggccucug gcccgcuggg gcgcgggcuu ucgcuuucag ucgagggcua    60
gcgagcgcag cggagccugg agagaaggcg cugggc                             96

<210> SEQ ID NO 470
<211> LENGTH: 69
<212> TYPE: RNA
<213> ORGANISM: Homo sapiens

<400> SEQUENCE: 470
uggagggcug cgggacugua gagggcauga gcucaggagc ucaggccagc ucauggugca    60
aggccucug                                                          69

<210> SEQ ID NO 471
<211> LENGTH: 76
<212> TYPE: RNA
<213> ORGANISM: Homo sapiens

<400> SEQUENCE: 471
uuuaaauccu guuuucccca cuuacuauuc uggucagaua ucccaugaag cagugguag    60 gaggacagga aaaagc                                                  76

<210> SEQ ID NO 472
<211> LENGTH: 65
<212> TYPE: RNA
<213> ORGANISM: Homo sapiens

<400> SEQUENCE: 472
cggccacaug gcccaggcuc uucuccgagu gaucucggug gacuggagug ggugguaggu    60
ggcag                                                              65

<210> SEQ ID NO 473
<211> LENGTH: 65
<212> TYPE: RNA
<213> ORGANISM: Homo sapiens

<400> SEQUENCE: 473
```

```
cggccacaug gcccaggcuc uucuccgagu gaucucggug gacuggagug ggugguaggu    60
ggcag                                                                65

<210> SEQ ID NO 474
<211> LENGTH: 72
<212> TYPE: RNA
<213> ORGANISM: Homo sapiens

<400> SEQUENCE: 474
gauuucagug accuggcagc agggagcguc gucaguguuu gacuguuuau gguaugucag    60
ggagcugguu cc                                                        72

<210> SEQ ID NO 475
<211> LENGTH: 78
<212> TYPE: RNA
<213> ORGANISM: Homo sapiens

<400> SEQUENCE: 475
uuagcccugc ggccccacgc accaggguaa gagagacucu cgcuuccugc ccuggcccga    60
gggaccgacu ggcugggc                                                  78

<210> SEQ ID NO 476
<211> LENGTH: 110
<212> TYPE: RNA
<213> ORGANISM: Homo sapiens

<400> SEQUENCE: 476
ggcuacaguc uuucuucaug ugacucgugg acuucccuuu gucauccuau gccugagaau    60
auaugaagga ggcugggaag gcaaagggac guucaauugu caucacuggc               110

<210> SEQ ID NO 477
<211> LENGTH: 84
<212> TYPE: RNA
<213> ORGANISM: Homo sapiens

<400> SEQUENCE: 477
ggccccuccu ucucagcccc agcucccgcu caccccugcc acgucaaagg aggcagaagg    60
ggaguuggga gcagagaggg gacc                                           84

<210> SEQ ID NO 478
<211> LENGTH: 91
<212> TYPE: RNA
<213> ORGANISM: Homo sapiens

<400> SEQUENCE: 478
ggcgccccgg cuccccgcgc ccccgaucgg ggccgccgcu aguaguggcg gcggcggagg    60 cggggggcagc ggcggcggcg gcggaggcgc c                                  91

<210> SEQ ID NO 479
<211> LENGTH: 58
<212> TYPE: RNA
<213> ORGANISM: Homo sapiens

<400> SEQUENCE: 479
agaagggugu guguguuuuu ccugagaaua agagaaggaa ggacagccaa auucuuca      58

<210> SEQ ID NO 480
<211> LENGTH: 58
<212> TYPE: RNA
<213> ORGANISM: Homo sapiens
```

<400> SEQUENCE: 480
cuucccagcu gcccuaaguc aggaguggcu uuccugacac ggaggguggc uugggaaa    58

<210> SEQ ID NO 481
<211> LENGTH: 70
<212> TYPE: RNA
<213> ORGANISM: Homo sapiens

<400> SEQUENCE: 481
aaaagccugu cccuaagucc cucccagccu uccagaguug gugccaggaa ggauuuaggg    60
acaggcuuug    70

<210> SEQ ID NO 482
<211> LENGTH: 70
<212> TYPE: RNA
<213> ORGANISM: Homo sapiens

<400> SEQUENCE: 482
aggacccagc ggggcugggc gcgcggagca gcgcugggug cagcgccugc gccggcagcu    60
gcaagggccg    70

<210> SEQ ID NO 483
<211> LENGTH: 80
<212> TYPE: RNA
<213> ORGANISM: Homo sapiens

<400> SEQUENCE: 483
accugaggag ccagcccucc ucccgcaccc aaacuuggag cacuugaccu uggcuguug    60 gaggggcag gcucgcgggu    80

<210> SEQ ID NO 484
<211> LENGTH: 76
<212> TYPE: RNA
<213> ORGANISM: Homo sapiens

<400> SEQUENCE: 484
gagggagcug uagagcaggg agcaggaagc ugugugyguc cagcccugac cguccuguu    60 cugcccccag ccccuc    76

<210> SEQ ID NO 485
<211> LENGTH: 74
<212> TYPE: RNA
<213> ORGANISM: Homo sapiens

<400> SEQUENCE: 485
gcucuagccu aauuuuagau cuggucugcu ucaguuucac uccaagcaga cuugaccuac    60
aauuagccua gagc    74

<210> SEQ ID NO 486
<211> LENGTH: 74
<212> TYPE: RNA
<213> ORGANISM: Homo sapiens

<400> SEQUENCE: 486
gcucuagccu aauuuuagau cuggucugcu ucaguuucac uccaagcaga cuugaccuac    60
aauuagccua gagc    74

<210> SEQ ID NO 487

```
<211> LENGTH: 97
<212> TYPE: RNA
<213> ORGANISM: Homo sapiens

<400> SEQUENCE: 487
aucugaguug ggagggucccc ucuccaaaug ugucuugggg uggggaauca agacacauuu    60
ggagagggaa ccucccaacu cggcucugc caucauu                              97

<210> SEQ ID NO 488
<211> LENGTH: 60
<212> TYPE: RNA
<213> ORGANISM: Homo sapiens

<400> SEQUENCE: 488
aggccuaggg gguggcaggc uggccaucag ugugggcuaa cccuguccuc ucccucccag    60

<210> SEQ ID NO 489
<211> LENGTH: 68
<212> TYPE: RNA
<213> ORGANISM: Homo sapiens

<400> SEQUENCE: 489
cagugcaggg agaaggugga agugcagagu gggcucaccu cucgcccaca cuguccccuu    60
cuccccag                                                             68

<210> SEQ ID NO 490
<211> LENGTH: 69
<212> TYPE: RNA
<213> ORGANISM: Homo sapiens

<400> SEQUENCE: 490
gaggagggga ggugugcagg gcuggggguca cugacucugc uuccccugcc cugcauggug    60
uccccacag                                                            69

<210> SEQ ID NO 491
<211> LENGTH: 62
<212> TYPE: RNA
<213> ORGANISM: Homo sapiens

<400> SEQUENCE: 491
ccuucugcgg cagagcuggg gucaccagcc cucauguacu ugugacuucu ccccugccac    60
ag                                                                   62

<210> SEQ ID NO 492
<211> LENGTH: 74
<212> TYPE: RNA
<213> ORGANISM: Homo sapiens

<400> SEQUENCE: 492
gugcguggug gcucgaggcg ggguggggg ccucgcccug cuugggcccu cccugaccuc    60
uccgcuccgc acag                                                      74

<210> SEQ ID NO 493
<211> LENGTH: 67
<212> TYPE: RNA
<213> ORGANISM: Homo sapiens

<400> SEQUENCE: 493
cagcgugggc ugcugagaag gggcaggguc cuccagcuca uuccuccugc cucuccgug    60 gccucag                                                              67
```

<210> SEQ ID NO 494
<211> LENGTH: 69
<212> TYPE: RNA
<213> ORGANISM: Homo sapiens

<400> SEQUENCE: 494
ccgggcaggc agguguaggg uggagcccac uguggcuccu gacucagccc ugcugccuuc    60
accugccag                                                           69

<210> SEQ ID NO 495
<211> LENGTH: 87
<212> TYPE: RNA
<213> ORGANISM: Homo sapiens

<400> SEQUENCE: 495
guguggccgg caggcgggug ggcggggcg gccgguggga accccgcccc gccccgcgcc     60
cgcacucacc cgcccgucuc cccacag                                       87

<210> SEQ ID NO 496
<211> LENGTH: 72
<212> TYPE: RNA
<213> ORGANISM: Homo sapiens

<400> SEQUENCE: 496 cuggggagg aaggacaggc caucugcuau ucguccacca accugacuug auccucucuu    60
cccuccuccc ag                                                       72

<210> SEQ ID NO 497
<211> LENGTH: 82
<212> TYPE: RNA
<213> ORGANISM: Homo sapiens

<400> SEQUENCE: 497
aaggagcacu cacuccaauu ucccuggacu gggggcaggc ugccaccucc uggggacagg    60
ggauuggggc aggauguucc ag                                            82

<210> SEQ ID NO 498
<211> LENGTH: 74
<212> TYPE: RNA
<213> ORGANISM: Homo sapiens

<400> SEQUENCE: 498
ccgcacucuc uccauuacac uacccugccu cuucuccaug agaggcagcg ggguguagug    60
gauagagcac gggu                                                     74

<210> SEQ ID NO 499
<211> LENGTH: 96
<212> TYPE: RNA
<213> ORGANISM: Homo sapiens

<400> SEQUENCE: 499
cgggccccgg gcgggcggga gggacgggac gcggugcagu guuguuuuu cccccgccaa     60 uauugcacuc gucccggccu ccggcccccc cggccc                             96

<210> SEQ ID NO 500
<211> LENGTH: 84
<212> TYPE: RNA
<213> ORGANISM: Homo sapiens

```
<400> SEQUENCE: 500
gcuggcgucg gugcuggggga gcggcccccg gguggccuc ugcucuggcc ccuccugggg    60
cccgcacucu cgcucugggc ccgc                                          84

<210> SEQ ID NO 501
<211> LENGTH: 63
<212> TYPE: RNA
<213> ORGANISM: Homo sapiens

<400> SEQUENCE: 501
cuugcccggg agaaggaggu ggccuggaga gcugcugucu ccagccgccg ccugucucca    60
cag                                                                 63

<210> SEQ ID NO 502
<211> LENGTH: 90
<212> TYPE: RNA
<213> ORGANISM: Homo sapiens

<400> SEQUENCE: 502
gagagaagca cuggacuuag ggucagaagg ccugagucuc ucugcugcag augggcucuc    60
ugucccugag ccaagcuuug uccucccugg                                    90

<210> SEQ ID NO 503
<211> LENGTH: 109
<212> TYPE: RNA
<213> ORGANISM: Homo sapiens

<400> SEQUENCE: 503
ggucgggcuc accaugacac agugugagac ucgggcuac aacacaggac ccgggcgcug    60
cucugacccc ucgugucuug uguugcagcc ggagggacgc agguccgca              109

<210> SEQ ID NO 504
<211> LENGTH: 61
<212> TYPE: RNA
<213> ORGANISM: Homo sapiens

<400> SEQUENCE: 504
gagggcagcg uggguguggc ggaggcaggc gugaccguuu gccgcccucu cgcugcucua    60
g                                                                   61

<210> SEQ ID NO 505
<211> LENGTH: 67
<212> TYPE: RNA
<213> ORGANISM: Homo sapiens

<400> SEQUENCE: 505
ccagaccccu ggggcugggc aggcggaaag aggucugaac ugccucugcc uccuuggucu    60
ccggcag                                                             67

<210> SEQ ID NO 506
<211> LENGTH: 78
<212> TYPE: RNA
<213> ORGANISM: Homo sapiens

<400> SEQUENCE: 506
uacugcccuc ggcuucuuua cagugcugcc uuguugcaua uggaucaagc agcauuguac    60
agggcuauga aggcauug                                                 78
```

```
<210> SEQ ID NO 507
<211> LENGTH: 78
<212> TYPE: RNA
<213> ORGANISM: Homo sapiens

<400> SEQUENCE: 507
uugugcuuuc agcuucuuua cagugcugcc uuguagcauu caggucaagc agcauuguac    60
agggcuauga aagaacca                                                 78

<210> SEQ ID NO 508
<211> LENGTH: 81
<212> TYPE: RNA
<213> ORGANISM: Homo sapiens

<400> SEQUENCE: 508
cucucugcuu ucagcuucuu uacaguguug ccuuguggca uggaguucaa gcagcauugu    60
acagggcuau caaagcacag a                                             81

<210> SEQ ID NO 509
<211> LENGTH: 119
<212> TYPE: RNA
<213> ORGANISM: Homo sapiens

<400> SEQUENCE: 509
agccugcgcc ggagccgggg ccugagcccg ggccgcgcag gccgugaacu cgucgagcug    60
cgcgugcggc cggugcucaa ccugccgggu ccuggccccg cgcucccgcg cgcccugga   119

<210> SEQ ID NO 510
<211> LENGTH: 90
<212> TYPE: RNA
<213> ORGANISM: Homo sapiens

<400> SEQUENCE: 510 gugggguacgg cccagugggg gggagaggga cacgcccugg gcucugccca gggugcagcc   60
ggacugacug agcccugug ccgcccccag                                     90

<210> SEQ ID NO 511
<211> LENGTH: 73
<212> TYPE: RNA
<213> ORGANISM: Homo sapiens

<400> SEQUENCE: 511
gugggcgggg gcaggugugu gguggugguu ggccugcggu gagcagggcc cucacaccug    60
ccucgccccc cag                                                      73

<210> SEQ ID NO 512
<211> LENGTH: 69
<212> TYPE: RNA
<213> ORGANISM: Homo sapiens

<400> SEQUENCE: 512
guggguaggg uuugggggag agcgugggcu ggggucagg gacacccucu caccacugcc    60
cucccacag                                                           69

<210> SEQ ID NO 513
<211> LENGTH: 82
<212> TYPE: RNA
<213> ORGANISM: Homo sapiens

<400> SEQUENCE: 513
```
gugaguggga ggccagggca cggcaggggg agcugcaggg cuauggagg ggccccagcg    60 ucugagcccu guccucccgc ag    82

<210> SEQ ID NO 514
<211> LENGTH: 82
<212> TYPE: RNA
<213> ORGANISM: Homo sapiens

<400> SEQUENCE: 514
gugaguggga ggccagggca cggcaggggg agcugcaggg cuauggagg ggccccagcg    60 ucugagcccu guccucccgc ag    82

<210> SEQ ID NO 515
<211> LENGTH: 102
<212> TYPE: RNA
<213> ORGANISM: Homo sapiens

<400> SEQUENCE: 515
gugggagggc ccaggcgcgg gcaggggugg ggguggcaga gcgcuguccc ggggggcgggg    60 ccgaagcgcg gcgaccguaa cuccuucugc uccguccccc ag    102

<210> SEQ ID NO 516
<211> LENGTH: 136
<212> TYPE: RNA
<213> ORGANISM: Homo sapiens

<400> SEQUENCE: 516
ccgcuugccu cgcccagcgc agcccggcc gcugggcgca cccguccgu ucgucccgg    60 acguugcucu cuaccccggg aacgucgaga cuggagcgcc cgaacugagc caccucgcg    120 gaccccgaga gcggcg    136

<210> SEQ ID NO 517
<211> LENGTH: 97
<212> TYPE: RNA
<213> ORGANISM: Homo sapiens

<400> SEQUENCE: 517 gguggagga uugcuugagc cuggaagcug gagccugcag ugaacuauca uugugccacu    60
guacuccagc cuaggcaaca aaaugaaauc cugucua    97

<210> SEQ ID NO 518
<211> LENGTH: 63
<212> TYPE: RNA
<213> ORGANISM: Homo sapiens

<400> SEQUENCE: 518
cugagccugg aagcuggagc cugcagugag cuaugaucau gucccuguac ucuagccugg    60
gca    63

<210> SEQ ID NO 519
<211> LENGTH: 89
<212> TYPE: RNA
<213> ORGANISM: Homo sapiens

<400> SEQUENCE: 519
ucuccguuua ucccaccacu gccaccauua uugcuacugu ucagcaggug cugcuggugg    60
ugauggugau agcucggugg gggcggugg    89

```
<210> SEQ ID NO 520
<211> LENGTH: 52
<212> TYPE: RNA
<213> ORGANISM: Homo sapiens

<400> SEQUENCE: 520
uagccgggcg ugguggugggg ggccuguggu cccagcuacu uuggaggcug ag        52

<210> SEQ ID NO 521
<211> LENGTH: 50
<212> TYPE: RNA
<213> ORGANISM: Homo sapiens

<400> SEQUENCE: 521
acccgggcgu ggugguggggg gugggugccu guaauuccag cuaguuggga           50

<210> SEQ ID NO 522
<211> LENGTH: 100
<212> TYPE: RNA
<213> ORGANISM: Homo sapiens

<400> SEQUENCE: 522
gaggugggag gauugcuuga gucagggugg uugaggcugc aguaaguugu gaucauacca  60
cugcacucca gccugaguga cagagcaaga ccuugucuca                        100

<210> SEQ ID NO 523
<211> LENGTH: 82
<212> TYPE: RNA
<213> ORGANISM: Homo sapiens

<400> SEQUENCE: 523
ugagcuguug gauucggggc cguagcacug ucugagaggu uuacauuucu cacagugaac  60
cggucucuuu uucagcugcu uc                                           82

<210> SEQ ID NO 524
<211> LENGTH: 84
<212> TYPE: RNA
<213> ORGANISM: Homo sapiens

<400> SEQUENCE: 524
ugugcagugg aagggggggc cgauacacug uacgagagug aguagcaggu cucacaguga  60
accggucucu uucccuacug uguc                                         84

<210> SEQ ID NO 525
<211> LENGTH: 78
<212> TYPE: RNA
<213> ORGANISM: Homo sapiens

<400> SEQUENCE: 525
gagcgucacg uugacacuca aaaaguuuca gauuuuggaa cauuucggau uuuggauuuu  60
uggaucaggg augcucaa                                                78

<210> SEQ ID NO 526
<211> LENGTH: 84
<212> TYPE: RNA
<213> ORGANISM: Homo sapiens

<400> SEQUENCE: 526
cuccccaugg cccugucucc caacccuugu accagugcug ggcucagacc cugguacagg  60
ccugggggac agggaccugg ggac                                         84
```

<210> SEQ ID NO 527
<211> LENGTH: 84
<212> TYPE: RNA
<213> ORGANISM: Homo sapiens

<400> SEQUENCE: 527
gucagaauaa ugucaaagug cuuacagugc agguagugau augugcaucu acugcaguga    60
aggcacuugu agcauuaugg ugac                                          84

<210> SEQ ID NO 528
<211> LENGTH: 80
<212> TYPE: RNA
<213> ORGANISM: Homo sapiens

<400> SEQUENCE: 528
cgggaaugcc gcggcgggga cggcgauugg uccguaugug uggugccacc ggccgccggc    60
uccgccccgg cccccgcccc                                               80

<210> SEQ ID NO 529
<211> LENGTH: 80
<212> TYPE: RNA
<213> ORGANISM: Homo sapiens

<400> SEQUENCE: 529
cauccaggac aauggugagu gccggugccu gcccuggggc cgucccugcg caggggccgg    60
gugcucaccg caucugcccc                                               80

<210> SEQ ID NO 530
<211> LENGTH: 80
<212> TYPE: RNA
<213> ORGANISM: Homo sapiens

<400> SEQUENCE: 530
cgugugagcc cgcccugugc ccggcccacu ucugcuuccu cuuagcgcag gagggguccc    60
gcacugggag gggcccucac                                               80

<210> SEQ ID NO 531
<211> LENGTH: 80
<212> TYPE: RNA
<213> ORGANISM: Homo sapiens

<400> SEQUENCE: 531
ugagaggccg caccuugccu ugcugcccgg gccgugcacc cgugggcccc agggcgacgc    60
ggcgggggcg gcccuagcga                                               80

<210> SEQ ID NO 532
<211> LENGTH: 92
<212> TYPE: RNA
<213> ORGANISM: Homo sapiens

<400> SEQUENCE: 532
cggcuggaca gcgggcaacg gaaucccaaa agcagcuguu gucuccagag cauuccagcu    60
gcgcuuggau uucguccccu gcucuccugc cu                                 92

<210> SEQ ID NO 533
<211> LENGTH: 85
<212> TYPE: RNA
<213> ORGANISM: Homo sapiens

<400> SEQUENCE: 533

-continued

```
ggcugagccg caguaguucu ucaguggcaa gcuuuaugu cugacccagc uaaagcugcc    60
aguugaagaa cuguugcccu cugcc                                        85

<210> SEQ ID NO 534
<211> LENGTH: 97
<212> TYPE: RNA
<213> ORGANISM: Homo sapiens

<400> SEQUENCE: 534
cucaggugcu cuggcugcuu ggguuccugg caugcugauu ugugacuuaa gauuaaaauc    60
acauugccag ggauuaccac gcaaccacga ccuuggc                            97

<210> SEQ ID NO 535
<211> LENGTH: 68
<212> TYPE: RNA
<213> ORGANISM: Homo sapiens

<400> SEQUENCE: 535
cuccggugcc uacugagcug auaucaguuc ucauuuuaca cacuggcuca guucagcagg    60
aacaggag                                                           68

<210> SEQ ID NO 536
<211> LENGTH: 73
<212> TYPE: RNA
<213> ORGANISM: Homo sapiens

<400> SEQUENCE: 536
cucugccucc cgugccuacu gagcugaaac acaguugguu uguguacacu ggcucaguuc    60
agcaggaaca ggg                                                     73

<210> SEQ ID NO 537
<211> LENGTH: 80
<212> TYPE: RNA
<213> ORGANISM: Homo sapiens

<400> SEQUENCE: 537
aggacccuuc cagagggccc ccccucaauc cuguugugcc uaauucagag gguugggugg    60
aggcucuccu gaagggcucu                                              80

<210> SEQ ID NO 538
<211> LENGTH: 63
<212> TYPE: RNA
<213> ORGANISM: Homo sapiens

<400> SEQUENCE: 538
gagucgagga cugguggaag ggccuuuccc cucagaccaa ggcccuggcc ccagcuucuu    60
cuc                                                                63

<210> SEQ ID NO 539
<211> LENGTH: 82
<212> TYPE: RNA
<213> ORGANISM: Homo sapiens

<400> SEQUENCE: 539
cugacuuuuu uagggaguag aagggugggg agcaugaaca auguuucuca cucccuaccc    60
cuccacuccc caaaaaaguc ag                                           82

<210> SEQ ID NO 540
```

```
<211> LENGTH: 85
<212> TYPE: RNA
<213> ORGANISM: Homo sapiens

<400> SEQUENCE: 540
ggcgccuccu gcucugcugu gccgccaggg ccuccccuag cgcgccuucu ggagaggcuu    60
ugugcggaua cggggcugga ggccu                                         85

<210> SEQ ID NO 541
<211> LENGTH: 64
<212> TYPE: RNA
<213> ORGANISM: Homo sapiens

<400> SEQUENCE: 541
gggugggggc ggggcggcag gggccuccccc cagugccagg ccccauucug cuucucuccc   60
agcu                                                                64

<210> SEQ ID NO 542
<211> LENGTH: 73
<212> TYPE: RNA
<213> ORGANISM: Homo sapiens

<400> SEQUENCE: 542
ggcgagggga ggcgcaggcu cggaaaggcg cgcgaggcuc caggcuccuu cccgauccac    60
cgcucuccuc gcu                                                      73

<210> SEQ ID NO 543
<211> LENGTH: 82
<212> TYPE: RNA
<213> ORGANISM: Homo sapiens

<400> SEQUENCE: 543
gcuucgcucc ccuccgccuu cucuucccgg uucuucccgg agucgggaaa agcuggguug    60
agagggcgaa aaaggaugag gu                                            82

<210> SEQ ID NO 544
<211> LENGTH: 99
<212> TYPE: RNA
<213> ORGANISM: Homo sapiens

<400> SEQUENCE: 544
gaaacugggc ucaaggugag gggugcuauc ugugauugag ggacaugguu aauggaauug    60
ucucacacag aaaucgcacc cgucaccuug gccuacuua                          99

<210> SEQ ID NO 545
<211> LENGTH: 85
<212> TYPE: RNA
<213> ORGANISM: Homo sapiens

<400> SEQUENCE: 545
gugagcugcu ggggacgcgg gucggggucu gcagggcggu cggcagccg ccaccugacg     60 ccgcgccuuu gucuguguvcc cacag                                        85

<210> SEQ ID NO 546
<211> LENGTH: 180
<212> TYPE: RNA
<213> ORGANISM: Homo sapiens

<400> SEQUENCE: 546
cgcgacugcg gcggcggugg uggggggagc cgcggggauc gccgagggcc ggucggccgc    60
``` cccggguqcc gcgcggugcc gccggcggcg gugaggcccc gcgcgugugu cccggcugcg    120
gucggccgcg cucgagggqu ccccguggcg uccccuuccc cgccggccgc cuuucucgcg    180

<210> SEQ ID NO 547
<211> LENGTH: 69
<212> TYPE: RNA
<213> ORGANISM: Homo sapiens

<400> SEQUENCE: 547
cuuucggcca gcgggacggc auccgaggug ggcuaggcuc gggcccgugg cgggugcggg     60
ggugggagg                                                             69

<210> SEQ ID NO 548
<211> LENGTH: 87
<212> TYPE: RNA
<213> ORGANISM: Homo sapiens

<400> SEQUENCE: 548
accgcaggga aaugaggga cuuuggggg cagaugaguu uccauccac uaucauaaug       60 ccccuaaaaa uccuuauugc ucuugca                                         87

<210> SEQ ID NO 549
<211> LENGTH: 105
<212> TYPE: RNA
<213> ORGANISM: Homo sapiens

<400> SEQUENCE: 549
gcgggcggcg gcggcggcag cagcagcagg ugcggggcgg cggccgcgcu ggccgcucga     60
cuccgcagcu gcucguucug cuucuccagc uugcgcacca gcucc                    105

<210> SEQ ID NO 550
<211> LENGTH: 68
<212> TYPE: RNA
<213> ORGANISM: Homo sapiens

<400> SEQUENCE: 550
cguggugagg auauggcagg gaagggagu ucccucuau ucccuucccc ccaguaaucu       60
ucaucaug                                                              68

<210> SEQ ID NO 551
<211> LENGTH: 67
<212> TYPE: RNA
<213> ORGANISM: Homo sapiens

<400> SEQUENCE: 551
guggcacuca aacugugggg gcacuuucug cucucugqug aaagugccgc caucuuuuga     60
guguuac                                                               67

<210> SEQ ID NO 552
<211> LENGTH: 102
<212> TYPE: RNA
<213> ORGANISM: Homo sapiens

<400> SEQUENCE: 552
gcuuaucgag gaaaagaucg aggugggquug gggcgggcuc uggggauuug gucucacagc    60
ccggauccca gcccacuuac cuugguuacu cuccuuccuu cu                       102

<210> SEQ ID NO 553

```
<211> LENGTH: 94
<212> TYPE: RNA
<213> ORGANISM: Homo sapiens

<400> SEQUENCE: 553
auaaaggaag uuaggcugag gggcagagag cgagacuuuu cuauuuucca aaagcucggu    60
cugaggcccc ucagucuugc uuccuaaccc gcgc                               94

<210> SEQ ID NO 554
<211> LENGTH: 86
<212> TYPE: RNA
<213> ORGANISM: Homo sapiens

<400> SEQUENCE: 554
ggcuuagaaa caguccuag guaggauuug gggaggagcu aagaagcccc uacagggccc    60
agaggugggg acugagccuu aguugg                                        86

<210> SEQ ID NO 555
<211> LENGTH: 70
<212> TYPE: RNA
<213> ORGANISM: Homo sapiens

<400> SEQUENCE: 555
acaaauagcu ucagggaguc aggggagggc agaaauagau ggccuucccc ugcugggaag    60
aaaguggguc                                                          70

<210> SEQ ID NO 556
<211> LENGTH: 67
<212> TYPE: RNA
<213> ORGANISM: Homo sapiens

<400> SEQUENCE: 556
aaaucucucu ccauaucuuu ccugcagccc ccaggugggg gggaagaaaa gguggggaau    60
uagauuc                                                             67

<210> SEQ ID NO 557
<211> LENGTH: 93
<212> TYPE: RNA
<213> ORGANISM: Homo sapiens

<400> SEQUENCE: 557
uacuuauggc acccacucc ugguaccaua gucauaaguu aggagauguu agagcuguga    60
guaccaugac uuaagugugg uggcuuaaac aug                                93

<210> SEQ ID NO 558
<211> LENGTH: 73
<212> TYPE: RNA
<213> ORGANISM: Homo sapiens

<400> SEQUENCE: 558
ggggagguac cugggacagg aggaggaggc agccuugccu cagaaaccaa acugucaaaa    60
guguagguuc cac                                                      73

<210> SEQ ID NO 559
<211> LENGTH: 73
<212> TYPE: RNA
<213> ORGANISM: Homo sapiens

<400> SEQUENCE: 559
gaaaacaacc aggugggcuu cccggagggc ggaacaccca gccccagcau ccagggcuca    60
```

| | |
|---|---|
| ccuaccacgu uug | 73 |

<210> SEQ ID NO 560
<211> LENGTH: 67
<212> TYPE: RNA
<213> ORGANISM: Homo sapiens

<400> SEQUENCE: 560

| | |
|---|---|
| gcgcccuccc ucucucccg gugugcaaau gugugugugc ggguguuaugc cggacaagag | 60 |
| ggaggug | 67 |

<210> SEQ ID NO 561
<211> LENGTH: 67
<212> TYPE: RNA
<213> ORGANISM: Homo sapiens

<400> SEQUENCE: 561

| | |
|---|---|
| cugguccauu ucccugccau ucccuuggcu ucaauuuacu cccagggcug gcagugacau | 60 |
| gggucaa | 67 |

<210> SEQ ID NO 562
<211> LENGTH: 86
<212> TYPE: RNA
<213> ORGANISM: Homo sapiens

<400> SEQUENCE: 562

| | |
|---|---|
| aggagugacc aaaagacaag agugcgagcc uucuauuaug cccagacagg gccaccagag | 60 |
| ggcuccuugg ucuagggua augcca | 86 |

<210> SEQ ID NO 563
<211> LENGTH: 55
<212> TYPE: RNA
<213> ORGANISM: Homo sapiens

<400> SEQUENCE: 563

| | |
|---|---|
| ccggauccga gucacggcac caaauuucau gcguguccgu gugaagagac cacca | 55 |

<210> SEQ ID NO 564
<211> LENGTH: 63
<212> TYPE: RNA
<213> ORGANISM: Homo sapiens

<400> SEQUENCE: 564

| | |
|---|---|
| ugguggcggc gguaguuaug ggcuucucuu ucucaccagc agccccuggg ccgccgccuc | 60 |
| ccu | 63 |

<210> SEQ ID NO 565
<211> LENGTH: 80
<212> TYPE: RNA
<213> ORGANISM: Homo sapiens

<400> SEQUENCE: 565

| | |
|---|---|
| uggcagaccc uugcucucuc acucucccua augggcuga agacagcuca ggggcagggu | 60 |
| gggggguguu guuuuuguuu | 80 |

<210> SEQ ID NO 566
<211> LENGTH: 67
<212> TYPE: RNA
<213> ORGANISM: Homo sapiens

```
<400> SEQUENCE: 566
uggugggggu gggggguguu guuuuuguuu uugagacaga gucuugcucc gucgcccagg    60
ccggagu                                                             67

<210> SEQ ID NO 567
<211> LENGTH: 52
<212> TYPE: RNA
<213> ORGANISM: Homo sapiens

<400> SEQUENCE: 567
ucugggcuga gccgagcugg guuaagccga gcugggguugg gcugggcugg gu          52

<210> SEQ ID NO 568
<211> LENGTH: 86
<212> TYPE: RNA
<213> ORGANISM: Homo sapiens

<400> SEQUENCE: 568
agggagaagg gucggggcag ggagggcagg gcaggcucug gggugggggg ucugugaguc    60
agccacggcu cugcccacgu cuccc                                         86

<210> SEQ ID NO 569
<211> LENGTH: 72
<212> TYPE: RNA
<213> ORGANISM: Homo sapiens

<400> SEQUENCE: 569
cuugggaaug gcaaggaaac cguuaccauu acugaguuua guaaugguaa ugguucucuu    60
gcuauaccca ga                                                       72

<210> SEQ ID NO 570
<211> LENGTH: 64
<212> TYPE: RNA
<213> ORGANISM: Homo sapiens

<400> SEQUENCE: 570
ucugggcgag gggugggcuc ucagaggggc uggcaguacu gcucugaggc cugccucucc    60
ccag                                                                64

<210> SEQ ID NO 571
<211> LENGTH: 73
<212> TYPE: RNA
<213> ORGANISM: Homo sapiens

<400> SEQUENCE: 571
cggcgacggc gggugggug aggucgggcc ccaagacucg ggguuugccg ggcgccucag     60
uucaccgcgg ccg                                                      73

<210> SEQ ID NO 572
<211> LENGTH: 87
<212> TYPE: RNA
<213> ORGANISM: Homo sapiens

<400> SEQUENCE: 572
cccaggcgcc cgcucccgac ccacgccgcg ccgccggguc ccuccucccc ggagaggcug    60
ggcucgggac gcgcggcuca gcucggg                                       87

<210> SEQ ID NO 573
<211> LENGTH: 77
```

```
<212> TYPE: RNA
<213> ORGANISM: Homo sapiens

<400> SEQUENCE: 573
caugagaaau ccugcugguc aaccauagcc cggucagac ucuccggggc ugugauugac      60
cagcaggacu ucucaug                                                    77

<210> SEQ ID NO 574
<211> LENGTH: 70
<212> TYPE: RNA
<213> ORGANISM: Homo sapiens

<400> SEQUENCE: 574
gguuucuccu ugaggagaca uggugggggc cggucaggca gcccaugcca ugugccuca      60 uggagaggcc                                                            70

<210> SEQ ID NO 575
<211> LENGTH: 74
<212> TYPE: RNA
<213> ORGANISM: Homo sapiens

<400> SEQUENCE: 575
ccugcaggag gcagugggcg agcaggcggg gcagcccaau gccaugggcc ugaucucacc      60
gcugccuccu uccc                                                       74

<210> SEQ ID NO 576
<211> LENGTH: 78
<212> TYPE: RNA
<213> ORGANISM: Homo sapiens

<400> SEQUENCE: 576
gggcccagaa gggggcgcag ucacugacgu gaagggacca caucccgcuu caugucagug      60
acuccugccc cuuggucu                                                   78

<210> SEQ ID NO 577
<211> LENGTH: 90
<212> TYPE: RNA
<213> ORGANISM: Homo sapiens

<400> SEQUENCE: 577
gugucucucu ggagacccug cagccuuccc acccaccagg gagcuuucca ugggcugugg      60
ggaaggcguc agugucgggu gagggaacac                                      90

<210> SEQ ID NO 578
<211> LENGTH: 74
<212> TYPE: RNA
<213> ORGANISM: Homo sapiens

<400> SEQUENCE: 578
gggaggaaga agggaggagg agcggagggg cccuugucuu cccagagccu cucccuuccu      60 ccccucccce uccc                                                       74

<210> SEQ ID NO 579
<211> LENGTH: 62
<212> TYPE: RNA
<213> ORGANISM: Homo sapiens

<400> SEQUENCE: 579
gugagugggg cucccgggac ggcgcccgcc cuggcccugg cccggcgacg ucucacgguc      60
```

-continued

| | |
|---|---|
| cc | 62 |

<210> SEQ ID NO 580
<211> LENGTH: 74
<212> TYPE: RNA
<213> ORGANISM: Homo sapiens

<400> SEQUENCE: 580

| | |
|---|---|
| gcagcccggu gagcgcucgc uggccuggca gugcgucgga agaacagggc ggguggggcc | 60 |
| gcgcacaucu cugc | 74 |

<210> SEQ ID NO 581
<211> LENGTH: 68
<212> TYPE: RNA
<213> ORGANISM: Homo sapiens

<400> SEQUENCE: 581

| | |
|---|---|
| gcauccugua cugagcugcc ccgaggcccu ucaugcugcc cagcucgggg cagcucagua | 60 |
| caggauac | 68 |

<210> SEQ ID NO 582
<211> LENGTH: 64
<212> TYPE: RNA
<213> ORGANISM: Homo sapiens

<400> SEQUENCE: 582

| | |
|---|---|
| uccuguacug agcugccccg agcugggcag caugaagggc cucggggcag cucaguacag | 60 |
| gaug | 64 |

<210> SEQ ID NO 583
<211> LENGTH: 100
<212> TYPE: RNA
<213> ORGANISM: Homo sapiens

<400> SEQUENCE: 583

| | |
|---|---|
| agcucagggc ggcugcgcag agggcuggac ucagcggcgg agcuggcugc uggccucagu | 60 |
| ucugccucug uccagguccu ugugacccgc ccgcucuccu | 100 |

<210> SEQ ID NO 584
<211> LENGTH: 115
<212> TYPE: RNA
<213> ORGANISM: Homo sapiens

<400> SEQUENCE: 584

| | |
|---|---|
| gagcaaaaac cagagaacaa caugggagcg uuccuaaccc cuaaggcaac uggaugggag | 60 |
| accugaccca uccaguucuc ugaggggcu cuugugguu cuacaagguu guuca | 115 |

<210> SEQ ID NO 585
<211> LENGTH: 97
<212> TYPE: RNA
<213> ORGANISM: Homo sapiens

<400> SEQUENCE: 585

| | |
|---|---|
| ugaugcuuug cuggcugguc cagugccuga gggaguaaga gcccuguugu uguaagauag | 60 |
| ugucuuacuc ccucaggcac aucccaaca agucucu | 97 |

<210> SEQ ID NO 586
<211> LENGTH: 97
<212> TYPE: RNA
<213> ORGANISM: Homo sapiens -continued

<400> SEQUENCE: 586
ugaugcuuug cuggcuggug cagugccuga gggaguaaga gcccuguugu ugucagauag    60
ugucuuacuc ccucaggcac aucuccagcg agucucu    97

<210> SEQ ID NO 587
<211> LENGTH: 72
<212> TYPE: RNA
<213> ORGANISM: Homo sapiens

<400> SEQUENCE: 587
cugugcaccu gggggagugc agugauugug gaaugcaaag ucccacaauc acuguacucc    60
ccaggugcac ag    72

<210> SEQ ID NO 588
<211> LENGTH: 95
<212> TYPE: RNA
<213> ORGANISM: Homo sapiens

<400> SEQUENCE: 588
gacaccacau gcuccuccag gccugccugc ccuccagguc auguuccagu gucccacaga    60
ugcagcacca cggcccaggc ggcauuggug ucacc    95

<210> SEQ ID NO 589
<211> LENGTH: 51
<212> TYPE: RNA
<213> ORGANISM: Homo sapiens

<400> SEQUENCE: 589
agagaugaag cgggggggcg gggucuugcu cuauugccua cgcugaucuc a    51

<210> SEQ ID NO 590
<211> LENGTH: 64
<212> TYPE: RNA
<213> ORGANISM: Homo sapiens

<400> SEQUENCE: 590
ccccgggccc ggcguucccu ccccuuccgu gcgccagugg aggccggggu ggggcgggc    60 gggg    64

<210> SEQ ID NO 591
<211> LENGTH: 64
<212> TYPE: RNA
<213> ORGANISM: Homo sapiens

<400> SEQUENCE: 591
ccccgggccc ggcguucccu ccccuuccgu gcgccagugg aggccggggu ggggcgggc    60 gggg    64

<210> SEQ ID NO 592
<211> LENGTH: 96
<212> TYPE: RNA
<213> ORGANISM: Homo sapiens

<400> SEQUENCE: 592
gcucuggggc gugccgccgc cgucgcugcc accuccccua ccgcuagugg aagaagaugg    60
cggaaggcgg agcggcggau cuggacaccc agcggu    96

<210> SEQ ID NO 593

```
<211> LENGTH: 89
<212> TYPE: RNA
<213> ORGANISM: Homo sapiens

<400> SEQUENCE: 593 agccugugggaaagagaagagcagggcagggugaaggcccggcggagacacucugcccac      60 cccacacccugccuaugggccacacagcu                                   89

<210> SEQ ID NO 594
<211> LENGTH: 90
<212> TYPE: RNA
<213> ORGANISM: Homo sapiens

<400> SEQUENCE: 594 ucuaagaaacgcagguggucucugaagccugcaggggcaggccagcccugcacugaacgcc    60 uguucuugccagguggcagaagguugcugc                                  90

<210> SEQ ID NO 595
<211> LENGTH: 96
<212> TYPE: RNA
<213> ORGANISM: Homo sapiens

<400> SEQUENCE: 595 cucgggagggcgggagggggguccccggugcucggaucucgagggugcuuauuguucgg    60 uccgagccugggucucccucuuccccccaaccccccc                           96

<210> SEQ ID NO 596
<211> LENGTH: 99
<212> TYPE: RNA
<213> ORGANISM: Homo sapiens

<400> SEQUENCE: 596 cgcccaccucagccucccaaaaugcugggauuacaggcaugagccacugcggucgaccau    60 gaccuggacauguuugugccccaguacugucaguuugcag                        99

<210> SEQ ID NO 597
<211> LENGTH: 100
<212> TYPE: RNA
<213> ORGANISM: Homo sapiens

<400> SEQUENCE: 597 gugagcgggcgcggcagggaucgcgggcggguggcggccuagggcgcggagggcggaccg    60 ggaauggcgcgccgugcgccgccggcguaacugcggcgcu                        100

<210> SEQ ID NO 598
<211> LENGTH: 77
<212> TYPE: RNA
<213> ORGANISM: Homo sapiens

<400> SEQUENCE: 598 gaguugggagguucccucuccaaaugugucuugauccccaccccaagacacauuuggag    60 agggacccucccaacuc                                               77

<210> SEQ ID NO 599
<211> LENGTH: 96
<212> TYPE: RNA
<213> ORGANISM: Homo sapiens

<400> SEQUENCE: 599 cagugcuggggucucaggaggcagcgcucucaggacgucaccaccauggccugggcucug    60
```

```
cuccuccuca cccuccucac ucagggcaca ggugau                                    96
```

<210> SEQ ID NO 600
<211> LENGTH: 93
<212> TYPE: RNA
<213> ORGANISM: Homo sapiens

<400> SEQUENCE: 600

```
ccuuccggcg uccaggcggg ggcgccgcgg gaccgcccuc gugucugugg cggugggauc     60
ccgcggccgu guuuuccugg uggcccggcc aug                                   93
```

<210> SEQ ID NO 601
<211> LENGTH: 115
<212> TYPE: RNA
<213> ORGANISM: Homo sapiens

<400> SEQUENCE: 601

```
ggugccgagg gccgccggc auccaggcg ggucgcugcg guaccucccu ccgucugug         60 gcggugggau cccguggccg uguuuccug guggcccggc cgugccgag guuuc            115
```

<210> SEQ ID NO 602
<211> LENGTH: 73
<212> TYPE: RNA
<213> ORGANISM: Homo sapiens

<400> SEQUENCE: 602

```
cugguguuug aggcgaugug gggauguaga gacaacuucc cagucucauu uccucauccu     60
gccaggccac cau                                                         73
```

<210> SEQ ID NO 603
<211> LENGTH: 87
<212> TYPE: RNA
<213> ORGANISM: Homo sapiens

<400> SEQUENCE: 603

```
cccucaucuc ugggcagggg cuuauuguag gagucucuga agagagcugu ggacugaccu     60
gcuuuaaccc uuccccaggu ucccauu                                          87
```

<210> SEQ ID NO 604
<211> LENGTH: 61
<212> TYPE: RNA
<213> ORGANISM: Homo sapiens

<400> SEQUENCE: 604

```
gggggcggga gcuggggucu gcagguucgc acugaugccu gcucgcccug ucucccgcua     60
g                                                                      61
```

<210> SEQ ID NO 605
<211> LENGTH: 65
<212> TYPE: RNA
<213> ORGANISM: Homo sapiens

<400> SEQUENCE: 605

```
gggugcucgg ggcaggcggc ugggagcggc ccucacauug auggcuccug ccaccuccuc     60
cgcag                                                                  65
```

<210> SEQ ID NO 606
<211> LENGTH: 64
<212> TYPE: RNA

<213> ORGANISM: Homo sapiens

<400> SEQUENCE: 606
gaaggcgagg gguagaagag cacaggggüu cugauaaacc cuucugccug cauucuacuc    60
ccag    64

<210> SEQ ID NO 607
<211> LENGTH: 63
<212> TYPE: RNA
<213> ORGANISM: Homo sapiens

<400> SEQUENCE: 607 aaugggüggg ugcuggüggg agccgugccc uggccacuca uucggcucuc ucccucaccc    60
uag    63

<210> SEQ ID NO 608
<211> LENGTH: 69
<212> TYPE: RNA
<213> ORGANISM: Homo sapiens

<400> SEQUENCE: 608
ggcccucggg ccugggguug ggggagcucu guccugucuc acucauugcu ccucccugc    60 cuggcccag    69

<210> SEQ ID NO 609
<211> LENGTH: 71
<212> TYPE: RNA
<213> ORGANISM: Homo sapiens

<400> SEQUENCE: 609
auggaggggg guguggagcc aggggccca ggucuacagc uucuccccgc ucccugcccc    60
cauacuccca g    71

<210> SEQ ID NO 610
<211> LENGTH: 73
<212> TYPE: RNA
<213> ORGANISM: Homo sapiens

<400> SEQUENCE: 610
cccagggucu ggugcggaga gggcccacag uggacuuggu gacgcuguau gcccucaccg    60
cucagccccu ggg    73

<210> SEQ ID NO 611
<211> LENGTH: 69
<212> TYPE: RNA
<213> ORGANISM: Homo sapiens

<400> SEQUENCE: 611
gggcuuaggg augggaggcc aggaugaaga uuaaucccua auccccaaca cuggccuugc    60
uaucccag    69

<210> SEQ ID NO 612
<211> LENGTH: 87
<212> TYPE: RNA
<213> ORGANISM: Homo sapiens

<400> SEQUENCE: 612
gugaggcggg gccaggaggg uguguggcgu gggugcugcg gggccgucag ggugccugcg    60
ggacgcucac cuggcuggcc cgcccag    87

<210> SEQ ID NO 613
<211> LENGTH: 69
<212> TYPE: RNA
<213> ORGANISM: Homo sapiens

<400> SEQUENCE: 613
gaaccucggg gcauggggga gggaggcugg acaggagagg gcucacccag gcccuguccu    60
cugccccag                                                            69

<210> SEQ ID NO 614
<211> LENGTH: 79
<212> TYPE: RNA
<213> ORGANISM: Homo sapiens

<400> SEQUENCE: 614
cagccugggg aaggcuuggc agggaagaca caugagcagu gccuccacuu cacgccucuc    60 ccugucucc uuucccuag                                                  79

<210> SEQ ID NO 615
<211> LENGTH: 69
<212> TYPE: RNA
<213> ORGANISM: Homo sapiens

<400> SEQUENCE: 615 uggggguaggg gugggggaau ucaggggugu cgaacucaug gcugccaccu uuguguccccc   60 auccugcag                                                            69

<210> SEQ ID NO 616
<211> LENGTH: 67
<212> TYPE: RNA
<213> ORGANISM: Homo sapiens

<400> SEQUENCE: 616
uacaggccgg ggcuuugggu gagggacccc cggagucugu cacgguucuca ccccaacucu   60 gccccag                                                              67

<210> SEQ ID NO 617
<211> LENGTH: 64
<212> TYPE: RNA
<213> ORGANISM: Homo sapiens

<400> SEQUENCE: 617
ugcucuguag gcaugaggca gggcccaggu uccaugugau gcugaagcuc ugacauuccu    60
gcag                                                                 64

<210> SEQ ID NO 618
<211> LENGTH: 71
<212> TYPE: RNA
<213> ORGANISM: Homo sapiens

<400> SEQUENCE: 618
ugaccacccc cgggcaaaga ccugcagauc cccguuaga gacgggccca ggacuuugug    60
cggggugccc a                                                         71

<210> SEQ ID NO 619
<211> LENGTH: 70
<212> TYPE: RNA
<213> ORGANISM: Homo sapiens

```
<400> SEQUENCE: 619
guccuggggg gcugggaugg gccauggugu gcucugaucc cccgugguc ucuuggcccc      60 caggaacucc                                                            70

<210> SEQ ID NO 620
<211> LENGTH: 67
<212> TYPE: RNA
<213> ORGANISM: Homo sapiens

<400> SEQUENCE: 620
cagggaggag ugguacuag gggccagcaa ccugauuacc ccucuuuggc ccuuuguacc      60
ccuccag                                                               67

<210> SEQ ID NO 621
<211> LENGTH: 60
<212> TYPE: RNA
<213> ORGANISM: Homo sapiens

<400> SEQUENCE: 621
caaggugggg gagauggggg uugaacuuca uuucucaugc ucaucccccau cuccuuucag   60

<210> SEQ ID NO 622
<211> LENGTH: 62
<212> TYPE: RNA
<213> ORGANISM: Homo sapiens

<400> SEQUENCE: 622
gugggucucg caucaggagg caaggccagg acccgcugac ccaugccucc ugccgcgguc   60
ag                                                                    62

<210> SEQ ID NO 623
<211> LENGTH: 72
<212> TYPE: RNA
<213> ORGANISM: Homo sapiens

<400> SEQUENCE: 623
gagucugagg gacccaggac aggagaaggc cuauggugau uugcauucuu ccugcccugg   60
cuccauccuc ag                                                         72

<210> SEQ ID NO 624
<211> LENGTH: 64
<212> TYPE: RNA
<213> ORGANISM: Homo sapiens

<400> SEQUENCE: 624
aguucagggc cgaagggugg aagcugcugg ugcucaucuc agccucugcc cuuggccucc   60
ccag                                                                  64

<210> SEQ ID NO 625
<211> LENGTH: 66
<212> TYPE: RNA
<213> ORGANISM: Homo sapiens

<400> SEQUENCE: 625
cagagcaggg cagggaaggu gggagagggg cccagcugac ccuccuguca cccgcuccuu   60
gcccag                                                                66

<210> SEQ ID NO 626
<211> LENGTH: 66
```

```
<212> TYPE: RNA
<213> ORGANISM: Homo sapiens

<400> SEQUENCE: 626
ccuggagggg ggcacugcgc aagcaaagcc agggacccug agaggcuuug cuuccugcuc    60
cccuag                                                               66

<210> SEQ ID NO 627
<211> LENGTH: 65
<212> TYPE: RNA
<213> ORGANISM: Homo sapiens

<400> SEQUENCE: 627
gagaaugggg ggacagaugg agaggacaca ggcuggcacu gagguccccu ccacuuuccu    60
ccuag                                                                65

<210> SEQ ID NO 628
<211> LENGTH: 76
<212> TYPE: RNA
<213> ORGANISM: Homo sapiens

<400> SEQUENCE: 628
acugacuuug agucucuccu cagggugcug caggcaaagc uggggaccca gggagagacg    60
uaagugaggg gagaug                                                    76

<210> SEQ ID NO 629
<211> LENGTH: 59
<212> TYPE: RNA
<213> ORGANISM: Homo sapiens

<400> SEQUENCE: 629
cuccagggag acagugugug aggccucuug ccauggccuc ccugcccgcc ucucugcag     59

<210> SEQ ID NO 630
<211> LENGTH: 98
<212> TYPE: RNA
<213> ORGANISM: Homo sapiens

<400> SEQUENCE: 630
uugggcaagg ugcggggcua gggcuaacag cagucuuacu gaagguuucc uggaaaccac    60
gcacaugcug uugccacuaa ccucaaccuu acucgguc                            98

<210> SEQ ID NO 631
<211> LENGTH: 80
<212> TYPE: RNA
<213> ORGANISM: Homo sapiens

<400> SEQUENCE: 631
ggcgcgucgc ccccucagu ccaccagagc ccggauaccu cagaaauucg gcucuggguc     60
uguggggagc gaaaugcaac                                                80

<210> SEQ ID NO 632
<211> LENGTH: 99
<212> TYPE: RNA
<213> ORGANISM: Homo sapiens

<400> SEQUENCE: 632
gcaagggaca gggagggucg uggcgacacu cgcgccagcu cccgggacgg cugggucgg     60 gcuggucgcc gaccuccgac ccuccacuag augccuggc                           99
```

<210> SEQ ID NO 633
<211> LENGTH: 103
<212> TYPE: RNA
<213> ORGANISM: Homo sapiens

<400> SEQUENCE: 633
gugucggcug uggcgugacu gucccucugu gucccccacu aggcccacug cucaguggag    60
cguggaggac gaggaggagg ccguccacga gcaaugccag cau                     103

<210> SEQ ID NO 634
<211> LENGTH: 49
<212> TYPE: RNA
<213> ORGANISM: Homo sapiens

<400> SEQUENCE: 634
uucccagcca acgcaccaaa aaugauaugg gucuguuguc uggagaaac                49

<210> SEQ ID NO 635
<211> LENGTH: 81
<212> TYPE: RNA
<213> ORGANISM: Homo sapiens

<400> SEQUENCE: 635
uacaggugca ggggaacugu agaugaaaag gcuuggcacu ugagggaaag ccucaguuca    60
uucucauuuu gcucaccugu u                                              81

<210> SEQ ID NO 636
<211> LENGTH: 81
<212> TYPE: RNA
<213> ORGANISM: Homo sapiens

<400> SEQUENCE: 636
uagaggcagu uucaacagau guguagacuu uugauaugag aaauuggu uu caaaaucagg    60 agucggggcu uuacugcuuu u                                              81

<210> SEQ ID NO 637
<211> LENGTH: 80
<212> TYPE: RNA
<213> ORGANISM: Homo sapiens

<400> SEQUENCE: 637
gcgucaagau ggcggcgggg agguaggcag agcaggacgc cgcugcugcc gccgccaccg    60
ccgccuccgc uccagucgcc                                                80

<210> SEQ ID NO 638
<211> LENGTH: 75
<212> TYPE: RNA
<213> ORGANISM: Homo sapiens

<400> SEQUENCE: 638
ucaucccugg gugggauuu guugcauuac uuguguucua uauaaaguau ugcacuuguc    60
ccggccugug gaaga                                                    75

<210> SEQ ID NO 639
<211> LENGTH: 94
<212> TYPE: RNA
<213> ORGANISM: Homo sapiens

<400> SEQUENCE: 639
gugaggugug ggcccggccc caggagcggg gccugggcag ccccgugugu ugaggaagga    60

| | |
|---|---|
| aggcagggcc cccgcucccc gggccugacc ccac | 94 |

<210> SEQ ID NO 640
<211> LENGTH: 80
<212> TYPE: RNA
<213> ORGANISM: Homo sapiens

<400> SEQUENCE: 640

| | |
|---|---|
| ccucugugag aaagggugug ggggagaggc ugucuugugu cuguaaguau gccaaacuua | 60 |
| uuuuccccaa ggcagaggga | 80 |

<210> SEQ ID NO 641
<211> LENGTH: 149
<212> TYPE: RNA
<213> ORGANISM: Homo sapiens

<400> SEQUENCE: 641

| | |
|---|---|
| caucaagacc cagcugaguc acugucacug ccuaccaauc ucgaccggac cucgaccggc | 60 |
| ucgucugugu ugccaaucga cucggcgugg cgucggucgu gguagauagg cggucaugca | 120 |
| uacgaauuuu cagcucuugu ucuggugac | 149 |

<210> SEQ ID NO 642
<211> LENGTH: 73
<212> TYPE: RNA
<213> ORGANISM: Homo sapiens

<400> SEQUENCE: 642

| | |
|---|---|
| ggccggcugg gguuccuggg gaugggauuu gcuuccuguc acaaaucaca uugccaggga | 60 |
| uuuccaaccg acc | 73 |

<210> SEQ ID NO 643
<211> LENGTH: 81
<212> TYPE: RNA
<213> ORGANISM: Homo sapiens

<400> SEQUENCE: 643

| | |
|---|---|
| cuucaggaag cugguuucau auggugguuu agauuuaaau agugauuguc uagcaccauu | 60 |
| ugaaaucagu guucuugggg g | 81 |

<210> SEQ ID NO 644
<211> LENGTH: 81
<212> TYPE: RNA
<213> ORGANISM: Homo sapiens

<400> SEQUENCE: 644

| | |
|---|---|
| cuucuggaag cugguuucac auggugggcuu agauuuuucc aucuuuguau cuagcaccau | 60 |
| uugaaaucag uguuuuagga g | 81 |

<210> SEQ ID NO 645
<211> LENGTH: 68
<212> TYPE: RNA
<213> ORGANISM: Homo sapiens

<400> SEQUENCE: 645

| | |
|---|---|
| ugcccaggcu ggagcgagug cagugguca gucagccua gcucacugca gccucgaacu | 60 |
| ccugggcu | 68 |

<210> SEQ ID NO 646

```
<211> LENGTH: 68
<212> TYPE: RNA
<213> ORGANISM: Homo sapiens

<400> SEQUENCE: 646
gaauggaaga agaaggcggu cggucugcgg gagccaggcc gcagagccau ccgccuucug    60
uccauguc                                                            68

<210> SEQ ID NO 647
<211> LENGTH: 51
<212> TYPE: RNA
<213> ORGANISM: Homo sapiens

<400> SEQUENCE: 647
acagaccccg gggagcccgg cggugaagcu ccugguaucc ugggugucug a             51

<210> SEQ ID NO 648
<211> LENGTH: 60
<212> TYPE: RNA
<213> ORGANISM: Homo sapiens

<400> SEQUENCE: 648
gagcaggcga ggcugggcug aacccguggg ugaggagugc agcccagcug aggccucugc    60

<210> SEQ ID NO 649
<211> LENGTH: 71
<212> TYPE: RNA
<213> ORGANISM: Homo sapiens

<400> SEQUENCE: 649
ggugaguggg agccgguggg gcuggaguaa gggcacgccc ggggcugccc caccugcuga    60
ccacccuccc c                                                        71

<210> SEQ ID NO 650
<211> LENGTH: 82
<212> TYPE: RNA
<213> ORGANISM: Homo sapiens

<400> SEQUENCE: 650
gggaaagcgg agggcgcgcc cagcucccgg gcugauugcg cuaacagugg ccccgguguu    60
ggggcgcguc ugccgcugcc cc                                            82

<210> SEQ ID NO 651
<211> LENGTH: 109
<212> TYPE: RNA
<213> ORGANISM: Homo sapiens

<400> SEQUENCE: 651
ucccgcauuc ccucugcuuu ggucaggugg ugcccuccuu ccaugggu ag agccagagau    60 gguggguucu ggcuggucag augggagugg acagagaccc ggggccuc               109

<210> SEQ ID NO 652
<211> LENGTH: 85
<212> TYPE: RNA
<213> ORGANISM: Homo sapiens

<400> SEQUENCE: 652 agggu agagg gaugagggg g aaaguucuau aguccuguaa uuagaucuca ggacuauaga    60
acuuuccccc ucaucccucu gcccu                                         85
```

-continued

```
<210> SEQ ID NO 653
<211> LENGTH: 67
<212> TYPE: RNA
<213> ORGANISM: Homo sapiens

<400> SEQUENCE: 653
ccugcaggca aagugggc ugacagggca gaggguugcg ccccucacc aucccuucug      60 ccugcag                                                             67

<210> SEQ ID NO 654
<211> LENGTH: 67
<212> TYPE: RNA
<213> ORGANISM: Homo sapiens

<400> SEQUENCE: 654
ccugcaggca aagugggc ugacagggca gaggguugcg ccccucacc aucccuucug      60 ccugcag                                                             67

<210> SEQ ID NO 655
<211> LENGTH: 67
<212> TYPE: RNA
<213> ORGANISM: Homo sapiens

<400> SEQUENCE: 655
ccugcaggca aagugggc ugacagggca gaggguugcg ccccucacc aucccuucug      60 ccugcag                                                             67

<210> SEQ ID NO 656
<211> LENGTH: 67
<212> TYPE: RNA
<213> ORGANISM: Homo sapiens

<400> SEQUENCE: 656
ccugcaggca aagugggc ugacagggca gaggguugcg ccccucacc aucccuucug      60 ccugcag                                                             67

<210> SEQ ID NO 657
<211> LENGTH: 66
<212> TYPE: RNA
<213> ORGANISM: Homo sapiens

<400> SEQUENCE: 657
ccgagugggg cggggcaggu cccugcaggg acugugacac ugaaggaccu gcaccuucgc   60
ccacag                                                              66

<210> SEQ ID NO 658
<211> LENGTH: 66
<212> TYPE: RNA
<213> ORGANISM: Homo sapiens

<400> SEQUENCE: 658
gggcaugggg aggugggag ucagcauggg gcuaggaggc cccgcgcuga cccgccuucu    60
ccgcag                                                              66

<210> SEQ ID NO 659
<211> LENGTH: 61
<212> TYPE: RNA
<213> ORGANISM: Homo sapiens

<400> SEQUENCE: 659
```

```
aacugcgggg ccagagcaga gagcccuugc acaccaccag ccucuccucc cugugcccca    60
g                                                                    61

<210> SEQ ID NO 660
<211> LENGTH: 94
<212> TYPE: RNA
<213> ORGANISM: Homo sapiens

<400> SEQUENCE: 660
cacggugucc ccugguggaa ccuggcaggg ggagagguaa ggucuuucag ccucuccaaa    60
gcccaugguc agguacucag guggggagc ccug                                 94

<210> SEQ ID NO 661
<211> LENGTH: 61
<212> TYPE: RNA
<213> ORGANISM: Homo sapiens

<400> SEQUENCE: 661
ucucguuuga ucucggaagc uaagcagggu ugggccuggu aguacuugg augggaaacu     60 u                                                                    61

<210> SEQ ID NO 662
<211> LENGTH: 53
<212> TYPE: RNA
<213> ORGANISM: Homo sapiens

<400> SEQUENCE: 662
guuugaucuc ggaagcuaag cagggucggg ccugguuagu acuggaugg gag            53

<210> SEQ ID NO 663
<211> LENGTH: 68
<212> TYPE: RNA
<213> ORGANISM: Homo sapiens

<400> SEQUENCE: 663
gugcaaagag caggaggaca ggggauuuau cucccaaggg aggucccug auccaguca      60 cggcacca                                                             68

<210> SEQ ID NO 664
<211> LENGTH: 78
<212> TYPE: RNA
<213> ORGANISM: Homo sapiens

<400> SEQUENCE: 664
cuuucuacac agguugggau cgguugcaau gcuguguuuc uguaugguau ugcacuuguc    60
ccggccuguu gaguuugg                                                  78

<210> SEQ ID NO 665
<211> LENGTH: 17
<212> TYPE: RNA
<213> ORGANISM: Homo sapiens

<400> SEQUENCE: 665
caggcacggg agcucag                                                   17

<210> SEQ ID NO 666
<211> LENGTH: 23
<212> TYPE: RNA
<213> ORGANISM: Homo sapiens

<400> SEQUENCE: 666
```
aauauacagg gggagacucu uau    23

<210> SEQ ID NO 667
<211> LENGTH: 15
<212> TYPE: RNA
<213> ORGANISM: Homo sapiens

<400> SEQUENCE: 667
auauacaggg ggaga    15

<210> SEQ ID NO 668
<211> LENGTH: 21
<212> TYPE: RNA
<213> ORGANISM: Homo sapiens

<400> SEQUENCE: 668
gugagucagg gugggcugg c    21

<210> SEQ ID NO 669
<211> LENGTH: 26
<212> TYPE: RNA
<213> ORGANISM: Homo sapiens

<400> SEQUENCE: 669
caagauggug gacuacagcg uguggg    26

<210> SEQ ID NO 670
<211> LENGTH: 15
<212> TYPE: RNA
<213> ORGANISM: Homo sapiens

<400> SEQUENCE: 670
aggcaagaug gugga    15

<210> SEQ ID NO 671
<211> LENGTH: 24
<212> TYPE: RNA
<213> ORGANISM: Homo sapiens

<400> SEQUENCE: 671
auauacaggg ggagacucuc auuu    24

<210> SEQ ID NO 672
<211> LENGTH: 15
<212> TYPE: RNA
<213> ORGANISM: Homo sapiens

<400> SEQUENCE: 672
auauacaggg ggaga    15

<210> SEQ ID NO 673
<211> LENGTH: 21
<212> TYPE: RNA
<213> ORGANISM: Homo sapiens

<400> SEQUENCE: 673
uaggucaccc guuugacuau c    21

<210> SEQ ID NO 674
<211> LENGTH: 21
<212> TYPE: RNA
<213> ORGANISM: Homo sapiens

```
<400> SEQUENCE: 674
gaauggauuu uuggagcagg a                                           21

<210> SEQ ID NO 675
<211> LENGTH: 15
<212> TYPE: RNA
<213> ORGANISM: Homo sapiens

<400> SEQUENCE: 675
gaauggauuu uugga                                                  15

<210> SEQ ID NO 676
<211> LENGTH: 26
<212> TYPE: RNA
<213> ORGANISM: Homo sapiens

<400> SEQUENCE: 676
aggagggagg agaugggcca aguucc                                      26

<210> SEQ ID NO 677
<211> LENGTH: 15
<212> TYPE: RNA
<213> ORGANISM: Homo sapiens

<400> SEQUENCE: 677
gggaggaggg aggag                                                  15

<210> SEQ ID NO 678
<211> LENGTH: 15
<212> TYPE: RNA
<213> ORGANISM: Homo sapiens

<400> SEQUENCE: 678
cccgcgggac gcgcc                                                  15

<210> SEQ ID NO 679
<211> LENGTH: 26
<212> TYPE: RNA
<213> ORGANISM: Homo sapiens

<400> SEQUENCE: 679
cggguagaga gggcaguggg agguaa                                      26

<210> SEQ ID NO 680
<211> LENGTH: 15
<212> TYPE: RNA
<213> ORGANISM: Homo sapiens

<400> SEQUENCE: 680
cggguagaga gggca                                                  15

<210> SEQ ID NO 681
<211> LENGTH: 28
<212> TYPE: RNA
<213> ORGANISM: Homo sapiens

<400> SEQUENCE: 681
uuggggaaac ggccgcugag ugaggcgu                                    28

<210> SEQ ID NO 682
<211> LENGTH: 15
<212> TYPE: RNA
<213> ORGANISM: Homo sapiens
```

-continued

<400> SEQUENCE: 682
ggggaaacgg ccgcu                                                    15

<210> SEQ ID NO 683
<211> LENGTH: 22
<212> TYPE: RNA
<213> ORGANISM: Homo sapiens

<400> SEQUENCE: 683
ggcagggaca gcaaagggu gc                                             22

<210> SEQ ID NO 684
<211> LENGTH: 18
<212> TYPE: RNA
<213> ORGANISM: Homo sapiens

<400> SEQUENCE: 684
gcagggacag caaagggg                                                 18

<210> SEQ ID NO 685
<211> LENGTH: 23
<212> TYPE: RNA
<213> ORGANISM: Homo sapiens

<400> SEQUENCE: 685
agcagaggca gagaggcuca ggg                                           23

<210> SEQ ID NO 686
<211> LENGTH: 15
<212> TYPE: RNA
<213> ORGANISM: Homo sapiens

<400> SEQUENCE: 686
agcagaggca gagag                                                    15

<210> SEQ ID NO 687
<211> LENGTH: 24
<212> TYPE: RNA
<213> ORGANISM: Homo sapiens

<400> SEQUENCE: 687
guugggacaa gaggacgguc uucu                                          24

<210> SEQ ID NO 688
<211> LENGTH: 20
<212> TYPE: RNA
<213> ORGANISM: Homo sapiens

<400> SEQUENCE: 688
guugggacaa gaggacgguc                                               20

<210> SEQ ID NO 689
<211> LENGTH: 15
<212> TYPE: RNA
<213> ORGANISM: Homo sapiens

<400> SEQUENCE: 689
gcggguggag gagga                                                    15

<210> SEQ ID NO 690
<211> LENGTH: 21
<212> TYPE: RNA

```
<213> ORGANISM: Homo sapiens

<400> SEQUENCE: 690
aaagaucugg aagugggaga c                                        21

<210> SEQ ID NO 691
<211> LENGTH: 22
<212> TYPE: RNA
<213> ORGANISM: Homo sapiens

<400> SEQUENCE: 691
uccugcagag aggaagcccu uc                                       22

<210> SEQ ID NO 692
<211> LENGTH: 18
<212> TYPE: RNA
<213> ORGANISM: Homo sapiens

<400> SEQUENCE: 692
ccugcagaga ggaagccc                                            18

<210> SEQ ID NO 693
<211> LENGTH: 23
<212> TYPE: RNA
<213> ORGANISM: Homo sapiens

<400> SEQUENCE: 693 ugggcggag cuuccggagg ccc                                       23

<210> SEQ ID NO 694
<211> LENGTH: 15
<212> TYPE: RNA
<213> ORGANISM: Homo sapiens

<400> SEQUENCE: 694
gccccgggaa agcgu                                               15

<210> SEQ ID NO 695
<211> LENGTH: 20
<212> TYPE: RNA
<213> ORGANISM: Homo sapiens

<400> SEQUENCE: 695
uggggacgua gcuggccaga                                          20

<210> SEQ ID NO 696
<211> LENGTH: 20
<212> TYPE: RNA
<213> ORGANISM: Homo sapiens

<400> SEQUENCE: 696
agcucugcug cucacuggca                                          20

<210> SEQ ID NO 697
<211> LENGTH: 24
<212> TYPE: RNA
<213> ORGANISM: Homo sapiens

<400> SEQUENCE: 697
gaaaagcugg guugagaggg caaa                                     24

<210> SEQ ID NO 698
<211> LENGTH: 15
```

```
<212> TYPE: RNA
<213> ORGANISM: Homo sapiens

<400> SEQUENCE: 698
gaaaagcugg guuga                                                    15

<210> SEQ ID NO 699
<211> LENGTH: 22
<212> TYPE: RNA
<213> ORGANISM: Homo sapiens

<400> SEQUENCE: 699 gggggcagg aggggcucag gg                                             22

<210> SEQ ID NO 700
<211> LENGTH: 16
<212> TYPE: RNA
<213> ORGANISM: Homo sapiens

<400> SEQUENCE: 700 guggggggc aggagg                                                    16

<210> SEQ ID NO 701
<211> LENGTH: 22
<212> TYPE: RNA
<213> ORGANISM: Homo sapiens

<400> SEQUENCE: 701
ugagugaauc ggaaaggagg cg                                            22

<210> SEQ ID NO 702
<211> LENGTH: 15
<212> TYPE: RNA
<213> ORGANISM: Homo sapiens

<400> SEQUENCE: 702
cggaaaggag gcgcc                                                    15

<210> SEQ ID NO 703
<211> LENGTH: 23
<212> TYPE: RNA
<213> ORGANISM: Homo sapiens

<400> SEQUENCE: 703
gugggcuggg cugggcuggg cca                                           23

<210> SEQ ID NO 704
<211> LENGTH: 15
<212> TYPE: RNA
<213> ORGANISM: Homo sapiens

<400> SEQUENCE: 704
gggcugggcu gggcu                                                    15

<210> SEQ ID NO 705
<211> LENGTH: 23
<212> TYPE: RNA
<213> ORGANISM: Homo sapiens

<400> SEQUENCE: 705
ugccugcugg gguggaaccu ggu                                           23

<210> SEQ ID NO 706
```

```
<211> LENGTH: 15
<212> TYPE: RNA
<213> ORGANISM: Homo sapiens

<400> SEQUENCE: 706
gccugcuggg gugga                                              15

<210> SEQ ID NO 707
<211> LENGTH: 29
<212> TYPE: RNA
<213> ORGANISM: Homo sapiens

<400> SEQUENCE: 707
ggucaggcgg cucggacuga gcagguggg                               29

<210> SEQ ID NO 708
<211> LENGTH: 15
<212> TYPE: RNA
<213> ORGANISM: Homo sapiens

<400> SEQUENCE: 708
agaguguggu caggc                                              15

<210> SEQ ID NO 709
<211> LENGTH: 16
<212> TYPE: RNA
<213> ORGANISM: Homo sapiens

<400> SEQUENCE: 709
cuggggaucc cccgac                                             16

<210> SEQ ID NO 710
<211> LENGTH: 15
<212> TYPE: RNA
<213> ORGANISM: Homo sapiens

<400> SEQUENCE: 710
guguggagcu ggggc                                              15

<210> SEQ ID NO 711
<211> LENGTH: 15
<212> TYPE: RNA
<213> ORGANISM: Homo sapiens

<400> SEQUENCE: 711
gaggcugaag gaaga                                              15

<210> SEQ ID NO 712
<211> LENGTH: 23
<212> TYPE: RNA
<213> ORGANISM: Homo sapiens

<400> SEQUENCE: 712
caaggagacg ggaacaugga gcc                                     23

<210> SEQ ID NO 713
<211> LENGTH: 22
<212> TYPE: RNA
<213> ORGANISM: Homo sapiens

<400> SEQUENCE: 713
aaaagcuggg cugagaggcg ac                                      22
```

```
<210> SEQ ID NO 714
<211> LENGTH: 15
<212> TYPE: RNA
<213> ORGANISM: Homo sapiens

<400> SEQUENCE: 714
aaagcugggc ugaga                                                    15

<210> SEQ ID NO 715
<211> LENGTH: 23
<212> TYPE: RNA
<213> ORGANISM: Homo sapiens

<400> SEQUENCE: 715
acaggagugg ggugggaca uaa                                            23

<210> SEQ ID NO 716
<211> LENGTH: 20
<212> TYPE: RNA
<213> ORGANISM: Homo sapiens

<400> SEQUENCE: 716
acaggagugg ggugggaca                                                20

<210> SEQ ID NO 717
<211> LENGTH: 26
<212> TYPE: RNA
<213> ORGANISM: Homo sapiens

<400> SEQUENCE: 717
gucccggggc ugcgcgaggc acaggc                                        26

<210> SEQ ID NO 718
<211> LENGTH: 15
<212> TYPE: RNA
<213> ORGANISM: Homo sapiens

<400> SEQUENCE: 718
ggcccggggg gcggg                                                    15

<210> SEQ ID NO 719
<211> LENGTH: 23
<212> TYPE: RNA
<213> ORGANISM: Homo sapiens

<400> SEQUENCE: 719
ccaggaggcg gaggaggugg agg                                           23

<210> SEQ ID NO 720
<211> LENGTH: 15
<212> TYPE: RNA
<213> ORGANISM: Homo sapiens

<400> SEQUENCE: 720
acccaggagg cggag                                                    15

<210> SEQ ID NO 721
<211> LENGTH: 24
<212> TYPE: RNA
<213> ORGANISM: Homo sapiens

<400> SEQUENCE: 721
agaggcaccg ccugcccagu gaca                                          24
```

```
<210> SEQ ID NO 722
<211> LENGTH: 15
<212> TYPE: RNA
<213> ORGANISM: Homo sapiens

<400> SEQUENCE: 722
gaggcaccgc cugcc                                                      15

<210> SEQ ID NO 723
<211> LENGTH: 19
<212> TYPE: RNA
<213> ORGANISM: Homo sapiens

<400> SEQUENCE: 723
gcugggcgag gcuggcauc                                                  19

<210> SEQ ID NO 724
<211> LENGTH: 19
<212> TYPE: RNA
<213> ORGANISM: Homo sapiens

<400> SEQUENCE: 724 aggggggcggg cuccggcgc                                                 19

<210> SEQ ID NO 725
<211> LENGTH: 15
<212> TYPE: RNA
<213> ORGANISM: Homo sapiens

<400> SEQUENCE: 725
guagggggcg ggcuc                                                      15

<210> SEQ ID NO 726
<211> LENGTH: 22
<212> TYPE: RNA
<213> ORGANISM: Homo sapiens

<400> SEQUENCE: 726 ggugggggcua gugaugcagg ac                                             22

<210> SEQ ID NO 727
<211> LENGTH: 19
<212> TYPE: RNA
<213> ORGANISM: Homo sapiens

<400> SEQUENCE: 727 ugggggcuagu gaugcagga                                                 19

<210> SEQ ID NO 728
<211> LENGTH: 30
<212> TYPE: RNA
<213> ORGANISM: Homo sapiens

<400> SEQUENCE: 728
gcugggcugg gacggacacc cggccuccac                                      30

<210> SEQ ID NO 729
<211> LENGTH: 19
<212> TYPE: RNA
<213> ORGANISM: Homo sapiens

<400> SEQUENCE: 729
gaggcugggc ugggacgga                                                  19
```

```
<210> SEQ ID NO 730
<211> LENGTH: 18
<212> TYPE: RNA
<213> ORGANISM: Homo sapiens

<400> SEQUENCE: 730
ucuagguggg gagacuga                                                   18

<210> SEQ ID NO 731
<211> LENGTH: 16
<212> TYPE: RNA
<213> ORGANISM: Homo sapiens

<400> SEQUENCE: 731 gugggagac ugacgg                                                      16

<210> SEQ ID NO 732
<211> LENGTH: 23
<212> TYPE: RNA
<213> ORGANISM: Homo sapiens

<400> SEQUENCE: 732
aggacuggac ucccggcagc ccc                                             23

<210> SEQ ID NO 733
<211> LENGTH: 18
<212> TYPE: RNA
<213> ORGANISM: Homo sapiens

<400> SEQUENCE: 733
gcguggggag cugguccu                                                   18

<210> SEQ ID NO 734
<211> LENGTH: 21
<212> TYPE: RNA
<213> ORGANISM: Homo sapiens

<400> SEQUENCE: 734
cccagcagga cgggagcgcg g                                               21

<210> SEQ ID NO 735
<211> LENGTH: 16
<212> TYPE: RNA
<213> ORGANISM: Homo sapiens

<400> SEQUENCE: 735
aagcuggguc aaggag                                                     16

<210> SEQ ID NO 736
<211> LENGTH: 25
<212> TYPE: RNA
<213> ORGANISM: Homo sapiens

<400> SEQUENCE: 736
cugggccagg gagcagcugg ugggu                                           25

<210> SEQ ID NO 737
<211> LENGTH: 20
<212> TYPE: RNA
<213> ORGANISM: Homo sapiens

<400> SEQUENCE: 737
```

```
ugggccaggg agcagcuggu                                                    20

<210> SEQ ID NO 738
<211> LENGTH: 26
<212> TYPE: RNA
<213> ORGANISM: Homo sapiens

<400> SEQUENCE: 738
acugggaaga ggagcugagg gacauu                                             26

<210> SEQ ID NO 739
<211> LENGTH: 19
<212> TYPE: RNA
<213> ORGANISM: Homo sapiens

<400> SEQUENCE: 739
acugggaaga ggagcugag                                                     19

<210> SEQ ID NO 740
<211> LENGTH: 21
<212> TYPE: RNA
<213> ORGANISM: Homo sapiens

<400> SEQUENCE: 740 cuggggacg cgugagcgcg a                                                   21

<210> SEQ ID NO 741
<211> LENGTH: 21
<212> TYPE: RNA
<213> ORGANISM: Homo sapiens

<400> SEQUENCE: 741
agcggggagg aagugggcgc u                                                  21

<210> SEQ ID NO 742
<211> LENGTH: 16
<212> TYPE: RNA
<213> ORGANISM: Homo sapiens

<400> SEQUENCE: 742
ggagccccgg cgcggg                                                        16

<210> SEQ ID NO 743
<211> LENGTH: 22
<212> TYPE: RNA
<213> ORGANISM: Homo sapiens

<400> SEQUENCE: 743
aggagcaagg cggcaucucu cu                                                 22

<210> SEQ ID NO 744
<211> LENGTH: 18
<212> TYPE: RNA
<213> ORGANISM: Homo sapiens

<400> SEQUENCE: 744
gagcaaggcg gcaucucu                                                      18

<210> SEQ ID NO 745
<211> LENGTH: 15
<212> TYPE: RNA
<213> ORGANISM: Homo sapiens

<400> SEQUENCE: 745
```

-continued gggugagggc aggug 15

<210> SEQ ID NO 746
<211> LENGTH: 17
<212> TYPE: RNA
<213> ORGANISM: Homo sapiens

<400> SEQUENCE: 746
ggcaggaggg cugugcc 17

<210> SEQ ID NO 747
<211> LENGTH: 19
<212> TYPE: RNA
<213> ORGANISM: Homo sapiens

<400> SEQUENCE: 747 auaguggggaa gcuggcaga 19

<210> SEQ ID NO 748
<211> LENGTH: 22
<212> TYPE: RNA
<213> ORGANISM: Homo sapiens

<400> SEQUENCE: 748
uggcggagcc cauuccaugc ca 22

<210> SEQ ID NO 749
<211> LENGTH: 21
<212> TYPE: RNA
<213> ORGANISM: Homo sapiens

<400> SEQUENCE: 749
cuggcggagc ccauuccaug c 21

<210> SEQ ID NO 750
<211> LENGTH: 24
<212> TYPE: RNA
<213> ORGANISM: Homo sapiens

<400> SEQUENCE: 750
gcugcgggcu gcggucaggg cgau 24

<210> SEQ ID NO 751
<211> LENGTH: 20
<212> TYPE: RNA
<213> ORGANISM: Homo sapiens

<400> SEQUENCE: 751
gcugcgggcu gcggucaggg 20

<210> SEQ ID NO 752
<211> LENGTH: 24
<212> TYPE: RNA
<213> ORGANISM: Homo sapiens

<400> SEQUENCE: 752
cugcggggac aggccagggc aucu 24

<210> SEQ ID NO 753
<211> LENGTH: 20
<212> TYPE: RNA
<213> ORGANISM: Homo sapiens

```
<400> SEQUENCE: 753
cugcggggac aggccagggc                                              20

<210> SEQ ID NO 754
<211> LENGTH: 22
<212> TYPE: RNA
<213> ORGANISM: Homo sapiens

<400> SEQUENCE: 754
agccaggcuc ugaagggaaa gu                                           22

<210> SEQ ID NO 755
<211> LENGTH: 15
<212> TYPE: RNA
<213> ORGANISM: Homo sapiens

<400> SEQUENCE: 755
gaagggaaag uugaa                                                   15

<210> SEQ ID NO 756
<211> LENGTH: 15
<212> TYPE: RNA
<213> ORGANISM: Homo sapiens

<400> SEQUENCE: 756
gcccacugcc ccgcg                                                   15

<210> SEQ ID NO 757
<211> LENGTH: 24
<212> TYPE: RNA
<213> ORGANISM: Homo sapiens

<400> SEQUENCE: 757 caggggaug gcagagcaaa auuc                                          24

<210> SEQ ID NO 758
<211> LENGTH: 17
<212> TYPE: RNA
<213> ORGANISM: Homo sapiens

<400> SEQUENCE: 758 aggggaugg cagagca                                                  17

<210> SEQ ID NO 759
<211> LENGTH: 22
<212> TYPE: RNA
<213> ORGANISM: Homo sapiens

<400> SEQUENCE: 759
gggagugcag ggcagguuu cc                                            22

<210> SEQ ID NO 760
<211> LENGTH: 18
<212> TYPE: RNA
<213> ORGANISM: Homo sapiens

<400> SEQUENCE: 760
agggagugca gggcaggg                                                18

<210> SEQ ID NO 761
<211> LENGTH: 24
<212> TYPE: RNA
<213> ORGANISM: Homo sapiens
```

```
<400> SEQUENCE: 761
cccggggcag auugguguag ggug                                          24

<210> SEQ ID NO 762
<211> LENGTH: 17
<212> TYPE: RNA
<213> ORGANISM: Homo sapiens

<400> SEQUENCE: 762
cggggcagau uggugua                                                  17

<210> SEQ ID NO 763
<211> LENGTH: 17
<212> TYPE: RNA
<213> ORGANISM: Homo sapiens

<400> SEQUENCE: 763
gaucccagcg gugccuc                                                  17

<210> SEQ ID NO 764
<211> LENGTH: 15
<212> TYPE: RNA
<213> ORGANISM: Homo sapiens

<400> SEQUENCE: 764
gaucccagcg gugcc                                                    15

<210> SEQ ID NO 765
<211> LENGTH: 25
<212> TYPE: RNA
<213> ORGANISM: Homo sapiens

<400> SEQUENCE: 765
gggacgaggg uugggaaca ggugg                                          25

<210> SEQ ID NO 766
<211> LENGTH: 15
<212> TYPE: RNA
<213> ORGANISM: Homo sapiens

<400> SEQUENCE: 766
uggggaacag guggu                                                    15

<210> SEQ ID NO 767
<211> LENGTH: 23
<212> TYPE: RNA
<213> ORGANISM: Homo sapiens

<400> SEQUENCE: 767
gaaaucaagc gugggugaga ccu                                           23

<210> SEQ ID NO 768
<211> LENGTH: 20
<212> TYPE: RNA
<213> ORGANISM: Homo sapiens

<400> SEQUENCE: 768
gaaaucaagc gugggugaga                                               20

<210> SEQ ID NO 769
<211> LENGTH: 15
<212> TYPE: RNA
```

```
<213> ORGANISM: Homo sapiens

<400> SEQUENCE: 769
ggcgcgggga ggugc                                              15

<210> SEQ ID NO 770
<211> LENGTH: 18
<212> TYPE: RNA
<213> ORGANISM: Homo sapiens

<400> SEQUENCE: 770
aaaaggaagg gggaggag                                           18

<210> SEQ ID NO 771
<211> LENGTH: 16
<212> TYPE: RNA
<213> ORGANISM: Homo sapiens

<400> SEQUENCE: 771
aaggaagggg gaggag                                             16

<210> SEQ ID NO 772
<211> LENGTH: 23
<212> TYPE: RNA
<213> ORGANISM: Homo sapiens

<400> SEQUENCE: 772
acagcagggc uggggauugc agu                                     23

<210> SEQ ID NO 773
<211> LENGTH: 19
<212> TYPE: RNA
<213> ORGANISM: Homo sapiens

<400> SEQUENCE: 773
ugcugcuccc aguccugcc                                          19

<210> SEQ ID NO 774
<211> LENGTH: 21
<212> TYPE: RNA
<213> ORGANISM: Homo sapiens

<400> SEQUENCE: 774
cagcagggga gagagaggag u                                       21

<210> SEQ ID NO 775
<211> LENGTH: 20
<212> TYPE: RNA
<213> ORGANISM: Homo sapiens

<400> SEQUENCE: 775
cagcagggga gagagaggag                                         20

<210> SEQ ID NO 776
<211> LENGTH: 25
<212> TYPE: RNA
<213> ORGANISM: Homo sapiens

<400> SEQUENCE: 776
cugcaggcag aagugggcu gacag                                    25

<210> SEQ ID NO 777
<211> LENGTH: 19
```

```
<212> TYPE: RNA
<213> ORGANISM: Homo sapiens

<400> SEQUENCE: 777
caggcagaag uggggcuga                                              19

<210> SEQ ID NO 778
<211> LENGTH: 21
<212> TYPE: RNA
<213> ORGANISM: Homo sapiens

<400> SEQUENCE: 778
caacucugau cucuucaucu a                                           21

<210> SEQ ID NO 779
<211> LENGTH: 23
<212> TYPE: RNA
<213> ORGANISM: Homo sapiens

<400> SEQUENCE: 779
uggugggccg cagaacaugu gcu                                         23

<210> SEQ ID NO 780
<211> LENGTH: 21
<212> TYPE: RNA
<213> ORGANISM: Homo sapiens

<400> SEQUENCE: 780
uggugggccg cagaacaugu g                                           21

<210> SEQ ID NO 781
<211> LENGTH: 22
<212> TYPE: RNA
<213> ORGANISM: Homo sapiens

<400> SEQUENCE: 781
gcacgacuca gggcggaggg aa                                          22

<210> SEQ ID NO 782
<211> LENGTH: 15
<212> TYPE: RNA
<213> ORGANISM: Homo sapiens

<400> SEQUENCE: 782
agggcggagg gaagu                                                  15

<210> SEQ ID NO 783
<211> LENGTH: 25
<212> TYPE: RNA
<213> ORGANISM: Homo sapiens

<400> SEQUENCE: 783
uucugggccc gcggcgggcg uggg                                        25

<210> SEQ ID NO 784
<211> LENGTH: 15
<212> TYPE: RNA
<213> ORGANISM: Homo sapiens

<400> SEQUENCE: 784
cgcggcgggc guggg                                                  15

<210> SEQ ID NO 785
```

```
<211> LENGTH: 22
<212> TYPE: RNA
<213> ORGANISM: Homo sapiens

<400> SEQUENCE: 785 uccccggcc ugcucauccc cc                                              22

<210> SEQ ID NO 786
<211> LENGTH: 15
<212> TYPE: RNA
<213> ORGANISM: Homo sapiens

<400> SEQUENCE: 786
accucuccug gcauc                                                     15

<210> SEQ ID NO 787
<211> LENGTH: 24
<212> TYPE: RNA
<213> ORGANISM: Homo sapiens

<400> SEQUENCE: 787
gcggccccac gcaccagggu aaga                                           24

<210> SEQ ID NO 788
<211> LENGTH: 19
<212> TYPE: RNA
<213> ORGANISM: Homo sapiens

<400> SEQUENCE: 788
cggccccacg caccagggu                                                 19

<210> SEQ ID NO 789
<211> LENGTH: 24
<212> TYPE: RNA
<213> ORGANISM: Homo sapiens

<400> SEQUENCE: 789
gaggcuggga aggcaaaggg acgu                                           24

<210> SEQ ID NO 790
<211> LENGTH: 15
<212> TYPE: RNA
<213> ORGANISM: Homo sapiens

<400> SEQUENCE: 790
gaaggaggcu gggaa                                                     15

<210> SEQ ID NO 791
<211> LENGTH: 16
<212> TYPE: RNA
<213> ORGANISM: Homo sapiens

<400> SEQUENCE: 791 gaagggagu ugggag                                                     16

<210> SEQ ID NO 792
<211> LENGTH: 18
<212> TYPE: RNA
<213> ORGANISM: Homo sapiens

<400> SEQUENCE: 792
ggcagcggcg gcggcggc                                                  18
```

```
<210> SEQ ID NO 793
<211> LENGTH: 15
<212> TYPE: RNA
<213> ORGANISM: Homo sapiens

<400> SEQUENCE: 793
gcuccccgcg ccccc                                                    15

<210> SEQ ID NO 794
<211> LENGTH: 19
<212> TYPE: RNA
<213> ORGANISM: Homo sapiens

<400> SEQUENCE: 794
cgucccaccc cccacuccu                                                19

<210> SEQ ID NO 795
<211> LENGTH: 25
<212> TYPE: RNA
<213> ORGANISM: Homo sapiens

<400> SEQUENCE: 795
caggaaggau uuagggacag gcuuu                                         25

<210> SEQ ID NO 796
<211> LENGTH: 19
<212> TYPE: RNA
<213> ORGANISM: Homo sapiens

<400> SEQUENCE: 796
caggaaggau uuagggaca                                                19

<210> SEQ ID NO 797
<211> LENGTH: 18
<212> TYPE: RNA
<213> ORGANISM: Homo sapiens

<400> SEQUENCE: 797
cagcggggcu gggcgcgc                                                 18

<210> SEQ ID NO 798
<211> LENGTH: 15
<212> TYPE: RNA
<213> ORGANISM: Homo sapiens

<400> SEQUENCE: 798
cagcggggcu gggcg                                                    15

<210> SEQ ID NO 799
<211> LENGTH: 20
<212> TYPE: RNA
<213> ORGANISM: Homo sapiens

<400> SEQUENCE: 799
uggcuguugg aggggggcagg                                              20

<210> SEQ ID NO 800
<211> LENGTH: 15
<212> TYPE: RNA
<213> ORGANISM: Homo sapiens

<400> SEQUENCE: 800 ggaggggggca ggcuc                                                   15
```

```
<210> SEQ ID NO 801
<211> LENGTH: 21
<212> TYPE: RNA
<213> ORGANISM: Homo sapiens

<400> SEQUENCE: 801
cagcccuccu cccgcaccca a                                              21

<210> SEQ ID NO 802
<211> LENGTH: 15
<212> TYPE: RNA
<213> ORGANISM: Homo sapiens

<400> SEQUENCE: 802
cagggagcag gaagc                                                     15

<210> SEQ ID NO 803
<211> LENGTH: 22
<212> TYPE: RNA
<213> ORGANISM: Homo sapiens

<400> SEQUENCE: 803
uaauuuuaga ucuggucugc uu                                             22

<210> SEQ ID NO 804
<211> LENGTH: 19
<212> TYPE: RNA
<213> ORGANISM: Homo sapiens

<400> SEQUENCE: 804
aauuuuagau cuggucugc                                                 19

<210> SEQ ID NO 805
<211> LENGTH: 24
<212> TYPE: RNA
<213> ORGANISM: Homo sapiens

<400> SEQUENCE: 805
agacacauuu ggagagggaa ccuc                                           24

<210> SEQ ID NO 806
<211> LENGTH: 16
<212> TYPE: RNA
<213> ORGANISM: Homo sapiens

<400> SEQUENCE: 806
agacacauuu ggagag                                                    16

<210> SEQ ID NO 807
<211> LENGTH: 21
<212> TYPE: RNA
<213> ORGANISM: Homo sapiens

<400> SEQUENCE: 807
aggcagcggg guguagugga u                                              21

<210> SEQ ID NO 808
<211> LENGTH: 24
<212> TYPE: RNA
<213> ORGANISM: Homo sapiens

<400> SEQUENCE: 808
aauauugcac ucgucccggc cucc                                           24
```

-continued

<210> SEQ ID NO 809
<211> LENGTH: 15
<212> TYPE: RNA
<213> ORGANISM: Homo sapiens

<400> SEQUENCE: 809
uauugcacuc guccc                                                    15

<210> SEQ ID NO 810
<211> LENGTH: 23
<212> TYPE: RNA
<213> ORGANISM: Homo sapiens

<400> SEQUENCE: 810
cuccuggggc ccgcacucuc gcu                                           23

<210> SEQ ID NO 811
<211> LENGTH: 18
<212> TYPE: RNA
<213> ORGANISM: Homo sapiens

<400> SEQUENCE: 811
cuccuggggc ccgcacuc                                                 18

<210> SEQ ID NO 812
<211> LENGTH: 23
<212> TYPE: RNA
<213> ORGANISM: Homo sapiens

<400> SEQUENCE: 812
ggcuacaaca caggacccgg gcg                                           23

<210> SEQ ID NO 813
<211> LENGTH: 21
<212> TYPE: RNA
<213> ORGANISM: Homo sapiens

<400> SEQUENCE: 813
ggcuacaaca caggacccgg g                                             21

<210> SEQ ID NO 814
<211> LENGTH: 21
<212> TYPE: RNA
<213> ORGANISM: Homo sapiens

<400> SEQUENCE: 814
gagggcagcg ugggugoggc g                                             21

<210> SEQ ID NO 815
<211> LENGTH: 29
<212> TYPE: RNA
<213> ORGANISM: Homo sapiens

<400> SEQUENCE: 815
agcagcauug uacagggcua ugaaggcau                                     29

<210> SEQ ID NO 816
<211> LENGTH: 15
<212> TYPE: RNA
<213> ORGANISM: Homo sapiens

<400> SEQUENCE: 816

```
agcagcauug uacag                                                        15

<210> SEQ ID NO 817
<211> LENGTH: 28
<212> TYPE: RNA
<213> ORGANISM: Homo sapiens

<400> SEQUENCE: 817
agcagcauug uacagggcua ucaaagca                                          28

<210> SEQ ID NO 818
<211> LENGTH: 15
<212> TYPE: RNA
<213> ORGANISM: Homo sapiens

<400> SEQUENCE: 818
agcagcauug uacag                                                        15

<210> SEQ ID NO 819
<211> LENGTH: 22
<212> TYPE: RNA
<213> ORGANISM: Homo sapiens

<400> SEQUENCE: 819
gugggcgggg gcaggugugu gg                                                22

<210> SEQ ID NO 820
<211> LENGTH: 15
<212> TYPE: RNA
<213> ORGANISM: Homo sapiens

<400> SEQUENCE: 820
cgggggcagg ugugu                                                        15

<210> SEQ ID NO 821
<211> LENGTH: 19
<212> TYPE: RNA
<213> ORGANISM: Homo sapiens

<400> SEQUENCE: 821
agugggaggc cagggcacg                                                    19

<210> SEQ ID NO 822
<211> LENGTH: 15
<212> TYPE: RNA
<213> ORGANISM: Homo sapiens

<400> SEQUENCE: 822 aggggggagcu gcagg                                                       15

<210> SEQ ID NO 823
<211> LENGTH: 15
<212> TYPE: RNA
<213> ORGANISM: Homo sapiens

<400> SEQUENCE: 823
uggcagagcg cuguc                                                        15

<210> SEQ ID NO 824
<211> LENGTH: 22
<212> TYPE: RNA
<213> ORGANISM: Homo sapiens

<400> SEQUENCE: 824
```

-continued ccgggaacgu cgagacugga gc                                           22

<210> SEQ ID NO 825
<211> LENGTH: 15
<212> TYPE: RNA
<213> ORGANISM: Homo sapiens

<400> SEQUENCE: 825
cgggaacguc gagac                                                   15

<210> SEQ ID NO 826
<211> LENGTH: 24
<212> TYPE: RNA
<213> ORGANISM: Homo sapiens

<400> SEQUENCE: 826
acgcccuucc ccccuucuu cacc                                          24

<210> SEQ ID NO 827
<211> LENGTH: 17
<212> TYPE: RNA
<213> ORGANISM: Homo sapiens

<400> SEQUENCE: 827
acgcccuucc ccccuu                                                  17

<210> SEQ ID NO 828
<211> LENGTH: 27
<212> TYPE: RNA
<213> ORGANISM: Homo sapiens

<400> SEQUENCE: 828
agccuggaag cuggagccug cagugaa                                      27

<210> SEQ ID NO 829
<211> LENGTH: 15
<212> TYPE: RNA
<213> ORGANISM: Homo sapiens

<400> SEQUENCE: 829
ggugggagga uugcu                                                   15

<210> SEQ ID NO 830
<211> LENGTH: 20
<212> TYPE: RNA
<213> ORGANISM: Homo sapiens

<400> SEQUENCE: 830
aucccaccac ugccaccauu                                              20

<210> SEQ ID NO 831
<211> LENGTH: 15
<212> TYPE: RNA
<213> ORGANISM: Homo sapiens

<400> SEQUENCE: 831
aucccaccac ugcca                                                   15

<210> SEQ ID NO 832
<211> LENGTH: 21
<212> TYPE: RNA
<213> ORGANISM: Homo sapiens -continued

```
<400> SEQUENCE: 832
gccgggcgug guggugggg c                                             21

<210> SEQ ID NO 833
<211> LENGTH: 15
<212> TYPE: RNA
<213> ORGANISM: Homo sapiens

<400> SEQUENCE: 833
uagccgggcg uggug                                                   15

<210> SEQ ID NO 834
<211> LENGTH: 24
<212> TYPE: RNA
<213> ORGANISM: Homo sapiens

<400> SEQUENCE: 834
cgggcguggu gguggggug ggug                                          24

<210> SEQ ID NO 835
<211> LENGTH: 15
<212> TYPE: RNA
<213> ORGANISM: Homo sapiens

<400> SEQUENCE: 835
cgggcguggu ggugg                                                   15

<210> SEQ ID NO 836
<211> LENGTH: 21
<212> TYPE: RNA
<213> ORGANISM: Homo sapiens

<400> SEQUENCE: 836
cagccugagu gacagagcaa g                                            21

<210> SEQ ID NO 837
<211> LENGTH: 15
<212> TYPE: RNA
<213> ORGANISM: Homo sapiens

<400> SEQUENCE: 837
acugcacucc agccu                                                   15

<210> SEQ ID NO 838
<211> LENGTH: 20
<212> TYPE: RNA
<213> ORGANISM: Homo sapiens

<400> SEQUENCE: 838
cggggccgua gcacugucug                                              20

<210> SEQ ID NO 839
<211> LENGTH: 20
<212> TYPE: RNA
<213> ORGANISM: Homo sapiens

<400> SEQUENCE: 839
gggggccgau acacuguacg                                              20

<210> SEQ ID NO 840
<211> LENGTH: 20
<212> TYPE: RNA
<213> ORGANISM: Homo sapiens
```

```
<400> SEQUENCE: 840
ggauuuuugg aucagggaug                                              20

<210> SEQ ID NO 841
<211> LENGTH: 15
<212> TYPE: RNA
<213> ORGANISM: Homo sapiens

<400> SEQUENCE: 841 auuuuggau caggg                                                    15

<210> SEQ ID NO 842
<211> LENGTH: 24
<212> TYPE: RNA
<213> ORGANISM: Homo sapiens

<400> SEQUENCE: 842
cugguacagg ccuggggac aggg                                          24

<210> SEQ ID NO 843
<211> LENGTH: 18
<212> TYPE: RNA
<213> ORGANISM: Homo sapiens

<400> SEQUENCE: 843
cugguacagg ccugggg                                                 18

<210> SEQ ID NO 844
<211> LENGTH: 25
<212> TYPE: RNA
<213> ORGANISM: Homo sapiens

<400> SEQUENCE: 844
acugcaguga aggcacuugu agcau                                        25

<210> SEQ ID NO 845
<211> LENGTH: 15
<212> TYPE: RNA
<213> ORGANISM: Homo sapiens

<400> SEQUENCE: 845
acugcaguga aggca                                                   15

<210> SEQ ID NO 846
<211> LENGTH: 22
<212> TYPE: RNA
<213> ORGANISM: Homo sapiens

<400> SEQUENCE: 846
cgcggcgggg acggcgauug gu                                           22

<210> SEQ ID NO 847
<211> LENGTH: 17
<212> TYPE: RNA
<213> ORGANISM: Homo sapiens

<400> SEQUENCE: 847
cggcggggac ggcgauu                                                 17

<210> SEQ ID NO 848
<211> LENGTH: 23
<212> TYPE: RNA
```

```
<213> ORGANISM: Homo sapiens

<400> SEQUENCE: 848
ugcgcagggg ccggugcuc acc                                            23

<210> SEQ ID NO 849
<211> LENGTH: 19
<212> TYPE: RNA
<213> ORGANISM: Homo sapiens

<400> SEQUENCE: 849
cgcaggggcc gggugcuca                                                19

<210> SEQ ID NO 850
<211> LENGTH: 23
<212> TYPE: RNA
<213> ORGANISM: Homo sapiens

<400> SEQUENCE: 850 aggaggggguc ccgcacuggg agg                                          23

<210> SEQ ID NO 851
<211> LENGTH: 15
<212> TYPE: RNA
<213> ORGANISM: Homo sapiens

<400> SEQUENCE: 851
ugggaggggc ccuca                                                    15

<210> SEQ ID NO 852
<211> LENGTH: 15
<212> TYPE: RNA
<213> ORGANISM: Homo sapiens

<400> SEQUENCE: 852
cgcggcgggg gcggc                                                    15

<210> SEQ ID NO 853
<211> LENGTH: 29
<212> TYPE: RNA
<213> ORGANISM: Homo sapiens

<400> SEQUENCE: 853
caacggaauc ccaaaagcag cuguugucu                                     29

<210> SEQ ID NO 854
<211> LENGTH: 15
<212> TYPE: RNA
<213> ORGANISM: Homo sapiens

<400> SEQUENCE: 854
caacggaauc ccaaa                                                    15

<210> SEQ ID NO 855
<211> LENGTH: 25
<212> TYPE: RNA
<213> ORGANISM: Homo sapiens

<400> SEQUENCE: 855
aagcugccag uugaagaacu guugc                                         25

<210> SEQ ID NO 856
<211> LENGTH: 15
```

```
<212> TYPE: RNA
<213> ORGANISM: Homo sapiens

<400> SEQUENCE: 856
aagcugccag uugaa                                              15

<210> SEQ ID NO 857
<211> LENGTH: 26
<212> TYPE: RNA
<213> ORGANISM: Homo sapiens

<400> SEQUENCE: 857
aaaaucacau ugccagggau uaccac                                  26

<210> SEQ ID NO 858
<211> LENGTH: 15
<212> TYPE: RNA
<213> ORGANISM: Homo sapiens

<400> SEQUENCE: 858
aaucacauug ccagg                                              15

<210> SEQ ID NO 859
<211> LENGTH: 24
<212> TYPE: RNA
<213> ORGANISM: Homo sapiens

<400> SEQUENCE: 859
acuggcucag uucagcagga acag                                    24

<210> SEQ ID NO 860
<211> LENGTH: 15
<212> TYPE: RNA
<213> ORGANISM: Homo sapiens

<400> SEQUENCE: 860
uggcucaguu cagca                                              15

<210> SEQ ID NO 861
<211> LENGTH: 15
<212> TYPE: RNA
<213> ORGANISM: Homo sapiens

<400> SEQUENCE: 861
gaggguuggg uggag                                              15

<210> SEQ ID NO 862
<211> LENGTH: 23
<212> TYPE: RNA
<213> ORGANISM: Homo sapiens

<400> SEQUENCE: 862
gagggccccc ccucaauccu guu                                     23

<210> SEQ ID NO 863
<211> LENGTH: 16
<212> TYPE: RNA
<213> ORGANISM: Homo sapiens

<400> SEQUENCE: 863 agggccccccc cucaau                                            16

<210> SEQ ID NO 864
```

```
<211> LENGTH: 24
<212> TYPE: RNA
<213> ORGANISM: Homo sapiens

<400> SEQUENCE: 864
ucgaggacug guggaagggc cuuu                                              24

<210> SEQ ID NO 865
<211> LENGTH: 16
<212> TYPE: RNA
<213> ORGANISM: Homo sapiens

<400> SEQUENCE: 865
ucgaggacug guggaa                                                       16

<210> SEQ ID NO 866
<211> LENGTH: 23
<212> TYPE: RNA
<213> ORGANISM: Homo sapiens

<400> SEQUENCE: 866
agggaguaga agguggggga gca                                               23

<210> SEQ ID NO 867
<211> LENGTH: 16
<212> TYPE: RNA
<213> ORGANISM: Homo sapiens

<400> SEQUENCE: 867
uagggaguag aagggu                                                       16

<210> SEQ ID NO 868
<211> LENGTH: 26
<212> TYPE: RNA
<213> ORGANISM: Homo sapiens

<400> SEQUENCE: 868
ccuucuggag aggcuuugug cggaua                                            26

<210> SEQ ID NO 869
<211> LENGTH: 15
<212> TYPE: RNA
<213> ORGANISM: Homo sapiens

<400> SEQUENCE: 869
ccuucuggag aggcu                                                        15

<210> SEQ ID NO 870
<211> LENGTH: 17
<212> TYPE: RNA
<213> ORGANISM: Homo sapiens

<400> SEQUENCE: 870
gcggggcggc aggggcc                                                      17

<210> SEQ ID NO 871
<211> LENGTH: 15
<212> TYPE: RNA
<213> ORGANISM: Homo sapiens

<400> SEQUENCE: 871
gggggcgggg cggca                                                        15
```

```
<210> SEQ ID NO 872
<211> LENGTH: 15
<212> TYPE: RNA
<213> ORGANISM: Homo sapiens

<400> SEQUENCE: 872
gcaggcucgg aaagg                                                      15

<210> SEQ ID NO 873
<211> LENGTH: 27
<212> TYPE: RNA
<213> ORGANISM: Homo sapiens

<400> SEQUENCE: 873
gaaaagcugg guugagaggg cgaaaaa                                         27

<210> SEQ ID NO 874
<211> LENGTH: 15
<212> TYPE: RNA
<213> ORGANISM: Homo sapiens

<400> SEQUENCE: 874
cuucucuucc cgguu                                                      15

<210> SEQ ID NO 875
<211> LENGTH: 28
<212> TYPE: RNA
<213> ORGANISM: Homo sapiens

<400> SEQUENCE: 875
aggggugcua ucugugauug agggacau                                        28

<210> SEQ ID NO 876
<211> LENGTH: 15
<212> TYPE: RNA
<213> ORGANISM: Homo sapiens

<400> SEQUENCE: 876
gcuaucugug auuga                                                      15

<210> SEQ ID NO 877
<211> LENGTH: 29
<212> TYPE: RNA
<213> ORGANISM: Homo sapiens

<400> SEQUENCE: 877
gggagccgcg gggaucgccg agggccggu                                       29

<210> SEQ ID NO 878
<211> LENGTH: 15
<212> TYPE: RNA
<213> ORGANISM: Homo sapiens

<400> SEQUENCE: 878
ggcggcggug guggg                                                      15

<210> SEQ ID NO 879
<211> LENGTH: 19
<212> TYPE: RNA
<213> ORGANISM: Homo sapiens

<400> SEQUENCE: 879
uggcgggugc ggggguggg                                                  19
```

<210> SEQ ID NO 880
<211> LENGTH: 15
<212> TYPE: RNA
<213> ORGANISM: Homo sapiens

<400> SEQUENCE: 880
uggcgggugc ggggg                                                    15

<210> SEQ ID NO 881
<211> LENGTH: 27
<212> TYPE: RNA
<213> ORGANISM: Homo sapiens

<400> SEQUENCE: 881
ugagggacuu uuggggcag auguguu                                        27

<210> SEQ ID NO 882
<211> LENGTH: 17
<212> TYPE: RNA
<213> ORGANISM: Homo sapiens

<400> SEQUENCE: 882
ggacuuuugg gggcaga                                                  17

<210> SEQ ID NO 883
<211> LENGTH: 18
<212> TYPE: RNA
<213> ORGANISM: Homo sapiens

<400> SEQUENCE: 883
gcggcggcgg cggcagca                                                 18

<210> SEQ ID NO 884
<211> LENGTH: 15
<212> TYPE: RNA
<213> ORGANISM: Homo sapiens

<400> SEQUENCE: 884
gcgggcggcg gcggc                                                    15

<210> SEQ ID NO 885
<211> LENGTH: 19
<212> TYPE: RNA
<213> ORGANISM: Homo sapiens

<400> SEQUENCE: 885
ugaggauaug gcagggaag                                                19

<210> SEQ ID NO 886
<211> LENGTH: 22
<212> TYPE: RNA
<213> ORGANISM: Homo sapiens

<400> SEQUENCE: 886
acucaaacug uggggcacu uu                                             22

<210> SEQ ID NO 887
<211> LENGTH: 19
<212> TYPE: RNA
<213> ORGANISM: Homo sapiens

<400> SEQUENCE: 887
acucaaacug uggggcac                                                 19

-continued

<210> SEQ ID NO 888
<211> LENGTH: 19
<212> TYPE: RNA
<213> ORGANISM: Homo sapiens

<400> SEQUENCE: 888
guggguuggg gcgggcucu                                                    19

<210> SEQ ID NO 889
<211> LENGTH: 30
<212> TYPE: RNA
<213> ORGANISM: Homo sapiens

<400> SEQUENCE: 889
ugaggggcag agagcgagac uuuucuauuu                                         30

<210> SEQ ID NO 890
<211> LENGTH: 15
<212> TYPE: RNA
<213> ORGANISM: Homo sapiens

<400> SEQUENCE: 890
ugaggggcag agagc                                                         15

<210> SEQ ID NO 891
<211> LENGTH: 16
<212> TYPE: RNA
<213> ORGANISM: Homo sapiens

<400> SEQUENCE: 891 uggggggaa gaaaag                                                         16

<210> SEQ ID NO 892
<211> LENGTH: 22
<212> TYPE: RNA
<213> ORGANISM: Homo sapiens

<400> SEQUENCE: 892
accccacucc ugguaccaua gu                                                 22

<210> SEQ ID NO 893
<211> LENGTH: 15
<212> TYPE: RNA
<213> ORGANISM: Homo sapiens

<400> SEQUENCE: 893
accccacucc uggua                                                         15

<210> SEQ ID NO 894
<211> LENGTH: 15
<212> TYPE: RNA
<213> ORGANISM: Homo sapiens

<400> SEQUENCE: 894
aggaggagga ggcag                                                         15

<210> SEQ ID NO 895
<211> LENGTH: 15
<212> TYPE: RNA
<213> ORGANISM: Homo sapiens

<400> SEQUENCE: 895

```
ggugggcuuc ccgga                                             15

<210> SEQ ID NO 896
<211> LENGTH: 20
<212> TYPE: RNA
<213> ORGANISM: Homo sapiens

<400> SEQUENCE: 896
cuccccggug ugcaaaugug                                        20

<210> SEQ ID NO 897
<211> LENGTH: 15
<212> TYPE: RNA
<213> ORGANISM: Homo sapiens

<400> SEQUENCE: 897
gugugcggug uuaug                                             15

<210> SEQ ID NO 898
<211> LENGTH: 23
<212> TYPE: RNA
<213> ORGANISM: Homo sapiens

<400> SEQUENCE: 898
ccagggcugg cagugacaug ggu                                    23

<210> SEQ ID NO 899
<211> LENGTH: 19
<212> TYPE: RNA
<213> ORGANISM: Homo sapiens

<400> SEQUENCE: 899
cagggcuggc agugacaug                                         19

<210> SEQ ID NO 900
<211> LENGTH: 15
<212> TYPE: RNA
<213> ORGANISM: Homo sapiens

<400> SEQUENCE: 900
cuuggucuag gggua                                             15

<210> SEQ ID NO 901
<211> LENGTH: 21
<212> TYPE: RNA
<213> ORGANISM: Homo sapiens

<400> SEQUENCE: 901
cggauccgag ucacggcacc a                                      21

<210> SEQ ID NO 902
<211> LENGTH: 15
<212> TYPE: RNA
<213> ORGANISM: Homo sapiens

<400> SEQUENCE: 902
ggauccgagu cacgg                                             15

<210> SEQ ID NO 903
<211> LENGTH: 25
<212> TYPE: RNA
<213> ORGANISM: Homo sapiens

<400> SEQUENCE: 903
```

-continued uggcggcggu aguuaugggc uucuc                                    25

<210> SEQ ID NO 904
<211> LENGTH: 29
<212> TYPE: RNA
<213> ORGANISM: Homo sapiens

<400> SEQUENCE: 904
gcuggguuaa gccgagcugg guugggcug                                29

<210> SEQ ID NO 905
<211> LENGTH: 19
<212> TYPE: RNA
<213> ORGANISM: Homo sapiens

<400> SEQUENCE: 905
cugguugggg cugggcugg                                           19

<210> SEQ ID NO 906
<211> LENGTH: 23
<212> TYPE: RNA
<213> ORGANISM: Homo sapiens

<400> SEQUENCE: 906
agggucgggg cagggagggc agg                                      23

<210> SEQ ID NO 907
<211> LENGTH: 15
<212> TYPE: RNA
<213> ORGANISM: Homo sapiens

<400> SEQUENCE: 907
gggagaaggg ucggg                                               15

<210> SEQ ID NO 908
<211> LENGTH: 27
<212> TYPE: RNA
<213> ORGANISM: Homo sapiens

<400> SEQUENCE: 908
aaaccguuac cauuacugag uuuagua                                  27

<210> SEQ ID NO 909
<211> LENGTH: 15
<212> TYPE: RNA
<213> ORGANISM: Homo sapiens

<400> SEQUENCE: 909
gaaaccguua ccauu                                               15

<210> SEQ ID NO 910
<211> LENGTH: 15
<212> TYPE: RNA
<213> ORGANISM: Homo sapiens

<400> SEQUENCE: 910
ucugggcgag gggug                                               15

<210> SEQ ID NO 911
<211> LENGTH: 23
<212> TYPE: RNA
<213> ORGANISM: Homo sapiens

```
<400> SEQUENCE: 911
gguggguhag gucgggcccc aag                                           23

<210> SEQ ID NO 912
<211> LENGTH: 22
<212> TYPE: RNA
<213> ORGANISM: Homo sapiens

<400> SEQUENCE: 912
cugggcucgg gacgcgcggc uc                                            22

<210> SEQ ID NO 913
<211> LENGTH: 19
<212> TYPE: RNA
<213> ORGANISM: Homo sapiens

<400> SEQUENCE: 913
cugggcucgg gacgcgcgg                                                19

<210> SEQ ID NO 914
<211> LENGTH: 21
<212> TYPE: RNA
<213> ORGANISM: Homo sapiens

<400> SEQUENCE: 914
uugaggagac augguggggg c                                             21

<210> SEQ ID NO 915
<211> LENGTH: 15
<212> TYPE: RNA
<213> ORGANISM: Homo sapiens

<400> SEQUENCE: 915
uugaggagac auggu                                                    15

<210> SEQ ID NO 916
<211> LENGTH: 21
<212> TYPE: RNA
<213> ORGANISM: Homo sapiens

<400> SEQUENCE: 916
aggaggcagu gggcgagcag g                                             21

<210> SEQ ID NO 917
<211> LENGTH: 23
<212> TYPE: RNA
<213> ORGANISM: Homo sapiens

<400> SEQUENCE: 917 ugggaaggc gucagugucg ggu                                            23

<210> SEQ ID NO 918
<211> LENGTH: 16
<212> TYPE: RNA
<213> ORGANISM: Homo sapiens

<400> SEQUENCE: 918 ugggaaggc gucagu                                                    16

<210> SEQ ID NO 919
<211> LENGTH: 23
<212> TYPE: RNA
<213> ORGANISM: Homo sapiens
```

-continued

<400> SEQUENCE: 919
aagggaggag gagcggaggg gcc                                            23

<210> SEQ ID NO 920
<211> LENGTH: 15
<212> TYPE: RNA
<213> ORGANISM: Homo sapiens

<400> SEQUENCE: 920
gggaggagga gcgga                                                     15

<210> SEQ ID NO 921
<211> LENGTH: 20
<212> TYPE: RNA
<213> ORGANISM: Homo sapiens

<400> SEQUENCE: 921
ugaguggggc ucccgggacg                                                20

<210> SEQ ID NO 922
<211> LENGTH: 15
<212> TYPE: RNA
<213> ORGANISM: Homo sapiens

<400> SEQUENCE: 922 gggcggggggg cggcg                                                    15

<210> SEQ ID NO 923
<211> LENGTH: 17
<212> TYPE: RNA
<213> ORGANISM: Homo sapiens

<400> SEQUENCE: 923
ggugagcgcu cgcuggc                                                   17

<210> SEQ ID NO 924
<211> LENGTH: 15
<212> TYPE: RNA
<213> ORGANISM: Homo sapiens

<400> SEQUENCE: 924
cggugagcgc ucgcu                                                     15

<210> SEQ ID NO 925
<211> LENGTH: 23
<212> TYPE: RNA
<213> ORGANISM: Homo sapiens

<400> SEQUENCE: 925
cggggcagcu caguacagga uac                                            23

<210> SEQ ID NO 926
<211> LENGTH: 15
<212> TYPE: RNA
<213> ORGANISM: Homo sapiens

<400> SEQUENCE: 926
agcucaguac aggau                                                     15

<210> SEQ ID NO 927
<211> LENGTH: 26
<212> TYPE: RNA

```
<213> ORGANISM: Homo sapiens

<400> SEQUENCE: 927
agggcuggac ucagcggcgg agcugg                                      26

<210> SEQ ID NO 928
<211> LENGTH: 17
<212> TYPE: RNA
<213> ORGANISM: Homo sapiens

<400> SEQUENCE: 928
gcggcggagc uggcugc                                                17

<210> SEQ ID NO 929
<211> LENGTH: 15
<212> TYPE: RNA
<213> ORGANISM: Homo sapiens

<400> SEQUENCE: 929
gagggaguaa gagcc                                                  15

<210> SEQ ID NO 930
<211> LENGTH: 24
<212> TYPE: RNA
<213> ORGANISM: Homo sapiens

<400> SEQUENCE: 930 uggggagug cagugauugu ggaa                                         24

<210> SEQ ID NO 931
<211> LENGTH: 19
<212> TYPE: RNA
<213> ORGANISM: Homo sapiens

<400> SEQUENCE: 931 uggggagug cagugauug                                               19

<210> SEQ ID NO 932
<211> LENGTH: 15
<212> TYPE: RNA
<213> ORGANISM: Homo sapiens

<400> SEQUENCE: 932
ugaagcgggg gggcg                                                  15

<210> SEQ ID NO 933
<211> LENGTH: 16
<212> TYPE: RNA
<213> ORGANISM: Homo sapiens

<400> SEQUENCE: 933
cgggcccggc guuccc                                                 16

<210> SEQ ID NO 934
<211> LENGTH: 15
<212> TYPE: RNA
<213> ORGANISM: Homo sapiens

<400> SEQUENCE: 934
ccgggcccgg cguuc                                                  15

<210> SEQ ID NO 935
<211> LENGTH: 23
```

```
<212> TYPE: RNA
<213> ORGANISM: Homo sapiens

<400> SEQUENCE: 935
cuaguggaag aagauggcgg aag                                              23

<210> SEQ ID NO 936
<211> LENGTH: 15
<212> TYPE: RNA
<213> ORGANISM: Homo sapiens

<400> SEQUENCE: 936
uaguggaaga agaug                                                       15

<210> SEQ ID NO 937
<211> LENGTH: 16
<212> TYPE: RNA
<213> ORGANISM: Homo sapiens

<400> SEQUENCE: 937
gugaaggccc ggcgga                                                      16

<210> SEQ ID NO 938
<211> LENGTH: 15
<212> TYPE: RNA
<213> ORGANISM: Homo sapiens

<400> SEQUENCE: 938
gugaaggccc ggcgg                                                       15

<210> SEQ ID NO 939
<211> LENGTH: 17
<212> TYPE: RNA
<213> ORGANISM: Homo sapiens

<400> SEQUENCE: 939
ugcaggggca ggccagc                                                     17

<210> SEQ ID NO 940
<211> LENGTH: 23
<212> TYPE: RNA
<213> ORGANISM: Homo sapiens

<400> SEQUENCE: 940
gggggucccc ggugcucgga ucu                                              23

<210> SEQ ID NO 941
<211> LENGTH: 16
<212> TYPE: RNA
<213> ORGANISM: Homo sapiens

<400> SEQUENCE: 941
ucgggagggg cgggag                                                      16

<210> SEQ ID NO 942
<211> LENGTH: 24
<212> TYPE: RNA
<213> ORGANISM: Homo sapiens

<400> SEQUENCE: 942
cccaaaaugc ugggauuaca ggca                                             24

<210> SEQ ID NO 943
```

```
<211> LENGTH: 15
<212> TYPE: RNA
<213> ORGANISM: Homo sapiens

<400> SEQUENCE: 943
gcccaccuca gccuc                                                    15

<210> SEQ ID NO 944
<211> LENGTH: 16
<212> TYPE: RNA
<213> ORGANISM: Homo sapiens

<400> SEQUENCE: 944
ggcgcggagg gcggac                                                   16

<210> SEQ ID NO 945
<211> LENGTH: 15
<212> TYPE: RNA
<213> ORGANISM: Homo sapiens

<400> SEQUENCE: 945
ggcgcggagg gcgga                                                    15

<210> SEQ ID NO 946
<211> LENGTH: 20
<212> TYPE: RNA
<213> ORGANISM: Homo sapiens

<400> SEQUENCE: 946
aagacacauu uggagaggga                                               20

<210> SEQ ID NO 947
<211> LENGTH: 16
<212> TYPE: RNA
<213> ORGANISM: Homo sapiens

<400> SEQUENCE: 947
agacacauuu ggagag                                                   16

<210> SEQ ID NO 948
<211> LENGTH: 27
<212> TYPE: RNA
<213> ORGANISM: Homo sapiens

<400> SEQUENCE: 948
gcuggggucu caggaggcag cgcucuc                                       27

<210> SEQ ID NO 949
<211> LENGTH: 17
<212> TYPE: RNA
<213> ORGANISM: Homo sapiens

<400> SEQUENCE: 949
gcuggggucu caggagg                                                  17

<210> SEQ ID NO 950
<211> LENGTH: 26
<212> TYPE: RNA
<213> ORGANISM: Homo sapiens

<400> SEQUENCE: 950
cgguggyauc ccgcggccgu guuuuc                                        26
```

```
<210> SEQ ID NO 951
<211> LENGTH: 15
<212> TYPE: RNA
<213> ORGANISM: Homo sapiens

<400> SEQUENCE: 951
ggggcgccgc gggac                                                   15

<210> SEQ ID NO 952
<211> LENGTH: 23
<212> TYPE: RNA
<213> ORGANISM: Homo sapiens

<400> SEQUENCE: 952
ggcccggccg ugccugaggu uuc                                          23

<210> SEQ ID NO 953
<211> LENGTH: 15
<212> TYPE: RNA
<213> ORGANISM: Homo sapiens

<400> SEQUENCE: 953
ggcgguggga ucccg                                                   15

<210> SEQ ID NO 954
<211> LENGTH: 21
<212> TYPE: RNA
<213> ORGANISM: Homo sapiens

<400> SEQUENCE: 954
gaggcgaugu ggggauguag a                                            21

<210> SEQ ID NO 955
<211> LENGTH: 20
<212> TYPE: RNA
<213> ORGANISM: Homo sapiens

<400> SEQUENCE: 955
cccagucuca uuuccucauc                                              20

<210> SEQ ID NO 956
<211> LENGTH: 25
<212> TYPE: RNA
<213> ORGANISM: Homo sapiens

<400> SEQUENCE: 956
ugggcagggg cuuauuguag gaguc                                        25

<210> SEQ ID NO 957
<211> LENGTH: 19
<212> TYPE: RNA
<213> ORGANISM: Homo sapiens

<400> SEQUENCE: 957
ugggcagggg cuuauugua                                               19

<210> SEQ ID NO 958
<211> LENGTH: 15
<212> TYPE: RNA
<213> ORGANISM: Homo sapiens

<400> SEQUENCE: 958
gggucuggug cggag                                                   15
```

-continued

```
<210> SEQ ID NO 959
<211> LENGTH: 16
<212> TYPE: RNA
<213> ORGANISM: Homo sapiens

<400> SEQUENCE: 959
ggacccaggg agagac                                                        16

<210> SEQ ID NO 960
<211> LENGTH: 25
<212> TYPE: RNA
<213> ORGANISM: Homo sapiens

<400> SEQUENCE: 960
ugcggggcua gggcuaacag caguc                                              25

<210> SEQ ID NO 961
<211> LENGTH: 15
<212> TYPE: RNA
<213> ORGANISM: Homo sapiens

<400> SEQUENCE: 961
ugcggggcua gggcu                                                         15

<210> SEQ ID NO 962
<211> LENGTH: 23
<212> TYPE: RNA
<213> ORGANISM: Homo sapiens

<400> SEQUENCE: 962
ucggcucugg gucugugggg agc                                                23

<210> SEQ ID NO 963
<211> LENGTH: 15
<212> TYPE: RNA
<213> ORGANISM: Homo sapiens

<400> SEQUENCE: 963
gcccggauac cucag                                                         15

<210> SEQ ID NO 964
<211> LENGTH: 24
<212> TYPE: RNA
<213> ORGANISM: Homo sapiens

<400> SEQUENCE: 964
cugcccuggc ccgagggacc gacu                                               24

<210> SEQ ID NO 965
<211> LENGTH: 15
<212> TYPE: RNA
<213> ORGANISM: Homo sapiens

<400> SEQUENCE: 965
cugcccuggc ccgag                                                         15

<210> SEQ ID NO 966
<211> LENGTH: 25
<212> TYPE: RNA
<213> ORGANISM: Homo sapiens

<400> SEQUENCE: 966
ggguggggau uuguugcauu acuug                                              25
```

<210> SEQ ID NO 967
<211> LENGTH: 20
<212> TYPE: RNA
<213> ORGANISM: Homo sapiens

<400> SEQUENCE: 967 gguggggau uguugcauu                                                  20

<210> SEQ ID NO 968
<211> LENGTH: 26
<212> TYPE: RNA
<213> ORGANISM: Homo sapiens

<400> SEQUENCE: 968
agggacggga cgcggugcag uguugu                                         26

<210> SEQ ID NO 969
<211> LENGTH: 15
<212> TYPE: RNA
<213> ORGANISM: Homo sapiens

<400> SEQUENCE: 969
ggcgggcggg aggga                                                     15

<210> SEQ ID NO 970
<211> LENGTH: 25
<212> TYPE: RNA
<213> ORGANISM: Homo sapiens

<400> SEQUENCE: 970
aaggcagggc ccccgcuccc cgggc                                          25

<210> SEQ ID NO 971
<211> LENGTH: 15
<212> TYPE: RNA
<213> ORGANISM: Homo sapiens

<400> SEQUENCE: 971
guguguugag gaagg                                                     15

<210> SEQ ID NO 972
<211> LENGTH: 22
<212> TYPE: RNA
<213> ORGANISM: Homo sapiens

<400> SEQUENCE: 972
ccucacaccu gccucgcccc cc                                             22

<210> SEQ ID NO 973
<211> LENGTH: 15
<212> TYPE: RNA
<213> ORGANISM: Homo sapiens

<400> SEQUENCE: 973
ucacaccugc cucgc                                                     15

<210> SEQ ID NO 974
<211> LENGTH: 23
<212> TYPE: RNA
<213> ORGANISM: Homo sapiens

<400> SEQUENCE: 974
gugggggaga ggcugucuug ugu                                          23

<210> SEQ ID NO 975
<211> LENGTH: 15
<212> TYPE: RNA
<213> ORGANISM: Homo sapiens

<400> SEQUENCE: 975
guguggggga gaggc                                                   15

<210> SEQ ID NO 976
<211> LENGTH: 25
<212> TYPE: RNA
<213> ORGANISM: Homo sapiens

<400> SEQUENCE: 976
acucggcgug gcgucggucg uggua                                        25

<210> SEQ ID NO 977
<211> LENGTH: 15
<212> TYPE: RNA
<213> ORGANISM: Homo sapiens

<400> SEQUENCE: 977
acucggcgug gcguc                                                   15

<210> SEQ ID NO 978
<211> LENGTH: 27
<212> TYPE: RNA
<213> ORGANISM: Homo sapiens

<400> SEQUENCE: 978
aucacauugc cagggauuuc caaccga                                      27

<210> SEQ ID NO 979
<211> LENGTH: 15
<212> TYPE: RNA
<213> ORGANISM: Homo sapiens

<400> SEQUENCE: 979
aaucacauug ccagg                                                   15

<210> SEQ ID NO 980
<211> LENGTH: 26
<212> TYPE: RNA
<213> ORGANISM: Homo sapiens

<400> SEQUENCE: 980
uagcaccauu ugaaaucagu guucuu                                       26

<210> SEQ ID NO 981
<211> LENGTH: 15
<212> TYPE: RNA
<213> ORGANISM: Homo sapiens

<400> SEQUENCE: 981
cuagcaccau uugaa                                                   15

<210> SEQ ID NO 982
<211> LENGTH: 21
<212> TYPE: RNA
<213> ORGANISM: Homo sapiens

<400> SEQUENCE: 982
cccaggcugg agcgagugca g                                              21

<210> SEQ ID NO 983
<211> LENGTH: 15
<212> TYPE: RNA
<213> ORGANISM: Homo sapiens

<400> SEQUENCE: 983
agcucacugc agccu                                                     15

<210> SEQ ID NO 984
<211> LENGTH: 21
<212> TYPE: RNA
<213> ORGANISM: Homo sapiens

<400> SEQUENCE: 984
aagaaggcgg ucggucugcg g                                              21

<210> SEQ ID NO 985
<211> LENGTH: 20
<212> TYPE: RNA
<213> ORGANISM: Homo sapiens

<400> SEQUENCE: 985
ccccggggag cccggcggug                                                20

<210> SEQ ID NO 986
<211> LENGTH: 15
<212> TYPE: RNA
<213> ORGANISM: Homo sapiens

<400> SEQUENCE: 986
accccgggga gcccg                                                     15

<210> SEQ ID NO 987
<211> LENGTH: 19
<212> TYPE: RNA
<213> ORGANISM: Homo sapiens

<400> SEQUENCE: 987
gcaggcgagg cugggcuga                                                 19

<210> SEQ ID NO 988
<211> LENGTH: 16
<212> TYPE: RNA
<213> ORGANISM: Homo sapiens

<400> SEQUENCE: 988
aggcgaggcu gggcug                                                    16

<210> SEQ ID NO 989
<211> LENGTH: 24
<212> TYPE: RNA
<213> ORGANISM: Homo sapiens

<400> SEQUENCE: 989
gugaguggga gccggugggg cugg                                           24

<210> SEQ ID NO 990
<211> LENGTH: 15
<212> TYPE: RNA
<213> ORGANISM: Homo sapiens -continued

```
<400> SEQUENCE: 990
ggggcuggag uaagg                                                  15

<210> SEQ ID NO 991
<211> LENGTH: 22
<212> TYPE: RNA
<213> ORGANISM: Homo sapiens

<400> SEQUENCE: 991
ccccguguuu ggggcgcguc ug                                          22

<210> SEQ ID NO 992
<211> LENGTH: 21
<212> TYPE: RNA
<213> ORGANISM: Homo sapiens

<400> SEQUENCE: 992
cccgguguug gggcgcgucu g                                           21

<210> SEQ ID NO 993
<211> LENGTH: 20
<212> TYPE: RNA
<213> ORGANISM: Homo sapiens

<400> SEQUENCE: 993
ggcuggucag augggagugg                                             20

<210> SEQ ID NO 994
<211> LENGTH: 26
<212> TYPE: RNA
<213> ORGANISM: Homo sapiens

<400> SEQUENCE: 994
gacuauagaa cuuuccccu cauccc                                       26

<210> SEQ ID NO 995
<211> LENGTH: 15
<212> TYPE: RNA
<213> ORGANISM: Homo sapiens

<400> SEQUENCE: 995
aacuuucccc cucau                                                  15

<210> SEQ ID NO 996
<211> LENGTH: 25
<212> TYPE: RNA
<213> ORGANISM: Homo sapiens

<400> SEQUENCE: 996
ugcaggcaga agugggcug acagg                                        25

<210> SEQ ID NO 997
<211> LENGTH: 20
<212> TYPE: RNA
<213> ORGANISM: Homo sapiens

<400> SEQUENCE: 997
cugcaggcag aaguggggcu                                             20

<210> SEQ ID NO 998
<211> LENGTH: 17
<212> TYPE: RNA
<213> ORGANISM: Homo sapiens
```

```
<400> SEQUENCE: 998
uccuagucac ggcacca                                                    17

<210> SEQ ID NO 999
<211> LENGTH: 28
<212> TYPE: RNA
<213> ORGANISM: Homo sapiens

<400> SEQUENCE: 999
guaugguauu gcacuugucc cggccugu                                        28

<210> SEQ ID NO 1000
<211> LENGTH: 15
<212> TYPE: RNA
<213> ORGANISM: Homo sapiens

<400> SEQUENCE: 1000
uauugcacuu guccc                                                      15
```

KIT, DEVICE, AND METHOD FOR DETECTING LUNG CANCER

TECHNICAL FIELD

The present invention relates to a kit or a device for detection of lung cancer, comprising a nucleic acid capable of specifically binding to a particular polynucleotide or a polynucleotide complementary to that of the polynucleotide, which is used for examining the presence or absence of lung cancer in a subject, and a method for detecting lung cancer by measuring an expression level of the miRNA using the nucleic acid.

BACKGROUND ART

Lung cancer is a cancerous change of some cells of the trachea, bronchi, or alveoli of the lungs for some reasons. According to the cancer statistics in the year of 2012 by site in Japan disclosed by the Center for Cancer Control and Information Services, National Cancer Center, the number of people affected by lung cancer is 107,241 people, and 1 out of every 10 men and 1 out of every 22 women are supposedly affected. The number of deaths from lung cancer in men and women all together climbed to 71,518 people which is the top cause of deaths among cancer types. In the United States, the estimated number of people affected by lung cancer in 2014 climbed to 224,210 people, out of which about 159,260 people are expected to die.

Lung cancer has several different tissue types, of which about 15% is small cell lung carcinoma, whereas the remaining tissue types are called non-small cell lung carcinoma. Non-small cell lung carcinoma contains various tissue types, including three major tissue types that are adenocarcinoma, squamous cell carcinoma, and large cell carcinoma. Depending on the tissue type of lung cancer, development site, form and speed of progression, and their symptoms notably vary, and appropriate approaches to therapy are accordingly different. For example, small cell carcinoma quickly grows and is highly malignant, but is said to be more susceptible to anticancer agents and radiation treatment than non-small cell carcinoma. Furthermore, classification by the development site of lung cancer primarily includes hilar type and lung field type. The hilar type which develops near the hilar area at which various tracheas come together is not easily detected by a typical X-ray examination compared to the lung field type which develops in the periphery of the lung.

A stage of progression of lung cancer is classified into stages 0, IA, IB, IIA, IIB, IIIA, IIIB, and IV according to spread of tumors (T1 to T4), lymph node metastasis (N0 to N3), and distant metastasis (M0, M1). Survival rate in lung cancer varies depending on the stage of progression. Five-year relative survival rates in non-small cell lung carcinoma are reported to be 45 to 49% in the case of stage I (IA and IB), 30 to 31% in the case of stage II (IIA and IIB), 5 to 14% in the case of stage III (IIIA and IIIB), and 1% in the case of stage IV. Thus, detection of lung cancer in an early stage, i.e., detection in stage 0 or stage I, and treatment thereof notably contribute to improvement in survival rate.

Lung cancer is mainly treated by surgery, radiation therapy, and anticancer agents. Particularly, surgery is suitable for an early stage lung cancer, and it is likely to be cured in such case. Furthermore, in the case of an early stage lung cancer, there are several treatment selections that are less burden on a patient are available; such treatment includes thoracoscopic surgery, stereotactic body radiation treatment (SBRT), photodynamic treatment, laser treatment, brachytherapy for irradiating radiation from inside the body, or the like.

Many lung cancer cases are, regardless of a stage of progression, almost asymptomatic, which makes early detection at routine health checkups important. The most common lung cancer screening is chest X-ray examination. When a suspecting result is obtained from chest X-ray examination, a more precise image diagnoses such as CT test, MRI test, PET test, or the like, are carried out. Additionally, in recent years effectiveness of low dose CT on lung cancer screening has been recognized. National Lung Screening Trial conducted in the United States revealed that a test subject group of high-risk for lung cancer such as chain smokers who took CT checkups had reduced mortalities compared to those who took chest X-ray checkups.

When an individual is strongly suspected of having lung cancer by an image diagnosis, final diagnosis would be made that includes determination of the lung cancer tissue type by collecting cells and tissues for a microscopic examination. Cytodiagnosis and tissue diagnosis include sputum cytodiagnosis, pleural effusion examination, bronchoscopy, percutaneous needle biopsy, and the like.

In conventional diagnostic methods, lung cancers are often found in a progressed state, and they were found by the methods that impose an innegligible burden on the examinee, such as biopsy test. Under the circumstance, there is an effort to detect lung cancers earlier in a simpler manner using tumor markers in blood. Examples of the lung cancer tumor markers used at present include CEA, CYFRA21-1, NSE, SCC, and the like. As shown in Patent Literatures 1 to 6 and Non-Patent Literatures 1 to 6, there are reports, albeit at a research stage, on the detection of lung cancer using the expression levels of microRNAs (miRNAs) in biological samples including blood.

Specifically, Patent Literature 1 discloses a method for discriminating lung cancer patients from healthy subjects and patients with cancers other than lung cancer using miR-1343-3p, miR-6746-5p, miR-187-5p, miR-4632-5p and the like in serum.

Patent Literature 2 discloses a method for discriminating lung cancer using a pair of expression levels of miR-296-5p, miR-422a, miR-638, miR-191-5p, miR-23a-3p, miR-24-3p, miR-320a, miR-29b-3p, miR-92-3p and the like in serum or plasma.

Patent Literature 3 discloses miR-150-3p, miR-103a-3p, miR-107 and the like in peripheral blood as biomarkers for non-small cell lung carcinoma.

Patent Literature 4 discloses a method for discriminating non-small cell lung carcinoma using miR-23b-3p, miR-29b-3p, miR-625-3p, miR-17-3p and the like in peripheral blood.

Patent Literature 5 discloses a method for diagnosing lung cancer or predicting prognosis for lung cancer using miR-1249-3p, miR-1275, miR-191-5p, miR-423-5p, miR-744, miR-874-3p and the like in tracheal cells.

Patent Literature 6 discloses a method for detecting lung cancer patients from high-risk people for lung cancer with high smoking amount using miR-23b-3p, miR-107, miR-103a-3p, miR-17-5p and the like in plasma.

Non-Patent Literature 1 discloses a method for discriminating lung adenocarcinoma from healthy subjects and lung benign diseases using twenty miRNAs including miR-1290 and miR-24-3p in serum.

Non-Patent Literature 2 discloses that expression levels of five miRNAs including miR-650 in bronchoalveolar lavage samples significantly increase in lung cancer patients whereby these miRNAs have potential for the use as lung cancer markers.

Non-Patent Literature 3 discloses a method for discriminating lung cancer patients from healthy subjects using expression levels of miR-3180-3p, miR-342-5p, miR-150 and the like contained in neutrophilic granulocyte.

Non-Patent Literature 4 discloses miR-550 and the like in serum as biomarkers for lung adenocarcinoma.

Non-Patent Literature 5 discloses miR-1229 and the like in serum as biomarkers for non-small cell lung carcinoma.

Non-Patent Literature 6 discloses miR-1254, miR-1275, miR-320a and the like in serum as biomarkers for non-small cell lung carcinoma.

PRIOR ART LITERATURE

Patent Literature

Patent Literature 1: International Publication No. WO 2015/194610
Patent Literature 2: JP Patent Publication (Kohyo) No. 2013-502931 A (2013)
Patent Literature 3: JP Patent Publication (Kohyo) No. 2011-505143 A (2011)
Patent Literature 4: Published U.S. Patent Application No. 2012/108462
Patent Literature 5: Published U.S. Patent Application No. 2015/080243
Patent Literature 6: International Publication No. WO 2015/115923

Non-Patent Literature

Non-Patent Literature 1: Tai M C et al. Sci Rep. 2016 Aug. 10; 6: 31389
Non-Patent Literature 2: Schmidt B et al. Adv Exp Med Biol. 2016; 924: 33-37.
Non-Patent Literature 3: Leidinger P et al. Oncotarget. 2014 Oct. 15; 5(19): 9484-97.
Non-Patent Literature 4: Rani S et al. Cancer Biol Ther. 2013 Dec.; 14(12): 1104-12.
Non-Patent Literature 5: Roth C et al. PLoS One. 2012; 7(6): e38248
Non-Patent Literature 6: Foss K M et al. J Thorac Oncol. 2011 March; 6(3): 482-8

SUMMARY OF INVENTION

Problem to be Solved by Invention

An object of the present invention is to find a novel tumor marker(s) for lung cancer practically usable in primary tests of lung cancer and to provide a method that can effectively detect lung cancer using a nucleic acid(s) that specifically bind(s) to the marker(s). Effective primary tests of lung cancer require four factors: 1. ability to detect early stages, 2. Ability to detect any histological type of lung cancer, 3. high detection sensitivity and specificity for lung cancer, and 4. low invasiveness to examinees. An object of the present invention is to provide a test method that satisfies these factors.

X-ray examination, which is currently used as a main primary test of lung cancer, has the difficulty in the early detection of small cell carcinoma or squamous cell carcinoma which develops mainly in the hilar area. Large cell carcinoma grows rapidly and often already has a large tumor size when detected. Furthermore, some who are detected as abnormal in low-dose CT examination often turn out to be non-cancer (false-positive) by additional examination. Such case could lead to more highly invasive needle biopsy or surgery if unattended.

For detection of lung cancer, CEA and CYFRA21-1 are known examples as tumor markers in blood. These tumor markers in blood, however, have been reported to have general lung cancer detection sensitivity of 69% (CEA) and 43% (CYFRA21-1), and are thus not very useful in lung cancer examination. Furthermore, the tumor markers such as CEA and CYFRA21-1 may elevate for reasons other than lung cancer, and therefore have the difficulty in identifying cancer types. The false diagnosis of other cancers as lung cancer wastes appropriate therapeutic opportunity or places unnecessary economical and physical burdens on patients due to the application of wrong medical approaches.

As described below, there are reports, albeit at a research stage, on the determination of lung cancer using the expression levels of microRNAs (miRNAs) in biological samples including blood, none of which, however, have yet been brought into practical use.

Patent Literature 1 discloses a method for discriminating a lung cancer patient from a healthy subject or a patient having a cancer other than lung cancer using miR-1343-3p, miR-6746-5p, miR-187-5p, miR-4632-5p and the like in serum. However, lung cancer sample groups include only adenocarcinoma and squamous cell carcinoma samples. Therefore, this method might be unable to detect the other types of lung cancers.

Patent Literature 2 discloses a method for determining lung cancer using a pair of expression levels of miR-296-5p, miR-422a, miR-638, miR-191-5p, miR-23a-3p, miR-24-3p, miR-320a, miR-29b-3p, miR-92-3p and the like in serum or plasma. However, any cancer sample other than lung cancer was not used in the Examples. Therefore, the method might misdiagnose lung cancer as another cancer.

Patent Literature 3 discloses miR-150-3p, miR-103a-3p, miR-107 and the like in peripheral blood as biomarkers for non-small cell lung carcinoma; however, it does not describe the specific detection performance, such as accuracy, sensitivity, or specificity, for determining lung cancer, making these miRNAs poor in industrially practical use.

Patent Literature 4 discloses a method for determining non-small cell lung carcinoma using miR-23b-3p, miR-29b-3p, miR-625-3p, miR-17-3p and the like in peripheral blood. However, any cancer sample other than lung cancer, or any other cancer type other than small cell carcinoma was not used in the Examples. Therefore, the method might misdiagnose lung cancer as another cancer, or might be unable to detect some types of lung cancers such as small cell carcinoma.

Patent Literature 5 discloses a method for diagnosing lung cancer or predicting prognosis for lung cancer using miR-1249-3p, miR-1275, miR-191-5p, miR-423-5p, miR-744, miR-874-3p and the like in tracheal cells. However, obtaining tissue samples requires tissue resection by surgery, and this step causes an undue physical burden on a patient, hence not preferable as a test method.

Patent Literature 6 discloses a method for detecting a lung cancer patient from people who have a large quantity of smoking and have a high risk of lung cancer using miR-23b-3p, miR-107, miR-103a-3p, miR-17-5p and the like in plasma. However, any cancer sample other than lung cancer was not used in the Examples. Therefore, the method might misdiagnose lung cancer as another cancer.

Non-Patent Literature 1 discloses a method for discriminating lung adenocarcinoma from normal health or benign lung disease using twenty miRNAs including miR-1290 and miR-24-3p in serum. However, the discriminant performance for squamous cell carcinoma or small cell carcinoma is as low as approximately 70%. Therefore, the method might overlook some histological types of lung cancer patients.

Non-Patent Literature 2 discloses that expression levels of five miRNAs including miR-650 in bronchoalveolar lavage samples were significantly increased in lung cancer patients, indicating their potentiality as lung cancer markers; however, it does not describe the specific detection performance, such as accuracy, sensitivity, or specificity, for determining lung cancer, making these miRNAs poor in industrially practical use.

Non-Patent Literature 3 discloses a method for discriminating a lung cancer patient from a healthy subject using expression levels of miR-3180-3p, miR-342-5p, miR-150 and the like contained in neutrophilic granulocytes. However, separation of immunocytes on a cell type basis from blood is laborious, making these miRNAs poor in industrially practical use.

Non-Patent Literature 4 discloses miR-550 and the like in serum as biomarkers for lung adenocarcinoma. However, any cancer sample other than lung cancer, or any lung cancer type other than adenocarcinoma was not used in the Examples. Therefore, use of these miRNAs as biomarkers might misdiagnose lung cancer as another cancer or might be unable to detect some histological types of lung cancers.

Non-Patent Literature 5 discloses miR-1229 and the like in serum as biomarkers for non-small cell lung carcinoma. However, any cancer sample other than lung cancer, or any small cell carcinoma sample was not used in the Examples. Therefore, use of these miRNAs as the biomarker might misdiagnose lung cancer as another cancer or might be unable to detect some histological types of lung cancers.

Non-Patent Literature 6 discloses miR-1254, miR-1275, miR-320a and the like in serum as biomarkers for non-small cell lung carcinoma. However, any cancer sample other than lung cancer, or any small cell carcinoma sample was not used in the Examples. Therefore, use of these miRNAs as the biomarker might misdiagnose lung cancer as another cancer, or might be unable to detect some types of lung cancers such as small cell carcinoma.

As mentioned above, chest X-ray examination or low-dose CT for use in lung cancer examination has the difficulty in detection of lung cancer, depending on the site of origin, and in some case detect non-cancer abnormality in an image that might lead to the execution of needless extra examination. Furthermore, the existing tumor markers exhibit low detection performance for lung cancer and cannot distinguish lung cancer from other cancers. Neither validation using samples of cancers other than lung cancer nor validation using some histological types of lung cancers such as small cell carcinoma or large cell carcinoma has been conducted as to the markers at a research stage. Therefore, use of these markers might require carrying out needless extra examination due to the false detection of normal subjects or other cancer patients as being lung cancer patients, or might waste therapeutic opportunity because of overlooking lung cancer patients. Furthermore, the collection of lung tissues for measuring the tumor markers is highly invasive to patients and is not favorable. Hence, there is a demand for a highly accurate lung cancer marker that is detectable from blood, which can be collected with less invasiveness, and is capable of correctly determining the presence or absence of lung cancer. Particularly, the early detection of lung cancer increases the applicability of surgery in treatment, and drastically improve the survival rates. For early-stage lung cancers, there are several therapeutic options available that place less burden on patients, such as thoracoscopic surgery and stereotactic body radiotherapy. Therefore, a highly sensitive lung cancer marker that can detect lung cancer even at a low stage of progression is desired.

Means for Solution of Problem

The present inventors have conducted diligent studies to attain the object and consequently completed the present invention by finding gene markers usable as markers for detection of lung cancer from blood, which can be collected with limited invasiveness, and finding that lung cancer such as lung adenocarcinoma, lung squamous cell carcinoma, large cell lung carcinoma, or small cell lung carcinoma can be significantly, preferably specifically, detected, using nucleic acids to detect such markers, for example, at least one nucleic acid selected from probes capable of specifically binding to any of these markers and primers for amplifying these markers.

SUMMARY OF INVENTION

The present invention has the following features:
(1) A kit for detection of lung cancer, comprising a nucleic acid(s) capable of specifically binding to at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide consisting of a nucleotide sequence complementary to that of the polynucleotide.

(2) The kit according to (1), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and (e) a polynucleotide hybridizing under stringent conditions to any of the polynucleotides (a) to (d).

(3) The kit according to (1) or (2), wherein the kit further comprises a nucleic acid(s) capable of specifically binding to at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

(4) The kit according to (3), wherein the nucleic acid(s) is a polynucleotide(s) selected from the group consisting of the following polynucleotides (f) to (j):

(f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and (j) a polynucleotide hybridizing under stringent conditions to any of the polynucleotides (f) to (i).

(5) A device for detection of lung cancer, comprising a nucleic acid(s) capable of specifically binding to at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide consisting of a nucleotide sequence complementary to that of the polynucleotide.

(6) The device according to (5), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and (e) a polynucleotide hybridizing under stringent conditions to any of the polynucleotides (a) to (d).

(7) The device according to (5) or (6), wherein the device further comprises a nucleic acid(s) capable of specifically binding to at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

(8) The device according to (7), wherein the nucleic acid(s) is a polynucleotide(s) selected from the group consisting of the following polynucleotides (f) to (j):

(f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and (j) a polynucleotide hybridizing under stringent conditions to any of the polynucleotides (f) to (i).

(9) The device according to any of (5) to (8), wherein the device is for measurement by a hybridization technique.

(10) The device according to (9), wherein the hybridization technique is a nucleic acid array technique.

(11) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-5p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-6665-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-

5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and evaluating in vitro whether or not the subject has lung cancer using the measured expression level(s).

(12) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and evaluating in vitro whether or not the subject has lung cancer using both of the measured expression level(s) and a control expression level(s) from healthy subjects measured in the same way.

(13) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and assigning the expression level(s) of the at least one polynucleotide in the sample from the subject to a discriminant, which is capable of discriminatorily determining the presence or absence of lung cancer, and is prepared with gene expression levels in samples from subjects known to have lung cancer and samples from subjects without lung cancer as training samples, and thereby evaluating in vitro the presence or absence of lung cancer.

(14) The method according to any of (11) to (13), wherein the measurement of the expression level(s) of the polynucleotide(s) is performed using a nucleic acid(s) capable of specifically binding to the polynucleotide(s) or a polynucleotide(s) consisting of a nucleotide sequence(s) complementary to the polynucleotide(s), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and (e) a polynucleotide hybridizing under stringent conditions to any of the polynucleotides (a) to (d).

(15) The method according to any of (11) to (14), wherein the method further comprises measuring an expression level(s) of at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p.

(16) The method according to (15), wherein the measurement of the expression level(s) of the polynucleotide(s) is performed using a nucleic acid(s) capable of specifically binding to the polynucleotide(s) or a polynucleotide(s) consisting of a nucleotide sequence(s) complementary to the polynucleotide(s), wherein the nucleic acid(s) is a polynucleotide(s) selected from the group consisting of the following polynucleotides (f) to (j):

(f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and (j) a polynucleotide hybridizing under stringent conditions to any of the polynucleotides (f) to (i).

(17) The method according to any of (11) to (16), wherein the expression level(s) of the polynucleotide(s) in the sample from the subject is measured using a kit according to any of (1) to (4) or a device according to any of (5) to (10), comprising a nucleic acid(s) capable of specifically binding to the polynucleotide(s) or a polynucleotide(s) consisting of a nucleotide sequence(s) complementary to the polynucleotide(s).

(18) The method according to any of (11) to (17), wherein the subject is a human.

(19) The method according to any of (11) to (18), wherein the sample is blood, serum, or plasma.

In one preferred aspect of the present invention, the kit, the device or the method for detecting lung cancer according to the present invention is a kit, a device or a method for detecting lung cancer, wherein a histological type of the lung cancer is adenocarcinoma, squamous cell carcinoma, large cell carcinoma or small cell carcinoma.

In another preferred aspect of the present invention, the kit, the device or the method for detecting lung cancer according to the present invention is a kit, a device or a method for detecting lung cancer, wherein as the lung cancer markers, miR-6787-5p is hsa-miR-6787-5p, miR-920 is hsa-miR-920, miR-3622a-5p is hsa-miR-3622a-5p, miR-1185-1-3p is hsa-miR-1185-1-3p, miR-4327 is hsa-miR-4327, miR-5739 is hsa-miR-5739, miR-937-5p is hsa-miR-937-5p, miR-1181 is hsa-miR-1181, miR-1185-2-3p is hsa-miR-1185-2-3p, miR-1193 is hsa-miR-1193, miR-1207-5p is hsa-miR-1207-5p, miR-1238-5p is hsa-miR-1238-5p, miR-1246 is hsa-miR-1246, miR-1249-5p is hsa-miR-1249-5p, miR-1292-3p is hsa-miR-1292-3p, miR-1469 is hsa-miR-1469, miR-1470 is hsa-miR-1470, miR-197-5p is hsa-miR-197-5p, miR-208a-5p is hsa-miR-208a-5p, miR-2110 is hsa-miR-2110, miR-211-3p is hsa-miR-211-3p, miR-2467-3p is hsa-miR-2467-3p, miR-3122 is hsa-miR-3122, miR-3141 is hsa-miR-3141, miR-3156-5p is hsa-miR-3156-5p, miR-3158-5p is hsa-miR-3158-5p, miR-3160-5p is hsa-miR-3160-5p, miR-3180-3p is hsa-miR-3180-3p, miR-3191-3p is hsa-miR-3191-3p, miR-3194-3p is hsa-miR-3194-3p, miR-320b is hsa-miR-320b, miR-328-5p is hsa-miR-328-5p, miR-3610 is hsa-miR-3610, miR-3619-3p is hsa-miR-3619-3p, miR-3620-5p is hsa-miR-3620-5p, miR-370-3p is hsa-miR-370-3p, miR-373-5p is hsa-miR-373-5p, miR-3917 is hsa-miR-3917, miR-3937 is hsa-miR-3937, miR-4259 is hsa-miR-4259, miR-4281 is hsa-miR-4281, miR-4294 is hsa-miR-4294, miR-4419b is hsa-miR-4419b, miR-4428 is hsa-miR-4428, miR-4429 is hsa-miR-4429, miR-4433a-3p is hsa-miR-4433a-3p, miR-4447 is hsa-miR-4447, miR-4449 is hsa-miR-4449, miR-4459 is hsa-miR-4459, miR-4480 is hsa-miR-4480, miR-4485-5p is hsa-miR-4485-5p, miR-4486 is hsa-miR-4486, miR-4488 is hsa-miR-4488, miR-4489 is hsa-miR-4489, miR-4505 is hsa-miR-4505, miR-4513 is hsa-miR-4513, miR-4515 is hsa-miR-4515, miR-4530 is hsa-miR-4530, miR-4535 is hsa-miR-4535, miR-4635 is hsa-miR-4635, miR-4640-5p is hsa-miR- 4640-5p, miR-4646-5p is hsa-miR-4646-5p, miR-4656 is hsa-miR-4656, miR-4663 is hsa-miR-4663, miR-4665-5p is hsa-miR-4665-5p, miR-4706 is hsa-miR-4706, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4727-3p is hsa-miR-4727-3p, miR-4730 is hsa-miR-4730, miR-4734 is hsa-miR-4734, miR-4740-5p is hsa-miR-4740-5p, miR-4747-3p is hsa-miR-4747-3p, miR-4749-5p is hsa-miR-4749-5p, miR-4755-3p is hsa-miR-4755-3p, miR-4763-5p is hsa-miR-4763-5p, miR-4787-3p is hsa-miR-4787-3p, miR-5008-5p is hsa-miR-5008-5p, miR-5010-5p is hsa-miR-5010-5p, miR-504-3p is hsa-miR-504-3p, miR-5090 is hsa-miR-5090, miR-5100 is hsa-miR-5100, miR-5196-5p is hsa-miR-5196-5p, miR-551b-5p is hsa-miR-551b-5p, miR-557 is hsa-miR-557, miR-5787 is hsa-miR-5787, miR-6090 is hsa-miR-6090, miR-6124 is hsa-miR-6124, miR-6132 is hsa-miR-6132, miR-6510-5p is hsa-miR-6510-5p, miR-6511b-5p is hsa-miR-6511b-5p, miR-6515-3p is hsa-miR-6515-3p, miR-654-5p is hsa-miR-654-5p, miR-658 is hsa-miR-658, miR-668-5p is hsa-miR-668-5p, miR-6722-5p is hsa-miR-6722-5p, miR-6724-5p is hsa-miR-6724-5p, miR-6729-3p is hsa-miR-6729-3p, miR-6737-5p is hsa-miR-6737-5p, miR-6756-5p is hsa-miR-6756-5p, miR-6762-5p is hsa-miR-6762-5p, miR-6763-3p is hsa-miR-6763-3p, miR-6766-5p is hsa-miR-6766-5p, miR-6769a-5p is hsa-miR-6769a-5p, miR-6771-5p is hsa-miR-6771-5p, miR-6786-5p is hsa-miR-6786-5p, miR-6789-5p is hsa-miR-6789-5p, miR-6794-5p is hsa-miR-6794-5p, miR-6796-3p is hsa-miR-6796-3p, miR-6797-5p is hsa-miR-6797-5p, miR-6800-3p is hsa-miR-6800-3p, miR-6802-5p is hsa-miR-6802-5p, miR-6803-5p is hsa-miR-6803-5p, miR-6805-3p is hsa-miR-6805-3p, miR-6805-5p is hsa-miR-6805-5p, miR-6807-5p is hsa-miR-6807-5p, miR-6812-5p is hsa-miR-6812-5p, miR-6819-5p is hsa-miR-6819-5p, miR-6822-5p is hsa-miR-6822-5p, miR-6824-5p is hsa-miR-6824-5p, miR-6826-5p is hsa-miR-6826-5p, miR-6850-5p is hsa-miR-6850-5p, miR-6858-5p is hsa-miR-6858-5p, miR-6861-5p is hsa-miR-6861-5p, miR-6880-3p is hsa-miR-6880-3p, miR-7107-5p is hsa-miR-7107-5p, miR-7109-5p is hsa-miR-7109-5p, miR-7114-5p is hsa-miR-7114-5p, miR-7704 is hsa-miR-7704, miR-7846-3p is hsa-miR-7846-3p, miR-8052 is hsa-miR-8052, miR-8060 is hsa-miR-8060, miR-8071 is hsa-miR-8071, miR-8073 is hsa-miR-8073, miR-874-5p is hsa-miR-874-5p, miR-204-3p is hsa-miR-204-3p, miR-3154 is hsa-miR-3154, miR-3960 is hsa-miR-3960, miR-4433a-5p is hsa-miR-4433a-5p, miR-4455 is hsa-miR-4455, miR-4462 is hsa-miR-4462, miR-4476 is hsa-miR-4476, miR-4508 is hsa-miR-4508, miR-4687-3p is hsa-miR-4687-3p, miR-4687-5p is hsa-miR-4687-5p, miR-4732-5p is hsa-miR-4732-5p, miR-4771 is hsa-miR-4771, miR-642a-3p is hsa-miR-642a-3p, miR-6732-5p is hsa-miR-6732-5p, miR-6760-5p is hsa-miR-6760-5p, miR-6799-5p is hsa-miR-6799-5p, miR-6820-5p is hsa-miR-6820-5p, miR-6821-5p is hsa-miR-6821-5p, miR-6829-5p is hsa-miR-6829-5p, miR-6893-5p is hsa-miR-6893-5p, miR-7108-3p is hsa-miR-7108-3p, miR-7111-5p is hsa-miR-7111-5p, miR-8089 is hsa-miR-8089, miR-885-3p is hsa-miR-885-3p, miR-92b-3p is hsa-miR-92b-3p, miR-1343-3p is hsa-miR-1343-3p, miR-6746-5p is hsa-miR-6746-5p, miR-422a is hsa-miR-422a, miR-187-5p is hsa-miR-187-5p, miR-4632-5p is hsa-miR-4632-5p, miR-6791-5p is hsa-miR-6791-5p, miR-103a-3p is hsa-miR-103a-3p, miR-107 is hsa-miR-107, miR-1199-5p is hsa-miR-1199-5p, miR-1225-3p is hsa-miR-1225-3p, miR-1225-5p is hsa-miR-1225-5p, miR-1228-5p is hsa-miR-1228-5p, miR-1229-5p is hsa-miR-1229-5p, miR-1233-5p is hsa-miR-1233-5p, miR-1237-5p is hsa-miR-1237-5p, miR-1247-3p is hsa-miR-1247-3p, miR-1249-3p is hsa-miR-1249-3p, miR-1254 is hsa-miR-1254, miR-1260b is hsa-miR-1260b, miR-1268a is hsa-miR-1268a, miR-1268b is hsa-miR-1268b, miR-1273g-3p is hsa-miR-1273g-3p, miR-128-1-5p is hsa-miR-128-1-5p, miR-128-2-5p is hsa-miR-128-2-5p, miR-1290 is hsa-miR-1290, miR-150-3p is hsa-miR-150-3p, miR-17-3p is hsa-miR-17-3p, miR-1908-5p is hsa-miR-1908-5p, miR-1909-3p is hsa-miR-1909-3p, miR-1914-3p is hsa-miR-1914-3p, miR-1915-3p is hsa-miR-1915-3p, miR-191-5p is hsa-miR-191-5p, miR-22-3p is hsa-miR-22-3p, miR-23b-3p is hsa-miR-23b-3p, miR-24-3p is hsa-miR-24-3p, miR-296-3p is hsa-miR-296-3p, miR-296-5p is hsa-miR-296-5p, miR-3131 is hsa-miR-3131, miR-3162-5p is hsa-miR-3162-5p, miR-3188 is hsa-miR-3188, miR-3196 is hsa-miR-3196, miR-3197 is hsa-miR-3197, miR-320a is hsa-miR-320a, miR-342-5p is hsa-miR-342-5p, miR-3621 is hsa-miR-3621, miR-3648 is hsa-miR-3648, miR-3656 is hsa-miR-3656, miR-365a-5p is hsa-miR-365a-5p, miR-3665 is hsa-miR-3665, miR-3679-5p is hsa-miR-3679-5p, miR-371a-5p is hsa-miR-371a-5p, miR-3940-5p is hsa-miR-3940-5p, miR-423-5p is hsa-miR-423-5p, miR-4257 is hsa-miR-4257, miR-4270 is hsa-miR-4270, miR-4271 is hsa-miR-4271, miR-4286 is hsa-miR-4286, miR-4298 is hsa-miR-4298, miR-4417 is hsa-miR-4417, miR-4442 is hsa-miR-4442, miR-4446-3p is hsa-miR-4446-3p, miR-4448 is hsa-miR-4448, miR-4454 is hsa-miR-4454, miR-4467 is hsa-miR-4467, miR-4472 is hsa-miR-4472, miR-4507 is hsa-miR-4507, miR-4516 is hsa-miR-4516, miR-451a is hsa-miR-451a, miR-4649-5p is hsa-miR-4649-5p, miR-4651 is hsa-miR-4651, miR-4665-3p is hsa-miR-4665-3p, miR-4674 is hsa-miR-4674, miR-4675 is hsa-miR-4675, miR-4689 is hsa-miR-4689, miR-4695-5p is hsa-miR-4695-5p, miR-4697-5p is hsa-miR-4697-5p, miR-4725-3p is hsa-miR-4725-3p, miR-4739 is hsa-miR-4739, miR-4745-5p is hsa-miR-4745-5p, miR-4763-3p is hsa-miR-4763-3p, miR-4792 is hsa-miR-4792, miR-486-3p is hsa-miR-486-3p, miR-5001-5p is hsa-miR-5001-5p, miR-5195-3p is hsa-miR-5195-3p, miR-550a-5p is hsa-miR-550a-5p, miR-5698 is hsa-miR-5698, miR-6075 is hsa-miR-6075, miR-6088 is hsa-miR-6088, miR-6089 is hsa-miR-6089, miR-6125 is hsa-miR-6125, miR-6126 is hsa-miR-6126, miR-614 is hsa-miR-614, miR-615-5p is hsa-miR-615-5p, miR-619-5p is hsa-miR-619-5p, miR-638 is hsa-miR-638, miR-642b-3p is hsa-miR-642b-3p, miR-650 is hsa-miR-650, miR-663a is hsa-miR-663a, miR-663b is hsa-miR-663b, miR-6717-5p is hsa-miR-6717-5p, miR-6721-5p is hsa-miR-6721-5p, miR-6726-5p is hsa-miR-6726-5p, miR-6727-5p is hsa-miR-6727-5p, miR-6738-5p is hsa-miR-6738-5p, miR-6741-5p is hsa-miR-6741-5p, miR-6749-5p is hsa-miR-6749-5p, miR-6752-5p is hsa-miR-6752-5p, miR-675-5p is hsa-miR-675-5p, miR-6757-5p is hsa-miR-6757-5p, miR-6763-5p is hsa-miR-6763-5p, miR-6765-5p is hsa-miR-6765-5p, miR-6775-5p is hsa-miR-6775-5p, miR-6780b-5p is hsa-miR-6780b-5p, miR-6782-5p is hsa-miR-6782-5p, miR-6784-5p is hsa-miR-6784-5p, miR-6800-5p is hsa-miR-6800-5p, miR-6806-5p is hsa-miR-6806-5p, miR-6840-3p is hsa-miR-6840-3p, miR-6848-5p is hsa-miR-6848-5p, miR-6851-5p is hsa-miR-6851-5p, miR-6870-5p is hsa-miR-6870-5p, miR-6872-3p is hsa-miR-6872-3p, miR-6875-5p is hsa-miR-6875-5p, miR-6877-5p is hsa-miR-6877-5p, miR-6879-5p is hsa-miR-6879-5p, miR-6880-5p is hsa-miR-6880-5p, miR-6885-5p is hsa-miR-6885-5p, miR-6887-5p is hsa-miR-6887-5p, miR-7108-5p is hsa-miR-7108-5p, miR-711 is hsa-miR-711, miR-7113-3p is hsa-miR-7113-3p, miR-744-5p is hsa-miR-744-5p, miR-760 is hsa-miR-760, miR-7845-5p is hsa-miR-7845-5p, miR-7847-3p is hsamiR-7847-3p, miR-7977 is hsa-miR-7977, miR-8059 is hsa-miR-8059, miR-8063 is hsa-miR-8063, miR-8072 is hsa-miR-8072, miR-874-3p is hsa-miR-874-3p, miR-92a-2-5p is hsa-miR-92a-2-5p, miR-92b-5p is hsa-miR-92b-5p, miR-940 is hsa-miR-940, miR-1228-3p is hsa-miR-1228-3p, miR-1275 is hsa-miR-1275, miR-1307-3p is hsa-miR-1307-3p, miR-1343-5p is hsa-miR-1343-5p, miR-23a-3p is hsa-miR-23a-3p, miR-29b-3p is hsa-miR-29b-3p, miR-3135b is hsa-miR-3135b, miR-3185 is hsa-miR-3185, miR-4532 is hsa-miR-4532, miR-4690-5p is hsa-miR-4690-5p, miR-4758-5p is hsa-miR-4758-5p, miR-4783-3p is hsa-miR-4783-3p, miR-6131 is hsa-miR-6131, miR-625-3p is hsa-miR-625-3p, miR-6511a-5p is hsa-miR-6511a-5p, miR-6765-3p is hsa-miR-6765-3p, miR-6816-5p is hsa-miR-6816-5p, miR-6825-5p is hsa-miR-6825-5p, miR-6845-5p is hsa-miR-6845-5p, miR-7150 is hsa-miR-7150, miR-7641 is hsa-miR-7641, miR-7975 is hsa-miR-7975, and miR-92a-3p is hsa-miR-92a-3p.

Definition of Terms

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus (+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 1000 or a nucleotide sequence derived from the nucleotide sequence in which the nucleic acid u is replaced with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID NO) but a "miRNA" comprising a precursor of the "miRNA" (pre-miRNA or pri-miRNA) and having biological functions equivalent to miRNAs encoded by these, for example, a "miRNA" encoding a congener (i.e., a homolog or an ortholog), a variant such as a genetic polymorph, and a derivative. Such a "miRNA" encoding a precursor, a congener, a variant, or a derivative can be specifically identified using miRBase Release 21 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 1000. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

The term "complementary polynucleotide" or "polynucleotide consisting of a complementary nucleotide sequence" (complementary strand or reverse strand) used herein means a polynucleotide in a complementary relationship based on A:T (U) and G:C base pairs with the full-length sequence of the nucleotide sequence of the target polynucleotide or a nucleotide sequence derived from the nucleotide sequence in which the nucleic acid u is replaced with t, or a partial sequence thereof (herein, these nucleotide sequences are referred to as a plus strand for the sake of convenience). Such a complementary polynucleotide is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID NO or a nucleotide sequence derived from the nucleotide sequence in which the nucleic acid u is replaced with t, or a partial sequence thereof; a variant containing the deletion, substitution, addition, or insertion of 1 or 2 or more nucleotides in a nucleotide sequence of a premature miRNA of the sequence of any of SEQ ID NOs 1 to 329 or a nucleotide sequence derived from the nucleotide sequence in which the nucleic acid u is replaced with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant used herein can be prepared by use of a well-known technique such as site-directed mutagenesis or mutagenesis using PCR.

The term "percent (%) identity" used herein can be determined with or without an introduced gap, using a protein or gene search system based on BLAST (https://blast.ncbi.nlm.nih.gov/Blast.cgi) or FASTA (http://www.genome.jp/tools/fasta/) (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include modified nucleic acids, unlimitedly for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the lung cancer marker miRNAs described above or to a polynucleotide consisting of a nucleotide sequence complementary to that of the polynucleotide is a synthesized or prepared nucleic acid and, for example, includes a "nucleic acid probe" or a "primer" capable of detecting the polynucleotide. These nucleic acids are utilized directly or indirectly for detecting the presence or absence of lung cancer in a subject, for diagnosing the presence or absence or the severity of lung cancer, the presence or absence or the degree of amelioration of lung cancer, or the therapeutic sensitivity of lung cancer, or for screening for a candidate substance useful in the prevention, amelioration, or treatment of lung cancer. The "nucleic acid" includes a nucleotide, an oligonucleotide, and a polynucleotide capable of specifically recognizing and binding to a transcript represented by any of SEQ ID NOs: 1 to 1000 or a synthetic cDNA nucleic acid thereof in vivo, particularly, in a sample such as a body fluid (e.g., blood or urine), in relation to the development of lung cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing- or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. The term "subject" herein may be optionally referred to as "test subject". The term "healthy subject" also means such a mammal, which is an animal or a subject without the cancer to be detected. The healthy subject is preferably a human.

The "lung cancer" used herein is malignant tumor that develops in the lungs, and is broadly divided into small cell lung carcinoma and non-small cell lung carcinoma. The non-small cell lung carcinoma is generic name for lung cancer other than the small cell lung carcinoma and, for example, includes lung adenocarcinoma, lung squamous cell carcinoma, and large cell lung carcinoma.

The term "lung adenocarcinoma" or "adenocarcinoma" used herein is lung cancer in which differentiation into a duct of the gland or mucus production is found.

The term "lung squamous cell carcinoma" or "squamous cell carcinoma" used herein is lung cancer that exhibits cornification or intercellular bridge.

The term "large cell lung carcinoma" or "large cell carcinoma" used herein is lung cancer that is undifferentiated malignant epithelial tumor, and that is not categorized to any of small cell carcinoma, adenocarcinoma, and squamous cell carcinoma.

The term "small cell lung carcinoma" or "small cell carcinoma" used herein is lung cancer consisting of cells having a small size. The tumor cells exhibit a round, oval, or spindle form or the like with poor cytoplasms and unclear boundaries between the cells.

The term "other lung cancers" used herein is lung cancers other than adenocarcinoma, squamous cell carcinoma, large cell carcinoma, and small cell carcinoma and, for example, includes carcinoid tumor, adenosquamous carcinoma, polymorphic cell cancer, and salivary gland-type cancer.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows lung cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being lung cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as lung cancer develops, as lung cancer progresses, or as therapeutic effects on lung cancer are exerted. Specifically, the sample refers to a lung tissue, lymph node and a surrounding organ thereof, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6787-5p gene" or "hsa-miR-6787-5p" used herein includes the hsa-miR-6787-5p gene (miRBase Accession No. MIMAT0027474) described in SEQ ID NO: 1, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 330) having a hairpin-like structure is known as a precursor of "hsa-miR-6787-5p".

The term "hsa-miR-920 gene" or "hsa-miR-920" used herein includes the hsa-miR-920 gene (miRBase Accession No. MIMAT0004970) described in SEQ ID NO: 2, a homolog or an ortholog of a different organism species, and the like. The hsa-miR-920 gene can be obtained by a method described in Novotny G W et al., 2007, Int J Androl, Vol. 30, p. 316-326. Also, "hsa-mir-920" (miRBase Accession No. MI0005712, SEQ ID NO: 331) having a hairpin-like structure is known as a precursor of "hsa-miR-920".

The term "hsa-miR-3622a-5p gene" or "hsa-miR-3622a-5p" used herein includes the hsa-miR-3622a-5p gene (miRBase Accession No. MIMAT0018003) described in SEQ ID NO: 3, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 332) having a hairpin-like structure is known as a precursor of "hsa-miR-3622a-5p".

The term "hsa-miR-1185-1-3p gene" or "hsa-miR-1185-1-3p" used herein includes the hsa-miR-1185-1-3p gene (miRBase Accession No. MIMAT0022838) described in SEQ ID NO: 4, a homolog or an ortholog of a different organism species, and the like. The hsa-miR-1185-1-3p gene can be obtained by a method described in Berezikov E et al., 2006, Genome Res, Vol. 16, p. 1289-1298. Also, "hsa-mir-1185-1" (miRBase Accession No. MI0003844, SEQ ID NO: 333) having a hairpin-like structure is known as a precursor of "hsa-miR-1185-1-3p".

The term "hsa-miR-4327 gene" or "hsa-miR-4327" used herein includes the hsa-miR-4327 gene (miRBase Accession No. MIMAT0016889) described in SEQ ID NO: 5, a homolog or an ortholog of a different organism species, and the like. The hsa-miR-4327 gene can be obtained by a method described in Goff L A et al., 2009, PLoS One, Vol. 4, e7192. Also, "hsa-mir-4327" (miRBase Accession No. MI0015867, SEQ ID NO: 334) having a hairpin-like structure is known as a precursor of "hsa-miR-4327".

The term "hsa-miR-5739 gene" or "hsa-miR-5739" used herein includes the hsa-miR-5739 gene (miRBase Accession No. MIMAT0023116) described in SEQ ID NO: 6, a homolog or an ortholog of a different organism species, and the like. The hsa-miR-5739 gene can be obtained by a method described in Yoo J K et al., 2011, Biochem Biophys Res Commun., Vol. 415, p. 258-262. Also, "hsa-mir-5739" (miRBase Accession No. MI0019412, SEQ ID NO: 335) having a hairpin-like structure is known as a precursor of "hsa-miR-5739".

The term "hsa-miR-937-5p gene" or "hsa-miR-937-5p" used herein includes the hsa-miR-937-5p gene (miRBase Accession No. MIMAT0022938) described in SEQ ID NO: 7, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 336) having a hairpin-like structure is known as a precursor of "hsa-miR-937-5p".

The term "hsa-miR-1181 gene" or "hsa-miR-1181" used herein includes the hsa-miR-1181 gene (miRBase Accession No. MIMAT0005826) described in SEQ ID NO: 8, a homolog or an ortholog of a different organism species, and the like. The hsa-miR-1181 gene can be obtained by a method described in Subramanian S et al., 2008, Oncogene, Vol. 27, p. 2015-2026. Also, "hsa-mir-1181" (miRBase Accession No. MI0006274, SEQ ID NO: 337) having a hairpin-like structure is known as a precursor of "hsa-miR-1181".

The term "hsa-miR-1185-2-3p gene" or "hsa-miR-1185-2-3p" used herein includes the hsa-miR-1185-2-3p gene (miRBase Accession No. MIMAT0022713) described in SEQ ID NO: 9, a homolog or an ortholog of a different organism species, and the like. The hsa-miR-1185-2-3p gene can be obtained by a method described in Berezikov E et al., 2006, Genome Res, Vol. 16, p. 1289-1298. Also, "hsa-mir-1185-2" (miRBase Accession No. MI0003821, SEQ ID NO: 338) having a hairpin-like structure is known as a precursor of "hsa-miR-1185-2-3p".

The term "hsa-miR-1193 gene" or "hsa-miR-1193" used herein includes the hsa-miR-1193 gene (miRBase Accession No. MIMAT0015049) described in SEQ ID NO: 10, a homolog or an ortholog of a different organism species, and the like. The hsa-miR-1193 gene can be obtained by a method described in Stark M S et al., 2010, PLoS One, Vol. 5, e9685. Also, "hsa-mir-1193" (miRBase Accession No. MI0014205, SEQ ID NO: 339) having a hairpin-like structure is known as a precursor of "hsa-miR-1193".

The term "hsa-miR-1207-5p gene" or "hsa-miR-1207-5p" used herein includes the hsa-miR-1207-5p gene (miRBase Accession No. MIMAT0005871) described in SEQ ID NO: 11, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. MI0006340, SEQ ID NO: 340) having a hairpin-like structure is known as a precursor of "hsa-miR-1207-5p".

The term "hsa-miR-1238-5p gene" or "hsa-miR-1238-5p" used herein includes the hsa-miR-1238-5p gene (miRBase Accession No. MIMAT0022947) described in SEQ ID NO: 12, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 341) having a hairpin-like structure is known as a precursor of "hsa-miR-1238-5p".

The term "hsa-miR-1246 gene" or "hsa-miR-1246" used herein includes the hsa-miR-1246 gene (miRBase Accession No. MIMAT0005898) described in SEQ ID NO: 13, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 342) having a hairpin-like structure is known as a precursor of "hsa-miR-1246".

The term "hsa-miR-1249-5p gene" or "hsa-miR-1249-5p" used herein includes the hsa-miR-1249-5p gene (miRBase Accession No. MIMAT0032029) described in SEQ ID NO: 14, a homolog or an ortholog of a different organism species, and the like. The hsa-miR-1249-5p gene can be obtained by a method described in Morin R D et al., 2008, Genome Res, Vol. 18, p. 610-621. Also, "hsa-mir-1249" (miRBase Accession No. MI0006384, SEQ ID NO: 343) having a hairpin-like structure is known as a precursor of "hsa-miR-1249-5p".

The term "hsa-miR-1292-3p gene" or "hsa-miR-1292-3p" used herein includes the hsa-miR-1292-3p gene (miRBase Accession No. MIMAT0022948) described in SEQ ID NO: 15, a homolog or an ortholog of a different organism species, and the like. The hsa-miR-1292-3p gene can be obtained by a method described in Morin R D et al., 2008, Genome Res, Vol. 18, p. 610-621. Also, "hsa-mir-1292" (miRBase Accession No. MI0006433, SEQ ID NO: 344) having a hairpin-like structure is known as a precursor of "hsa-miR-1292-3p".

The term "hsa-miR-1469 gene" or "hsa-miR-1469" used herein includes the hsa-miR-1469 gene (miRBase Accession No. MIMAT0007347) described in SEQ ID NO: 16, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 345) having a hairpin-like structure is known as a precursor of "hsa-miR-1469".

The term "hsa-miR-1470 gene" or "hsa-miR-1470" used herein includes the hsa-miR-1470 gene (miRBase Accession No. MIMAT0007348) described in SEQ ID NO: 17, a homolog or an ortholog of a different organism species, and the like. The hsa-miR-1470 gene can be obtained by a method described in Kawaji H et al., 2008, BMC Genomics, Vol. 9, p. 157. Also, "hsa-mir-1470" (miRBase Accession No. MI0007075, SEQ ID NO: 346) having a hairpin-like structure is known as a precursor of "hsa-miR-1470".

The term "hsa-miR-197-5p gene" or "hsa-miR-197-5p" used herein includes the hsa-miR-197-5p gene (miRBase Accession No. MIMAT0022691) described in SEQ ID NO: 18, a homolog or an ortholog of a different organism species, and the like. The hsa-miR-197-5p gene can be obtained by a method described in 'Lagos-Quintana M et al., 2003, RNA, Vol. 9, p. 175-179'. Also, "hsa-mir-197" (miRBase Accession No. MI0000239, SEQ ID NO: 347) having a hairpin-like structure is known as a precursor of "hsa-miR-197-5p".

The term "hsa-miR-208a-5p gene" or "hsa-miR-208a-5p" used herein includes the hsa-miR-208a-5p gene (miRBase Accession No. MIMAT0026474) described in SEQ ID NO: 19, a homolog or an ortholog of a different organism species, and the like. The hsa-miR-208a-5p gene can be obtained by a method described in Lagos-Quintana M et al., 2003, RNA, Vol. 9, p. 175-179. Also, "hsa-mir-208a" (miRBase Accession No. MI0000251, SEQ ID NO: 348) having a hairpin-like structure is known as a precursor of "hsa-miR-208a-5p".

The term "hsa-miR-2110 gene" or "hsa-miR-2110" used herein includes the hsa-miR-2110 gene (miRBase Accession No. MIMAT0010133) described in SEQ ID NO: 20, a homolog or an ortholog of a different organism species, and the like. The hsa-miR-2110 gene can be obtained by a method described in Zhu J Y et al., 2009, J Virol, Vol. 83, p. 3333-3341. Also, "hsa-mir-2110" (miRBase Accession No. MI0010629, SEQ ID NO: 349) having a hairpin-like structure is known as a precursor of "hsa-miR-2110".

The term "hsa-miR-211-3p gene" or "hsa-miR-211-3p" used herein includes the hsa-miR-211-3p gene (miRBase Accession No. MIMAT0022694) described in SEQ ID NO: 21, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 350) having a hairpin-like structure is known as a precursor of "hsa-miR-211-3p".

The term "hsa-miR-2467-3p gene" or "hsa-miR-2467-3p" used herein includes the hsa-miR-2467-3p gene (miRBase Accession No. MIMAT0019953) described in SEQ ID NO: 22, a homolog or an ortholog of a different organism species, and the like. The hsa-miR-2467-3p gene can be obtained by a method described in Persson H et al., 2011, Cancer Res, Vol. 71, p. 78-86. Also, "hsa-mir-2467" (miRBase Accession No. MI0017432, SEQ ID NO: 351) having a hairpin-like structure is known as a precursor of "hsa-miR-2467-3p".

The term "hsa-miR-3122 gene" or "hsa-miR-3122" used herein includes the hsa-miR-3122 gene (miRBase Accession No. MIMAT0014984) described in SEQ ID NO: 23, a homolog or an ortholog of a different organism species, and the like. The hsa-miR-3122 gene can be obtained by a method described in Stark M S et al., 2010, PLoS One., Vol.

5, e9685. Also, "hsa-mir-3122" (miRBase Accession No. MI0014138, SEQ ID NO: 352) having a hairpin-like structure is known as a precursor of "hsa-miR-3122".

The term "hsa-miR-3141 gene" or "hsa-miR-3141" used herein includes the hsa-miR-3141 gene (miRBase Accession No. MIMAT0015010) described in SEQ ID NO: 24, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 353) having a hairpin-like structure is known as a precursor of "hsa-miR-3141".

The term "hsa-miR-3156-5p gene" or "hsa-miR-3156-5p" used herein includes the hsa-miR-3156-5p gene (miRBase Accession No. MIMAT0015030) described in SEQ ID NO: 25, a homolog or an ortholog of a different organism species, and the like. The hsa-miR-3156-5p gene can be obtained by a method described in Stark M S et al., 2010, PLoS One., Vol. 5, e9685. Also, "hsa-mir-3156-1, hsa-mir-3156-2, and hsa-mir-3156-3" (miRBase Accession Nos. MI0014184, MI0014230, and MI0014242, SEQ ID NOs: 354, 355, and 356) having a hairpin-like structure are known as precursors of "hsa-miR-3156-5p".

The term "hsa-miR-3158-5p gene" or "hsa-miR-3158-5p" used herein includes the hsa-miR-3158-5p gene (miRBase Accession No. MIMAT0019211) described in SEQ ID NO: 26, a homolog or an ortholog of a different organism species, and the like. The hsa-miR-3158-5p gene can be obtained by a method described in Creighton C J et al., 2010, PLoS One, Vol. 5, e9637. Also, "hsa-mir-3158-1 and hsa-mir-3158-2" (miRBase Accession Nos. MI0014186 and MI0014187, SEQ ID NOs: 357 and 358) having a hairpin-like structure are known as precursors of "hsa-miR-3158-5p".

The term "hsa-miR-3160-5p gene" or "hsa-miR-3160-5p" used herein includes the hsa-miR-3160-5p gene (miRBase Accession No. MIMAT0019212) described in SEQ ID NO: 27, a homolog or an ortholog of a different organism species, and the like. The hsa-miR-3160-5p gene can be obtained by a method described in Stark M S et al., 2010, PLoS One, Vol. 5, e9685. Also, "hsa-mir-3160-1 and hsa-mir-3160-2" (miRBase Accession Nos. MI0014189 and MI0014190, SEQ ID NOs: 359 and 360) having a hairpin-like structure are known as precursors of "hsa-miR-3160-5p".

The term "hsa-miR-3180-3p gene" or "hsa-miR-3180-3p" used herein includes the hsa-miR-3180-3p gene (miRBase Accession No. MIMAT0015058) described in SEQ ID NO: 28, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 361, 362, and 363) having a hairpin-like structure are known as precursors of "hsa-miR-3180-3p".

The term "hsa-miR-3191-3p gene" or "hsa-miR-3191-3p" used herein includes the hsa-miR-3191-3p gene (miRBase Accession No. MIMAT0015075) described in SEQ ID NO: 29, a homolog or an ortholog of a different organism species, and the like. The hsa-miR-3191-3p gene can be obtained by a method described in Stark M S et al., 2010, PLoS One, Vol. 5, e9685. Also, "hsa-mir-3191" (miRBase Accession No. MI0014236, SEQ ID NO: 364) having a hairpin-like structure is known as a precursor of "hsa-miR-3191-3p".

The term "hsa-miR-3194-3p gene" or "hsa-miR-3194-3p" used herein includes the hsa-miR-3194-3p gene (miRBase Accession No. MIMAT0019218) described in SEQ ID NO: 30, a homolog or an ortholog of a different organism species, and the like. The hsa-miR-3194-3p gene can be obtained by a method described in Stark M S et al., 2010, PLoS One, Vol. 5, e9685. Also, "hsa-mir-3194" (miRBase Accession No. MI0014239, SEQ ID NO: 365) having a hairpin-like structure is known as a precursor of "hsa-miR-3194-3p".

The term "hsa-miR-320b gene" or "hsa-miR-320b" used herein includes the hsa-miR-320b gene (miRBase Accession No. MIMAT0005792) described in SEQ ID NO: 31, a homolog or an ortholog of a different organism species, and the like. The hsa-miR-320b gene can be obtained by a method described in Berezikov E et al., 2006, Genome Res, Vol. 16, p. 1289-1298. Also, "hsa-mir-320b-1 and hsa-mir-320b-2" (miRBase Accession Nos. MI0003776 and MI0003839, SEQ ID NOs: 366 and 367) having a hairpin-like structure are known as precursors of "hsa-miR-320b".

The term "hsa-miR-328-5p gene" or "hsa-miR-328-5p" used herein includes the hsa-miR-328-5p gene (miRBase Accession No. MIMAT0026486) described in SEQ ID NO: 32, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. M10000804, SEQ ID NO: 368) having a hairpin-like structure is known as a precursor of "hsa-miR-328-5p".

The term "hsa-miR-3610 gene" or "hsa-miR-3610" used herein includes the hsa-miR-3610 gene (miRBase Accession No. MIMAT0017987) described in SEQ ID NO: 33, a homolog or an ortholog of a different organism species, and the like. The hsa-miR-3610 gene can be obtained by a method described in Witten D et al., 2010, BMC Biol., Vol. 8, 58. Also, "hsa-mir-3610" (miRBase Accession No. MI0016000, SEQ ID NO: 369) having a hairpin-like structure is known as a precursor of "hsa-miR-3610".

The term "hsa-miR-3619-3p gene" or "hsa-miR-3619-3p" used herein includes the hsa-miR-3619-3p gene (miRBase Accession No. MIMAT0019219) described in SEQ ID NO: 34, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 370) having a hairpin-like structure is known as a precursor of "hsa-miR-3619-3p".

The term "hsa-miR-3620-5p gene" or "hsa-miR-3620-5p" used herein includes the hsa-miR-3620-5p gene (miRBase Accession No. MIMAT0022967) described in SEQ ID NO: 35, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 371) having a hairpin-like structure is known as a precursor of "hsa-miR-3620-5p".

The term "hsa-miR-370-3p gene" or "hsa-miR-370-3p" used herein includes the hsa-miR-370-3p gene (miRBase Accession No. MIMAT0000722) described in SEQ ID NO: 36, a homolog or an ortholog of a different organism species, and the like. The hsa-miR-370-3p gene can be obtained by a method described in Suh M R et al., 2004, Dev Biol., Vol. 270, 488-498. Also, "hsa-mir-370" (miRBase Accession No. MI0000778, SEQ ID NO: 372) having a hairpin-like structure is known as a precursor of "hsa-miR-370-3p".

The term "hsa-miR-373-5p gene" or "hsa-miR-373-5p" used herein includes the hsa-miR-373-5p gene (miRBase Accession No. MIMAT0000725) described in SEQ ID NO: 37, a homolog or an ortholog of a different organism species, and the like. The hsa-miR-373-5p gene can be obtained by a method described in Suh M R et al., 2004, Dev Biol, Vol.

270, p. 488-498. Also, "hsa-mir-373" (miRBase Accession No. MI0000781, SEQ ID NO: 373) having a hairpin-like structure is known as a precursor of "hsa-miR-373-5p".

The term "hsa-miR-3917 gene" or "hsa-miR-3917" used herein includes the hsa-miR-3917 gene (miRBase Accession No. MIMAT0018191) described in SEQ ID NO: 38, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 374) having a hairpin-like structure is known as a precursor of "hsa-miR-3917".

The term "hsa-miR-3937 gene" or "hsa-miR-3937" used herein includes the hsa-miR-3937 gene (miRBase Accession No. MIMAT0018352) described in SEQ ID NO: 39, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 375) having a hairpin-like structure is known as a precursor of "hsa-miR-3937".

The term "hsa-miR-4259 gene" or "hsa-miR-4259" used herein includes the hsa-miR-4259 gene (miRBase Accession No. MIMAT0016880) described in SEQ ID NO: 40, a homolog or an ortholog of a different organism species, and the like. The hsa-miR-4259 gene can be obtained by a method described in Goff L A et al., 2009, PLoS One, Vol. 4, e7192. Also, "hsa-mir-4259" (miRBase Accession No. MI0015858, SEQ ID NO: 376) having a hairpin-like structure is known as a precursor of "hsa-miR-4259".

The term "hsa-miR-4281 gene" or "hsa-miR-4281" used herein includes the hsa-miR-4281 gene (miRBase Accession No. MIMAT0016907) described in SEQ ID NO: 41, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 377) having a hairpin-like structure is known as a precursor of "hsa-miR-4281".

The term "hsa-miR-4294 gene" or "hsa-miR-4294" used herein includes the hsa-miR-4294 gene (miRBase Accession No. MIMAT0016849) described in SEQ ID NO: 42, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827, SEQ ID NO: 378) having a hairpin-like structure is known as a precursor of "hsa-miR-4294".

The term "hsa-miR-4419b gene" or "hsa-miR-4419b" used herein includes the hsa-miR-4419b gene (miRBase Accession No. MIMAT0019034) described in SEQ ID NO: 43, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 379) having a hairpin-like structure is known as a precursor of "hsa-miR-4419b".

The term "hsa-miR-4428 gene" or "hsa-miR-4428" used herein includes the hsa-miR-4428 gene (miRBase Accession No. MIMAT0018943) described in SEQ ID NO: 44, a homolog or an ortholog of a different organism species, and the like. The hsa-miR-4428 gene can be obtained by a method described in Jima D D et al., 2010, Blood., Vol. 116, e118-e127. Also, "hsa-mir-4428" (miRBase Accession No. MI0016767, SEQ ID NO: 380) having a hairpin-like structure is known as a precursor of "hsa-miR-4428".

The term "hsa-miR-4429 gene" or "hsa-miR-4429" used herein includes the hsa-miR-4429 gene (miRBase Accession No. MIMAT0018944) described in SEQ ID NO: 45, a homolog or an ortholog of a different organism species, and the like. The hsa-miR-4429 gene can be obtained by a method described in Jima D D et al., 2010, Blood, Vol. 116, e118-e127. Also, "hsa-mir-4429" (miRBase Accession No. MI0016768, SEQ ID NO: 381) having a hairpin-like structure is known as a precursor of "hsa-miR-4429".

The term "hsa-miR-4433a-3p gene" or "hsa-miR-4433a-3p" used herein includes the hsa-miR-4433a-3p gene (miRBase Accession No. MIMAT0018949) described in SEQ ID NO: 46, a homolog or an ortholog of a different organism species, and the like. The hsa-miR-4433a-3p gene can be obtained by a method described in Jima D D et al., 2010, Blood, Vol. 116, e118-e127. Also, "hsa-mir-4433a" (miRBase Accession No. MI0016773, SEQ ID NO: 382) having a hairpin-like structure is known as a precursor of "hsa-miR-4433a-3p".

The term "hsa-miR-4447 gene" or "hsa-miR-4447" used herein includes the hsa-miR-4447 gene (miRBase Accession No. MIMAT0018966) described in SEQ ID NO: 47, a homolog or an ortholog of a different organism species, and the like. The hsa-miR-4447 gene can be obtained by a method described in Jima D D et al., 2010, Blood, Vol. 116, e118-e127. Also, "hsa-mir-4447" (miRBase Accession No. MI0016790, SEQ ID NO: 383) having a hairpin-like structure is known as a precursor of "hsa-miR-4447".

The term "hsa-miR-4449 gene" or "hsa-miR-4449" used herein includes the hsa-miR-4449 gene (miRBase Accession No. MIMAT0018968) described in SEQ ID NO: 48, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 384) having a hairpin-like structure is known as a precursor of "hsa-miR-4449".

The term "hsa-miR-4459 gene" or "hsa-miR-4459" used herein includes the hsa-miR-4459 gene (miRBase Accession No. MIMAT0018981) described in SEQ ID NO: 49, a homolog or an ortholog of a different organism species, and the like. The hsa-miR-4459 gene can be obtained by a method described in Jima D D et al., 2010, Blood, Vol. 116, e118-e127. Also, "hsa-miR-4459" (miRBase Accession No. MI0016805, SEQ ID NO: 385) having a hairpin-like structure is known as a precursor of "hsa-miR-4459".

The term "hsa-miR-4480 gene" or "hsa-miR-4480" used herein includes the hsa-miR-4480 gene (miRBase Accession No. MIMAT0019014) described in SEQ ID NO: 50, a homolog or an ortholog of a different organism species, and the like. The hsa-miR-4480 gene can be obtained by a method described in Jima D D et al., 2010, Blood, Vol. 116, e118-e127. Also, "hsa-mir-4480" (miRBase Accession No. MI0016841, SEQ ID NO: 386) having a hairpin-like structure is known as a precursor of "hsa-miR-4480".

The term "hsa-miR-4485-5p gene" or "hsa-miR-4485-5p" used herein includes the hsa-miR-4485-5p gene (miRBase Accession No. MIMAT0032116) described in SEQ ID NO: 51, a homolog or an ortholog of a different organism species, and the like. The hsa-miR-4485-5p gene can be obtained by a method described in Jima D D et al., 2010, Blood., Vol. 116, e118-e127. Also, "hsa-mir-4485" (miRBase Accession No. MI0016846, SEQ ID NO: 387) having a hairpin-like structure is known as a precursor of "hsa-miR-4485-5p".

The term "hsa-miR-4486 gene" or "hsa-miR-4486" used herein includes the hsa-miR-4486 gene (miRBase Accession No. MIMAT0019020) described in SEQ ID NO: 52, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 388) having a hairpin-like structure is known as a precursor of "hsa-miR-4486".

The term "hsa-miR-4488 gene" or "hsa-miR-4488" used herein includes the hsa-miR-4488 gene (miRBase Accession No. MIMAT0019022) described in SEQ ID NO: 53, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 389) having a hairpin-like structure is known as a precursor of "hsa-miR-4488".

The term "hsa-miR-4489 gene" or "hsa-miR-4489" used herein includes the hsa-miR-4489 gene (miRBase Accession No. MIMAT0019023) described in SEQ ID NO: 54, a homolog or an ortholog of a different organism species, and the like. The hsa-miR-4489 gene can be obtained by a method described in Jima D D et al., 2010, Blood., Vol. 116, e118-e127. Also, "hsa-mir-4489" (miRBase Accession No. MI0016850, SEQ ID NO: 390) having a hairpin-like structure is known as a precursor of "hsa-miR-4489".

The term "hsa-miR-4505 gene" or "hsa-miR-4505" used herein includes the hsa-miR-4505 gene (miRBase Accession No. MIMAT0019041) described in SEQ ID NO: 55, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 391) having a hairpin-like structure is known as a precursor of "hsa-miR-4505".

The term "hsa-miR-4513 gene" or "hsa-miR-4513" used herein includes the hsa-miR-4513 gene (miRBase Accession No. MIMAT0019050) described in SEQ ID NO: 56, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 392) having a hairpin-like structure is known as a precursor of "hsa-miR-4513".

The term "hsa-miR-4515 gene" or "hsa-miR-4515" used herein includes the hsa-miR-4515 gene (miRBase Accession No. MIMAT0019052) described in SEQ ID NO: 57, a homolog or an ortholog of a different organism species, and the like. The hsa-miR-4515 gene can be obtained by a method described in Jima D D et al., 2010, Blood, Vol. 116, e118-e127. Also, "hsa-mir-4515" (miRBase Accession No. MI0016881, SEQ ID NO: 393) having a hairpin-like structure is known as a precursor of "hsa-miR-4515".

The term "hsa-miR-4530 gene" or "hsa-miR-4530" used herein includes the hsa-miR-4530 gene (miRBase Accession No. MIMAT0019069) described in SEQ ID NO: 58, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 394) having a hairpin-like structure is known as a precursor of "hsa-miR-4530".

The term "hsa-miR-4535 gene" or "hsa-miR-4535" used herein includes the hsa-miR-4535 gene (miRBase Accession No. MIMAT0019075) described in SEQ ID NO: 59, a homolog or an ortholog of a different organism species, and the like. The hsa-miR-4535 gene can be obtained by a method described in Jima D D et al., 2010, Blood., Vol. 116, e118-e127. Also, "hsa-mir-4535" (miRBase Accession No. MI0016903, SEQ ID NO: 395) having a hairpin-like structure is known as a precursor of "hsa-miR-4535".

The term "hsa-miR-4635 gene" or "hsa-miR-4635" used herein includes the hsa-miR-4635 gene (miRBase Accession No. MIMAT0019692) described in SEQ ID NO: 60, a homolog or an ortholog of a different organism species, and the like. The hsa-miR-4635 gene can be obtained by a method described in Persson H et al., 2011, Cancer Res., Vol. 71, p. 78-86. Also, "hsa-mir-4635" (miRBase Accession No. MI0017262, SEQ ID NO: 396) having a hairpin-like structure is known as a precursor of "hsa-miR-4635".

The term "hsa-miR-4640-5p gene" or "hsa-miR-4640-5p" used herein includes the hsa-miR-4640-5p gene (miRBase Accession No. MIMAT0019699) described in SEQ ID NO: 61, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 397) having a hairpin-like structure is known as a precursor of "hsa-miR-4640-5p".

The term "hsa-miR-4646-5p gene" or "hsa-miR-4646-5p" used herein includes the hsa-miR-4646-5p gene (miRBase Accession No. MIMAT0019707) described in SEQ ID NO: 62, a homolog or an ortholog of a different organism species, and the like. The hsa-miR-4646-5p gene can be obtained by a method described in Persson H et al., 2011, Cancer Res., Vol. 71, p. 78-86. Also, "hsa-mir-4646" (miRBase Accession No. MI0017273, SEQ ID NO: 398) having a hairpin-like structure is known as a precursor of "hsa-miR-4646-5p".

The term "hsa-miR-4656 gene" or "hsa-miR-4656" used herein includes the hsa-miR-4656 gene (miRBase Accession No. MIMAT0019723) described in SEQ ID NO: 63, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 399) having a hairpin-like structure is known as a precursor of "hsa-miR-4656".

The term "hsa-miR-4663 gene" or "hsa-miR-4663" used herein includes the hsa-miR-4663 gene (miRBase Accession No. MIMAT0019735) described in SEQ ID NO: 64, a homolog or an ortholog of a different organism species, and the like. The hsa-miR-4663 gene can be obtained by a method described in Persson H. et al., 2011, Cancer Research, Vol. 71, p. 78-86. Also, "hsa-mir-4663" (miRBase Accession No. MI0017292, SEQ ID NO: 400) having a hairpin-like structure is known as a precursor of "hsa-miR-4663".

The term "hsa-miR-4665-5p gene" or "hsa-miR-4665-5p" used herein includes the hsa-miR-4665-5p gene (miRBase Accession No. MIMAT0019739) described in SEQ ID NO: 65, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 401) having a hairpin-like structure is known as a precursor of "hsa-miR-4665-5p".

The term "hsa-miR-4706 gene" or "hsa-miR-4706" used herein includes the hsa-miR-4706 gene (miRBase Accession No. MIMAT0019806) described in SEQ ID NO: 66, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 402) having a hairpin-like structure is known as a precursor of "hsa-miR-4706".

The term "hsa-miR-4707-5p gene" or "hsa-miR-4707-5p" used herein includes the hsa-miR-4707-5p gene (miRBase Accession No. MIMAT0019807) described in SEQ ID NO: 67, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 403) having a hairpin-like structure is known as a precursor of "hsa-miR-4707-5p".

The term "hsa-miR-4708-3p gene" or "hsa-miR-4708-3p" used herein includes the hsa-miR-4708-3p gene (miRBase Accession No. MIMAT0019810) described in SEQ ID NO: 68, a homolog or an ortholog of a different organism species, and the like. The hsa-miR-4708-3p gene can be obtained by a method described in Persson H et al., 2011, Cancer Res, Vol. 71, p. 78-86. Also, "hsa-mir-4708" (miRBase Accession No. MI0017341, SEQ ID NO: 404) having a hairpin-like structure is known as a precursor of "hsa-miR-4708-3p".

The term "hsa-miR-4710 gene" or "hsa-miR-4710" used herein includes the hsa-miR-4710 gene (miRBase Accession No. MIMAT0019815) described in SEQ ID NO: 69, a homolog or an ortholog of a different organism species, and the like. The hsa-miR-4710 gene can be obtained by a method described in Persson H et al., 2011, Cancer Res, Vol. 71, p. 78-86. Also, "hsa-mir-4710" (miRBase Accession No. MI0017344, SEQ ID NO: 405) having a hairpin-like structure is known as a precursor of "hsa-miR-4710".

The term "hsa-miR-4718 gene" or "hsa-miR-4718" used herein includes the hsa-miR-4718 gene (miRBase Accession No. MIMAT0019831) described in SEQ ID NO: 70, a homolog or an ortholog of a different organism species, and the like. The hsa-miR-4718 gene can be obtained by a method described in Persson H et al., 2011, Cancer Res, Vol. 71, p. 78-86. Also, "hsa-mir-4718" (miRBase Accession No. MI0017353, SEQ ID NO: 406) having a hairpin-like structure is known as a precursor of "hsa-miR-4718".

The term "hsa-miR-4722-5p gene" or "hsa-miR-4722-5p" used herein includes the hsa-miR-4722-5p gene (miRBase Accession No. MIMAT0019836) described in SEQ ID NO: 71, a homolog or an ortholog of a different organism species, and the like. The hsa-miR-4722-5p gene can be obtained by a method described in Persson H et al., 2011, Cancer Res, Vol. 71, p. 78-86. Also, "hsa-mir-4722" (miRBase Accession No. MI0017357, SEQ ID NO: 407) having a hairpin-like structure is known as a precursor of "hsa-miR-4722-5p".

The term "hsa-miR-4727-3p gene" or "hsa-miR-4727-3p" used herein includes the hsa-miR-4727-3p gene (miRBase Accession No. MIMAT0019848) described in SEQ ID NO: 72, a homolog or an ortholog of a different organism species, and the like. The hsa-miR-4727-3p gene can be obtained by a method described in Persson H et al., 2011, Cancer Res, Vol. 71, p. 78-86. Also, "hsa-mir-4727" (miRBase Accession No. MI0017364, SEQ ID NO: 408) having a hairpin-like structure is known as a precursor of "hsa-miR-4727-3p".

The term "hsa-miR-4730 gene" or "hsa-miR-4730" used herein includes the hsa-miR-4730 gene (miRBase Accession No. MIMAT0019852) described in SEQ ID NO: 73, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 409) having a hairpin-like structure is known as a precursor of "hsa-miR-4730".

The term "hsa-miR-4734 gene" or "hsa-miR-4734" used herein includes the hsa-miR-4734 gene (miRBase Accession No. MIMAT0019859) described in SEQ ID NO: 74, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 410) having a hairpin-like structure is known as a precursor of "hsa-miR-4734".

The term "hsa-miR-4740-5p gene" or "hsa-miR-4740-5p" used herein includes the hsa-miR-4740-5p gene (miRBase Accession No. MIMAT0019869) described in SEQ ID NO: 75, a homolog or an ortholog of a different organism species, and the like. The hsa-miR-4740-5p gene can be obtained by a method described in Persson H et al., 2011, Cancer Res, Vol. 71, p. 78-86. Also, "hsa-mir-4740" (miRBase Accession No. MI0017378, SEQ ID NO: 411) having a hairpin-like structure is known as a precursor of "hsa-miR-4740-5p".

The term "hsa-miR-4747-3p gene" or "hsa-miR-4747-3p" used herein includes the hsa-miR-4747-3p gene (miRBase Accession No. MIMAT0019883) described in SEQ ID NO: 76, a homolog or an ortholog of a different organism species, and the like. The hsa-miR-4747-3p gene can be obtained by a method described in Persson H et al., 2011, Cancer Res, Vol. 71, p. 78-86. Also, "hsa-mir-4747" (miRBase Accession No. MI0017386, SEQ ID NO: 412) having a hairpin-like structure is known as a precursor of "hsa-miR-4747-3p".

The term "hsa-miR-4749-5p gene" or "hsa-miR-4749-5p" used herein includes the hsa-miR-4749-5p gene (miRBase Accession No. MIMAT0019885) described in SEQ ID NO: 77, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 413) having a hairpin-like structure is known as a precursor of "hsa-miR-4749-5p".

The term "hsa-miR-4755-3p gene" or "hsa-miR-4755-3p" used herein includes the hsa-miR-4755-3p gene (miRBase Accession No. MIMAT0019896) described in SEQ ID NO: 78, a homolog or an ortholog of a different organism species, and the like. The hsa-miR-4755-3p gene can be obtained by a method described in Persson H. et al., 2011, Cancer Research, Vol. 71, p. 78-86. Also, "hsa-mir-4755" (miRBase Accession No. MI0017395, SEQ ID NO: 414) having a hairpin-like structure is known as a precursor of "hsa-miR-4755-3p".

The term "hsa-miR-4763-5p gene" or "hsa-miR-4763-5p" used herein includes the hsa-miR-4763-5p gene (miRBase Accession No. MIMAT0019912) described in SEQ ID NO: 79, a homolog or an ortholog of a different organism species, and the like. The hsa-miR-4763-5p gene can be obtained by a method described in Persson H et al., 2011, Cancer Res., Vol. 71, p. 78-86. Also, "hsa-mir-4763" (miRBase Accession No. MI0017404, SEQ ID NO: 415) having a hairpin-like structure is known as a precursor of "hsa-miR-4763-5p".

The term "hsa-miR-4787-3p gene" or "hsa-miR-4787-3p" used herein includes the hsa-miR-4787-3p gene (miRBase Accession No. MIMAT0019957) described in SEQ ID NO: 80, a homolog or an ortholog of a different organism species, and the like. The hsa-miR-4787-3p gene can be obtained by a method described in Persson H et al., 2011, Cancer Res, Vol. 71, p. 78-86. Also, "hsa-mir-4787" (miRBase Accession No. MI0017434, SEQ ID NO: 416) having a hairpin-like structure is known as a precursor of "hsa-miR-4787-3p".

The term "hsa-miR-5008-5p gene" or "hsa-miR-5008-5p" used herein includes the hsa-miR-5008-5p gene (miRBase Accession No. MIMAT0021039) described in SEQ ID NO: 81, a homolog or an ortholog of a different organism species, and the like. The hsa-miR-5008-5p gene can be obtained by a method described in Hansen T B et al., 2011, RNA Biol, Vol. 8, p. 378-383. Also, "hsa-mir-5008" (miRBase Accession No. MI0017876, SEQ ID NO: 417) having a hairpin-like structure is known as a precursor of "hsa-miR-5008-5p".

The term "hsa-miR-5010-5p gene" or "hsa-miR-5010-5p" used herein includes the hsa-miR-5010-5p gene (miRBase Accession No. MIMAT0021043) described in SEQ ID NO: 82, a homolog or an ortholog of a different organism species, and the like. The hsa-miR-5010-5p gene can be obtained by a method described in Hansen T B et al., 2011, RNA Biol, Vol. 8, p. 378-383. Also, "hsa-mir-5010" (miRBase Accession No. MI0017878, SEQ ID NO: 418) having a hairpin-like structure is known as a precursor of "hsa-miR-5010-5p".

The term "hsa-miR-504-3p gene" or "hsa-miR-504-3p" used herein includes the hsa-miR-504-3p gene (miRBase Accession No. MIMAT0026612) described in SEQ ID NO: 83, a homolog or an ortholog of a different organism species, and the like. The hsa-miR-504-3p gene can be obtained by a method described in Bentwich I et al., 2005, Nat Genet, Vol. 37, p. 766-770. Also, "hsa-mir-504" (miRBase Accession No. MI0003189, SEQ ID NO: 419) having a hairpin-like structure is known as a precursor of "hsa-miR-504-3p".

The term "hsa-miR-5090 gene" or "hsa-miR-5090" used herein includes the hsa-miR-5090 gene (miRBase Accession No. MIMAT0021082) described in SEQ ID NO: 84, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 420) having a hairpin-like structure is known as a precursor of "hsa-miR-5090".

The term "hsa-miR-5100 gene" or "hsa-miR-5100" used herein includes the hsa-miR-5100 gene (miRBase Accession No. MIMAT0022259) described in SEQ ID NO: 85, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 421) having a hairpin-like structure is known as a precursor of "hsa-miR-5100".

The term "hsa-miR-5196-5p gene" or "hsa-miR-5196-5p" used herein includes the hsa-miR-5196-5p gene (miRBase Accession No. MIMAT0021128) described in SEQ ID NO: 86, a homolog or an ortholog of a different organism species, and the like. The hsa-miR-5196-5p gene can be obtained by a method described in Schotte D et al., 2011, Leukemia, Vol. 25, p. 1389-1399. Also, "hsa-mir-5196" (miRBase Accession No. MI0018175, SEQ ID NO: 422) having a hairpin-like structure is known as a precursor of "hsa-miR-5196-5p".

The term "hsa-miR-551b-5p gene" or "hsa-miR-551b-5p" used herein includes the hsa-miR-551b-5p gene (miRBase Accession No. MIMAT0004794) described in SEQ ID NO: 87, a homolog or an ortholog of a different organism species, and the like. The hsa-miR-551b-5p gene can be obtained by a method described in Cummins J M et al., 2006, Proc Natl Acad Sci USA, Vol. 103, p. 3687-3692. Also, "hsa-mir-551b" (miRBase Accession No. MI0003575, SEQ ID NO: 423) having a hairpin-like structure is known as a precursor of "hsa-miR-551b-5p".

The term "hsa-miR-557 gene" or "hsa-miR-557" used herein includes the hsa-miR-557 gene (miRBase Accession No. MIMAT0003221) described in SEQ ID NO: 88, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 424) having a hairpin-like structure is known as a precursor of "hsa-miR-557".

The term "hsa-miR-5787 gene" or "hsa-miR-5787" used herein includes the hsa-miR-5787 gene (miRBase Accession No. MIMAT0023252) described in SEQ ID NO: 89, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 425) having a hairpin-like structure is known as a precursor of "hsa-miR-5787".

The term "hsa-miR-6090 gene" or "hsa-miR-6090" used herein includes the hsa-miR-6090 gene (miRBase Accession No. MIMAT0023715) described in SEQ ID NO: 90, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 426) having a hairpin-like structure is known as a precursor of "hsa-miR-6090".

The term "hsa-miR-6124 gene" or "hsa-miR-6124" used herein includes the hsa-miR-6124 gene (miRBase Accession No. MIMAT0024597) described in SEQ ID NO: 91, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 427) having a hairpin-like structure is known as a precursor of "hsa-miR-6124".

The term "hsa-miR-6132 gene" or "hsa-miR-6132" used herein includes the hsa-miR-6132 gene (miRBase Accession No. MIMAT0024616) described in SEQ ID NO: 92, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 428) having a hairpin-like structure is known as a precursor of "hsa-miR-6132".

The term "hsa-miR-6510-5p gene" or "hsa-miR-6510-5p" used herein includes the hsa-miR-6510-5p gene (miRBase Accession No. MIMAT0025476) described in SEQ ID NO: 93, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 429) having a hairpin-like structure is known as a precursor of "hsa-miR-6510-5p".

The term "hsa-miR-6511b-5p gene" or "hsa-miR-6511b-5p" used herein includes the hsa-miR-6511b-5p gene (miRBase Accession No. MIMAT0025847) described in SEQ ID NO: 94, a homolog or an ortholog of a different organism species, and the like. The hsa-miR-6511b-5p gene can be obtained by a method described in Li Y et al., 2012, Gene, Vol. 497, p. 330-335. Also, "hsa-mir-6511b-1 and hsa-mir-6511b-2" (miRBase Accession Nos. MI0022552 and MI0023431, SEQ ID NOs: 430 and 431) having a hairpin-like structure are known as precursors of "hsa-miR-6511b-5p".

The term "hsa-miR-6515-3p gene" or "hsa-miR-6515-3p" used herein includes the hsa-miR-6515-3p gene (miRBase Accession No. MIMAT0025487) described in SEQ ID NO: 95, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 432) having a hairpin-like structure is known as a precursor of "hsa-miR-6515-3p".

The term "hsa-miR-654-5p gene" or "hsa-miR-654-5p" used herein includes the hsa-miR-654-5p gene (miRBase Accession No. MIMAT0003330) described in SEQ ID NO: 96, a homolog or an ortholog of a different organism species, and the like. The hsa-miR-654-5p gene can be obtained by a method described in Cummins J M et al., 2006, Proc Natl Acad Sci USA., Vol. 103, p. 3687-3692. Also, "hsa-mir-654" (miRBase Accession No. MI0003676, SEQ ID NO: 433) having a hairpin-like structure is known as a precursor of "hsa-miR-654-5p".

The term "hsa-miR-658 gene" or "hsa-miR-658" used herein includes the hsa-miR-658 gene (miRBase Accession No. MIMAT0003336) described in SEQ ID NO: 97, a homolog or an ortholog of a different organism species, and the like. The hsa-miR-658 gene can be obtained by a method described in Cummins J M et al., 2006, Proc Natl Acad Sci USA, Vol. 103, p. 3687-3692. Also, "hsa-mir-658" (miRBase Accession No. MI0003682, SEQ ID NO: 434) having a hairpin-like structure is known as a precursor of "hsa-miR-658".

The term "hsa-miR-668-5p gene" or "hsa-miR-668-5p" used herein includes the hsa-miR-668-5p gene (miRBase Accession No. MIMAT0026636) described in SEQ ID NO: 98, a homolog or an ortholog of a different organism species, and the like. The hsa-miR-668-5p gene can be obtained by a method described in Berezikov E et al., 2006, Genome Res., Vol. 16, p. 1289-1298. Also, "hsa-mir-668" (miRBase Accession No. MI0003761, SEQ ID NO: 435) having a hairpin-like structure is known as a precursor of "hsa-miR-668-5p".

The term "hsa-miR-6722-5p gene" or "hsa-miR-6722-5p" used herein includes the hsa-miR-6722-5p gene (miRBase Accession No. MIMAT0025853) described in SEQ ID NO: 99, a homolog or an ortholog of a different organism species, and the like. The hsa-miR-6722-5p gene can be obtained by a method described in Li Y et al., 2012, Gene., Vol. 497, p. 330-335. Also, "hsa-mir-6722" (miRBase Accession No. MI0022557, SEQ ID NO: 436) having a hairpin-like structure is known as a precursor of "hsa-miR-6722-5p".

The term "hsa-miR-6724-5p gene" or "hsa-miR-6724-5p" used herein includes the hsa-miR-6724-5p gene (miRBase Accession No. MIMAT0025856) described in SEQ ID NO: 100, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 437) having a hairpin-like structure is known as a precursor of "hsa-miR-6724-5p".

The term "hsa-miR-6729-3p gene" or "hsa-miR-6729-3p" used herein includes the hsa-miR-6729-3p gene (miRBase Accession No. MIMAT0027360) described in SEQ ID NO: 101, a homolog or an ortholog of a different organism species, and the like. The hsa-miR-6729-3p gene can be obtained by a method described in Ladewig E et al., 2012, Genome Res, Vol. 22, p. 1634-1645. Also, "hsa-mir-6729" (miRBase Accession No. MI0022574, SEQ ID NO: 438) having a hairpin-like structure is known as a precursor of "hsa-miR-6729-3p".

The term "hsa-miR-6737-5p gene" or "hsa-miR-6737-5p" used herein includes the hsa-miR-6737-5p gene (miRBase Accession No. MIMAT0027375) described in SEQ ID NO: 102, a homolog or an ortholog of a different organism species, and the like. The hsa-miR-6737-5p gene can be obtained by a method described in Ladewig E et al., 2012, Genome Res, Vol. 22, p. 1634-1645. Also, "hsa-mir-6737" (miRBase Accession No. MI0022582, SEQ ID NO: 439) having a hairpin-like structure is known as a precursor of "hsa-miR-6737-5p".

The term "hsa-miR-6756-5p gene" or "hsa-miR-6756-5p" used herein includes the hsa-miR-6756-5p gene (miRBase Accession No. MIMAT0027412) described in SEQ ID NO: 103, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 440) having a hairpin-like structure is known as a precursor of "hsa-miR-6756-5p".

The term "hsa-miR-6762-5p gene" or "hsa-miR-6762-5p" used herein includes the hsa-miR-6762-5p gene (miRBase Accession No. MIMAT0027424) described in SEQ ID NO: 104, a homolog or an ortholog of a different organism species, and the like. The hsa-miR-6762-5p gene can be obtained by a method described in Ladewig E et al., 2012, Genome Res, Vol. 22, p. 1634-1645. Also, "hsa-mir-6762" (miRBase Accession No. MI0022607, SEQ ID NO: 441) having a hairpin-like structure is known as a precursor of "hsa-miR-6762-5p".

The term "hsa-miR-6763-3p gene" or "hsa-miR-6763-3p" used herein includes the hsa-miR-6763-3p gene (miRBase Accession No. MIMAT0027427) described in SEQ ID NO: 105, a homolog or an ortholog of a different organism species, and the like. The hsa-miR-6763-3p gene can be obtained by a method described in Ladewig E et al., 2012, Genome Res, Vol. 22, p. 1634-1645. Also, "hsa-mir-6763" (miRBase Accession No. MI0022608, SEQ ID NO: 442) having a hairpin-like structure is known as a precursor of "hsa-miR-6763-3p".

The term "hsa-miR-6766-5p gene" or "hsa-miR-6766-5p" used herein includes the hsa-miR-6766-5p gene (miRBase Accession No. MIMAT0027432) described in SEQ ID NO: 106, a homolog or an ortholog of a different organism species, and the like. The hsa-miR-6766-5p gene can be obtained by a method described in Ladewig E et al., 2012, Genome Res, Vol. 22, p. 1634-1645. Also, "hsa-mir-6766" (miRBase Accession No. MI0022611, SEQ ID NO: 443) having a hairpin-like structure is known as a precursor of "hsa-miR-6766-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 107, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 444) having a hairpin-like structure is known as a precursor of "hsa-miR-6769a-5p".

The term "hsa-miR-6771-5p gene" or "hsa-miR-6771-5p" used herein includes the hsa-miR-6771-5p gene (miRBase Accession No. MIMAT0027442) described in SEQ ID NO: 108, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771"

(miRBase Accession No. MI0022616, SEQ ID NO: 445) having a hairpin-like structure is known as a precursor of "hsa-miR-6771-5p".

The term "hsa-miR-6786-5p gene" or "hsa-miR-6786-5p" used herein includes the hsa-miR-6786-5p gene (miRBase Accession No. MIMAT0027472) described in SEQ ID NO: 109, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 446) having a hairpin-like structure is known as a precursor of "hsa-miR-6786-5p".

The term "hsa-miR-6789-5p gene" or "hsa-miR-6789-5p" used herein includes the hsa-miR-6789-5p gene (miRBase Accession No. MIMAT0027478) described in SEQ ID NO: 110, a homolog or an ortholog of a different organism species, and the like. The hsa-miR-6789-5p gene can be obtained by a method described in Ladewig E et al., 2012, Genome Res., No. 22, p. 1634-1645. Also, "hsa-mir-6789" (miRBase Accession No. MI0022634, SEQ ID NO: 447) having a hairpin-like structure is known as a precursor of "hsa-miR-6789-5p".

The term "hsa-miR-6794-5p gene" or "hsa-miR-6794-5p" used herein includes the hsa-miR-6794-5p gene (miRBase Accession No. MIMAT0027488) described in SEQ ID NO: 111, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 448) having a hairpin-like structure is known as a precursor of "hsa-miR-6794-5p".

The term "hsa-miR-6796-3p gene" or "hsa-miR-6796-3p" used herein includes the hsa-miR-6796-3p gene (miRBase Accession No. MIMAT0027493) described in SEQ ID NO: 112, a homolog or an ortholog of a different organism species, and the like. The hsa-miR-6796-3p gene can be obtained by a method described in Ladewig E et al., 2012, Genome Res, Vol. 22, p. 1634-1645. Also, "hsa-mir-6796" (miRBase Accession No. MI0022641, SEQ ID NO: 449) having a hairpin-like structure is known as a precursor of "hsa-miR-6796-3p".

The term "hsa-miR-6797-5p gene" or "hsa-miR-6797-5p" used herein includes the hsa-miR-6797-5p gene (miRBase Accession No. MIMAT0027494) described in SEQ ID NO: 113, a homolog or an ortholog of a different organism species, and the like. The hsa-miR-6797-5p gene can be obtained by a method described in Ladewig E et al., 2012, Genome Res, Vol. 22, p. 1634-1645. Also, "hsa-mir-6797" (miRBase Accession No. MI0022642, SEQ ID NO: 450) having a hairpin-like structure is known as a precursor of "hsa-miR-6797-5p".

The term "hsa-miR-6800-3p gene" or "hsa-miR-6800-3p" used herein includes the hsa-miR-6800-3p gene (miRBase Accession No. MIMAT0027501) described in SEQ ID NO: 114, a homolog or an ortholog of a different organism species, and the like. The hsa-miR-6800-3p gene can be obtained by a method described in Ladewig E et al., 2012, Genome Res, Vol. 22, p. 1634-1645. Also, "hsa-mir-6800" (miRBase Accession No. MI0022645, SEQ ID NO: 451) having a hairpin-like structure is known as a precursor of "hsa-miR-6800-3p".

The term "hsa-miR-6802-5p gene" or "hsa-miR-6802-5p" used herein includes the hsa-miR-6802-5p gene (miRBase Accession No. MIMAT0027504) described in SEQ ID NO: 115, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 452) having a hairpin-like structure is known as a precursor of "hsa-miR-6802-5p".

The term "hsa-miR-6803-5p gene" or "hsa-miR-6803-5p" used herein includes the hsa-miR-6803-5p gene (miRBase Accession No. MIMAT0027506) described in SEQ ID NO: 116, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 453) having a hairpin-like structure is known as a precursor of "hsa-miR-6803-5p".

The term "hsa-miR-6805-3p gene" or "hsa-miR-6805-3p" used herein includes the hsa-miR-6805-3p gene (miRBase Accession No. MIMAT0027511) described in SEQ ID NO: 117, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 454) having a hairpin-like structure is known as a precursor of "hsa-miR-6805-3p".

The term "hsa-miR-6805-5p gene" or "hsa-miR-6805-5p" used herein includes the hsa-miR-6805-5p gene (miRBase Accession No. MIMAT0027510) described in SEQ ID NO: 118, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 454) having a hairpin-like structure is known as a precursor of "hsa-miR-6805-5p".

The term "hsa-miR-6807-5p gene" or "hsa-miR-6807-5p" used herein includes the hsa-miR-6807-5p gene (miRBase Accession No. MIMAT0027514) described in SEQ ID NO: 119, a homolog or an ortholog of a different organism species, and the like. The hsa-miR-6807-5p gene can be obtained by a method described in Ladewig E et al., 2012, Genome Res, Vol. 22, p. 1634-1645. Also, "hsa-mir-6807" (miRBase Accession No. MI0022652, SEQ ID NO: 455) having a hairpin-like structure is known as a precursor of "hsa-miR-6807-5p".

The term "hsa-miR-6812-5p gene" or "hsa-miR-6812-5p" used herein includes the hsa-miR-6812-5p gene (miRBase Accession No. MIMAT0027524) described in SEQ ID NO: 120, a homolog or an ortholog of a different organism species, and the like. The hsa-miR-6812-5p gene can be obtained by a method described in Ladewig E et al., 2012, Genome Res, Vol. 22, p. 1634-1645. Also, "hsa-mir-6812" (miRBase Accession No. MI0022657, SEQ ID NO: 456) having a hairpin-like structure is known as a precursor of "hsa-miR-6812-5p".

The term "hsa-miR-6819-5p gene" or "hsa-miR-6819-5p" used herein includes the hsa-miR-6819-5p gene (miRBase Accession No. MIMAT0027538) described in SEQ ID NO: 121, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 457) having a hairpin-like structure is known as a precursor of "hsa-miR-6819-5p".

The term "hsa-miR-6822-5p gene" or "hsa-miR-6822-5p" used herein includes the hsa-miR-6822-5p gene (miRBase Accession No. MIMAT0027544) described in SEQ ID NO: 122, a homolog or an ortholog of a different organism species, and the like. The hsa-miR-6822-5p gene can be obtained by a method described in Ladewig E et al., 2012, Genome Res, Vol. 22, p. 1634-1645. Also, "hsa-mir-6822" (miRBase Accession No. MI0022667, SEQ ID NO: 458) having a hairpin-like structure is known as a precursor of "hsa-miR-6822-5p".

The term "hsa-miR-6824-5p gene" or "hsa-miR-6824-5p" used herein includes the hsa-miR-6824-5p gene (miRBase Accession No. MIMAT0027548) described in SEQ ID NO: 123, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 459) having a hairpin-like structure is known as a precursor of "hsa-miR-6824-5p".

The term "hsa-miR-6826-5p gene" or "hsa-miR-6826-5p" used herein includes the hsa-miR-6826-5p gene (miRBase Accession No. MIMAT0027552) described in SEQ ID NO: 124, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 460) having a hairpin-like structure is known as a precursor of "hsa-miR-6826-5p".

The term "hsa-miR-6850-5p gene" or "hsa-miR-6850-5p" used herein includes the hsa-miR-6850-5p gene (miRBase Accession No. MIMAT0027600) described in SEQ ID NO: 125, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 461) having a hairpin-like structure is known as a precursor of "hsa-miR-6850-5p".

The term "hsa-miR-6858-5p gene" or "hsa-miR-6858-5p" used herein includes the hsa-miR-6858-5p gene (miRBase Accession No. MIMAT0027616) described in SEQ ID NO: 126, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 462) having a hairpin-like structure is known as a precursor of "hsa-miR-6858-5p".

The term "hsa-miR-6861-5p gene" or "hsa-miR-6861-5p" used herein includes the hsa-miR-6861-5p gene (miRBase Accession No. MIMAT0027623) described in SEQ ID NO: 127, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 463) having a hairpin-like structure is known as a precursor of "hsa-miR-6861-5p".

The term "hsa-miR-6880-3p gene" or "hsa-miR-6880-3p" used herein includes the hsa-miR-6880-3p gene (miRBase Accession No. MIMAT0027661) described in SEQ ID NO: 128, a homolog or an ortholog of a different organism species, and the like. The hsa-miR-6880-3p gene can be obtained by a method described in Ladewig E et al., 2012, Genome Res, Vol. 22, p. 1634-1645. Also, "hsa-mir-6880" (miRBase Accession No. MI0022727, SEQ ID NO: 464) having a hairpin-like structure is known as a precursor of "hsa-miR-6880-3p".

The term "hsa-miR-7107-5p gene" or "hsa-miR-7107-5p" used herein includes the hsa-miR-7107-5p gene (miRBase Accession No. MIMAT0028111) described in SEQ ID NO: 129, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 465) having a hairpin-like structure is known as a precursor of "hsa-miR-7107-5p".

The term "hsa-miR-7109-5p gene" or "hsa-miR-7109-5p" used herein includes the hsa-miR-7109-5p gene (miRBase Accession No. MIMAT0028115) described in SEQ ID NO: 130, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 466) having a hairpin-like structure is known as a precursor of "hsa-miR-7109-5p".

The term "hsa-miR-7114-5p gene" or "hsa-miR-7114-5p" used herein includes the hsa-miR-7114-5p gene (miRBase Accession No. MIMAT0028125) described in SEQ ID NO: 131, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 467) having a hairpin-like structure is known as a precursor of "hsa-miR-7114-5p".

The term "hsa-miR-7704 gene" or "hsa-miR-7704" used herein includes the hsa-miR-7704 gene (miRBase Accession No. MIMAT0030019) described in SEQ ID NO: 132, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 468) having a hairpin-like structure is known as a precursor of "hsa-miR-7704".

The term "hsa-miR-7846-3p gene" or "hsa-miR-7846-3p" used herein includes the hsa-miR-7846-3p gene (miRBase Accession No. MIMAT0030421) described in SEQ ID NO: 133, a homolog or an ortholog of a different organism species, and the like. The hsa-miR-7846-3p gene can be obtained by a method described in Ple H et al., 2012, PLoS One., Vol. 7, e50746. Also, "hsa-mir-7846" (miRBase Accession No. MI0025516, SEQ ID NO: 469) having a hairpin-like structure is known as a precursor of "hsa-miR-7846-3p".

The term "hsa-miR-8052 gene" or "hsa-miR-8052" used herein includes the hsa-miR-8052 gene (miRBase Accession No. MIMAT0030979) described in SEQ ID NO: 134, a homolog or an ortholog of a different organism species, and the like. The hsa-miR-8052 gene can be obtained by a method described in Wang H J et al., 2013, Shock., Vol. 39, 480-487. Also, "hsa-mir-8052" (miRBase Accession No. MI0025888, SEQ ID NO: 470) having a hairpin-like structure is known as a precursor of "hsa-miR-8052".

The term "hsa-miR-8060 gene" or "hsa-miR-8060" used herein includes the hsa-miR-8060 gene (miRBase Accession No. MIMAT0030987) described in SEQ ID NO: 135, a homolog or an ortholog of a different organism species, and the like. The hsa-miR-8060 gene can be obtained by a method described in Wang H J et al., 2013, Shock., Vol. 39, 480-487. Also, "hsa-mir-8060" (miRBase Accession No. MI0025896, SEQ ID NO: 471) having a hairpin-like structure is known as a precursor of "hsa-miR-8060".

The term "hsa-miR-8071 gene" or "hsa-miR-8071" used herein includes the hsa-miR-8071 gene (miRBase Accession No. MIMAT0030998) described in SEQ ID NO: 136, a homolog or an ortholog of a different organism species, and the like. The hsa-miR-8071 gene can be obtained by a method described in Wang H J et al., 2013, Shock, Vol. 39, p. 480-487. Also, "hsa-mir-8071-1 and hsa-mir-8071-2" (miRBase Accession Nos. MI0025907 and M10026417, SEQ ID NOs: 472 and 473) having a hairpin-like structure are known as precursors of "hsa-miR-8071".

The term "hsa-miR-8073 gene" or "hsa-miR-8073" used herein includes the hsa-miR-8073 gene (miRBase Accession No. MIMAT0031000) described in SEQ ID NO: 137, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 474) having a hairpin-like structure is known as a precursor of "hsa-miR-8073".

The term "hsa-miR-874-5p gene" or "hsa-miR-874-5p" used herein includes the hsa-miR-874-5p gene (miRBase Accession No. MIMAT0026718) described in SEQ ID NO: 138, a homolog or an ortholog of a different organism species, and the like. The hsa-miR-874-5p gene can be obtained by a method described in Landgraf P et al., 2007, Cell., Vol. 129, p. 1401-1414. Also, "hsa-mir-874" (miRBase Accession No. MI0005532, SEQ ID NO: 475) having a hairpin-like structure is known as a precursor of "hsa-miR-874-5p".

The term "hsa-miR-204-3p gene" or "hsa-miR-204-3p" used herein includes the hsa-miR-204-3p gene (miRBase Accession No. MIMAT0022693) described in SEQ ID NO: 139, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 476) having a hairpin-like structure is known as a precursor of "hsa-miR-204-3p".

The term "hsa-miR-3154 gene" or "hsa-miR-3154" used herein includes the hsa-miR-3154 gene (miRBase Accession No. MIMAT0015028) described in SEQ ID NO: 140, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 477) having a hairpin-like structure is known as a precursor of "hsa-miR-3154".

The term "hsa-miR-3960 gene" or "hsa-miR-3960" used herein includes the hsa-miR-3960 gene (miRBase Accession No. MIMAT0019337) described in SEQ ID NO: 141, a homolog or an ortholog of a different organism species, and the like. The hsa-miR-3960 gene can be obtained by a method described in Hu R et al., 2011, J Biol Chem, Vol. 286, p. 12328-12339. Also, "hsa-mir-3960" (miRBase Accession No. MI0016964, SEQ ID NO: 478) having a hairpin-like structure is known as a precursor of "hsa-miR-3960".

The term "hsa-miR-4433a-5p gene" or "hsa-miR-4433a-5p" used herein includes the hsa-miR-4433a-5p gene (miRBase Accession No. MIMAT0020956) described in SEQ ID NO: 142, a homolog or an ortholog of a different organism species, and the like. The hsa-miR-4433a-5p gene can be obtained by a method described in Jima D D et al., 2010, Blood, Vol. 116, e118-e127. Also, "hsa-mir-4433a" (miRBase Accession No. MI0016773, SEQ ID NO: 382) having a hairpin-like structure is known as a precursor of "hsa-miR-4433a-5p".

The term "hsa-miR-4455 gene" or "hsa-miR-4455" used herein includes the hsa-miR-4455 gene (miRBase Accession No. MIMAT0018977) described in SEQ ID NO: 143, a homolog or an ortholog of a different organism species, and the like. The hsa-miR-4455 gene can be obtained by a method described in Jima D D et al., 2010, Blood., Vol. 116, e118-e127. Also, "hsa-mir-4455" (miRBase Accession No. MI0016801, SEQ ID NO: 479) having a hairpin-like structure is known as a precursor of "hsa-miR-4455".

The term "hsa-miR-4462 gene" or "hsa-miR-4462" used herein includes the hsa-miR-4462 gene (miRBase Accession No. MIMAT0018986) described in SEQ ID NO: 144, a homolog or an ortholog of a different organism species, and the like. The hsa-miR-4462 gene can be obtained by a method described in Jima D D et al., 2010, Blood., Vol. 116, e118-e127. Also, "hsa-mir-4462" (miRBase Accession No. M10016810, SEQ ID NO: 480) having a hairpin-like structure is known as a precursor of "hsa-miR-4462".

The term "hsa-miR-4476 gene" or "hsa-miR-4476" used herein includes the hsa-miR-4476 gene (miRBase Accession No. MIMAT0019003) described in SEQ ID NO: 145, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 481) having a hairpin-like structure is known as a precursor of "hsa-miR-4476".

The term "hsa-miR-4508 gene" or "hsa-miR-4508" used herein includes the hsa-miR-4508 gene (miRBase Accession No. MIMAT0019045) described in SEQ ID NO: 146, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 482) having a hairpin-like structure is known as a precursor of "hsa-miR-4508".

The term "hsa-miR-4687-3p gene" or "hsa-miR-4687-3p" used herein includes the hsa-miR-4687-3p gene (miRBase Accession No. MIMAT0019775) described in SEQ ID NO: 147, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 483) having a hairpin-like structure is known as a precursor of "hsa-miR-4687-3p".

The term "hsa-miR-4687-5p gene" or "hsa-miR-4687-5p" used herein includes the hsa-miR-4687-5p gene (miRBase Accession No. MIMAT0019774) described in SEQ ID NO: 148, a homolog or an ortholog of a different organism species, and the like. The hsa-miR-4687-5p gene can be obtained by a method described in Persson H et al., 2011, Cancer Res, Vol. 71, p. 78-86. Also, "hsa-mir-4687" (miRBase Accession No. M10017319, SEQ ID NO: 483) having a hairpin-like structure is known as a precursor of "hsa-miR-4687-5p".

The term "hsa-miR-4732-5p gene" or "hsa-miR-4732-5p" used herein includes the hsa-miR-4732-5p gene (miRBase Accession No. MIMAT0019855) described in SEQ ID NO: 149, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miR-Base Accession No. MI0017369, SEQ ID NO: 484) having a hairpin-like structure is known as a precursor of "hsa-miR-4732-5p".

The term "hsa-miR-4771 gene" or "hsa-miR-4771" used herein includes the hsa-miR-4771 gene (miRBase Accession No. MIMAT0019925) described in SEQ ID NO: 150, a homolog or an ortholog of a different organism species, and the like. The hsa-miR-4771 gene can be obtained by a method described in Persson H et al., 2011, Cancer Res, Vol. 71, p. 78-86. Also, "hsa-mir-4771-1 and hsa-mir-4771-2" (miRBase Accession Nos. MI0017412 and MI0017413, SEQ ID NOs: 485 and 486) having a hairpin-like structure are known as precursors of "hsa-miR-4771".

The term "hsa-miR-642a-3p gene" or "hsa-miR-642a-3p" used herein includes the hsa-miR-642a-3p gene (miRBase Accession No. MIMAT0020924) described in SEQ ID NO: 151, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 487) having a hairpin-like structure is known as a precursor of "hsa-miR-642a-3p".

The term "hsa-miR-6732-5p gene" or "hsa-miR-6732-5p" used herein includes the hsa-miR-6732-5p gene (miRBase Accession No. MIMAT0027365) described in SEQ ID NO: 152, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 488) having a hairpin-like structure is known as a precursor of "hsa-miR-6732-5p".

The term "hsa-miR-6760-5p gene" or "hsa-miR-6760-5p" used herein includes the hsa-miR-6760-5p gene (miRBase Accession No. MIMAT0027420) described in SEQ ID NO: 153, a homolog or an ortholog of a different organism species, and the like. The hsa-miR-6760-5p gene can be obtained by a method described in Ladewig E et al., 2012, Genome Res., Vol. 22, p. 1634-1645. Also, "hsa-mir-6760" (miRBase Accession No. MI0022605, SEQ ID NO: 489) having a hairpin-like structure is known as a precursor of "hsa-miR-6760-5p".

The term "hsa-miR-6799-5p gene" or "hsa-miR-6799-5p" used herein includes the hsa-miR-6799-5p gene (miRBase Accession No. MIMAT0027498) described in SEQ ID NO: 154, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 490) having a hairpin-like structure is known as a precursor of "hsa-miR-6799-5p".

The term "hsa-miR-6820-5p gene" or "hsa-miR-6820-5p" used herein includes the hsa-miR-6820-5p gene (miRBase Accession No. MIMAT0027540) described in SEQ ID NO: 155, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 491) having a hairpin-like structure is known as a precursor of "hsa-miR-6820-5p".

The term "hsa-miR-6821-5p gene" or "hsa-miR-6821-5p" used herein includes the hsa-miR-6821-5p gene (miRBase Accession No. MIMAT0027542) described in SEQ ID NO: 156, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 492) having a hairpin-like structure is known as a precursor of "hsa-miR-6821-5p".

The term "hsa-miR-6829-5p gene" or "hsa-miR-6829-5p" used herein includes the hsa-miR-6829-5p gene (miRBase Accession No. MIMAT0027558) described in SEQ ID NO: 157, a homolog or an ortholog of a different organism species, and the like. The hsa-miR-6829-5p gene can be obtained by a method described in Ladewig E et al., 2012, Genome Res, Vol. 22, p. 1634-1645. Also, "hsa-mir-6829" (miRBase Accession No. MI0022674, SEQ ID NO: 493) having a hairpin-like structure is known as a precursor of "hsa-miR-6829-5p".

The term "hsa-miR-6893-5p gene" or "hsa-miR-6893-5p" used herein includes the hsa-miR-6893-5p gene (miRBase Accession No. MIMAT0027686) described in SEQ ID NO: 158, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 494) having a hairpin-like structure is known as a precursor of "hsa-miR-6893-5p".

The term "hsa-miR-7108-3p gene" or "hsa-miR-7108-3p" used herein includes the hsa-miR-7108-3p gene (miRBase Accession No. MIMAT0028114) described in SEQ ID NO: 159, a homolog or an ortholog of a different organism species, and the like. The hsa-miR-7108-3p gene can be obtained by a method described in Ladewig E et al., 2012, Genome Res, Vol. 22, p. 1634-1645. Also, "hsa-mir-7108" (miRBase Accession No. MI0022959, SEQ ID NO: 495) having a hairpin-like structure is known as a precursor of "hsa-miR-7108-3p".

The term "hsa-miR-7111-5p gene" or "hsa-miR-7111-5p" used herein includes the hsa-miR-7111-5p gene (miRBase Accession No. MIMAT0028119) described in SEQ ID NO: 160, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 496) having a hairpin-like structure is known as a precursor of "hsa-miR-7111-5p".

The term "hsa-miR-8089 gene" or "hsa-miR-8089" used herein includes the hsa-miR-8089 gene (miRBase Accession No. MIMAT0031016) described in SEQ ID NO: 161, a homolog or an ortholog of a different organism species, and the like. The hsa-miR-8089 gene can be obtained by a method described in Wang H J et al., 2013, Shock, Vol. 39, p. 480-487. Also, "hsa-mir-8089" (miRBase Accession No. MI0025925, SEQ ID NO: 497) having a hairpin-like structure is known as a precursor of "hsa-miR-8089".

The term "hsa-miR-885-3p gene" or "hsa-miR-885-3p" used herein includes the hsa-miR-885-3p gene (miRBase Accession No. MIMAT0004948) described in SEQ ID NO: 162, a homolog or an ortholog of a different organism species, and the like. The hsa-miR-885-3p gene can be obtained by a method described in Berezikov E et al., 2006, Genome Res, Vol. 16, p. 1289-1298. Also, "hsa-mir-885" (miRBase Accession No. MI0005560, SEQ ID NO: 498) having a hairpin-like structure is known as a precursor of "hsa-miR-885-3p".

The term "hsa-miR-92b-3p gene" or "hsa-miR-92b-3p" used herein includes the hsa-miR-92b-3p gene (miRBase Accession No. MIMAT0003218) described in SEQ ID NO: 163, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 499) having a hairpin-like structure is known as a precursor of "hsa-miR-92b-3p".

The term "hsa-miR-1343-3p gene" or "hsa-miR-1343-3p" used herein includes the hsa-miR-1343-3p gene (miRBase Accession No. MIMAT0019776) described in SEQ ID NO: 164, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 500) having a hairpin-like structure is known as a precursor of "hsa-miR-1343-3p".

The term "hsa-miR-6746-5p gene" or "hsa-miR-6746-5p" used herein includes the hsa-miR-6746-5p gene (miRBase Accession No. MIMAT0027392) described in SEQ ID NO: 165, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 501) having a hairpin-like structure is known as a precursor of "hsa-miR-6746-5p".

The term "hsa-miR-422a gene" or "hsa-miR-422a" used herein includes the hsa-miR-422a gene (miRBase Accession No. MIMAT0001339) described in SEQ ID NO: 166, a homolog or an ortholog of a different organism species, and the like. The hsa-miR-422a gene can be obtained by a method described in Kasashima K et al., 2004, Biochem Biophys Res Commun, Vol. 322, p. 403-410. Also, "hsa-mir-422a" (miRBase Accession No. MI0001444, SEQ ID NO: 502) having a hairpin-like structure is known as a precursor of "hsa-miR-422a".

The term "hsa-miR-187-5p gene" or "hsa-miR-187-5p" used herein includes the hsa-miR-187-5p gene (miRBase Accession No. MIMAT0004561) described in SEQ ID NO: 167, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 503) having a hairpin-like structure is known as a precursor of "hsa-miR-187-5p".

The term "hsa-miR-4632-5p gene" or "hsa-miR-4632-5p" used herein includes the hsa-miR-4632-5p gene (miRBase Accession No. MIMAT0022977) described in SEQ ID NO: 168, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 504) having a hairpin-like structure is known as a precursor of "hsa-miR-4632-5p".

The term "hsa-miR-6791-5p gene" or "hsa-miR-6791-5p" used herein includes the hsa-miR-6791-5p gene (miRBase Accession No. MIMAT0027482) described in SEQ ID NO: 169, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 505) having a hairpin-like structure is known as a precursor of "hsa-miR-6791-5p".

The term "hsa-miR-103a-3p gene" or "hsa-miR-103a-3p" used herein includes the hsa-miR-103a-3p gene (miRBase Accession No. MIMAT0000101) described in SEQ ID NO: 170, a homolog or an ortholog of a different organism species, and the like. The hsa-miR-103a-3p gene can be obtained by a method described in Mourelatos Z et al., 2002, Genes Dev. Vol. 16: p. 720-728. Also, "hsa-mir-103a-2 and hsa-mir-103a-1" (miRBase Accession Nos. MI0000109 and MI0000108, SEQ ID NOs: 506 and 507) having a hairpin-like structure are known as precursors of "hsa-miR-103a-3p".

The term "hsa-miR-107 gene" or "hsa-miR-107" used herein includes the hsa-miR-107 gene (miRBase Accession No. MIMAT0000104) described in SEQ ID NO: 171, a homolog or an ortholog of a different organism species, and the like. The hsa-miR-107 gene can be obtained by a method described in Mourelatos Z et al., 2002, Genes Dev., Vol. 16, p. 720-728. Also, "hsa-mir-107" (miRBase Accession No. MI0000114, SEQ ID NO: 508) having a hairpin-like structure is known as a precursor of "hsa-miR-107".

The term "hsa-miR-1199-5p gene" or "hsa-miR-1199-5p" used herein includes the hsa-miR-1199-5p gene (miRBase Accession No. MIMAT0031119) described in SEQ ID NO: 172, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 509) having a hairpin-like structure is known as a precursor of "hsa-miR-1199-5p".

The term "hsa-miR-1225-3p gene" or "hsa-miR-1225-3p" used herein includes the hsa-miR-1225-3p gene (miRBase Accession No. MIMAT0005573) described in SEQ ID NO: 173, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 510) having a hairpin-like structure is known as a precursor of "hsa-miR-1225-3p".

The term "hsa-miR-1225-5p gene" or "hsa-miR-1225-5p" used herein includes the hsa-miR-1225-5p gene (miRBase Accession No. MIMAT0005572) described in SEQ ID NO: 174, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 510) having a hairpin-like structure is known as a precursor of "hsa-miR-1225-5p".

The term "hsa-miR-1228-5p gene" or "hsa-miR-1228-5p" used herein includes the hsa-miR-1228-5p gene (miRBase Accession No. MIMAT0005582) described in SEQ ID NO: 175, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 511) having a hairpin-like structure is known as a precursor of "hsa-miR-1228-5p".

The term "hsa-miR-1229-5p gene" or "hsa-miR-1229-5p" used herein includes the hsa-miR-1229-5p gene (miRBase Accession No. MIMAT0022942) described in SEQ ID NO: 176, a homolog or an ortholog of a different organism species, and the like. The hsa-miR-1229-5p gene can be obtained by a method described in Berezikov E et al., 2007, Mol Cell, Vol. 28, p. 328-336. Also, "hsa-mir-1229" (miRBase Accession No. MI0006319, SEQ ID NO: 512) having a hairpin-like structure is known as a precursor of "hsa-miR-1229-5p".

The term "hsa-miR-1233-5p gene" or "hsa-miR-1233-5p" used herein includes the hsa-miR-1233-5p gene (miRBase Accession No. MIMAT0022943) described in SEQ ID NO: 177, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 513 and 514) having a hairpin-like structure are known as precursors of "hsa-miR-1233-5p".

The term "hsa-miR-1237-5p gene" or "hsa-miR-1237-5p" used herein includes the hsa-miR-1237-5p gene (miRBase Accession No. MIMAT0022946) described in SEQ ID NO: 178, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 515) having a hairpin-like structure is known as a precursor of "hsa-miR-1237-5p".

The term "hsa-miR-1247-3p gene" or "hsa-miR-1247-3p" used herein includes the hsa-miR-1247-3p gene (miRBase Accession No. MIMAT0022721) described in SEQ ID NO: 179, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 516) having a hairpin-like structure is known as a precursor of "hsa-miR-1247-3p".

The term "hsa-miR-1249-3p gene" or "hsa-miR-1249-3p" used herein includes the hsa-miR-1249-3p gene (miRBase Accession No. MIMAT0005901) described in SEQ ID NO: 180, a homolog or an ortholog of a different organism species, and the like. The hsa-miR-1249-3p gene can be obtained by a method described in Morin R D et al., 2008, Genome Res, Vol. 18, p. 610-621. Also, "hsa-mir-1249" (miRBase Accession No. MI0006384, SEQ ID NO: 343) having a hairpin-like structure is known as a precursor of "hsa-miR-1249-3p".

The term "hsa-miR-1254 gene" or "hsa-miR-1254" used herein includes the hsa-miR-1254 gene (miRBase Accession No. MIMAT0005905) described in SEQ ID NO: 181, a homolog or an ortholog of a different organism species, and the like. The hsa-miR-1254 gene can be obtained by a method described in Morin R D et al., 2008, Genome Res, Vol. 18, p. 610-621. Also, "hsa-mir-1254-1 and hsa-mir-1254-2" (miRBase Accession Nos. MI0006388 and MI0016747, SEQ ID NOs: 517 and 518) having a hairpin-like structure are known as precursors of "hsa-miR-1254".

The term "hsa-miR-1260b gene" or "hsa-miR-1260b" used herein includes the hsa-miR-1260b gene (miRBase Accession No. MIMAT0015041) described in SEQ ID NO: 182, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 519) having a hairpin-like structure is known as a precursor of "hsa-miR-1260b".

The term "hsa-miR-1268a gene" or "hsa-miR-1268a" used herein includes the hsa-miR-1268a gene (miRBase Accession No. MIMAT0005922) described in SEQ ID NO: 183, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 520) having a hairpin-like structure is known as a precursor of "hsa-miR-1268a".

The term "hsa-miR-1268b gene" or "hsa-miR-1268b" used herein includes the hsa-miR-1268b gene (miRBase Accession No. MIMAT0018925) described in SEQ ID NO: 184, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 521) having a hairpin-like structure is known as a precursor of "hsa-miR-1268b".

The term "hsa-miR-1273g-3p gene" or "hsa-miR-1273g-3p" used herein includes the hsa-miR-1273g-3p gene (miRBase Accession No. MIMAT0022742) described in SEQ ID NO: 185, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 522) having a hairpin-like structure is known as a precursor of "hsa-miR-1273g-3p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 186, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 523) having a hairpin-like structure is known as a precursor of "hsa-miR-128-1-5p".

The term "hsa-miR-128-2-5p gene" or "hsa-miR-128-2-5p" used herein includes the hsa-miR-128-2-5p gene (miRBase Accession No. MIMAT0031095) described in SEQ ID NO: 187, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 524) having a hairpin-like structure is known as a precursor of "hsa-miR-128-2-5p".

The term "hsa-miR-1290 gene" or "hsa-miR-1290" used herein includes the hsa-miR-1290 gene (miRBase Accession No. MIMAT0005880) described in SEQ ID NO: 188, a homolog or an ortholog of a different organism species, and the like. The hsa-miR-1290 gene can be obtained by a method described in Morin R D et al., 2008, Genome Res, Vol. 18, p. 610-621. Also, "hsa-mir-1290" (miRBase Accession No. MI0006352, SEQ ID NO: 525) having a hairpin-like structure is known as a precursor of "hsa-miR-1290".

The term "hsa-miR-150-3p gene" or "hsa-miR-150-3p" used herein includes the hsa-miR-150-3p gene (miRBase Accession No. MIMAT0004610) described in SEQ ID NO: 189, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150"

(miRBase Accession No. MI0000479, SEQ ID NO: 526) having a hairpin-like structure is known as a precursor of "hsa-miR-150-3p".

The term "hsa-miR-17-3p gene" or "hsa-miR-17-3p" used herein includes the hsa-miR-17-3p gene (miRBase Accession No. MIMAT0000071) described in SEQ ID NO: 190, a homolog or an ortholog of a different organism species, and the like. The hsa-miR-17-3p gene can be obtained by a method described in Lagos-Quintana M et al., 2001, Science., Vol. 294, p. 853-858. Also, "hsa-mir-17" (miRBase Accession No. MI0000071, SEQ ID NO: 527) having a hairpin-like structure is known as a precursor of "hsa-miR-17-3p".

The term "hsa-miR-1908-5p gene" or "hsa-miR-1908-5p" used herein includes the hsa-miR-1908-5p gene (miRBase Accession No. MIMAT0007881) described in SEQ ID NO: 191, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 528) having a hairpin-like structure is known as a precursor of "hsa-miR-1908-5p".

The term "hsa-miR-1909-3p gene" or "hsa-miR-1909-3p" used herein includes the hsa-miR-1909-3p gene (miRBase Accession No. MIMAT0007883) described in SEQ ID NO: 192, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 529) having a hairpin-like structure is known as a precursor of "hsa-miR-1909-3p".

The term "hsa-miR-1914-3p gene" or "hsa-miR-1914-3p" used herein includes the hsa-miR-1914-3p gene (miRBase Accession No. MIMAT0007890) described in SEQ ID NO: 193, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 530) having a hairpin-like structure is known as a precursor of "hsa-miR-1914-3p".

The term "hsa-miR-1915-3p gene" or "hsa-miR-1915-3p" used herein includes the hsa-miR-1915-3p gene (miRBase Accession No. MIMAT0007892) described in SEQ ID NO: 194, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 531) having a hairpin-like structure is known as a precursor of "hsa-miR-1915-3p".

The term "hsa-miR-191-5p gene" or "hsa-miR-191-5p" used herein includes the hsa-miR-191-5p gene (miRBase Accession No. MIMAT0000440) described in SEQ ID NO: 195, a homolog or an ortholog of a different organism species, and the like. The hsa-miR-191-5p gene can be obtained by a method described in Lagos-Quintana M et al., 2003, RNA, Vol. 9, p. 175-179. Also, "hsa-mir-191" (miRBase Accession No. MI0000465, SEQ ID NO: 532) having a hairpin-like structure is known as a precursor of "hsa-miR-191-5p".

The term "hsa-miR-22-3p gene" or "hsa-miR-22-3p" used herein includes the hsa-miR-22-3p gene (miRBase Accession No. MIMAT0000077) described in SEQ ID NO: 196, a homolog or an ortholog of a different organism species, and the like. The hsa-miR-22-3p gene can be obtained by a method described in Lagos-Quintana M et al., 2001, Science, Vol. 294, p. 853-858. Also, "hsa-mir-22" (miRBase Accession No. MI0000078, SEQ ID NO: 533) having a hairpin-like structure is known as a precursor of "hsa-miR-22-3p".

The term "hsa-miR-23b-3p gene" or "hsa-miR-23b-3p" used herein includes the hsa-miR-23b-3p gene (miRBase Accession No. MIMAT0000418) described in SEQ ID NO: 197, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 534) having a hairpin-like structure is known as a precursor of "hsa-miR-23b-3p".

The term "hsa-miR-24-3p gene" or "hsa-miR-24-3p" used herein includes the hsa-miR-24-3p gene (miRBase Accession No. MIMAT0000080) described in SEQ ID NO: 198, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 535 and 536) having a hairpin-like structure are known as precursors of "hsa-miR-24-3p".

The term "hsa-miR-296-3p gene" or "hsa-miR-296-3p" used herein includes the hsa-miR-296-3p gene (miRBase Accession No. MIMAT0004679) described in SEQ ID NO: 199, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 537) having a hairpin-like structure is known as a precursor of "hsa-miR-296-3p".

The term "hsa-miR-296-5p gene" or "hsa-miR-296-5p" used herein includes the hsa-miR-296-5p gene (miRBase Accession No. MIMAT0000690) described in SEQ ID NO: 200, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 537) having a hairpin-like structure is known as a precursor of "hsa-miR-296-5p".

The term "hsa-miR-3131 gene" or "hsa-miR-3131" used herein includes the hsa-miR-3131 gene (miRBase Accession No. MIMAT0014996) described in SEQ ID NO: 201, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 538) having a hairpin-like structure is known as a precursor of "hsa-miR-3131".

The term "hsa-miR-3162-5p gene" or "hsa-miR-3162-5p" used herein includes the hsa-miR-3162-5p gene (miRBase Accession No. MIMAT0015036) described in SEQ ID NO: 202, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 539) having a hairpin-like structure is known as a precursor of "hsa-miR-3162-5p".

The term "hsa-miR-3188 gene" or "hsa-miR-3188" used herein includes the hsa-miR-3188 gene (miRBase Accession No. MIMAT0015070) described in SEQ ID NO: 203, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 540) having a hairpin-like structure is known as a precursor of "hsa-miR-3188".

The term "hsa-miR-3196 gene" or "hsa-miR-3196" used herein includes the hsa-miR-3196 gene (miRBase Accession No. MIMAT0015080) described in SEQ ID NO: 204, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 541) having a hairpin-like structure is known as a precursor of "hsa-miR-3196".

The term "hsa-miR-3197 gene" or "hsa-miR-3197" used herein includes the hsa-miR-3197 gene (miRBase Accession No. MIMAT0015082) described in SEQ ID NO: 205, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 542) having a hairpin-like structure is known as a precursor of "hsa-miR-3197".

The term "hsa-miR-320a gene" or "hsa-miR-320a" used herein includes the hsa-miR-320a gene (miRBase Accession No. MIMAT0000510) described in SEQ ID NO: 206, a homolog or an ortholog of a different organism species, and the like. The hsa-miR-320a gene can be obtained by a method described in Michael M Z et al., 2003, Mol Cancer Res, Vol. 1, p. 882-891. Also, "hsa-mir-320a" (miRBase Accession No. MI0000542, SEQ ID NO: 543) having a hairpin-like structure is known as a precursor of "hsa-miR-320a".

The term "hsa-miR-342-5p gene" or "hsa-miR-342-5p" used herein includes the hsa-miR-342-5p gene (miRBase Accession No. MIMAT0004694) described in SEQ ID NO: 207, a homolog or an ortholog of a different organism species, and the like. The hsa-miR-342-5p gene can be obtained by a method described in Kim J et al., 2004, Proc Natl Acad Sci USA, Vol. 101, p. 360-365. Also, "hsa-mir-342" (miRBase Accession No. MI0000805, SEQ ID NO: 544) having a hairpin-like structure is known as a precursor of "hsa-miR-342-5p".

The term "hsa-miR-3621 gene" or "hsa-miR-3621" used herein includes the hsa-miR-3621 gene (miRBase Accession No. MIMAT0018002) described in SEQ ID NO: 208, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 545) having a hairpin-like structure is known as a precursor of "hsa-miR-3621".

The term "hsa-miR-3648 gene" or "hsa-miR-3648" used herein includes the hsa-miR-3648 gene (miRBase Accession No. MIMAT0018068) described in SEQ ID NO: 209, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 546) having a hairpin-like structure is known as a precursor of "hsa-miR-3648".

The term "hsa-miR-3656 gene" or "hsa-miR-3656" used herein includes the hsa-miR-3656 gene (miRBase Accession No. MIMAT0018076) described in SEQ ID NO: 210, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 547) having a hairpin-like structure is known as a precursor of "hsa-miR-3656".

The term "hsa-miR-365a-5p gene" or "hsa-miR-365a-5p" used herein includes the hsa-miR-365a-5p gene (miRBase Accession No. MIMAT0009199) described in SEQ ID NO: 211, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 548) having a hairpin-like structure is known as a precursor of "hsa-miR-365a-5p".

The term "hsa-miR-3665 gene" or "hsa-miR-3665" used herein includes the hsa-miR-3665 gene (miRBase Accession No. MIMAT0018087) described in SEQ ID NO: 212, a homolog or an ortholog of a different organism species, and the like. The hsa-miR-3665 gene can be obtained by a method described in 'Xie X et al., 2005, Nature, Vol. 434, p. 338-345'. Also, "hsa-mir-3665" (miRBase Accession No. MI0016066, SEQ ID NO: 549) having a hairpin-like structure is known as a precursor of "hsa-miR-3665".

The term "hsa-miR-3679-5p gene" or "hsa-miR-3679-5p" used herein includes the hsa-miR-3679-5p gene (miRBase Accession No. MIMAT0018104) described in SEQ ID NO: 213, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 550) having a hairpin-like structure is known as a precursor of "hsa-miR-3679-5p".

The term "hsa-miR-371a-5p gene" or "hsa-miR-371a-5p" used herein includes the hsa-miR-371a-5p gene (miRBase Accession No. MIMAT0004687) described in SEQ ID NO: 214, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 551) having a hairpin-like structure is known as a precursor of "hsa-miR-371a-5p".

The term "hsa-miR-3940-5p gene" or "hsa-miR-3940-5p" used herein includes the hsa-miR-3940-5p gene (miRBase Accession No. MIMAT0019229) described in SEQ ID NO: 215, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 552) having a hairpin-like structure is known as a precursor of "hsa-miR-3940-5p".

The term "hsa-miR-423-5p gene" or "hsa-miR-423-5p" used herein includes the hsa-miR-423-5p gene (miRBase Accession No. MIMAT0004748) described in SEQ ID NO: 216, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 553) having a hairpin-like structure is known as a precursor of "hsa-miR-423-5p".

The term "hsa-miR-4257 gene" or "hsa-miR-4257" used herein includes the hsa-miR-4257 gene (miRBase Accession No. MIMAT0016878) described in SEQ ID NO: 217, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 554) having a hairpin-like structure is known as a precursor of "hsa-miR-4257".

The term "hsa-miR-4270 gene" or "hsa-miR-4270" used herein includes the hsa-miR-4270 gene (miRBase Accession No. MIMAT0016900) described in SEQ ID NO: 218, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 555) having a hairpin-like structure is known as a precursor of "hsa-miR-4270".

The term "hsa-miR-4271 gene" or "hsa-miR-4271" used herein includes the hsa-miR-4271 gene (miRBase Accession No. MIMAT0016901) described in SEQ ID NO: 219, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 556) having a hairpin-like structure is known as a precursor of "hsa-miR-4271".

The term "hsa-miR-4286 gene" or "hsa-miR-4286" used herein includes the hsa-miR-4286 gene (miRBase Accession No. MIMAT0016916) described in SEQ ID NO: 220, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 557) having a hairpin-like structure is known as a precursor of "hsa-miR-4286".

The term "hsa-miR-4298 gene" or "hsa-miR-4298" used herein includes the hsa-miR-4298 gene (miRBase Accession No. MIMAT0016852) described in SEQ ID NO: 221, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 558) having a hairpin-like structure is known as a precursor of "hsa-miR-4298".

The term "hsa-miR-4417 gene" or "hsa-miR-4417" used herein includes the hsa-miR-4417 gene (miRBase Accession No. MIMAT0018929) described in SEQ ID NO: 222, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 559) having a hairpin-like structure is known as a precursor of "hsa-miR-4417".

The term "hsa-miR-4442 gene" or "hsa-miR-4442" used herein includes the hsa-miR-4442 gene (miRBase Accession No. MIMAT0018960) described in SEQ ID NO: 223, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 560) having a hairpin-like structure is known as a precursor of "hsa-miR-4442".

The term "hsa-miR-4446-3p gene" or "hsa-miR-4446-3p" used herein includes the hsa-miR-4446-3p gene (miRBase Accession No. MIMAT0018965) described in SEQ ID NO: 224, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 561) having a hairpin-like structure is known as a precursor of "hsa-miR-4446-3p".

The term "hsa-miR-4448 gene" or "hsa-miR-4448" used herein includes the hsa-miR-4448 gene (miRBase Accession No. MIMAT0018967) described in SEQ ID NO: 225, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 562) having a hairpin-like structure is known as a precursor of "hsa-miR-4448".

The term "hsa-miR-4454 gene" or "hsa-miR-4454" used herein includes the hsa-miR-4454 gene (miRBase Accession No. MIMAT0018976) described in SEQ ID NO: 226, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 563) having a hairpin-like structure is known as a precursor of "hsa-miR-4454".

The term "hsa-miR-4467 gene" or "hsa-miR-4467" used herein includes the hsa-miR-4467 gene (miRBase Accession No. MIMAT0018994) described in SEQ ID NO: 227, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 564) having a hairpin-like structure is known as a precursor of "hsa-miR-4467".

The term "hsa-miR-4472 gene" or "hsa-miR-4472" used herein includes the hsa-miR-4472 gene (miRBase Accession No. MIMAT0018999) described in SEQ ID NO: 228, a homolog or an ortholog of a different organism species, and the like. The hsa-miR-4472 gene can be obtained by a method described in Jima D D et al., 2010, Blood, Vol. 116, e118-e127. Also, "hsa-mir-4472-1 and hsa-mir-4472-2" (miRBase Accession Nos. MI0016823 and MI0016824, SEQ ID NOs: 565 and 566) having a hairpin-like structure are known as precursors of "hsa-miR-4472".

The term "hsa-miR-4507 gene" or "hsa-miR-4507" used herein includes the hsa-miR-4507 gene (miRBase Accession No. MIMAT0019044) described in SEQ ID NO: 229, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 567) having a hairpin-like structure is known as a precursor of "hsa-miR-4507".

The term "hsa-miR-4516 gene" or "hsa-miR-4516" used herein includes the hsa-miR-4516 gene (miRBase Accession No. MIMAT0019053) described in SEQ ID NO: 230, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 568) having a hairpin-like structure is known as a precursor of "hsa-miR-4516".

The term "hsa-miR-451a gene" or "hsa-miR-451a" used herein includes the hsa-miR-451a gene (miRBase Accession No. MIMAT0001631) described in SEQ ID NO: 231, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 569) having a hairpin-like structure is known as a precursor of "hsa-miR-451a".

The term "hsa-miR-4649-5p gene" or "hsa-miR-4649-5p" used herein includes the hsa-miR-4649-5p gene (miRBase Accession No. MIMAT0019711) described in SEQ ID NO: 232, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 570) having a hairpin-like structure is known as a precursor of "hsa-miR-4649-5p".

The term "hsa-miR-4651 gene" or "hsa-miR-4651" used herein includes the hsa-miR-4651 gene (miRBase Accession No. MIMAT0019715) described in SEQ ID NO: 233, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 571) having a hairpin-like structure is known as a precursor of "hsa-miR-4651".

The term "hsa-miR-4665-3p gene" or "hsa-miR-4665-3p" used herein includes the hsa-miR-4665-3p gene (miRBase Accession No. MIMAT0019740) described in SEQ ID NO: 234, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 401) having a hairpin-like structure is known as a precursor of "hsa-miR-4665-3p".

The term "hsa-miR-4674 gene" or "hsa-miR-4674" used herein includes the hsa-miR-4674 gene (miRBase Accession No. MIMAT0019756) described in SEQ ID NO: 235, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 572) having a hairpin-like structure is known as a precursor of "hsa-miR-4674".

The term "hsa-miR-4675 gene" or "hsa-miR-4675" used herein includes the hsa-miR-4675 gene (miRBase Accession No. MIMAT0019757) described in SEQ ID NO: 236, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 573) having a hairpin-like structure is known as a precursor of "hsa-miR-4675".

The term "hsa-miR-4689 gene" or "hsa-miR-4689" used herein includes the hsa-miR-4689 gene (miRBase Accession No. MIMAT0019778) described in SEQ ID NO: 237, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 574) having a hairpin-like structure is known as a precursor of "hsa-miR-4689".

The term "hsa-miR-4695-5p gene" or "hsa-miR-4695-5p" used herein includes the hsa-miR-4695-5p gene (miRBase Accession No. MIMAT0019788) described in SEQ ID NO: 238, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 575) having a hairpin-like structure is known as a precursor of "hsa-miR-4695-5p".

The term "hsa-miR-4697-5p gene" or "hsa-miR-4697-5p" used herein includes the hsa-miR-4697-5p gene (miRBase Accession No. MIMAT0019791) described in SEQ ID NO: 239, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 576) having a hairpin-like structure is known as a precursor of "hsa-miR-4697-5p".

The term "hsa-miR-4725-3p gene" or "hsa-miR-4725-3p" used herein includes the hsa-miR-4725-3p gene (miRBase Accession No. MIMAT0019844) described in SEQ ID NO: 240, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 577) having a hairpin-like structure is known as a precursor of "hsa-miR-4725-3p".

The term "hsa-miR-4739 gene" or "hsa-miR-4739" used herein includes the hsa-miR-4739 gene (miRBase Accession No. MIMAT0019868) described in SEQ ID NO: 241, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 578) having a hairpin-like structure is known as a precursor of "hsa-miR-4739".

The term "hsa-miR-4745-5p gene" or "hsa-miR-4745-5p" used herein includes the hsa-miR-4745-5p gene (miRBase Accession No. MIMAT0019878) described in SEQ ID NO: 242, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 579) having a hairpin-like structure is known as a precursor of "hsa-miR-4745-5p".

The term "hsa-miR-4763-3p gene" or "hsa-miR-4763-3p" used herein includes the hsa-miR-4763-3p gene (miRBase Accession No. MIMAT0019913) described in SEQ ID NO: 243, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 415) having a hairpin-like structure is known as a precursor of "hsa-miR-4763-3p".

The term "hsa-miR-4792 gene" or "hsa-miR-4792" used herein includes the hsa-miR-4792 gene (miRBase Accession No. MIMAT0019964) described in SEQ ID NO: 244, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 580) having a hairpin-like structure is known as a precursor of "hsa-miR-4792".

The term "hsa-miR-486-3p gene" or "hsa-miR-486-3p" used herein includes the hsa-miR-486-3p gene (miRBase Accession No. MIMAT0004762) described in SEQ ID NO: 245, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 581 and 582) having a hairpin-like structure are known as precursors of "hsa-miR-486-3p".

The term "hsa-miR-5001-5p gene" or "hsa-miR-5001-5p" used herein includes the hsa-miR-5001-5p gene (miRBase Accession No. MIMAT0021021) described in SEQ ID NO: 246, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 583) having a hairpin-like structure is known as a precursor of "hsa-miR-5001-5p".

The term "hsa-miR-5195-3p gene" or "hsa-miR-5195-3p" used herein includes the hsa-miR-5195-3p gene (miRBase Accession No. MIMAT0021127) described in SEQ ID NO: 247, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 584) having a hairpin-like structure is known as a precursor of "hsa-miR-5195-3p".

The term "hsa-miR-550a-5p gene" or "hsa-miR-550a-5p" used herein includes the hsa-miR-550a-5p gene (miRBase Accession No. MIMAT0004800) described in SEQ ID NO: 248, a homolog or an ortholog of a different organism species, and the like. The hsa-miR-550a-5p gene can be obtained by a method described in Cummins J M, 2006, Proc Natl Acad Sci, Vol. 103, p. 3687-3692. Also, "hsa-mir-550a-1 and hsa-mir-550a-2" (miRBase Accession Nos. MI0003600 and MI0003601, SEQ ID NOs: 585 and 586) having a hairpin-like structure are known as precursors of "hsa-miR-550a-5p".

The term "hsa-miR-5698 gene" or "hsa-miR-5698" used herein includes the hsa-miR-5698 gene (miRBase Accession No. MIMAT0022491) described in SEQ ID NO: 249, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 587) having a hairpin-like structure is known as a precursor of "hsa-miR-5698".

The term "hsa-miR-6075 gene" or "hsa-miR-6075" used herein includes the hsa-miR-6075 gene (miRBase Accession No. MIMAT0023700) described in SEQ ID NO: 250, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 588) having a hairpin-like structure is known as a precursor of "hsa-miR-6075".

The term "hsa-miR-6088 gene" or "hsa-miR-6088" used herein includes the hsa-miR-6088 gene (miRBase Accession No. MIMAT0023713) described in SEQ ID NO: 251, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 589) having a hairpin-like structure is known as a precursor of "hsa-miR-6088".

The term "hsa-miR-6089 gene" or "hsa-miR-6089" used herein includes the hsa-miR-6089 gene (miRBase Accession No. MIMAT0023714) described in SEQ ID NO: 252, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 590 and 591) having a hairpin-like structure are known as precursors of "hsa-miR-6089".

The term "hsa-miR-6125 gene" or "hsa-miR-6125" used herein includes the hsa-miR-6125 gene (miRBase Accession No. MIMAT0024598) described in SEQ ID NO: 253, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 592) having a hairpin-like structure is known as a precursor of "hsa-miR-6125".

The term "hsa-miR-6126 gene" or "hsa-miR-6126" used herein includes the hsa-miR-6126 gene (miRBase Accession No. MIMAT0024599) described in SEQ ID NO: 254, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 593) having a hairpin-like structure is known as a precursor of "hsa-miR-6126".

The term "hsa-miR-614 gene" or "hsa-miR-614" used herein includes the hsa-miR-614 gene (miRBase Accession No. MIMAT0003282) described in SEQ ID NO: 255, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 594) having a hairpin-like structure is known as a precursor of "hsa-miR-614".

The term "hsa-miR-615-5p gene" or "hsa-miR-615-5p" used herein includes the hsa-miR-615-5p gene (miRBase Accession No. MIMAT0004804) described in SEQ ID NO: 256, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. M10003628, SEQ ID NO: 595) having a hairpin-like structure is known as a precursor of "hsa-miR-615-5p".

The term "hsa-miR-619-5p gene" or "hsa-miR-619-5p" used herein includes the hsa-miR-619-5p gene (miRBase Accession No. MIMAT0026622) described in SEQ ID NO: 257, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 596) having a hairpin-like structure is known as a precursor of "hsa-miR-619-5p".

The term "hsa-miR-638 gene" or "hsa-miR-638" used herein includes the hsa-miR-638 gene (miRBase Accession No. MIMAT0003308) described in SEQ ID NO: 258, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 597) having a hairpin-like structure is known as a precursor of "hsa-miR-638".

The term "hsa-miR-642b-3p gene" or "hsa-miR-642b-3p" used herein includes the hsa-miR-642b-3p gene (miRBase Accession No. MIMAT0018444) described in SEQ ID NO: 259, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 598) having a hairpin-like structure is known as a precursor of "hsa-miR-642b-3p".

The term "hsa-miR-650 gene" or "hsa-miR-650" used herein includes the hsa-miR-650 gene (miRBase Accession No. MIMAT0003320) described in SEQ ID NO: 260, a homolog or an ortholog of a different organism species, and the like. The hsa-miR-650 gene can be obtained by a method described in Cummins J M et al., 2006, Proc Natl Acad Sci USA., Vol. 103, 3687-3692. Also, "hsa-mir-650" (miRBase Accession No. MI0003665, SEQ ID NO: 599) having a hairpin-like structure is known as a precursor of "hsa-miR-650".

The term "hsa-miR-663a gene" or "hsa-miR-663a" used herein includes the hsa-miR-663a gene (miRBase Accession No. MIMAT0003326) described in SEQ ID NO: 261, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 600) having a hairpin-like structure is known as a precursor of "hsa-miR-663a".

The term "hsa-miR-663b gene" or "hsa-miR-663b" used herein includes the hsa-miR-663b gene (miRBase Accession No. MIMAT0005867) described in SEQ ID NO: 262, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 601) having a hairpin-like structure is known as a precursor of "hsa-miR-663b".

The term "hsa-miR-6717-5p gene" or "hsa-miR-6717-5p" used herein includes the hsa-miR-6717-5p gene (miRBase Accession No. MIMAT0025846) described in SEQ ID NO: 263, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 602) having a hairpin-like structure is known as a precursor of "hsa-miR-6717-5p".

The term "hsa-miR-6721-5p gene" or "hsa-miR-6721-5p" used herein includes the hsa-miR-6721-5p gene (miRBase Accession No. MIMAT0025852) described in SEQ ID NO: 264, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 603) having a hairpin-like structure is known as a precursor of "hsa-miR-6721-5p".

The term "hsa-miR-6726-5p gene" or "hsa-miR-6726-5p" used herein includes the hsa-miR-6726-5p gene (miRBase Accession No. MIMAT0027353) described in SEQ ID NO: 265, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 604) having a hairpin-like structure is known as a precursor of "hsa-miR-6726-5p".

The term "hsa-miR-6727-5p gene" or "hsa-miR-6727-5p" used herein includes the hsa-miR-6727-5p gene (miRBase Accession No. MIMAT0027355) described in SEQ ID NO: 266, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 605) having a hairpin-like structure is known as a precursor of "hsa-miR-6727-5p".

The term "hsa-miR-6738-5p gene" or "hsa-miR-6738-5p" used herein includes the hsa-miR-6738-5p gene (miRBase Accession No. MIMAT0027377) described in SEQ ID NO: 267, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 606) having a hairpin-like structure is known as a precursor of "hsa-miR-6738-5p".

The term "hsa-miR-6741-5p gene" or "hsa-miR-6741-5p" used herein includes the hsa-miR-6741-5p gene (miRBase Accession No. MIMAT0027383) described in SEQ ID NO: 268, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 607) having a hairpin-like structure is known as a precursor of "hsa-miR-6741-5p".

The term "hsa-miR-6749-5p gene" or "hsa-miR-6749-5p" used herein includes the hsa-miR-6749-5p gene (miRBase Accession No. MIMAT0027398) described in SEQ ID NO: 269, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 608) having a hairpin-like structure is known as a precursor of "hsa-miR-6749-5p".

The term "hsa-miR-6752-5p gene" or "hsa-miR-6752-5p" used herein includes the hsa-miR-6752-5p gene (miRBase Accession No. MIMAT0027404) described in SEQ ID NO: 270, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 609) having a hairpin-like structure is known as a precursor of "hsa-miR-6752-5p".

The term "hsa-miR-675-5p gene" or "hsa-miR-675-5p" used herein includes the hsa-miR-675-5p gene (miRBase Accession No. MIMAT0004284) described in SEQ ID NO: 271, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 610) having a hairpin-like structure is known as a precursor of "hsa-miR-675-5p".

The term "hsa-miR-6757-5p gene" or "hsa-miR-6757-5p" used herein includes the hsa-miR-6757-5p gene (miRBase Accession No. MIMAT0027414) described in SEQ ID NO: 272, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 611) having a hairpin-like structure is known as a precursor of "hsa-miR-6757-5p".

The term "hsa-miR-6763-5p gene" or "hsa-miR-6763-5p" used herein includes the hsa-miR-6763-5p gene (miRBase Accession No. MIMAT0027426) described in SEQ ID NO: 273, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 442) having a hairpin-like structure is known as a precursor of "hsa-miR-6763-5p".

The term "hsa-miR-6765-5p gene" or "hsa-miR-6765-5p" used herein includes the hsa-miR-6765-5p gene (miRBase Accession No. MIMAT0027430) described in SEQ ID NO: 274, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 612) having a hairpin-like structure is known as a precursor of "hsa-miR-6765-5p".

The term "hsa-miR-6775-5p gene" or "hsa-miR-6775-5p" used herein includes the hsa-miR-6775-5p gene (miRBase Accession No. MIMAT0027450) described in SEQ ID NO: 275, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 613) having a hairpin-like structure is known as a precursor of "hsa-miR-6775-5p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 276, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 614) having a hairpin-like structure is known as a precursor of "hsa-miR-6780b-5p".

The term "hsa-miR-6782-5p gene" or "hsa-miR-6782-5p" used herein includes the hsa-miR-6782-5p gene (miRBase Accession No. MIMAT0027464) described in SEQ ID NO: 277, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 615) having a hairpin-like structure is known as a precursor of "hsa-miR-6782-5p".

The term "hsa-miR-6784-5p gene" or "hsa-miR-6784-5p" used herein includes the hsa-miR-6784-5p gene (miRBase Accession No. MIMAT0027468) described in SEQ ID NO: 278, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 616) having a hairpin-like structure is known as a precursor of "hsa-miR-6784-5p".

The term "hsa-miR-6800-5p gene" or "hsa-miR-6800-5p" used herein includes the hsa-miR-6800-5p gene (miRBase Accession No. MIMAT0027500) described in SEQ ID NO: 279, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 451) having a hairpin-like structure is known as a precursor of "hsa-miR-6800-5p".

The term "hsa-miR-6806-5p gene" or "hsa-miR-6806-5p" used herein includes the hsa-miR-6806-5p gene (miRBase Accession No. MIMAT0027512) described in SEQ ID NO: 280, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 617) having a hairpin-like structure is known as a precursor of "hsa-miR-6806-5p".

The term "hsa-miR-6840-3p gene" or "hsa-miR-6840-3p" used herein includes the hsa-miR-6840-3p gene (miRBase Accession No. MIMAT0027583) described in SEQ ID NO: 281, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 618) having a hairpin-like structure is known as a precursor of "hsa-miR-6840-3p".

The term "hsa-miR-6848-5p gene" or "hsa-miR-6848-5p" used herein includes the hsa-miR-6848-5p gene (miRBase Accession No. MIMAT0027596) described in SEQ ID NO: 282, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 619) having a hairpin-like structure is known as a precursor of "hsa-miR-6848-5p".

The term "hsa-miR-6851-5p gene" or "hsa-miR-6851-5p" used herein includes the hsa-miR-6851-5p gene (miRBase Accession No. MIMAT0027602) described in SEQ ID NO: 283, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 620) having a hairpin-like structure is known as a precursor of "hsa-miR-6851-5p".

The term "hsa-miR-6870-5p gene" or "hsa-miR-6870-5p" used herein includes the hsa-miR-6870-5p gene (miRBase Accession No. MIMAT0027640) described in SEQ ID NO: 284, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 621) having a hairpin-like structure is known as a precursor of "hsa-miR-6870-5p".

The term "hsa-miR-6872-3p gene" or "hsa-miR-6872-3p" used herein includes the hsa-miR-6872-3p gene (miRBase Accession No. MIMAT0027645) described in SEQ ID NO: 285, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872"

(miRBase Accession No. MI0022719, SEQ ID NO: 622) having a hairpin-like structure is known as a precursor of "hsa-miR-6872-3p".

The term "hsa-miR-6875-5p gene" or "hsa-miR-6875-5p" used herein includes the hsa-miR-6875-5p gene (miRBase Accession No. MIMAT0027650) described in SEQ ID NO: 286, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 623) having a hairpin-like structure is known as a precursor of "hsa-miR-6875-5p".

The term "hsa-miR-6877-5p gene" or "hsa-miR-6877-5p" used herein includes the hsa-miR-6877-5p gene (miRBase Accession No. MIMAT0027654) described in SEQ ID NO: 287, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 624) having a hairpin-like structure is known as a precursor of "hsa-miR-6877-5p".

The term "hsa-miR-6879-5p gene" or "hsa-miR-6879-5p" used herein includes the hsa-miR-6879-5p gene (miRBase Accession No. MIMAT0027658) described in SEQ ID NO: 288, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 625) having a hairpin-like structure is known as a precursor of "hsa-miR-6879-5p".

The term "hsa-miR-6880-5p gene" or "hsa-miR-6880-5p" used herein includes the hsa-miR-6880-5p gene (miRBase Accession No. MIMAT0027660) described in SEQ ID NO: 289, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 464) having a hairpin-like structure is known as a precursor of "hsa-miR-6880-5p".

The term "hsa-miR-6885-5p gene" or "hsa-miR-6885-5p" used herein includes the hsa-miR-6885-5p gene (miRBase Accession No. MIMAT0027670) described in SEQ ID NO: 290, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 626) having a hairpin-like structure is known as a precursor of "hsa-miR-6885-5p".

The term "hsa-miR-6887-5p gene" or "hsa-miR-6887-5p" used herein includes the hsa-miR-6887-5p gene (miRBase Accession No. MIMAT0027674) described in SEQ ID NO: 291, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 627) having a hairpin-like structure is known as a precursor of "hsa-miR-6887-5p".

The term "hsa-miR-7108-5p gene" or "hsa-miR-7108-5p" used herein includes the hsa-miR-7108-5p gene (miRBase Accession No. MIMAT0028113) described in SEQ ID NO: 292, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. M10022959, SEQ ID NO: 495) having a hairpin-like structure is known as a precursor of "hsa-miR-7108-5p".

The term "hsa-miR-711 gene" or "hsa-miR-711" used herein includes the hsa-miR-711 gene (miRBase Accession No. MIMAT0012734) described in SEQ ID NO: 293, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 628) having a hairpin-like structure is known as a precursor of "hsa-miR-711".

The term "hsa-miR-7113-3p gene" or "hsa-miR-7113-3p" used herein includes the hsa-miR-7113-3p gene (miRBase Accession No. MIMAT0028124) described in SEQ ID NO: 294, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 629) having a hairpin-like structure is known as a precursor of "hsa-miR-7113-3p".

The term "hsa-miR-744-5p gene" or "hsa-miR-744-5p" used herein includes the hsa-miR-744-5p gene (miRBase Accession No. MIMAT0004945) described in SEQ ID NO: 295, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 630) having a hairpin-like structure is known as a precursor of "hsa-miR-744-5p".

The term "hsa-miR-760 gene" or "hsa-miR-760" used herein includes the hsa-miR-760 gene (miRBase Accession No. MIMAT0004957) described in SEQ ID NO: 296, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. M10005567, SEQ ID NO: 631) having a hairpin-like structure is known as a precursor of "hsa-miR-760".

The term "hsa-miR-7845-5p gene" or "hsa-miR-7845-5p" used herein includes the hsa-miR-7845-5p gene (miRBase Accession No. MIMAT0030420) described in SEQ ID NO: 297, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 632) having a hairpin-like structure is known as a precursor of "hsa-miR-7845-5p".

The term "hsa-miR-7847-3p gene" or "hsa-miR-7847-3p" used herein includes the hsa-miR-7847-3p gene (miRBase Accession No. MIMAT0030422) described in SEQ ID NO: 298, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 633) having a hairpin-like structure is known as a precursor of "hsa-miR-7847-3p".

The term "hsa-miR-7977 gene" or "hsa-miR-7977" used herein includes the hsa-miR-7977 gene (miRBase Accession No. MIMAT0031180) described in SEQ ID NO: 299, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 634) having a hairpin-like structure is known as a precursor of "hsa-miR-7977".

The term "hsa-miR-8059 gene" or "hsa-miR-8059" used herein includes the hsa-miR-8059 gene (miRBase Accession No. MIMAT0030986) described in SEQ ID NO: 300, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 635) having a hairpin-like structure is known as a precursor of "hsa-miR-8059".

The term "hsa-miR-8063 gene" or "hsa-miR-8063" used herein includes the hsa-miR-8063 gene (miRBase Accession No. MIMAT0030990) described in SEQ ID NO: 301, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 636) having a hairpin-like structure is known as a precursor of "hsa-miR-8063".

The term "hsa-miR-8072 gene" or "hsa-miR-8072" used herein includes the hsa-miR-8072 gene (miRBase Accession No. MIMAT0030999) described in SEQ ID NO: 302, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 637) having a hairpin-like structure is known as a precursor of "hsa-miR-8072".

The term "hsa-miR-874-3p gene" or "hsa-miR-874-3p" used herein includes the hsa-miR-874-3p gene (miRBase Accession No. MIMAT0004911) described in SEQ ID NO: 303, a homolog or an ortholog of a different organism species, and the like. The hsa-miR-874-3p gene can be obtained by a method described in Landgraf P et al., 2007, Cell., Vol. 129, p. 1401-1414. Also, "hsa-mir-874" (miRBase Accession No. MI0005532, SEQ ID NO: 475) having a hairpin-like structure is known as a precursor of "hsa-miR-874-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 304, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 638) having a hairpin-like structure is known as a precursor of "hsa-miR-92a-2-5p".

The term "hsa-miR-92b-5p gene" or "hsa-miR-92b-5p" used herein includes the hsa-miR-92b-5p gene (miRBase Accession No. MIMAT0004792) described in SEQ ID NO: 305, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 499) having a hairpin-like structure is known as a precursor of "hsa-miR-92b-5p".

The term "hsa-miR-940 gene" or "hsa-miR-940" used herein includes the hsa-miR-940 gene (miRBase Accession No. MIMAT0004983) described in SEQ ID NO: 306, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 639) having a hairpin-like structure is known as a precursor of "hsa-miR-940".

The term "hsa-miR-1228-3p gene" or "hsa-miR-1228-3p" used herein includes the hsa-miR-1228-3p gene (miRBase Accession No. MIMAT0005583) described in SEQ ID NO: 307, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 511) having a hairpin-like structure is known as a precursor of "hsa-miR-1228-3p".

The term "hsa-miR-1275 gene" or "hsa-miR-1275" used herein includes the hsa-miR-1275 gene (miRBase Accession No. MIMAT0005929) described in SEQ ID NO: 308, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 640) having a hairpin-like structure is known as a precursor of "hsa-miR-1275".

The term "hsa-miR-1307-3p gene" or "hsa-miR-1307-3p" used herein includes the hsa-miR-1307-3p gene (miRBase Accession No. MIMAT0005951) described in SEQ ID NO: 309, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 641) having a hairpin-like structure is known as a precursor of "hsa-miR-1307-3p".

The term "hsa-miR-1343-5p gene" or "hsa-miR-1343-5p" used herein includes the hsa-miR-1343-5p gene (miRBase Accession No. MIMAT0027038) described in SEQ ID NO: 310, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 500) having a hairpin-like structure is known as a precursor of "hsa-miR-1343-5p".

The term "hsa-miR-23a-3p gene" or "hsa-miR-23a-3p" used herein includes the hsa-miR-23a-3p gene (miRBase Accession No. MIMAT0000078) described in SEQ ID NO: 311, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 642) having a hairpin-like structure is known as a precursor of "hsa-miR-23a-3p".

The term "hsa-miR-29b-3p gene" or "hsa-miR-29b-3p" used herein includes the hsa-miR-29b-3p gene (miRBase Accession No. MIMAT0000100) described in SEQ ID NO: 312, a homolog or an ortholog of a different organism species, and the like. The hsa-miR-29b-3p gene can be obtained by a method described in Mourelatos Z et al., 2002, Genes Dev., Vol. 16, p. 720-728. Also, "hsa-mir-29b-1 and hsa-mir-29b-2" (miRBase Accession Nos. MI0000105 and MI0000107, SEQ ID NOs: 643 and 644) having a hairpin-like structure are known as precursors of "hsa-miR-29b-3p".

The term "hsa-miR-3135b gene" or "hsa-miR-3135b" used herein includes the hsa-miR-3135b gene (miRBase Accession No. MIMAT0018985) described in SEQ ID NO:

313, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 645) having a hairpin-like structure is known as a precursor of "hsa-miR-3135b".

The term "hsa-miR-3185 gene" or "hsa-miR-3185" used herein includes the hsa-miR-3185 gene (miRBase Accession No. MIMAT0015065) described in SEQ ID NO: 314, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 646) having a hairpin-like structure is known as a precursor of "hsa-miR-3185".

The term "hsa-miR-4532 gene" or "hsa-miR-4532" used herein includes the hsa-miR-4532 gene (miRBase Accession No. MIMAT0019071) described in SEQ ID NO: 315, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 647) having a hairpin-like structure is known as a precursor of "hsa-miR-4532".

The term "hsa-miR-4690-5p gene" or "hsa-miR-4690-5p" used herein includes the hsa-miR-4690-5p gene (miRBase Accession No. MIMAT0019779) described in SEQ ID NO: 316, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 648) having a hairpin-like structure is known as a precursor of "hsa-miR-4690-5p".

The term "hsa-miR-4758-5p gene" or "hsa-miR-4758-5p" used herein includes the hsa-miR-4758-5p gene (miRBase Accession No. MIMAT0019903) described in SEQ ID NO: 317, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 649) having a hairpin-like structure is known as a precursor of "hsa-miR-4758-5p".

The term "hsa-miR-4783-3p gene" or "hsa-miR-4783-3p" used herein includes the hsa-miR-4783-3p gene (miRBase Accession No. MIMAT0019947) described in SEQ ID NO: 318, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 650) having a hairpin-like structure is known as a precursor of "hsa-miR-4783-3p".

The term "hsa-miR-6131 gene" or "hsa-miR-6131" used herein includes the hsa-miR-6131 gene (miRBase Accession No. MIMAT0024615) described in SEQ ID NO: 319, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 651) having a hairpin-like structure is known as a precursor of "hsa-miR-6131".

The term "hsa-miR-625-3p gene" or "hsa-miR-625-3p" used herein includes the hsa-miR-625-3p gene (miRBase Accession No. MIMAT0004808) described in SEQ ID NO: 320, a homolog or an ortholog of a different organism species, and the like. The hsa-miR-625-3p gene can be obtained by a method described in Cummins J M et al., 2006, Proc Natl Acad Sci USA, Vol. 103, p. 3687-3692. Also, "hsa-mir-625" (miRBase Accession No. MI0003639, SEQ ID NO: 652) having a hairpin-like structure is known as a precursor of "hsa-miR-625-3p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 321, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566, SEQ ID NOs: 653, 654, 655, and 656) having a hairpin-like structure are known as precursors of "hsa-miR-6511a-5p".

The term "hsa-miR-6765-3p gene" or "hsa-miR-6765-3p" used herein includes the hsa-miR-6765-3p gene (miRBase Accession No. MIMAT0027431) described in SEQ ID NO: 322, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 612) having a hairpin-like structure is known as a precursor of "hsa-miR-6765-3p".

The term "hsa-miR-6816-5p gene" or "hsa-miR-6816-5p" used herein includes the hsa-miR-6816-5p gene (miRBase Accession No. MIMAT0027532) described in SEQ ID NO: 323, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 657) having a hairpin-like structure is known as a precursor of "hsa-miR-6816-5p".

The term "hsa-miR-6825-5p gene" or "hsa-miR-6825-5p" used herein includes the hsa-miR-6825-5p gene (miRBase Accession No. MIMAT0027550) described in SEQ ID NO: 324, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 658) having a hairpin-like structure is known as a precursor of "hsa-miR-6825-5p".

The term "hsa-miR-6845-5p gene" or "hsa-miR-6845-5p" used herein includes the hsa-miR-6845-5p gene (miRBase Accession No. MIMAT0027590) described in SEQ ID NO: 325, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 659) having a hairpin-like structure is known as a precursor of "hsa-miR-6845-5p".

The term "hsa-miR-7150 gene" or "hsa-miR-7150" used herein includes the hsa-miR-7150 gene (miRBase Accession No. MIMAT0028211) described in SEQ ID NO: 326, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 660) having a hairpin-like structure is known as a precursor of "hsa-miR-7150".

The term "hsa-miR-7641 gene" or "hsa-miR-7641" used herein includes the hsa-miR-7641 gene (miRBase Accession No. MIMAT0029782) described in SEQ ID NO: 327, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 661 and 662) having a hairpin-like structure are known as precursors of "hsa-miR-7641".

The term "hsa-miR-7975 gene" or "hsa-miR-7975" used herein includes the hsa-miR-7975 gene (miRBase Accession No. MIMAT0031178) described in SEQ ID NO: 328, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 663) having a hairpin-like structure is known as a precursor of "hsa-miR-7975".

The term "hsa-miR-92a-3p gene" or "hsa-miR-92a-3p" used herein includes the hsa-miR-92a-3p gene (miRBase Accession No. MIMAT0000092) described in SEQ ID NO: 329, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 664 and 638) having a hairpin-like structure are known as precursors of "hsa-miR-92a-3p".

A mature miRNA may become a variant shorter or longer by one to several flanking nucleotides due to the sequence cleavage, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 21 shows the nucleotide sequences represented by SEQ ID NOs: 1 to 329 as well as a large number of the nucleotide sequence variants and fragments represented by SEQ ID NOs: 665 to 1000, called isomiRs. These variants can also be obtained as miRNAs having a nucleotide sequence represented by any of SEQ ID NOs: 1 to 329. Specifically, according to the present invention, among the variants of polynucleotides consisting of the nucleotide sequence represented by any of SEQ ID NOs: 4, 7, 8, 9, 13, 14, 18, 20, 21, 22, 23, 26, 28, 31, 32, 33, 35, 36, 38, 41, 44, 45, 46, 48, 49, 51, 52, 53, 54, 55, 56, 57, 58, 61, 62, 68, 73, 74, 77, 78, 82, 83, 84, 85, 86, 87, 91, 92, 93, 94, 95, 96, 97, 100, 101, 138, 139, 141, 145, 146, 147, 150, 151, 163, 164, 167, 170, 171, 175, 177, 179, 180, 181, 182, 183, 184, 185, 188, 189, 190, 191, 192, 193, 195, 196, 197, 198, 200, 201, 202, 203, 204, 206, 207, 209, 210, 211, 212, 214, 216, 220, 223, 224, 226, 227, 229, 230, 231, 233, 235, 237, 240, 241, 244, 245, 246, 249, 252, 253, 254, 256, 257, 258, 259, 260, 261, 262, 263, 264, 295, 296, 303, 304, 305, 306, 307, 308, 309, 311, 312, 313, 315, 316, 317, 318, 319, 320, 321, and 329, or the nucleotide sequence in which the nucleic acid u is replaced with t, examples of the longest variants registered in miRBase Release 21 include polynucleotides represented by SEQ ID NOs: 666, 668, 669, 671, 674, 676, 679, 681, 683, 685, 687, 691, 693, 697, 699, 701, 703, 705, 707, 709, 712, 713, 715, 717, 719, 721, 723, 724, 726, 728, 730, 732, 734, 736, 738, 743, 748, 750, 752, 754, 757, 759, 761, 763, 765, 767, 770, 772, 774, 776, 778, 779, 781, 783, 785, 787, 789, 792, 795, 797, 799, 803, 805, 808, 810, 812, 815, 817, 819, 821, 824, 826, 828, 830, 832, 834, 836, 840, 842, 844, 846, 848, 850, 853, 855, 857, 859, 862, 864, 866, 868, 870, 873, 875, 877, 879, 881, 883, 886, 889, 892, 896, 898, 901, 903, 904, 906, 908, 911, 912, 914, 917, 919, 923, 925, 927, 930, 933, 935, 937, 940, 942, 944, 946, 948, 950, 952, 954, 956, 960, 962, 964, 966, 968, 970, 972, 974, 976, 978, 980, 982, 985, 987, 989, 991, 993, 994, 996, and 999, respectively. Also, according to the present invention, among the variants of polynucleotides consisting of the nucleotide sequence represented by any of SEQ ID NOs: 3, 4, 8, 9, 10, 13, 14, 17, 18, 20, 21, 22, 23, 24, 25, 26, 28, 29, 30, 31, 32, 33, 35, 36, 38, 41, 43, 45, 46, 48, 49, 51, 53, 54, 55, 56, 57, 58, 61, 62, 65, 66, 67, 68, 69, 71, 72, 73, 74, 77, 78, 80, 82, 83, 84, 85, 86, 87, 89, 91, 92, 93, 94, 96, 97, 100, 114, 138, 139, 140, 141, 142, 145, 146, 147, 148, 149, 150, 151, 162, 163, 164, 167, 168, 170, 171, 175, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 209, 210, 211, 212, 213, 214, 215, 216, 219, 220, 221, 222, 223, 224, 225, 226, 229, 230, 231, 232, 235, 237, 238, 240, 241, 242, 243, 244, 245, 246, 248, 249, 251, 252, 253, 254, 255, 256, 257, 258, 259, 260, 261, 262, 263, 264, 271, 293, 295, 296, 303, 304, 305, 306, 307, 308, 309, 311, 312, 313, 314, 315, 316, 317, 318, 320, 321, 328, and 329, or the nucleotide sequence in which the nucleic acid u is replaced with t, examples of the shortest variants registered in the miRBase Release 21 include polynucleotides having sequences represented by SEQ ID NOs: 665, 667, 670, 672, 673, 675, 677, 678, 680, 682, 684, 686, 688, 689, 690, 692, 694, 695, 696, 698, 700, 702, 704, 706, 708, 710, 711, 714, 716, 718, 720, 722, 725, 727, 729, 731, 733, 735, 737, 739, 740, 741, 742, 744, 745, 746, 747, 749, 751, 753, 755, 756, 758, 760, 762, 764, 766, 768, 769, 771, 773, 775, 777, 780, 782, 784, 786, 788, 790, 791, 793, 794, 796, 798, 800, 801, 802, 804, 806, 807, 809, 811, 813, 814, 816, 818, 820, 822, 823, 825, 827, 829, 831, 833, 835, 837, 838, 839, 841, 843, 845, 847, 849, 851, 852, 854, 856, 858, 860, 861, 863, 865, 867, 869, 871, 872, 874, 876, 878, 880, 882, 884, 885, 887, 888, 890, 891, 893, 894, 895, 897, 899, 900, 902, 905, 907, 909, 910, 913, 915, 916, 918, 920, 921, 922, 924, 926, 928, 929, 931, 932, 934, 936, 938, 939, 941, 943, 945, 947, 949, 951, 953, 955, 957, 958, 959, 961, 963, 965, 967, 969, 971, 973, 975, 977, 979, 981, 983, 984, 986, 988, 990, 992, 995, 997, 998, and 1000, respectively. In addition to these variants and fragments, examples thereof include a large number of isomiR polynucleotides of SEQ ID NOs: 1 to 329 registered in the miRBase. Examples of the polynucleotide comprising a nucleotide sequence represented by any of SEQ ID NOs: 1 to 329 include a polynucleotide represented by any of SEQ ID NOs: 330 to 664, which are their respective precursors.

The names and miRBase Accession Nos. (registration numbers) of the genes represented by SEQ ID NOs: 1 to 1000 are shown in Table 1.

As used herein, the term "capable of specifically binding" means that nucleic acids such as the nucleic acid probe or the primer used in the present invention binds to a particular target nucleic acid and cannot substantially bind to other nucleic acids.

TABLE 1

| SEQ ID NO: | Name of gene | Accession No. of miRBase |
|---|---|---|
| 1 | hsa-miR-6787-5p | MIMAT0027474 |
| 2 | hsa-miR-920 | MIMAT0004970 |

TABLE 1-continued

| SEQ ID NO: | Name of gene | Accession No. of miRBase |
|---|---|---|
| 3 | hsa-miR-3622a-5p | MIMAT0018003 |
| 4 | hsa-miR-1185-1-3p | MIMAT0022838 |
| 5 | hsa-miR-4327 | MIMAT0016889 |
| 6 | hsa-miR-5739 | MIMAT0023116 |
| 7 | hsa-miR-937-5p | MIMAT0022938 |
| 8 | hsa-miR-1181 | MIMAT0005826 |
| 9 | hsa-miR-1185-2-3p | MIMAT0022713 |
| 10 | hsa-miR-1193 | MIMAT0015049 |
| 11 | hsa-miR-1207-5p | MIMAT0005871 |
| 12 | hsa-miR-1238-5p | MIMAT0022947 |
| 13 | hsa-miR-1246 | MIMAT0005898 |
| 14 | hsa-miR-1249-5p | MIMAT0032029 |
| 15 | hsa-miR-1292-3p | MIMAT0022948 |
| 16 | hsa-miR-1469 | MIMAT0007347 |
| 17 | hsa-miR-1470 | MIMAT0007348 |
| 18 | hsa-miR-197-5p | MIMAT0022691 |
| 19 | hsa-miR-208a-5p | MIMAT0026474 |
| 20 | hsa-miR-2110 | MIMAT0010133 |
| 21 | hsa-miR-211-3p | MIMAT0022694 |
| 22 | hsa-miR-2467-3p | MIMAT0019953 |
| 23 | hsa-miR-3122 | MIMAT0014984 |
| 24 | hsa-miR-3141 | MIMAT0015010 |
| 25 | hsa-miR-3156-5p | MIMAT0015030 |
| 26 | hsa-miR-3158-5p | MIMAT0019211 |
| 27 | hsa-miR-3160-5p | MIMAT0019212 |
| 28 | hsa-miR-3180-3p | MIMAT0015058 |
| 29 | hsa-miR-3191-3p | MIMAT0015075 |
| 30 | hsa-miR-3194-3p | MIMAT0019218 |
| 31 | hsa-miR-320b | MIMAT0005792 |
| 32 | hsa-miR-328-5p | MIMAT0026486 |
| 33 | hsa-miR-3610 | MIMAT0017987 |
| 34 | hsa-miR-3619-3p | MIMAT0019219 |
| 35 | hsa-miR-3620-5p | MIMAT0022967 |
| 36 | hsa-miR-370-3p | MIMAT0000722 |
| 37 | hsa-miR-373-5p | MIMAT0000725 |
| 38 | hsa-miR-3917 | MIMAT0018191 |
| 39 | hsa-miR-3937 | MIMAT0018352 |
| 40 | hsa-miR-4259 | MIMAT0016880 |
| 41 | hsa-miR-4281 | MIMAT0016907 |
| 42 | hsa-miR-4294 | MIMAT0016849 |
| 43 | hsa-miR-4419b | MIMAT0019034 |
| 44 | hsa-miR-4428 | MIMAT0018943 |
| 45 | hsa-miR-4429 | MIMAT0018944 |
| 46 | hsa-miR-4433a-3p | MIMAT0018949 |
| 47 | hsa-miR-4447 | MIMAT0018966 |
| 48 | hsa-miR-4449 | MIMAT0018968 |
| 49 | hsa-miR-4459 | MIMAT0018981 |
| 50 | hsa-miR-4480 | MIMAT0019014 |
| 51 | hsa-miR-4485-5p | MIMAT0032116 |
| 52 | hsa-miR-4486 | MIMAT0019020 |
| 53 | hsa-miR-4488 | MIMAT0019022 |
| 54 | hsa-miR-4489 | MIMAT0019023 |
| 55 | hsa-miR-4505 | MIMAT0019041 |
| 56 | hsa-miR-4513 | MIMAT0019050 |
| 57 | hsa-miR-4515 | MIMAT0019052 |
| 58 | hsa-miR-4530 | MIMAT0019069 |
| 59 | hsa-miR-4535 | MIMAT0019075 |
| 60 | hsa-miR-4635 | MIMAT0019692 |
| 61 | hsa-miR-4640-5p | MIMAT0019699 |
| 62 | hsa-miR-4646-5p | MIMAT0019707 |
| 63 | hsa-miR-4656 | MIMAT0019723 |
| 64 | hsa-miR-4663 | MIMAT0019735 |
| 65 | hsa-miR-4665-5p | MIMAT0019739 |
| 66 | hsa-miR-4706 | MIMAT0019806 |
| 67 | hsa-miR-4707-5p | MIMAT0019807 |
| 68 | hsa-miR-4708-3p | MIMAT0019810 |
| 69 | hsa-miR-4710 | MIMAT0019815 |
| 70 | hsa-miR-4718 | MIMAT0019831 |
| 71 | hsa-miR-4722-5p | MIMAT0019836 |
| 72 | hsa-miR-4727-3p | MIMAT0019848 |
| 73 | hsa-miR-4730 | MIMAT0019852 |
| 74 | hsa-miR-4734 | MIMAT0019859 |
| 75 | hsa-miR-4740-5p | MIMAT0019869 |
| 76 | hsa-miR-4747-3p | MIMAT0019883 |
| 77 | hsa-miR-4749-5p | MIMAT0019885 |
| 78 | hsa-miR-4755-3p | MIMAT0019896 |
| 79 | hsa-miR-4763-5p | MIMAT0019912 |
| 80 | hsa-miR-4787-3p | MIMAT0019957 |
| 81 | hsa-miR-5008-5p | MIMAT0021039 |
| 82 | hsa-miR-5010-5p | MIMAT0021043 |
| 83 | hsa-miR-504-3p | MIMAT0026612 |
| 84 | hsa-miR-5090 | MIMAT0021082 |
| 85 | hsa-miR-5100 | MIMAT0022259 |
| 86 | hsa-miR-5196-5p | MIMAT0021128 |
| 87 | hsa-miR-551b-5p | MIMAT0004794 |
| 88 | hsa-miR-557 | MIMAT0003221 |
| 89 | hsa-miR-5787 | MIMAT0023252 |
| 90 | hsa-miR-6090 | MIMAT0023715 |
| 91 | hsa-miR-6124 | MIMAT0024597 |
| 92 | hsa-miR-6132 | MIMAT0024616 |
| 93 | hsa-miR-6510-5p | MIMAT0025476 |
| 94 | hsa-miR-6511b-5p | MIMAT0025847 |
| 95 | hsa-miR-6515-3p | MIMAT0025487 |
| 96 | hsa-miR-654-5p | MIMAT0003330 |
| 97 | hsa-miR-658 | MIMAT0003336 |
| 98 | hsa-miR-668-5p | MIMAT0026636 |
| 99 | hsa-miR-6722-5p | MIMAT0025853 |
| 100 | hsa-miR-6724-5p | MIMAT0025856 |
| 101 | hsa-miR-6729-3p | MIMAT0027360 |
| 102 | hsa-miR-6737-5p | MIMAT0027375 |
| 103 | hsa-miR-6756-5p | MIMAT0027412 |
| 104 | hsa-miR-6762-5p | MIMAT0027424 |
| 105 | hsa-miR-6763-3p | MIMAT0027427 |
| 106 | hsa-miR-6766-5p | MIMAT0027432 |
| 107 | hsa-miR-6769a-5p | MIMAT0027438 |
| 108 | hsa-miR-6771-5p | MIMAT0027442 |
| 109 | hsa-miR-6786-5p | MIMAT0027472 |
| 110 | hsa-miR-6789-5p | MIMAT0027478 |
| 111 | hsa-miR-6794-5p | MIMAT0027488 |
| 112 | hsa-miR-6796-3p | MIMAT0027493 |
| 113 | hsa-miR-6797-5p | MIMAT0027494 |
| 114 | hsa-miR-6800-3p | MIMAT0027501 |
| 115 | hsa-miR-6802-5p | MIMAT0027504 |
| 116 | hsa-miR-6803-5p | MIMAT0027506 |
| 117 | hsa-miR-6805-3p | MIMAT0027511 |
| 118 | hsa-miR-6805-5p | MIMAT0027510 |
| 119 | hsa-miR-6807-5p | MIMAT0027514 |
| 120 | hsa-miR-6812-5p | MIMAT0027524 |
| 121 | hsa-miR-6819-5p | MIMAT0027538 |
| 122 | hsa-miR-6822-5p | MIMAT0027544 |
| 123 | hsa-miR-6824-5p | MIMAT0027548 |
| 124 | hsa-miR-6826-5p | MIMAT0027552 |
| 125 | hsa-miR-6850-5p | MIMAT0027600 |
| 126 | hsa-miR-6858-5p | MIMAT0027616 |
| 127 | hsa-miR-6861-5p | MIMAT0027623 |
| 128 | hsa-miR-6880-3p | MIMAT0027661 |
| 129 | hsa-miR-7107-5p | MIMAT0028111 |
| 130 | hsa-miR-7109-5p | MIMAT0028115 |
| 131 | hsa-miR-7114-5p | MIMAT0028125 |
| 132 | hsa-miR-7704 | MIMAT0030019 |
| 133 | hsa-miR-7846-3p | MIMAT0030421 |
| 134 | hsa-miR-8052 | MIMAT0030979 |
| 135 | hsa-miR-8060 | MIMAT0030987 |
| 136 | hsa-miR-8071 | MIMAT0030998 |
| 137 | hsa-miR-8073 | MIMAT0031000 |
| 138 | hsa-miR-874-5p | MIMAT0026718 |
| 139 | hsa-miR-204-3p | MIMAT0022693 |
| 140 | hsa-miR-3154 | MIMAT0015028 |
| 141 | hsa-miR-3960 | MIMAT0019337 |
| 142 | hsa-miR-4433a-5p | MIMAT0020956 |
| 143 | hsa-miR-4455 | MIMAT0018974 |
| 144 | hsa-miR-4462 | MIMAT0018986 |
| 145 | hsa-miR-4476 | MIMAT0019003 |
| 146 | hsa-miR-4508 | MIMAT0019045 |
| 147 | hsa-miR-4687-3p | MIMAT0019775 |
| 148 | hsa-miR-4687-5p | MIMAT0019774 |
| 149 | hsa-miR-4732-5p | MIMAT0019855 |
| 150 | hsa-miR-4771 | MIMAT0019925 |
| 151 | hsa-miR-642a-3p | MIMAT0020924 |
| 152 | hsa-miR-6732-5p | MIMAT0027365 |
| 153 | hsa-miR-6760-5p | MIMAT0027420 |
| 154 | hsa-miR-6799-5p | MIMAT0027498 |
| 155 | hsa-miR-6820-5p | MIMAT0027540 |
| 156 | hsa-miR-6821-5p | MIMAT0027542 |

TABLE 1-continued

| SEQ ID NO: | Name of gene | Accession No. of miRBase |
|---|---|---|
| 157 | hsa-miR-6829-5p | MIMAT0027558 |
| 158 | hsa-miR-6893-5p | MIMAT0027686 |
| 159 | hsa-miR-7108-3p | MIMAT0028114 |
| 160 | hsa-miR-7111-5p | MIMAT0028119 |
| 161 | hsa-miR-8089 | MIMAT0031016 |
| 162 | hsa-miR-885-3p | MIMAT0004948 |
| 163 | hsa-miR-92b-3p | MIMAT0003218 |
| 164 | hsa-miR-1343-3p | MIMAT0019776 |
| 165 | hsa-miR-6746-5p | MIMAT0027392 |
| 166 | hsa-miR-422a | MIMAT0001339 |
| 167 | hsa-miR-187-5p | MIMAT0004561 |
| 168 | hsa-miR-4632-5p | MIMAT0022977 |
| 169 | hsa-miR-6791-5p | MIMAT0027482 |
| 170 | hsa-miR-103a-3p | MIMAT0000101 |
| 171 | hsa-miR-107 | MIMAT0000104 |
| 172 | hsa-miR-1199-5p | MIMAT0031119 |
| 173 | hsa-miR-1225-3p | MIMAT0005573 |
| 174 | hsa-miR-1225-5p | MIMAT0005572 |
| 175 | hsa-miR-1228-5p | MIMAT0005582 |
| 176 | hsa-miR-1229-5p | MIMAT0022942 |
| 177 | hsa-miR-1233-5p | MIMAT0022943 |
| 178 | hsa-miR-1237-5p | MIMAT0022946 |
| 179 | hsa-miR-1247-3p | MIMAT0022721 |
| 180 | hsa-miR-1249-3p | MIMAT0005901 |
| 181 | hsa-miR-1254 | MIMAT0005905 |
| 182 | hsa-miR-1260b | MIMAT0015041 |
| 183 | hsa-miR-1268a | MIMAT0005922 |
| 184 | hsa-miR-1268b | MIMAT0018925 |
| 185 | hsa-miR-1273g-3p | MIMAT0022742 |
| 186 | hsa-miR-128-1-5p | MIMAT0026477 |
| 187 | hsa-miR-128-2-5p | MIMAT0031095 |
| 188 | hsa-miR-1290 | MIMAT0005880 |
| 189 | hsa-miR-150-3p | MIMAT0004610 |
| 190 | hsa-miR-17-3p | MIMAT0000071 |
| 191 | hsa-miR-1908-5p | MIMAT0007881 |
| 192 | hsa-miR-1909-3p | MIMAT0007883 |
| 193 | hsa-miR-1914-3p | MIMAT0007890 |
| 194 | hsa-miR-1915-3p | MIMAT0007892 |
| 195 | hsa-miR-191-5p | MIMAT0000440 |
| 196 | hsa-miR-22-3p | MIMAT0000077 |
| 197 | hsa-miR-23b-3p | MIMAT0000418 |
| 198 | hsa-miR-24-3p | MIMAT0000080 |
| 199 | hsa-miR-296-3p | MIMAT0004679 |
| 200 | hsa-miR-296-5p | MIMAT0000690 |
| 201 | hsa-miR-3131 | MIMAT0014996 |
| 202 | hsa-miR-3162-5p | MIMAT0015036 |
| 203 | hsa-miR-3188 | MIMAT0015070 |
| 204 | hsa-miR-3196 | MIMAT0015080 |
| 205 | hsa-miR-3197 | MIMAT0015082 |
| 206 | hsa-miR-320a | MIMAT0000510 |
| 207 | hsa-miR-342-5p | MIMAT0004694 |
| 208 | hsa-miR-3621 | MIMAT0018002 |
| 209 | hsa-miR-3648 | MIMAT0018068 |
| 210 | hsa-miR-3656 | MIMAT0018076 |
| 211 | hsa-miR-365a-5p | MIMAT0009199 |
| 212 | hsa-miR-3665 | MIMAT0018087 |
| 213 | hsa-miR-3679-5p | MIMAT0018104 |
| 214 | hsa-miR-371a-5p | MIMAT0004687 |
| 215 | hsa-miR-3940-5p | MIMAT0019229 |
| 216 | hsa-miR-423-5p | MIMAT0004748 |
| 217 | hsa-miR-4257 | MIMAT0016878 |
| 218 | hsa-miR-4270 | MIMAT0016900 |
| 219 | hsa-miR-4271 | MIMAT0016901 |
| 220 | hsa-miR-4286 | MIMAT0016916 |
| 221 | hsa-miR-4298 | MIMAT0016852 |
| 222 | hsa-miR-4417 | MIMAT0018929 |
| 223 | hsa-miR-4442 | MIMAT0018960 |
| 224 | hsa-miR-4446-3p | MIMAT0018965 |
| 225 | hsa-miR-4448 | MIMAT0018967 |
| 226 | hsa-miR-4454 | MIMAT0018976 |
| 227 | hsa-miR-4467 | MIMAT0018994 |
| 228 | hsa-miR-4472 | MIMAT0018999 |
| 229 | hsa-miR-4507 | MIMAT0019044 |
| 230 | hsa-miR-4516 | MIMAT0019053 |
| 231 | hsa-miR-451a | MIMAT0001631 |
| 232 | hsa-miR-4649-5p | MIMAT0019711 |
| 233 | hsa-miR-4651 | MIMAT0019715 |
| 234 | hsa-miR-4665-3p | MIMAT0019740 |
| 235 | hsa-miR-4674 | MIMAT0019756 |
| 236 | hsa-miR-4675 | MIMAT0019757 |
| 237 | hsa-miR-4689 | MIMAT0019778 |
| 238 | hsa-miR-4695-5p | MIMAT0019788 |
| 239 | hsa-miR-4697-5p | MIMAT0019791 |
| 240 | hsa-miR-4725-3p | MIMAT0019844 |
| 241 | hsa-miR-4739 | MIMAT0019868 |
| 242 | hsa-miR-4745-5p | MIMAT0019878 |
| 243 | hsa-miR-4763-3p | MIMAT0019913 |
| 244 | hsa-miR-4792 | MIMAT0019964 |
| 245 | hsa-miR-486-3p | MIMAT0004762 |
| 246 | hsa-miR-5001-5p | MIMAT0021021 |
| 247 | hsa-miR-5195-3p | MIMAT0021127 |
| 248 | hsa-miR-550a-5p | MIMAT0004800 |
| 249 | hsa-miR-5698 | MIMAT0022491 |
| 250 | hsa-miR-6075 | MIMAT0023700 |
| 251 | hsa-miR-6088 | MIMAT0023713 |
| 252 | hsa-miR-6089 | MIMAT0023714 |
| 253 | hsa-miR-6125 | MIMAT0024598 |
| 254 | hsa-miR-6126 | MIMAT0024599 |
| 255 | hsa-miR-614 | MIMAT0003282 |
| 256 | hsa-miR-615-5p | MIMAT0004804 |
| 257 | hsa-miR-619-5p | MIMAT0026622 |
| 258 | hsa-miR-638 | MIMAT0003308 |
| 259 | hsa-miR-642b-3p | MIMAT0018444 |
| 260 | hsa-miR-650 | MIMAT0003320 |
| 261 | hsa-miR-663a | MIMAT0003326 |
| 262 | hsa-miR-663b | MIMAT0005867 |
| 263 | hsa-miR-6717-5p | MIMAT0025846 |
| 264 | hsa-miR-6721-5p | MIMAT0025852 |
| 265 | hsa-miR-6726-5p | MIMAT0027353 |
| 266 | hsa-miR-6727-5p | MIMAT0027355 |
| 267 | hsa-miR-6738-5p | MIMAT0027377 |
| 268 | hsa-miR-6741-5p | MIMAT0027383 |
| 269 | hsa-miR-6749-5p | MIMAT0027398 |
| 270 | hsa-miR-6752-5p | MIMAT0027404 |
| 271 | hsa-miR-675-5p | MIMAT0004284 |
| 272 | hsa-miR-6757-5p | MIMAT0027414 |
| 273 | hsa-miR-6763-5p | MIMAT0027426 |
| 274 | hsa-miR-6765-5p | MIMAT0027430 |
| 275 | hsa-miR-6775-5p | MIMAT0027450 |
| 276 | hsa-miR-6780b-5p | MIMAT0027572 |
| 277 | hsa-miR-6782-5p | MIMAT0027464 |
| 278 | hsa-miR-6784-5p | MIMAT0027468 |
| 279 | hsa-miR-6800-5p | MIMAT0027500 |
| 280 | hsa-miR-6806-5p | MIMAT0027512 |
| 281 | hsa-miR-6840-3p | MIMAT0027583 |
| 282 | hsa-miR-6848-5p | MIMAT0027596 |
| 283 | hsa-miR-6851-5p | MIMAT0027602 |
| 284 | hsa-miR-6870-5p | MIMAT0027640 |
| 285 | hsa-miR-6872-3p | MIMAT0027645 |
| 286 | hsa-miR-6875-5p | MIMAT0027650 |
| 287 | hsa-miR-6877-5p | MIMAT0027654 |
| 288 | hsa-miR-6879-5p | MIMAT0027658 |
| 289 | hsa-miR-6880-5p | MIMAT0027660 |
| 290 | hsa-miR-6885-5p | MIMAT0027670 |
| 291 | hsa-miR-6887-5p | MIMAT0027674 |
| 292 | hsa-miR-7108-5p | MIMAT0028113 |
| 293 | hsa-miR-711 | MIMAT0012734 |
| 294 | hsa-miR-7113-3p | MIMAT0028124 |
| 295 | hsa-miR-744-5p | MIMAT0004945 |
| 296 | hsa-miR-760 | MIMAT0004957 |
| 297 | hsa-miR-7845-5p | MIMAT0030420 |
| 298 | hsa-miR-7847-3p | MIMAT0030422 |
| 299 | hsa-miR-7977 | MIMAT0031180 |
| 300 | hsa-miR-8059 | MIMAT0030986 |
| 301 | hsa-miR-8063 | MIMAT0030990 |
| 302 | hsa-miR-8072 | MIMAT0030999 |
| 303 | hsa-miR-874-3p | MIMAT0004911 |
| 304 | hsa-miR-92a-2-5p | MIMAT0004508 |
| 305 | hsa-miR-92b-5p | MIMAT0004792 |
| 306 | hsa-miR-940 | MIMAT0004983 |
| 307 | hsa-miR-1228-3p | MIMAT0005583 |
| 308 | hsa-miR-1275 | MIMAT0005929 |
| 309 | hsa-miR-1307-3p | MIMAT0005951 |
| 310 | hsa-miR-1343-5p | MIMAT0027038 |

TABLE 1-continued

| SEQ ID NO: | Name of gene | Accession No. of miRBase |
|---|---|---|
| 311 | hsa-miR-23a-3p | MIMAT0000078 |
| 312 | hsa-miR-29b-3p | MIMAT0000100 |
| 313 | hsa-miR-3135b | MIMAT0018985 |
| 314 | hsa-miR-3185 | MIMAT0015065 |
| 315 | hsa-miR-4532 | MIMAT0019071 |
| 316 | hsa-miR-4690-5p | MIMAT0019779 |
| 317 | hsa-miR-4758-5p | MIMAT0019903 |
| 318 | hsa-miR-4783-3p | MIMAT0019947 |
| 319 | hsa-miR-6131 | MIMAT0024615 |
| 320 | hsa-miR-625-3p | MIMAT0004808 |
| 321 | hsa-miR-6511a-5p | MIMAT0025478 |
| 322 | hsa-miR-6765-3p | MIMAT0027431 |
| 323 | hsa-miR-6816-5p | MIMAT0027532 |
| 324 | hsa-miR-6825-5p | MIMAT0027550 |
| 325 | hsa-miR-6845-5p | MIMAT0027590 |
| 326 | hsa-miR-7150 | MIMAT0028211 |
| 327 | hsa-miR-7641 | MIMAT0029782 |
| 328 | hsa-miR-7975 | MIMAT0031178 |
| 329 | hsa-miR-92a-3p | MIMAT0000092 |
| 330 | hsa-mir-6787 | MI0022632 |
| 331 | hsa-mir-920 | MI0005712 |
| 332 | hsa-mir-3622a | MI0016013 |
| 333 | hsa-mir-1185-1 | MI0003844 |
| 334 | hsa-mir-4327 | MI0015867 |
| 335 | hsa-mir-5739 | MI0019412 |
| 336 | hsa-mir-937 | MI0005759 |
| 337 | hsa-mir-1181 | MI0006274 |
| 338 | hsa-mir-1185-2 | MI0003821 |
| 339 | hsa-mir-1193 | MI0014205 |
| 340 | hsa-mir-1207 | MI0006340 |
| 341 | hsa-mir-1238 | MI0006328 |
| 342 | hsa-mir-1246 | MI0006381 |
| 343 | hsa-mir-1249 | MI0006384 |
| 344 | hsa-mir-1292 | MI0006433 |
| 345 | hsa-mir-1469 | MI0007074 |
| 346 | hsa-mir-1470 | MI0007075 |
| 347 | hsa-mir-197 | MI0000239 |
| 348 | hsa-mir-208a | MI0000251 |
| 349 | hsa-mir-2110 | MI0010629 |
| 350 | hsa-mir-211 | MI0000287 |
| 351 | hsa-mir-2467 | MI0017432 |
| 352 | hsa-mir-3122 | MI0014138 |
| 353 | hsa-mir-3141 | MI0014165 |
| 354 | hsa-mir-3156-1 | MI0014184 |
| 355 | hsa-mir-3156-2 | MI0014230 |
| 356 | hsa-mir-3156-3 | MI0014242 |
| 357 | hsa-mir-3158-1 | MI0014186 |
| 358 | hsa-mir-3158-2 | MI0014187 |
| 359 | hsa-mir-3160-1 | MI0014189 |
| 360 | hsa-mir-3160-2 | MI0014190 |
| 361 | hsa-mir-3180-1 | MI0014214 |
| 362 | hsa-mir-3180-2 | MI0014215 |
| 363 | hsa-mir-3180-3 | MI0014217 |
| 364 | hsa-mir-3191 | MI0014236 |
| 365 | hsa-mir-3194 | MI0014239 |
| 366 | hsa-mir-320b-1 | MI0003776 |
| 367 | hsa-mir-320b-2 | MI0003839 |
| 368 | hsa-mir-328 | MI0000804 |
| 369 | hsa-mir-3610 | MI0016000 |
| 370 | hsa-mir-3619 | MI0016009 |
| 371 | hsa-mir-3620 | MI0016011 |
| 372 | hsa-mir-370 | MI0000778 |
| 373 | hsa-mir-373 | MI0000781 |
| 374 | hsa-mir-3917 | MI0016423 |
| 375 | hsa-mir-3937 | MI0016593 |
| 376 | hsa-mir-4259 | MI0015858 |
| 377 | hsa-mir-4281 | MI0015885 |
| 378 | hsa-mir-4294 | MI0015827 |
| 379 | hsa-mir-4419b | MI0016861 |
| 380 | hsa-mir-4428 | MI0016767 |
| 381 | hsa-mir-4429 | MI0016768 |
| 382 | hsa-mir-4433a | MI0016773 |
| 383 | hsa-mir-4447 | MI0016790 |
| 384 | hsa-mir-4449 | MI0016792 |
| 385 | hsa-mir-4459 | MI0016805 |
| 386 | hsa-mir-4480 | MI0016841 |
| 387 | hsa-mir-4485 | MI0016846 |
| 388 | hsa-mir-4486 | MI0016847 |
| 389 | hsa-mir-4488 | MI0016849 |
| 390 | hsa-mir-4489 | MI0016850 |
| 391 | hsa-mir-4505 | MI0016868 |
| 392 | hsa-mir-4513 | MI0016879 |
| 393 | hsa-mir-4515 | MI0016881 |
| 394 | hsa-mir-4530 | MI0016897 |
| 395 | hsa-mir-4535 | MI0016903 |
| 396 | hsa-mir-4635 | MI0017262 |
| 397 | hsa-mir-4640 | MI0017267 |
| 398 | hsa-mir-4646 | MI0017273 |
| 399 | hsa-mir-4656 | MI0017284 |
| 400 | hsa-mir-4663 | MI0017292 |
| 401 | hsa-mir-4665 | MI0017295 |
| 402 | hsa-mir-4706 | MI0017339 |
| 403 | hsa-mir-4707 | MI0017340 |
| 404 | hsa-mir-4708 | MI0017341 |
| 405 | hsa-mir-4710 | MI0017344 |
| 406 | hsa-mir-4718 | MI0017353 |
| 407 | hsa-mir-4722 | MI0017357 |
| 408 | hsa-mir-4727 | MI0017364 |
| 409 | hsa-mir-4730 | MI0017367 |
| 410 | hsa-mir-4734 | MI0017371 |
| 411 | hsa-mir-4740 | MI0017378 |
| 412 | hsa-mir-4747 | MI0017386 |
| 413 | hsa-mir-4749 | MI0017388 |
| 414 | hsa-mir-4755 | MI0017395 |
| 415 | hsa-mir-4763 | MI0017404 |
| 416 | hsa-mir-4787 | MI0017434 |
| 417 | hsa-mir-5008 | MI0017876 |
| 418 | hsa-mir-5010 | MI0017878 |
| 419 | hsa-mir-504 | MI0003189 |
| 420 | hsa-mir-5090 | MI0017979 |
| 421 | hsa-mir-5100 | MI0019116 |
| 422 | hsa-mir-5196 | MI0018175 |
| 423 | hsa-mir-551b | MI0003575 |
| 424 | hsa-mir-557 | MI0003563 |
| 425 | hsa-mir-5787 | MI0019797 |
| 426 | hsa-mir-6090 | MI0020367 |
| 427 | hsa-mir-6124 | MI0021258 |
| 428 | hsa-mir-6132 | MI0021277 |
| 429 | hsa-mir-6510 | MI0022222 |
| 430 | hsa-mir-6511b-1 | MI0022552 |
| 431 | hsa-mir-6511b-2 | MI0023431 |
| 432 | hsa-mir-6515 | MI0022227 |
| 433 | hsa-mir-654 | MI0003676 |
| 434 | hsa-mir-658 | MI0003682 |
| 435 | hsa-mir-668 | MI0003761 |
| 436 | hsa-mir-6722 | MI0022557 |
| 437 | hsa-mir-6724 | MI0022559 |
| 438 | hsa-mir-6729 | MI0022574 |
| 439 | hsa-mir-6737 | MI0022582 |
| 440 | hsa-mir-6756 | MI0022601 |
| 441 | hsa-mir-6762 | MI0022607 |
| 442 | hsa-mir-6763 | MI0022608 |
| 443 | hsa-mir-6766 | MI0022611 |
| 444 | hsa-mir-6769a | MI0022614 |
| 445 | hsa-mir-6771 | MI0022616 |
| 446 | hsa-mir-6786 | MI0022631 |
| 447 | hsa-mir-6789 | MI0022634 |
| 448 | hsa-mir-6794 | MI0022639 |
| 449 | hsa-mir-6796 | MI0022641 |
| 450 | hsa-mir-6797 | MI0022642 |
| 451 | hsa-mir-6800 | MI0022645 |
| 452 | hsa-mir-6802 | MI0022647 |
| 453 | hsa-mir-6803 | MI0022648 |
| 454 | hsa-mir-6805 | MI0022650 |
| 455 | hsa-mir-6807 | MI0022652 |
| 456 | hsa-mir-6812 | MI0022657 |
| 457 | hsa-mir-6819 | MI0022664 |
| 458 | hsa-mir-6822 | MI0022667 |
| 459 | hsa-mir-6824 | MI0022669 |
| 460 | hsa-mir-6826 | MI0022671 |
| 461 | hsa-mir-6850 | MI0022696 |
| 462 | hsa-mir-6858 | MI0022704 |
| 463 | hsa-mir-6861 | MI0022708 |
| 464 | hsa-mir-6880 | MI0022727 |

TABLE 1-continued

| SEQ ID NO: | Name of gene | Accession No. of miRBase |
|---|---|---|
| 465 | hsa-mir-7107 | MI0022958 |
| 466 | hsa-mir-7109 | MI0022960 |
| 467 | hsa-mir-7114 | MI0022965 |
| 468 | hsa-mir-7704 | MI0025240 |
| 469 | hsa-mir-7846 | MI0025516 |
| 470 | hsa-mir-8052 | MI0025888 |
| 471 | hsa-mir-8060 | MI0025896 |
| 472 | hsa-mir-8071-1 | MI0025907 |
| 473 | hsa-mir-8071-2 | MI0026417 |
| 474 | hsa-mir-8073 | MI0025909 |
| 475 | hsa-mir-874 | MI0005532 |
| 476 | hsa-mir-204 | MI0000284 |
| 477 | hsa-mir-3154 | MI0014182 |
| 478 | hsa-mir-3960 | MI0016964 |
| 479 | hsa-mir-4455 | MI0016801 |
| 480 | hsa-mir-4462 | MI0016810 |
| 481 | hsa-mir-4476 | MI0016828 |
| 482 | hsa-mir-4508 | MI0016872 |
| 483 | hsa-mir-4687 | MI0017319 |
| 484 | hsa-mir-4732 | MI0017369 |
| 485 | hsa-mir-4771-1 | MI0017412 |
| 486 | hsa-mir-4771-2 | MI0017413 |
| 487 | hsa-mir-642a | MI0003657 |
| 488 | hsa-mir-6732 | MI0022577 |
| 489 | hsa-mir-6760 | MI0022605 |
| 490 | hsa-mir-6799 | MI0022644 |
| 491 | hsa-mir-6820 | MI0022665 |
| 492 | hsa-mir-6821 | MI0022666 |
| 493 | hsa-mir-6829 | MI0022674 |
| 494 | hsa-mir-6893 | MI0022740 |
| 495 | hsa-mir-7108 | MI0022959 |
| 496 | hsa-mir-7111 | MI0022962 |
| 497 | hsa-mir-8089 | MI0025925 |
| 498 | hsa-mir-885 | MI0005560 |
| 499 | hsa-mir-92b | MI0003560 |
| 500 | hsa-mir-1343 | MI0017320 |
| 501 | hsa-mir-6746 | MI0022591 |
| 502 | hsa-mir-422a | MI0001444 |
| 503 | hsa-mir-187 | MI0000274 |
| 504 | hsa-mir-4632 | MI0017259 |
| 505 | hsa-mir-6791 | MI0022636 |
| 506 | hsa-mir-103a-2 | MI0000109 |
| 507 | hsa-mir-103a-1 | MI0000108 |
| 508 | hsa-mir-107 | MI0000114 |
| 509 | hsa-mir-1199 | MI0020340 |
| 510 | hsa-mir-1225 | MI0006311 |
| 511 | hsa-mir-1228 | MI0006318 |
| 512 | hsa-mir-1229 | MI0006319 |
| 513 | hsa-mir-1233-1 | MI0006323 |
| 514 | hsa-mir-1233-2 | MI0015973 |
| 515 | hsa-mir-1237 | MI0006327 |
| 516 | hsa-mir-1247 | MI0006382 |
| 517 | hsa-mir-1254-1 | MI0006388 |
| 518 | hsa-mir-1254-2 | MI0016747 |
| 519 | hsa-mir-1260b | MI0014197 |
| 520 | hsa-mir-1268a | MI0006405 |
| 521 | hsa-mir-1268b | MI0016748 |
| 522 | hsa-mir-1273g | MI0018003 |
| 523 | hsa-mir-128-1 | MI0000447 |
| 524 | hsa-mir-128-2 | MI0000727 |
| 525 | hsa-mir-1290 | MI0006352 |
| 526 | hsa-mir-150 | MI0000479 |
| 527 | hsa-mir-17 | MI0000071 |
| 528 | hsa-mir-1908 | MI0008329 |
| 529 | hsa-mir-1909 | MI0008330 |
| 530 | hsa-mir-1914 | MI0008335 |
| 531 | hsa-mir-1915 | MI0008336 |
| 532 | hsa-mir-191 | MI0000465 |
| 533 | hsa-mir-22 | MI0000078 |
| 534 | hsa-mir-23b | MI0000439 |
| 535 | hsa-mir-24-1 | MI0000080 |
| 536 | hsa-mir-24-2 | MI0000081 |
| 537 | hsa-mir-296 | MI0000747 |
| 538 | hsa-mir-3131 | MI0014151 |
| 539 | hsa-mir-3162 | MI0014192 |
| 540 | hsa-mir-3188 | MI0014232 |
| 541 | hsa-mir-3196 | MI0014241 |
| 542 | hsa-mir-3197 | MI0014245 |
| 543 | hsa-mir-320a | MI0000542 |
| 544 | hsa-mir-342 | MI0000805 |
| 545 | hsa-mir-3621 | MI0016012 |
| 546 | hsa-mir-3648 | MI0016048 |
| 547 | hsa-mir-3656 | MI0016056 |
| 548 | hsa-mir-365a | MI0000767 |
| 549 | hsa-mir-3665 | MI0016066 |
| 550 | hsa-mir-3679 | MI0016080 |
| 551 | hsa-mir-371a | MI0000779 |
| 552 | hsa-mir-3940 | MI0016597 |
| 553 | hsa-mir-423 | MI0001445 |
| 554 | hsa-mir-4257 | MI0015856 |
| 555 | hsa-mir-4270 | MI0015878 |
| 556 | hsa-mir-4271 | MI0015879 |
| 557 | hsa-mir-4286 | MI0015894 |
| 558 | hsa-mir-4298 | MI0015830 |
| 559 | hsa-mir-4417 | MI0016753 |
| 560 | hsa-mir-4442 | MI0016785 |
| 561 | hsa-mir-4446 | MI0016789 |
| 562 | hsa-mir-4448 | MI0016791 |
| 563 | hsa-mir-4454 | MI0016800 |
| 564 | hsa-mir-4467 | MI0016818 |
| 565 | hsa-mir-4472-1 | MI0016823 |
| 566 | hsa-mir-4472-2 | MI0016824 |
| 567 | hsa-mir-4507 | MI0016871 |
| 568 | hsa-mir-4516 | MI0016882 |
| 569 | hsa-mir-451a | MI0001729 |
| 570 | hsa-mir-4649 | MI0017276 |
| 571 | hsa-mir-4651 | MI0017279 |
| 572 | hsa-mir-4674 | MI0017305 |
| 573 | hsa-mir-4675 | MI0017306 |
| 574 | hsa-mir-4689 | MI0017322 |
| 575 | hsa-mir-4695 | MI0017328 |
| 576 | hsa-mir-4697 | MI0017330 |
| 577 | hsa-mir-4725 | MI0017362 |
| 578 | hsa-mir-4739 | MI0017377 |
| 579 | hsa-mir-4745 | MI0017384 |
| 580 | hsa-mir-4792 | MI0017439 |
| 581 | hsa-mir-486 | MI0002470 |
| 582 | hsa-mir-486-2 | MI0023622 |
| 583 | hsa-mir-5001 | MI0017867 |
| 584 | hsa-mir-5195 | MI0018174 |
| 585 | hsa-mir-550a-1 | MI0003600 |
| 586 | hsa-mir-550a-2 | MI0003601 |
| 587 | hsa-mir-5698 | MI0019305 |
| 588 | hsa-mir-6075 | MI0020352 |
| 589 | hsa-mir-6088 | MI0020365 |
| 590 | hsa-mir-6089-1 | MI0020366 |
| 591 | hsa-mir-6089-2 | MI0023563 |
| 592 | hsa-mir-6125 | MI0021259 |
| 593 | hsa-mir-6126 | MI0021260 |
| 594 | hsa-mir-614 | MI0003627 |
| 595 | hsa-mir-615 | MI0003628 |
| 596 | hsa-mir-619 | MI0003633 |
| 597 | hsa-mir-638 | MI0003653 |
| 598 | hsa-mir-642b | MI0016685 |
| 599 | hsa-mir-650 | MI0003665 |
| 600 | hsa-mir-663a | MI0003672 |
| 601 | hsa-mir-663b | MI0006336 |
| 602 | hsa-mir-6717 | MI0022551 |
| 603 | hsa-mir-6721 | MI0022556 |
| 604 | hsa-mir-6726 | MI0022571 |
| 605 | hsa-mir-6727 | MI0022572 |
| 606 | hsa-mir-6738 | MI0022583 |
| 607 | hsa-mir-6741 | MI0022586 |
| 608 | hsa-mir-6749 | MI0022594 |
| 609 | hsa-mir-6752 | MI0022597 |
| 610 | hsa-mir-675 | MI0005416 |
| 611 | hsa-mir-6757 | MI0022602 |
| 612 | hsa-mir-6765 | MI0022610 |
| 613 | hsa-mir-6775 | MI0022620 |
| 614 | hsa-mir-6780b | MI0022681 |
| 615 | hsa-mir-6782 | MI0022627 |
| 616 | hsa-mir-6784 | MI0022629 |
| 617 | hsa-mir-6806 | MI0022651 |
| 618 | hsa-mir-6840 | MI0022686 |

TABLE 1-continued

| SEQ ID NO: | Name of gene | Accession No. of miRBase |
|---|---|---|
| 619 | hsa-mir-6848 | MI0022694 |
| 620 | hsa-mir-6851 | MI0022697 |
| 621 | hsa-mir-6870 | MI0022717 |
| 622 | hsa-mir-6872 | MI0022719 |
| 623 | hsa-mir-6875 | MI0022722 |
| 624 | hsa-mir-6877 | MI0022724 |
| 625 | hsa-mir-6879 | MI0022726 |
| 626 | hsa-mir-6885 | MI0022732 |
| 627 | hsa-mir-6887 | MI0022734 |
| 628 | hsa-mir-711 | MI0012488 |
| 629 | hsa-mir-7113 | MI0022964 |
| 630 | hsa-mir-744 | MI0005559 |
| 631 | hsa-mir-760 | MI0005567 |
| 632 | hsa-mir-7845 | MI0025515 |
| 633 | hsa-mir-7847 | MI0025517 |
| 634 | hsa-mir-7977 | MI0025753 |
| 635 | hsa-mir-8059 | MI0025895 |
| 636 | hsa-mir-8063 | MI0025899 |
| 637 | hsa-mir-8072 | MI0025908 |
| 638 | hsa-mir-92a-2 | MI0000094 |
| 639 | hsa-mir-940 | MI0005762 |
| 640 | hsa-mir-1275 | MI0006415 |
| 641 | hsa-mir-1307 | MI0006444 |
| 642 | hsa-mir-23a | MI0000079 |
| 643 | hsa-mir-29b-1 | MI0000105 |
| 644 | hsa-mir-29b-2 | MI0000107 |
| 645 | hsa-mir-3135b | MI0016809 |
| 646 | hsa-mir-3185 | MI0014227 |
| 647 | hsa-mir-4532 | MI0016899 |
| 648 | hsa-mir-4690 | MI0017323 |
| 649 | hsa-mir-4758 | MI0017399 |
| 650 | hsa-mir-4783 | MI0017428 |
| 651 | hsa-mir-6131 | MI0021276 |
| 652 | hsa-mir-625 | MI0003639 |
| 653 | hsa-mir-6511a-1 | MI0022223 |
| 654 | hsa-mir-6511a-2 | MI0023564 |
| 655 | hsa-mir-6511a-3 | MI0023565 |
| 656 | hsa-mir-6511a-4 | MI0023566 |
| 657 | hsa-mir-6816 | MI0022661 |
| 658 | hsa-mir-6825 | MI0022670 |
| 659 | hsa-mir-6845 | MI0022691 |
| 660 | hsa-mir-7150 | MI0023610 |
| 661 | hsa-mir-7641-1 | MI0024975 |
| 662 | hsa-mir-7641-2 | MI0024976 |
| 663 | hsa-mir-7975 | MI0025751 |
| 664 | hsa-mir-92a-1 | MI0000093 |
| 665 | isomiR Example 1 of SEQ ID NO: 3 | — |
| 666 | isomiR Example 1 of SEQ ID NO: 4 | — |
| 667 | isomiR Example 2 of SEQ ID NO: 4 | — |
| 668 | isomiR Example 1 of SEQ ID NO: 7 | — |
| 669 | isomiR Example 1 of SEQ ID NO: 8 | — |
| 670 | isomiR Example 2 of SEQ ID NO: 8 | — |
| 671 | isomiR Example 1 of SEQ ID NO: 9 | — |
| 672 | isomiR Example 2 of SEQ ID NO: 9 | — |
| 673 | isomiR Example 1 of SEQ ID NO: 10 | — |
| 674 | isomiR Example 1 of SEQ ID NO: 13 | — |
| 675 | isomiR Example 2 of SEQ ID NO: 13 | — |
| 676 | isomiR Example 1 of SEQ ID NO: 14 | — |
| 677 | isomiR Example 2 of SEQ ID NO: 14 | — |
| 678 | isomiR Example 1 of SEQ ID NO: 17 | — |
| 679 | isomiR Example 1 of SEQ ID NO: 18 | — |
| 680 | isomiR Example 2 of SEQ ID NO: 18 | — |
| 681 | isomiR Example 1 of SEQ ID NO: 20 | — |
| 682 | isomiR Example 2 of SEQ ID NO: 20 | — |
| 683 | isomiR Example 1 of SEQ ID NO: 21 | — |
| 684 | isomiR Example 2 of SEQ ID NO: 21 | — |
| 685 | isomiR Example 1 of SEQ ID NO: 22 | — |
| 686 | isomiR Example 2 of SEQ ID NO: 22 | — |
| 687 | isomiR Example 1 of SEQ ID NO: 23 | — |
| 688 | isomiR Example 2 of SEQ ID NO: 23 | — |
| 689 | isomiR Example 1 of SEQ ID NO: 24 | — |
| 690 | isomiR Example 1 of SEQ ID NO: 25 | — |
| 691 | isomiR Example 1 of SEQ ID NO: 26 | — |
| 692 | isomiR Example 2 of SEQ ID NO: 26 | — |
| 693 | isomiR Example 1 of SEQ ID NO: 28 | — |
| 694 | isomiR Example 2 of SEQ ID NO: 28 | — |
| 695 | isomiR Example 1 of SEQ ID NO: 29 | — |
| 696 | isomiR Example 1 of SEQ ID NO: 30 | — |
| 697 | isomiR Example 1 of SEQ ID NO: 31 | — |
| 698 | isomiR Example 2 of SEQ ID NO: 31 | — |
| 699 | isomiR Example 1 of SEQ ID NO: 32 | — |
| 700 | isomiR Example 2 of SEQ ID NO: 32 | — |
| 701 | isomiR Example 1 of SEQ ID NO: 33 | — |
| 702 | isomiR Example 2 of SEQ ID NO: 33 | — |
| 703 | isomiR Example 1 of SEQ ID NO: 35 | — |
| 704 | isomiR Example 2 of SEQ ID NO: 35 | — |
| 705 | isomiR Example 1 of SEQ ID NO: 36 | — |
| 706 | isomiR Example 2 of SEQ ID NO: 36 | — |
| 707 | isomiR Example 1 of SEQ ID NO: 38 | — |
| 708 | isomiR Example 2 of SEQ ID NO: 38 | — |
| 709 | isomiR Example 1 of SEQ ID NO: 41 | — |
| 710 | isomiR Example 2 of SEQ ID NO: 41 | — |
| 711 | isomiR Example 1 of SEQ ID NO: 43 | — |
| 712 | isomiR Example 1 of SEQ ID NO: 44 | — |
| 713 | isomiR Example 1 of SEQ ID NO: 45 | — |
| 714 | isomiR Example 2 of SEQ ID NO: 45 | — |
| 715 | isomiR Example 1 of SEQ ID NO: 46 | — |
| 716 | isomiR Example 2 of SEQ ID NO: 46 | — |
| 717 | isomiR Example 1 of SEQ ID NO: 48 | — |
| 718 | isomiR Example 2 of SEQ ID NO: 48 | — |
| 719 | isomiR Example 1 of SEQ ID NO: 49 | — |
| 720 | isomiR Example 2 of SEQ ID NO: 49 | — |
| 721 | isomiR Example 1 of SEQ ID NO: 51 | — |
| 722 | isomiR Example 2 of SEQ ID NO: 51 | — |
| 723 | isomiR Example 1 of SEQ ID NO: 52 | — |
| 724 | isomiR Example 1 of SEQ ID NO: 53 | — |
| 725 | isomiR Example 2 of SEQ ID NO: 53 | — |
| 726 | isomiR Example 1 of SEQ ID NO: 54 | — |
| 727 | isomiR Example 2 of SEQ ID NO: 54 | — |
| 728 | isomiR Example 1 of SEQ ID NO: 55 | — |
| 729 | isomiR Example 2 of SEQ ID NO: 55 | — |
| 730 | isomiR Example 1 of SEQ ID NO: 56 | — |
| 731 | isomiR Example 2 of SEQ ID NO: 56 | — |
| 732 | isomiR Example 1 of SEQ ID NO: 57 | — |
| 733 | isomiR Example 2 of SEQ ID NO: 57 | — |
| 734 | isomiR Example 1 of SEQ ID NO: 58 | — |
| 735 | isomiR Example 2 of SEQ ID NO: 58 | — |
| 736 | isomiR Example 1 of SEQ ID NO: 61 | — |
| 737 | isomiR Example 2 of SEQ ID NO: 61 | — |
| 738 | isomiR Example 1 of SEQ ID NO: 62 | — |
| 739 | isomiR Example 2 of SEQ ID NO: 62 | — |
| 740 | isomiR Example 1 of SEQ ID NO: 65 | — |
| 741 | isomiR Example 1 of SEQ ID NO: 66 | — |
| 742 | isomiR Example 1 of SEQ ID NO: 67 | — |
| 743 | isomiR Example 1 of SEQ ID NO: 68 | — |
| 744 | isomiR Example 2 of SEQ ID NO: 68 | — |
| 745 | isomiR Example 1 of SEQ ID NO: 69 | — |
| 746 | isomiR Example 1 of SEQ ID NO: 71 | — |
| 747 | isomiR Example 1 of SEQ ID NO: 72 | — |
| 748 | isomiR Example 1 of SEQ ID NO: 73 | — |
| 749 | isomiR Example 2 of SEQ ID NO: 73 | — |
| 750 | isomiR Example 1 of SEQ ID NO: 74 | — |
| 751 | isomiR Example 2 of SEQ ID NO: 74 | — |
| 752 | isomiR Example 1 of SEQ ID NO: 77 | — |
| 753 | isomiR Example 2 of SEQ ID NO: 77 | — |
| 754 | isomiR Example 1 of SEQ ID NO: 78 | — |
| 755 | isomiR Example 2 of SEQ ID NO: 78 | — |
| 756 | isomiR Example 1 of SEQ ID NO: 80 | — |
| 757 | isomiR Example 1 of SEQ ID NO: 82 | — |
| 758 | isomiR Example 2 of SEQ ID NO: 82 | — |
| 759 | isomiR Example 1 of SEQ ID NO: 83 | — |
| 760 | isomiR Example 2 of SEQ ID NO: 83 | — |
| 761 | isomiR Example 1 of SEQ ID NO: 84 | — |
| 762 | isomiR Example 2 of SEQ ID NO: 84 | — |
| 763 | isomiR Example 1 of SEQ ID NO: 85 | — |
| 764 | isomiR Example 2 of SEQ ID NO: 85 | — |
| 765 | isomiR Example 1 of SEQ ID NO: 86 | — |
| 766 | isomiR Example 2 of SEQ ID NO: 86 | — |
| 767 | isomiR Example 1 of SEQ ID NO: 87 | — |
| 768 | isomiR Example 2 of SEQ ID NO: 87 | — |
| 769 | isomiR Example 1 of SEQ ID NO: 89 | — |
| 770 | isomiR Example 1 of SEQ ID NO: 91 | — |
| 771 | isomiR Example 2 of SEQ ID NO: 91 | — |
| 772 | isomiR Example 1 of SEQ ID NO: 92 | — |

TABLE 1-continued

| SEQ ID NO: | Name of gene | Accession No. of miRBase |
|---|---|---|
| 773 | isomiR Example 2 of SEQ ID NO: 92 | — |
| 774 | isomiR Example 1 of SEQ ID NO: 93 | — |
| 775 | isomiR Example 2 of SEQ ID NO: 93 | — |
| 776 | isomiR Example 1 of SEQ ID NO: 94 | — |
| 777 | isomiR Example 2 of SEQ ID NO: 94 | — |
| 778 | isomiR Example 1 of SEQ ID NO: 95 | — |
| 779 | isomiR Example 1 of SEQ ID NO: 96 | — |
| 780 | isomiR Example 2 of SEQ ID NO: 96 | — |
| 781 | isomiR Example 1 of SEQ ID NO: 97 | — |
| 782 | isomiR Example 2 of SEQ ID NO: 97 | — |
| 783 | isomiR Example 1 of SEQ ID NO: 100 | — |
| 784 | isomiR Example 2 of SEQ ID NO: 100 | — |
| 785 | isomiR Example 1 of SEQ ID NO: 101 | — |
| 786 | isomiR Example 1 of SEQ ID NO: 114 | — |
| 787 | isomiR Example 1 of SEQ ID NO: 138 | — |
| 788 | isomiR Example 2 of SEQ ID NO: 138 | — |
| 789 | isomiR Example 1 of SEQ ID NO: 139 | — |
| 790 | isomiR Example 2 of SEQ ID NO: 139 | — |
| 791 | isomiR Example 1 of SEQ ID NO: 140 | — |
| 792 | isomiR Example 1 of SEQ ID NO: 141 | — |
| 793 | isomiR Example 2 of SEQ ID NO: 141 | — |
| 794 | isomiR Example 1 of SEQ ID NO: 142 | — |
| 795 | isomiR Example 1 of SEQ ID NO: 145 | — |
| 796 | isomiR Example 2 of SEQ ID NO: 145 | — |
| 797 | isomiR Example 1 of SEQ ID NO: 146 | — |
| 798 | isomiR Example 2 of SEQ ID NO: 146 | — |
| 799 | isomiR Example 1 of SEQ ID NO: 147 | — |
| 800 | isomiR Example 2 of SEQ ID NO: 147 | — |
| 801 | isomiR Example 1 of SEQ ID NO: 148 | — |
| 802 | isomiR Example 1 of SEQ ID NO: 149 | — |
| 803 | isomiR Example 1 of SEQ ID NO: 150 | — |
| 804 | isomiR Example 2 of SEQ ID NO: 150 | — |
| 805 | isomiR Example 1 of SEQ ID NO: 151 | — |
| 806 | isomiR Example 2 of SEQ ID NO: 151 | — |
| 807 | isomiR Example 1 of SEQ ID NO: 162 | — |
| 808 | isomiR Example 1 of SEQ ID NO: 163 | — |
| 809 | isomiR Example 2 of SEQ ID NO: 163 | — |
| 810 | isomiR Example 1 of SEQ ID NO: 164 | — |
| 811 | isomiR Example 2 of SEQ ID NO: 164 | — |
| 812 | isomiR Example 1 of SEQ ID NO: 167 | — |
| 813 | isomiR Example 2 of SEQ ID NO: 167 | — |
| 814 | isomiR Example 1 of SEQ ID NO: 168 | — |
| 815 | isomiR Example 1 of SEQ ID NO: 170 | — |
| 816 | isomiR Example 2 of SEQ ID NO: 170 | — |
| 817 | isomiR Example 1 of SEQ ID NO: 171 | — |
| 818 | isomiR Example 2 of SEQ ID NO: 171 | — |
| 819 | isomiR Example 1 of SEQ ID NO: 175 | — |
| 820 | isomiR Example 2 of SEQ ID NO: 175 | — |
| 821 | isomiR Example 1 of SEQ ID NO: 177 | — |
| 822 | isomiR Example 2 of SEQ ID NO: 177 | — |
| 823 | isomiR Example 1 of SEQ ID NO: 178 | — |
| 824 | isomiR Example 1 of SEQ ID NO: 179 | — |
| 825 | isomiR Example 2 of SEQ ID NO: 179 | — |
| 826 | isomiR Example 1 of SEQ ID NO: 180 | — |
| 827 | isomiR Example 2 of SEQ ID NO: 180 | — |
| 828 | isomiR Example 1 of SEQ ID NO: 181 | — |
| 829 | isomiR Example 2 of SEQ ID NO: 181 | — |
| 830 | isomiR Example 1 of SEQ ID NO: 182 | — |
| 831 | isomiR Example 2 of SEQ ID NO: 182 | — |
| 832 | isomiR Example 1 of SEQ ID NO: 183 | — |
| 833 | isomiR Example 2 of SEQ ID NO: 183 | — |
| 834 | isomiR Example 1 of SEQ ID NO: 184 | — |
| 835 | isomiR Example 2 of SEQ ID NO: 184 | — |
| 836 | isomiR Example 1 of SEQ ID NO: 185 | — |
| 837 | isomiR Example 2 of SEQ ID NO: 185 | — |
| 838 | isomiR Example 1 of SEQ ID NO: 186 | — |
| 839 | isomiR Example 1 of SEQ ID NO: 187 | — |
| 840 | isomiR Example 1 of SEQ ID NO: 188 | — |
| 841 | isomiR Example 2 of SEQ ID NO: 188 | — |
| 842 | isomiR Example 1 of SEQ ID NO: 189 | — |
| 843 | isomiR Example 2 of SEQ ID NO: 189 | — |
| 844 | isomiR Example 1 of SEQ ID NO: 190 | — |
| 845 | isomiR Example 2 of SEQ ID NO: 190 | — |
| 846 | isomiR Example 1 of SEQ ID NO: 191 | — |
| 847 | isomiR Example 2 of SEQ ID NO: 191 | — |
| 848 | isomiR Example 1 of SEQ ID NO: 192 | — |
| 849 | isomiR Example 2 of SEQ ID NO: 192 | — |
| 850 | isomiR Example 1 of SEQ ID NO: 193 | — |
| 851 | isomiR Example 2 of SEQ ID NO: 193 | — |
| 852 | isomiR Example 1 of SEQ ID NO: 194 | — |
| 853 | isomiR Example 1 of SEQ ID NO: 195 | — |
| 854 | isomiR Example 2 of SEQ ID NO: 195 | — |
| 855 | isomiR Example 1 of SEQ ID NO: 196 | — |
| 856 | isomiR Example 2 of SEQ ID NO: 196 | — |
| 857 | isomiR Example 1 of SEQ ID NO: 197 | — |
| 858 | isomiR Example 2 of SEQ ID NO: 197 | — |
| 859 | isomiR Example 1 of SEQ ID NO: 198 | — |
| 860 | isomiR Example 2 of SEQ ID NO: 198 | — |
| 861 | isomiR Example 1 of SEQ ID NO: 199 | — |
| 862 | isomiR Example 1 of SEQ ID NO: 200 | — |
| 863 | isomiR Example 2 of SEQ ID NO: 200 | — |
| 864 | isomiR Example 1 of SEQ ID NO: 201 | — |
| 865 | isomiR Example 2 of SEQ ID NO: 201 | — |
| 866 | isomiR Example 1 of SEQ ID NO: 202 | — |
| 867 | isomiR Example 2 of SEQ ID NO: 202 | — |
| 868 | isomiR Example 1 of SEQ ID NO: 203 | — |
| 869 | isomiR Example 2 of SEQ ID NO: 203 | — |
| 870 | isomiR Example 1 of SEQ ID NO: 204 | — |
| 871 | isomiR Example 2 of SEQ ID NO: 204 | — |
| 872 | isomiR Example 1 of SEQ ID NO: 205 | — |
| 873 | isomiR Example 1 of SEQ ID NO: 206 | — |
| 874 | isomiR Example 2 of SEQ ID NO: 206 | — |
| 875 | isomiR Example 1 of SEQ ID NO: 207 | — |
| 876 | isomiR Example 2 of SEQ ID NO: 207 | — |
| 877 | isomiR Example 1 of SEQ ID NO: 209 | — |
| 878 | isomiR Example 2 of SEQ ID NO: 209 | — |
| 879 | isomiR Example 1 of SEQ ID NO: 210 | — |
| 880 | isomiR Example 2 of SEQ ID NO: 210 | — |
| 881 | isomiR Example 1 of SEQ ID NO: 211 | — |
| 882 | isomiR Example 2 of SEQ ID NO: 211 | — |
| 883 | isomiR Example 1 of SEQ ID NO: 212 | — |
| 884 | isomiR Example 2 of SEQ ID NO: 212 | — |
| 885 | isomiR Example 1 of SEQ ID NO: 213 | — |
| 886 | isomiR Example 1 of SEQ ID NO: 214 | — |
| 887 | isomiR Example 2 of SEQ ID NO: 214 | — |
| 888 | isomiR Example 1 of SEQ ID NO: 215 | — |
| 889 | isomiR Example 1 of SEQ ID NO: 216 | — |
| 890 | isomiR Example 2 of SEQ ID NO: 216 | — |
| 891 | isomiR Example 1 of SEQ ID NO: 219 | — |
| 892 | isomiR Example 1 of SEQ ID NO: 220 | — |
| 893 | isomiR Example 2 of SEQ ID NO: 220 | — |
| 894 | isomiR Example 1 of SEQ ID NO: 221 | — |
| 895 | isomiR Example 1 of SEQ ID NO: 222 | — |
| 896 | isomiR Example 1 of SEQ ID NO: 223 | — |
| 897 | isomiR Example 2 of SEQ ID NO: 223 | — |
| 898 | isomiR Example 1 of SEQ ID NO: 224 | — |
| 899 | isomiR Example 2 of SEQ ID NO: 224 | — |
| 900 | isomiR Example 1 of SEQ ID NO: 225 | — |
| 901 | isomiR Example 1 of SEQ ID NO: 226 | — |
| 902 | isomiR Example 2 of SEQ ID NO: 226 | — |
| 903 | isomiR Example 1 of SEQ ID NO: 227 | — |
| 904 | isomiR Example 1 of SEQ ID NO: 229 | — |
| 905 | isomiR Example 2 of SEQ ID NO: 229 | — |
| 906 | isomiR Example 1 of SEQ ID NO: 230 | — |
| 907 | isomiR Example 2 of SEQ ID NO: 230 | — |
| 908 | isomiR Example 1 of SEQ ID NO: 231 | — |
| 909 | isomiR Example 2 of SEQ ID NO: 231 | — |
| 910 | isomiR Example 1 of SEQ ID NO: 232 | — |
| 911 | isomiR Example 1 of SEQ ID NO: 233 | — |
| 912 | isomiR Example 1 of SEQ ID NO: 235 | — |
| 913 | isomiR Example 2 of SEQ ID NO: 235 | — |
| 914 | isomiR Example 1 of SEQ ID NO: 237 | — |
| 915 | isomiR Example 2 of SEQ ID NO: 237 | — |
| 916 | isomiR Example 1 of SEQ ID NO: 238 | — |
| 917 | isomiR Example 1 of SEQ ID NO: 240 | — |
| 918 | isomiR Example 2 of SEQ ID NO: 240 | — |
| 919 | isomiR Example 1 of SEQ ID NO: 241 | — |
| 920 | isomiR Example 2 of SEQ ID NO: 241 | — |
| 921 | isomiR Example 1 of SEQ ID NO: 242 | — |
| 922 | isomiR Example 1 of SEQ ID NO: 243 | — |
| 923 | isomiR Example 1 of SEQ ID NO: 244 | — |
| 924 | isomiR Example 2 of SEQ ID NO: 244 | — |
| 925 | isomiR Example 1 of SEQ ID NO: 245 | — |
| 926 | isomiR Example 2 of SEQ ID NO: 245 | — |

TABLE 1-continued

| SEQ ID NO: | Name of gene | Accession No. of miRBase |
|---|---|---|
| 927 | isomiR Example 1 of SEQ ID NO: 246 | — |
| 928 | isomiR Example 2 of SEQ ID NO: 246 | — |
| 929 | isomiR Example 1 of SEQ ID NO: 248 | — |
| 930 | isomiR Example 1 of SEQ ID NO: 249 | — |
| 931 | isomiR Example 2 of SEQ ID NO: 249 | — |
| 932 | isomiR Example 1 of SEQ ID NO: 251 | — |
| 933 | isomiR Example 1 of SEQ ID NO: 252 | — |
| 934 | isomiR Example 2 of SEQ ID NO: 252 | — |
| 935 | isomiR Example 1 of SEQ ID NO: 253 | — |
| 936 | isomiR Example 2 of SEQ ID NO: 253 | — |
| 937 | isomiR Example 1 of SEQ ID NO: 254 | — |
| 938 | isomiR Example 2 of SEQ ID NO: 254 | — |
| 939 | isomiR Example 1 of SEQ ID NO: 255 | — |
| 940 | isomiR Example 1 of SEQ ID NO: 256 | — |
| 941 | isomiR Example 2 of SEQ ID NO: 256 | — |
| 942 | isomiR Example 1 of SEQ ID NO: 257 | — |
| 943 | isomiR Example 2 of SEQ ID NO: 257 | — |
| 944 | isomiR Example 1 of SEQ ID NO: 258 | — |
| 945 | isomiR Example 2 of SEQ ID NO: 258 | — |
| 946 | isomiR Example 1 of SEQ ID NO: 259 | — |
| 947 | isomiR Example 2 of SEQ ID NO: 259 | — |
| 948 | isomiR Example 1 of SEQ ID NO: 260 | — |
| 949 | isomiR Example 2 of SEQ ID NO: 260 | — |
| 950 | isomiR Example 1 of SEQ ID NO: 261 | — |
| 951 | isomiR Example 2 of SEQ ID NO: 261 | — |
| 952 | isomiR Example 1 of SEQ ID NO: 262 | — |
| 953 | isomiR Example 2 of SEQ ID NO: 262 | — |
| 954 | isomiR Example 1 of SEQ ID NO: 263 | — |
| 955 | isomiR Example 2 of SEQ ID NO: 263 | — |
| 956 | isomiR Example 1 of SEQ ID NO: 264 | — |
| 957 | isomiR Example 2 of SEQ ID NO: 264 | — |
| 958 | isomiR Example 1 of SEQ ID NO: 271 | — |
| 959 | isomiR Example 1 of SEQ ID NO: 293 | — |
| 960 | isomiR Example 1 of SEQ ID NO: 295 | — |
| 961 | isomiR Example 2 of SEQ ID NO: 295 | — |
| 962 | isomiR Example 1 of SEQ ID NO: 296 | — |
| 963 | isomiR Example 2 of SEQ ID NO: 296 | — |
| 964 | isomiR Example 1 of SEQ ID NO: 303 | — |
| 965 | isomiR Example 2 of SEQ ID NO: 303 | — |
| 966 | isomiR Example 1 of SEQ ID NO: 304 | — |
| 967 | isomiR Example 2 of SEQ ID NO: 304 | — |
| 968 | isomiR Example 1 of SEQ ID NO: 305 | — |
| 969 | isomiR Example 2 of SEQ ID NO: 305 | — |
| 970 | isomiR Example 1 of SEQ ID NO: 306 | — |
| 971 | isomiR Example 2 of SEQ ID NO: 306 | — |
| 972 | isomiR Example 1 of SEQ ID NO: 307 | — |
| 973 | isomiR Example 2 of SEQ ID NO: 307 | — |
| 974 | isomiR Example 1 of SEQ ID NO: 308 | — |
| 975 | isomiR Example 2 of SEQ ID NO: 308 | — |
| 976 | isomiR Example 1 of SEQ ID NO: 309 | — |
| 977 | isomiR Example 2 of SEQ ID NO: 309 | — |
| 978 | isomiR Example 1 of SEQ ID NO: 311 | — |
| 979 | isomiR Example 2 of SEQ ID NO: 311 | — |
| 980 | isomiR Example 1 of SEQ ID NO: 312 | — |
| 981 | isomiR Example 2 of SEQ ID NO: 312 | — |
| 982 | isomiR Example 1 of SEQ ID NO: 313 | — |
| 983 | isomiR Example 2 of SEQ ID NO: 313 | — |
| 984 | isomiR Example 1 of SEQ ID NO: 314 | — |
| 985 | isomiR Example 1 of SEQ ID NO: 315 | — |
| 986 | isomiR Example 2 of SEQ ID NO: 315 | — |
| 987 | isomiR Example 1 of SEQ ID NO: 316 | — |
| 988 | isomiR Example 2 of SEQ ID NO: 316 | — |
| 989 | isomiR Example 1 of SEQ ID NO: 317 | — |
| 990 | isomiR Example 2 of SEQ ID NO: 317 | — |
| 991 | isomiR Example 1 of SEQ ID NO: 318 | — |
| 992 | isomiR Example 2 of SEQ ID NO: 318 | — |
| 993 | isomiR Example 1 of SEQ ID NO: 319 | — |
| 994 | isomiR Example 1 of SEQ ID NO: 320 | — |
| 995 | isomiR Example 2 of SEQ ID NO: 320 | — |
| 996 | isomiR Example 1 of SEQ ID NO: 321 | — |
| 997 | isomiR Example 2 of SEQ ID NO: 321 | — |
| 998 | isomiR Example 1 of SEQ ID NO: 328 | — |
| 999 | isomiR Example 1 of SEQ ID NO: 329 | — |
| 1000 | isomiR Example 2 of SEQ ID NO: 329 | — |

Effect of Invention

According to the present invention, lung cancer can be detected easily and in high accuracy. For example, the presence or absence of lung cancer in patients can be easily detected by using, as indicators, the determined expression levels of one to several miRNAs in blood, serum, and/or plasma of the patients, which can be collected with limited invasiveness.

The present specification encompasses the contents disclosed in Japanese Patent Application No. 2017-126933 from which the present application claims priority.

MODES FOR CARRYING OUT THE INVENTION

Figure 1:
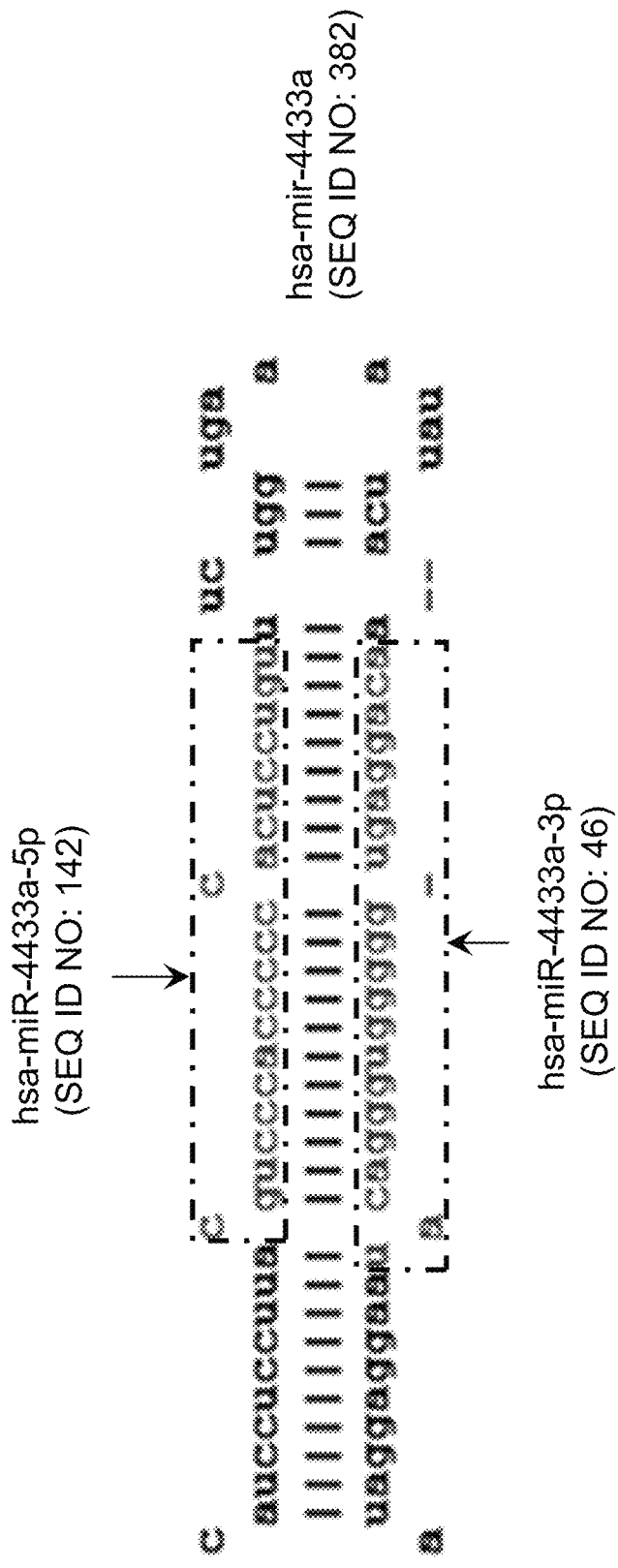
FIG. 1 This figure shows the relationship between the nucleotide sequences of hsa-miR-4433a-5p represented by SEQ ID NO: 142 and hsa-miR-4433a-3p represented by SEQ ID NO: 46, which are produced from the precursor hsa-mir-4433a represented by SEQ ID NO: 382.

Hereinafter, the present invention will be further described in detail.

1. Target Nucleic Acid for Lung Cancer

Primary target nucleic acids, as lung cancer markers, for detecting the presence and/or absence of lung cancer or lung cancer cells using the nucleic acids such as the nucleic acid probes or the primers for detection of lung cancer defined above according to the present invention comprise at least one miRNA selected from the group consisting of the following miRNAs: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or a polynucleotide complementary to the miRNA. Furthermore, at least one miRNA selected from the group consisting of the following other lung cancer markers that can be combined with these miRNAs, i.e., miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-5p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or a polynucleotide complementary to the miRNA can also be preferably used as target nucleic acids.

These miRNAs include, for example, a human gene comprising a nucleotide sequence represented by any of SEQ ID NOs: 1 to 329 (i.e., miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-13p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR- 6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-13413-13p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 329 or a transcript thereof, more preferably the transcript, i.e., a miRNA or its precursor RNA, pri-miRNA or pre-miRNA, or a polynucleotide complementary thereto.

The first target gene is the hsa-miR-6787-5p gene, a congener thereof, a transcript thereof, or a variant or a derivative thereof. None of the previously known report shows that change in the expression of the gene or the transcript thereof can serve as a marker for lung cancer.

The second target gene is the hsa-miR-920 gene, a congener thereof, a transcript thereof, or a variant or a derivative thereof. None of the previously known report shows that change in the expression of the gene or the transcript thereof can serve as a marker for lung cancer.

The third target gene is the hsa-miR-3622a-5p gene, a congener thereof, a transcript thereof, or a variant or a derivative thereof. None of the previously known report shows that change in the expression of the gene or the transcript thereof can serve as a marker for lung cancer.

The fourth target gene is the hsa-miR-1185-1-3p gene, a congener thereof, a transcript thereof, or a variant or a derivative thereof. None of the previously known report shows that change in the expression of the gene or the transcript thereof can serve as a marker for lung cancer.

The fifth target gene is the hsa-miR-4327 gene, a congener thereof, a transcript thereof, or a variant or a derivative thereof. None of the previously known report shows that change in the expression of the gene or the transcript thereof can serve as a marker for lung cancer.

The sixth target gene is the hsa-miR-5739 gene, a congener thereof, a transcript thereof, or a variant or a derivative thereof. None of the previously known report shows that change in the expression of the gene or the transcript thereof can serve as a marker for lung cancer.

The seventh target gene is the hsa-miR-937-5p gene, a congener thereof, a transcript thereof, or a variant or a derivative thereof. None of the previously known report shows that change in the expression of the gene or the transcript thereof can serve as a marker for lung cancer.

The eighth target gene is the hsa-miR-1181 gene, a congener thereof, a transcript thereof, or a variant or a derivative thereof. None of the previously known report shows that change in the expression of the gene or the transcript thereof can serve as a marker for lung cancer.

The ninth target gene is the hsa-miR-1185-2-3p gene, a congener thereof, a transcript thereof, or a variant or a derivative thereof. None of the previously known report shows that change in the expression of the gene or the transcript thereof can serve as a marker for lung cancer.

The 10th target gene is the hsa-miR-1193 gene, a congener thereof, a transcript thereof, or a variant or a derivative thereof. None of the previously known report shows that change in the expression of the gene or the transcript thereof can serve as a marker for lung cancer.

The 11th target gene is the hsa-miR-1207-5p gene, a congener thereof, a transcript thereof, or a variant or a derivative thereof. None of the previously known report shows that change in the expression of the gene or the transcript thereof can serve as a marker for lung cancer.

The 12th target gene is the hsa-miR-1238-5p gene, a congener thereof, a transcript thereof, or a variant or a derivative thereof. None of the previously known report shows that change in the expression of the gene or the transcript thereof can serve as a marker for lung cancer.

The 13th target gene is the hsa-miR-1246 gene, a congener thereof, a transcript thereof, or a variant or a derivative thereof. None of the previously known report shows that change in the expression of the gene or the transcript thereof can serve as a marker for lung cancer.

The 14th target gene is the hsa-miR-1249-5p gene, a congener thereof, a transcript thereof, or a variant or a derivative thereof. None of the previously known report shows that change in the expression of the gene or the transcript thereof can serve as a marker for lung cancer.

The 15th target gene is the hsa-miR-1292-3p gene, a congener thereof, a transcript thereof, or a variant or a derivative thereof. None of the previously known report shows that change in the expression of the gene or the transcript thereof can serve as a marker for lung cancer.

The 16th target gene is the hsa-miR-1469 gene, a congener thereof, a transcript thereof, or a variant or a derivative thereof. None of the previously known report shows that change in the expression of the gene or the transcript thereof can serve as a marker for lung cancer.

The 17th target gene is the hsa-miR-1470 gene, a congener thereof, a transcript thereof, or a variant or a derivative thereof. None of the previously known report shows that change in the expression of the gene or the transcript thereof can serve as a marker for lung cancer.

The 18th target gene is the hsa-miR-197-5p gene, a congener thereof, a transcript thereof, or a variant or a derivative thereof. None of the previously known report shows that change in the expression of the gene or the transcript thereof can serve as a marker for lung cancer.

The 19th target gene is the hsa-miR-208a-5p gene, a congener thereof, a transcript thereof, or a variant or a derivative thereof. None of the previously known report shows that change in the expression of the gene or the transcript thereof can serve as a marker for lung cancer.

The 20th target gene is the hsa-miR-2110 gene, a congener thereof, a transcript thereof, or a variant or a derivative thereof. None of the previously known report shows that change in the expression of the gene or the transcript thereof can serve as a marker for lung cancer.

The 21st target gene is the hsa-miR-211-3p gene, a congener thereof, a transcript thereof, or a variant or a derivative thereof. None of the previously known report shows that change in the expression of the gene or the transcript thereof can serve as a marker for lung cancer.

The 22nd target gene is the hsa-miR-2467-3p gene, a congener thereof, a transcript thereof, or a variant or a derivative thereof. None of the previously known report shows that change in the expression of the gene or the transcript thereof can serve as a marker for lung cancer.

The 23rd target gene is the hsa-miR-3122 gene, a congener thereof, a transcript thereof, or a variant or a derivative thereof. None of the previously known report shows that change in the expression of the gene or the transcript thereof can serve as a marker for lung cancer.

The 24th target gene is the hsa-miR-3141 gene, a congener thereof, a transcript thereof, or a variant or a derivative thereof. None of the previously known report shows that change in the expression of the gene or the transcript thereof can serve as a marker for lung cancer.

The 25th target gene is the hsa-miR-3156-5p gene, a congener thereof, a transcript thereof, or a variant or a derivative thereof. None of the previously known report shows that change in the expression of the gene or the transcript thereof can serve as a marker for lung cancer.

The 26th target gene is the hsa-miR-3158-5p gene, a congener thereof, a transcript thereof, or a variant or a derivative thereof. None of the previously known report shows that change in the expression of the gene or the transcript thereof can serve as a marker for lung cancer.

The 27th target gene is the hsa-miR-3160-5p gene, a congener thereof, a transcript thereof, or a variant or a derivative thereof. None of the previously known report shows that change in the expression of the gene or the transcript thereof can serve as a marker for lung cancer.

The 28th target gene is the hsa-miR-3180-3p gene, a congener thereof, a transcript thereof, or a variant or a derivative thereof. None of the previously known report shows that change in the expression of the gene or the transcript thereof can serve as a marker for lung cancer.

The 29th target gene is the hsa-miR-3191-3p gene, a congener thereof, a transcript thereof, or a variant or a derivative thereof. None of the previously known report shows that change in the expression of the gene or the transcript thereof can serve as a marker for lung cancer.

The 30th target gene is the hsa-miR-3194-3p gene, a congener thereof, a transcript thereof, or a variant or a derivative thereof. None of the previously known report shows that change in the expression of the gene or the transcript thereof can serve as a marker for lung cancer.

The 31st target gene is the hsa-miR-320b gene, a congener thereof, a transcript thereof, or a variant or a derivative thereof. None of the previously known report shows that change in the expression of the gene or the transcript thereof can serve as a marker for lung cancer.

The 32nd target gene is the hsa-miR-328-5p gene, a congener thereof, a transcript thereof, or a variant or a derivative thereof. None of the previously known report shows that change in the expression of the gene or the transcript thereof can serve as a marker for lung cancer.

The 33rd target gene is the hsa-miR-3610 gene, a congener thereof, a transcript thereof, or a variant or a derivative thereof. None of the previously known report shows that change in the expression of the gene or the transcript thereof can serve as a marker for lung cancer.

The 34th target gene is the hsa-miR-3619-3p gene, a congener thereof, a transcript thereof, or a variant or a derivative thereof. None of the previously known report shows that change in the expression of the gene or the transcript thereof can serve as a marker for lung cancer.

The 35th target gene is the hsa-miR-3620-5p gene, a congener thereof, a transcript thereof, or a variant or a derivative thereof. None of the previously known report shows that change in the expression of the gene or the transcript thereof can serve as a marker for lung cancer.

The 36th target gene is the hsa-miR-370-3p gene, a congener thereof, a transcript thereof, or a variant or a derivative thereof. None of the previously known report shows that change in the expression of the gene or the transcript thereof can serve as a marker for lung cancer.

The 37th target gene is the hsa-miR-373-5p gene, a congener thereof, a transcript thereof, or a variant or a derivative thereof. None of the previously known report shows that change in the expression of the gene or the transcript thereof can serve as a marker for lung cancer.

The 38th target gene is the hsa-miR-3917 gene, a congener thereof, a transcript thereof, or a variant or a derivative thereof. None of the previously known report shows that change in the expression of the gene or the transcript thereof can serve as a marker for lung cancer.

The 39th target gene is the hsa-miR-3937 gene, a congener thereof, a transcript thereof, or a variant or a derivative thereof. None of the previously known report shows that change in the expression of the gene or the transcript thereof can serve as a marker for lung cancer.

The 40th target gene is the hsa-miR-4259 gene, a congener thereof, a transcript thereof, or a variant or a derivative thereof. None of the previously known report shows that change in the expression of the gene or the transcript thereof can serve as a marker for lung cancer.

The 41st target gene is the hsa-miR-4281 gene, a congener thereof, a transcript thereof, or a variant or a derivative thereof. None of the previously known report shows that change in the expression of the gene or the transcript thereof can serve as a marker for lung cancer.

The 42nd target gene is the hsa-miR-4294 gene, a congener thereof, a transcript thereof, or a variant or a derivative thereof. None of the previously known report shows that change in the expression of the gene or the transcript thereof can serve as a marker for lung cancer.

The 43rd target gene is the hsa-miR-4419b gene, a congener thereof, a transcript thereof, or a variant or a derivative thereof. None of the previously known report shows that change in the expression of the gene or the transcript thereof can serve as a marker for lung cancer.

The 44th target gene is the hsa-miR-4428 gene, a congener thereof, a transcript thereof, or a variant or a derivative thereof. None of the previously known report shows that change in the expression of the gene or the transcript thereof can serve as a marker for lung cancer.

The 45th target gene is the hsa-miR-4429 gene, a congener thereof, a transcript thereof, or a variant or a derivative thereof. None of the previously known report shows that change in the expression of the gene or the transcript thereof can serve as a marker for lung cancer.

The 46th target gene is the hsa-miR-4433a-3p gene, a congener thereof, a transcript thereof, or a variant or a derivative thereof. None of the previously known report shows that change in the expression of the gene or the transcript thereof can serve as a marker for lung cancer.

The 47th target gene is the hsa-miR-4447 gene, a congener thereof, a transcript thereof, or a variant or a derivative thereof. None of the previously known report shows that change in the expression of the gene or the transcript thereof can serve as a marker for lung cancer.

The 48th target gene is the hsa-miR-4449 gene, a congener thereof, a transcript thereof, or a variant or a derivative thereof. None of the previously known report shows that change in the expression of the gene or the transcript thereof can serve as a marker for lung cancer.

The 49th target gene is the hsa-miR-4459 gene, a congener thereof, a transcript thereof, or a variant or a derivative thereof. None of the previously known report shows that change in the expression of the gene or the transcript thereof can serve as a marker for lung cancer.

The 50th target gene is the hsa-miR-4480 gene, a congener thereof, a transcript thereof, or a variant or a derivative thereof. None of the previously known report shows that change in the expression of the gene or the transcript thereof can serve as a marker for lung cancer.

The 51st target gene is the hsa-miR-4485-5p gene, a congener thereof, a transcript thereof, or a variant or a derivative thereof. None of the previously known report shows that change in the expression of the gene or the transcript thereof can serve as a marker for lung cancer.

The 52nd target gene is the hsa-miR-4486 gene, a congener thereof, a transcript thereof, or a variant or a derivative thereof. None of the previously known report shows that change in the expression of the gene or the transcript thereof can serve as a marker for lung cancer.

The 53rd target gene is the hsa-miR-4488 gene, a congener thereof, a transcript thereof, or a variant or a derivative thereof. None of the previously known report shows that change in the expression of the gene or the transcript thereof can serve as a marker for lung cancer.

The 54th target gene is the hsa-miR-4489 gene, a congener thereof, a transcript thereof, or a variant or a derivative thereof. None of the previously known report shows that change in the expression of the gene or the transcript thereof can serve as a marker for lung cancer.

The 55th target gene is the hsa-miR-4505 gene, a congener thereof, a transcript thereof, or a variant or a derivative thereof. None of the previously known report shows that change in the expression of the gene or the transcript thereof can serve as a marker for lung cancer.

The 56th target gene is the hsa-miR-4513 gene, a congener thereof, a transcript thereof, or a variant or a derivative thereof. None of the previously known report shows that change in the expression of the gene or the transcript thereof can serve as a marker for lung cancer.

The 57th target gene is the hsa-miR-4515 gene, a congener thereof, a transcript thereof, or a variant or a derivative thereof. None of the previously known report shows that change in the expression of the gene or the transcript thereof can serve as a marker for lung cancer.

The 58th target gene is the hsa-miR-4530 gene, a congener thereof, a transcript thereof, or a variant or a derivative thereof. None of the previously known report shows that change in the expression of the gene or the transcript thereof can serve as a marker for lung cancer.

The 59th target gene is the hsa-miR-4535 gene, a congener thereof, a transcript thereof, or a variant or a derivative thereof. None of the previously known report shows that change in the expression of the gene or the transcript thereof can serve as a marker for lung cancer.

The 60th target gene is the hsa-miR-4635 gene, a congener thereof, a transcript thereof, or a variant or a derivative thereof. None of the previously known report shows that change in the expression of the gene or the transcript thereof can serve as a marker for lung cancer.

The 61st target gene is the hsa-miR-4640-5p gene, a congener thereof, a transcript thereof, or a variant or a derivative thereof. None of the previously known report shows that change in the expression of the gene or the transcript thereof can serve as a marker for lung cancer.

The 62nd target gene is the hsa-miR-4646-5p gene, a congener thereof, a transcript thereof, or a variant or a derivative thereof. None of the previously known report shows that change in the expression of the gene or the transcript thereof can serve as a marker for lung cancer.

The 63rd target gene is the hsa-miR-4656 gene, a congener thereof, a transcript thereof, or a variant or a derivative thereof. None of the previously known report shows that change in the expression of the gene or the transcript thereof can serve as a marker for lung cancer.

The 64th target gene is the hsa-miR-4663 gene, a congener thereof, a transcript thereof, or a variant or a derivative thereof. None of the previously known report shows that change in the expression of the gene or the transcript thereof can serve as a marker for lung cancer.

The 65th target gene is the hsa-miR-4665-5p gene, a congener thereof, a transcript thereof, or a variant or a derivative thereof. None of the previously known report shows that change in the expression of the gene or the transcript thereof can serve as a marker for lung cancer.

The 66th target gene is the hsa-miR-4706 gene, a congener thereof, a transcript thereof, or a variant or a derivative thereof. None of the previously known report shows that change in the expression of the gene or the transcript thereof can serve as a marker for lung cancer.

The 67th target gene is the hsa-miR-4707-5p gene, a congener thereof, a transcript thereof, or a variant or a derivative thereof. None of the previously known report shows that change in the expression of the gene or the transcript thereof can serve as a marker for lung cancer.

The 68th target gene is the hsa-miR-4708-3p gene, a congener thereof, a transcript thereof, or a variant or a derivative thereof. None of the previously known report shows that change in the expression of the gene or the transcript thereof can serve as a marker for lung cancer.

The 69th target gene is the hsa-miR-4710 gene, a congener thereof, a transcript thereof, or a variant or a derivative thereof. None of the previously known report shows that change in the expression of the gene or the transcript thereof can serve as a marker for lung cancer.

The 70th target gene is the hsa-miR-4718 gene, a congener thereof, a transcript thereof, or a variant or a derivative thereof. None of the previously known report shows that change in the expression of the gene or the transcript thereof can serve as a marker for lung cancer.

The 71st target gene is the hsa-miR-4722-5p gene, a congener thereof, a transcript thereof, or a variant or a derivative thereof. None of the previously known report shows that change in the expression of the gene or the transcript thereof can serve as a marker for lung cancer.

The 72nd target gene is the hsa-miR-4727-3p gene, a congener thereof, a transcript thereof, or a variant or a derivative thereof. None of the previously known report shows that change in the expression of the gene or the transcript thereof can serve as a marker for lung cancer.

The 73rd target gene is the hsa-miR-4730 gene, a congener thereof, a transcript thereof, or a variant or a derivative thereof. None of the previously known report shows that change in the expression of the gene or the transcript thereof can serve as a marker for lung cancer.

The 74th target gene is the hsa-miR-4734 gene, a congener thereof, a transcript thereof, or a variant or a derivative thereof. None of the previously known report shows that change in the expression of the gene or the transcript thereof can serve as a marker for lung cancer.

The 75th target gene is the hsa-miR-4740-5p gene, a congener thereof, a transcript thereof, or a variant or a derivative thereof. None of the previously known report shows that change in the expression of the gene or the transcript thereof can serve as a marker for lung cancer.

The 76th target gene is the hsa-miR-4747-3p gene, a congener thereof, a transcript thereof, or a variant or a derivative thereof. None of the previously known report shows that change in the expression of the gene or the transcript thereof can serve as a marker for lung cancer.

The 77th target gene is the hsa-miR-4749-5p gene, a congener thereof, a transcript thereof, or a variant or a derivative thereof. None of the previously known report shows that change in the expression of the gene or the transcript thereof can serve as a marker for lung cancer.

The 78th target gene is the hsa-miR-4755-3p gene, a congener thereof, a transcript thereof, or a variant or a derivative thereof. None of the previously known report shows that change in the expression of the gene or the transcript thereof can serve as a marker for lung cancer.

The 79th target gene is the hsa-miR-4763-5p gene, a congener thereof, a transcript thereof, or a variant or a derivative thereof. None of the previously known report shows that change in the expression of the gene or the transcript thereof can serve as a marker for lung cancer.

The 80th target gene is the hsa-miR-4787-3p gene, a congener thereof, a transcript thereof, or a variant or a derivative thereof. None of the previously known report shows that change in the expression of the gene or the transcript thereof can serve as a marker for lung cancer.

The 81st target gene is the hsa-miR-5008-5p gene, a congener thereof, a transcript thereof, or a variant or a derivative thereof. None of the previously known report shows that change in the expression of the gene or the transcript thereof can serve as a marker for lung cancer.

The 82nd target gene is the hsa-miR-5010-5p gene, a congener thereof, a transcript thereof, or a variant or a derivative thereof. None of the previously known report shows that change in the expression of the gene or the transcript thereof can serve as a marker for lung cancer.

The 83rd target gene is the hsa-miR-504-3p gene, a congener thereof, a transcript thereof, or a variant or a derivative thereof. None of the previously known report shows that change in the expression of the gene or the transcript thereof can serve as a marker for lung cancer.

The 84th target gene is the hsa-miR-5090 gene, a congener thereof, a transcript thereof, or a variant or a derivative thereof. None of the previously known report shows that change in the expression of the gene or the transcript thereof can serve as a marker for lung cancer.

The 85th target gene is the hsa-miR-5100 gene, a congener thereof, a transcript thereof, or a variant or a derivative thereof. None of the previously known report shows that change in the expression of the gene or the transcript thereof can serve as a marker for lung cancer.

The 86th target gene is the hsa-miR-5196-5p gene, a congener thereof, a transcript thereof, or a variant or a derivative thereof. None of the previously known report shows that change in the expression of the gene or the transcript thereof can serve as a marker for lung cancer.

The 87th target gene is the hsa-miR-551b-5p gene, a congener thereof, a transcript thereof, or a variant or a derivative thereof. None of the previously known report shows that change in the expression of the gene or the transcript thereof can serve as a marker for lung cancer.

The 88th target gene is the hsa-miR-557 gene, a congener thereof, a transcript thereof, or a variant or a derivative thereof. None of the previously known report shows that change in the expression of the gene or the transcript thereof can serve as a marker for lung cancer.

The 89th target gene is the hsa-miR-5787 gene, a congener thereof, a transcript thereof, or a variant or a derivative thereof. None of the previously known report shows that change in the expression of the gene or the transcript thereof can serve as a marker for lung cancer.

The 90th target gene is the hsa-miR-6090 gene, a congener thereof, a transcript thereof, or a variant or a derivative thereof. None of the previously known report shows that change in the expression of the gene or the transcript thereof can serve as a marker for lung cancer.

The 91st target gene is the hsa-miR-6124 gene, a congener thereof, a transcript thereof, or a variant or a derivative thereof. None of the previously known report shows that change in the expression of the gene or the transcript thereof can serve as a marker for lung cancer.

The 92nd target gene is the hsa-miR-6132 gene, a congener thereof, a transcript thereof, or a variant or a derivative thereof. None of the previously known report shows that change in the expression of the gene or the transcript thereof can serve as a marker for lung cancer.

The 93rd target gene is the hsa-miR-6510-5p gene, a congener thereof, a transcript thereof, or a variant or a derivative thereof. None of the previously known report shows that change in the expression of the gene or the transcript thereof can serve as a marker for lung cancer.

The 94th target gene is the hsa-miR-6511b-5p gene, a congener thereof, a transcript thereof, or a variant or a derivative thereof. None of the previously known report shows that change in the expression of the gene or the transcript thereof can serve as a marker for lung cancer.

The 95th target gene is the hsa-miR-6515-3p gene, a congener thereof, a transcript thereof, or a variant or a derivative thereof. None of the previously known report shows that change in the expression of the gene or the transcript thereof can serve as a marker for lung cancer.

The 96th target gene is the hsa-miR-654-5p gene, a congener thereof, a transcript thereof, or a variant or a derivative thereof. None of the previously known report shows that change in the expression of the gene or the transcript thereof can serve as a marker for lung cancer.

The 97th target gene is the hsa-miR-658 gene, a congener thereof, a transcript thereof, or a variant or a derivative thereof. None of the previously known report shows that change in the expression of the gene or the transcript thereof can serve as a marker for lung cancer.

The 98th target gene is the hsa-miR-668-5p gene, a congener thereof, a transcript thereof, or a variant or a derivative thereof. None of the previously known report shows that change in the expression of the gene or the transcript thereof can serve as a marker for lung cancer.

The 99th target gene is the hsa-miR-6722-5p gene, a congener thereof, a transcript thereof, or a variant or a derivative thereof. None of the previously known report shows that change in the expression of the gene or the transcript thereof can serve as a marker for lung cancer.

The 100th target gene is the hsa-miR-6724-5p gene, a congener thereof, a transcript thereof, or a variant or a derivative thereof. None of the previously known report shows that change in the expression of the gene or the transcript thereof can serve as a marker for lung cancer.

The 101st target gene is the hsa-miR-6729-3p gene, a congener thereof, a transcript thereof, or a variant or a derivative thereof. None of the previously known report shows that change in the expression of the gene or the transcript thereof can serve as a marker for lung cancer.

The 102nd target gene is the hsa-miR-6737-5p gene, a congener thereof, a transcript thereof, or a variant or a derivative thereof. None of the previously known report shows that change in the expression of the gene or the transcript thereof can serve as a marker for lung cancer.

The 103rd target gene is the hsa-miR-6756-5p gene, a congener thereof, a transcript thereof, or a variant or a derivative thereof. None of the previously known report shows that change in the expression of the gene or the transcript thereof can serve as a marker for lung cancer.

The 104th target gene is the hsa-miR-6762-5p gene, a congener thereof, a transcript thereof, or a variant or a derivative thereof. None of the previously known report shows that change in the expression of the gene or the transcript thereof can serve as a marker for lung cancer.

The 105th target gene is the hsa-miR-6763-3p gene, a congener thereof, a transcript thereof, or a variant or a derivative thereof. None of the previously known report shows that change in the expression of the gene or the transcript thereof can serve as a marker for lung cancer.

The 106th target gene is the hsa-miR-6766-5p gene, a congener thereof, a transcript thereof, or a variant or a derivative thereof. None of the previously known report shows that change in the expression of the gene or the transcript thereof can serve as a marker for lung cancer.

The 107th target gene is the hsa-miR-6769a-5p gene, a congener thereof, a transcript thereof, or a variant or a derivative thereof. None of the previously known report shows that change in the expression of the gene or the transcript thereof can serve as a marker for lung cancer.

The 108th target gene is the hsa-miR-6771-5p gene, a congener thereof, a transcript thereof, or a variant or a derivative thereof. None of the previously known report shows that change in the expression of the gene or the transcript thereof can serve as a marker for lung cancer.

The 109th target gene is the hsa-miR-6786-5p gene, a congener thereof, a transcript thereof, or a variant or a derivative thereof. None of the previously known report shows that change in the expression of the gene or the transcript thereof can serve as a marker for lung cancer.

The 110th target gene is the hsa-miR-6789-5p gene, a congener thereof, a transcript thereof, or a variant or a derivative thereof. None of the previously known report shows that change in the expression of the gene or the transcript thereof can serve as a marker for lung cancer.

The 111th target gene is the hsa-miR-6794-5p gene, a congener thereof, a transcript thereof, or a variant or a derivative thereof. None of the previously known report shows that change in the expression of the gene or the transcript thereof can serve as a marker for lung cancer.

The 112th target gene is the hsa-miR-6796-3p gene, a congener thereof, a transcript thereof, or a variant or a derivative thereof. None of the previously known report shows that change in the expression of the gene or the transcript thereof can serve as a marker for lung cancer.

The 113th target gene is the hsa-miR-6797-5p gene, a congener thereof, a transcript thereof, or a variant or a derivative thereof. None of the previously known report shows that change in the expression of the gene or the transcript thereof can serve as a marker for lung cancer.

The 114th target gene is the hsa-miR-6800-3p gene, a congener thereof, a transcript thereof, or a variant or a derivative thereof. None of the previously known report shows that change in the expression of the gene or the transcript thereof can serve as a marker for lung cancer.

The 115th target gene is the hsa-miR-6802-5p gene, a congener thereof, a transcript thereof, or a variant or a derivative thereof. None of the previously known report shows that change in the expression of the gene or the transcript thereof can serve as a marker for lung cancer.

The 116th target gene is the hsa-miR-6803-5p gene, a congener thereof, a transcript thereof, or a variant or a derivative thereof. None of the previously known report shows that change in the expression of the gene or the transcript thereof can serve as a marker for lung cancer.

The 117th target gene is the hsa-miR-6805-3p gene, a congener thereof, a transcript thereof, or a variant or a derivative thereof. None of the previously known report shows that change in the expression of the gene or the transcript thereof can serve as a marker for lung cancer.

The 118th target gene is the hsa-miR-6805-5p gene, a congener thereof, a transcript thereof, or a variant or a derivative thereof. None of the previously known report shows that change in the expression of the gene or the transcript thereof can serve as a marker for lung cancer.

The 119th target gene is the hsa-miR-6807-5p gene, a congener thereof, a transcript thereof, or a variant or a derivative thereof. None of the previously known report shows that change in the expression of the gene or the transcript thereof can serve as a marker for lung cancer.

The 120th target gene is the hsa-miR-6812-5p gene, a congener thereof, a transcript thereof, or a variant or a derivative thereof. None of the previously known report shows that change in the expression of the gene or the transcript thereof can serve as a marker for lung cancer.

The 121st target gene is the hsa-miR-6819-5p gene, a congener thereof, a transcript thereof, or a variant or a derivative thereof. None of the previously known report shows that change in the expression of the gene or the transcript thereof can serve as a marker for lung cancer.

The 122nd target gene is the hsa-miR-6822-5p gene, a congener thereof, a transcript thereof, or a variant or a derivative thereof. None of the previously known report shows that change in the expression of the gene or the transcript thereof can serve as a marker for lung cancer.

The 123rd target gene is the hsa-miR-6824-5p gene, a congener thereof, a transcript thereof, or a variant or a derivative thereof. None of the previously known report shows that change in the expression of the gene or the transcript thereof can serve as a marker for lung cancer.

The 124th target gene is the hsa-miR-6826-5p gene, a congener thereof, a transcript thereof, or a variant or a derivative thereof. None of the previously known report shows that change in the expression of the gene or the transcript thereof can serve as a marker for lung cancer.

The 125th target gene is the hsa-miR-6850-5p gene, a congener thereof, a transcript thereof, or a variant or a derivative thereof. None of the previously known report shows that change in the expression of the gene or the transcript thereof can serve as a marker for lung cancer.

The 126th target gene is the hsa-miR-6858-5p gene, a congener thereof, a transcript thereof, or a variant or a derivative thereof. None of the previously known report shows that change in the expression of the gene or the transcript thereof can serve as a marker for lung cancer.

The 127th target gene is the hsa-miR-6861-5p gene, a congener thereof, a transcript thereof, or a variant or a derivative thereof. None of the previously known report shows that change in the expression of the gene or the transcript thereof can serve as a marker for lung cancer.

The 128th target gene is the hsa-miR-6880-3p gene, a congener thereof, a transcript thereof, or a variant or a derivative thereof. None of the previously known report shows that change in the expression of the gene or the transcript thereof can serve as a marker for lung cancer.

The 129th target gene is the hsa-miR-7107-5p gene, a congener thereof, a transcript thereof, or a variant or a derivative thereof. None of the previously known report shows that change in the expression of the gene or the transcript thereof can serve as a marker for lung cancer.

The 130th target gene is the hsa-miR-7109-5p gene, a congener thereof, a transcript thereof, or a variant or a derivative thereof. None of the previously known report shows that change in the expression of the gene or the transcript thereof can serve as a marker for lung cancer.

The 131st target gene is the hsa-miR-7114-5p gene, a congener thereof, a transcript thereof, or a variant or a derivative thereof. None of the previously known report shows that change in the expression of the gene or the transcript thereof can serve as a marker for lung cancer.

The 132nd target gene is the hsa-miR-7704 gene, a congener thereof, a transcript thereof, or a variant or a derivative thereof. None of the previously known report shows that change in the expression of the gene or the transcript thereof can serve as a marker for lung cancer.

The 133rd target gene is the hsa-miR-7846-3p gene, a congener thereof, a transcript thereof, or a variant or a derivative thereof. None of the previously known report shows that change in the expression of the gene or the transcript thereof can serve as a marker for lung cancer.

The 134th target gene is the hsa-miR-8052 gene, a congener thereof, a transcript thereof, or a variant or a derivative thereof. None of the previously known report shows that change in the expression of the gene or the transcript thereof can serve as a marker for lung cancer.

The 135th target gene is the hsa-miR-8060 gene, a congener thereof, a transcript thereof, or a variant or a derivative thereof. None of the previously known report shows that change in the expression of the gene or the transcript thereof can serve as a marker for lung cancer.

The 136th target gene is the hsa-miR-8071 gene, a congener thereof, a transcript thereof, or a variant or a derivative thereof. None of the previously known report shows that change in the expression of the gene or the transcript thereof can serve as a marker for lung cancer.

The 137th target gene is the hsa-miR-8073 gene, a congener thereof, a transcript thereof, or a variant or a derivative thereof. None of the previously known report shows that change in the expression of the gene or the transcript thereof can serve as a marker for lung cancer.

The 138th target gene is the hsa-miR-874-5p gene, a congener thereof, a transcript thereof, or a variant or a derivative thereof. None of the previously known report shows that change in the expression of the gene or the transcript thereof can serve as a marker for lung cancer.

The 139th target gene is the hsa-miR-204-3p gene, a congener thereof, a transcript thereof, or a variant or a derivative thereof. None of the previously known report shows that change in the expression of the gene or the transcript thereof can serve as a marker for lung cancer.

The 140th target gene is the hsa-miR-3154 gene, a congener thereof, a transcript thereof, or a variant or a derivative thereof. None of the previously known report shows that change in the expression of the gene or the transcript thereof can serve as a marker for lung cancer.

The 141st target gene is the hsa-miR-3960 gene, a congener thereof, a transcript thereof, or a variant or a derivative thereof. None of the previously known report shows that change in the expression of the gene or the transcript thereof can serve as a marker for lung cancer.

The 142nd target gene is the hsa-miR-4433a-5p gene, a congener thereof, a transcript thereof, or a variant or a derivative thereof. None of the previously known report shows that change in the expression of the gene or the transcript thereof can serve as a marker for lung cancer.

The 143rd target gene is the hsa-miR-4455 gene, a congener thereof, a transcript thereof, or a variant or a derivative thereof. None of the previously known report shows that change in the expression of the gene or the transcript thereof can serve as a marker for lung cancer.

The 144th target gene is the hsa-miR-4462 gene, a congener thereof, a transcript thereof, or a variant or a derivative thereof. None of the previously known report shows that change in the expression of the gene or the transcript thereof can serve as a marker for lung cancer.

The 145th target gene is the hsa-miR-4476 gene, a congener thereof, a transcript thereof, or a variant or a derivative thereof. None of the previously known report shows that change in the expression of the gene or the transcript thereof can serve as a marker for lung cancer.

The 146th target gene is the hsa-miR-4508 gene, a congener thereof, a transcript thereof, or a variant or a derivative thereof. None of the previously known report shows that change in the expression of the gene or the transcript thereof can serve as a marker for lung cancer.

The 147th target gene is the hsa-miR-4687-3p gene, a congener thereof, a transcript thereof, or a variant or a derivative thereof. None of the previously known report shows that change in the expression of the gene or the transcript thereof can serve as a marker for lung cancer.

The 148th target gene is the hsa-miR-4687-5p gene, a congener thereof, a transcript thereof, or a variant or a derivative thereof. None of the previously known report shows that change in the expression of the gene or the transcript thereof can serve as a marker for lung cancer.

The 149th target gene is the hsa-miR-4732-5p gene, a congener thereof, a transcript thereof, or a variant or a derivative thereof. None of the previously known report shows that change in the expression of the gene or the transcript thereof can serve as a marker for lung cancer.

The 150th target gene is the hsa-miR-4771 gene, a congener thereof, a transcript thereof, or a variant or a derivative thereof. None of the previously known report shows that change in the expression of the gene or the transcript thereof can serve as a marker for lung cancer.

The 151st target gene is the hsa-miR-642a-3p gene, a congener thereof, a transcript thereof, or a variant or a derivative thereof. None of the previously known report shows that change in the expression of the gene or the transcript thereof can serve as a marker for lung cancer.

The 152nd target gene is the hsa-miR-6732-5p gene, a congener thereof, a transcript thereof, or a variant or a derivative thereof. None of the previously known report shows that change in the expression of the gene or the transcript thereof can serve as a marker for lung cancer.

The 153rd target gene is the hsa-miR-6760-5p gene, a congener thereof, a transcript thereof, or a variant or a derivative thereof. None of the previously known report shows that change in the expression of the gene or the transcript thereof can serve as a marker for lung cancer.

The 154th target gene is the hsa-miR-6799-5p gene, a congener thereof, a transcript thereof, or a variant or a derivative thereof. None of the previously known report shows that change in the expression of the gene or the transcript thereof can serve as a marker for lung cancer.

The 155th target gene is the hsa-miR-6820-5p gene, a congener thereof, a transcript thereof, or a variant or a derivative thereof. None of the previously known report shows that change in the expression of the gene or the transcript thereof can serve as a marker for lung cancer.

The 156th target gene is the hsa-miR-6821-5p gene, a congener thereof, a transcript thereof, or a variant or a derivative thereof. None of the previously known report shows that change in the expression of the gene or the transcript thereof can serve as a marker for lung cancer.

The 157th target gene is the hsa-miR-6829-5p gene, a congener thereof, a transcript thereof, or a variant or a derivative thereof. None of the previously known report shows that change in the expression of the gene or the transcript thereof can serve as a marker for lung cancer.

The 158th target gene is the hsa-miR-6893-5p gene, a congener thereof, a transcript thereof, or a variant or a derivative thereof. None of the previously known report shows that change in the expression of the gene or the transcript thereof can serve as a marker for lung cancer.

The 159th target gene is the hsa-miR-7108-3p gene, a congener thereof, a transcript thereof, or a variant or a derivative thereof. None of the previously known report shows that change in the expression of the gene or the transcript thereof can serve as a marker for lung cancer.

The 160th target gene is the hsa-miR-7111-5p gene, a congener thereof, a transcript thereof, or a variant or a derivative thereof. None of the previously known report shows that change in the expression of the gene or the transcript thereof can serve as a marker for lung cancer.

The 161st target gene is the hsa-miR-8089 gene, a congener thereof, a transcript thereof, or a variant or a derivative thereof. None of the previously known report shows that change in the expression of the gene or the transcript thereof can serve as a marker for lung cancer.

The 162nd target gene is the hsa-miR-885-3p gene, a congener thereof, a transcript thereof, or a variant or a derivative thereof. None of the previously known report shows that change in the expression of the gene or the transcript thereof can serve as a marker for lung cancer.

The 163rd target gene is the hsa-miR-92b-3p gene, a congener thereof, a transcript thereof, or a variant or a derivative thereof. None of the previously known report shows that change in the expression of the gene or the transcript thereof can serve as a marker for lung cancer.

The 164th target gene is the hsa-miR-1343-3p gene, a congener thereof, a transcript thereof, or a variant or a derivative thereof. The previously known report shows that change in the expression of the gene or the transcript thereof can serve as a marker for lung cancer (Patent Literature 1).

The 165th target gene is the hsa-miR-6746-5p gene, a congener thereof, a transcript thereof, or a variant or a derivative thereof. The previously known report shows that change in the expression of the gene or the transcript thereof can serve as a marker for lung cancer (Patent Literature 1).

The 166th target gene is the hsa-miR-422a gene, a congener thereof, a transcript thereof, or a variant or a derivative thereof. The previously known report shows that change in the expression of the gene or the transcript thereof can serve as a marker for lung cancer (Patent Literature 2).

The 167th target gene is the hsa-miR-187-5p gene, a congener thereof, a transcript thereof, or a variant or a derivative thereof. The previously known report shows that change in the expression of the gene or the transcript thereof can serve as a marker for lung cancer (Patent Literature 1).

The 168th target gene is the hsa-miR-4632-5p gene, a congener thereof, a transcript thereof, or a variant or a derivative thereof. The previously known report shows that change in the expression of the gene or the transcript thereof can serve as a marker for lung cancer (Patent Literature 1).

The 169th target gene is the hsa-miR-6791-5p gene, a congener thereof, a transcript thereof, or a variant or a derivative thereof. The previously known report shows that change in the expression of the gene or the transcript thereof can serve as a marker for lung cancer (Patent Literature 1).

The 170th target gene is the hsa-miR-103a-3p gene, a congener thereof, a transcript thereof, or a variant or a derivative thereof. The previously known report shows that change in the expression of the gene or the transcript thereof can serve as a marker for lung cancer (Patent Literature 3).

The 171st target gene is the hsa-miR-107 gene, a congener thereof, a transcript thereof, or a variant or a derivative thereof. The previously known report shows that change in the expression of the gene or the transcript thereof can serve as a marker for lung cancer (Patent Literature 3).

The 172nd target gene is the hsa-miR-1199-5p gene, a congener thereof, a transcript thereof, or a variant or a derivative thereof. The previously known report shows that change in the expression of the gene or the transcript thereof can serve as a marker for lung cancer (Patent Literature 1).

The 173rd target gene is the hsa-miR-1225-3p gene, a congener thereof, a transcript thereof, or a variant or a derivative thereof. The previously known report shows that change in the expression of the gene or the transcript thereof can serve as a marker for lung cancer (Patent Literature 1).

The 174th target gene is the hsa-miR-1225-5p gene, a congener thereof, a transcript thereof, or a variant or a derivative thereof. The previously known report shows that change in the expression of the gene or the transcript thereof can serve as a marker for lung cancer (Patent Literature 1).

The 175th target gene is the hsa-miR-1228-5p gene, a congener thereof, a transcript thereof, or a variant or a derivative thereof. The previously known report shows that change in the expression of the gene or the transcript thereof can serve as a marker for lung cancer (Patent Literature 1).

The 176th target gene is the hsa-miR-1229-5p gene, a congener thereof, a transcript thereof, or a variant or a derivative thereof. The previously known report shows that change in the expression of the gene or the transcript thereof can serve as a marker for lung cancer (Non-Patent Literature 5).

The 177th target gene is the hsa-miR-1233-5p gene, a congener thereof, a transcript thereof, or a variant or a derivative thereof. The previously known report shows that change in the expression of the gene or the transcript thereof can serve as a marker for lung cancer (Patent Literature 1).

The 178th target gene is the hsa-miR-1237-5p gene, a congener thereof, a transcript thereof, or a variant or a derivative thereof. The previously known report shows that change in the expression of the gene or the transcript thereof can serve as a marker for lung cancer (Patent Literature 1).

The 179th target gene is the hsa-miR-1247-3p gene, a congener thereof, a transcript thereof, or a variant or a derivative thereof. The previously known report shows that change in the expression of the gene or the transcript thereof can serve as a marker for lung cancer (Patent Literature 1).

The 180th target gene is the hsa-miR-1249-3p gene, a congener thereof, a transcript thereof, or a variant or a derivative thereof. The previously known report shows that change in the expression of the gene or the transcript thereof can serve as a marker for lung cancer (Patent Literature 5).

The 181st target gene is the hsa-miR-1254 gene, a congener thereof, a transcript thereof, or a variant or a derivative thereof. The previously known report shows that change in the expression of the gene or the transcript thereof can serve as a marker for lung cancer (Non-Patent Literature 6).

The 182nd target gene is the hsa-miR-1260b gene, a congener thereof, a transcript thereof, or a variant or a derivative thereof. The previously known report shows that change in the expression of the gene or the transcript thereof can serve as a marker for lung cancer (Patent Literature 1).

The 183rd target gene is the hsa-miR-1268a gene, a congener thereof, a transcript thereof, or a variant or a derivative thereof. The previously known report shows that change in the expression of the gene or the transcript thereof can serve as a marker for lung cancer (Patent Literature 1).

The 184th target gene is the hsa-miR-1268b gene, a congener thereof, a transcript thereof, or a variant or a derivative thereof. The previously known report shows that change in the expression of the gene or the transcript thereof can serve as a marker for lung cancer (Patent Literature 1).

The 185th target gene is the hsa-miR-1273g-3p gene, a congener thereof, a transcript thereof, or a variant or a derivative thereof. The previously known report shows that change in the expression of the gene or the transcript thereof can serve as a marker for lung cancer (Patent Literature 1).

The 186th target gene is the hsa-miR-128-1-5p gene, a congener thereof, a transcript thereof, or a variant or a derivative thereof. The previously known report shows that change in the expression of the gene or the transcript thereof can serve as a marker for lung cancer (Patent Literature 1).

The 187th target gene is the hsa-miR-128-2-5p gene, a congener thereof, a transcript thereof, or a variant or a derivative thereof. The previously known report shows that change in the expression of the gene or the transcript thereof can serve as a marker for lung cancer (Patent Literature 1).

The 188th target gene is the hsa-miR-1290 gene, a congener thereof, a transcript thereof, or a variant or a derivative thereof. The previously known report shows that change in the expression of the gene or the transcript thereof can serve as a marker for lung cancer (Non-Patent Literature 1).

The 189th target gene is the hsa-miR-150-3p gene, a congener thereof, a transcript thereof, or a variant or a derivative thereof. The previously known report shows that change in the expression of the gene or the transcript thereof can serve as a marker for lung cancer (Patent Literature 3).

The 190th target gene is the hsa-miR-17-3p gene, a congener thereof, a transcript thereof, or a variant or a derivative thereof. The previously known report shows that change in the expression of the gene or the transcript thereof can serve as a marker for lung cancer (Patent Literature 1).

The 191st target gene is the hsa-miR-1908-5p gene, a congener thereof, a transcript thereof, or a variant or a derivative thereof. The previously known report shows that change in the expression of the gene or the transcript thereof can serve as a marker for lung cancer (Patent Literature 1).

The 192nd target gene is the hsa-miR-1909-3p gene, a congener thereof, a transcript thereof, or a variant or a derivative thereof. The previously known report shows that change in the expression of the gene or the transcript thereof can serve as a marker for lung cancer (Patent Literature 4).

The 193rd target gene is the hsa-miR-1914-3p gene, a congener thereof, a transcript thereof, or a variant or a derivative thereof. The previously known report shows that change in the expression of the gene or the transcript thereof can serve as a marker for lung cancer (Patent Literature 1).

The 194th target gene is the hsa-miR-1915-3p gene, a congener thereof, a transcript thereof, or a variant or a derivative thereof. The previously known report shows that change in the expression of the gene or the transcript thereof can serve as a marker for lung cancer (Patent Literature 1).

The 195th target gene is the hsa-miR-191-5p gene, a congener thereof, a transcript thereof, or a variant or a derivative thereof. The previously known report shows that change in the expression of the gene or the transcript thereof can serve as a marker for lung cancer (Patent Literature 1).

The 196th target gene is the hsa-miR-22-3p gene, a congener thereof, a transcript thereof, or a variant or a derivative thereof. The previously known report shows that change in the expression of the gene or the transcript thereof can serve as a marker for lung cancer (Patent Literature 1).

The 197th target gene is the hsa-miR-23b-3p gene, a congener thereof, a transcript thereof, or a variant or a derivative thereof. The previously known report shows that change in the expression of the gene or the transcript thereof can serve as a marker for lung cancer (Patent Literature 4).

The 198th target gene is the hsa-miR-24-3p gene, a congener thereof, a transcript thereof, or a variant or a derivative thereof. The previously known report shows that change in the expression of the gene or the transcript thereof can serve as a marker for lung cancer (Patent Literature 2).

The 199th target gene is the hsa-miR-296-3p gene, a congener thereof, a transcript thereof, or a variant or a derivative thereof. The previously known report shows that change in the expression of the gene or the transcript thereof can serve as a marker for lung cancer (Patent Literature 1).

The 200th target gene is the hsa-miR-296-5p gene, a congener thereof, a transcript thereof, or a variant or a derivative thereof. The previously known report shows that change in the expression of the gene or the transcript thereof can serve as a marker for lung cancer (Patent Literature 2).

The 201st target gene is the hsa-miR-3131 gene, a congener thereof, a transcript thereof, or a variant or a derivative thereof. The previously known report shows that change in the expression of the gene or the transcript thereof can serve as a marker for lung cancer (Patent Literature 1).

The 202nd target gene is the hsa-miR-3162-5p gene, a congener thereof, a transcript thereof, or a variant or a derivative thereof. The previously known report shows that change in the expression of the gene or the transcript thereof can serve as a marker for lung cancer (Patent Literature 1).

The 203rd target gene is the hsa-miR-3188 gene, a congener thereof, a transcript thereof, or a variant or a derivative thereof. The previously known report shows that change in the expression of the gene or the transcript thereof can serve as a marker for lung cancer (Patent Literature 1).

The 204th target gene is the hsa-miR-3196 gene, a congener thereof, a transcript thereof, or a variant or a derivative thereof. The previously known report shows that change in the expression of the gene or the transcript thereof can serve as a marker for lung cancer (Patent Literature 1).

The 205th target gene is the hsa-miR-3197 gene, a congener thereof, a transcript thereof, or a variant or a derivative thereof. The previously known report shows that change in the expression of the gene or the transcript thereof can serve as a marker for lung cancer (Patent Literature 1).

The 206th target gene is the hsa-miR-320a gene, a congener thereof, a transcript thereof, or a variant or a derivative thereof. The previously known report shows that change in the expression of the gene or the transcript thereof can serve as a marker for lung cancer (Patent Literature 2).

The 207th target gene is the hsa-miR-342-5p gene, a congener thereof, a transcript thereof, or a variant or a derivative thereof. The previously known report shows that change in the expression of the gene or the transcript thereof can serve as a marker for lung cancer (Non-Patent Literature 3).

The 208th target gene is the hsa-miR-3621 gene, a congener thereof, a transcript thereof, or a variant or a derivative thereof. The previously known report shows that change in the expression of the gene or the transcript thereof can serve as a marker for lung cancer (Patent Literature 1).

The 209th target gene is the hsa-miR-3648 gene, a congener thereof, a transcript thereof, or a variant or a derivative thereof. The previously known report shows that change in the expression of the gene or the transcript thereof can serve as a marker for lung cancer (Patent Literature 1).

The 210th target gene is the hsa-miR-3656 gene, a congener thereof, a transcript thereof, or a variant or a derivative thereof. The previously known report shows that change in the expression of the gene or the transcript thereof can serve as a marker for lung cancer (Patent Literature 1).

The 211th target gene is the hsa-miR-365a-5p gene, a congener thereof, a transcript thereof, or a variant or a derivative thereof. The previously known report shows that change in the expression of the gene or the transcript thereof can serve as a marker for lung cancer (Patent Literature 1).

The 212th target gene is the hsa-miR-3665 gene, a congener thereof, a transcript thereof, or a variant or a derivative thereof. The previously known report shows that change in the expression of the gene or the transcript thereof can serve as a marker for lung cancer (Patent Literature 1).

The 213th target gene is the hsa-miR-3679-5p gene, a congener thereof, a transcript thereof, or a variant or a derivative thereof. The previously known report shows that change in the expression of the gene or the transcript thereof can serve as a marker for lung cancer (Patent Literature 1).

The 214th target gene is the hsa-miR-371a-5p gene, a congener thereof, a transcript thereof, or a variant or a derivative thereof. The previously known report shows that change in the expression of the gene or the transcript thereof can serve as a marker for lung cancer (Patent Literature 1).

The 215th target gene is the hsa-miR-3940-5p gene, a congener thereof, a transcript thereof, or a variant or a derivative thereof. The previously known report shows that change in the expression of the gene or the transcript thereof can serve as a marker for lung cancer (Patent Literature 1).

The 216th target gene is the hsa-miR-423-5p gene, a congener thereof, a transcript thereof, or a variant or a derivative thereof. The previously known report shows that change in the expression of the gene or the transcript thereof can serve as a marker for lung cancer (Patent Literature 4).

The 217th target gene is the hsa-miR-4257 gene, a congener thereof, a transcript thereof, or a variant or a derivative thereof. The previously known report shows that change in the expression of the gene or the transcript thereof can serve as a marker for lung cancer (Patent Literature 1).

The 218th target gene is the hsa-miR-4270 gene, a congener thereof, a transcript thereof, or a variant or a derivative thereof. The previously known report shows that change in the expression of the gene or the transcript thereof can serve as a marker for lung cancer (Patent Literature 1).

The 219th target gene is the hsa-miR-4271 gene, a congener thereof, a transcript thereof, or a variant or a derivative thereof. The previously known report shows that change in the expression of the gene or the transcript thereof can serve as a marker for lung cancer (Patent Literature 1).

The 220th target gene is the hsa-miR-4286 gene, a congener thereof, a transcript thereof, or a variant or a derivative thereof. The previously known report shows that change in the expression of the gene or the transcript thereof can serve as a marker for lung cancer (Patent Literature 1).

The 221st target gene is the hsa-miR-4298 gene, a congener thereof, a transcript thereof, or a variant or a derivative thereof. The previously known report shows that change in the expression of the gene or the transcript thereof can serve as a marker for lung cancer (Patent Literature 1).

The 222nd target gene is the hsa-miR-4417 gene, a congener thereof, a transcript thereof, or a variant or a derivative thereof. The previously known report shows that change in the expression of the gene or the transcript thereof can serve as a marker for lung cancer (Patent Literature 1).

The 223rd target gene is the hsa-miR-4442 gene, a congener thereof, a transcript thereof, or a variant or a derivative thereof. The previously known report shows that change in the expression of the gene or the transcript thereof can serve as a marker for lung cancer (Patent Literature 1).

The 224th target gene is the hsa-miR-4446-3p gene, a congener thereof, a transcript thereof, or a variant or a derivative thereof. The previously known report shows that change in the expression of the gene or the transcript thereof can serve as a marker for lung cancer (Patent Literature 1).

The 225th target gene is the hsa-miR-4448 gene, a congener thereof, a transcript thereof, or a variant or a derivative thereof. The previously known report shows that change in the expression of the gene or the transcript thereof can serve as a marker for lung cancer (Patent Literature 1).

The 226th target gene is the hsa-miR-4454 gene, a congener thereof, a transcript thereof, or a variant or a derivative thereof. The previously known report shows that change in the expression of the gene or the transcript thereof can serve as a marker for lung cancer (Patent Literature 1).

The 227th target gene is the hsa-miR-4467 gene, a congener thereof, a transcript thereof, or a variant or a derivative thereof. The previously known report shows that change in the expression of the gene or the transcript thereof can serve as a marker for lung cancer (Patent Literature 1).

The 228th target gene is the hsa-miR-4472 gene, a congener thereof, a transcript thereof, or a variant or a derivative thereof. The previously known report shows that change in the expression of the gene or the transcript thereof can serve as a marker for lung cancer (Patent Literature 1).

The 229th target gene is the hsa-miR-4507 gene, a congener thereof, a transcript thereof, or a variant or a derivative The 230th target gene is the hsa-miR-4516 gene, a congener thereof, a transcript thereof, or a variant or a derivative thereof. The previously known report shows that change in the expression of the gene or the transcript thereof can serve as a marker for lung cancer (Patent Literature 1).

The 231st target gene is the hsa-miR-451a gene, a congener thereof, a transcript thereof, or a variant or a derivative thereof. The previously known report shows that change in the expression of the gene or the transcript thereof can serve as a marker for lung cancer (Patent Literature 1).

The 232nd target gene is the hsa-miR-4649-5p gene, a congener thereof, a transcript thereof, or a variant or a derivative thereof. The previously known report shows that change in the expression of the gene or the transcript thereof can serve as a marker for lung cancer (Patent Literature 1).

The 233rd target gene is the hsa-miR-4651 gene, a congener thereof, a transcript thereof, or a variant or a derivative thereof. The previously known report shows that change in the expression of the gene or the transcript thereof can serve as a marker for lung cancer (Patent Literature 1).

The 234th target gene is the hsa-miR-4665-3p gene, a congener thereof, a transcript thereof, or a variant or a derivative thereof. The previously known report shows that change in the expression of the gene or the transcript thereof can serve as a marker for lung cancer (Patent Literature 1).

The 235th target gene is the hsa-miR-4674 gene, a congener thereof, a transcript thereof, or a variant or a derivative thereof. The previously known report shows that change in the expression of the gene or the transcript thereof can serve as a marker for lung cancer (Patent Literature 1).

The 236th target gene is the hsa-miR-4675 gene, a congener thereof, a transcript thereof, or a variant or a derivative thereof. The previously known report shows that change in the expression of the gene or the transcript thereof can serve as a marker for lung cancer (Patent Literature 1).

The 237th target gene is the hsa-miR-4689 gene, a congener thereof, a transcript thereof, or a variant or a derivative thereof. The previously known report shows that change in the expression of the gene or the transcript thereof can serve as a marker for lung cancer (Patent Literature 1).

The 238th target gene is the hsa-miR-4695-5p gene, a congener thereof, a transcript thereof, or a variant or a derivative thereof. The previously known report shows that change in the expression of the gene or the transcript thereof can serve as a marker for lung cancer (Patent Literature 1).

The 239th target gene is the hsa-miR-4697-5p gene, a congener thereof, a transcript thereof, or a variant or a derivative thereof. The previously known report shows that change in the expression of the gene or the transcript thereof can serve as a marker for lung cancer (Patent Literature 1).

The 240th target gene is the hsa-miR-4725-3p gene, a congener thereof, a transcript thereof, or a variant or a derivative thereof. The previously known report shows that change in the expression of the gene or the transcript thereof can serve as a marker for lung cancer (Patent Literature 1).

The 241st target gene is the hsa-miR-4739 gene, a congener thereof, a transcript thereof, or a variant or a derivative thereof. The previously known report shows that change in the expression of the gene or the transcript thereof can serve as a marker for lung cancer (Patent Literature 1).

The 242nd target gene is the hsa-miR-4745-5p gene, a congener thereof, a transcript thereof, or a variant or a derivative thereof. The previously known report shows that change in the expression of the gene or the transcript thereof can serve as a marker for lung cancer (Patent Literature 1).

The 243rd target gene is the hsa-miR-4763-3p gene, a congener thereof, a transcript thereof, or a variant or a derivative thereof. The previously known report shows that change in the expression of the gene or the transcript thereof can serve as a marker for lung cancer (Patent Literature 1).

The 244th target gene is the hsa-miR-4792 gene, a congener thereof, a transcript thereof, or a variant or a derivative thereof. The previously known report shows that change in the expression of the gene or the transcript thereof can serve as a marker for lung cancer (Patent Literature 1).

The 245th target gene is the hsa-miR-486-3p gene, a congener thereof, a transcript thereof, or a variant or a derivative thereof. The previously known report shows that change in the expression of the gene or the transcript thereof can serve as a marker for lung cancer (Patent Literature 1).

The 246th target gene is the hsa-miR-5001-5p gene, a congener thereof, a transcript thereof, or a variant or a derivative thereof. The previously known report shows that change in the expression of the gene or the transcript thereof can serve as a marker for lung cancer (Patent Literature 1).

The 247th target gene is the hsa-miR-5195-3p gene, a congener thereof, a transcript thereof, or a variant or a derivative thereof. The previously known report shows that change in the expression of the gene or the transcript thereof can serve as a marker for lung cancer (Patent Literature 1).

The 248th target gene is the hsa-miR-550a-5p gene, a congener thereof, a transcript thereof, or a variant or a derivative thereof. The previously known report shows that change in the expression of the gene or the transcript thereof can serve as a marker for lung cancer (Non-Patent Literature 4).

The 249th target gene is the hsa-miR-5698 gene, a congener thereof, a transcript thereof, or a variant or a derivative thereof. The previously known report shows that change in the expression of the gene or the transcript thereof can serve as a marker for lung cancer (Patent Literature 1).

The 250th target gene is the hsa-miR-6075 gene, a congener thereof, a transcript thereof, or a variant or a derivative thereof. The previously known report shows that change in the expression of the gene or the transcript thereof can serve as a marker for lung cancer (Patent Literature 1).

The 251st target gene is the hsa-miR-6088 gene, a congener thereof, a transcript thereof, or a variant or a derivative thereof. The previously known report shows that change in the expression of the gene or the transcript thereof can serve as a marker for lung cancer (Patent Literature 1).

The 252nd target gene is the hsa-miR-6089 gene, a congener thereof, a transcript thereof, or a variant or a derivative thereof. The previously known report shows that change in the expression of the gene or the transcript thereof can serve as a marker for lung cancer (Patent Literature 1).

The 253rd target gene is the hsa-miR-6125 gene, a congener thereof, a transcript thereof, or a variant or a derivative thereof. The previously known report shows that change in the expression of the gene or the transcript thereof can serve as a marker for lung cancer (Patent Literature 1).

The 254th target gene is the hsa-miR-6126 gene, a congener thereof, a transcript thereof, or a variant or a derivative thereof. The previously known report shows that change in the expression of the gene or the transcript thereof can serve as a marker for lung cancer (Patent Literature 1).

The 255th target gene is the hsa-miR-614 gene, a congener thereof, a transcript thereof, or a variant or a derivative thereof. The previously known report shows that change in the expression of the gene or the transcript thereof can serve as a marker for lung cancer (Patent Literature 1).

The 256th target gene is the hsa-miR-615-5p gene, a congener thereof, a transcript thereof, or a variant or a derivative thereof. The previously known report shows that change in the expression of the gene or the transcript thereof can serve as a marker for lung cancer (Patent Literature 1).

The 257th target gene is the hsa-miR-619-5p gene, a congener thereof, a transcript thereof, or a variant or a derivative thereof. The previously known report shows that change in the expression of the gene or the transcript thereof can serve as a marker for lung cancer (Patent Literature 1).

The 258th target gene is the hsa-miR-638 gene, a congener thereof, a transcript thereof, or a variant or a derivative thereof. The previously known report shows that change in the expression of the gene or the transcript thereof can serve as a marker for lung cancer (Patent Literature 2).

The 259th target gene is the hsa-miR-642b-3p gene, a congener thereof, a transcript thereof, or a variant or a derivative thereof. The previously known report shows that change in the expression of the gene or the transcript thereof can serve as a marker for lung cancer (Patent Literature 1).

The 260th target gene is the hsa-miR-650 gene, a congener thereof, a transcript thereof, or a variant or a derivative thereof. The previously known report shows that change in the expression of the gene or the transcript thereof can serve as a marker for lung cancer (Non-Patent Literature 2).

The 261st target gene is the hsa-miR-663a gene, a congener thereof, a transcript thereof, or a variant or a derivative thereof. The previously known report shows that change in the expression of the gene or the transcript thereof can serve as a marker for lung cancer (Patent Literature 1).

The 262nd target gene is the hsa-miR-663b gene, a congener thereof, a transcript thereof, or a variant or a derivative thereof. The previously known report shows that change in the expression of the gene or the transcript thereof can serve as a marker for lung cancer (Patent Literature 1).

The 263rd target gene is the hsa-miR-6717-5p gene, a congener thereof, a transcript thereof, or a variant or a derivative thereof. The previously known report shows that change in the expression of the gene or the transcript thereof can serve as a marker for lung cancer (Patent Literature 1).

The 264th target gene is the hsa-miR-6721-5p gene, a congener thereof, a transcript thereof, or a variant or a derivative thereof. The previously known report shows that change in the expression of the gene or the transcript thereof can serve as a marker for lung cancer (Patent Literature 1).

The 265th target gene is the hsa-miR-6726-5p gene, a congener thereof, a transcript thereof, or a variant or a derivative thereof. The previously known report shows that change in the expression of the gene or the transcript thereof can serve as a marker for lung cancer (Patent Literature 1).

The 266th target gene is the hsa-miR-6727-5p gene, a congener thereof, a transcript thereof, or a variant or a derivative thereof. The previously known report shows that change in the expression of the gene or the transcript thereof can serve as a marker for lung cancer (Patent Literature 1).

The 267th target gene is the hsa-miR-6738-5p gene, a congener thereof, a transcript thereof, or a variant or a derivative thereof. The previously known report shows that change in the expression of the gene or the transcript thereof can serve as a marker for lung cancer (Patent Literature 1).

The 268th target gene is the hsa-miR-6741-5p gene, a congener thereof, a transcript thereof, or a variant or a derivative thereof. The previously known report shows that change in the expression of the gene or the transcript thereof can serve as a marker for lung cancer (Patent Literature 1).

The 269th target gene is the hsa-miR-6749-5p gene, a congener thereof, a transcript thereof, or a variant or a derivative thereof. The previously known report shows that change in the expression of the gene or the transcript thereof can serve as a marker for lung cancer (Patent Literature 1).

The 270th target gene is the hsa-miR-6752-5p gene, a congener thereof, a transcript thereof, or a variant or a derivative thereof. The previously known report shows that change in the expression of the gene or the transcript thereof can serve as a marker for lung cancer (Patent Literature 1).

The 271st target gene is the hsa-miR-675-5p gene, a congener thereof, a transcript thereof, or a variant or a derivative thereof. The previously known report shows that change in the expression of the gene or the transcript thereof can serve as a marker for lung cancer (Patent Literature 1).

The 272nd target gene is the hsa-miR-6757-5p gene, a congener thereof, a transcript thereof, or a variant or a derivative thereof. The previously known report shows that change in the expression of the gene or the transcript thereof can serve as a marker for lung cancer (Patent Literature 1).

The 273rd target gene is the hsa-miR-6763-5p gene, a congener thereof, a transcript thereof, or a variant or a derivative thereof. The previously known report shows that change in the expression of the gene or the transcript thereof can serve as a marker for lung cancer (Patent Literature 1).

The 274th target gene is the hsa-miR-6765-5p gene, a congener thereof, a transcript thereof, or a variant or a derivative thereof. The previously known report shows that change in the expression of the gene or the transcript thereof can serve as a marker for lung cancer (Patent Literature 1).

The 275th target gene is the hsa-miR-6775-5p gene, a congener thereof, a transcript thereof, or a variant or a derivative thereof. The previously known report shows that change in the expression of the gene or the transcript thereof can serve as a marker for lung cancer (Patent Literature 1).

The 276th target gene is the hsa-miR-6780b-5p gene, a congener thereof, a transcript thereof, or a variant or a derivative thereof. The previously known report shows that change in the expression of the gene or the transcript thereof can serve as a marker for lung cancer (Patent Literature 1).

The 277th target gene is the hsa-miR-6782-5p gene, a congener thereof, a transcript thereof, or a variant or a derivative thereof. The previously known report shows that change in the expression of the gene or the transcript thereof can serve as a marker for lung cancer (Patent Literature 1).

The 278th target gene is the hsa-miR-6784-5p gene, a congener thereof, a transcript thereof, or a variant or a derivative thereof. The previously known report shows that change in the expression of the gene or the transcript thereof can serve as a marker for lung cancer (Patent Literature 1).

The 279th target gene is the hsa-miR-6800-5p gene, a congener thereof, a transcript thereof, or a variant or a derivative thereof. The previously known report shows that change in the expression of the gene or the transcript thereof can serve as a marker for lung cancer (Patent Literature 1).

The 280th target gene is the hsa-miR-6806-5p gene, a congener thereof, a transcript thereof, or a variant or a derivative thereof. The previously known report shows that change in the expression of the gene or the transcript thereof can serve as a marker for lung cancer (Patent Literature 1).

The 281st target gene is the hsa-miR-6840-3p gene, a congener thereof, a transcript thereof, or a variant or a derivative thereof. The previously known report shows that change in the expression of the gene or the transcript thereof can serve as a marker for lung cancer (Patent Literature 1).

The 282nd target gene is the hsa-miR-6848-5p gene, a congener thereof, a transcript thereof, or a variant or a derivative thereof. The previously known report shows that change in the expression of the gene or the transcript thereof can serve as a marker for lung cancer (Patent Literature 1).

The 283rd target gene is the hsa-miR-6851-5p gene, a congener thereof, a transcript thereof, or a variant or a derivative thereof. The previously known report shows that change in the expression of the gene or the transcript thereof can serve as a marker for lung cancer (Patent Literature 1).

The 284th target gene is the hsa-miR-6870-5p gene, a congener thereof, a transcript thereof, or a variant or a derivative thereof. The previously known report shows that change in the expression of the gene or the transcript thereof can serve as a marker for lung cancer (Patent Literature 1).

The 285th target gene is the hsa-miR-6872-3p gene, a congener thereof, a transcript thereof, or a variant or a derivative thereof. The previously known report shows that change in the expression of the gene or the transcript thereof can serve as a marker for lung cancer (Patent Literature 1).

The 286th target gene is the hsa-miR-6875-5p gene, a congener thereof, a transcript thereof, or a variant or a derivative thereof. The previously known report shows that change in the expression of the gene or the transcript thereof can serve as a marker for lung cancer (Patent Literature 1).

The 287th target gene is the hsa-miR-6877-5p gene, a congener thereof, a transcript thereof, or a variant or a derivative thereof. The previously known report shows that change in the expression of the gene or the transcript thereof can serve as a marker for lung cancer (Patent Literature 1).

The 288th target gene is the hsa-miR-6879-5p gene, a congener thereof, a transcript thereof, or a variant or a derivative thereof. The previously known report shows that change in the expression of the gene or the transcript thereof can serve as a marker for lung cancer (Patent Literature 1).

The 289th target gene is the hsa-miR-6880-5p gene, a congener thereof, a transcript thereof, or a variant or a derivative thereof. The previously known report shows that change in the expression of the gene or the transcript thereof can serve as a marker for lung cancer (Patent Literature 1).

The 290th target gene is the hsa-miR-6885-5p gene, a congener thereof, a transcript thereof, or a variant or a derivative thereof. The previously known report shows that change in the expression of the gene or the transcript thereof can serve as a marker for lung cancer (Patent Literature 1).

The 291st target gene is the hsa-miR-6887-5p gene, a congener thereof, a transcript thereof, or a variant or a derivative thereof. The previously known report shows that change in the expression of the gene or the transcript thereof can serve as a marker for lung cancer (Patent Literature 1).

The 292nd target gene is the hsa-miR-7108-5p gene, a congener thereof, a transcript thereof, or a variant or a derivative thereof. The previously known report shows that change in the expression of the gene or the transcript thereof can serve as a marker for lung cancer (Patent Literature 1).

The 293rd target gene is the hsa-miR-711 gene, a congener thereof, a transcript thereof, or a variant or a derivative thereof. The previously known report shows that change in the expression of the gene or the transcript thereof can serve as a marker for lung cancer (Patent Literature 1).

The 294th target gene is the hsa-miR-7113-3p gene, a congener thereof, a transcript thereof, or a variant or a derivative thereof. The previously known report shows that change in the expression of the gene or the transcript thereof can serve as a marker for lung cancer (Patent Literature 1).

The 295th target gene is the hsa-miR-744-5p gene, a congener thereof, a transcript thereof, or a variant or a derivative thereof. The previously known report shows that change in the expression of the gene or the transcript thereof can serve as a marker for lung cancer (Patent Literature 5).

The 296th target gene is the hsa-miR-760 gene, a congener thereof, a transcript thereof, or a variant or a derivative thereof. The previously known report shows that change in the expression of the gene or the transcript thereof can serve as a marker for lung cancer (Patent Literature 1).

The 297th target gene is the hsa-miR-7845-5p gene, a congener thereof, a transcript thereof, or a variant or a derivative thereof. The previously known report shows that change in the expression of the gene or the transcript thereof can serve as a marker for lung cancer (Patent Literature 1).

The 298th target gene is the hsa-miR-7847-3p gene, a congener thereof, a transcript thereof, or a variant or a derivative thereof. The previously known report shows that change in the expression of the gene or the transcript thereof can serve as a marker for lung cancer (Patent Literature 1).

The 299th target gene is the hsa-miR-7977 gene, a congener thereof, a transcript thereof, or a variant or a derivative thereof. The previously known report shows that change in the expression of the gene or the transcript thereof can serve as a marker for lung cancer (Patent Literature 1).

The 300th target gene is the hsa-miR-8059 gene, a congener thereof, a transcript thereof, or a variant or a derivative thereof. The previously known report shows that change in the expression of the gene or the transcript thereof can serve as a marker for lung cancer (Patent Literature 1).

The 301st target gene is the hsa-miR-8063 gene, a congener thereof, a transcript thereof, or a variant or a derivative thereof. The previously known report shows that change in the expression of the gene or the transcript thereof can serve as a marker for lung cancer (Patent Literature 1).

The 302nd target gene is the hsa-miR-8072 gene, a congener thereof, a transcript thereof, or a variant or a derivative thereof. The previously known report shows that change in the expression of the gene or the transcript thereof can serve as a marker for lung cancer (Patent Literature 1).

The 303rd target gene is the hsa-miR-874-3p gene, a congener thereof, a transcript thereof, or a variant or a derivative thereof. The previously known report shows that change in the expression of the gene or the transcript thereof can serve as a marker for lung cancer (Patent Literature 5).

The 304th target gene is the hsa-miR-92a-2-5p gene, a congener thereof, a transcript thereof, or a variant or a derivative thereof. The previously known report shows that change in the expression of the gene or the transcript thereof can serve as a marker for lung cancer (Patent Literature 1).

The 305th target gene is the hsa-miR-92b-5p gene, a congener thereof, a transcript thereof, or a variant or a derivative thereof. The previously known report shows that change in the expression of the gene or the transcript thereof can serve as a marker for lung cancer (Patent Literature 1).

The 306th target gene is the hsa-miR-940 gene, a congener thereof, a transcript thereof, or a variant or a derivative thereof. The previously known report shows that change in the expression of the gene or the transcript thereof can serve as a marker for lung cancer (Patent Literature 1).

The 307th target gene is the hsa-miR-1228-3p gene, a congener thereof, a transcript thereof, or a variant or a derivative thereof. The previously known report shows that change in the expression of the gene or the transcript thereof can serve as a marker for lung cancer (Patent Literature 1).

The 308th target gene is the hsa-miR-1275 gene, a congener thereof, a transcript thereof, or a variant or a derivative thereof. The previously known report shows that change in the expression of the gene or the transcript thereof can serve as a marker for lung cancer (Patent Literature 5).

The 309th target gene is the hsa-miR-1307-3p gene, a congener thereof, a transcript thereof, or a variant or a derivative thereof. The previously known report shows that change in the expression of the gene or the transcript thereof can serve as a marker for lung cancer (Patent Literature 1).

The 310th target gene is the hsa-miR-1343-5p gene, a congener thereof, a transcript thereof, or a variant or a derivative thereof. The previously known report shows that change in the expression of the gene or the transcript thereof can serve as a marker for lung cancer (Patent Literature 1).

The 311th target gene is the hsa-miR-23a-3p gene, a congener thereof, a transcript thereof, or a variant or a derivative thereof. The previously known report shows that change in the expression of the gene or the transcript thereof can serve as a marker for lung cancer (Patent Literature 2).

The 312th target gene is the hsa-miR-29b-3p gene, a congener thereof, a transcript thereof, or a variant or a derivative thereof. The previously known report shows that change in the expression of the gene or the transcript thereof can serve as a marker for lung cancer (Patent Literature 2).

The 313th target gene is the hsa-miR-3135b gene, a congener thereof, a transcript thereof, or a variant or a derivative thereof. The previously known report shows that change in the expression of the gene or the transcript thereof can serve as a marker for lung cancer (Patent Literature 1).

The 314th target gene is the hsa-miR-3185 gene, a congener thereof, a transcript thereof, or a variant or a derivative thereof. The previously known report shows that change in the expression of the gene or the transcript thereof can serve as a marker for lung cancer (Patent Literature 1).

The 315th target gene is the hsa-miR-4532 gene, a congener thereof, a transcript thereof, or a variant or a derivative thereof. The previously known report shows that change in the expression of the gene or the transcript thereof can serve as a marker for lung cancer (Patent Literature 1).

The 316th target gene is the hsa-miR-4690-5p gene, a congener thereof, a transcript thereof, or a variant or a derivative thereof. The previously known report shows that change in the expression of the gene or the transcript thereof can serve as a marker for lung cancer (Patent Literature 1).

The 317th target gene is the hsa-miR-4758-5p gene, a congener thereof, a transcript thereof, or a variant or a derivative thereof. The previously known report shows that change in the expression of the gene or the transcript thereof can serve as a marker for lung cancer (Patent Literature 1).

The 318th target gene is the hsa-miR-4783-3p gene, a congener thereof, a transcript thereof, or a variant or a derivative thereof. The previously known report shows that change in the expression of the gene or the transcript thereof can serve as a marker for lung cancer (Patent Literature 1).

The 319th target gene is the hsa-miR-6131 gene, a congener thereof, a transcript thereof, or a variant or a derivative thereof. The previously known report shows that change in the expression of the gene or the transcript thereof can serve as a marker for lung cancer (Patent Literature 1).

The 320th target gene is the hsa-miR-625-3p gene, a congener thereof, a transcript thereof, or a variant or a derivative thereof. The previously known report shows that change in the expression of the gene or the transcript thereof can serve as a marker for lung cancer (Patent Literature 4).

The 321st target gene is the hsa-miR-65111a-5p gene, a congener thereof, a transcript thereof, or a variant or a derivative thereof. The previously known report shows that change in the expression of the gene or the transcript thereof can serve as a marker for lung cancer (Patent Literature 1).

The 322nd target gene is the hsa-miR-6765-3p gene, a congener thereof, a transcript thereof, or a variant or a derivative thereof. The previously known report shows that change in the expression of the gene or the transcript thereof can serve as a marker for lung cancer (Patent Literature 1).

The 323rd target gene is the hsa-miR-6816-5p gene, a congener thereof, a transcript thereof, or a variant or a derivative thereof. The previously known report shows that change in the expression of the gene or the transcript thereof can serve as a marker for lung cancer (Patent Literature 1).

The 324th target gene is the hsa-miR-6825-5p gene, a congener thereof, a transcript thereof, or a variant or a derivative thereof. The previously known report shows that change in the expression of the gene or the transcript thereof can serve as a marker for lung cancer (Patent Literature 1).

The 325th target gene is the hsa-miR-6845-5p gene, a congener thereof, a transcript thereof, or a variant or a derivative thereof. The previously known report shows that change in the expression of the gene or the transcript thereof can serve as a marker for lung cancer (Patent Literature 1).

The 326th target gene is the hsa-miR-7150 gene, a congener thereof, a transcript thereof, or a variant or a derivative thereof. The previously known report shows that change in the expression of the gene or the transcript thereof can serve as a marker for lung cancer (Patent Literature 1).

The 327th target gene is the hsa-miR-7641 gene, a congener thereof, a transcript thereof, or a variant or a derivative thereof. The previously known report shows that change in the expression of the gene or the transcript thereof can serve as a marker for lung cancer (Patent Literature 1).

The 328th target gene is the hsa-miR-7975 gene, a congener thereof, a transcript thereof, or a variant or a derivative thereof. The previously known report shows that change in the expression of the gene or the transcript thereof can serve as a marker for lung cancer (Patent Literature 1).

The 329th target gene is the hsa-miR-92a-3p gene, a congener thereof, a transcript thereof, or a variant or a derivative thereof. The previously known report shows that change in the expression of the gene or the transcript thereof can serve as a marker for lung cancer (Patent Literature 1).

In one aspect, the present invention relates to a marker containing at least one of the target nucleic acids described above for detecting lung cancer or for diagnosing lung cancer.

In one aspect, the present invention relates to use of at least one of the target nucleic acids described above for detecting lung cancer or for diagnosing lung cancer.

2. Nucleic Acid for Detection of Lung Cancer

In the present invention, the nucleic acids for detecting lung cancer, e.g., nucleic acid probes or primers that can be used for diagnosing lung cancer enable qualitative and/or quantitative measurement of the presence, expression levels, or existing amounts (abundance) of: human-derived miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR- 4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-1191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, as target nucleic acids for lung cancer, or combinations thereof, congeners thereof, transcripts thereof, or variants or derivatives thereof.

The expression levels of the target nucleic acids described above are increased or decreased (hereinafter, referred to as "increased/decreased") depending on the types of the target nucleic acids in subjects having lung cancer as compared with healthy subjects, benign bone and soft tissue tumor patients and benign breast disease patients, and subjects having a cancer other than lung cancer. Hence, the kit or device of the present invention can be effectively used for measuring expression levels of the target nucleic acids in body fluids from subjects (e.g., humans) suspected of having lung cancer and body fluids from healthy subjects, benign bone and soft tissue tumor patients and benign breast disease patients (or diseased animals), and patients (or cancer animals) having a cancer other than lung cancer, and thereby detecting lung cancer through the comparison thereof.

The nucleic acid probe or primer(s) that can be used in the present invention is, for example, a nucleic acid probe capable of specifically binding to a polynucleotide consisting of a nucleotide sequence represented by at least one of SEQ ID NOs: 1 to 163; or a primer(s) for amplifying a polynucleotide consisting of a nucleotide sequence represented by at least one of SEQ ID NOs: 1 to 163.

The nucleic acid probe or primer(s) that can be used in the present invention may further comprise, for example, a nucleic acid probe capable of specifically binding to a polynucleotide consisting of a nucleotide sequence represented by at least one of SEQ ID NOs: 164 to 329; or a primer(s) for amplifying a polynucleotide consisting of a nucleotide sequence represented by at least one of SEQ ID NOs: 164 to 329.

In a preferred embodiment of the present invention, specifically, these nucleic acid probes or primers comprise a combination of one or more polynucleotides selected from: a group of polynucleotides comprising nucleotide sequences represented by any of SEQ ID NOs: 1 to 1000, or the nucleotide sequences in which the nucleic acid u is replaced with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides and being from the nucleotide sequences of these polynucleotide groups. These polynucleotides can be used as nucleic acid probes and primers for detecting the lung cancer markers as target nucleic acids.

More specifically, examples of the nucleic acid probes or primers that can be used in the present invention include one or more polynucleotides selected from the group consisting of the following polynucleotides (a) to (e):

(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163, or a nucleotide sequence derived from the nucleotide sequence in which the nucleic acid u is replaced with t; and (e) a polynucleotide hybridizing under stringent conditions to any of the polynucleotides (a) to (d).

In addition to at least one polynucleotide selected from any of the polynucleotides (a) to (e), the nucleic acid probes or the primers that can be used in the present invention may further comprise any of the following polynucleotides (f) to (j):

(f) a polynucleotide consisting of a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329, or a nucleotide sequence derived from the nucleotide sequence in which the nucleic acid u is replaced with t; and (j) a polynucleotide hybridizing under stringent conditions to any of the polynucleotides (f) to (i).

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p represented by SEQ ID NOs: 1 to 329 are known, and methods to obtain them are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA in length of up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 329 do not exist as miRNAs or precursors thereof in the living body or in vivo. For example, the nucleotide sequences represented by SEQ ID NO: 142 and SEQ ID NO: 46 are produced from the precursor represented by SEQ ID NO: 382. This precursor has a hairpin-like structure as shown in FIG. 1, and the nucleotide sequences represented by SEQ ID NO: 142 and SEQ ID NO: 46 have mismatch sequences with each other. As such, a nucleotide sequence completely complementary to the nucleotide sequence represented by SEQ ID NO: 142 or SEQ ID NO: 46 does not naturally occur in vivo. Therefore, the nucleic acid probes and the primers for detecting the nucleotide sequence represented by any of SEQ ID NOs: 1 to 329 can have artificial nucleotide sequences that do not exist in the living body or in vivo.

3. Kit or Device for Detection of Lung Cancer

The present invention also provides a kit or a device for detecting lung cancer, comprising one or more polynucleotides (which may include a variant, a fragment, or a derivative thereof) that can be used as nucleic acid probes or primers in the present invention for measuring target nucleic acids as lung cancer markers.

The target nucleic acids as lung cancer markers according to the present invention are preferably selected from the following group A:

Group A:
miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p.

Additional target nucleic acids that may be optionally used in the measurement are preferably selected from the following group B:

Group B:
miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p.

The kit or the device of the present invention comprises one or more nucleic acids capable of specifically binding to any of the target nucleic acids as the lung cancer markers described above or nucleic acids for detecting the target nucleic acids, preferably one or more polynucleotides selected from the polynucleotides described in the preceding Section 2, or variants thereof.

Specifically, the kit or the device of the present invention can comprise at least one polynucleotide comprising (or consisting of), for example, a nucleotide sequence represented by any of SEQ ID NOs: 1 to 163, or a nucleotide sequence derived from the nucleotide sequence in which the nucleic acid u is replaced with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more polynucleotides comprising (or consisting of), for example, a nucleotide sequence represented by any of SEQ ID NOs: 164 to 329, or a nucleotide sequence derived from the nucleotide sequence in which the nucleic acid u is replaced with t, a polynucleotide(s) comprising (or consisting of) a complementary sequence thereof, a polynucleotide(s) hybridizing under stringent conditions to any of these polynucleotides, a variant(s) or a fragment(s) comprising 15 or more consecutive nucleotides of any of these polynucleotide sequences.

The fragment or fragments that can be comprised in the kit or the device of the present invention is/are, for example, one or more polynucleotides, preferably two or more polynucleotides, selected from the group consisting of the following polynucleotides (1) and (2):

(1) a polynucleotide comprising 15 or more consecutive nucleotides derived from a nucleotide sequence represented by any of SEQ ID NOs: 1 to 163 in which the nucleic acid u is replaced with t, or a complementary sequence thereof; and (2) a polynucleotide comprising 15 or more consecutive nucleotides derived from a nucleotide sequence represented by any of SEQ ID NOs: 164 to 329 in which the nucleic acid u is replaced with t, or a complementary sequence thereof.

In a preferred embodiment, the polynucleotide is a polynucleotide consisting of a nucleotide sequence represented by any of SEQ ID NOs: 1 to 163, or a nucleotide sequence derived from the nucleotide sequence in which the nucleic acid u is replaced with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 164 to 329, or a nucleotide sequence derived from the nucleotide sequence in which the nucleic acid u is replaced with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Examples of the combination of the above-mentioned polynucleotides as target nucleic acids in the kit or the device of the present invention can include a single (one) polynucleotide or combinations of 2, 3, 4, 5, 6, 7, 8, 9, 10 or more of the above-mentioned polynucleotides consisting of the nucleotide sequences represented by SEQ ID NOs: 1 to 329 as shown in Table 1 above. However, these are given merely for illustrative purposes, and all of various other possible combinations are included in the present invention.

Examples of the combinations of target nucleic acids in the kit or the device for discriminating lung cancer patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1.

For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected. Among them, particularly, a combination comprising at least one polynucleotide selected from the group consisting of the polynucleotides of SEQ ID NOs: 18, 4, 130, 2, 9, 17, and 121 (hereinafter, this group is referred to as "cancer type-specific polynucleotide group") is more preferred.

Non-limiting examples of the combination comprising the polynucleotide consisting of the nucleotide sequence represented by SEQ ID NO: 18 or a complementary sequence thereof are listed below as combinations of target nucleic acids:

(1) a combination of SEQ ID NOs: 18, and 164;
(2) a combination of SEQ ID NOs: 18, 164, and 255;
(3) a combination of SEQ ID NOs: 18, 164, and 300;
(4) a combination of SEQ ID NOs: 18, 164, and 190;
(5) a combination of SEQ ID NOs: 18, 85, and 164;
(6) a combination of SEQ ID NOs: 18, 147, and 164;
(7) a combination of SEQ ID NOs: 18, 22, and 164;
(8) a combination of SEQ ID NOs: 18, 164, and 312;
(9) a combination of SEQ ID NOs: 18, 66, and 164;
(10) a combination of SEQ ID NOs: 18, 78, and 164;
(11) a combination of SEQ ID NOs: 18, 27, and 164;
(12) a combination of SEQ ID NOs: 18, 164, and 207;
(13) a combination of SEQ ID NOs: 18, 82, and 164;
(14) a combination of SEQ ID NOs: 18, 164, and 263;
(15) a combination of SEQ ID NOs: 18, 164, and 168;
(16) a combination of SEQ ID NOs: 18, 34, and 164;
(17) a combination of SEQ ID NOs: 18, 39, and 164;
(18) a combination of SEQ ID NOs: 18, 57, and 164;
(19) a combination of SEQ ID NOs: 18, 121, and 164;
(20) a combination of SEQ ID NOs: 18, 107, and 164;
(21) a combination of SEQ ID NOs: 18, 70, and 164;
(22) a combination of SEQ ID NOs: 18, 50, and 164;
(23) a combination of SEQ ID NOs: 18, 164, and 250;
(24) a combination of SEQ ID NOs: 18, 164, and 315;
(25) a combination of SEQ ID NOs: 18, 164, and 211;
(26) a combination of SEQ ID NOs: 18, 164, and 326;
(27) a combination of SEQ ID NOs: 18, 164, and 308;
(28) a combination of SEQ ID NOs: 18, 164, and 268;
(29) a combination of SEQ ID NOs: 18, 164, and 191;
(30) a combination of SEQ ID NOs: 18, 149, and 165;
(31) a combination of SEQ ID NOs: 18, 121, 130, and 164;
(32) a combination of SEQ ID NOs: 18, 164, 255, and 316;
(33) a combination of SEQ ID NOs: 18, 121, 164, and 255;
(34) a combination of SEQ ID NOs: 18, 147, 164, and 255;
(35) a combination of SEQ ID NOs: 18, 27, 164, and 255;
(36) a combination of SEQ ID NOs: 18, 34, 164, and 255;
(37) a combination of SEQ ID NOs: 18, 47, 164, and 255;
(38) a combination of SEQ ID NOs: 18, 158, 164, and 255;
(39) a combination of SEQ ID NOs: 18, 164, 220, and 255;
(40) a combination of SEQ ID NOs: 18, 88, 164, and 255;
(41) a combination of SEQ ID NOs: 18, 130, 164, and 268;
(42) a combination of SEQ ID NOs: 18, 164, 255, and 321;

(43) a combination of SEQ ID NOs: 18, 164, 184, and 255;
(44) a combination of SEQ ID NOs: 18, 152, 164, and 255;
(45) a combination of SEQ ID NOs: 18, 164, 185, and 255;
(46) a combination of SEQ ID NOs: 18, 164, 238, and 255;
(47) a combination of SEQ ID NOs: 18, 164, 255, and 256;
(48) a combination of SEQ ID NOs: 18, 127, 164, and 255;
(49) a combination of SEQ ID NOs: 18, 164, 222, and 255;
(50) a combination of SEQ ID NOs: 18, 139, 164, and 255;
(51) a combination of SEQ ID NOs: 18, 39, 164, and 255;
(52) a combination of SEQ ID NOs: 18, 164, 255, and 295;
(53) a combination of SEQ ID NOs: 18, 146, 164, and 255;
(54) a combination of SEQ ID NOs: 18, 164, 211, and 255;
(55) a combination of SEQ ID NOs: 18, 164, 255, and 322;
(56) a combination of SEQ ID NOs: 18, 164, 255, and 318;
(57) a combination of SEQ ID NOs: 18, 121, 164, and 201;
(58) a combination of SEQ ID NOs: 18, 147, 164, and 300;
(59) a combination of SEQ ID NOs: 18, 121, 151, and 164;
(60) a combination of SEQ ID NOs: 18, 164, 211, and 300;
(61) a combination of SEQ ID NOs: 18, 95, 164, and 268;
(62) a combination of SEQ ID NOs: 18, 164, 231, and 268;
(63) a combination of SEQ ID NOs: 18, 147, 164, and 268;
(64) a combination of SEQ ID NOs: 18, 164, 188, and 268;
(65) a combination of SEQ ID NOs: 18, 164, 268, and 312;
(66) a combination of SEQ ID NOs: 18, 39, 164, and 300;
(67) a combination of SEQ ID NOs: 18, 95, 121, and 164;
(68) a combination of SEQ ID NOs: 18, 93, 164, and 268;
(69) a combination of SEQ ID NOs: 18, 164, 268, and 308;
(70) a combination of SEQ ID NOs: 18, 107, 121, and 164;
(71) a combination of SEQ ID NOs: 18, 164, 218, and 268;
(72) a combination of SEQ ID NOs: 18, 164, 202, and 268;
(73) a combination of SEQ ID NOs: 13, 18, 130, and 165;
(74) a combination of SEQ ID NOs: 18, 149, 165, and 168;
(75) a combination of SEQ ID NOs: 18, 164, 242, and 268;
(76) a combination of SEQ ID NOs: 18, 164, 214, and 268;
(77) a combination of SEQ ID NOs: 18, 164, 268, and 313;
(78) a combination of SEQ ID NOs: 18, 162, 164, and 268;
(79) a combination of SEQ ID NOs: 18, 150, 164, and 268;
(80) a combination of SEQ ID NOs: 18, 164, 268, and 315;
(81) a combination of SEQ ID NOs: 18, 152, 164, and 268;
(82) a combination of SEQ ID NOs: 18, 164, 268, and 325;
(83) a combination of SEQ ID NOs: 18, 121, 149, and 165;
(84) a combination of SEQ ID NOs: 13, 18, 165, and 260;
(85) a combination of SEQ ID NOs: 13, 18, 165, and 268;
(86) a combination of SEQ ID NOs: 13, 18, 121, and 165;
(87) a combination of SEQ ID NOs: 13, 18, 165, and 168;
(88) a combination of SEQ ID NOs: 18, 149, 165, and 268;
(89) a combination of SEQ ID NOs: 13, 18, 83, and 165;
(90) a combination of SEQ ID NOs: 13, 18, 165, and 263;
(91) a combination of SEQ ID NOs: 2, 18, 165, and 268;
(92) a combination of SEQ ID NOs: 13, 18, 165, and 211;
(93) a combination of SEQ ID NOs: 13, 18, 165, and 256;
(94) a combination of SEQ ID NOs: 13, 18, 165, and 276;
(95) a combination of SEQ ID NOs: 13, 18, 165, and 302;
(96) a combination of SEQ ID NOs: 13, 18, 165, and 190;
(97) a combination of SEQ ID NOs: 18, 121, 130, 136, and 164;
(98) a combination of SEQ ID NOs: 18, 121, 130, 164, and 314;
(99) a combination of SEQ ID NOs: 18, 114, 121, 130, and 164;
(100) a combination of SEQ ID NOs: 18, 121, 130, 164, and 214;
(101) a combination of SEQ ID NOs: 18, 121, 130, 164, and 193;
(102) a combination of SEQ ID NOs: 18, 130, 164, 255, and 268;
(103) a combination of SEQ ID NOs: 18, 121, 130, 164, and 320;
(104) a combination of SEQ ID NOs: 18, 121, 130, 164, and 301;
(105) a combination of SEQ ID NOs: 18, 121, 130, 144, and 164;
(106) a combination of SEQ ID NOs: 18, 121, 130, 164, and 168;
(107) a combination of SEQ ID NOs: 18, 121, 130, 164, and 205;
(108) a combination of SEQ ID NOs: 18, 121, 130, 158, and 164;
(109) a combination of SEQ ID NOs: 18, 121, 130, 164, and 260;
(110) a combination of SEQ ID NOs: 18, 106, 121, 130, and 164;
(111) a combination of SEQ ID NOs: 18, 121, 130, 164, and 318;
(112) a combination of SEQ ID NOs: 18, 121, 130, 164, and 286;
(113) a combination of SEQ ID NOs: 18, 121, 130, 164, and 315;
(114) a combination of SEQ ID NOs: 18, 121, 130, 164, and 237;
(115) a combination of SEQ ID NOs: 18, 121, 130, 164, and 184;
(116) a combination of SEQ ID NOs: 18, 121, 130, 164, and 270;
(117) a combination of SEQ ID NOs: 18, 121, 130, 164, and 309;

(118) a combination of SEQ ID NOs: 18, 121, 130, 164, and 278;
(119) a combination of SEQ ID NOs: 18, 82, 121, 130, and 164;
(120) a combination of SEQ ID NOs: 18, 23, 121, 130, and 164;
(121) a combination of SEQ ID NOs: 18, 121, 130, 164, and 189;
(122) a combination of SEQ ID NOs: 18, 121, 130, 152, and 164;
(123) a combination of SEQ ID NOs: 18, 121, 130, 164, and 213;
(124) a combination of SEQ ID NOs: 18, 121, 130, 164, and 229;
(125) a combination of SEQ ID NOs: 18, 57, 121, 130, and 164;
(126) a combination of SEQ ID NOs: 18, 121, 130, 142, and 164;
(127) a combination of SEQ ID NOs: 18, 121, 130, 155, and 164;
(128) a combination of SEQ ID NOs: 18, 39, 121, 130, and 164;
(129) a combination of SEQ ID NOs: 18, 27, 130, 164, and 268;
(130) a combination of SEQ ID NOs: 18, 33, 121, 130, and 164;
(131) a combination of SEQ ID NOs: 18, 121, 126, 130, and 164;
(132) a combination of SEQ ID NOs: 18, 121, 130, 164, and 319;
(133) a combination of SEQ ID NOs: 18, 22, 121, 130, and 164;
(134) a combination of SEQ ID NOs: 18, 59, 121, 130, and 164;
(135) a combination of SEQ ID NOs: 18, 27, 121, 130, and 164;
(136) a combination of SEQ ID NOs: 18, 130, 164, 268, and 317;
(137) a combination of SEQ ID NOs: 18, 121, 130, 164, and 201;
(138) a combination of SEQ ID NOs: 18, 34, 164, 211, and 255;
(139) a combination of SEQ ID NOs: 18, 19, 121, 130, and 164;
(140) a combination of SEQ ID NOs: 18, 74, 130, 164, and 268;
(141) a combination of SEQ ID NOs: 18, 130, 164, 264, and 268;
(142) a combination of SEQ ID NOs: 18, 39, 164, 255, and 328;
(143) a combination of SEQ ID NOs: 18, 39, 164, 226, and 255;
(144) a combination of SEQ ID NOs: 18, 95, 121, 164, and 188;
(145) a combination of SEQ ID NOs: 13, 18, 121, 130, and 165;
(146) a combination of SEQ ID NOs: 13, 18, 130, 165, and 268;
(147) a combination of SEQ ID NOs: 18, 151, 164, 268, and 315;
(148) a combination of SEQ ID NOs: 18, 147, 164, 184, and 268;
(149) a combination of SEQ ID NOs: 18, 149, 165, 168, and 268;
(150) a combination of SEQ ID NOs: 13, 18, 165, 268, and 276;
(151) a combination of SEQ ID NOs: 2, 18, 165, 268, and 301;
(152) a combination of SEQ ID NOs: 2, 18, 165, 268, and 315;
(153) a combination of SEQ ID NOs: 13, 18, 165, 183, and 268; and
(154) a combination of SEQ ID NOs: 13, 18, 165, 184, and 268.

Non-limiting examples of the combination comprising the polynucleotide consisting of the nucleotide sequence represented by SEQ ID NO: 4 or a complementary sequence thereof are further listed below as combinations of target nucleic acids:

(1) a combination of SEQ ID NOs: 4, and 164;
(2) a combination of SEQ ID NOs: 4, 165, and 168;
(3) a combination of SEQ ID NOs: 4, 165, 168, and 246;
(4) a combination of SEQ ID NOs: 4, 128, 165, and 168;
(5) a combination of SEQ ID NOs: 4, 117, 165, and 168;
(6) a combination of SEQ ID NOs: 4, 159, 165, and 168;
(7) a combination of SEQ ID NOs: 4, 165, 168, and 260;
(8) a combination of SEQ ID NOs: 4, 17, 165, and 168;
(9) a combination of SEQ ID NOs: 4, 165, 168, and 173;
(10) a combination of SEQ ID NOs: 4, 80, 165, and 168;
(11) a combination of SEQ ID NOs: 4, 99, 165, and 168;
(12) a combination of SEQ ID NOs: 2, 4, 168, and 246;
(13) a combination of SEQ ID NOs: 4, 17, 115, and 168;
(14) a combination of SEQ ID NOs: 4, 17, 115, and 302;
(15) a combination of SEQ ID NOs: 4, 94, 173, and 183;
(16) a combination of SEQ ID NOs: 2, 4, 173, and 183;
(17) a combination of SEQ ID NOs: 2, 4, 115, and 168;
(18) a combination of SEQ ID NOs: 4, 17, 115, and 184;
(19) a combination of SEQ ID NOs: 4, 17, 165, 168, and 173;
(20) a combination of SEQ ID NOs: 4, 17, 165, 168, and 223;
(21) a combination of SEQ ID NOs: 4, 128, 129, 165, and 168;
(22) a combination of SEQ ID NOs: 2, 4, 130, 168, and 246;
(23) a combination of SEQ ID NOs: 4, 17, 128, 165, and 168;
(24) a combination of SEQ ID NOs: 4, 17, 165, 168, and 169;
(25) a combination of SEQ ID NOs: 4, 17, 117, 165, and 168;
(26) a combination of SEQ ID NOs: 4, 17, 165, 168, and 323;
(27) a combination of SEQ ID NOs: 4, 17, 81, 165, and 168;
(28) a combination of SEQ ID NOs: 4, 17, 165, 168, and 253;
(29) a combination of SEQ ID NOs: 4, 17, 162, 165, and 168;
(30) a combination of SEQ ID NOs: 2, 4, 168, 201, and 246;
(31) a combination of SEQ ID NOs: 4, 17, 141, 165, and 168;
(32) a combination of SEQ ID NOs: 4, 17, 129, 165, and 168;
(33) a combination of SEQ ID NOs: 4, 17, 165, 168, and 258;
(34) a combination of SEQ ID NOs: 4, 17, 165, 168, and 190;
(35) a combination of SEQ ID NOs: 4, 17, 115, 168, and 177;
(36) a combination of SEQ ID NOs: 4, 17, 165, 168, and 191;

(37) a combination of SEQ ID NOs: 4, 17, 158, 165, and 168;
(38) a combination of SEQ ID NOs: 4, 17, 165, 168, and 184;
(39) a combination of SEQ ID NOs: 4, 17, 94, 165, and 168;
(40) a combination of SEQ ID NOs: 4, 17, 165, 168, and 296;
(41) a combination of SEQ ID NOs: 4, 17, 165, 168, and 307;
(42) a combination of SEQ ID NOs: 4, 17, 123, 165, and 168;
(43) a combination of SEQ ID NOs: 4, 17, 39, 165, and 168;
(44) a combination of SEQ ID NOs: 4, 17, 145, 165, and 168;
(45) a combination of SEQ ID NOs: 4, 17, 165, 168, and 286;
(46) a combination of SEQ ID NOs: 4, 17, 73, 165, and 168;
(47) a combination of SEQ ID NOs: 4, 17, 115, 165, and 168;
(48) a combination of SEQ ID NOs: 4, 17, 108, 165, and 168;
(49) a combination of SEQ ID NOs: 4, 17, 156, 165, and 168;
(50) a combination of SEQ ID NOs: 4, 17, 165, 168, and 249;
(51) a combination of SEQ ID NOs: 4, 17, 131, 165, and 168;
(52) a combination of SEQ ID NOs: 4, 17, 165, 168, and 304;
(53) a combination of SEQ ID NOs: 4, 17, 157, 165, and 168;
(54) a combination of SEQ ID NOs: 4, 17, 165, 168, and 318;
(55) a combination of SEQ ID NOs: 4, 17, 74, 165, and 168;
(56) a combination of SEQ ID NOs: 4, 17, 165, 168, and 216;
(57) a combination of SEQ ID NOs: 4, 17, 165, 168, and 309;
(58) a combination of SEQ ID NOs: 4, 17, 165, 168, and 236;
(59) a combination of SEQ ID NOs: 4, 17, 165, 168, and 324;
(60) a combination of SEQ ID NOs: 2, 4, 111, 168, and 173;
(61) a combination of SEQ ID NOs: 4, 17, 115, 130, and 168;
(62) a combination of SEQ ID NOs: 2, 4, 130, 168, and 173;
(63) a combination of SEQ ID NOs: 4, 17, 111, 115, and 168;
(64) a combination of SEQ ID NOs: 2, 4, 168, 173, and 201;
(65) a combination of SEQ ID NOs: 4, 17, 115, 160, and 168;
(66) a combination of SEQ ID NOs: 4, 17, 115, 168, and 246;
(67) a combination of SEQ ID NOs: 2, 4, 115, 168, and 173;
(68) a combination of SEQ ID NOs: 4, 17, 115, 168, and 201;
(69) a combination of SEQ ID NOs: 4, 17, 115, 168, and 217;
(70) a combination of SEQ ID NOs: 2, 4, 17, 115, and 168;
(71) a combination of SEQ ID NOs: 4, 17, 115, 140, and 168; and
(72) a combination of SEQ ID NOs: 4, 17, 102, 115, and 168.

Non-limiting examples of the combination comprising the polynucleotide consisting of the nucleotide sequence represented by SEQ ID NO: 130 or a complementary sequence thereof are further listed below as combinations of target nucleic acids:
(1) a combination of SEQ ID NOs: 121, 130, and 164;
(2) a combination of SEQ ID NOs: 18, 121, 130, and 164;
(3) a combination of SEQ ID NOs: 18, 130, 164, and 268;
(4) a combination of SEQ ID NOs: 13, 18, 130, and 165;
(5) a combination of SEQ ID NOs: 18, 121, 130, 136, and 164;
(6) a combination of SEQ ID NOs: 18, 121, 130, 164, and 314;
(7) a combination of SEQ ID NOs: 18, 114, 121, 130, and 164;
(8) a combination of SEQ ID NOs: 18, 121, 130, 164, and 214;
(9) a combination of SEQ ID NOs: 18, 121, 130, 164, and 193;
(10) a combination of SEQ ID NOs: 18, 130, 164, 255, and 268;
(11) a combination of SEQ ID NOs: 18, 121, 130, 164, and 320;
(12) a combination of SEQ ID NOs: 18, 121, 130, 164, and 301;
(13) a combination of SEQ ID NOs: 18, 121, 130, 144, and 164;
(14) a combination of SEQ ID NOs: 18, 121, 130, 164, and 168;
(15) a combination of SEQ ID NOs: 18, 121, 130, 164, and 205;
(16) a combination of SEQ ID NOs: 18, 121, 130, 158, and 164;
(17) a combination of SEQ ID NOs: 18, 121, 130, 164, and 260;
(18) a combination of SEQ ID NOs: 18, 106, 121, 130, and 164;
(19) a combination of SEQ ID NOs: 18, 121, 130, 164, and 318;
(20) a combination of SEQ ID NOs: 18, 121, 130, 164, and 286;
(21) a combination of SEQ ID NOs: 18, 121, 130, 164, and 315;
(22) a combination of SEQ ID NOs: 18, 121, 130, 164, and 237;
(23) a combination of SEQ ID NOs: 18, 121, 130, 164, and 184;
(24) a combination of SEQ ID NOs: 18, 121, 130, 164, and 270;
(25) a combination of SEQ ID NOs: 18, 121, 130, 164, and 309;
(26) a combination of SEQ ID NOs: 18, 121, 130, 164, and 278;
(27) a combination of SEQ ID NOs: 18, 82, 121, 130, and 164;
(28) a combination of SEQ ID NOs: 18, 23, 121, 130, and 164;
(29) a combination of SEQ ID NOs: 18, 121, 130, 164, and 189;
(30) a combination of SEQ ID NOs: 18, 121, 130, 152, and 164;

(31) a combination of SEQ ID NOs: 18, 121, 130, 164, and 213;
(32) a combination of SEQ ID NOs: 18, 121, 130, 164, and 229;
(33) a combination of SEQ ID NOs: 18, 57, 121, 130, and 164;
(34) a combination of SEQ ID NOs: 18, 121, 130, 142, and 164;
(35) a combination of SEQ ID NOs: 18, 121, 130, 155, and 164;
(36) a combination of SEQ ID NOs: 18, 39, 121, 130, and 164;
(37) a combination of SEQ ID NOs: 18, 27, 130, 164, and 268;
(38) a combination of SEQ ID NOs: 18, 33, 121, 130, and 164;
(39) a combination of SEQ ID NOs: 18, 121, 126, 130, and 164;
(40) a combination of SEQ ID NOs: 18, 121, 130, 164, and 319;
(41) a combination of SEQ ID NOs: 18, 22, 121, 130, and 164;
(42) a combination of SEQ ID NOs: 18, 59, 121, 130, and 164;
(43) a combination of SEQ ID NOs: 18, 27, 121, 130, and 164;
(44) a combination of SEQ ID NOs: 18, 130, 164, 268, and 317;
(45) a combination of SEQ ID NOs: 18, 121, 130, 164, and 201;
(46) a combination of SEQ ID NOs: 18, 19, 121, 130, and 164;
(47) a combination of SEQ ID NOs: 18, 74, 130, 164, and 268;
(48) a combination of SEQ ID NOs: 18, 130, 164, 264, and 268;
(49) a combination of SEQ ID NOs: 2, 4, 130, 168, and 246;
(50) a combination of SEQ ID NOs: 2, 9, 130, 168, and 246;
(51) a combination of SEQ ID NOs: 13, 18, 121, 130, and 165;
(52) a combination of SEQ ID NOs: 13, 18, 130, 165, and 268;
(53) a combination of SEQ ID NOs: 4, 17, 115, 130, and 168;
(54) a combination of SEQ ID NOs: 2, 4, 130, 168, and 173;
(55) a combination of SEQ ID NOs: 2, 9, 130, 168, and 173;
(56) a combination of SEQ ID NOs: 2, 111, 130, 168, and 173;
(57) a combination of SEQ ID NOs: 2, 83, 130, 168, and 173;
(58) a combination of SEQ ID NOs: 2, 6, 130, 168, and 173;
(59) a combination of SEQ ID NOs: 2, 6, 130, 173, and 184;
(60) a combination of SEQ ID NOs: 2, 130, 168, 173, and 213;
(61) a combination of SEQ ID NOs: 2, 5, 130, 168, and 173; and
(62) a combination of SEQ ID NOs: 2, 130, 168, 173, and 249.

Non-limiting examples of the combination comprising the polynucleotide consisting of the nucleotide sequence represented by SEQ ID NO: 2 or a complementary sequence thereof are further listed below as combinations of target nucleic acids:
(1) a combination of SEQ ID NOs: 2, 121, 165, and 168;
(2) a combination of SEQ ID NOs: 2, 165, 168, and 268;
(3) a combination of SEQ ID NOs: 2, 4, 168, and 246;
(4) a combination of SEQ ID NOs: 2, 18, 165, and 268;
(5) a combination of SEQ ID NOs: 2, 4, 173, and 183;
(6) a combination of SEQ ID NOs: 2, 4, 115, and 168;
(7) a combination of SEQ ID NOs: 2, 9, 168, and 246;
(8) a combination of SEQ ID NOs: 2, 111, 168, and 246;
(9) a combination of SEQ ID NOs: 2, 111, 168, and 173;
(10) a combination of SEQ ID NOs: 2, 102, 168, and 246;
(11) a combination of SEQ ID NOs: 2, 4, 130, 168, and 246;
(12) a combination of SEQ ID NOs: 2, 4, 168, 201, and 246;
(13) a combination of SEQ ID NOs: 2, 9, 130, 168, and 246;
(14) a combination of SEQ ID NOs: 2, 4, 111, 168, and 173;
(15) a combination of SEQ ID NOs: 2, 4, 130, 168, and 173;
(16) a combination of SEQ ID NOs: 2, 4, 168, 173, and 201;
(17) a combination of SEQ ID NOs: 2, 4, 115, 168, and 173;
(18) a combination of SEQ ID NOs: 2, 9, 130, 168, and 173;
(19) a combination of SEQ ID NOs: 2, 4, 17, 115, and 168;
(20) a combination of SEQ ID NOs: 2, 111, 168, 173, and 268;
(21) a combination of SEQ ID NOs: 2, 18, 165, 268, and 301;
(22) a combination of SEQ ID NOs: 2, 18, 165, 268, and 315;
(23) a combination of SEQ ID NOs: 2, 111, 130, 168, and 173;
(24) a combination of SEQ ID NOs: 2, 83, 130, 168, and 173;
(25) a combination of SEQ ID NOs: 2, 6, 130, 168, and 173;
(26) a combination of SEQ ID NOs: 2, 111, 168, 173, and 223;
(27) a combination of SEQ ID NOs: 2, 5, 111, 168, and 173;
(28) a combination of SEQ ID NOs: 2, 6, 130, 173, and 184;
(29) a combination of SEQ ID NOs: 2, 39, 111, 168, and 173;
(30) a combination of SEQ ID NOs: 2, 111, 168, 173, and 222;
(31) a combination of SEQ ID NOs: 2, 111, 152, 168, and 173;
(32) a combination of SEQ ID NOs: 2, 111, 168, 173, and 241;
(33) a combination of SEQ ID NOs: 2, 130, 168, 173, and 213;
(34) a combination of SEQ ID NOs: 2, 111, 168, 173, and 184;
(35) a combination of SEQ ID NOs: 2, 102, 111, 168, and 173;
(36) a combination of SEQ ID NOs: 2, 5, 130, 168, and 173;
(37) a combination of SEQ ID NOs: 2, 111, 168, 173, and 234;

(38) a combination of SEQ ID NOs: 2, 111, 168, 173, and 230;
(39) a combination of SEQ ID NOs: 2, 111, 168, 173, and 307;
(40) a combination of SEQ ID NOs: 2, 130, 168, 173, and 249;
(41) a combination of SEQ ID NOs: 2, 111, 158, 168, and 173; and
(42) a combination of SEQ ID NOs: 2, 39, 168, 169, and 173.

Non-limiting examples of the combination comprising the polynucleotide consisting of the nucleotide sequence represented by SEQ ID NO: 9 or a complementary sequence thereof are further listed below as combinations of target nucleic acids:
(1) a combination of SEQ ID NOs: 9, 165, and 168;
(2) a combination of SEQ ID NOs: 9, 165, 168, and 173;
(3) a combination of SEQ ID NOs: 9, 128, 165, and 168;
(4) a combination of SEQ ID NOs: 9, 17, 165, and 168;
(5) a combination of SEQ ID NOs: 9, 80, 165, and 168;
(6) a combination of SEQ ID NOs: 2, 9, 168, and 246;
(7) a combination of SEQ ID NOs: 5, 9, 165, 168, and 173;
(8) a combination of SEQ ID NOs: 9, 128, 129, 165, and 168;
(9) a combination of SEQ ID NOs: 2, 9, 130, 168, and 246;
(10) a combination of SEQ ID NOs: 9, 17, 159, 165, and 168;
(11) a combination of SEQ ID NOs: 9, 17, 165, 168, and 173; and
(12) a combination of SEQ ID NOs: 2, 9, 130, 168, and 173.

Non-limiting examples of the combination comprising the polynucleotide consisting of the nucleotide sequence represented by SEQ ID NO: 17 or a complementary sequence thereof are further listed below as combinations of target nucleic acids:
(1) a combination of SEQ ID NOs: 17, 164, and 168;
(2) a combination of SEQ ID NOs: 4, 17, 165, and 168;
(3) a combination of SEQ ID NOs: 9, 17, 165, and 168;
(4) a combination of SEQ ID NOs: 4, 17, 115, and 168;
(5) a combination of SEQ ID NOs: 4, 17, 115, and 302;
(6) a combination of SEQ ID NOs: 4, 17, 115, and 184;
(7) a combination of SEQ ID NOs: 4, 17, 165, 168, and 173;
(8) a combination of SEQ ID NOs: 4, 17, 165, 168, and 223;
(9) a combination of SEQ ID NOs: 4, 17, 128, 165, and 168;
(10) a combination of SEQ ID NOs: 4, 17, 165, 168, and 169;
(11) a combination of SEQ ID NOs: 4, 17, 117, 165, and 168;
(12) a combination of SEQ ID NOs: 4, 17, 165, 168, and 323;
(13) a combination of SEQ ID NOs: 4, 17, 81, 165, and 168;
(14) a combination of SEQ ID NOs: 4, 17, 165, 168, and 253;
(15) a combination of SEQ ID NOs: 4, 17, 162, 165, and 168;
(16) a combination of SEQ ID NOs: 4, 17, 141, 165, and 168;
(17) a combination of SEQ ID NOs: 4, 17, 129, 165, and 168;
(18) a combination of SEQ ID NOs: 4, 17, 165, 168, and 258;
(19) a combination of SEQ ID NOs: 4, 17, 165, 168, and 190;
(20) a combination of SEQ ID NOs: 4, 17, 115, 168, and 177;
(21) a combination of SEQ ID NOs: 4, 17, 165, 168, and 191;
(22) a combination of SEQ ID NOs: 4, 17, 158, 165, and 168;
(23) a combination of SEQ ID NOs: 4, 17, 165, 168, and 184;
(24) a combination of SEQ ID NOs: 4, 17, 94, 165, and 168;
(25) a combination of SEQ ID NOs: 4, 17, 165, 168, and 296;
(26) a combination of SEQ ID NOs: 4, 17, 165, 168, and 307;
(27) a combination of SEQ ID NOs: 4, 17, 123, 165, and 168;
(28) a combination of SEQ ID NOs: 4, 17, 39, 165, and 168;
(29) a combination of SEQ ID NOs: 4, 17, 145, 165, and 168;
(30) a combination of SEQ ID NOs: 4, 17, 165, 168, and 286;
(31) a combination of SEQ ID NOs: 4, 17, 73, 165, and 168;
(32) a combination of SEQ ID NOs: 4, 17, 115, 165, and 168;
(33) a combination of SEQ ID NOs: 4, 17, 108, 165, and 168;
(34) a combination of SEQ ID NOs: 4, 17, 156, 165, and 168;
(35) a combination of SEQ ID NOs: 4, 17, 165, 168, and 249;
(36) a combination of SEQ ID NOs: 4, 17, 131, 165, and 168;
(37) a combination of SEQ ID NOs: 4, 17, 165, 168, and 304;
(38) a combination of SEQ ID NOs: 4, 17, 157, 165, and 168;
(39) a combination of SEQ ID NOs: 4, 17, 165, 168, and 318;
(40) a combination of SEQ ID NOs: 4, 17, 74, 165, and 168;
(41) a combination of SEQ ID NOs: 4, 17, 165, 168, and 216;
(42) a combination of SEQ ID NOs: 4, 17, 165, 168, and 309;
(43) a combination of SEQ ID NOs: 4, 17, 165, 168, and 236;
(44) a combination of SEQ ID NOs: 4, 17, 165, 168, and 324;
(45) a combination of SEQ ID NOs: 9, 17, 159, 165, and 168;
(46) a combination of SEQ ID NOs: 4, 17, 115, 130, and 168;
(47) a combination of SEQ ID NOs: 4, 17, 111, 115, and 168;
(48) a combination of SEQ ID NOs: 9, 17, 165, 168, and 173;
(49) a combination of SEQ ID NOs: 4, 17, 115, 160, and 168;
(50) a combination of SEQ ID NOs: 4, 17, 115, 168, and 246;

(51) a combination of SEQ ID NOs: 4, 17, 115, 168, and 201;
(52) a combination of SEQ ID NOs: 4, 17, 115, 168, and 217;
(53) a combination of SEQ ID NOs: 2, 4, 17, 115, and 168;
(54) a combination of SEQ ID NOs: 4, 17, 115, 140, and 168; and
(55) a combination of SEQ ID NOs: 4, 17, 102, 115, and 168.

Non-limiting examples of the combination comprising the polynucleotide consisting of the nucleotide sequence represented by SEQ ID NO: 121 or a complementary sequence thereof are further listed below as combinations of target nucleic acids:

(1) a combination of SEQ ID NOs: 121, 130, and 164;
(2) a combination of SEQ ID NOs: 18, 121, and 164;
(3) a combination of SEQ ID NOs: 121, 164, and 168;
(4) a combination of SEQ ID NOs: 121, 164, and 328;
(5) a combination of SEQ ID NOs: 121, 164, and 211;
(6) a combination of SEQ ID NOs: 95, 121, and 164;
(7) a combination of SEQ ID NOs: 6, 121, and 165;
(8) a combination of SEQ ID NOs: 18, 121, 130, and 164;
(9) a combination of SEQ ID NOs: 18, 121, 164, and 255;
(10) a combination of SEQ ID NOs: 18, 121, 164, and 201;
(11) a combination of SEQ ID NOs: 18, 121, 151, and 164;
(12) a combination of SEQ ID NOs: 18, 95, 121, and 164;
(13) a combination of SEQ ID NOs: 18, 107, 121, and 164;
(14) a combination of SEQ ID NOs: 2, 121, 165, and 168;
(15) a combination of SEQ ID NOs: 18, 121, 149, and 165;
(16) a combination of SEQ ID NOs: 13, 18, 121, and 165;
(17) a combination of SEQ ID NOs: 18, 121, 130, 136, and 164;
(18) a combination of SEQ ID NOs: 18, 121, 130, 164, and 314;
(19) a combination of SEQ ID NOs: 18, 114, 121, 130, and 164;
(20) a combination of SEQ ID NOs: 18, 121, 130, 164, and 214;
(21) a combination of SEQ ID NOs: 18, 121, 130, 164, and 193;
(22) a combination of SEQ ID NOs: 18, 121, 130, 164, and 320;
(23) a combination of SEQ ID NOs: 18, 121, 130, 164, and 301;
(24) a combination of SEQ ID NOs: 18, 121, 130, 144, and 164;
(25) a combination of SEQ ID NOs: 18, 121, 130, 164, and 168;
(26) a combination of SEQ ID NOs: 18, 121, 130, 164, and 205;
(27) a combination of SEQ ID NOs: 18, 121, 130, 158, and 164;
(28) a combination of SEQ ID NOs: 18, 121, 130, 164, and 260;
(29) a combination of SEQ ID NOs: 18, 106, 121, 130, and 164;
(30) a combination of SEQ ID NOs: 18, 121, 130, 164, and 318;
(31) a combination of SEQ ID NOs: 18, 121, 130, 164, and 286;
(32) a combination of SEQ ID NOs: 18, 121, 130, 164, and 315;
(33) a combination of SEQ ID NOs: 18, 121, 130, 164, and 237;
(34) a combination of SEQ ID NOs: 18, 121, 130, 164, and 184;
(35) a combination of SEQ ID NOs: 18, 121, 130, 164, and 270;
(36) a combination of SEQ ID NOs: 18, 121, 130, 164, and 309;
(37) a combination of SEQ ID NOs: 18, 121, 130, 164, and 278;
(38) a combination of SEQ ID NOs: 18, 82, 121, 130, and 164;
(39) a combination of SEQ ID NOs: 18, 23, 121, 130, and 164;
(40) a combination of SEQ ID NOs: 18, 121, 130, 164, and 189;
(41) a combination of SEQ ID NOs: 18, 121, 130, 152, and 164;
(42) a combination of SEQ ID NOs: 18, 121, 130, 164, and 213;
(43) a combination of SEQ ID NOs: 18, 121, 130, 164, and 229;
(44) a combination of SEQ ID NOs: 18, 57, 121, 130, and 164;
(45) a combination of SEQ ID NOs: 18, 121, 130, 142, and 164;
(46) a combination of SEQ ID NOs: 18, 121, 130, 155, and 164;
(47) a combination of SEQ ID NOs: 18, 39, 121, 130, and 164;
(48) a combination of SEQ ID NOs: 18, 33, 121, 130, and 164;
(49) a combination of SEQ ID NOs: 18, 121, 126, 130, and 164;
(50) a combination of SEQ ID NOs: 18, 121, 130, 164, and 319;
(51) a combination of SEQ ID NOs: 18, 22, 121, 130, and 164;
(52) a combination of SEQ ID NOs: 18, 59, 121, 130, and 164;
(53) a combination of SEQ ID NOs: 18, 27, 121, 130, and 164;
(54) a combination of SEQ ID NOs: 18, 121, 130, 164, and 201;
(55) a combination of SEQ ID NOs: 18, 19, 121, 130, and 164;
(56) a combination of SEQ ID NOs: 18, 95, 121, 164, and 188; and
(57) a combination of SEQ ID NOs: 13, 18, 121, 130, and 165.

Examples of the combinations of target nucleic acids in the kit or the device for discriminating lung adenocarcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating squamous cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating large cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating small cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

The kit or device of the present invention can also comprise polynucleotide(s) which can detect lung cancer and are known in the art or will be found in the future in addition to the polynucleotide(s) (that can comprise variant(s), fragments, or derivative(s)) according to the present invention as described above.

The kit or device of the present invention can also comprise an antibody for measuring a marker or markers for lung cancer examination known in the art, such as CEA and CYFRA21-1, in addition to the polynucleotide(s) according to the present invention as described above.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for measurement of cancer markers in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to all of the lung cancer marker miRNAs, respectively, of the group A described above, or to a polynucleotide(s) consisting of a nucleotide sequence(s) complementary to that of the polynucleotide(s). The kit or the device of the present invention can optionally further comprise nucleic acids capable of specifically binding to the polynucleotides of at least one, preferably at least two, more preferably at least three, most preferably at least five to all of the lung cancer marker miRNAs, respectively, of the group B described above, or to a polynucleotide(s) consisting of a nucleotide sequence(s) complementary to that of the polynucleotide(s).

The kit or the device of the present invention can be used for detecting lung cancer as described in Section 4 below.

4. Method for Detecting Lung Cancer

The present invention further provides a method for detecting lung cancer, using the above-mentioned nucleic acid(s) that can be used in the present invention (alternatively, e.g., the kit or the device of the present invention as described in Section 3 above) to measure one or more expression levels of lung cancer-derived genes represented by: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR- 4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p; and optionally an expression level(s) of lung cancer-derived gene(s) represented by: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, in a sample, and evaluating in vitro whether or not the subject has lung cancer, based on the expression levels measured (and control expression levels of healthy subjects optionally measured in the same way as above). In the method, for example, using samples, such as blood, serum, or plasma, collected from a subject suspected of having lung cancer and a subject without lung cancer, the expression levels of the above mentioned genes obtained from these subjects are compared, and if the expression level(s) of the target nucleic acid(s) is different between these samples, the subject is evaluated to have lung cancer.

This method of the present invention enables a limitedly invasive, early diagnosis of lung adenocarcinoma, lung squamous cell carcinoma, large cell lung carcinoma, small cell lung carcinoma and other lung cancers with high sensitivity and high specificity and thereby brings about early treatment and improved prognosis. In addition, the disease progression or the effectiveness of surgical, radiotherapeutic, and chemotherapeutic treatments can be monitored by the present invention.

According to the present invention, the method for extracting the lung cancer-derived gene(s) from the sample such as blood, serum, or plasma prepared by the addition of a reagent for RNA extraction in 3D-Gene™ RNA extraction reagent from liquid sample kit (Toray Industries, Inc., Japan) is particularly preferable. A general acidic phenol method (acid guanidinium-phenol-chloroform (AGPC)) or Trizol™ (Life Technologies Corp.) may be used. The lung cancer-derived gene(s) may be also prepared by the addition of a reagent for RNA extraction containing acidic phenol, such as Trizol (Life Technologies Corp.) or Isogen (Nippon Gene Co., Ltd., Japan). Alternatively, a kit such as miRNeasy™ Mini Kit (Qiagen N.V.) may be used, although the method is not limited thereto.

The present invention also provides use of the kit or the device of the present invention for detecting in vitro an expression product(s) of a lung cancer-derived miRNA gene(s) in a sample from a subject.

In the method of the present invention, the kit or the device described above comprises a single polynucleotide or any possible combination of polynucleotides that can be used in the present invention as described above.

In the detection or (genetic) diagnosis of lung cancer according to the present invention, each polynucleotide contained in the kit or the device of the present invention can be used as a probe or a primer. In the case of using the polynucleotides as primers, TaqMan™ MicroRNA Assays from Life Technologies Corp., miScript PCR System from Qiagen N.V., or the like can be used, although the method is not limited thereto.

In the method of the present invention, measurement of the gene expression levels can be performed using the above-mentioned primers or probes according to a routine method in a method known in the art specifically for detecting particular genes, for example, a hybridization technique such as Northern blot, Southern blot, in situ hybridization, Northern hybridization, or Southern hybridization, a quantitative amplification technique such as quantitative RT-PCR, or a method with a next-generation sequencer. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The method, the kit or the device of the present invention is useful for diagnosis of lung cancer or the detection of the presence or absence of lung cancer. Specifically, the detection of lung cancer using the method, the kit or the device can be performed by detecting in vitro an expression level(s) of a gene(s) which is detected by the method or detected using the nucleic acid probe(s) or the primer(s) contained in the kit or the device, in a sample such as blood, serum, plasma, or urine from a subject suspected of having lung cancer. The subject suspected of having lung cancer can be evaluated as having lung cancer when the expression level(s) of a polynucleotide(s) consisting of a nucleotide sequence(s) represented by at least one of, for example, SEQ ID NOs: 1 to 163 and optionally a nucleotide sequence(s) represented by one or more of, for example, SEQ ID NOs: 164 to 329, as target nucleic acids, in the sample such as blood, serum, plasma, or urine of the subject, is significantly high in statistic compared to an expression level(s) of the nucleotide sequences in the sample such as blood, serum, or plasma, or urine of a subject without lung cancer (i.e., also referred to as a control animal).

In the method of the present invention, or the method using the kit or the device of the present invention, the method for detecting the presence or the absence of lung cancer in a sample from a subject comprises collecting a body fluid such as blood, serum, plasma, or urine of a subject, and measuring the expression level(s) of the target gene(s) (or target nucleic acid(s)) contained therein using one or more polynucleotides (including a variant(s), a fragment(s), or a derivative(s)) selected from the groups of polynucleotides of the present invention, to evaluate the presence or absence of lung cancer or to detect lung cancer.

The method for detecting lung cancer according to the present invention can be used in combination with an imaging test method such as chest X-ray examination, CT examination, MRI examination, or PET examination. The method for detecting lung cancer according to the present invention can also be used in combination with sputum cytology, pleural fluid analysis, bronchoscopy, percutaneous needle biopsy or the like, which is a pathological examination method involving the microscopic examination of collected cells or tissues. The method for detecting lung cancer according to the present invention is capable of specifically detecting lung cancer and therefore, can substantially discriminate lung cancer from cancer other than lung cancer and can determine lung cancer with higher reliability by combination with another examination method such as the imaging test method or the pathological examination method described above. Furthermore, the method of the present invention can also be utilized to confirm the necessity of carrying out another examination method such an imaging test or a pathological examination.

The method for detecting lung cancer according to the present invention can also be used to evaluate or diagnose, for example, the presence or absence of amelioration of the disease or the degree of amelioration thereof in a lung cancer patient in the case that a lung cancer-related therapeutic drug which is known or on a development stage (including cisplatin, gefitinib, docetaxel, etoposide, carboplatin, paclitaxel, and combination drugs thereof as non-limiting examples) is administered to the patient for treatment or amelioration of the disease.

The method of the present invention can comprise, for example, the following steps (a), (b), and (c):

(a) a step of contacting in vitro a sample from a subject with a polynucleotide(s) contained in the kit or the device of the present invention;

(b) a step of measuring an expression level(s) of the target nucleic acid(s) in the sample using the polynucleotide(s) as a nucleic acid probe(s) or primer(s); and (c) a step of evaluating the presence or absence of lung cancer (cells) in the subject on the basis of the measurement results in the step (b).

In one embodiment, the present invention provides a method for detecting lung cancer, comprising: measuring an expression level(s) of a target nucleic acid(s) in a sample of a subject using a nucleic acid(s) capable of specifically binding to at least one, preferably at least two polynucleotides selected from the group consisting of the following miRNAs: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide(s) consisting of a nucleotide sequence(s) complementary to that of the polynucleotide(s); or a nucleic acid(s) for detecting the polynucleotide(s); and evaluating in vitro whether or not the subject has lung cancer using the above-measured expression levels and control expression levels of a subject(s) without lung cancer measured in the same way as above.

As used herein, the term "evaluating" is evaluation support based on results of in vitro examination, not physician's judgment.

As described above, in the method of the present invention, specifically, miR-6787-5p is hsa-miR-6787-5p, miR-920 is hsa-miR-920, miR-3622a-5p is hsa-miR-3622a-5p, miR-1185-1-3p is hsa-miR-1185-1-3p, miR-4327 is hsa-miR-4327, miR-5739 is hsa-miR-5739, miR-937-5p is hsa-miR-937-5p, miR-1181 is hsa-miR-1181, miR-1185-2-3p is hsa-miR-1185-2-3p, miR-1193 is hsa-miR-1193, miR-1207-5p is hsa-miR-1207-5p, miR-1238-5p is hsa-miR-1238-5p, miR-1246 is hsa-miR-1246, miR-1249-5p is hsa-miR-1249-5p, miR-1292-3p is hsa-miR-1292-3p, miR-1469 is hsamiR-1469, miR-1470 is hsa-miR-1470, miR-197-5p is hsa-miR-197-5p, miR-208a-5p is hsa-miR-208a-5p, miR-2110 is hsa-miR-2110, miR-211-3p is hsa-miR-211-3p, miR-2467-3p is hsa-miR-2467-3p, miR-3122 is hsa-miR-3122, miR-3141 is hsa-miR-3141, miR-3156-5p is hsa-miR-3156-5p, miR-3158-5p is hsa-miR-3158-5p, miR-3160-5p is hsa-miR-3160-5p, miR-3180-3p is hsa-miR-3180-3p, miR-3191-3p is hsa-miR-3191-3p, miR-3194-3p is hsa-miR-3194-3p, miR-320b is hsa-miR-320b, miR-328-5p is hsa-miR-328-5p, miR-3610 is hsa-miR-3610, miR-3619-3p is hsa-miR-3619-3p, miR-3620-5p is hsa-miR-3620-5p, miR-370-3p is hsa-miR-370-3p, miR-373-5p is hsa-miR-373-5p, miR-3917 is hsa-miR-3917, miR-3937 is hsa-miR-3937, miR-4259 is hsa-miR-4259, miR-4281 is hsa-miR-4281, miR-4294 is hsa-miR-4294, miR-4419b is hsa-miR-4419b, miR-4428 is hsa-miR-4428, miR-4429 is hsa-miR-4429, miR-4433a-3p is hsa-miR-4433a-3p, miR-4447 is hsa-miR-4447, miR-4449 is hsa-miR-4449, miR-4459 is hsa-miR-4459, miR-4480 is hsa-miR-4480, miR-4485-5p is hsa-miR-4485-5p, miR-4486 is hsa-miR-4486, miR-4488 is hsa-miR-4488, miR-4489 is hsa-miR-4489, miR-4505 is hsa-miR-4505, miR-4513 is hsa-miR-4513, miR-4515 is hsa-miR-4515, miR-4530 is hsa-miR-4530, miR-4535 is hsa-miR-4535, miR-4635 is hsa-miR-4635, miR-4640-5p is hsa-miR-4640-5p, miR-4646-5p is hsa-miR-4646-5p, miR-4656 is hsa-miR-4656, miR-4663 is hsa-miR-4663, miR-4665-5p is hsa-miR-4665-5p, miR-4706 is hsa-miR-4706, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4727-3p is hsa-miR-4727-3p, miR-4730 is hsa-miR-4730, miR-4734 is hsa-miR-4734, miR-4740-5p is hsa-miR-4740-5p, miR-4747-3p is hsa-miR-4747-3p, miR-4749-5p is hsa-miR-4749-5p, miR-4755-3p is hsa-miR-4755-3p, miR-4763-5p is hsa-miR-4763-5p, miR-4787-3p is hsa-miR-4787-3p, miR-5008-5p is hsa-miR-5008-5p, miR-5010-5p is hsa-miR-5010-5p, miR-504-3p is hsa-miR-504-3p, miR-5090 is hsa-miR-5090, miR-5100 is hsa-miR-5100, miR-5196-5p is hsa-miR-5196-5p, miR-551b-5p is hsa-miR-551b-5p, miR-557 is hsa-miR-557, miR-5787 is hsa-miR-5787, miR-6090 is hsa-miR-6090, miR-6124 is hsa-miR-6124, miR-6132 is hsa-miR-6132, miR-6510-5p is hsa-miR-6510-5p, miR-6511b-5p is hsa-miR-6511b-5p, miR-6515-3p is hsa-miR-6515-3p, miR-654-5p is hsa-miR-654-5p, miR-658 is hsa-miR-658, miR-668-5p is hsa-miR-668-5p, miR-6722-5p is hsa-miR-6722-5p, miR-6724-5p is hsa-miR-6724-5p, miR-6729-3p is hsa-miR-6729-3p, miR-6737-5p is hsa-miR-6737-5p, miR-6756-5p is hsa-miR-6756-5p, miR-6762-5p is hsa-miR-6762-5p, miR-6763-3p is hsa-miR-6763-3p, miR-6766-5p is hsa-miR-6766-5p, miR-6769a-5p is hsa-miR-6769a-5p, miR-6771-5p is hsa-miR-6771-5p, miR-6786-5p is hsa-miR-6786-5p, miR-6789-5p is hsa-miR-6789-5p, miR-6794-5p is hsa-miR-6794-5p, miR-6796-3p is hsa-miR-6796-3p, miR-6797-5p is hsa-miR-6797-5p, miR-6800-3p is hsa-miR-6800-3p, miR-6802-5p is hsa-miR-6802-5p, miR-6803-5p is hsa-miR-6803-5p, miR-6805-3p is hsa-miR-6805-3p, miR-6805-5p is hsa-miR-6805-5p, miR-6807-5p is hsa-miR-6807-5p, miR-6812-5p is hsa-miR-6812-5p, miR-6819-5p is hsa-miR-6819-5p, miR-6822-5p is hsa-miR-6822-5p, miR-6824-5p is hsa-miR-6824-5p, miR-6826-5p is hsa-miR-6826-5p, miR-6850-5p is hsa-miR-6850-5p, miR-6858-5p is hsa-miR-6858-5p, miR-6861-5p is hsa-miR-6861-5p, miR-6880-3p is hsa-miR-6880-3p, miR-7107-5p is hsa-miR-7107-5p, miR-7109-5p is hsa-miR-7109-5p, miR-7114-5p is hsa-miR-7114-5p, miR-7704 is hsa-miR-7704, miR-7846-3p is hsa-miR-7846-3p, miR-8052 is hsa-miR-8052, miR-8060 is hsa-miR-8060, miR-8071 is hsa-miR-8071, miR-8073 is hsa-miR-8073, miR-874-5p is hsa-miR-874-5p, miR-204-3p is hsa-miR-204-3p, miR-3154 is hsa-miR-3154, miR-3960 is hsa-miR-3960, miR-4433a-5p is hsa-miR-4433a-5p, miR-4455 is hsa-miR-4455, miR-4462 is hsa-miR-4462, miR-4476 is hsa-miR-4476, miR-4508 is hsa-miR-4508, miR-4687-3p is hsa-miR-4687-3p, miR-4687-5p is hsa-miR-4687-5p, miR-4732-5p is hsa-miR-4732-5p, miR-4771 is hsa-miR-4771, miR-642a-3p is hsa-miR-642a-3p, miR-6732-5p is hsa-miR-6732-5p, miR-6760-5p is hsa-miR-6760-5p, miR-6799-5p is hsa-miR-6799-5p, miR-6820-5p is hsa-miR-6820-5p, miR-6821-5p is hsa-miR-6821-5p, miR-6829-5p is hsa-miR-6829-5p, miR-6893-5p is hsa-miR-6893-5p, miR-7108-3p is hsa-miR-7108-3p, miR-7111-5p is hsa-miR-7111-5p, miR-8089 is hsa-miR-8089, miR-885-3p is hsa-miR-885-3p, and miR-92b-3p is hsa-miR-92b-3p.

Additionally, in one embodiment, the nucleic acid(s) (e.g., a probe(s) or a primer(s)) in the method of the present invention is selected from the group consisting of, for example, the following polynucleotides (a) to (e):

(a) a polynucleotide consisting of a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163, or a nucleotide sequence derived from the nucleotide sequence in which the nucleic acid u is replaced with t; and (e) a polynucleotide hybridizing under stringent conditions to any of the polynucleotides (a) to (d).

The nucleic acid(s) used in the method of the present invention can further comprise a nucleic acid(s) capable of specifically binding to at least one polynucleotide selected from the group consisting of the following miRNAs: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-5p, miR-550a-5p, miR-5698, miR-6075, miR-6088, miR-6089, miR-6125, miR-6126, miR-614, miR-615-5p, miR-619-5p, miR- 638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

Specifically, miR-1343-3p is hsa-miR-1343-3p, miR-6746-5p is hsa-miR-6746-5p, miR-422a is hsa-miR-422a, miR-187-5p is hsa-miR-187-5p, miR-4632-5p is hsa-miR-4632-5p, miR-6791-5p is hsa-miR-6791-5p, miR-103a-3p is hsa-miR-103a-3p, miR-107 is hsa-miR-107, miR-1199-5p is hsa-miR-1199-5p, miR-1225-3p is hsa-miR-1225-3p, miR-1225-5p is hsa-miR-1225-5p, miR-1228-5p is hsa-miR-1228-5p, miR-1229-5p is hsa-miR-1229-5p, miR-1233-5p is hsa-miR-1233-5p, miR-1237-5p is hsa-miR-1237-5p, miR-1247-3p is hsa-miR-1247-3p, miR-1249-3p is hsa-miR-1249-3p, miR-1254 is hsa-miR-1254, miR-1260b is hsa-miR-1260b, miR-1268a is hsa-miR-1268a, miR-1268b is hsa-miR-1268b, miR-1273g-3p is hsa-miR-1273g-3p, miR-128-1-5p is hsa-miR-128-1-5p, miR-128-2-5p is hsa-miR-128-2-5p, miR-1290 is hsa-miR-1290, miR-150-3p is hsa-miR-150-3p, miR-17-3p is hsa-miR-17-3p, miR-1908-5p is hsa-miR-1908-5p, miR-1909-3p is hsa-miR-1909-3p, miR-1914-3p is hsa-miR-1914-3p, miR-1915-3p is hsa-miR-1915-3p, miR-191-5p is hsa-miR-191-5p, miR-22-3p is hsa-miR-22-3p, miR-23b-3p is hsa-miR-23b-3p, miR-24-3p is hsa-miR-24-3p, miR-296-3p is hsa-miR-296-3p, miR-296-5p is hsa-miR-296-5p, miR-3131 is hsa-miR-3131, miR-3162-5p is hsa-miR-3162-5p, miR-3188 is hsa-miR-3188, miR-3196 is hsa-miR-3196, miR-3197 is hsa-miR-3197, miR-320a is hsa-miR-320a, miR-342-5p is hsa-miR-342-5p, miR-3621 is hsa-miR-3621, miR-3648 is hsa-miR-3648, miR-3656 is hsa-miR-3656, miR-365a-5p is hsa-miR-365a-5p, miR-3665 is hsa-miR-3665, miR-3679-5p is hsa-miR-3679-5p, miR-371a-5p is hsa-miR-371a-5p, miR-3940-5p is hsa-miR-3940-5p, miR-423-5p is hsa-miR-423-5p, miR-4257 is hsa-miR-4257, miR-4270 is hsa-miR-4270, miR-4271 is hsa-miR-4271, miR-4286 is hsa-miR-4286, miR-4298 is hsa-miR-4298, miR-4417 is hsa-miR-4417, miR-4442 is hsa-miR-4442, miR-4446-3p is hsa-miR-4446-3p, miR-4448 is hsa-miR-4448, miR-4454 is hsa-miR-4454, miR-4467 is hsa-miR-4467, miR-4472 is hsa-miR-4472, miR-4507 is hsa-miR-4507, miR-4516 is hsa-miR-4516, miR-451a is hsa-miR-451a, miR-4649-5p is hsa-miR-4649-5p, miR-4651 is hsa-miR-4651, miR-4665-3p is hsa-miR-4665-3p, miR-4674 is hsa-miR-4674, miR-4675 is hsa-miR-4675, miR-4689 is hsa-miR-4689, miR-4695-5p is hsa-miR-4695-5p, miR-4697-5p is hsa-miR-4697-5p, miR-4725-3p is hsa-miR-4725-3p, miR-4739 is hsa-miR-4739, miR-4745-5p is hsa-miR-4745-5p, miR-4763-3p is hsa-miR-4763-3p, miR-4792 is hsa-miR-4792, miR-486-3p is hsa-miR-486-3p, miR-5001-5p is hsa-miR-5001-5p, miR-5195-3p is hsa-miR-5195-3p, miR-550a-5p is hsa-miR-550a-5p, miR-5698 is hsa-miR-5698, miR-6075 is hsa-miR-6075, miR-6088 is hsa-miR-6088, miR-6089 is hsa-miR-6089, miR-6125 is hsa-miR-6125, miR-6126 is hsa-miR-6126, miR-614 is hsa-miR-614, miR-615-5p is hsa-miR-615-5p, miR-619-5p is hsa-miR-619-5p, miR-638 is hsa-miR-638, miR-642b-3p is hsa-miR-642b-3p, miR-650 is hsa-miR-650, miR-663a is hsa-miR-663a, miR-663b is hsa-miR-663b, miR-6717-5p is hsa-miR-6717-5p, miR-6721-5p is hsa-miR-6721-5p, miR-6726-5p is hsa-miR-6726-5p, miR-6727-5p is hsa-miR-6727-5p, miR-6738-5p is hsa-miR-6738-5p, miR-6741-5p is hsa-miR-6741-5p, miR-6749-5p is hsa-miR-6749-5p, miR-6752-5p is hsa-miR-6752-5p, miR-675-5p is hsa-miR-675-5p, miR-6757-5p is hsa-miR-6757-5p, miR-6763-5p is hsa-miR-6763-5p, miR-6765-5p is hsa-miR-6765-5p, miR-6775-5p is hsa-miR-6775-5p, miR-6780b-5p is hsa-miR-6780b-5p, miR-6782-5p is hsa-miR-6782-5p, miR-6784-5p is hsa-miR-6784-5p, miR-6800-5p is hsa-miR-6800-5p, miR-6806-5p is hsa-miR-6806-5p, miR-6840-3p is hsa-miR-6840-3p, miR-6848-5p is hsa-miR-6848-5p, miR-6851-5p is hsa-miR-6851-5p, miR-6870-5p is hsa-miR-6870-5p, miR-6872-3p is hsa-miR-6872-3p, miR-6875-5p is hsa-miR-6875-5p, miR-6877-5p is hsa-miR-6877-5p, miR-6879-5p is hsa-miR-6879-5p, miR-6880-5p is hsa-miR-6880-5p, miR-6885-5p is hsa-miR-6885-5p, miR-6887-5p is hsa-miR-6887-5p, miR-7108-5p is hsa-miR-7108-5p, miR-711 is hsa-miR-711, miR-7113-3p is hsa-miR-7113-3p, miR-744-5p is hsa-miR-744-5p, miR-760 is hsa-miR-760, miR-7845-5p is hsa-miR-7845-5p, miR-7847-3p is hsa-miR-7847-3p, miR-7977 is hsa-miR-7977, miR-8059 is hsa-miR-8059, miR-8063 is hsa-miR-8063, miR-8072 is hsa-miR-8072, miR-874-3p is hsa-miR-874-3p, miR-92a-2-5p is hsa-miR-92a-2-5p, miR-92b-5p is hsa-miR-92b-5p, miR-940 is hsa-miR-940, miR-1228-3p is hsa-miR-1228-3p, miR-1275 is hsa-miR-1275, miR-1307-3p is hsa-miR-1307-3p, miR-1343-5p is hsa-miR-1343-5p, miR-23a-3p is hsa-miR-23a-3p, miR-29b-3p is hsa-miR-29b-3p, miR-3135b is hsa-miR-3135b, miR-3185 is hsa-miR-3185, miR-4532 is hsa-miR-4532, miR-4690-5p is hsa-miR-4690-5p, miR-4758-5p is hsa-miR-4758-5p, miR-4783-3p is hsa-miR-4783-3p, miR-6131 is hsa-miR-6131, miR-625-3p is hsa-miR-625-3p, miR-6511a-5p is hsa-miR-6511a-5p, miR-6765-3p is hsa-miR-6765-3p, miR-6816-5p is hsa-miR-6816-5p, miR-6825-5p is hsa-miR-6825-5p, miR-6845-5p is hsa-miR-6845-5p, miR-7150 is hsa-miR-7150, miR-7641 is hsa-miR-7641, miR-7975 is hsa-miR-7975, and miR-92a-3p is hsa-miR-92a-3p.

In one embodiment, the nucleic acid(s) may further be selected from, for example, the group consisting of the following polynucleotides (f) to (j):

(f) a polynucleotide consisting of a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329, or a nucleotide sequence derived from the nucleotide sequence in which the nucleic acid u is replaced with t; and (j) a polynucleotide hybridizing under stringent conditions to any of the polynucleotides (f) to (i).

Examples of the sample used in the method of the present invention can include samples prepared from living tissues (preferably lung tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed according to the type of the sample to be measured.

In the case of using RNA as an analyte, the method for detecting lung cancer (cells) can comprise, for example, the following steps (a), (b), and (c):

(a) a step of binding RNA prepared from a sample from a subject (wherein, for example, the 3' end of the RNA may be polyadenylated for quantitative RT-PCR in step (b)) or complementary polynucleotides (cDNAs) transcribed from the RNA to a polynucleotide(s) in the kit of the present invention;

(b) a step of measuring the sample-derived RNA or the cDNAs synthesized from the RNA, which is/are bound to the polynucleotide(s), by hybridization using the polynucleotide(s) as a nucleic acid probe(s) or by quantitative RT-PCR using the polynucleotide(s) as a primer(s); and (c) a step of evaluating the presence or absence of lung cancer (or lung cancer-derived gene) on the basis of the measurement results of the step (b).

For example, various hybridization methods can be used for measuring the expression level(s) of a target gene(s), or detecting, examining, evaluating, or diagnosing lung cancer (or lung cancer-derived gene) in vitro according to the present invention. For example, Northern blot, Southern blot, DNA chip analysis, in situ hybridization, Northern hybridization, or Southern hybridization can be used as such a hybridization method. PCR such as quantitative RT-PCR can also be used in combination with hybridization method, or as an alternative thereof.

In the case of using the Northern blot, the presence or absence of expression of each gene or the expression level thereof in the RNA can be detected or measured by use of, for example, the nucleic acid probe(s) that can be used in the present invention. Specific examples thereof can include a method which comprises labeling the nucleic acid probe (or a complementary strand) with a radioisotope (32P, 33P, 35S, etc.), a fluorescent material, or the like, hybridizing the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of, for example, the primer that can be used in the present invention. Specific examples thereof can include a method which comprises recovering the tissue-derived RNA from a subject, preparing cDNAs according to reverse transcription using 3'-end polyadenylation treatment, specific primers, and the like, hybridizing a pair of primers (consisting of a plus strand and a reverse strand binding to the cDNA) prepared from the kit for detection of the present invention with the cDNA such that the region of each target gene marker can be amplified with the cDNA as a template, and performing PCR according to a routine method to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA to a labeled nucleic acid probe for detection.

In the case of using the nucleic acid array analysis, an RNA chip or a DNA chip in which the kit or device for detection of the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene™ Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene™ scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

In the method of the present invention, measurement of the gene expression level(s) may be performed with a sequencer, in addition to hybridization methods described above. In use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specifically designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p. 308 and Int. Neurourol. J., 2016, 20 (Suppl. 2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be enriched or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably three times, more preferably six times the standard deviation of the measurement values of the blank spots are added to the average measurement value of the blank spots on the DNA chip, and probe spots having a signal value equal to or larger than the resulting value can be regarded as detected spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only genes that show gene expression levels of $2^6$, preferably $2^8$, more preferably 210 or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method of detecting a lung cancer (or assisting detection thereof) in a subject, comprising measuring target genes or gene expression levels in a sample from the subject using the gene markers (or target nucleic acids) of the present invention, the nucleic acids (or polynucleotides for detection or diagnosis), the kit, or the device (e.g., chip) for detecting the gene marker or a combination thereof; and assigning the expression levels of the target genes in a sample from the subject to a discriminant (discriminant function), which is prepared using gene expression levels of a sample(s) from a subject(s) (for example, a patient(s)) known to have a lung cancer and a sample(s) from a subject(s) (also referred to as control animal) having no lung cancer, as a training sample(s), and which can distinguishably discriminate the presence or absence of a lung cancer, thereby evaluating the presence or absence of the lung cancer, for example.

Specifically, the present invention further provides the method comprising a first step of measuring in vitro expression levels of target genes, which are known to determine or evaluate that a subject has a lung cancer and/or not, in multiple samples, using the gene marker (or target nucleic acid) of the present invention, the nucleic acids (or polynucleotides for detection or diagnosis), the kit, the device (e.g., chip) for detecting the gene marker or a combination thereof; a second step of preparing a discriminant with the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether the subject has a lung cancer or not on the basis of the results obtained from the discriminant, for example. The above target genes are those that can be detected, for example, by the polynucleotides for detection or diagnosis, the polynucleotides contained in the kit or device, and variants thereof or fragments thereof.

The discriminant herein can be prepared by use of any discriminant analysis method that can create a discriminant that distinguishably discriminate the presence or absence of a lung cancer, such as Fisher's discriminant analysis, nonlinear discriminant analysis based on the Mahalanobis' distance, neural network or Support Vector Machine (SVM), although the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and $w_0$ represents a constant term.

[Expression 1]

$$f(x) = w_0 + \sum_{i=1}^{n} w_i x_i \quad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimension-reducing method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, µ represents an average input, ng represents the number of data belonging to class g, and µg represents an average input of the data belonging to class g. The numerator and the denominator are the interclass variance and the intraclass variance, respectively, when each of data is projected in the direction of the vector w. Discriminant coefficient $w_i$ is determined by maximizing this ratio (Takafumi Kanamori et al., "Pattern Recognition", KYORITSU SHUPPAN CO., LTD. (Tokyo, Japan) (2009); Richard O. et al., Pattern Classification, Second Edition, Wiley-Interscience, 2000).

[Expression 2]

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \quad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, µ represents a central vector of each cluster, and $S^{-1}$ represents an inverse matrix of the variance-covariance matrix of the cluster. The central vector is calculated from explanatory variable x, and an average vector, a median value vector, or the like can be used.

[Expression 3]

$$D(x, \mu) = \{(x - \mu)^t S^{-1}(x - \mu)\}^{\frac{1}{2}} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be a distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of lung cancer patients and a group of test subjects having no lung cancer. For example, lung tissue examination can be used for a reference under which each subject is confirmed to have a lung cancer or not.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

[Expression 4]

$$\min_{a} \frac{1}{2} a^T Q a - e^T a \qquad \text{Formula 4}$$
$$\text{subject to } y^T a = 0, 0 \leq a_i \leq C, i = 1, \ldots, l,$$

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

[Expression 5]

$$f(x) = \text{sgn}\left(\sum_{i=1}^{l} y_i a_i K(x_i, x) + b\right) \qquad \text{Formula 5}$$

For example, a RBF kernel defined by Formula 6 can be used as the kernel function. In this formula, x represents a support vector, and y represents a kernel parameter for adjusting the complexity of the hyperplane.

[Expression 6]

$$K(x_i, x_j) = \exp(-r\|x_i - x_j\|^2), r < 0 \qquad \text{Formula 6}$$

In addition, an approach such as neural network, k-nearest neighbor algorithms, decision trees, or logistic regression analysis can be selected as a method for determining or evaluating the presence or absence of lung cancer in a sample from a subject.

In an embodiment, the method of the present invention can comprise, for example, the following steps (a), (b) and (c):

(a) a step of measuring an expression level(s) of a target gene(s) in samples from subjects who are already known to have lung cancer or known to have no lung cancer, using the polynucleotide(s), the kit, or the device (e.g., DNA chip) for detection or diagnosis according to the present invention;

(b) a step of preparing the discriminants of Formulas 1 to 3, 5 and 6 described above from the measurement values of the expression level determined in the step (a), and (c) a step of measuring the expression level(s) of the target gene(s) in a sample from a subject using the polynucleotide(s), the kit, or the device (e.g., DNA chip) for detection or diagnosis according to the present invention, and assigning the obtained measurement value(s) to the discriminants prepared in the step (b), and determining or evaluating that the subject has a lung cancer or not on the basis of the obtained results, or evaluating the expression level derived from a lung cancer patient by comparison with a control from a subject having no lung cancer (including, e.g., a healthy subject). In this context, in the discriminants of Formulas 1 to 3, 5 and 6, x represents an explanatory variable and includes a value obtained by measuring a polynucleotide(s) or a fragment(s) thereof selected from the polynucleotides serving as target nucleic acids described in Section 2 above. Specifically, the explanatory variable of the present invention for discriminating a lung cancer patient and a subject having no lung cancer is a gene expression level(s) selected from, for example, the following expression level (1) or (2).

(1) a gene expression level(s) in the serum of a lung cancer patient and a subject having no lung cancer measured by any nucleic acid (e.g., DNA or RNA) comprising 15 or more consecutive nucleotides in the nucleotide sequence represented by any of SEQ ID NOs: 1 to 163 or a complementary sequence thereof; and (2) a gene expression level(s) in the serum of a lung cancer patient and a subject having no lung cancer measured by any nucleic acid (e.g., DNA or RNA) comprising 15 or more consecutive nucleotides in the nucleotide sequence represented by any of SEQ ID NOs: 164 to 329 or a complementary sequence thereof.

As described above, as the method for determining or evaluating whether a subject has a lung cancer or not in a sample from the subject, it is necessary to use a discriminant employing one or more gene expression levels as an explanatory variable(s). In particular, for enhancing the discrimination accuracy of the discriminant using a single gene expression level alone, it is necessary to use a gene having a clear difference in expression level between two groups consisting of a group of lung cancer patients and a group of healthy subjects, in a discriminant.

Specifically, the gene that is used for an explanatory variable of a discriminant is preferably determined as follows. First, using comprehensive gene expression levels of a group of lung cancer patients and comprehensive gene expression levels of a group of test subjects having no lung cancer, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of statistical tests, the absolute value of an expression ratio of a median value of each gene expression level (fold change) between gene expression levels of a group of patients having lung cancer and gene expression levels of a group of test subjects having no lung cancer may be calculated to select a gene that is used for an explanatory variable in a discriminant. Alternatively, ROC curves may be prepared using gene expression levels of a group of patients having lung cancer and a group of test subjects having no lung cancer, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). To the discriminant, the gene expression level of another independent patient having a lung cancer or a test subject having no lung cancer is assigned as an explanatory variable to calculate discrimination results of the group to which the independent patient having a lung cancer or the test subject having no lung cancer belongs. Specifically, the gene set for diagnosis found and the discriminant constructed using the gene set for diagnosis can be evaluated in an independent sample cohort to find more universal gene set for diagnosis that can detect a lung cancer and a more universal method for discriminating a lung cancer.

In preparing a discriminant using expression levels of multiple genes as an explanatory variable, it is not necessary to select a gene having a clear difference in expression level between the group of lung cancer patients and the group of test subjects having no lung cancer as described above. Specifically, if expression levels of multiple genes are used in combination even though the expression levels of individual genes do not clearly differ, a discriminant having high discriminant performance can be obtained, as the case may be. Because of this, a method of directly searching a discriminant having high discriminant performance without prior selection of the gene to be employed in the discriminant can also be used.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for detection or diagnosis of a disease useful for diagnosing and treating a lung cancer, a method for detecting a lung cancer using the polynucleotide(s), and a kit and device for detecting or diagnosing a lung cancer, comprising the polynucleotide(s). Particularly, in order to select a gene(s) for diagnosis and prepare a discriminant so as to exhibit accuracy beyond the lung cancer diagnosis method using the existing tumor marker CEA, a gene set for diagnosis and a discriminant for the method of present invention can be constructed, which exhibit accuracy beyond CEA, for example, by comparing expressed genes in serum from a patient confirmed to be negative using CEA but finally found to have a lung cancer by detailed examination such as computed tomography using a contrast medium, with genes expressed in serum from a patient having no lung cancer.

For example, the gene set for diagnosis is set to any combination selected from: one or two or more of the polynucleotides based on a nucleotide sequence(s) represented by any of SEQ ID NOs: 1 to 163 as described above; and optionally one or two or more of the polynucleotides based on a nucleotide sequence(s) represented by any of SEQ ID NOs: 164 to 329. Further, a discriminant is constructed using the expression levels of the gene set for diagnosis in samples from a lung cancer patient as a result of tissue diagnosis and samples from a test subject having no lung cancer as a result of tissue diagnosis. As a result, whether a subject, from which a sample with unknown lung cancer status is provided, has a lung cancer or not can be determined with 100% accuracy at the maximum by measuring expression levels of the gene set for diagnosis in the sample.

EXAMPLES

The present invention will be described further specifically with reference to Examples below. However, the scope of the present invention is not intended to be limited by these Examples.

Reference Example

<Collection of Samples>

Sera were collected using VENOJECT II vacuum blood collecting tube VP-AS109K60 (Terumo Corp. (Japan)) from total 10,869 people (Table 11a) including 4,660 healthy subjects, 327 benign bone and soft tissue tumor patients, 41 benign breast disease patients, 1,694 lung cancer patients, 1,417 stomach cancer patients, 595 esophagus cancer patients, 355 liver cancer patients, 862 pancreatic cancer patients, 406 biliary cancer patients, and 512 bladder cancer patients, after receiving their informed consents. The histological types of the lung cancer patients were adenocarcinoma in 1,308 people, squamous cell carcinoma in 243 people, large cell carcinoma in 23 people, small cell carcinoma in 25 people, adenosquamous carcinoma in 18 people, polymorphic cell cancer in 33 people, salivary gland-type cancer in 2 people, carcinoid tumor in 13 people, preinvasive lesion in 1 person, and other lung cancers in 28 people. Also, the stages of the lung cancer patients were stage IA in 1,068 people, stage IB in 337 people, stage IIA in 97 people, stage IIB in 89 people, stage IIIA in 46 people, stage IIIB in 29 people, stage IV in 4 people, unknown stages in 24 people (Table 2).

<Extraction of Total RNA>

Total RNA was obtained using a reagent for "RNA extraction in 3D-Gene™ RNA extraction reagent from liquid sample kit" (Toray Industries, Inc. (Japan)) according to the protocol provided by the manufacturer, from 300 µL of the serum sample obtained from each of 10,869 people in total.

<Measurement of Gene Expression Level>

MicroRNA in the total RNA that was obtained from the serum samples of a total of 10,869 people was fluorescently labeled by use of 3D-Gene™ miRNA Labeling kit (Toray Industries, Inc.) according to the protocol provided by the manufacturer. The oligo DNA chip used was 3D-Gene™ Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for the 10,869 people described above.

Subsequently, the samples were extracted for use in the discriminant analysis of lung cancer. In the description below, healthy subjects, benign bone and soft tissue tumor patients and benign breast disease patients, and patients having a cancer other than lung cancer will be collectively referred to as "test subjects without lung cancer". Also, stomach cancer, esophagus cancer, liver cancer, pancreatic cancer, biliary cancer and bladder cancer patients will be collectively referred to as "patients having a cancer other than lung cancer". Firstly, 1,694 lung cancer patients were used as a positive sample group. Secondly, 1,800 people from the healthy subjects described above, and a total of 1,800 people including 300 people having each cancer other than lung cancer were extracted at random, and combined with 368 benign bone and soft tissue tumor patients and benign breast disease patients to select a total of 3,968 people as a negative sample group (Table 11b). Thirdly, 70% of each sample group was used as a training cohort and the remaining 30% thereof as a validation cohort. Specifically, the training cohort consisted of 1,233 healthy subjects, 263 benign bone and soft tissue tumor patients and benign breast disease patients, 1,186 lung cancer patients and 1,281 patients having a cancer other than lung cancer; while the validation cohort consisted of 567 healthy subjects, 105 benign bone and soft tissue tumor patients and benign breast disease patients, 508 lung cancer patients and 519 patients having a cancer other than lung cancer. Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

TABLE 2

| | | Stage | | | | | | | | |
|---|---|---|---|---|---|---|---|---|---|---|
| | | IA | IB | IIA | IIB | IIIA | IIIB | IV | Unknown | Total |
| Histological type | Adenocarcinoma | 917 | 250 | 57 | 36 | 19 | 20 | 2 | 7 | 1308 |
| | Squamous cell carcinoma | 95 | 54 | 30 | 39 | 18 | 6 | 0 | 1 | 243 |
| | Large cell carcinoma | 11 | 5 | 2 | 2 | 2 | 0 | 0 | 1 | 23 |
| | Small cell carcinoma | 7 | 2 | 1 | 0 | 0 | 0 | 0 | 1 | 11 |
| | Combined small cell carcinoma | 8 | 3 | 2 | 0 | 0 | 0 | 1 | 0 | 14 |
| | Adenosquamous carcinoma | 10 | 5 | 0 | 3 | 0 | 0 | 0 | 0 | 18 |
| | Polymorphic cell cancer | 6 | 11 | 4 | 6 | 4 | 0 | 1 | 1 | 33 |
| | Salivary gland-type cancer | 0 | 0 | 0 | 0 | 0 | 1 | 0 | 1 | 2 |
| | Carcinoid tumor | 3 | 1 | 0 | 0 | 1 | 0 | 0 | 8 | 13 |
| | Preinvasive lesion | 1 | 0 | 0 | 0 | 0 | 0 | 0 | 0 | 1 |
| | Others | 10 | 6 | 1 | 3 | 2 | 2 | 0 | 4 | 28 |
| | Total | 1068 | 337 | 97 | 89 | 46 | 29 | 4 | 24 | 1694 |

TABLE 11

| Subject | a. All samples | b. All samples used in discriminant analysis | b1. Training cohort used in discriminant analysis | b2. Validation cohort used in discriminant analysis |
|---|---|---|---|---|
| Healthy | 4660 | 1800 | 1233 | 567 |
| Benign bone and soft tissue tumor | 327 | 368 | 263 | 105 |
| Benign breast disease | 41 | | | |
| Lung cancer | 1694 | 1694 | 1186 | 508 |
| Stomach cancer | 1417 | 1800 | 1281 | 519 |
| Esophagus cancer | 595 | | | |
| Liver cancer | 355 | | | |
| Pancreatic cancer | 862 | | | |
| Biliary cancer | 406 | | | |
| Bladder cancer | 512 | | | |

Example 1

<Discriminant Analysis Using Up to Two miRNAs in Combination>

In this Example, a discriminant(s) was prepared using one or two gene markers in the training cohort including the lung cancer patients and the test subjects without lung cancer (Table 11 b1), and then, the discriminant performance was evaluated in the validation cohort (Table 11b2). Based on the evaluation, gene(s) used in discriminant(s) with high performance were extracted to obtain gene marker(s) that was able to detect lung cancer.

To be more specific, firstly the miRNA expression levels of the training cohort and the validation cohort obtained in the preceding Reference Examples were combined and normalized by global normalization. Secondly, in order to acquire diagnostic markers with higher reliability, only 396 genes having the expression level of $2^6$ or higher in 50% or more of the samples in either of the group of the lung cancer patients or the group of the test subjects without lung cancer were selected as analytes.

Thirdly, one and two in combination of the 396 gene expression level measurement values described above were subjected to the Fisher's discriminant analysis to construct discriminants to discriminate the presence or absence of lung cancer. Accuracy, sensitivity, and specificity in the validation cohort were further calculated using the discriminants prepared above and the discriminant performance was validated using the independent samples. As a result, 645 discriminants with 80% or more discrimination accuracy in the validation cohort were obtained. Among these discriminants, for the discriminants that used a combination of two gene expression levels, only those whose discrimination accuracy is better than the discriminant that used any single one of the gene expression levels were selected, which led to 490 discriminants with 80% or more discrimination accuracy. The 281 genes used in these discriminants were selected as diagnostic markers for the lung cancer patients and the test subjects without lung cancer. In this way, miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, and miR-940, and the relevant polynucleotides consisting of nucleotide sequences of SEQ ID NOs: 1 to 138 and 164 to 306, were found. Among them, the genes newly found as the markers for examining the presence or absence of lung cancer are polynucleotides consisting of the nucleotide sequences represented by SEQ ID NOs: 1 to 138.

The sensitivities in the validation cohort determined by the discriminants obtained using any single one of the polynucleotides consisting of the nucleotide sequences represented by SEQ ID NOs: 188, 164, 85, 13, 175, 137, 231, 195, 263, 165, 226, 94, 45, 190, 274, 80, 220, 198, 98, 43, 2, 115, 299, 50, 196, 31, 182, 72, 96, 70, 40, 127, 183, 68, 3, 60, 66, 25, 75, 12, 255, 7, 1, 291, 87, 199, 120, 222, 278, 260, 246, 197, 103, 22, 106, 57, 29, 184, 206, 135, 179, 287, 56, 207, 261, 201, 217, 172, 300, 102, 285, 20, 21, 73, 78, 15, 30, 134, 76, 107, 97, 23, 33, 215, 122, 38, 54, 225, 26, 298, 114, 185, 128, 109, 104, 277, 303, 181, 59, 209, 236, 214, 51, 99, 105, 294, 58, 272, 101, 42, 180, 170, 47, 44, 16, 124, 241, 46, 130, 79, 247, 262, 95, 267, 69, 259, 118, 234, 138, 286, 110, 173, 200, 257, 167, 8, 111, 27, 64, 304, 177, 74, 34, 17, 36, 171, 251, 211, 193, and 256 among the polynucleotides described above, are shown in Table 3. Also, discriminant coefficients and constant terms are shown in Table 4. In this context, the general sensitivity of the existing marker CEA has been reported as being 69%. Accordingly, it was demonstrated that the polynucleotides represented by these SEQ ID NOs singly detect lung cancer with sensitivity beyond CEA.

Discriminants that were all able to discriminate lung cancer with 80% or more accuracy were also able to be prepared by combining each of the expression levels of the 281 genes represented by the nucleotide sequences of SEQ ID NOs: 1 to 138 and 164 to 306 with another gene expression level (Table 5). In this respect, discriminant coefficients and constant terms are shown in Table 6. The performance of all the discriminants using these combinations exceeded the discriminant performance of the existing marker CEA. Note that, in the tables, in the column of "SEQ ID NO or Gene", the combinations of multiple polynucleotides used are described by SEQ ID NOs. (the same applies to tables described later).

From the above, it was demonstrated that all polynucleotides consisting of the nucleotide sequences represented by SEQ ID NOs: 1 to 138 and 164 to 306 are genes capable of discriminating a lung cancer patient from a test subject without lung cancer with high accuracy if these are used alone or in combination of two or more.

TABLE 3

| SEQ ID NO: | Training cohort | | | Validation cohort | | |
|---|---|---|---|---|---|---|
| | Accuracy | Sensitivity | Specificity | Accuracy | Sensitivity | Specificity |
| 188 | 71.9 | 98.1 | 60.8 | 72.7 | 97.0 | 62.3 |
| 164 | 83.4 | 97.0 | 77.7 | 83.8 | 95.9 | 78.6 |
| 85 | 73.2 | 95.3 | 63.8 | 74.0 | 94.3 | 65.4 |
| 13 | 73.4 | 93.4 | 64.9 | 73.0 | 91.7 | 65.1 |
| 175 | 71.3 | 91.4 | 62.7 | 71.5 | 91.5 | 62.9 |
| 137 | 74.9 | 93.9 | 66.8 | 74.4 | 91.1 | 67.3 |
| 231 | 74.4 | 91.8 | 66.9 | 75.8 | 90.2 | 69.6 |
| 319 | 72.2 | 92.6 | 63.5 | 72.7 | 90.2 | 65.2 |
| 195 | 71.1 | 92.2 | 62.0 | 71.9 | 90.2 | 64.1 |
| 263 | 71.5 | 91.0 | 63.2 | 73.0 | 90.0 | 65.7 |
| 165 | 78.4 | 89.7 | 73.6 | 79.7 | 89.8 | 75.4 |
| 226 | 72.0 | 89.5 | 64.5 | 74.5 | 89.6 | 68.0 |
| 94 | 77.3 | 87.6 | 72.9 | 77.3 | 88.8 | 72.5 |
| 45 | 73.3 | 88.9 | 66.6 | 75.0 | 88.8 | 69.1 |
| 190 | 68.7 | 89.0 | 60.0 | 70.3 | 88.4 | 62.6 |
| 274 | 74.2 | 85.7 | 69.2 | 75.0 | 88.2 | 69.4 |
| 328 | 72.1 | 89.4 | 64.7 | 74.4 | 87.2 | 68.9 |
| 80 | 68.9 | 86.8 | 61.2 | 70.6 | 87.0 | 63.6 |
| 220 | 74.1 | 87.9 | 68.2 | 75.5 | 86.8 | 70.7 |
| 198 | 73.1 | 87.5 | 67.0 | 73.7 | 86.6 | 68.2 |
| 98 | 76.2 | 86.6 | 71.7 | 77.6 | 86.4 | 73.8 |
| 43 | 72.0 | 84.2 | 66.7 | 73.7 | 86.4 | 68.3 |
| 316 | 69.2 | 86.0 | 62.1 | 71.5 | 86.4 | 65.2 |
| 2 | 79.7 | 87.4 | 76.4 | 78.3 | 86.2 | 75.0 |
| 115 | 73.4 | 88.0 | 67.2 | 74.5 | 86.0 | 69.5 |
| 299 | 71.7 | 88.0 | 64.7 | 73.2 | 85.8 | 67.8 |
| 50 | 70.4 | 87.4 | 63.2 | 70.9 | 85.8 | 64.6 |
| 150 | 71.6 | 88.5 | 64.4 | 71.0 | 85.6 | 64.8 |
| 196 | 73.0 | 86.9 | 67.1 | 72.8 | 85.2 | 67.5 |
| 31 | 64.1 | 83.6 | 55.7 | 67.3 | 85.2 | 59.7 |
| 182 | 70.0 | 86.0 | 63.2 | 71.8 | 85.0 | 66.2 |
| 72 | 74.0 | 87.0 | 68.5 | 75.5 | 84.8 | 71.5 |
| 318 | 67.8 | 84.7 | 60.5 | 69.3 | 84.8 | 62.6 |
| 149 | 75.5 | 85.8 | 71.2 | 75.0 | 84.6 | 70.9 |
| 312 | 73.1 | 87.4 | 67.0 | 73.8 | 84.6 | 69.2 |
| 96 | 71.4 | 84.3 | 65.9 | 72.7 | 84.3 | 67.8 |
| 329 | 73.7 | 84.1 | 69.3 | 74.7 | 84.1 | 70.7 |
| 70 | 71.4 | 86.5 | 64.9 | 72.1 | 84.1 | 67.0 |
| 40 | 76.4 | 88.7 | 71.2 | 76.4 | 83.7 | 73.3 |
| 127 | 68.7 | 84.5 | 62.0 | 71.3 | 83.3 | 66.2 |
| 153 | 76.4 | 86.1 | 72.3 | 76.8 | 83.1 | 74.1 |
| 183 | 72.9 | 81.8 | 69.1 | 73.9 | 83.1 | 69.9 |
| 148 | 70.6 | 83.5 | 65.1 | 71.7 | 83.1 | 66.9 |
| 68 | 73.3 | 86.4 | 67.7 | 73.3 | 82.9 | 69.2 |
| 3 | 79.2 | 85.7 | 76.4 | 79.7 | 82.7 | 78.4 |
| 60 | 77.8 | 84.4 | 75.0 | 78.2 | 82.5 | 76.4 |
| 66 | 74.8 | 85.5 | 70.2 | 76.3 | 82.5 | 73.7 |
| 25 | 66.3 | 81.6 | 59.8 | 68.6 | 82.5 | 62.6 |
| 75 | 70.7 | 83.8 | 65.1 | 71.8 | 82.3 | 67.3 |
| 12 | 69.2 | 84.7 | 62.6 | 70.5 | 82.3 | 65.4 |
| 255 | 68.9 | 86.3 | 61.5 | 69.6 | 82.3 | 64.2 |
| 7 | 75.4 | 81.6 | 72.8 | 76.7 | 82.1 | 74.4 |
| 1 | 79.4 | 84.7 | 77.1 | 79.4 | 81.9 | 78.3 |
| 291 | 73.3 | 81.6 | 69.7 | 73.9 | 81.9 | 70.4 |
| 162 | 64.6 | 81.5 | 57.4 | 66.3 | 81.9 | 59.6 |
| 163 | 75.3 | 83.0 | 72.1 | 74.7 | 81.7 | 71.8 |
| 87 | 72.6 | 84.2 | 67.6 | 73.3 | 81.7 | 69.7 |
| 199 | 68.4 | 81.3 | 62.9 | 70.9 | 81.7 | 66.2 |
| 120 | 73.7 | 80.9 | 70.6 | 73.3 | 81.5 | 69.9 |
| 222 | 70.2 | 77.2 | 67.3 | 71.3 | 81.5 | 67.0 |
| 311 | 74.5 | 82.6 | 71.0 | 75.2 | 81.3 | 72.5 |
| 278 | 64.5 | 83.7 | 56.4 | 65.7 | 81.3 | 59.1 |
| 260 | 76.7 | 84.3 | 73.4 | 76.5 | 81.1 | 74.6 |
| 246 | 71.6 | 85.2 | 65.8 | 72.1 | 81.1 | 68.3 |
| 197 | 73.7 | 84.1 | 69.3 | 73.9 | 80.9 | 70.9 |
| 103 | 68.4 | 80.9 | 63.1 | 70.1 | 80.9 | 65.5 |
| 22 | 70.3 | 82.6 | 65.1 | 71.4 | 80.7 | 67.4 |
| 106 | 70.9 | 83.2 | 65.7 | 71.6 | 80.5 | 67.8 |
| 322 | 69.4 | 81.3 | 64.3 | 71.5 | 80.5 | 67.7 |
| 57 | 69.1 | 83.5 | 63.0 | 70.9 | 80.5 | 66.8 |
| 309 | 68.2 | 80.9 | 62.7 | 69.6 | 80.5 | 64.9 |
| 29 | 78.1 | 82.6 | 76.2 | 78.2 | 80.1 | 77.4 |
| 184 | 71.5 | 78.2 | 68.6 | 72.2 | 80.1 | 68.8 |
| 206 | 63.7 | 81.3 | 56.2 | 65.0 | 80.1 | 58.5 |
| 135 | 78.9 | 83.3 | 77.0 | 77.9 | 79.9 | 77.1 |
| 179 | 73.5 | 81.5 | 70.0 | 75.0 | 79.9 | 72.9 |
| 287 | 75.9 | 82.5 | 73.1 | 77.1 | 79.5 | 76.1 |
| 56 | 71.9 | 79.9 | 68.5 | 73.9 | 79.5 | 71.5 |
| 207 | 67.0 | 81.8 | 60.7 | 68.9 | 79.5 | 64.3 |
| 261 | 64.4 | 78.8 | 58.3 | 66.2 | 79.5 | 60.5 |
| 201 | 71.8 | 80.4 | 68.1 | 71.6 | 79.1 | 68.3 |
| 217 | 74.7 | 80.6 | 72.2 | 76.3 | 78.9 | 75.1 |
| 317 | 71.9 | 79.0 | 68.9 | 72.7 | 78.9 | 70.0 |
| 172 | 69.4 | 78.4 | 65.6 | 71.3 | 78.9 | 68.1 |
| 300 | 69.6 | 82.7 | 64.1 | 70.7 | 78.7 | 67.3 |
| 102 | 77.1 | 78.6 | 76.5 | 76.0 | 78.5 | 75.0 |
| 285 | 69.5 | 81.0 | 64.6 | 69.9 | 78.5 | 66.2 |
| 20 | 73.8 | 80.1 | 71.2 | 74.3 | 78.3 | 72.5 |
| 159 | 70.9 | 80.7 | 66.8 | 70.6 | 78.3 | 67.3 |
| 21 | 68.4 | 80.2 | 63.4 | 70.5 | 78.1 | 67.2 |
| 73 | 61.6 | 79.0 | 54.2 | 64.0 | 78.1 | 57.9 |
| 78 | 70.5 | 80.9 | 66.1 | 70.9 | 78.0 | 67.8 |
| 15 | 68.6 | 76.5 | 65.2 | 70.5 | 78.0 | 67.3 |
| 30 | 70.3 | 79.8 | 66.3 | 71.3 | 77.8 | 68.5 |
| 134 | 70.6 | 78.7 | 67.2 | 72.9 | 77.6 | 70.9 |
| 315 | 67.4 | 73.5 | 64.8 | 70.6 | 77.6 | 67.6 |
| 76 | 66.5 | 76.5 | 62.2 | 67.3 | 77.6 | 63.0 |
| 107 | 71.3 | 80.2 | 67.5 | 72.5 | 77.2 | 70.4 |
| 97 | 61.8 | 75.8 | 55.8 | 63.0 | 77.0 | 57.0 |
| 23 | 74.8 | 81.2 | 72.0 | 74.7 | 76.8 | 73.9 |
| 33 | 71.7 | 78.5 | 68.7 | 72.0 | 76.4 | 70.2 |
| 307 | 67.9 | 76.0 | 64.4 | 69.7 | 76.2 | 67.0 |
| 215 | 63.0 | 78.6 | 56.4 | 64.4 | 76.2 | 59.4 |
| 122 | 71.9 | 79.0 | 68.8 | 71.3 | 76.0 | 69.4 |
| 38 | 66.4 | 77.9 | 61.5 | 68.1 | 76.0 | 64.7 |
| 54 | 71.4 | 78.5 | 68.3 | 70.8 | 75.8 | 68.7 |
| 225 | 71.0 | 78.1 | 68.0 | 70.6 | 75.6 | 68.5 |
| 26 | 65.7 | 76.6 | 61.0 | 65.8 | 75.6 | 61.6 |
| 298 | 66.3 | 76.8 | 61.8 | 66.5 | 75.4 | 62.6 |
| 114 | 64.7 | 74.2 | 60.6 | 66.3 | 75.4 | 62.4 |
| 185 | 69.0 | 76.4 | 65.8 | 70.6 | 75.2 | 68.6 |
| 128 | 68.6 | 77.7 | 64.7 | 69.6 | 75.2 | 67.2 |
| 109 | 68.2 | 75.0 | 65.3 | 69.4 | 75.2 | 66.9 |
| 104 | 67.4 | 71.8 | 65.6 | 66.0 | 75.2 | 62.1 |
| 277 | 65.8 | 74.5 | 62.2 | 64.6 | 75.2 | 60.0 |
| 327 | 65.0 | 76.4 | 60.1 | 64.6 | 75.2 | 60.0 |
| 303 | 68.3 | 76.1 | 65.0 | 68.9 | 75.0 | 66.3 |
| 181 | 69.1 | 76.3 | 66.0 | 69.8 | 74.8 | 67.7 |
| 59 | 66.8 | 74.9 | 63.4 | 67.7 | 74.8 | 64.7 |
| 209 | 63.2 | 73.2 | 58.9 | 65.3 | 74.8 | 61.2 |
| 236 | 61.7 | 76.1 | 55.6 | 63.2 | 74.8 | 58.3 |
| 214 | 66.6 | 74.7 | 63.2 | 67.9 | 74.4 | 65.1 |
| 51 | 65.1 | 76.6 | 60.1 | 65.0 | 74.2 | 61.0 |
| 140 | 65.9 | 75.5 | 61.8 | 64.7 | 74.2 | 60.7 |
| 99 | 69.2 | 75.5 | 66.5 | 69.1 | 74.0 | 67.0 |
| 105 | 66.8 | 75.6 | 63.0 | 67.3 | 74.0 | 64.4 |
| 294 | 63.2 | 74.6 | 58.4 | 64.4 | 74.0 | 60.4 |
| 58 | 59.4 | 75.0 | 52.8 | 59.7 | 73.8 | 53.7 |
| 143 | 70.1 | 75.9 | 67.6 | 71.2 | 73.6 | 70.2 |
| 272 | 65.6 | 78.1 | 60.2 | 65.8 | 73.6 | 62.5 |
| 101 | 65.1 | 74.5 | 61.1 | 65.7 | 73.4 | 62.4 |
| 144 | 68.3 | 75.4 | 65.3 | 68.2 | 73.0 | 66.1 |
| 42 | 68.3 | 77.5 | 64.4 | 67.6 | 73.0 | 65.3 |
| 180 | 68.3 | 76.6 | 64.8 | 67.7 | 72.8 | 65.5 |
| 170 | 72.0 | 74.7 | 70.9 | 72.7 | 72.6 | 72.7 |
| 47 | 68.5 | 71.0 | 67.4 | 69.7 | 72.6 | 68.4 |
| 44 | 68.7 | 77.6 | 64.9 | 68.5 | 72.6 | 66.8 |
| 16 | 65.2 | 71.8 | 62.4 | 67.8 | 72.4 | 65.8 |
| 124 | 65.1 | 74.7 | 61.0 | 66.5 | 72.4 | 63.9 |
| 241 | 64.8 | 72.1 | 61.7 | 66.0 | 72.4 | 63.3 |
| 46 | 68.2 | 73.0 | 66.2 | 67.4 | 72.2 | 65.3 |
| 321 | 65.7 | 75.6 | 61.4 | 66.5 | 72.2 | 64.1 |
| 130 | 69.1 | 72.4 | 67.7 | 69.9 | 72.0 | 68.9 |
| 79 | 64.3 | 71.8 | 61.1 | 66.3 | 72.0 | 63.8 |

TABLE 3-continued

| SEQ ID NO: | Training cohort | | | Validation cohort | | |
|---|---|---|---|---|---|---|
| | Accuracy | Sensitivity | Specificity | Accuracy | Sensitivity | Specificity |
| 247 | 62.1 | 71.2 | 58.2 | 64.4 | 72.0 | 61.2 |
| 262 | 65.3 | 70.0 | 63.2 | 68.0 | 71.7 | 66.4 |
| 95 | 66.6 | 72.4 | 64.1 | 67.0 | 71.7 | 65.0 |
| 142 | 65.5 | 71.2 | 63.0 | 65.0 | 71.7 | 62.1 |
| 267 | 64.0 | 73.4 | 60.0 | 64.3 | 71.7 | 61.2 |
| 69 | 67.8 | 71.4 | 66.2 | 68.9 | 71.5 | 67.8 |
| 259 | 62.7 | 69.6 | 59.8 | 65.5 | 71.5 | 63.0 |
| 118 | 65.4 | 72.6 | 62.3 | 67.2 | 71.3 | 65.4 |
| 234 | 65.5 | 71.1 | 63.1 | 65.0 | 71.3 | 62.3 |
| 138 | 65.3 | 71.8 | 62.5 | 64.0 | 71.3 | 60.9 |
| 286 | 69.0 | 68.8 | 69.1 | 69.7 | 71.1 | 69.1 |
| 110 | 67.2 | 68.0 | 66.9 | 69.1 | 71.1 | 68.3 |
| 173 | 70.2 | 78.0 | 66.9 | 68.6 | 71.1 | 67.6 |
| 320 | 65.1 | 69.9 | 63.1 | 65.9 | 71.1 | 63.6 |
| 200 | 64.6 | 72.3 | 61.3 | 64.9 | 71.1 | 62.2 |
| 257 | 67.4 | 69.6 | 66.5 | 69.6 | 70.9 | 69.1 |
| 167 | 67.1 | 72.7 | 64.7 | 66.9 | 70.9 | 65.2 |
| 314 | 68.0 | 74.3 | 65.3 | 65.4 | 70.9 | 63.1 |
| 8 | 62.7 | 76.5 | 56.8 | 60.0 | 70.9 | 55.3 |
| 111 | 78.3 | 74.3 | 80.0 | 76.2 | 70.7 | 78.5 |
| 27 | 68.2 | 72.8 | 66.2 | 69.2 | 70.5 | 68.7 |
| 64 | 68.0 | 75.0 | 65.0 | 68.5 | 70.1 | 67.8 |
| 304 | 64.1 | 69.5 | 61.9 | 65.1 | 70.1 | 63.0 |
| 177 | 59.3 | 67.5 | 55.9 | 63.5 | 70.1 | 60.7 |
| 74 | 68.2 | 67.5 | 68.6 | 70.9 | 69.7 | 71.4 |
| 34 | 66.3 | 69.8 | 64.8 | 66.9 | 69.7 | 65.7 |
| 17 | 66.3 | 72.9 | 63.4 | 65.1 | 69.7 | 63.1 |
| 36 | 64.3 | 73.6 | 60.4 | 64.4 | 69.7 | 62.1 |
| 171 | 72.0 | 73.4 | 71.3 | 72.3 | 69.5 | 73.6 |
| 251 | 62.8 | 70.9 | 59.3 | 64.0 | 69.5 | 61.7 |
| 211 | 65.2 | 71.9 | 62.3 | 65.5 | 69.3 | 63.9 |
| 193 | 69.5 | 71.7 | 68.6 | 69.7 | 69.1 | 69.9 |
| 256 | 62.4 | 69.0 | 59.6 | 65.2 | 69.1 | 63.6 |

TABLE 4

| SEQ ID NO: | Coefficient | Constant term |
|---|---|---|
| 188 | 0.46 | −3.96 |
| 164 | 1.52 | −12.87 |
| 85 | 0.76 | −9.89 |
| 13 | 0.44 | −3.44 |
| 175 | −2.56 | 28.63 |
| 137 | 1.19 | −9.35 |
| 231 | 0.52 | −3.92 |
| 319 | 0.50 | −5.37 |
| 195 | 0.52 | −2.98 |
| 263 | 0.74 | −5.56 |
| 165 | 1.72 | −13.28 |
| 226 | 0.90 | −9.97 |
| 94 | 1.04 | −6.31 |
| 45 | 1.09 | −7.88 |
| 190 | 0.52 | −2.78 |
| 274 | −3.35 | 34.66 |
| 328 | 0.90 | −8.02 |
| 80 | 1.00 | −7.29 |
| 220 | 1.16 | −8.43 |
| 198 | 0.71 | −4.51 |
| 98 | 0.90 | −4.61 |
| 43 | 1.05 | −7.31 |
| 316 | 1.29 | −8.88 |
| 2 | 1.01 | −6.10 |
| 115 | 2.20 | −20.21 |
| 299 | 1.00 | −9.37 |
| 50 | 0.47 | −2.72 |
| 150 | 0.56 | −3.02 |
| 196 | 0.56 | −3.19 |
| 31 | 0.53 | −3.07 |
| 182 | 1.11 | −10.40 |
| 72 | 0.75 | −4.45 |
| 318 | 0.74 | −5.73 |
| 149 | 0.81 | −5.37 |

TABLE 4-continued

| SEQ ID NO: | Coefficient | Constant term |
|---|---|---|
| 312 | 0.61 | −2.91 |
| 96 | 0.70 | −3.37 |
| 329 | 0.81 | −5.51 |
| 70 | 0.53 | −4.19 |
| 40 | 0.86 | −4.96 |
| 127 | 1.53 | −12.09 |
| 153 | 0.76 | −4.05 |
| 183 | −3.32 | 35.60 |
| 148 | 1.25 | −8.23 |
| 68 | 0.68 | −5.43 |
| 3 | 1.39 | −9.03 |
| 60 | 0.86 | −4.09 |
| 66 | 1.97 | −16.60 |
| 25 | 0.56 | −3.00 |
| 75 | 0.61 | −3.65 |
| 12 | 0.98 | −7.25 |
| 255 | 0.72 | −7.17 |
| 7 | 2.37 | −19.98 |
| 1 | 2.02 | −19.02 |
| 291 | 1.25 | −8.99 |
| 162 | 0.63 | −3.74 |
| 163 | 0.81 | −4.70 |
| 87 | 0.73 | −3.97 |
| 199 | 0.90 | −6.60 |
| 120 | 1.00 | −6.11 |
| 222 | 3.07 | −26.17 |
| 311 | 0.59 | −3.50 |
| 278 | −1.45 | 16.91 |
| 260 | 0.90 | −4.36 |
| 246 | 1.85 | −16.38 |
| 197 | 0.57 | −3.42 |
| 103 | 2.01 | −17.60 |
| 22 | 0.53 | −4.56 |
| 106 | 1.05 | −6.86 |
| 322 | 0.95 | −7.58 |
| 57 | 0.56 | −3.59 |
| 309 | 0.71 | −5.45 |
| 29 | 1.18 | −6.74 |
| 184 | −3.26 | 31.56 |
| 206 | 0.66 | −4.32 |
| 135 | 0.89 | −4.22 |
| 179 | 1.56 | −11.11 |
| 287 | 1.88 | −15.11 |
| 56 | 1.31 | −8.81 |
| 207 | 0.63 | −3.95 |
| 261 | 1.04 | −12.53 |
| 201 | 1.27 | −10.31 |
| 217 | 1.58 | −12.07 |
| 317 | 2.32 | −21.17 |
| 172 | 0.85 | −5.07 |
| 300 | 0.91 | −9.12 |
| 102 | 1.40 | −9.99 |
| 285 | 0.94 | −5.62 |
| 20 | 1.03 | −6.33 |
| 159 | 1.19 | −7.36 |
| 21 | 1.16 | −8.70 |
| 73 | −0.53 | 4.41 |
| 78 | 0.48 | −2.44 |
| 15 | 0.87 | −5.39 |
| 30 | 0.43 | −3.27 |
| 134 | 1.00 | −6.04 |
| 315 | 0.74 | −9.76 |
| 76 | 0.75 | −4.45 |
| 107 | 1.18 | −8.80 |
| 97 | 0.57 | −3.71 |
| 23 | 0.91 | −4.91 |
| 33 | 0.86 | −4.72 |
| 307 | 1.66 | −11.62 |
| 215 | −1.63 | 18.47 |
| 122 | 0.80 | −4.37 |
| 38 | 0.83 | −5.46 |
| 54 | 0.67 | −3.37 |
| 225 | 0.63 | −5.27 |
| 26 | 0.52 | −3.11 |
| 298 | 0.87 | −6.15 |
| 114 | 0.64 | −3.71 |
| 185 | 0.81 | −6.70 |
| 128 | 1.01 | −6.33 |

TABLE 4-continued

| SEQ ID NO: | Coefficient | Constant term |
|---|---|---|
| 109 | −2.71 | 33.33 |
| 104 | 1.28 | −10.29 |
| 277 | 0.63 | −3.80 |
| 327 | 0.52 | −3.47 |
| 303 | 0.78 | −4.47 |
| 181 | 0.87 | −5.65 |
| 59 | 0.67 | −3.76 |
| 209 | 1.09 | −14.30 |
| 236 | 0.88 | −7.04 |
| 214 | 1.28 | −9.55 |
| 51 | 0.64 | −3.99 |
| 140 | 0.81 | −5.16 |
| 99 | 0.73 | −3.95 |
| 105 | 0.77 | −4.44 |
| 294 | 0.62 | −3.83 |
| 58 | −1.09 | 10.55 |
| 143 | 0.62 | −3.40 |
| 272 | 0.96 | −7.96 |
| 101 | 0.93 | −5.82 |
| 144 | 0.67 | −3.81 |
| 42 | −1.55 | 15.71 |
| 180 | 1.31 | −9.04 |
| 170 | 0.57 | −2.49 |
| 47 | 1.03 | −7.03 |
| 44 | 0.64 | −3.54 |
| 16 | 1.18 | −13.90 |
| 124 | 0.97 | −7.04 |
| 241 | −2.20 | 24.78 |
| 46 | 1.29 | −9.94 |
| 321 | 1.00 | −7.64 |
| 130 | 1.67 | −13.02 |
| 79 | 0.65 | −3.61 |
| 247 | 0.69 | −4.92 |
| 262 | 0.84 | −7.44 |
| 95 | 1.45 | −10.46 |
| 142 | 0.65 | −3.63 |
| 267 | 0.69 | −4.79 |
| 69 | 0.55 | −4.42 |
| 259 | 0.64 | −6.21 |
| 118 | −1.78 | 19.05 |
| 234 | 0.72 | −4.36 |
| 138 | 0.57 | −3.21 |
| 286 | −1.05 | 8.89 |
| 110 | 1.63 | −16.52 |
| 173 | 1.60 | −11.35 |
| 320 | 0.62 | −3.53 |
| 200 | 1.40 | −10.95 |
| 257 | 0.51 | −3.87 |
| 167 | 1.29 | −11.15 |
| 314 | 1.59 | −12.95 |
| 8 | 0.66 | −4.07 |
| 111 | 2.44 | −20.94 |
| 27 | 0.38 | −2.72 |
| 64 | 0.45 | −2.24 |
| 304 | −0.61 | 4.99 |
| 177 | 0.59 | −7.14 |
| 74 | 0.86 | −10.97 |
| 34 | 0.84 | −6.99 |
| 17 | 0.77 | −4.63 |
| 36 | 0.69 | −4.14 |
| 171 | 0.57 | −2.50 |
| 251 | 0.85 | −9.59 |
| 211 | 1.02 | −7.34 |
| 193 | 1.57 | −12.18 |
| 256 | 0.47 | −3.00 |

TABLE 5

| | Training cohort | | | Validation cohort | | |
|---|---|---|---|---|---|---|
| Gene | Accuracy | Sensitivity | Specificity | Accuracy | Sensitivity | Specificity |
| 18_164 | 86.4 | 98.0 | 81.4 | 86.7 | 98.2 | 81.8 |
| 255_164 | 86.9 | 96.1 | 83.0 | 86.6 | 96.1 | 82.5 |
| 177_164 | 86.1 | 94.6 | 82.5 | 86.3 | 94.5 | 82.9 |
| 4_164 | 85.8 | 91.1 | 83.5 | 86.0 | 91.3 | 83.7 |
| 164_9 | 85.4 | 92.0 | 82.6 | 85.9 | 91.5 | 83.5 |
| 300_164 | 85.8 | 96.1 | 81.5 | 85.7 | 96.1 | 81.3 |
| 272_164 | 84.8 | 97.6 | 79.4 | 85.7 | 97.0 | 80.9 |
| 206_164 | 86.0 | 95.3 | 82.0 | 85.6 | 93.9 | 82.0 |
| 12_164 | 85.6 | 96.0 | 81.2 | 85.6 | 95.5 | 81.4 |
| 166_164 | 85.6 | 92.8 | 82.5 | 85.6 | 91.7 | 83.0 |
| 168_164 | 85.3 | 97.6 | 80.1 | 85.6 | 97.4 | 80.6 |
| 6_164 | 85.0 | 97.1 | 79.8 | 85.6 | 97.0 | 80.8 |
| 259_164 | 85.0 | 94.7 | 80.8 | 85.5 | 93.9 | 81.9 |
| 115_164 | 84.8 | 96.4 | 79.8 | 85.5 | 96.1 | 81.0 |
| 164_129 | 84.5 | 95.8 | 79.7 | 85.4 | 95.3 | 81.2 |
| 190_164 | 85.5 | 95.4 | 81.3 | 85.3 | 95.1 | 81.2 |
| 199_164 | 85.4 | 95.9 | 81.0 | 85.3 | 95.9 | 80.8 |
| 66_164 | 85.4 | 96.3 | 80.7 | 85.3 | 96.5 | 80.5 |
| 164_107 | 85.4 | 97.1 | 80.4 | 85.3 | 97.2 | 80.3 |
| 207_164 | 85.3 | 96.8 | 80.4 | 85.3 | 95.3 | 81.0 |
| 263_164 | 85.1 | 97.5 | 79.8 | 85.3 | 97.0 | 80.4 |
| 16_164 | 85.0 | 95.3 | 80.6 | 85.3 | 95.1 | 81.2 |
| 37_164 | 84.9 | 94.9 | 80.6 | 85.3 | 94.1 | 81.5 |
| 38_164 | 84.9 | 96.9 | 79.8 | 85.3 | 96.3 | 80.7 |
| 261_164 | 85.5 | 94.8 | 81.6 | 85.2 | 93.9 | 81.5 |
| 305_164 | 85.2 | 94.7 | 81.2 | 85.2 | 93.7 | 81.6 |
| 55_164 | 85.1 | 94.2 | 81.2 | 85.2 | 93.1 | 81.9 |
| 127_164 | 84.6 | 95.6 | 79.9 | 85.2 | 95.1 | 80.9 |
| 104_164 | 84.2 | 96.2 | 79.1 | 85.2 | 96.1 | 80.5 |
| 31_164 | 85.2 | 95.9 | 80.6 | 85.1 | 94.3 | 81.2 |
| 121_164 | 84.7 | 97.8 | 79.0 | 85.1 | 97.4 | 79.8 |
| 81_164 | 84.6 | 95.4 | 79.9 | 85.1 | 95.5 | 80.7 |
| 295_164 | 84.6 | 93.8 | 80.7 | 85.1 | 93.1 | 81.6 |
| 6_165 | 84.5 | 95.3 | 79.9 | 85.1 | 95.9 | 80.5 |
| 25_164 | 84.5 | 96.1 | 79.5 | 85.1 | 95.5 | 80.6 |
| 83_164 | 84.4 | 97.1 | 79.0 | 85.1 | 96.7 | 80.2 |
| 32_164 | 85.1 | 94.7 | 81.0 | 85.0 | 94.1 | 81.1 |
| 247_164 | 84.5 | 95.8 | 79.7 | 85.0 | 95.1 | 80.7 |
| 26_164 | 84.1 | 96.2 | 78.9 | 85.0 | 96.3 | 80.2 |
| 302_164 | 84.5 | 95.4 | 79.8 | 84.9 | 94.7 | 80.7 |
| 268_164 | 84.5 | 97.3 | 79.0 | 84.9 | 96.9 | 79.8 |
| 90_164 | 84.4 | 95.8 | 79.5 | 84.9 | 95.9 | 80.2 |
| 287_164 | 84.2 | 96.9 | 78.8 | 84.9 | 96.7 | 79.9 |
| 278_164 | 84.9 | 96.0 | 80.1 | 84.8 | 94.7 | 80.5 |
| 5_164 | 84.7 | 93.6 | 80.9 | 84.8 | 93.7 | 81.0 |
| 137_164 | 84.5 | 95.9 | 79.7 | 84.8 | 95.5 | 80.3 |
| 276_164 | 84.5 | 94.9 | 80.0 | 84.8 | 94.9 | 80.5 |
| 164_271 | 84.1 | 96.6 | 78.8 | 84.8 | 95.9 | 80.0 |
| 167_164 | 83.8 | 97.4 | 78.0 | 84.8 | 97.2 | 79.4 |
| 126_164 | 84.7 | 96.8 | 79.5 | 84.7 | 96.1 | 79.8 |
| 211_164 | 84.3 | 96.6 | 79.0 | 84.7 | 96.7 | 79.6 |
| 67_164 | 84.2 | 95.2 | 79.4 | 84.7 | 93.7 | 80.9 |
| 39_164 | 83.9 | 95.9 | 78.8 | 84.7 | 96.1 | 79.8 |
| 186_164 | 85.1 | 95.7 | 80.6 | 84.6 | 94.3 | 80.5 |
| 182_164 | 85.0 | 96.0 | 80.3 | 84.6 | 94.7 | 80.4 |
| 226_164 | 85.0 | 96.0 | 80.3 | 84.6 | 95.1 | 80.1 |
| 27_164 | 84.7 | 96.3 | 79.7 | 84.6 | 95.3 | 80.0 |
| 275_164 | 84.6 | 95.7 | 79.8 | 84.6 | 94.1 | 80.5 |
| 185_164 | 84.3 | 95.8 | 79.3 | 84.6 | 95.1 | 80.2 |
| 92_164 | 84.2 | 93.8 | 80.1 | 84.6 | 93.3 | 80.9 |
| 10_164 | 85.0 | 95.9 | 80.4 | 84.5 | 94.7 | 80.1 |
| 279_164 | 84.7 | 93.3 | 81.1 | 84.5 | 92.7 | 80.9 |
| 256_164 | 84.7 | 96.5 | 79.6 | 84.5 | 96.1 | 79.5 |
| 80_164 | 84.6 | 94.8 | 80.2 | 84.5 | 93.3 | 80.8 |
| 164_195 | 84.6 | 95.6 | 79.9 | 84.5 | 94.9 | 80.1 |
| 243_164 | 84.5 | 96.9 | 79.2 | 84.5 | 96.5 | 79.3 |
| 22_164 | 84.5 | 95.4 | 79.8 | 84.5 | 94.7 | 80.1 |
| 164_97 | 84.4 | 96.4 | 79.2 | 84.5 | 95.9 | 79.6 |
| 34_164 | 84.2 | 97.6 | 78.4 | 84.5 | 96.9 | 79.3 |
| 215_164 | 84.2 | 95.1 | 79.5 | 84.5 | 94.1 | 80.4 |
| 187_164 | 84.0 | 95.1 | 79.3 | 84.5 | 93.7 | 80.6 |
| 164_174 | 84.0 | 96.5 | 78.6 | 84.5 | 96.3 | 79.4 |
| 50_164 | 83.9 | 95.8 | 78.8 | 84.5 | 94.9 | 80.0 |
| 62_164 | 83.8 | 96.9 | 78.2 | 84.5 | 96.7 | 79.3 |
| 75_164 | 83.8 | 96.0 | 78.6 | 84.5 | 95.9 | 79.7 |
| 61_164 | 83.8 | 95.4 | 78.9 | 84.5 | 95.9 | 79.6 |
| 89_164 | 83.7 | 96.6 | 78.2 | 84.5 | 96.1 | 79.6 |

TABLE 5-continued

| Gene | Training cohort | | | Validation cohort | | |
|---|---|---|---|---|---|---|
| | Accuracy | Sensitivity | Specificity | Accuracy | Sensitivity | Specificity |
| 306_164 | 83.6 | 95.5 | 78.5 | 84.5 | 94.1 | 80.4 |
| 164_286 | 83.5 | 97.5 | 77.6 | 84.5 | 96.9 | 79.3 |
| 85_164 | 84.6 | 95.6 | 79.8 | 84.4 | 94.9 | 79.9 |
| 192_164 | 83.9 | 97.0 | 78.3 | 84.4 | 96.1 | 79.4 |
| 223_164 | 85.1 | 95.6 | 80.6 | 84.3 | 94.3 | 80.1 |
| 299_164 | 84.8 | 96.4 | 79.8 | 84.3 | 95.1 | 79.8 |
| 73_164 | 84.5 | 96.0 | 79.7 | 84.3 | 95.1 | 79.7 |
| 241_164 | 84.2 | 96.5 | 78.9 | 84.3 | 95.9 | 79.4 |
| 118_164 | 84.1 | 97.0 | 78.6 | 84.3 | 95.9 | 79.4 |
| 283_164 | 84.1 | 96.8 | 78.7 | 84.3 | 95.1 | 79.8 |
| 164_77 | 84.0 | 96.5 | 78.6 | 84.3 | 95.9 | 79.3 |
| 175_164 | 83.9 | 95.2 | 79.1 | 84.3 | 93.5 | 80.4 |
| 164_65 | 83.8 | 95.9 | 78.6 | 84.3 | 95.3 | 79.6 |
| 7_164 | 83.6 | 96.4 | 78.2 | 84.3 | 95.3 | 79.6 |
| 205_164 | 83.3 | 97.3 | 77.3 | 84.3 | 96.5 | 79.2 |
| 188_164 | 84.2 | 96.5 | 78.9 | 84.2 | 95.1 | 79.6 |
| 100_164 | 84.1 | 94.8 | 79.5 | 84.2 | 94.1 | 79.9 |
| 13_164 | 84.0 | 96.2 | 78.8 | 84.2 | 95.7 | 79.3 |
| 106_164 | 84.0 | 97.3 | 78.4 | 84.2 | 96.3 | 79.1 |
| 53_164 | 84.0 | 95.6 | 79.0 | 84.2 | 93.5 | 80.3 |
| 64_164 | 83.9 | 96.1 | 78.7 | 84.2 | 96.1 | 79.2 |
| 210_164 | 83.9 | 93.6 | 79.7 | 84.2 | 91.3 | 81.2 |
| 290_164 | 83.9 | 95.4 | 78.9 | 84.2 | 94.1 | 79.9 |
| 164_43 | 83.9 | 98.1 | 77.9 | 84.2 | 96.3 | 79.1 |
| 164_44 | 83.9 | 97.0 | 78.3 | 84.2 | 96.3 | 79.0 |
| 30_164 | 83.8 | 95.9 | 78.7 | 84.2 | 95.1 | 79.6 |
| 21_164 | 83.8 | 96.4 | 78.4 | 84.2 | 95.9 | 79.3 |
| 301_164 | 83.8 | 97.6 | 77.9 | 84.2 | 96.3 | 79.1 |
| 24_164 | 83.7 | 97.2 | 77.9 | 84.2 | 96.5 | 78.9 |
| 45_164 | 83.7 | 96.9 | 78.0 | 84.2 | 96.7 | 78.9 |
| 200_164 | 83.7 | 96.0 | 78.5 | 84.2 | 95.1 | 79.6 |
| 214_164 | 83.6 | 96.8 | 78.0 | 84.2 | 95.7 | 79.3 |
| 170_164 | 83.5 | 97.0 | 77.7 | 84.2 | 96.3 | 79.0 |
| 213_164 | 83.5 | 97.0 | 77.7 | 84.2 | 96.1 | 79.1 |
| 184_164 | 83.5 | 97.6 | 77.5 | 84.2 | 97.0 | 78.8 |
| 292_164 | 83.4 | 95.4 | 78.3 | 84.2 | 93.7 | 80.2 |
| 171_164 | 83.3 | 96.5 | 77.7 | 84.2 | 96.5 | 79.0 |
| 172_164 | 83.3 | 97.6 | 77.3 | 84.2 | 97.0 | 78.8 |
| 264_164 | 84.7 | 95.4 | 80.2 | 84.1 | 94.3 | 79.8 |
| 70_164 | 84.2 | 95.9 | 79.2 | 84.1 | 95.1 | 79.4 |
| 269_164 | 84.1 | 95.3 | 79.3 | 84.1 | 94.1 | 79.8 |
| 239_164 | 84.0 | 96.9 | 78.5 | 84.1 | 95.9 | 79.1 |
| 71_164 | 84.0 | 97.0 | 78.4 | 84.1 | 96.7 | 78.8 |
| 234_164 | 83.7 | 97.4 | 77.9 | 84.1 | 96.7 | 78.8 |
| 78_164 | 83.6 | 96.1 | 78.3 | 84.1 | 95.3 | 79.3 |
| 96_164 | 83.6 | 96.3 | 78.1 | 84.1 | 95.7 | 79.2 |
| 19_164 | 83.6 | 97.6 | 77.7 | 84.1 | 96.7 | 78.8 |
| 138_164 | 83.6 | 97.0 | 77.9 | 84.1 | 95.7 | 79.2 |
| 245_164 | 83.3 | 97.0 | 77.5 | 84.1 | 96.3 | 78.9 |
| 111_164 | 84.1 | 94.7 | 79.6 | 84.0 | 94.1 | 79.7 |
| 304_164 | 84.1 | 96.2 | 78.9 | 84.0 | 94.9 | 79.4 |
| 250_164 | 83.9 | 95.0 | 79.2 | 84.0 | 94.9 | 79.4 |
| 178_164 | 83.9 | 96.2 | 78.6 | 84.0 | 94.9 | 79.4 |
| 289_164 | 83.9 | 94.9 | 79.3 | 84.0 | 93.7 | 79.9 |
| 84_164 | 83.9 | 95.9 | 78.8 | 84.0 | 94.9 | 79.3 |
| 116_164 | 83.9 | 95.8 | 78.8 | 84.0 | 94.9 | 79.3 |
| 180_164 | 83.7 | 96.7 | 78.1 | 84.0 | 96.1 | 78.8 |
| 94_164 | 83.7 | 96.5 | 78.2 | 84.0 | 95.1 | 79.3 |
| 164_253 | 83.7 | 96.5 | 78.3 | 84.0 | 95.3 | 79.3 |
| 82_164 | 83.6 | 97.0 | 77.9 | 84.0 | 95.9 | 78.9 |
| 132_164 | 83.6 | 96.7 | 78.0 | 84.0 | 96.1 | 78.8 |
| 265_164 | 83.6 | 94.8 | 78.8 | 84.0 | 93.7 | 79.8 |
| 274_164 | 83.6 | 97.4 | 77.8 | 84.0 | 96.1 | 78.9 |
| 164_252 | 83.6 | 97.0 | 78.0 | 84.0 | 96.1 | 78.9 |
| 41_164 | 83.5 | 96.5 | 78.0 | 84.0 | 95.7 | 79.1 |
| 230_164 | 83.5 | 97.0 | 77.7 | 84.0 | 96.5 | 78.7 |
| 191_164 | 83.5 | 96.1 | 78.1 | 84.0 | 95.1 | 79.3 |
| 196_164 | 83.5 | 96.5 | 77.9 | 84.0 | 96.3 | 78.8 |
| 112_164 | 83.5 | 96.9 | 77.8 | 84.0 | 96.3 | 78.8 |
| 280_164 | 83.4 | 96.6 | 77.7 | 84.0 | 96.3 | 78.8 |
| 99_164 | 83.4 | 97.0 | 77.6 | 84.0 | 96.1 | 78.8 |
| 224_164 | 83.4 | 96.3 | 78.0 | 84.0 | 95.7 | 79.0 |
| 193_164 | 83.4 | 97.5 | 77.4 | 84.0 | 96.5 | 78.7 |
| 17_164 | 83.4 | 97.7 | 77.3 | 84.0 | 96.7 | 78.6 |
| 20_164 | 83.4 | 96.5 | 77.8 | 84.0 | 95.5 | 79.1 |
| 164_108 | 83.4 | 97.1 | 77.5 | 84.0 | 96.1 | 78.8 |
| 28_164 | 83.3 | 96.7 | 77.6 | 84.0 | 95.7 | 79.1 |
| 298_164 | 83.3 | 97.3 | 77.3 | 84.0 | 96.5 | 78.7 |
| 240_164 | 83.3 | 95.3 | 78.2 | 84.0 | 94.9 | 79.4 |
| 198_164 | 83.2 | 97.0 | 77.3 | 84.0 | 96.3 | 78.8 |
| 220_164 | 84.2 | 96.7 | 78.9 | 83.9 | 95.7 | 78.8 |
| 124_164 | 84.1 | 97.4 | 78.4 | 83.9 | 96.1 | 78.8 |
| 236_164 | 84.0 | 94.7 | 79.5 | 83.9 | 93.9 | 79.7 |
| 282_164 | 83.9 | 96.0 | 78.8 | 83.9 | 94.9 | 79.2 |
| 235_164 | 83.9 | 96.6 | 78.4 | 83.9 | 96.1 | 78.8 |
| 232_164 | 83.9 | 95.1 | 79.2 | 83.9 | 93.1 | 80.0 |
| 57_164 | 83.8 | 95.5 | 78.8 | 83.9 | 94.3 | 79.4 |
| 277_164 | 83.8 | 96.8 | 78.2 | 83.9 | 95.5 | 78.9 |
| 173_164 | 83.7 | 96.8 | 78.1 | 83.9 | 95.5 | 78.9 |
| 227_164 | 83.7 | 96.0 | 78.4 | 83.9 | 94.9 | 79.2 |
| 69_164 | 83.7 | 97.0 | 78.1 | 83.9 | 95.9 | 78.8 |
| 47_164 | 83.7 | 97.0 | 78.0 | 83.9 | 95.9 | 78.8 |
| 122_164 | 83.6 | 96.5 | 78.1 | 83.9 | 95.5 | 79.0 |
| 242_164 | 83.6 | 97.2 | 77.8 | 83.9 | 96.1 | 78.8 |
| 176_164 | 83.6 | 97.2 | 77.7 | 83.9 | 96.3 | 78.6 |
| 202_164 | 83.6 | 97.3 | 77.7 | 83.9 | 96.1 | 78.7 |
| 197_164 | 83.6 | 97.1 | 77.8 | 83.9 | 96.3 | 78.7 |
| 218_164 | 83.6 | 97.1 | 77.9 | 83.9 | 96.1 | 78.8 |
| 46_164 | 83.5 | 97.0 | 77.7 | 83.9 | 96.3 | 78.7 |
| 86_164 | 83.5 | 97.4 | 77.6 | 83.9 | 96.5 | 78.5 |
| 93_164 | 83.5 | 97.0 | 77.8 | 83.9 | 96.3 | 78.6 |
| 63_164 | 83.5 | 96.5 | 78.0 | 83.9 | 96.1 | 78.7 |
| 109_164 | 83.5 | 96.9 | 77.9 | 83.9 | 95.7 | 78.9 |
| 204_164 | 83.5 | 96.9 | 77.8 | 83.9 | 95.7 | 78.8 |
| 216_164 | 83.5 | 97.1 | 77.7 | 83.9 | 96.3 | 78.6 |
| 169_164 | 83.5 | 96.7 | 77.9 | 83.9 | 95.7 | 78.8 |
| 164_254 | 83.5 | 96.6 | 77.9 | 83.9 | 95.9 | 78.8 |
| 164_203 | 83.5 | 97.0 | 77.7 | 83.9 | 96.3 | 78.7 |
| 98_164 | 83.4 | 97.0 | 77.7 | 83.9 | 96.1 | 78.7 |
| 221_164 | 83.4 | 97.3 | 77.5 | 83.9 | 96.7 | 78.4 |
| 233_164 | 83.4 | 96.0 | 78.0 | 83.9 | 95.1 | 79.1 |
| 284_164 | 83.4 | 96.9 | 77.6 | 83.9 | 96.5 | 78.6 |
| 42_164 | 83.4 | 97.1 | 77.6 | 83.9 | 96.1 | 78.8 |
| 56_164 | 83.4 | 97.2 | 77.6 | 83.9 | 95.9 | 78.8 |
| 296_164 | 83.4 | 97.1 | 77.5 | 83.9 | 96.3 | 78.6 |
| 36_164 | 83.4 | 97.0 | 77.6 | 83.9 | 96.1 | 78.8 |
| 164_229 | 83.4 | 97.1 | 77.5 | 83.9 | 96.7 | 78.4 |
| 134_164 | 83.3 | 97.0 | 77.4 | 83.9 | 96.7 | 78.4 |
| 294_164 | 83.3 | 97.1 | 77.3 | 83.9 | 96.5 | 78.5 |
| 113_164 | 83.3 | 97.3 | 77.3 | 83.9 | 96.5 | 78.5 |
| 164_273 | 83.3 | 97.6 | 77.2 | 83.9 | 96.5 | 78.6 |
| 164_238 | 83.2 | 97.6 | 77.1 | 83.9 | 97.2 | 78.3 |
| 74_164 | 83.0 | 96.9 | 77.1 | 83.9 | 95.9 | 78.8 |
| 102_164 | 84.5 | 95.9 | 79.6 | 83.8 | 93.5 | 79.7 |
| 270_164 | 84.3 | 95.8 | 79.4 | 83.8 | 93.5 | 79.6 |
| 189_164 | 84.0 | 95.5 | 79.0 | 83.8 | 95.1 | 79.0 |
| 262_164 | 84.0 | 95.5 | 79.0 | 83.8 | 94.5 | 79.2 |
| 164_58 | 83.9 | 94.2 | 79.5 | 83.8 | 92.7 | 79.9 |
| 164_251 | 83.9 | 96.0 | 78.7 | 83.8 | 94.1 | 79.4 |
| 103_164 | 83.8 | 96.5 | 78.3 | 83.8 | 95.7 | 78.8 |
| 208_164 | 83.8 | 97.1 | 78.1 | 83.8 | 96.5 | 78.4 |
| 110_164 | 83.8 | 95.5 | 78.8 | 83.8 | 94.5 | 79.2 |
| 281_164 | 83.7 | 96.0 | 78.4 | 83.8 | 95.3 | 78.9 |
| 68_164 | 83.7 | 96.6 | 78.1 | 83.8 | 95.3 | 78.8 |
| 249_164 | 83.7 | 97.0 | 78.1 | 83.8 | 96.5 | 78.3 |
| 219_164 | 83.6 | 97.2 | 77.9 | 83.8 | 95.7 | 78.8 |
| 120_164 | 83.6 | 96.8 | 77.9 | 83.8 | 95.9 | 78.7 |
| 225_164 | 83.6 | 96.5 | 78.1 | 83.8 | 95.3 | 78.9 |
| 52_164 | 83.6 | 97.0 | 77.9 | 83.8 | 96.1 | 78.6 |
| 297_164 | 83.6 | 97.0 | 77.9 | 83.8 | 95.7 | 78.7 |
| 212_164 | 83.6 | 97.0 | 77.8 | 83.8 | 95.9 | 78.6 |
| 248_164 | 83.6 | 97.0 | 77.8 | 83.8 | 95.9 | 78.6 |
| 88_164 | 83.6 | 97.3 | 77.8 | 83.8 | 96.1 | 78.6 |
| 257_164 | 83.6 | 96.8 | 78.0 | 83.8 | 96.1 | 78.5 |
| 244_164 | 83.6 | 97.4 | 77.7 | 83.8 | 96.1 | 78.6 |
| 258_164 | 83.6 | 97.0 | 77.9 | 83.8 | 95.9 | 78.7 |
| 164_79 | 83.6 | 97.3 | 77.7 | 83.8 | 96.3 | 78.5 |
| 181_164 | 83.5 | 97.0 | 77.7 | 83.8 | 96.1 | 78.6 |
| 117_164 | 83.5 | 97.0 | 77.7 | 83.8 | 96.1 | 78.5 |
| 51_164 | 83.5 | 96.7 | 77.9 | 83.8 | 96.1 | 78.5 |

TABLE 5-continued

| Gene | Training cohort | | | Validation cohort | | |
|---|---|---|---|---|---|---|
| | Accuracy | Sensitivity | Specificity | Accuracy | Sensitivity | Specificity |
| 209_164 | 83.5 | 97.0 | 77.7 | 83.8 | 95.9 | 78.6 |
| 72_164 | 83.5 | 96.8 | 77.9 | 83.8 | 96.1 | 78.6 |
| 101_164 | 83.5 | 96.8 | 77.9 | 83.8 | 95.7 | 78.7 |
| 59_164 | 83.5 | 97.0 | 77.7 | 83.8 | 96.1 | 78.5 |
| 222_164 | 83.5 | 96.5 | 77.9 | 83.8 | 95.9 | 78.6 |
| 123_164 | 83.5 | 96.8 | 77.9 | 83.8 | 95.7 | 78.7 |
| 266_164 | 83.5 | 96.9 | 77.8 | 83.8 | 95.9 | 78.7 |
| 133_164 | 83.5 | 97.0 | 77.7 | 83.8 | 95.9 | 78.6 |
| 91_164 | 83.5 | 96.7 | 77.9 | 83.8 | 96.1 | 78.6 |
| 35_164 | 83.5 | 97.1 | 77.6 | 83.8 | 96.3 | 78.5 |
| 54_164 | 83.5 | 97.1 | 77.7 | 83.8 | 96.3 | 78.5 |
| 293_164 | 83.5 | 96.9 | 77.9 | 83.8 | 95.9 | 78.7 |
| 291_164 | 83.5 | 97.4 | 77.6 | 83.8 | 96.1 | 78.5 |
| 164_267 | 83.5 | 97.0 | 77.8 | 83.8 | 96.1 | 78.6 |
| 164_285 | 83.5 | 96.4 | 78.0 | 83.8 | 95.9 | 78.6 |
| 164 | 83.4 | 97.0 | 77.7 | 83.8 | 95.9 | 78.6 |
| 167_1 | 81.9 | 89.1 | 78.8 | 82.6 | 86.0 | 81.1 |
| 166_217 | 82.3 | 82.4 | 82.3 | 82.3 | 80.7 | 83.0 |
| 183_169 | 81.9 | 89.3 | 78.7 | 82.3 | 89.0 | 79.4 |
| 246_5 | 81.0 | 86.8 | 78.6 | 82.2 | 87.6 | 79.9 |
| 3_168 | 81.3 | 89.0 | 78.1 | 82.0 | 86.8 | 80.0 |
| 165_2 | 81.2 | 90.1 | 77.4 | 81.8 | 90.2 | 78.3 |
| 166_87 | 82.9 | 88.5 | 80.5 | 81.5 | 86.6 | 79.3 |
| 60_166 | 81.3 | 84.3 | 80.0 | 81.5 | 83.9 | 80.5 |
| 165_136 | 80.0 | 94.4 | 73.9 | 81.5 | 94.9 | 75.7 |
| 7_29 | 80.5 | 84.8 | 78.7 | 81.3 | 84.1 | 80.1 |
| 49_165 | 80.4 | 93.5 | 74.8 | 81.3 | 93.9 | 75.9 |
| 231_165 | 80.2 | 92.7 | 74.8 | 81.3 | 92.9 | 76.2 |
| 165_237 | 80.1 | 90.4 | 75.7 | 81.2 | 92.3 | 76.5 |
| 2_260 | 81.0 | 88.6 | 77.7 | 81.0 | 87.4 | 78.3 |
| 165_288 | 80.4 | 93.6 | 74.8 | 81.0 | 94.7 | 75.1 |
| 165_131 | 80.3 | 95.7 | 73.7 | 81.0 | 96.1 | 74.6 |
| 303_1 | 80.2 | 86.7 | 77.5 | 80.8 | 84.4 | 79.3 |
| 1_15 | 80.0 | 86.2 | 77.4 | 80.7 | 83.3 | 79.6 |
| 119_2 | 80.8 | 88.6 | 77.4 | 80.6 | 86.8 | 77.9 |
| 135_167 | 80.6 | 85.9 | 78.3 | 80.6 | 85.2 | 78.7 |
| 3_228 | 80.1 | 83.0 | 78.8 | 80.6 | 81.9 | 80.1 |
| 3_130 | 80.7 | 85.0 | 78.8 | 80.5 | 83.3 | 79.3 |
| 2_128 | 80.6 | 87.3 | 77.8 | 80.5 | 87.4 | 77.5 |
| 23_2 | 80.7 | 87.9 | 77.6 | 80.4 | 86.2 | 77.9 |
| 33_1 | 80.6 | 85.8 | 78.5 | 80.4 | 83.5 | 79.1 |
| 194_1 | 80.5 | 85.4 | 78.5 | 80.4 | 81.9 | 79.8 |
| 8_1 | 80.9 | 87.4 | 78.1 | 80.3 | 82.5 | 79.4 |
| 201_1 | 80.4 | 86.1 | 78.0 | 80.3 | 83.3 | 79.0 |
| 125_1 | 80.0 | 84.7 | 78.1 | 80.3 | 81.7 | 79.8 |
| 48_1 | 81.2 | 88.3 | 78.2 | 80.1 | 82.9 | 78.9 |
| 3_11 | 80.1 | 85.2 | 77.9 | 80.1 | 82.1 | 79.3 |
| 105_2 | 80.1 | 86.9 | 77.1 | 80.1 | 88.4 | 76.6 |
| 4_179 | 80.8 | 81.7 | 80.4 | 80.0 | 82.3 | 79.1 |
| 14_2 | 80.5 | 87.8 | 77.4 | 80.0 | 87.4 | 76.8 |
| 2_40 | 80.4 | 87.8 | 77.3 | 80.0 | 87.2 | 77.0 |
| 95_2 | 80.1 | 87.9 | 76.8 | 80.0 | 86.6 | 77.2 |
| 76_1 | 80.0 | 87.0 | 77.1 | 80.0 | 82.7 | 78.8 |
| 114_1 | 80.0 | 85.9 | 77.4 | 80.0 | 82.7 | 78.9 |

TABLE 6

| SEQ ID NO: | Coefficient 1 | Coefficient 2 | Constant term |
|---|---|---|---|
| 18_164 | −1.60 | 2.07 | −4.82 |
| 255_164 | −0.98 | 2.48 | −11.23 |
| 177_164 | −1.10 | 2.10 | −4.44 |
| 4_164 | −0.85 | 1.78 | −8.30 |
| 164_9 | 1.73 | −0.66 | −9.70 |
| 300_164 | −1.00 | 2.32 | −9.50 |
| 272_164 | −0.85 | 1.91 | −9.04 |
| 206_164 | −0.91 | 2.23 | −12.83 |
| 12_164 | −0.92 | 2.10 | −10.95 |
| 166_164 | −0.55 | 1.58 | −9.95 |
| 168_164 | −1.98 | 1.65 | 3.77 |
| 6_164 | −1.20 | 1.67 | −5.70 |
| 259_164 | −0.82 | 1.95 | −8.42 |
| 115_164 | −1.79 | 2.29 | −2.81 |
| 164_129 | 1.72 | −1.15 | −5.57 |
| 190_164 | −0.48 | 2.13 | −15.45 |
| 199_164 | −1.10 | 2.33 | −11.65 |
| 66_164 | −1.88 | 2.44 | −4.75 |
| 164_107 | 2.03 | −0.94 | −10.10 |
| 207_164 | −0.64 | 2.08 | −13.57 |
| 263_164 | −0.56 | 2.11 | −13.68 |
| 16_164 | −0.88 | 1.86 | −5.46 |
| 37_164 | −1.04 | 1.96 | −9.42 |
| 38_164 | −1.07 | 2.09 | −10.66 |
| 261_164 | −1.03 | 2.07 | −5.02 |
| 305_164 | −1.09 | 1.82 | −5.02 |
| 55_164 | −1.62 | 1.94 | −0.70 |
| 127_164 | −1.50 | 2.16 | −6.33 |
| 104_164 | 0.60 | 1.44 | −17.01 |
| 31_164 | −0.56 | 2.05 | −14.07 |
| 121_164 | −1.11 | 1.74 | −5.58 |
| 81_164 | −0.53 | 1.74 | −11.39 |
| 295_164 | −1.02 | 1.89 | −7.03 |
| 6_165 | −1.66 | 2.22 | −5.42 |
| 25_164 | −0.40 | 1.88 | −13.73 |
| 83_164 | −0.57 | 1.59 | −9.82 |
| 32_164 | −2.50 | 1.64 | 14.46 |
| 247_164 | −0.67 | 1.75 | −9.95 |
| 26_164 | −0.32 | 1.70 | −12.40 |
| 302_164 | −1.77 | 1.59 | 9.32 |
| 268_164 | −0.92 | 1.75 | −7.57 |
| 90_164 | −0.98 | 1.71 | −1.22 |
| 287_164 | −0.85 | 1.89 | −9.10 |
| 278_164 | 1.28 | 2.03 | −32.12 |
| 5_164 | −1.83 | 1.84 | 1.34 |
| 137_164 | −0.56 | 1.98 | −12.35 |
| 276_164 | −1.05 | 1.76 | −3.97 |
| 164_271 | 1.61 | −0.44 | −10.57 |
| 167_164 | 0.63 | 1.44 | −17.66 |
| 126_164 | −1.58 | 1.79 | −1.86 |
| 211_164 | −0.88 | 1.83 | −9.18 |
| 67_164 | −1.06 | 1.72 | −5.62 |
| 39_164 | −1.38 | 1.62 | −2.09 |
| 186_164 | 0.55 | 1.66 | −17.66 |
| 182_164 | −0.93 | 2.15 | −9.42 |
| 226_164 | −0.68 | 2.13 | −10.43 |
| 27_164 | −0.27 | 1.80 | −13.29 |
| 275_164 | −1.38 | 1.65 | −1.88 |
| 185_164 | −0.40 | 1.75 | −11.50 |
| 92_164 | −0.97 | 1.81 | −6.28 |
| 10_164 | −0.86 | 1.79 | −9.84 |
| 279_164 | 0.87 | 1.72 | −21.61 |
| 256_164 | −0.69 | 1.70 | −10.03 |
| 80_164 | −0.65 | 2.02 | −12.33 |
| 164_195 | 1.96 | −0.27 | −15.00 |
| 243_164 | −1.46 | 1.66 | −0.44 |
| 22_164 | −0.39 | 1.97 | −13.31 |
| 164_97 | 1.69 | −0.48 | −11.18 |
| 34_164 | −0.46 | 1.67 | −10.31 |
| 215_164 | 1.34 | 1.94 | −31.62 |
| 187_164 | −0.51 | 1.68 | −8.56 |
| 164_174 | 1.59 | 0.59 | −17.66 |
| 50_164 | −0.24 | 1.85 | −14.26 |
| 62_164 | −0.22 | 1.65 | −12.75 |
| 75_164 | −0.23 | 1.77 | −13.59 |
| 61_164 | 0.79 | 1.52 | −18.90 |
| 89_164 | −0.43 | 1.57 | −7.48 |
| 306_164 | −0.59 | 1.72 | −10.12 |
| 164_286 | 1.45 | −0.32 | −9.57 |
| 85_164 | −0.39 | 1.98 | −11.58 |
| 192_164 | 0.78 | 1.60 | −20.45 |
| 223_164 | −1.58 | 1.66 | 0.62 |
| 299_164 | −0.75 | 2.07 | −10.44 |
| 73_164 | 0.45 | 1.81 | −19.02 |
| 241_164 | −1.09 | 1.46 | −0.04 |
| 118_164 | 0.71 | 1.67 | −21.70 |
| 283_164 | 0.29 | 1.54 | −14.75 |
| 164_77 | 1.74 | −1.41 | −2.70 |
| 175_164 | 1.39 | 1.98 | −32.32 |
| 164_65 | 1.68 | −0.74 | −7.18 |
| 7_164 | 0.43 | 1.43 | −15.72 |

TABLE 6-continued

| SEQ ID NO: | Coefficient 1 | Coefficient 2 | Constant term |
|---|---|---|---|
| 205_164 | −0.92 | 1.57 | −3.72 |
| 188_164 | −0.14 | 1.73 | −13.43 |
| 100_164 | −1.13 | 1.66 | −2.07 |
| 13_164 | −0.12 | 1.76 | −13.99 |
| 106_164 | −0.71 | 1.92 | −11.57 |
| 53_164 | −1.10 | 1.61 | 0.96 |
| 64_164 | −0.15 | 1.69 | −13.55 |
| 210_164 | −1.94 | 1.61 | 8.98 |
| 290_164 | −0.45 | 1.65 | −8.84 |
| 164_43 | 1.88 | −0.56 | −12.03 |
| 164_44 | 1.66 | −0.22 | −12.81 |
| 30_164 | −0.17 | 1.76 | −13.60 |
| 21_164 | −0.44 | 1.74 | −11.46 |
| 301_164 | 0.22 | 1.50 | −14.48 |
| 24_164 | −0.37 | 1.51 | −10.00 |
| 45_164 | −0.46 | 1.84 | −12.20 |
| 200_164 | −0.47 | 1.62 | −10.00 |
| 214_164 | −0.45 | 1.66 | −10.68 |
| 170_164 | −0.15 | 1.72 | −13.87 |
| 213_164 | −0.41 | 1.52 | −9.71 |
| 184_164 | −1.04 | 1.39 | −1.69 |
| 292_164 | −1.29 | 1.60 | −1.13 |
| 171_164 | −0.13 | 1.68 | −13.66 |
| 172_164 | 0.26 | 1.46 | −13.87 |
| 264_164 | 0.70 | 1.63 | −18.75 |
| 70_164 | −0.24 | 1.83 | −13.58 |
| 269_164 | −0.78 | 1.69 | −6.52 |
| 239_164 | −0.35 | 1.61 | −10.55 |
| 71_164 | −0.45 | 1.65 | −10.96 |
| 234_164 | 0.38 | 1.49 | −14.91 |
| 78_164 | −0.19 | 1.76 | −13.93 |
| 96_164 | −0.14 | 1.66 | −13.34 |
| 19_164 | 0.27 | 1.52 | −14.36 |
| 138_164 | 0.11 | 1.51 | −13.33 |
| 245_164 | 0.34 | 1.54 | −15.75 |
| 111_164 | 0.71 | 1.38 | −17.76 |
| 304_164 | 0.35 | 1.67 | −16.93 |
| 250_164 | −1.07 | 1.82 | −5.84 |
| 178_164 | −0.65 | 1.54 | −4.79 |
| 289_164 | 0.36 | 1.54 | −15.62 |
| 84_164 | 0.51 | 1.64 | −17.49 |
| 116_164 | −1.61 | 1.54 | 4.66 |
| 180_164 | −0.16 | 1.56 | −12.08 |
| 94_164 | 0.22 | 1.39 | −13.09 |
| 164_253 | 1.50 | −1.23 | 2.24 |
| 82_164 | −0.25 | 1.57 | −11.81 |
| 132_164 | 0.52 | 1.56 | −20.15 |
| 265_164 | −0.76 | 1.67 | −6.92 |
| 274_164 | −0.87 | 1.35 | −2.46 |
| 164_252 | 1.51 | −0.40 | −7.36 |
| 41_164 | −0.28 | 1.55 | −9.93 |
| 230_164 | 0.39 | 1.52 | −17.97 |
| 191_164 | −0.96 | 1.49 | −1.36 |
| 196_164 | −0.13 | 1.70 | −13.61 |
| 112_164 | −0.12 | 1.54 | −12.28 |
| 280_164 | 0.17 | 1.50 | −13.80 |
| 99_164 | 0.05 | 1.51 | −13.01 |
| 224_164 | 0.33 | 1.58 | −15.79 |
| 193_164 | −0.38 | 1.61 | −10.63 |
| 17_164 | 0.27 | 1.48 | −14.10 |
| 20_164 | 0.15 | 1.47 | −13.35 |
| 164_108 | 1.51 | −0.31 | −10.06 |
| 28_164 | −0.59 | 1.54 | −7.68 |
| 298_164 | −0.13 | 1.56 | −12.24 |
| 240_164 | −0.80 | 1.61 | −6.09 |
| 198_164 | −0.14 | 1.65 | −13.04 |
| 220_164 | −0.50 | 1.90 | −12.49 |
| 124_164 | −0.50 | 1.72 | −10.87 |
| 236_164 | −0.51 | 1.71 | −10.38 |
| 282_164 | 0.37 | 1.57 | −15.84 |
| 235_164 | 0.45 | 1.60 | −17.95 |
| 232_164 | −0.54 | 1.69 | −8.55 |
| 57_164 | −0.35 | 1.91 | −13.90 |
| 277_164 | 0.21 | 1.49 | −13.91 |
| 173_164 | −0.09 | 1.55 | −12.45 |
| 227_164 | −0.70 | 1.57 | −5.93 |
| 69_164 | −0.08 | 1.59 | −12.80 |
| 47_164 | −0.15 | 1.58 | −12.28 |
| 122_164 | 0.10 | 1.46 | −12.92 |
| 242_164 | −0.07 | 1.53 | −12.07 |
| 176_164 | −0.29 | 1.55 | −10.76 |
| 202_164 | −0.36 | 1.61 | −10.87 |
| 197_164 | −0.08 | 1.64 | −13.36 |
| 218_164 | −0.51 | 1.52 | −8.70 |
| 46_164 | 0.31 | 1.49 | −14.95 |
| 86_164 | −0.13 | 1.55 | −12.25 |
| 93_164 | −0.13 | 1.52 | −11.99 |
| 63_164 | −0.49 | 1.60 | −9.70 |
| 109_164 | 0.38 | 1.58 | −17.95 |
| 204_164 | −0.20 | 1.51 | −10.38 |
| 216_164 | −0.28 | 1.53 | −10.91 |
| 169_164 | 0.20 | 1.50 | −14.62 |
| 164_254 | 1.53 | −0.24 | −10.19 |
| 164_203 | 1.53 | 0.17 | −14.06 |
| 98_164 | 0.04 | 1.48 | −12.76 |
| 221_164 | −0.15 | 1.56 | −12.18 |
| 233_164 | −0.71 | 1.54 | −5.44 |
| 284_164 | −0.08 | 1.51 | −12.23 |
| 42_164 | −0.10 | 1.50 | −11.66 |
| 56_164 | −0.14 | 1.57 | −12.32 |
| 296_164 | −0.03 | 1.52 | −12.58 |
| 36_164 | −0.02 | 1.53 | −12.80 |
| 164_229 | 1.51 | −0.10 | −12.23 |
| 134_164 | −0.31 | 1.66 | −12.15 |
| 294_164 | 0.11 | 1.51 | −13.40 |
| 113_164 | −0.24 | 1.57 | −11.89 |
| 164_273 | 1.55 | −0.12 | −12.21 |
| 164_238 | 1.60 | −0.63 | −8.26 |
| 74_164 | 0.43 | 1.47 | −17.92 |
| 102_164 | 0.68 | 1.42 | −16.82 |
| 270_164 | 2.03 | 1.83 | −37.88 |
| 189_164 | 0.34 | 1.52 | −15.01 |
| 262_164 | −0.26 | 1.62 | −11.37 |
| 164_58 | 1.71 | 0.83 | −22.48 |
| 164_251 | 1.63 | −0.46 | −8.53 |
| 103_164 | −1.28 | 1.84 | −4.36 |
| 208_164 | 0.68 | 1.60 | −21.40 |
| 110_164 | −0.50 | 1.64 | −8.76 |
| 281_164 | −0.36 | 1.62 | −10.57 |
| 68_164 | −0.12 | 1.66 | −13.02 |
| 249_164 | −0.44 | 1.52 | −10.19 |
| 219_164 | −0.30 | 1.53 | −10.58 |
| 120_164 | 0.14 | 1.46 | −13.23 |
| 225_164 | −0.16 | 1.67 | −12.79 |
| 52_164 | 0.06 | 1.52 | −13.28 |
| 297_164 | 0.05 | 1.53 | −13.21 |
| 212_164 | 0.06 | 1.52 | −13.64 |
| 248_164 | −0.16 | 1.54 | −11.99 |
| 88_164 | 0.27 | 1.52 | −14.70 |
| 257_164 | −0.08 | 1.57 | −12.63 |
| 244_164 | 0.25 | 1.55 | −14.58 |
| 258_164 | −0.30 | 1.50 | −8.85 |
| 164_79 | 1.50 | 0.13 | −13.38 |
| 181_164 | −0.03 | 1.53 | −12.75 |
| 117_164 | 0.04 | 1.52 | −13.21 |
| 51_164 | −0.12 | 1.56 | −12.44 |
| 209_164 | −0.01 | 1.53 | −12.74 |
| 72_164 | −0.07 | 1.59 | −13.05 |
| 101_164 | −0.14 | 1.55 | −12.27 |
| 59_164 | −0.01 | 1.53 | −12.84 |
| 222_164 | −0.23 | 1.56 | −11.22 |
| 123_164 | 0.07 | 1.52 | −13.33 |
| 266_164 | 0.21 | 1.54 | −15.65 |
| 133_164 | 0.01 | 1.52 | −12.92 |
| 91_164 | −0.20 | 1.51 | −11.31 |
| 35_164 | −0.30 | 1.49 | −10.30 |
| 54_164 | −0.11 | 1.61 | −13.01 |
| 293_164 | 0.06 | 1.53 | −13.43 |
| 291_164 | −0.15 | 1.59 | −12.36 |
| 164_267 | 1.61 | −0.32 | −11.40 |
| 164_285 | 1.61 | −0.19 | −12.48 |
| 164 | 1.52 | NA | −12.87 |
| 167_1 | 1.12 | 1.96 | −28.15 |
| 166_217 | −0.69 | 1.95 | −10.62 |
| 183_169 | −4.31 | 3.31 | 14.07 |
| 246_5 | 3.66 | −3.20 | −2.97 |

TABLE 6-continued

| SEQ ID NO: | Coefficient 1 | Coefficient 2 | Constant term |
|---|---|---|---|
| 3_168 | 1.58 | −1.82 | 6.03 |
| 165_2 | 1.07 | 0.64 | −12.10 |
| 166_87 | −0.74 | 0.95 | −0.57 |
| 60_166 | 0.88 | −0.48 | −1.19 |
| 165_136 | 1.72 | −0.72 | −8.51 |
| 7_29 | 1.53 | 0.90 | −18.05 |
| 49_165 | −1.32 | 1.80 | −1.73 |
| 231_165 | 0.32 | 1.27 | −12.22 |
| 165_237 | 1.91 | −0.81 | −7.22 |
| 2_260 | 0.72 | 0.50 | −6.78 |
| 165_288 | 2.06 | −1.38 | −3.16 |
| 165_131 | 1.75 | −0.84 | −7.21 |
| 303_1 | 0.47 | 1.93 | −20.83 |
| 1_15 | 1.91 | 0.36 | −20.23 |
| 119_2 | −0.51 | 1.19 | −4.27 |
| 135_167 | 0.83 | 0.98 | −12.50 |
| 3_228 | 1.32 | 0.32 | −10.30 |
| 3_130 | 1.22 | 0.90 | −14.91 |
| 2_128 | 0.95 | 0.77 | −10.55 |
| 23_2 | 0.39 | 0.88 | −7.42 |
| 33_1 | 0.44 | 1.82 | −19.51 |
| 194_1 | 0.96 | 2.15 | −30.54 |
| 8_1 | 0.69 | 2.03 | −23.35 |
| 201_1 | 0.56 | 1.75 | −20.94 |
| 125_1 | 0.73 | 2.11 | −28.03 |
| 48_1 | 0.61 | 2.08 | −23.93 |
| 3_11 | 1.45 | −0.64 | −4.99 |
| 105_2 | 0.51 | 0.97 | −8.76 |
| 4_179 | −0.78 | 2.02 | −8.19 |
| 14_2 | −0.38 | 1.01 | −3.29 |
| 2_40 | 0.74 | 0.42 | −6.86 |
| 95_2 | 0.94 | 0.94 | −12.41 |
| 76_1 | 0.40 | 1.90 | −20.30 |
| 114_1 | 0.42 | 1.97 | −20.95 |

Example 2

<Discriminant Analysis Using Up to Five miRNAs in Combination>

In this Example, discriminants were prepared using one to five gene markers in the training cohort including the lung cancer patients and the test subjects without lung cancer (Table 11b1), and then, the discriminant performance was evaluated in the validation cohort (Table 11b2). Based on the evaluation, genes used in discriminants with high performance were extracted to obtain gene markers that were able to detect lung cancer.

To be more specific, firstly, the miRNA expression levels of the training cohort and the validation cohort obtained in the preceding Reference Examples were combined and normalized by global normalization. Secondly, in order to acquire diagnostic markers with higher reliability, only 396 genes having the gene expression level of $2^6$ or higher in 50% or more of the samples in either of the positive sample group (lung cancer patients) or the negative sample group (healthy subjects, benign bone and soft tissue tumor patients and benign breast disease patients and patients having a cancer other than lung cancer), were selected as analytes.

Thirdly, combinations of one to five genes of the 396 gene above were subjected to the Fisher's discriminant analysis using the 396 gene expression level measurement values described above to construct discriminants for discriminating the presence or absence of lung cancer. In this relation, discriminants with high discriminant performance were searched for using a modified greedy algorithm. Accuracy, sensitivity, and specificity in the validation cohort were further calculated using the discriminants prepared above, and the discriminant performance was validated using independent samples. As a result, total 750 discriminants including top 150 discriminants having higher performance as to the combinations of one to five genes were obtained. The genes contained in these discriminants were selected as other diagnostic markers for the lung cancer patients and the test subjects without lung cancer. In this way, miR-920, miR-1185-1-3p, miR-4327, miR-5739, miR-1185-2-3p, miR-1238-5p, miR-1246, miR-1470, miR-197-5p, miR-208a-5p, miR-2467-3p, miR-3122, miR-3160-5p, miR-320b, miR-3610, miR-3619-3p, miR-3937, miR-4447, miR-4480, miR-4505, miR-4515, miR-4535, miR-4706, miR-4718, miR-4730, miR-4734, miR-4755-3p, miR-4787-3p, miR-5008-5p, miR-5010-5p, miR-504-3p, miR-5100, miR-557, miR-6510-5p, miR-6511b-5p, miR-6515-3p, miR-6722-5p, miR-6737-5p, miR-6766-5p, miR-6769a-5p, miR-6771-5p, miR-6786-5p, miR-6794-5p, miR-6800-3p, miR-6802-5p, miR-6805-3p, miR-6819-5p, miR-6824-5p, miR-6858-5p, miR-6861-5p, miR-6880-3p, miR-7107-5p, miR-7109-5p, miR-7114-5p, miR-8071, miR-204-3p, miR-3154, miR-3960, miR-4433a-5p, miR-4462, miR-4476, miR-4508, miR-4687-3p, miR-4732-5p, miR-4771, miR-642a-3p, miR-6732-5p, miR-6820-5p, miR-6821-5p, miR-6829-5p, miR-6893-5p, miR-7108-3p, miR-7111-5p, miR-885-3p, miR-1343-3p, miR-6746-5p, miR-422a, miR-4632-5p, miR-6791-5p, miR-1225-3p, miR-1233-5p, miR-1268a, miR-1268b, miR-1273g-3p, miR-1290, miR-150-3p, miR-17-3p, miR-1908-5p, miR-1914-3p, miR-296-3p, miR-3131, miR-3162-5p, miR-3197, miR-320a, miR-342-5p, miR-365a-5p, miR-3679-5p, miR-371a-5p, miR-423-5p, miR-4257, miR-4270, miR-4286, miR-4417, miR-4442, miR-4454, miR-4507, miR-4516, miR-451a, miR-4665-3p, miR-4675, miR-4689, miR-4695-5p, miR-4739, miR-4745-5p, miR-5001-5p, miR-5698, miR-6075, miR-6125, miR-614, miR-615-5p, miR-638, miR-650, miR-6717-5p, miR-6721-5p, miR-6741-5p, miR-6752-5p, miR-6780b-5p, miR-6784-5p, miR-6875-5p, miR-744-5p, miR-760, miR-7977, miR-8059, miR-8063, miR-8072, miR-92a-2-5p, miR-1228-3p, miR-1275, miR-1307-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, and miR-7975, and the relevant polynucleotides consisting of nucleotide sequences of SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121,123, 126 to 131, 136, 139 to 142, 144, 145, 146, 147, 149 to 152, 155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328, were found. Among them, the genes newly found as the marker for examining the presence or absence of lung cancer are polynucleotides consisting of the nucleotide sequences represented by SEQ ID NOs: 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328.

The sensitivities in the validation cohort determined by the discriminants obtained using any single one of the 88 polynucleotides consisting of the nucleotide sequences represented by SEQ ID NOs: 188, 164, 85, 13, 231, 319, 263, 165, 226, 94, 190, 328, 80, 220, 316, 2, 115, 299, 50, 150, 31, 318, 149, 312, 70, 127, 183, 66, 12, 255, 162, 199, 222, 278, 260, 246, 22, 106, 322, 57, 309, 184, 206, 207, 201, 217, 317, 300, 102, 159, 73, 78, 315, 107, 23, 33, 307, 114, 185, 128, 109, 59, 236, 214, 140, 99, 144, 47, 241, 321, 130, 95, 142, 234, 286, 173, 320, 314, 111, 27, 304, 177, 74, 34, 17, 211, 193, and 256 among the polynucleotides described above are shown in Table 3. Also, discriminant coefficients and constant terms are shown in Table 4. In this context, the general sensitivity of the existing marker CEA has been reported as being 69%. Accordingly, it was demonstrated that the polynucleotides represented by these SEQ ID NOs singly detect lung cancer with sensitivity beyond CEA.

The genes represented by SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121, 123, 126 to 131, 136, 139 to 142, 144, 145, 146, 147, 149 to 152, 155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328 provide excellent lung cancer discriminant performance, when the genes are used not only alone but also in combinations of, for example, 2, 3, 4, 5, 6, 7, 8, 9, 10 or more genes. For example, when a discriminant was prepared using gene expression level of the nucleotide sequence represented by SEQ ID NO: 18 alone, the discrimination accuracy in the validation cohort was 61.6%; however, when a discriminant was prepared using two genes (SEQ ID NOs: 18 and 164) in combination, the discrimination accuracy in the validation cohort was 86.7%, if a discriminant was prepared using three genes (SEQ ID NOs: 18, 164 and 255), the discrimination accuracy in the validation cohort was 88.2%, when a discriminant was prepared using four genes (SEQ ID NOs: 18, 121, 130 and 164), the discrimination accuracy in the validation cohort was 88.6%, and when a discriminant was prepared using five genes (SEQ ID NOs: 18, 121, 130, 136 and 164), the discrimination accuracy in the validation cohort was 88.8%.

Figure 2:
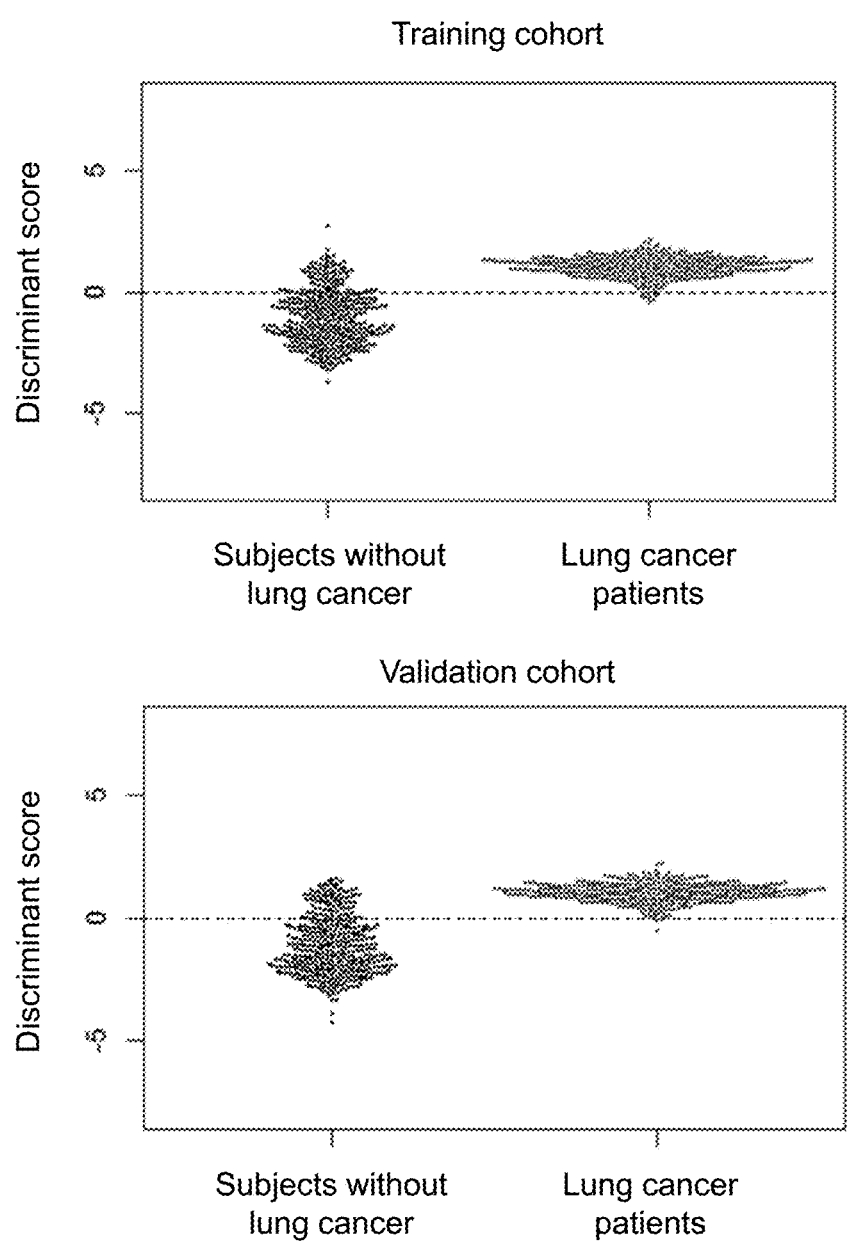
FIG. 2 Upper panel: a discriminant (0.960×hsa-miR-1343-3p-0.703×hsa-miR-197-5p-0.184×hsa-miR-6741-5p+0.506×hsa-miR-4687-3p-0.471×hsa-miR-1268b-1.273) was prepared by use of Fisher's discriminant analysis from the measured expression level values of hsa-miR-1343-3p (SEQ ID NO: 164), hsa-miR-197-5p (SEQ ID NO: 18), hsa-miR-6741-5p (SEQ ID NO: 268), hsa-miR-4687-3p (SEQ ID NO: 147), and hsa-miR-1268b (SEQ ID NO: 184) in sera of test subjects without lung cancer (total 2,777 people including 1,233 healthy subjects, 263 benign bone and soft tissue tumor patients and benign breast disease patients, 1,281 patients having a cancer other than lung cancer) and lung cancer patients (1,186 people) selected as a training cohort, and discriminant scores obtained from the discriminant were plotted on the ordinate against the sample groups on the abscissa. In consideration of easy viewability of the figure, the discriminant scores are shown as to 400 people each extracted at random from the test subjects without lung cancer and the patients with lung cancer. The dotted line in the panel depicts a discriminant boundary that offered a discriminant score of 0 and discriminated between the two groups. Lower panel: discriminant scores obtained from assignment to the discriminant (0.960×hsa-miR-1343-3p-0.703×hsa-miR-197-5p-0.184×hsa-miR-6741-5p+0.506× hsa-miR-4687-3p-0.471×hsa-miR-1268b-1.273) prepared from the training cohort as to the measured expression level values of hsa-miR-1343-3p (SEQ ID NO: 164), hsa-miR-197-5p (SEQ ID NO: 18), hsa-miR-6741-5p (SEQ ID NO: 268), hsa-miR-4687-3p (SEQ ID NO: 147), and hsa-miR-1268b (SEQ ID NO: 184) in sera of test subjects without lung cancer (total 1,191 people including 567 healthy subjects, 105 benign bone and soft tissue tumor patients and benign breast disease patients, 519 patients having a cancer other than lung cancer) and lung cancer patients (508 people) selected as a validation cohort were plotted on the ordinate against the sample groups on the abscissa. In consideration of easy viewability of the figure, the discriminant scores are shown as to 400 people each extracted at random from the test subjects without lung cancer and the patients with lung cancer. The dotted line in the panel depicts the discriminant boundary that offered a discriminant score of 0 and discriminated between the two groups.

As to the discriminant prepared using measurement values of nucleotide sequences represented by SEQ ID NOs: 164, 18, 268, 147 and 184 in combination, discriminant scores of 1,186 lung cancer patients and 2,777 test subjects without lung cancer in the training cohort were significantly separated, as shown in the upper panel of FIG. 2.

The same results were able to be reproduced also in the validation cohort (FIG. 2, lower panel).

Figure 3:
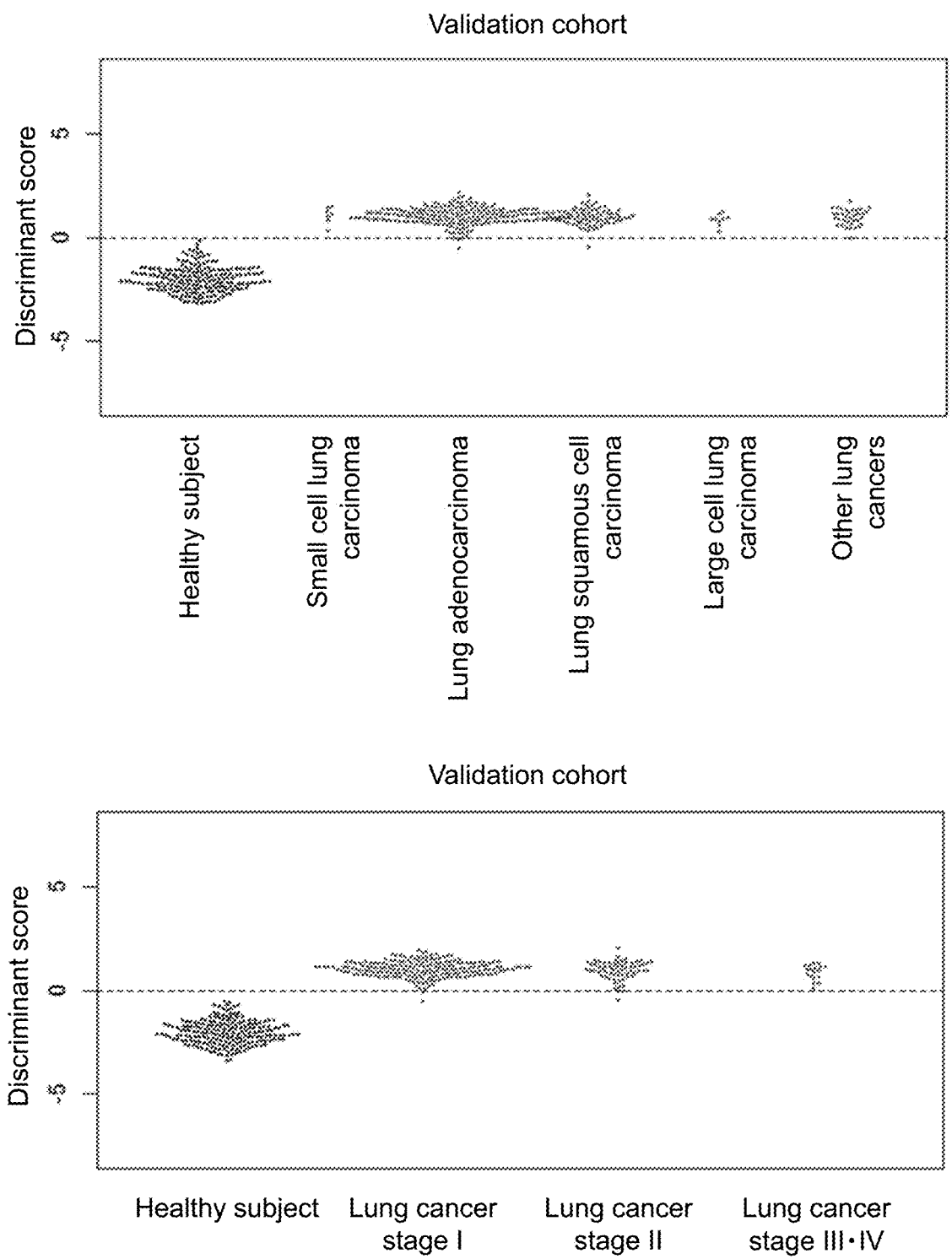
FIG. 3 Upper panel: the discriminant scores of the validation cohort described above are categorized on the basis of the healthy subjects and each histological type of lung cancer (small cell carcinoma, adenocarcinoma, squamous cell carcinoma, large cell carcinoma, and other lung cancers). The dotted line in the panel depicts the discriminant boundary that offered a discriminant score of 0 and discriminated between the two groups. Lower panel: the discriminant scores of the validation cohort described above are categorized on the basis of the healthy subjects and the progressive stages of lung cancer (stage I, stage II, and stage III/IV (stage III and stage IV)). The dotted line in the panel depicts the discriminant boundary that offered a discriminant score of 0 and discriminated between the two groups.

The discriminant scores were categorized on the basis of the histological types and stages of the lung cancer patients. As a result, it was confirmed that lung cancer in all of the categories was able to be detected with high sensitivity (FIG. 3).

Of the 750 discriminants obtained above, the number of discriminants exhibiting a discrimination accuracy of 85% or more both in the training cohort and the validation cohort was 305. These discriminants having particularly high discriminant performance contained at least one of the genes represented by SEQ ID NOs: 18, 4, 130, 2, 9, 17, and 121. These seven genes are referred to as "cancer type-specific polynucleotide group".

Specifically, when measurement was carried out using a polynucleotide consisting of the nucleotide sequence represented by SEQ ID NO: 18 or a complementary sequence thereof as a target nucleic acid, discrimination accuracy is shown in Table 7-1. The measurement using a combination of 2, 3, 4 or 5 genes comprising the polynucleotide consisting of the nucleotide sequence represented by SEQ ID NO: 18 or a complementary sequence thereof exhibited the highest accuracy of 86.7%, 88.2%, 88.6% and 88.8%, respectively, in the validation cohort.

Further, when measurement was carried out using a polynucleotide consisting of the nucleotide sequence represented by SEQ ID NO: 4 or a complementary sequence thereof as a target nucleic acid, discrimination accuracy is shown in Table 7-2. The measurement using a combination of 2, 3, 4 or 5 genes comprising the polynucleotide consisting of the nucleotide sequence represented by SEQ ID NO: 4 or a complementary sequence thereof exhibited the highest accuracy of 86.0%, 87.1%, 87.8% and 87.8%, respectively, in the validation cohort.

Further, when measurement was carried out using a polynucleotide consisting of the nucleotide sequence represented by SEQ ID NO: 130 or a complementary sequence thereof as a target nucleic acid, discrimination accuracy is shown in Table 7-3. The measurement using a combination of 3, 4 or 5 genes comprising the polynucleotide consisting of the nucleotide sequence represented by SEQ ID NO: 130 or a complementary sequence thereof exhibited the highest accuracy of 86.9%, 88.6% and 88.8%, respectively, in the validation cohort.

Further, when measurement was carried out using a polynucleotide consisting of the nucleotide sequence represented by SEQ ID NO: 2 or a complementary sequence thereof as a target nucleic acid, discrimination accuracy is shown in Table 7-4. The measurement using a combination of 4 or 5 genes comprising the polynucleotide consisting of the nucleotide sequence represented by SEQ ID NO: 2 or a complementary sequence thereof exhibited the highest accuracy of 86.3% and 87.8%, respectively, in the validation cohort.

Further, when measurement was carried out using a polynucleotide consisting of the nucleotide sequence represented by SEQ ID NO: 9 or a complementary sequence thereof as a target nucleic acid, discrimination accuracy is shown in Table 7-5. The measurement using a combination of 3, 4 or 5 genes comprising the polynucleotide consisting of the nucleotide sequence represented by SEQ ID NO: 9 or a complementary sequence thereof exhibited the highest accuracy of 86.9%, 87.2% and 87.6%, respectively, in the validation cohort.

Further, when measurement was carried out using a polynucleotide consisting of the nucleotide sequence represented by SEQ ID NO: 17 or a complementary sequence thereof as a target nucleic acid, discrimination accuracy is shown in Table 7-6. The measurement using a combination of 3, 4 or 5 genes comprising the polynucleotide consisting of the nucleotide sequence represented by SEQ ID NO: 17 or a complementary sequence thereof exhibited the highest accuracy of 85.6%, 87.5% and 87.8%, respectively, in the validation cohort.

Further, when measurement was carried out using a polynucleotide consisting of the nucleotide sequence represented by SEQ ID NO: 121 or a complementary sequence thereof as a target nucleic acid, discrimination accuracy is shown in Table 7-7. The measurement using a combination of 3, 4 or 5 genes comprising the polynucleotide consisting of the nucleotide sequence represented by SEQ ID NO: 121 or a complementary sequence thereof exhibited the highest accuracy of 86.9%, 88.6% and 88.8%, respectively, in the validation cohort.

Further, lung adenocarcinoma, lung squamous cell carcinoma, small cell lung carcinoma and large cell lung carcinoma were able to be detected with average sensitivities of 96.4%, 97.1%, 97.8% and 97.6%, respectively, determined by the 305 discriminants obtained using the polynucleotides consisting of SEQ ID NOs described in Tables 7-1 to 7-7 in combination. In addition, stage I (IA and IIA), stage II (IIA and IIB), and stage III/IV (IIIA, IIIB and IV) of lung cancer were able to be detected with average sensitivities of 96.9%, 94.0% and 94.6%, respectively, determined by the 305 discriminants obtained using the polynucleotides consisting of SEQ ID NOs described in Tables 7-1 to 7-7 in combination. Accordingly, the polynucleotides obtained in this Example exerted a high detection ability without missing a particular histological type or stage of progression of lung cancer.

From the above-mentioned results, the polynucleotides consisting of the nucleotide sequences of SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121, 123, 126 to 131, 136, 139 to 142, 144, 145, 146, 147, 149 to 152, 155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328, obtained in this Example, are deemed to be gene groups that lung cancer patients can be specifically discriminated from any of healthy subjects, benign bone and soft tissue tumor patients and benign breast disease patients, and patients having a cancer other than lung cancer. It was further demonstrated that high lung cancer discriminant performance can be obtained by using multiple polynucleotides in combination as target nucleic acids rather than using a single polynucleotide or fewer polynucleotides in combination. In this relation, particularly high discriminant performance can be obtained by using the polynucleotides contained in the cancer type-specific polynucleotide group in combination, wherein the combination of the multiple polynucleotides is not limited to those mentioned above. Even if the polynucleotides are used in any combination, lung cancer can be detected.

Specifically, as shown in the preceding Examples 1 or 2, it is concluded that in all of the polynucleotides consisting of the nucleotide sequences represented by SEQ ID NOs: 1 to 329 or complementary sequences thereof as the target nucleic acids, there exist combinations of 1, 2, 3, 4 or 5 genes that exhibit discriminant performance beyond the existing lung cancer markers, thus indicating that the polynucleotides are excellent diagnostic markers for lung cancer that can detect any histological type or stage of progression of lung cancer described in the preceding Reference Example.

TABLE 7-1

| Combined gene number | SEQ ID NO: | Validation cohort Sensitivity | Specificity | Accuracy |
|---|---|---|---|---|
| 2 | 18_164 | 98.2 | 81.8 | 86.7 |
| 3 | 18_164_255 | 98.2 | 83.9 | 88.2 |
| 3 | 18_164_300 | 97.8 | 83.0 | 87.5 |
| 3 | 18_164_190 | 97.6 | 83.0 | 87.4 |
| 3 | 18_85_164 | 97.2 | 83.2 | 87.4 |
| 3 | 18_147_164 | 98.2 | 82.5 | 87.2 |
| 3 | 18_22_164 | 97.4 | 82.8 | 87.2 |
| 3 | 18_164_312 | 98.2 | 82.3 | 87.1 |
| 3 | 18_66_164 | 97.8 | 82.5 | 87.1 |
| 3 | 18_78_164 | 97.8 | 82.4 | 87.0 |
| 3 | 18_27_164 | 97.4 | 82.5 | 87.0 |

TABLE 7-1-continued

| Combined gene number | SEQ ID NO: | Validation cohort Sensitivity | Specificity | Accuracy |
|---|---|---|---|---|
| 3 | 18_164_207 | 98.2 | 82.0 | 86.9 |
| 3 | 18_82_164 | 98.0 | 82.1 | 86.9 |
| 3 | 18_164_263 | 98.4 | 81.9 | 86.8 |
| 3 | 18_164_168 | 98.2 | 82.0 | 86.8 |
| 3 | 18_34_164 | 98.0 | 82.0 | 86.8 |
| 3 | 18_39_164 | 97.6 | 82.1 | 86.8 |
| 3 | 18_57_164 | 97.6 | 82.2 | 86.8 |
| 3 | 18_121_164 | 98.6 | 81.6 | 86.7 |
| 3 | 18_107_164 | 98.2 | 81.8 | 86.7 |
| 3 | 18_70_164 | 97.6 | 82.0 | 86.7 |
| 3 | 18_50_164 | 97.6 | 82.0 | 86.7 |
| 3 | 18_164_250 | 96.9 | 82.4 | 86.7 |
| 3 | 18_164_315 | 98.2 | 81.6 | 86.6 |
| 3 | 18_164_211 | 98.0 | 81.8 | 86.6 |
| 3 | 18_164_326 | 97.2 | 82.1 | 86.6 |
| 3 | 18_164_308 | 98.4 | 81.3 | 86.4 |
| 3 | 18_164_268 | 98.2 | 81.4 | 86.4 |
| 3 | 18_164_191 | 97.8 | 81.4 | 86.3 |
| 3 | 18_149_165 | 95.5 | 81.2 | 85.5 |
| 4 | 18_121_130_164 | 98.6 | 84.4 | 88.6 |
| 4 | 18_164_255_316 | 98.4 | 84.3 | 88.5 |
| 4 | 18_121_164_255 | 98.0 | 84.2 | 88.4 |
| 4 | 18_147_164_255 | 98.0 | 84.3 | 88.4 |
| 4 | 18_27_164_255 | 97.8 | 84.3 | 88.4 |
| 4 | 18_34_164_255 | 98.0 | 84.1 | 88.3 |
| 4 | 18_47_164_255 | 98.2 | 84.0 | 88.2 |
| 4 | 18_158_164_255 | 98.0 | 84.1 | 88.2 |
| 4 | 18_164_220_255 | 98.0 | 84.0 | 88.2 |
| 4 | 18_88_164_255 | 97.8 | 84.1 | 88.2 |
| 4 | 18_130_164_268 | 98.4 | 83.7 | 88.1 |
| 4 | 18_164_255_321 | 98.2 | 83.8 | 88.1 |
| 4 | 18_164_184_255 | 98.2 | 83.7 | 88.1 |
| 4 | 18_152_164_255 | 98.0 | 83.8 | 88.1 |
| 4 | 18_164_185_255 | 98.0 | 83.9 | 88.1 |
| 4 | 18_164_238_255 | 98.0 | 83.8 | 88.1 |
| 4 | 18_164_255_256 | 97.8 | 83.9 | 88.1 |
| 4 | 18_127_164_255 | 97.6 | 84.1 | 88.1 |
| 4 | 18_164_222_255 | 98.2 | 83.6 | 88.0 |
| 4 | 18_139_164_255 | 98.0 | 83.7 | 88.0 |
| 4 | 18_39_164_255 | 97.6 | 83.9 | 88.0 |
| 4 | 18_164_255_295 | 96.9 | 84.2 | 88.0 |
| 4 | 18_146_164_255 | 97.6 | 83.7 | 87.9 |
| 4 | 18_164_211_255 | 97.4 | 83.7 | 87.8 |
| 4 | 18_164_255_322 | 97.4 | 83.7 | 87.8 |
| 4 | 18_164_255_318 | 98.0 | 83.3 | 87.7 |
| 4 | 18_121_164_201 | 98.2 | 83.0 | 87.6 |
| 4 | 18_147_164_300 | 98.2 | 83.1 | 87.6 |
| 4 | 18_121_151_164 | 98.2 | 83.1 | 87.6 |
| 4 | 18_164_211_300 | 97.2 | 83.0 | 87.3 |
| 4 | 18_95_164_268 | 98.8 | 82.0 | 87.1 |
| 4 | 18_164_231_268 | 98.4 | 82.2 | 87.1 |
| 4 | 18_147_164_268 | 98.4 | 82.2 | 87.1 |
| 4 | 18_164_188_268 | 98.2 | 82.4 | 87.1 |
| 4 | 18_164_268_312 | 98.0 | 82.5 | 87.1 |
| 4 | 18_39_164_300 | 97.4 | 82.6 | 87.1 |
| 4 | 18_95_121_164 | 99.0 | 81.5 | 86.8 |
| 4 | 18_93_164_268 | 98.6 | 81.7 | 86.8 |
| 4 | 18_164_268_308 | 98.6 | 81.6 | 86.7 |
| 4 | 18_107_121_164 | 98.6 | 81.6 | 86.7 |
| 4 | 18_164_218_268 | 98.4 | 81.5 | 86.6 |
| 4 | 18_164_202_268 | 98.2 | 81.6 | 86.6 |
| 4 | 13_18_130_165 | 98.2 | 81.5 | 86.5 |
| 4 | 18_149_165_168 | 96.7 | 82.1 | 86.5 |
| 4 | 18_164_242_268 | 98.2 | 81.5 | 86.5 |
| 4 | 18_164_214_268 | 98.2 | 81.5 | 86.5 |
| 4 | 18_164_268_313 | 98.2 | 81.4 | 86.5 |
| 4 | 18_162_164_268 | 98.0 | 81.5 | 86.5 |
| 4 | 18_150_164_268 | 98.0 | 81.6 | 86.5 |
| 4 | 18_164_268_315 | 98.6 | 81.2 | 86.4 |
| 4 | 18_152_164_268 | 98.6 | 81.2 | 86.4 |
| 4 | 18_164_268_325 | 98.2 | 81.4 | 86.4 |
| 4 | 18_121_149_165 | 97.1 | 81.7 | 86.3 |
| 4 | 13_18_165_260 | 98.6 | 80.8 | 86.1 |
| 4 | 13_18_165_268 | 98.8 | 80.6 | 86.1 |
| 4 | 13_18_121_165 | 99.2 | 80.4 | 86.1 |
| 4 | 13_18_165_168 | 98.2 | 80.9 | 86.1 |

TABLE 7-1-continued

| Combined gene number | SEQ ID NO: | Sensitivity | Specificity | Accuracy |
|---|---|---|---|---|
| 4 | 18_149_165_268 | 96.1 | 81.7 | 86.0 |
| 4 | 13_18_83_165 | 98.0 | 80.9 | 86.0 |
| 4 | 13_18_165_263 | 98.6 | 80.5 | 85.9 |
| 4 | 2_18_165_268 | 95.5 | 81.7 | 85.8 |
| 4 | 13_18_165_211 | 98.2 | 80.4 | 85.8 |
| 4 | 13_18_165_256 | 98.2 | 80.4 | 85.7 |
| 4 | 13_18_165_276 | 98.0 | 80.2 | 85.5 |
| 4 | 13_18_165_302 | 98.0 | 80.1 | 85.5 |
| 4 | 13_18_165_190 | 98.2 | 79.9 | 85.3 |
| 5 | 18_121_130_136_164 | 98.6 | 84.6 | 88.8 |
| 5 | 18_121_130_164_314 | 98.4 | 84.6 | 88.8 |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_130_164_255_268 | 98.6 | 84.4 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_27_130_164_268 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_130_164_268_317 | 98.2 | 84.1 | 88.3 |
| 5 | 18_121_130_164_201 | 98.2 | 84.1 | 88.3 |
| 5 | 18_34_164_211_255 | 97.6 | 84.3 | 88.3 |
| 5 | 18_19_121_130_164 | 98.4 | 83.9 | 88.2 |
| 5 | 18_74_130_164_268 | 98.4 | 83.7 | 88.1 |
| 5 | 18_130_164_264_268 | 97.2 | 84.1 | 88.0 |
| 5 | 18_39_164_255_328 | 97.4 | 83.9 | 87.9 |
| 5 | 18_39_164_226_255 | 97.4 | 83.9 | 87.9 |
| 5 | 18_95_121_164_188 | 99.0 | 83.0 | 87.8 |
| 5 | 13_18_121_130_165 | 98.4 | 82.5 | 87.2 |
| 5 | 13_18_130_165_268 | 98.6 | 82.3 | 87.2 |
| 5 | 18_151_164_268_315 | 98.0 | 82.3 | 87.0 |
| 5 | 18_147_164_184_268 | 98.8 | 81.9 | 86.9 |
| 5 | 18_149_165_168_268 | 96.7 | 82.6 | 86.8 |
| 5 | 13_18_165_268_276 | 98.0 | 81.3 | 86.3 |
| 5 | 2_18_165_268_301 | 95.3 | 82.2 | 86.1 |
| 5 | 2_18_165_268_315 | 96.3 | 81.8 | 86.1 |
| 5 | 13_18_165_183_268 | 99.0 | 80.2 | 85.8 |
| 5 | 13_18_165_184_268 | 99.0 | 80.1 | 85.8 |

TABLE 7-2

| Combined gene number | SEQ ID NO: | Sensitivity | Specificity | Accuracy |
|---|---|---|---|---|
| 2 | 4_164 | 91.3 | 83.7 | 86.0 |
| 3 | 4_165_168 | 95.3 | 83.5 | 87.1 |
| 4 | 4_165_168_246 | 97.4 | 83.7 | 87.8 |
| 4 | 4_128_165_168 | 96.3 | 84.0 | 87.6 |
| 4 | 4_117_165_168 | 96.5 | 83.8 | 87.6 |
| 4 | 4_159_165_168 | 95.5 | 84.1 | 87.5 |
| 4 | 4_165_168_260 | 95.3 | 84.2 | 87.5 |
| 4 | 4_17_165_168 | 95.1 | 84.2 | 87.5 |
| 4 | 4_165_168_173 | 96.3 | 83.6 | 87.4 |
| 4 | 4_80_165_168 | 96.5 | 82.6 | 86.8 |
| 4 | 4_99_165_168 | 94.5 | 83.4 | 86.7 |
| 4 | 2_4_168_246 | 93.3 | 82.8 | 85.9 |
| 4 | 4_17_115_168 | 92.1 | 83.3 | 85.9 |
| 4 | 4_17_115_302 | 89.8 | 84.1 | 85.8 |
| 4 | 4_94_173_183 | 93.9 | 82.2 | 85.7 |
| 4 | 2_4_173_183 | 93.3 | 82.2 | 85.5 |
| 4 | 2_4_115_168 | 90.8 | 83.3 | 85.5 |
| 4 | 4_17_115_184 | 91.5 | 82.7 | 85.3 |
| 5 | 4_17_165_168_173 | 96.5 | 84.1 | 87.8 |
| 5 | 4_17_165_168_223 | 95.7 | 84.5 | 87.8 |
| 5 | 4_128_129_165_168 | 94.5 | 84.9 | 87.8 |
| 5 | 2_4_130_168_246 | 95.9 | 84.3 | 87.8 |
| 5 | 4_17_128_165_168 | 95.5 | 84.4 | 87.7 |
| 5 | 4_17_165_168_169 | 95.3 | 84.5 | 87.7 |
| 5 | 4_17_117_165_168 | 95.3 | 84.4 | 87.6 |
| 5 | 4_17_165_168_323 | 95.3 | 84.3 | 87.6 |
| 5 | 4_17_81_165_168 | 94.7 | 84.6 | 87.6 |
| 5 | 4_17_165_168_253 | 95.1 | 84.4 | 87.6 |
| 5 | 4_17_162_165_168 | 95.5 | 84.2 | 87.6 |
| 5 | 2_4_168_201_246 | 94.5 | 84.7 | 87.6 |
| 5 | 4_17_141_165_168 | 94.7 | 84.5 | 87.5 |
| 5 | 4_17_129_165_168 | 94.3 | 84.6 | 87.5 |
| 5 | 4_17_165_168_258 | 94.7 | 84.4 | 87.5 |
| 5 | 4_17_165_168_190 | 95.7 | 84.0 | 87.5 |
| 5 | 4_17_115_168_177 | 92.7 | 85.3 | 87.5 |
| 5 | 4_17_165_168_191 | 94.9 | 84.2 | 87.4 |
| 5 | 4_17_158_165_168 | 95.3 | 84.1 | 87.4 |
| 5 | 4_17_165_168_184 | 95.7 | 83.9 | 87.4 |
| 5 | 4_17_94_165_168 | 95.3 | 84.1 | 87.4 |
| 5 | 4_17_165_168_296 | 95.5 | 83.9 | 87.4 |
| 5 | 4_17_165_168_307 | 95.1 | 84.1 | 87.4 |
| 5 | 4_17_123_165_168 | 95.5 | 83.9 | 87.4 |
| 5 | 4_17_39_165_168 | 94.9 | 84.1 | 87.4 |
| 5 | 4_17_145_165_168 | 95.3 | 83.9 | 87.3 |
| 5 | 4_17_165_168_286 | 94.9 | 84.1 | 87.3 |
| 5 | 4_17_73_165_168 | 95.3 | 83.8 | 87.2 |
| 5 | 4_17_115_165_168 | 94.9 | 84.0 | 87.2 |
| 5 | 4_17_108_165_168 | 94.7 | 84.1 | 87.2 |
| 5 | 4_17_156_165_168 | 94.9 | 84.0 | 87.2 |
| 5 | 4_17_165_168_249 | 95.5 | 83.6 | 87.2 |
| 5 | 4_17_131_165_168 | 95.3 | 83.7 | 87.2 |
| 5 | 4_17_165_168_304 | 94.9 | 83.9 | 87.2 |
| 5 | 4_17_157_165_168 | 95.1 | 83.8 | 87.2 |
| 5 | 4_17_165_168_318 | 94.9 | 83.8 | 87.1 |
| 5 | 4_17_74_165_168 | 94.3 | 84.1 | 87.1 |
| 5 | 4_17_165_168_216 | 94.9 | 83.6 | 87.0 |
| 5 | 4_17_165_168_309 | 94.5 | 83.8 | 87.0 |
| 5 | 4_17_165_168_236 | 94.7 | 83.7 | 87.0 |
| 5 | 4_17_165_168_324 | 95.3 | 83.5 | 87.0 |
| 5 | 2_4_111_168_173 | 92.7 | 84.5 | 86.9 |
| 5 | 4_17_115_130_168 | 92.7 | 84.3 | 86.8 |
| 5 | 2_4_130_168_173 | 93.7 | 83.9 | 86.8 |
| 5 | 4_17_111_115_168 | 91.9 | 84.6 | 86.8 |
| 5 | 2_4_168_173_201 | 93.5 | 83.7 | 86.6 |
| 5 | 4_17_115_160_168 | 92.1 | 84.3 | 86.6 |
| 5 | 4_17_115_168_246 | 94.1 | 83.5 | 86.6 |
| 5 | 2_4_115_168_173 | 94.3 | 83.3 | 86.6 |
| 5 | 4_17_115_168_201 | 92.3 | 84.1 | 86.5 |
| 5 | 4_17_115_168_217 | 92.9 | 83.8 | 86.5 |
| 5 | 2_4_17_115_168 | 92.5 | 83.6 | 86.3 |
| 5 | 4_17_115_140_168 | 90.9 | 84.1 | 86.1 |
| 5 | 4_17_102_115_168 | 92.1 | 83.3 | 85.9 |

TABLE 7-3

| Combined gene number | SEQ ID NO: | Validation cohort Sensitivity | Specificity | Accuracy |
|---|---|---|---|---|
| 3 | 121_130_164 | 97.6 | 82.3 | 86.9 |
| 4 | 18_121_130_164 | 98.6 | 84.4 | 88.6 |
| 4 | 18_130_164_268 | 98.4 | 83.7 | 88.1 |
| 4 | 13_18_130_165 | 98.2 | 81.5 | 86.5 |
| 5 | 18_121_130_136_164 | 98.6 | 84.6 | 88.8 |
| 5 | 18_121_130_164_314 | 98.4 | 84.6 | 88.8 |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_130_164_255_268 | 98.6 | 84.4 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_27_130_164_268 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_130_164_268_317 | 98.2 | 84.1 | 88.3 |
| 5 | 18_121_130_164_201 | 98.2 | 84.1 | 88.3 |
| 5 | 18_19_121_130_164 | 98.4 | 83.9 | 88.2 |
| 5 | 18_74_130_164_268 | 98.4 | 83.7 | 88.1 |
| 5 | 18_130_164_264_268 | 97.2 | 84.1 | 88.0 |
| 5 | 2_4_130_168_246 | 95.9 | 84.3 | 87.8 |
| 5 | 2_9_130_168_246 | 95.9 | 84.0 | 87.5 |
| 5 | 13_18_121_130_165 | 98.4 | 82.5 | 87.2 |
| 5 | 13_18_130_165_268 | 98.6 | 82.3 | 87.2 |
| 5 | 4_17_115_130_168 | 92.7 | 84.3 | 86.8 |
| 5 | 2_4_130_168_173 | 93.7 | 83.9 | 86.8 |
| 5 | 2_9_130_168_173 | 93.7 | 83.2 | 86.3 |
| 5 | 2_111_130_168_173 | 93.3 | 83.0 | 86.1 |
| 5 | 2_83_130_168_173 | 94.5 | 82.2 | 85.9 |
| 5 | 2_6_130_168_173 | 94.5 | 82.0 | 85.7 |
| 5 | 2_6_130_173_184 | 95.9 | 81.3 | 85.6 |
| 5 | 2_130_168_173_213 | 94.9 | 81.4 | 85.4 |
| 5 | 2_5_130_168_173 | 92.9 | 82.1 | 85.3 |
| 5 | 2_130_168_173_249 | 93.9 | 81.5 | 85.2 |

TABLE 7-4

| Combined gene number | SEQ ID NO: | Validation cohort Sensitivity | Specificity | Accuracy |
|---|---|---|---|---|
| 4 | 2_121_165_168 | 95.3 | 82.5 | 86.3 |
| 4 | 2_165_168_268 | 94.9 | 82.0 | 85.9 |
| 4 | 2_4_168_246 | 93.3 | 82.8 | 85.9 |
| 4 | 2_18_165_268 | 95.5 | 81.7 | 85.8 |
| 4 | 2_4_173_183 | 93.3 | 82.2 | 85.5 |
| 4 | 2_4_115_168 | 90.8 | 83.3 | 85.5 |
| 4 | 2_9_168_246 | 93.3 | 82.1 | 85.5 |
| 4 | 2_111_168_246 | 92.7 | 82.3 | 85.4 |
| 4 | 2_111_168_173 | 92.9 | 82.1 | 85.3 |
| 4 | 2_102_168_246 | 93.1 | 81.7 | 85.1 |
| 5 | 2_4_130_168_246 | 95.9 | 84.3 | 87.8 |
| 5 | 2_4_168_201_246 | 94.5 | 84.7 | 87.6 |
| 5 | 2_9_130_168_246 | 95.9 | 84.0 | 87.5 |
| 5 | 2_4_111_168_173 | 92.7 | 84.5 | 86.9 |
| 5 | 2_4_130_168_173 | 93.7 | 83.9 | 86.8 |
| 5 | 2_4_168_173_201 | 93.5 | 83.7 | 86.6 |
| 5 | 2_4_115_168_173 | 94.3 | 83.3 | 86.6 |
| 5 | 2_9_130_168_173 | 93.7 | 83.2 | 86.3 |
| 5 | 2_4_17_115_168 | 92.5 | 83.6 | 86.3 |
| 5 | 2_111_168_173_268 | 93.7 | 83.1 | 86.3 |
| 5 | 2_18_165_268_301 | 95.3 | 82.2 | 86.1 |
| 5 | 2_18_165_268_315 | 96.3 | 81.8 | 86.1 |
| 5 | 2_111_130_168_173 | 93.3 | 83.0 | 86.1 |
| 5 | 2_83_130_168_173 | 94.5 | 82.2 | 85.9 |
| 5 | 2_6_130_168_173 | 94.5 | 82.0 | 85.7 |
| 5 | 2_111_168_173_223 | 92.7 | 82.7 | 85.7 |
| 5 | 2_5_111_168_173 | 92.1 | 83.0 | 85.7 |
| 5 | 2_6_130_173_184 | 95.9 | 81.3 | 85.6 |
| 5 | 2_39_111_168_173 | 93.3 | 82.3 | 85.6 |
| 5 | 2_111_168_173_222 | 93.9 | 82.0 | 85.5 |
| 5 | 2_111_152_168_173 | 93.5 | 82.0 | 85.5 |
| 5 | 2_111_168_173_241 | 93.1 | 82.2 | 85.5 |
| 5 | 2_130_168_173_213 | 94.9 | 81.4 | 85.4 |
| 5 | 2_111_168_173_184 | 94.1 | 81.7 | 85.4 |
| 5 | 2_102_111_168_173 | 92.3 | 82.5 | 85.4 |
| 5 | 2_5_130_168_173 | 92.9 | 82.1 | 85.3 |
| 5 | 2_111_168_173_234 | 92.3 | 82.4 | 85.3 |
| 5 | 2_111_168_173_230 | 93.1 | 82.0 | 85.3 |
| 5 | 2_111_168_173_307 | 93.3 | 81.9 | 85.3 |
| 5 | 2_130_168_173_249 | 93.9 | 81.5 | 85.2 |
| 5 | 2_111_158_168_173 | 92.9 | 81.8 | 85.1 |
| 5 | 2_39_168_169_173 | 93.3 | 81.5 | 85.1 |

TABLE 7-5

| Combined gene number | SEQ ID NO: | Validation cohort Sensitivity | Specificity | Accuracy |
|---|---|---|---|---|
| 3 | 9_165_168 | 95.9 | 83.0 | 86.9 |
| 4 | 9_165_168_173 | 96.5 | 83.2 | 87.2 |
| 4 | 9_128_165_168 | 95.3 | 83.6 | 87.1 |
| 4 | 9_17_165_168 | 94.7 | 83.5 | 86.9 |
| 4 | 9_80_165_168 | 97.4 | 82.2 | 86.8 |
| 4 | 2_9_168_246 | 93.3 | 82.1 | 85.5 |
| 5 | 5_9_165_168_173 | 96.5 | 83.9 | 87.6 |
| 5 | 9_128_129_165_168 | 94.5 | 84.6 | 87.5 |
| 5 | 2_9_130_168_246 | 95.9 | 84.0 | 87.5 |
| 5 | 9_17_159_165_168 | 94.7 | 83.4 | 86.8 |
| 5 | 9_17_165_168_173 | 95.1 | 83.1 | 86.7 |
| 5 | 2_9_130_168_173 | 93.7 | 83.2 | 86.3 |

TABLE 7-6

| Combined gene number | SEQ ID NO: | Validation cohort Sensitivity | Specificity | Accuracy |
|---|---|---|---|---|
| 3 | 17_164_168 | 97.8 | 80.4 | 85.6 |
| 4 | 4_17_165_168 | 95.1 | 84.2 | 87.5 |
| 4 | 9_17_165_168 | 94.7 | 83.5 | 86.9 |
| 4 | 4_17_115_168 | 92.1 | 83.3 | 85.9 |
| 4 | 4_17_115_302 | 89.8 | 84.1 | 85.8 |
| 4 | 4_17_115_184 | 91.5 | 82.7 | 85.3 |
| 5 | 4_17_165_168_173 | 96.5 | 84.1 | 87.8 |

TABLE 7-6-continued

| Combined gene number | SEQ ID NO: | Validation cohort | | |
|---|---|---|---|---|
| | | Sensitivity | Specificity | Accuracy |
| 5 | 4_17_165_168_223 | 95.7 | 84.5 | 87.8 |
| 5 | 4_17_128_165_168 | 95.5 | 84.4 | 87.7 |
| 5 | 4_17_165_168_169 | 95.3 | 84.5 | 87.7 |
| 5 | 4_17_117_165_168 | 95.3 | 84.4 | 87.6 |
| 5 | 4_17_165_168_323 | 95.3 | 84.3 | 87.6 |
| 5 | 4_17_81_165_168 | 94.7 | 84.6 | 87.6 |
| 5 | 4_17_165_168_253 | 95.1 | 84.4 | 87.6 |
| 5 | 4_17_162_165_168 | 95.5 | 84.2 | 87.6 |
| 5 | 4_17_141_165_168 | 94.7 | 84.5 | 87.5 |
| 5 | 4_17_129_165_168 | 94.3 | 84.6 | 87.5 |
| 5 | 4_17_165_168_258 | 94.7 | 84.4 | 87.5 |
| 5 | 4_17_165_168_190 | 95.7 | 84.0 | 87.5 |
| 5 | 4_17_115_168_177 | 92.7 | 85.3 | 87.5 |
| 5 | 4_17_165_168_191 | 94.9 | 84.2 | 87.4 |
| 5 | 4_17_158_165_168 | 95.3 | 84.1 | 87.4 |
| 5 | 4_17_165_168_184 | 95.7 | 83.9 | 87.4 |
| 5 | 4_17_94_165_168 | 95.3 | 84.1 | 87.4 |
| 5 | 4_17_165_168_296 | 95.5 | 83.9 | 87.4 |
| 5 | 4_17_165_168_307 | 95.1 | 84.1 | 87.4 |
| 5 | 4_17_123_165_168 | 95.5 | 83.9 | 87.4 |
| 5 | 4_17_39_165_168 | 94.9 | 84.1 | 87.4 |
| 5 | 4_17_145_165_168 | 95.3 | 83.9 | 87.3 |
| 5 | 4_17_165_168_286 | 94.9 | 84.1 | 87.3 |
| 5 | 4_17_73_165_168 | 95.3 | 83.8 | 87.2 |
| 5 | 4_17_115_165_168 | 94.9 | 84.0 | 87.2 |
| 5 | 4_17_108_165_168 | 94.7 | 84.1 | 87.2 |
| 5 | 4_17_156_165_168 | 94.9 | 84.0 | 87.2 |
| 5 | 4_17_165_168_249 | 95.5 | 83.6 | 87.2 |
| 5 | 4_17_131_165_168 | 95.3 | 83.7 | 87.2 |
| 5 | 4_17_165_168_304 | 94.9 | 83.9 | 87.2 |
| 5 | 4_17_157_165_168 | 95.1 | 83.8 | 87.2 |
| 5 | 4_17_165_168_318 | 94.9 | 83.8 | 87.1 |
| 5 | 4_17_74_165_168 | 94.3 | 84.1 | 87.1 |
| 5 | 4_17_165_168_216 | 94.9 | 83.6 | 87.0 |
| 5 | 4_17_165_168_309 | 94.5 | 83.8 | 87.0 |
| 5 | 4_17_165_168_236 | 94.7 | 83.7 | 87.0 |
| 5 | 4_17_165_168_324 | 95.3 | 83.5 | 87.0 |
| 5 | 9_17_159_165_168 | 94.7 | 83.4 | 86.8 |
| 5 | 4_17_115_130_168 | 92.7 | 84.3 | 86.8 |
| 5 | 4_17_111_115_168 | 91.9 | 84.6 | 86.8 |
| 5 | 9_17_165_168_173 | 95.1 | 83.1 | 86.7 |
| 5 | 4_17_115_160_168 | 92.1 | 84.3 | 86.6 |
| 5 | 4_17_115_168_246 | 94.1 | 83.5 | 86.6 |
| 5 | 4_17_115_168_201 | 92.3 | 84.1 | 86.5 |
| 5 | 4_17_115_168_217 | 92.9 | 83.8 | 86.5 |
| 5 | 2_4_17_115_168 | 92.5 | 83.6 | 86.3 |
| 5 | 4_17_115_140_168 | 90.9 | 84.1 | 86.1 |
| 5 | 4_17_102_115_168 | 92.1 | 83.3 | 85.9 |

TABLE 7-7

| Combined gene number | SEQIDNO: | Validation cohort | | |
|---|---|---|---|---|
| | | Sensitivity | Specificity | Accuracy |
| 3 | 121_130_164 | 97.6 | 82.3 | 86.9 |
| 3 | 18_121_164 | 98.6 | 81.6 | 86.7 |
| 3 | 121_164_168 | 97.8 | 80.9 | 85.9 |
| 3 | 121_164_328 | 96.3 | 81.1 | 85.6 |
| 3 | 121_164_211 | 97.6 | 80.2 | 85.4 |
| 3 | 95_121_164 | 98.4 | 79.7 | 85.3 |
| 3 | 6_121_165 | 96.3 | 80.3 | 85.1 |
| 4 | 18_121_130_164 | 98.6 | 84.4 | 88.6 |
| 4 | 18_121_164_255 | 98.0 | 84.2 | 88.4 |
| 4 | 18_121_164_201 | 98.2 | 83.0 | 87.6 |
| 4 | 18_121_151_164 | 98.2 | 83.1 | 87.6 |
| 4 | 18_95_121_164 | 99.0 | 81.5 | 86.8 |
| 4 | 18_107_121_164 | 98.6 | 81.6 | 86.7 |
| 4 | 2_121_165_168 | 95.3 | 82.5 | 86.3 |
| 4 | 18_121_149_165 | 97.1 | 81.7 | 86.3 |
| 4 | 13_18_121_165 | 99.2 | 80.4 | 86.1 |
| 5 | 18_121_130_136_164 | 98.6 | 84.6 | 88.8 |
| 5 | 18_121_130_164_314 | 98.4 | 84.6 | 88.8 |

TABLE 7-7-continued

| Combined gene number | SEQIDNO: | Validation cohort | | |
|---|---|---|---|---|
| | | Sensitivity | Specificity | Accuracy |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_121_130_164_201 | 98.2 | 84.1 | 88.3 |
| 5 | 18_19_121_130_164 | 98.4 | 83.9 | 88.2 |
| 5 | 18_95_121_164_188 | 99.0 | 83.0 | 87.8 |
| 5 | 13_18_121_130_165 | 98.4 | 82.5 | 87.2 |

Example 3

<Comparison of miRNA Expression Levels in Serum Between Lung Cancer Patient and Healthy Subject>

In this Example, miRNA expression levels in sera were compared between lung cancer patients and healthy subjects in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples were used (Table 11a). To be more specific, firstly, the miRNA expression levels of 1,694 lung cancer patients and 4,660 healthy subjects obtained in the preceding Reference Examples were combined and normalized by global normalization. Secondly, in order to evaluate diagnostic markers with higher reliability, only genes having the expression level of $2^6$ or higher in 50% or more of the samples in either of the lung cancer patient group or the healthy subject group, were selected. Thirdly, in order to evaluate a gene whose expression level significantly differs in statistics between a lung cancer patient group and the healthy subject group, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the lung cancer patient group and the healthy subject group, was calculated. Genes having a P value after the correction which was 0.05 or less and having an absolute value of fold change which was 0.5 or more, were extracted as genes varying in expression. The results are shown in Table 8.

TABLE 8

| SEQ ID NO: | P value after Bonferroni correction | Fold change of lung cancer patient to healthy subject |
|---|---|---|
| 1 | <1E−308 | 2.02 |
| 2 | <1E−308 | 2.95 |
| 3 | <1E−308 | 1.63 |
| 7 | <1E−308 | 0.81 |
| 10 | 5.30E−284 | 0.67 |
| 12 | <1E−308 | 2.04 |
| 13 | <1E−308 | 7.81 |
| 14 | 4.44E−148 | −0.52 |
| 15 | <1E−308 | 1.00 |
| 16 | <1E−308 | 1.41 |
| 17 | <1E−308 | 0.86 |
| 18 | <1E−308 | 0.85 |
| 19 | 4.47E−85 | 0.65 |
| 20 | <1E−308 | 1.29 |
| 21 | <1E−308 | 1.85 |
| 22 | <1E−308 | 3.64 |
| 23 | <1E−308 | 1.60 |
| 25 | <1E−308 | 3.01 |
| 26 | <1E−308 | 1.87 |
| 27 | <1E−308 | 3.01 |
| 29 | <1E−308 | 1.91 |
| 30 | <1E−308 | 4.83 |
| 31 | <1E−308 | 3.23 |
| 33 | <1E−308 | 1.53 |
| 34 | 3.29E−303 | 0.82 |
| 35 | <1E−308 | −0.54 |
| 36 | 2.02E−291 | 0.99 |
| 37 | <1E−308 | 1.21 |
| 38 | <1E−308 | 1.53 |
| 40 | <1E−308 | 3.15 |
| 42 | <1E−308 | −0.94 |
| 43 | <1E−308 | 2.13 |
| 44 | <1E−308 | 1.95 |
| 45 | <1E−308 | 2.38 |
| 46 | <1E−308 | 0.58 |
| 47 | <1E−308 | 1.30 |
| 50 | <1E−308 | 4.63 |
| 51 | <1E−308 | 1.09 |
| 55 | <1E−308 | 0.68 |
| 56 | <1E−308 | 1.19 |
| 57 | <1E−308 | 3.71 |
| 58 | <1E−308 | −0.92 |
| 59 | <1E−308 | 1.27 |
| 60 | <1E−308 | 3.87 |
| 64 | <1E−308 | 4.03 |
| 65 | <1E−308 | 0.58 |
| 66 | <1E−308 | 1.62 |
| 67 | <1E−308 | 0.60 |
| 68 | <1E−308 | 3.95 |
| 69 | <1E−308 | 3.20 |
| 70 | <1E−308 | 4.36 |
| 71 | <1E−308 | 0.81 |
| 72 | <1E−308 | 3.83 |
| 73 | <1E−308 | −2.42 |
| 74 | <1E−308 | 0.97 |
| 75 | <1E−308 | 3.76 |
| 76 | <1E−308 | 1.16 |
| 78 | <1E−308 | 4.29 |
| 79 | 7.77E−294 | 0.77 |
| 80 | <1E−308 | 2.72 |
| 81 | <1E−308 | 1.08 |
| 84 | <1E−308 | −0.80 |
| 85 | <1E−308 | 3.89 |
| 86 | 4.63E−209 | 0.57 |
| 87 | <1E−308 | 3.01 |
| 90 | <1E−308 | 0.67 |
| 92 | <1E−308 | 0.86 |

TABLE 8-continued

| SEQ ID NO: | P value after Bonferroni correction | Fold change of lung cancer patient to healthy subject |
|---|---|---|
| 94 | <1E−308 | 2.29 |
| 95 | <1E−308 | 0.75 |
| 96 | <1E−308 | 3.61 |
| 97 | <1E−308 | 1.15 |
| 98 | <1E−308 | 3.35 |
| 99 | <1E−308 | 1.22 |
| 101 | <1E−308 | 0.87 |
| 102 | <1E−308 | 0.58 |
| 103 | <1E−308 | 0.85 |
| 104 | <1E−308 | 0.78 |
| 105 | <1E−308 | 0.75 |
| 106 | <1E−308 | 1.77 |
| 107 | <1E−308 | 1.61 |
| 109 | <1E−308 | −0.58 |
| 110 | <1E−308 | 0.89 |
| 111 | <1E−308 | 0.72 |
| 113 | 8.52E−107 | 0.52 |
| 114 | 3.97E−267 | 0.63 |
| 115 | <1E−308 | 1.51 |
| 118 | <1E−308 | −0.80 |
| 120 | <1E−308 | 1.56 |
| 122 | <1E−308 | 2.26 |
| 124 | <1E−308 | 1.24 |
| 127 | <1E−308 | 1.40 |
| 128 | <1E−308 | 1.05 |
| 130 | <1E−308 | 0.55 |
| 131 | <1E−308 | −1.09 |
| 134 | <1E−308 | 1.38 |
| 135 | <1E−308 | 3.67 |
| 136 | <1E−308 | −1.41 |
| 137 | <1E−308 | 2.98 |
| 138 | 9.35E−164 | 0.54 |
| 140 | 8.27E−232 | 0.63 |
| 142 | 7.60E−293 | 0.73 |
| 143 | <1E−308 | 2.39 |
| 144 | <1E−308 | 1.12 |
| 145 | <1E−308 | −1.21 |
| 148 | <1E−308 | 1.55 |
| 149 | <1E−308 | 3.33 |
| 150 | <1E−308 | 4.64 |
| 153 | <1E−308 | 2.85 |
| 159 | <1E−308 | 1.19 |
| 162 | <1E−308 | 2.23 |
| 163 | <1E−308 | 3.49 |
| 164 | <1E−308 | 3.66 |
| 165 | <1E−308 | 1.98 |
| 166 | 3.76E−62 | −0.65 |
| 167 | 2.34E−248 | 0.61 |
| 170 | <1E−308 | 4.76 |
| 172 | <1E−308 | 1.30 |
| 173 | <1E−308 | 1.13 |
| 175 | <1E−308 | −1.26 |
| 177 | <1E−308 | 1.68 |
| 179 | <1E−308 | 1.49 |
| 180 | <1E−308 | 0.90 |
| 181 | <1E−308 | 1.16 |
| 182 | <1E−308 | 2.32 |
| 183 | <1E−308 | −0.85 |
| 184 | <1E−308 | −0.69 |
| 185 | <1E−308 | 1.96 |
| 186 | <1E−308 | −0.95 |
| 187 | <1E−308 | 1.14 |
| 188 | <1E−308 | 4.99 |
| 190 | <1E−308 | 4.22 |
| 193 | <1E−308 | 0.65 |
| 195 | <1E−308 | 5.97 |
| 196 | <1E−308 | 4.90 |
| 197 | <1E−308 | 5.16 |
| 198 | <1E−308 | 3.04 |
| 199 | <1E−308 | 2.28 |
| 200 | <1E−308 | 0.74 |
| 201 | <1E−308 | 1.42 |
| 202 | <1E−308 | 0.72 |
| 206 | <1E−308 | 2.54 |
| 207 | <1E−308 | 2.68 |
| 209 | <1E−308 | 1.03 |

TABLE 8-continued

| SEQ ID NO: | P value after Bonferroni correction | Fold change of lung cancer patient to healthy subject |
|---|---|---|
| 211 | <1E−308 | 1.06 |
| 214 | <1E−308 | 1.09 |
| 215 | <1E−308 | −1.12 |
| 217 | <1E−308 | 1.32 |
| 220 | <1E−308 | 2.71 |
| 221 | <1E−308 | 0.79 |
| 222 | <1E−308 | 0.64 |
| 225 | <1E−308 | 3.19 |
| 226 | <1E−308 | 3.05 |
| 229 | 4.55E−203 | −0.63 |
| 231 | <1E−308 | 5.80 |
| 232 | <1E−308 | 1.10 |
| 235 | 7.77E−196 | −0.55 |
| 236 | <1E−308 | 1.52 |
| 239 | <1E−308 | 0.95 |
| 246 | <1E−308 | 1.36 |
| 247 | <1E−308 | 1.17 |
| 249 | 3.06E−90 | −0.65 |
| 250 | <1E−308 | 0.81 |
| 251 | <1E−308 | 1.01 |
| 255 | <1E−308 | 3.10 |
| 256 | 3.79E−269 | 0.56 |
| 257 | <1E−308 | 1.99 |
| 259 | <1E−308 | 1.72 |
| 260 | <1E−308 | 3.26 |
| 261 | <1E−308 | 1.88 |
| 262 | <1E−308 | 1.54 |
| 263 | <1E−308 | 3.49 |
| 265 | 2.97E−266 | 0.55 |
| 267 | <1E−308 | 0.91 |
| 268 | 1.19E−234 | 0.55 |
| 269 | <1E−308 | 0.77 |
| 272 | <1E−308 | 1.43 |
| 273 | 1.04E−304 | 0.57 |
| 274 | <1E−308 | −0.92 |
| 276 | <1E−308 | 0.73 |
| 277 | 6.62E−218 | 0.64 |
| 278 | <1E−308 | −1.41 |
| 279 | <1E−308 | −0.83 |
| 280 | 1.54E−225 | 0.57 |
| 281 | <1E−308 | 1.05 |
| 282 | <1E−308 | −0.50 |
| 284 | 2.35E−278 | −0.60 |
| 285 | <1E−308 | 1.67 |
| 286 | <1E−308 | −1.27 |
| 287 | <1E−308 | 1.31 |
| 290 | <1E−308 | 1.08 |
| 291 | <1E−308 | 1.57 |
| 293 | <1E−308 | −0.51 |
| 294 | 2.90E−300 | 0.64 |
| 295 | <1E−308 | 1.12 |
| 296 | 5.92E−276 | −0.64 |
| 297 | 6.60E−269 | −0.60 |
| 298 | <1E−308 | 0.87 |
| 299 | <1E−308 | 2.46 |
| 300 | <1E−308 | 2.52 |
| 301 | <1E−308 | 0.87 |
| 303 | <1E−308 | 0.88 |
| 304 | <1E−308 | −1.68 |
| 305 | <1E−308 | 0.87 |
| 306 | <1E−308 | 1.06 |
| 307 | <1E−308 | 0.79 |
| 309 | <1E−308 | 3.01 |
| 311 | <1E−308 | 5.07 |
| 312 | <1E−308 | 4.83 |
| 313 | <1E−308 | 1.14 |
| 314 | <1E−308 | 0.75 |
| 315 | <1E−308 | 2.69 |
| 316 | <1E−308 | 1.63 |
| 317 | <1E−308 | 0.97 |
| 318 | <1E−308 | 3.19 |
| 319 | <1E−308 | 5.62 |
| 320 | <1E−308 | 1.02 |
| 321 | <1E−308 | 1.24 |
| 322 | <1E−308 | 2.07 |
| 324 | <1E−308 | −1.84 |
| 327 | 5.87E−261 | 1.52 |
| 328 | <1E−308 | 2.66 |
| 329 | <1E−308 | 3.30 |

Example 4

<Comparison of miRNA Expression Levels in Serum Between Lung Cancer Patient and Benign Bone and Soft Tissue Tumor Patients and Benign Breast Disease Patients>

In this Example, miRNA expression levels in sera were compared between lung cancer patients and benign bone and soft tissue tumor patients and benign breast disease patients in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples were used (Table 11a). To be more specific, firstly, the miRNA expression levels of 1,694 lung cancer patients and 368 benign bone and soft tissue tumor patients and benign breast disease patients obtained in the preceding Reference Examples were combined and normalized by global normalization.

Secondly, in order to evaluate diagnostic markers with higher reliability, only genes having the expression level of $2^6$ or higher in 50% or more of the samples in either of the group of lung cancer patients or the group of benign bone and soft tissue tumor patients and benign breast disease patients, were selected. Thirdly, in order to evaluate a gene whose expression level significantly differs in statistics between the group of lung cancer patients and the group of benign bone and soft tissue tumor patients and benign breast disease patients, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the group of lung cancer patients and the group of benign bone and soft tissue tumor patients and benign breast disease patients, was calculated. A gene having a P value after the correction which was 0.05 or less and having an absolute value of fold change which was 0.5 or more, was extracted as a gene varying in expression. The results are shown in Table 9.

TABLE 9

| SEQ ID NO: | P value after Bonferroni correction | Fold change of lung cancer patient to benign bone and soft tissue tumor patients and benign breast disease patients |
|---|---|---|
| 1 | 2.39E−129 | 0.94 |
| 2 | 1.31E−199 | 2.34 |
| 3 | 7.47E−167 | 1.49 |
| 4 | 3.64E−68 | −1.48 |
| 8 | 2.49E−75 | 1.03 |
| 9 | 9.04E−40 | −1.17 |
| 11 | 8.51E−43 | −0.55 |
| 12 | 7.12E−163 | 1.24 |

TABLE 9-continued

| SEQ ID NO: | P value after Bonferroni correction | Fold change of lung cancer patient to benign bone and soft tissue tumor patients and benign breast disease patients |
|---|---|---|
| 13 | 1.57E-149 | 2.56 |
| 15 | 1.26E-108 | 1.26 |
| 20 | 5.02E-73 | 1.03 |
| 22 | 2.96E-67 | 1.33 |
| 23 | 2.55E-128 | 1.57 |
| 24 | 7.59E-83 | -0.55 |
| 25 | 1.04E-58 | 1.12 |
| 27 | 1.98E-75 | 1.76 |
| 29 | 2.82E-175 | 1.91 |
| 30 | 2.35E-57 | 1.78 |
| 31 | 9.31E-74 | 1.14 |
| 32 | 3.51E-288 | -0.51 |
| 33 | 2.39E-102 | 1.50 |
| 34 | 1.65E-117 | 0.87 |
| 36 | 2.38E-48 | 0.85 |
| 40 | 7.11E-197 | 2.24 |
| 43 | 4.45E-73 | 0.88 |
| 44 | 6.93E-34 | 0.88 |
| 45 | 1.20E-84 | 0.83 |
| 47 | 2.20E-55 | 0.84 |
| 48 | 7.93E-64 | 0.79 |
| 50 | 4.47E-86 | 1.69 |
| 56 | 6.73E-93 | 0.90 |
| 57 | 6.51E-65 | 1.24 |
| 59 | 1.22E-39 | 0.85 |
| 60 | 6.33E-158 | 2.26 |
| 64 | 8.48E-18 | 1.00 |
| 66 | 1.35E-144 | 0.77 |
| 68 | 4.04E-101 | 1.61 |
| 69 | 1.85E-27 | 1.00 |
| 70 | 5.91E-114 | 1.85 |
| 72 | 1.62E-91 | 1.67 |
| 73 | 2.55E-32 | 0.62 |
| 75 | 2.81E-85 | 1.55 |
| 76 | 4.11E-23 | 0.59 |
| 78 | 2.75E-73 | 1.79 |
| 79 | 1.95E-45 | 0.85 |
| 80 | 1.21E-150 | 1.33 |
| 85 | <1E-308 | 4.19 |
| 87 | 2.13E-115 | 1.66 |
| 94 | 7.34E-131 | 1.46 |
| 96 | 8.87E-95 | 1.42 |
| 98 | 4.83E-171 | 2.02 |
| 99 | 1.02E-39 | 0.84 |
| 102 | 6.67E-165 | 1.11 |
| 106 | 5.24E-29 | 0.50 |
| 107 | 7.47E-61 | 0.67 |
| 110 | 5.98E-82 | 0.53 |
| 114 | 2.73E-20 | 0.52 |
| 115 | 8.65E-115 | 0.54 |
| 120 | 3.91E-46 | 0.81 |
| 122 | 4.73E-52 | 1.17 |
| 126 | 1.19E-154 | -0.53 |
| 128 | 9.40E-33 | 0.64 |
| 134 | 1.36E-41 | 0.72 |
| 135 | 5.46E-172 | 2.32 |
| 136 | 4.38E-35 | -0.70 |
| 137 | <1E-308 | 1.71 |
| 138 | 9.15E-27 | 0.64 |
| 139 | 9.22E-34 | 0.62 |
| 140 | 1.08E-44 | 0.74 |
| 143 | 2.03E-70 | 1.52 |
| 144 | 3.76E-22 | 0.62 |
| 148 | 1.34E-47 | 0.66 |
| 149 | 8.40E-110 | 1.76 |
| 150 | 1.98E-89 | 1.68 |
| 153 | 1.39E-161 | 2.04 |
| 159 | 1.11E-50 | 0.74 |
| 163 | 1.05E-120 | 1.98 |
| 164 | <1E-308 | 2.51 |
| 165 | 9.44E-220 | 1.28 |
| 166 | 5.85E-66 | -1.73 |
| 167 | 6.22E-235 | 1.31 |
| 170 | 7.90E-67 | 1.84 |
| 172 | 2.04E-94 | 1.31 |
| 173 | 9.00E-61 | 0.60 |
| 179 | 5.55E-45 | 0.55 |
| 181 | 7.23E-54 | 0.81 |
| 182 | 1.03E-104 | 0.81 |
| 185 | 1.24E-82 | 1.06 |
| 186 | 8.97E-59 | 0.86 |
| 188 | <1E-308 | 6.00 |
| 189 | 6.66E-102 | 1.18 |
| 190 | 2.48E-177 | 2.08 |
| 194 | 3.50E-122 | 0.67 |
| 195 | 6.34E-123 | 1.89 |
| 196 | 1.24E-104 | 2.05 |
| 197 | 5.84E-97 | 2.35 |
| 198 | 1.14E-114 | 1.54 |
| 199 | 8.95E-90 | 0.93 |
| 201 | 1.58E-195 | 1.24 |
| 202 | 6.22E-55 | 0.58 |
| 206 | 2.35E-30 | 0.56 |
| 209 | 2.52E-75 | 0.52 |
| 213 | 1.88E-68 | -0.66 |
| 217 | 3.25E-133 | 0.94 |
| 220 | 2.19E-173 | 1.30 |
| 225 | 4.62E-84 | 1.58 |
| 226 | 8.00E-184 | 1.32 |
| 228 | 1.25E-59 | 1.42 |
| 231 | <1E-308 | 4.03 |
| 235 | 2.68E-20 | 0.52 |
| 241 | 2.57E-182 | -0.57 |
| 244 | 1.26E-14 | 0.53 |
| 249 | 2.46E-25 | -0.78 |
| 250 | 2.66E-89 | 0.58 |
| 255 | 8.95E-34 | 0.58 |
| 257 | 5.57E-54 | 1.34 |
| 260 | 4.52E-157 | 1.97 |
| 262 | 3.71E-31 | 0.53 |
| 263 | 4.51E-89 | 1.03 |
| 285 | 6.31E-83 | 1.16 |
| 287 | 2.36E-295 | 1.36 |
| 289 | 5.59E-114 | 1.04 |
| 291 | 4.37E-44 | 0.55 |
| 294 | 2.77E-20 | 0.51 |
| 299 | 6.64E-135 | 1.05 |
| 303 | 7.57E-59 | 0.95 |
| 311 | 2.95E-83 | 2.16 |
| 312 | 3.35E-238 | 2.89 |
| 313 | 1.44E-53 | 0.76 |
| 315 | 1.73E-20 | 0.68 |
| 319 | 7.52E-85 | 1.75 |
| 320 | 3.60E-29 | 0.71 |
| 322 | 9.40E-116 | 1.07 |
| 325 | 3.44E-130 | -0.55 |
| 327 | 2.41E-29 | 0.90 |
| 328 | 2.19E-125 | 1.08 |
| 329 | 2.60E-73 | 1.31 |

Example 5

<Comparison of miRNA Expression Levels in Serum Between Lung Cancer Patient and Patient Having a Cancer Other than Lung Cancer>

In this Example, miRNA expression levels in sera were compared between lung cancer patients and other cancer patients in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples, were used (Table 11a). To be specific, firstly, the miRNA expression levels of 1,694 lung cancer patients and 4,147 other cancer patients obtained in the preceding Reference Examples were combined and normalized by global normalization. Secondly, in order to evaluate diagnostic markers with higher reliability, only genes having the expression level of $2^6$ or higher in 50% or more of the samples in either of the group of lung cancer patients or the group of other cancer patients, were selected. Thirdly, in order to evaluate a gene whose gene expression level significantly differs in statistics between the group of lung cancer patients and the group of other cancer patients, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the group of lung cancer patients and the group of patients having a cancer other than lung cancer, was calculated. A gene having a P value after the correction which was 0.05 or less and having an absolute value of fold change which was 0.5 or more, was extracted as a gene varying in expression. The results are shown in Table 10.

TABLE 10

| SEQ ID NO: | P value after Bonferroni correction | Fold change of lung cancer patient to patient having cancer other than lung cancer |
|---|---|---|
| 1 | 4.58E−123 | 0.55 |
| 2 | 1.88E−145 | 1.27 |
| 3 | 6.31E−96 | 0.66 |
| 4 | 1.76E−150 | −1.08 |
| 9 | 8.54E−95 | −0.93 |
| 13 | 1.21E−114 | 1.38 |
| 20 | 1.20E−69 | 0.57 |
| 23 | 2.52E−48 | 0.53 |
| 29 | 3.77E−99 | 0.77 |
| 30 | 3.12E−43 | 0.83 |
| 33 | 1.61E−53 | 0.57 |
| 40 | 8.43E−82 | 0.78 |
| 50 | 2.76E−40 | 0.67 |
| 60 | 7.34E−122 | 1.10 |
| 64 | 4.67E−30 | 0.64 |
| 68 | 4.99E−91 | 0.92 |
| 69 | 9.36E−39 | 0.58 |
| 70 | 8.65E−59 | 0.77 |
| 72 | 5.35E−106 | 0.91 |
| 75 | 2.31E−52 | 0.67 |
| 78 | 3.67E−39 | 0.73 |
| 87 | 6.09E−57 | 0.66 |
| 94 | 1.00E−113 | 0.90 |
| 96 | 3.83E−68 | 0.65 |
| 98 | 6.51E−115 | 0.93 |
| 102 | 4.09E−92 | 0.51 |
| 120 | 2.93E−63 | 0.61 |
| 122 | 5.74E−73 | 0.76 |
| 135 | 2.97E−118 | 1.08 |
| 140 | 1.69E−67 | 0.56 |
| 143 | 1.34E−60 | 0.74 |
| 149 | 8.83E−80 | 0.88 |
| 150 | 2.47E−76 | 0.89 |
| 153 | 3.64E−76 | 0.80 |
| 163 | 1.53E−95 | 0.91 |
| 164 | 5.78E−212 | 0.92 |
| 165 | 2.37E−104 | 0.56 |
| 166 | 2.06E−83 | −1.03 |
| 170 | 9.80E−60 | 0.85 |
| 188 | 1.53E−44 | 0.57 |
| 195 | 1.39E−75 | 0.83 |
| 196 | 5.59E−82 | 1.00 |
| 197 | 1.10E−77 | 1.09 |
| 198 | 1.49E−75 | 0.74 |
| 220 | 6.63E−89 | 0.56 |
| 225 | 3.64E−51 | 0.67 |
| 228 | 1.25E−100 | 0.86 |
| 231 | 2.36E−114 | 1.27 |
| 260 | 8.14E−106 | 0.92 |
| 263 | 6.10E−65 | 0.66 |
| 311 | 6.14E−102 | 1.34 |
| 312 | 9.19E−63 | 0.80 |
| 319 | 4.08E−58 | 0.97 |
| 327 | 4.54E−51 | 0.69 |
| 329 | 4.55E−101 | 0.92 |

As shown in the above Examples, the kit, device and method of the present invention can detect lung adenocarcinoma, lung squamous cell carcinoma, large cell lung carcinoma, small cell lung carcinoma and other lung cancers with higher sensitivity than the existing tumor markers and therefore permit early detection of lung cancer. As a result, a treatment such as a chemotherapy, a radiotherapy, an immunotherapy, a molecular targeted therapy, or surgery with a high degree of probability for complete therapy can be applied early, thereby significantly improving a survival rate.

INDUSTRIAL APPLICABILITY

According to the present invention, various histological types or stages of progression of lung cancer can be effectively detected by a simple and inexpensive method. This enables early detection, diagnosis and treatment of lung cancer. Also, the method of the present invention enables less-invasive detection of lung cancer using patient's blood and therefore lung cancer can be simply and quickly detected.

All publications, patents, and patent applications cited herein are incorporated herein by reference in their entirety.

The invention claimed is:

1. A method for detecting and treating or performing a diagnostic procedure for lung cancer, comprising: determining an expression level of hsa-miR-2467-3p in a sample from a human subject using a nucleic acid(s) capable of specifically binding to hsa-miR-2467-3p, or using a kit or device comprising a nucleic acid(s) capable of specifically binding to hsa-miR-2467-3p, wherein the determining comprises the following steps of:
(a) contacting hsa-miR-2467-3p in the sample or complementary polynucleotide(s) thereof prepared from hsa-miR-2467-3p with the nucleic acid(s);
(b) measuring an expression level of hsa-miR-2467-3p;
(c) comparing the expression level of hsa-miR-2467-3p measured in the step (b) to a control expression level of hsa-miR-2467-3p in a control sample from a healthy human subject measured in the same way as in the step (b) to allow for diagnosis of lung cancer;
(d) detecting an increased level of hsa-miR-2467-3p in the sample from the human subject as compared to the control expression level of hsa-miR-2467-3p from the sample from the human subject that does not have lung cancer, wherein the increased level of hsa-miR-2467-3p indicates that the human subject has lung cancer; and
(e) treating the human subject having lung cancer or performing a diagnostic procedure on the human subject having lung cancer;
wherein the sample is blood, serum, or plasma;
wherein the treatment comprises chemotherapy, radiotherapy, immunotherapy, molecular targeted therapy, surgery or a combination thereof; and
wherein the diagnostic procedure comprises an imaging test method selected from the group consisting of a chest X-ray examination, CT examination, MRI examination, and PET examination; a pathological examination method selected from the group consisting of sputum cytology, pleural fluid analysis, bronchoscopy, and percutaneous needle biopsy; or a combination thereof.

2. The method according to claim 1, wherein the nucleic acid(s) is a polynucleotide(s) selected from the group consisting of the following polynucleotides (a) to (e):

(a) a polynucleotide consisting of a nucleotide sequence of SEQ ID NO: 22, or a nucleotide sequence derived from the nucleotide sequence in which the nucleic acid u is replaced with t, a variant thereof, a derivative thereof, or a fragment thereof comprising 15 or more consecutive nucleotides;
(b) a polynucleotide comprising a nucleotide sequence of SEQ ID NO: 22;
(c) a polynucleotide consisting of a nucleotide sequence complementary to a nucleotide sequence of SEQ ID NO: 22, or a nucleotide sequence derived from the nucleotide sequence in which the nucleic acid u is replaced with t, a variant thereof, a derivative thereof, or a fragment thereof comprising 15 or more consecutive nucleotides;
(d) a polynucleotide comprising a nucleotide sequence complementary to a nucleotide sequence of SEQ ID NO: 22, or a nucleotide sequence derived from the nucleotide sequence in which the nucleic acid u is replaced with t; and
(e) a polynucleotide hybridizing under stringent conditions to any of the polynucleotides (a) to (d).

3. The method according to claim 1, wherein the method further comprises:

determining an expression level(s) of one or more other miRNA(s) selected from the following other lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a complementary strand of the polynucleotide, in the sample from the human subject by the same way as in the steps (a) and (b) using a nucleic acid(s) capable of specifically binding to the miRNA(s), or using a kit or device comprising a nucleic acid(s) capable of specifically binding to the miRNA(s).

4. The method according to claim 1, wherein the measuring in the step (b) is performed by quantitative RT-PCR using the nucleic acid(s) as primer(s).

5. The method according to claim 1, wherein the measuring in the step (b) is performed by hybridization using the nucleic acid(s) as probe(s).

6. The method according to claim 3, wherein the measuring in the step (b) is performed by quantitative RT-PCR using the nucleic acid(s) as primer(s).

7. The method according to claim 3, wherein the measuring in the step (b) is performed by hybridization using the nucleic acid(s) as probe(s).

* * * * *